(12) United States Patent
Song et al.

(10) Patent No.: US 10,287,255 B2
(45) Date of Patent: May 14, 2019

(54) COMPOUNDS AS HISTONE DEACETYLASE 6 INHIBITORS AND PHARMACEUTICAL COMPOSITIONS COMPRISING THE SAME

(71) Applicant: CHONG KUN DANG PHARMACEUTICAL CORP., Seoul (KR)

(72) Inventors: Hyeseung Song, Gyeonggi-do (KR); Changgon Lee, Gyeonggi-do (KR); Dalyong Kwak, Gyeonggi-do (KR); Jaeyoung Lee, Gyeonggi-do (KR); Suyeal Bae, Gyeonggi-do (KR); Yuntae Kim, Gyeonggi-do (KR); Daekwon Bae, Gyeonggi-do (KR); Nina Ha, Gyeonggi-do (KR); Miseon Bae, Gyeonggi-do (KR); Jihyun Kim, Gyeonggi-do (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 0 days.

(21) Appl. No.: 15/125,256

(22) PCT Filed: Mar. 12, 2015

(86) PCT No.: PCT/KR2015/002417
§ 371 (c)(1),
(2) Date: Sep. 12, 2016

(87) PCT Pub. No.: WO2015/137750
PCT Pub. Date: Sep. 17, 2015

(65) Prior Publication Data
US 2017/0096405 A1    Apr. 6, 2017

(30) Foreign Application Priority Data
Mar. 12, 2014  (KR) ........................ 10-2014-0028920

(51) Int. Cl.
| | | |
|---|---|---|
| *C07D 241/04* | (2006.01) | |
| *C07D 401/06* | (2006.01) | |
| *C07D 401/10* | (2006.01) | |
| *C07D 401/12* | (2006.01) | |
| *C07D 403/06* | (2006.01) | |
| *C07D 403/10* | (2006.01) | |
| *C07D 403/12* | (2006.01) | |
| *C07D 405/06* | (2006.01) | |

(Continued)

(52) U.S. Cl.
CPC ......... *C07D 241/04* (2013.01); *C07D 401/06* (2013.01); *C07D 401/10* (2013.01); *C07D 401/12* (2013.01); *C07D 403/10* (2013.01); *C07D 403/12* (2013.01); *C07D 405/06* (2013.01); *C07D 405/10* (2013.01); *C07D 405/12* (2013.01); *C07D 409/06* (2013.01); *C07D 409/10* (2013.01); *C07D 413/06* (2013.01)

(58) Field of Classification Search
CPC .. C07D 241/04; C07D 401/06; C07D 401/10; C07D 401/12; C07D 403/06; C07D 403/10; C07D 403/12; C07D 405/06; C07D 405/10; C07D 405/12; C07D 409/06; C07D 409/10; C07D 413/06; C07D 413/10
See application file for complete search history.

(56) References Cited

U.S. PATENT DOCUMENTS

2002/0022628 A1    2/2002  Barlaam et al.
2003/0013757 A1    1/2003  Leser-Reiff et al.
(Continued)

FOREIGN PATENT DOCUMENTS

WO    03/011851 A2    2/2003
WO    03/076400 A1    9/2003
(Continued)

OTHER PUBLICATIONS

Supplementary European Search Report dated Dec. 7, 2016 for Application No. EP 15 76 2410.
(Continued)

*Primary Examiner* — Emily A Bernhardt
(74) *Attorney, Agent, or Firm* — Ladas & Parry LLP; Malcolm J. MacDonald

(57) ABSTRACT

A compound of formula (I), having histone deacetylase 6 (HDAC6) inhibitory activity,

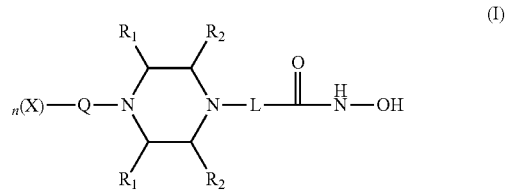

wherein X, Q, N, $R_1$, $R_2$, L, and n are as described, isomers thereof, or pharmaceutically acceptable salts thereof, the use thereof for the preparation of therapeutic medicaments, pharmaceutical compositions comprising the same, a method of treating disease using the composition, and methods for preparing the novel compounds. The novel compounds according to the present invention have histone deacetylase 6 (HDAC6) inhibitory activity, and are effective for the prevention or treatment of HDAC6-associated diseases, including cancer, inflammatory diseases, autoimmune diseases, neurological diseases and neurodegenerative disorders.

8 Claims, No Drawings

(51) Int. Cl.
   *C07D 405/10*   (2006.01)
   *C07D 405/12*   (2006.01)
   *C07D 409/06*   (2006.01)
   *C07D 409/10*   (2006.01)
   *C07D 413/06*   (2006.01)
   *C07D 413/10*   (2006.01)
   *A61K 31/496*   (2006.01)
   *A61K 31/5375*  (2006.01)

(56) References Cited

U.S. PATENT DOCUMENTS

2005/0234033 A1   10/2005   Anandan et al.
2011/0105474 A1   5/2011    Thaler et al.

FOREIGN PATENT DOCUMENTS

| WO | 03/076422 A1   | 9/2003 |
| WO | 2005/040101    | 5/2005 |
| WO | 2012/106343 A2 | 8/2012 |
| WO | 2013/041407 A1 | 3/2013 |
| WO | 2013/134467 A1 | 9/2013 |

OTHER PUBLICATIONS

Yu, L., et al., "Pharmacophore Identification of Hydroxamate HDAC 1 Inhibitors", Chinese Journal of Chemistry, vol. 27, No. 3, 2009, pp. 557-564.
International Search Report dated Jul. 9, 2015 for Application No. PCT/KR2015/002417.
Hassig, C.A., et al., "Nuclear histone acetylases and deacetylases and transcriptional regulation: HATs off to HDACs" Curr. Opin. Chem. Biol., 1997, 1, pp. 300-308.
Warrell, R.P., Jr., et al., "Therapeutic Targeting of Transcription in Acute Promyelocytic Leukemia by Use of an Inhibitor of Histone Deacetylase", Journal of the National Cancer Institute, Nov. 4, 1998, vol. 90, No. 21, pp. 1621-1625.
Bolden, J. E., et al., "Anticancer activities of histone deacetylase inhibitors", Nat. Rev. Drug Discovery, Sep. 2006, vol. 5, pp. 769-784.
Subramanian, S., et al., "Clinical Toxicities of Histone Deacetylase Inhibitors", Pharmaceuticals 2010, 3, pp. 2751-2767.
Witt, O, et al., "HDAC family: What are the cancer relevant targets?", Cancer Letters, 277, 2009, pp. 8-21.
Zhang, Y, et al., "Mice Lacking Histone Deacetylase 6 Have Hyperacetylated Tubulin but Are Viable and Develop Normally", Mol. and Cell. Biol., Mar. 2008, vol. 28, No. 5, pp. 1688-1701.
Kovacs, J.J., et al., "HDAC6 Regulates Hsp90 Acetylation and Chaperone-Dependent Activation of Glucocorticoid Receptor", Mol. Cell, May 27, 2005, vol. 18, pp. 601-607.
Santo, L., et al., "Preclinical activity, pharmacodynamic, and pharmacokinetic properties of a selective HDAC6 inhibitor, ACY-1215, in combination with bortezomib in multiple myeloma", Blood, Mar. 15, 2012, vol. 119, No. 11, pp. 2579-2589.
Vishwakarma, S., et al., "Tubastatin, a selective histone deacetylase 6 inhibitor shows anti-inflammatory and anti-rheumatic effects", International Immunopharmacology 2013, vol. 16, pp. 72-78.
Li, G., et al., "HDAC6 α-tubulin deacetylase: A potential therapeutic target in neurodegenerative diseases", Journal of the Neurological Sciences 2011, vol. 304, pp. 1-8.
Smil, D.V., et al., "Novel HDAC6 isoform selective chiral small molecule histone deacetylase inhibitors", Bioorganic & Medicinal Chemistry Letters, 2009, vol. 19, pp. 688-692.
Russian Office Action dated Nov. 3, 2007, for Russian Application No. 2016139690/04(063372).
Rossi, Cristina, et al., "Alkyl piperidine and piperazine hydroxamic acids as HDAC inhibitors", Bioorganic & Medicinal Chemistry Letters, vol. 21, No. 8, Oct. 22, 2011, pp. 2305-2308.
Chinese Office Action, including English translation, dated Feb. 11, 2018, corresponding to Chinese Application No. 201580020544.7.

COMPOUNDS AS HISTONE DEACETYLASE 6 INHIBITORS AND PHARMACEUTICAL COMPOSITIONS COMPRISING THE SAME

This application is a 371 of PCT/KR2015/002417, filed on Mar. 12, 2015, which claims priority to Korean patent application number 10-2014-0028920, filed on Mar. 12, 2014.

TECHNICAL FIELD

The present invention relates to novel compounds having histone deacetylase 6 (HDAC6) inhibitory activity, isomers thereof, pharmaceutically acceptable salts thereof, the use thereof for the preparation of therapeutic medicaments, pharmaceutical compositions comprising the same, a method of treating disease using the composition, and methods for preparing the novel compounds.

BACKGROUND ART

Post-translational modifications such as acetylation are very crucial regulatory modules at the heart of biological processes in the cells and are tightly regulated by a multitude of enzymes. Histones are the chief protein components of chromatin and act as spools around which DNA strands. Also, the balance of histone acetylation and deacetylation is a critical role in the regulation of gene expression.

Histone deacetylases (HDACs) are enzymes that remove acetyl groups from lysine residues on histone proteins of chromatin, and are known to be associated with gene silencing and induce cell cycle arrest, angiogenic inhibition, immune regulation, cell death, etc. (Hassig et al., Curr. Opin. Chem. Biol. 1997, 1, 300-308). In addition, it was reported that the inhibition of enzymatic function of HDACs induces the apoptosis of cancer cells in vivo by reducing the activity of cancer cell survival-associated factors and activating cancer cell apoptosis-associated factors (Warrell et al, J. Natl. Cancer Inst. 1998, 90, 1621-1625).

In humans, 18 HDACs have been identified and are subdivided into four classes based on their homology to yeast HDACs. Among them, 11 HDACs use zinc as a cofactor and can be divided into three groups: Class I (HDAC1, 2, 3 and 8), Class II (IIa: HDAC4, 5, 7 and 9; IIb: HDAC6 and 10), Class IV (HDAC 11). Additionally, 7 HDACs of Class III (SIRT 1-7) require $NAD^+$ instead of zinc as a cofactor (Bolden et al., Nat. Rev. Drug Discov. 2006, 5(9), 769-784).

Various HDAC inhibitors are in preclinical or clinical development, but to date, only non-selective HDAC inhibitors have been identified as anticancer agents, and only vorinostat (SAHA) and romidepsin (FK228) have been approved for the treatment of cutaneous T-cell lymphoma. However, non-selective HDAC inhibitors are known to cause side effects such as fatigue and nausea, generally at high doses (Piekarz et al., Pharmaceuticals 2010, 3, 2751-2767). Such side effects have been reported to be due to the inhibition of class I HDACs. Due to such side effects, the use of non-selective HDAC inhibitors in the development of drugs other than anticancer drugs has been limited (Witt et al., Cancer Letters, 2009, 277, 8-21).

Meanwhile, it was reported that the selective inhibition of class II HDACs would not show toxicity shown in the inhibition of class I HDACs. Also, when selective HDAC inhibitors are developed, side effects such as toxicity, which are caused by the non-selective HDAC inhibition, can be overcome. Thus, selective HDAC inhibitors have potential to be developed as therapeutic agents effective for the treatment of various diseases (Matthias et al., Mol. Cell. Biol. 2008, 28, 1688-1701).

It is known that HDAC6, a member of Class IIb HDACs, is present mainly in the cytoplasm and is involved in the deacetylation of a number of non-histone substrates (HSP90, cortactin, etc.), including tubulin, (Yao et al., Mol. Cell 2005, 18, 601-607). HDAC6 has two catalytic domains, and the zinc finger domain of C-terminal can bind to ubiquitinated proteins. It is known that HDAC6 has a number of non-histone proteins as substrates, and thus plays an important role in various diseases, including cancer, inflammatory diseases, autoimmune diseases, neurological diseases and neurodegenerative disorders (Santo et al., Blood 2012 119: 2579-258; Vishwakarma et al., International Immunopharmacology 2013, 16, 72-78; Hu et al., J. Neurol. Sci. 2011, 304, 1-8).

Accordingly, there is a need for the development of selective HDAC 6 inhibitors for treatment of cancer, inflammatory diseases, autoimmune diseases, neurological diseases and neurodegenerative disorders, which cause no side effects, unlike non-selective inhibitors.

DISCLOSURE

Technical Problem

It is an object of the present invention to provide novel compounds having selective HDAC6 inhibitory activity, isomers thereof, or pharmaceutically acceptable salts thereof.

Another object of the present invention is to provide pharmaceutical compositions containing novel compounds having selective HDAC6 inhibitory activity, isomers thereof, or pharmaceutically acceptable salts thereof.

Still another object of the present invention is to provide methods for preparing the novel compounds.

Still another object of the present invention is to provide pharmaceutical compositions for prevention or treatment of HDAC6 activity-associated diseases, including cancer, inflammatory diseases, autoimmune diseases, neurological diseases and neurodegenerative disorders, which contain the above compound.

Still another object of the present invention is to provide the use of the compounds for the preparation of therapeutic medicaments against HDAC6 activity-associated diseases.

Yet another object of the present invention is to provide methods for treating HDAC6 activity-associated diseases, which comprise administering a therapeutically effective amount of the pharmaceutical compositions containing the compounds.

Technical Solution

The present inventors have discovered novel dimethylpiperazine derivative compounds, particularly dimethylpiperazine hydroxamic acid derivative compounds, which have histone deacetylase 6 (HDAC6) inhibitory activity, and have found that these compounds can be used for the inhibition or treatment of histone deacetylase 6 (HDAC6) activity-associated diseases, thereby completing the present invention.

Novel HDAC6 Inhibitors

To achieve the above objects, the present invention provides compounds represented by the following formula I, isomers thereof, or pharmaceutically acceptable salts thereof:

Formula I

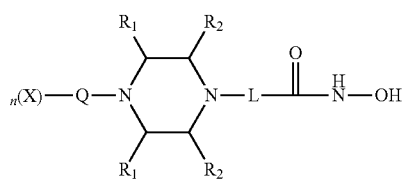

wherein
R$_1$ is hydrogen or —CH$_3$,
R$_2$ is hydrogen or —CH$_3$, provided that R$_2$ is —CH$_3$ when R$_1$ is hydrogen, and R$_2$ is hydrogen when R$_1$ is —CH$_3$
L is —(C$_4$-C$_5$ alkyl)-; —(C$_1$-C$_3$ alkyl)-L$_1$-; —C(=O)-L$_1$- or —S(=O)$_2$-L$_1$-,
wherein —(C$_4$-C$_5$ alkyl)- and —(C$_1$-C$_3$ alkyl)- may be unsubstituted or substituted with —CH$_3$,
L$_1$ is —(C$_3$-C$_6$)cycloalkyl-;

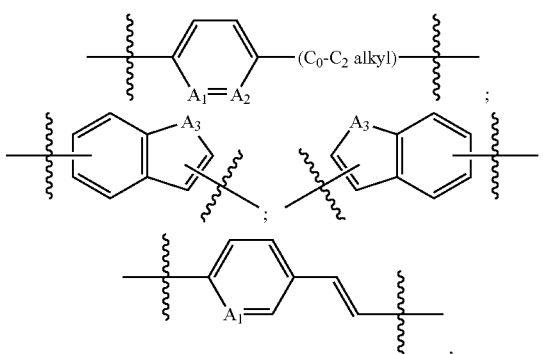

A$_1$ and A$_2$ are each independently —N— or —CR$_3$—, provided that both A$_1$ and A$_2$ cannot be —N—,
R$_3$ is hydrogen; —F, —Cl, —Br, —I or —OH, and
A$_3$ is —NH— or —O—,
Q is selected from the group consisting of —(C$_1$-C$_6$) alkyl-; —(C$_2$-C$_6$)alkenyl-; —C(=O)—; —C(=S)—; —S(=O)$_2$— or

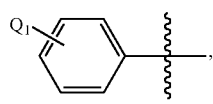

wherein —(C$_1$-C$_6$)alkyl- and —(C$_2$-C$_6$)alkenyl- may be unsubstituted or each independently substituted 1 to 3-CH$_3$ groups or halogen atoms,
Q$_1$ is hydrogen; —F, —Cl, —Br or —I
n is an integer of 0, 1 or 2, provided that n is 0 when Q is

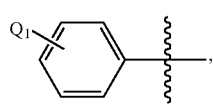

n is 1 when Q is —C(=O)—; —C(=S)— or —S(=O)$_2$—, and n is 1 or 2 when Q is —(C$_1$-C$_6$) alkyl- or —(C$_2$-C$_6$)alkenyl-, and
X may be selected from the group consisting of —C$_1$-C$_6$ alkyl; —C$_3$-C$_6$ cycloalkyl; —C$_2$-C$_6$ alkenyl; —C$_3$-C$_6$ cycloalkenyl; —(C$_0$-C$_2$ alkyl)Ar; —OAr; —(C$_0$-C$_2$ alkyl)Het; naphthyl and following groups:

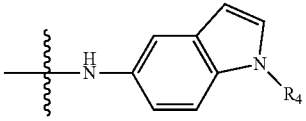

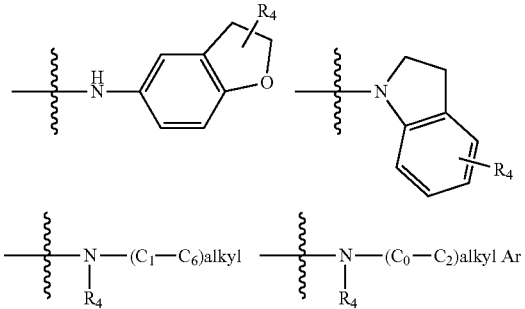

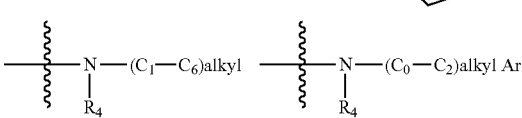

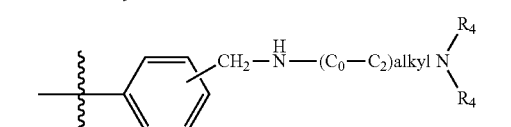

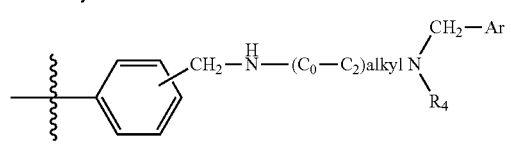

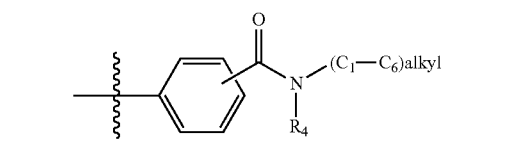

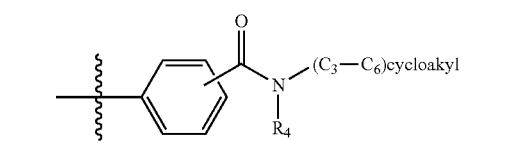

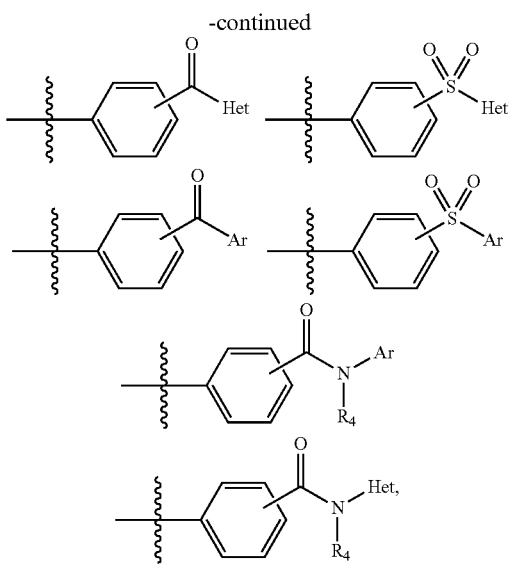

wherein R₄ is H or —$C_1$-$C_4$ alkyl,
—$C_0$-$C_2$ alkyl, —$C_2$-$C_6$ alkenyl and —$C_1$-$C_6$ alkyl may be unsubstituted or substituted with 1 to 2-$CH_3$ groups; 1 to 3—F groups, or a combination thereof, Ar is a $C_6$ monocyclic aromatic compound, which may be unsubstituted or substituted with one or more halogen atoms; —OH; —$NH_2$; —$C_1$-$C_6$ alkyl; —O($C_1$-$C_6$)alkyl; —$C_3$-$C_6$ cycloalkenyl; —NH($C_1$-$C_6$ alkyl); —N($C_1$-$C_3$ alkyl)₂; —$CH_2$N($C_1$-$C_3$ alkyl)₂; —S(=O)₂—($C_1$-$C_3$ alkyl) or phenyl groups, wherein —$C_1$-$C_3$ alkyl; —$C_1$-$C_6$ alkyl and —$C_3$-$C_6$ cycloalkenyl may be each independently substituted with 1 to 5 —F or —$CH_3$ groups, and Het is a 4- to 6-membered heteroaromatic or non-aromatic ring compound containing 1 to 3 elements selected from the group consisting of N, O and S while having 0 to 3 double bonds, and may be unsubstituted or substituted with one or more halogen atoms; —$C_1$-$C_6$ alkyl; —C(=O) ($C_1$-$C_3$ alkyl); —S(=O)₂($C_1$-$C_3$ alkyl) or benzyl groups, wherein —$C_1$-$C_3$ alkyl and —$C_1$-$C_6$ alkyl may be each independently substituted with —OH; 1 to 5 —F or —$CH_3$ groups.

As used herein, "$C_0$ alkyl" means that there is no carbon and therefore represents a bond. For example, "—($C_0$ alkyl) Ar" means —Ar.

The compounds represented by formula I according to the present invention may be compounds represented by the following formula II or formula III:

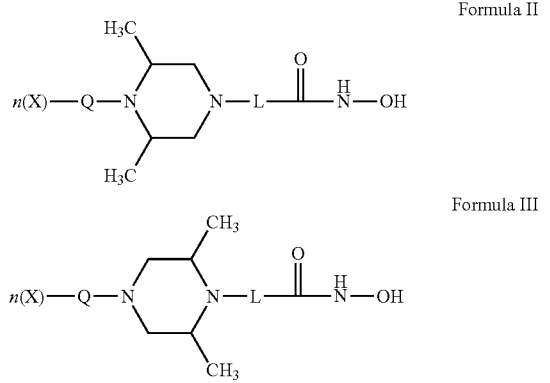

Formula II

Formula III wherein
L is —($C_5$ alkyl)-; —($C_1$-$C_2$ alkyl)-$L_1$-; —C(=O)-$L_1$- or —S(=O)₂-$L_1$-, wherein —($C_5$ alkyl)- and —($C_1$-$C_2$ alkyl)- are straight-chain and may be unsubstituted or substituted with —$CH_3$,
$L_1$ is —($C_3$-$C_6$) cycloalkyl-;

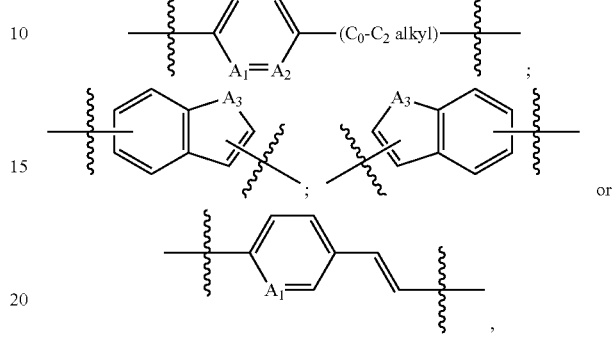

$A_1$ and $A_2$ are each independently —N— or —$CR_3$—, provided that both $A_1$ and $A_2$ cannot be —N—,
$R_3$ is hydrogen; —F or —OH, and
$A_3$ is —NH— or —O—,
Q is selected from the group consisting of —($C_1$-$C_3$) alkyl-; —C(=O)—; —C(=S)—; —S(=O)₂— or

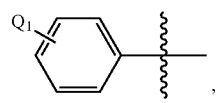

wherein —($C_1$-$C_3$)alkyl- may be unsubstituted or substituted with 1 to 3 —$CH_3$ groups or halogen atoms,
$Q_1$ is hydrogen; —F or —Cl,
n is an integer of 0 or 1, provided that n is 0 when Q is

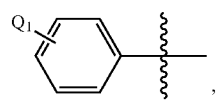

and n is 1 when Q is —C(=O)—, —C(=S)—, —S(=O)₂— or —($C_1$-$C_3$)alkyl-, and
X may be selected from the group consisting of —$C_1$-$C_6$ alkyl; —$C_3$-$C_6$ cycloalkyl; —$C_2$-$C_6$ alkenyl; —$C_3$-$C_6$ cycloalkenyl; —($C_0$-$C_2$ alkyl)Ar; —OAr; —($C_0$-$C_2$ alkyl)Het; naphthyl; and following groups:

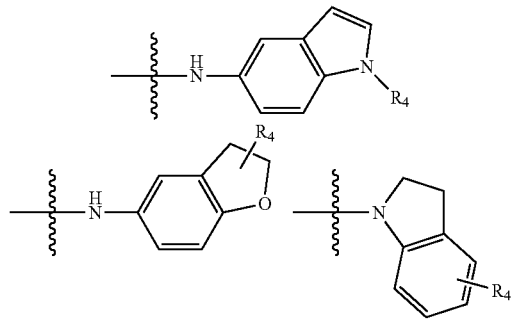

-continued

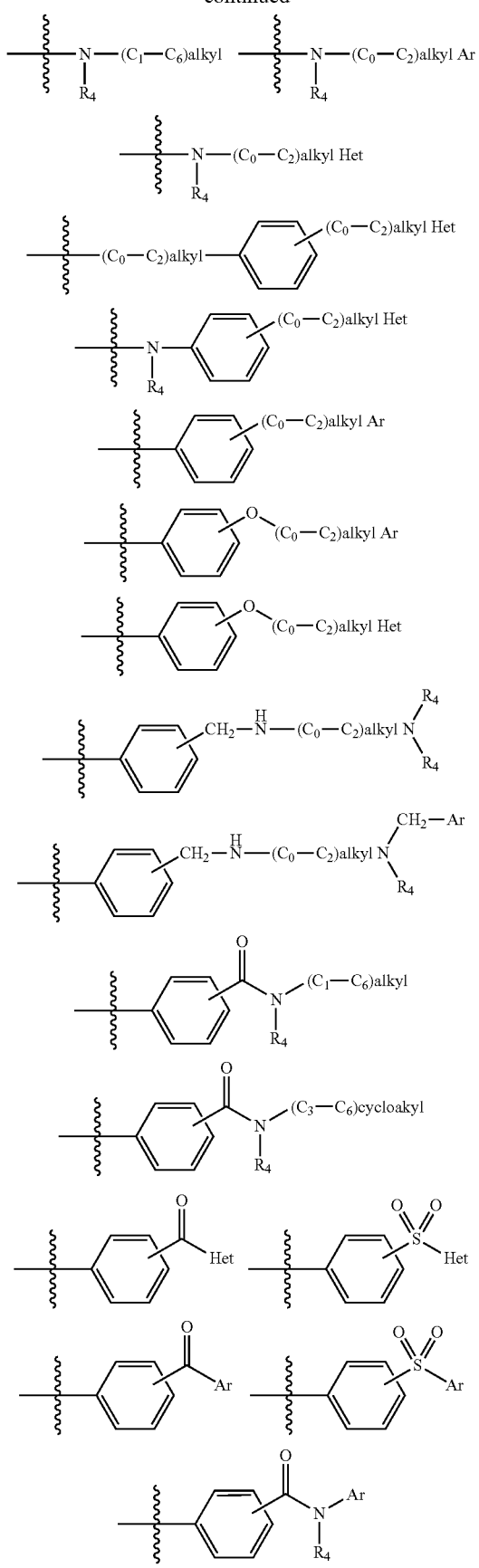

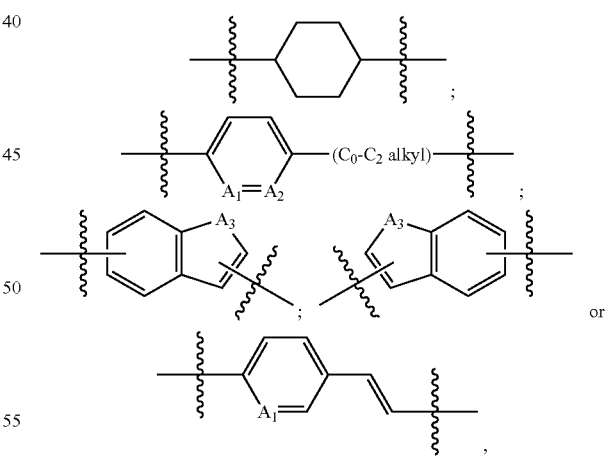

wherein $R_4$ is H or —$C_1$-$C_4$ alkyl,

—$C_0$-$C_2$ alkyl; —$C_2$-$C_6$ alkenyl and —$C_1$-$C_6$ alkyl may be unsubstituted or substituted with 1 or 2 —$CH_3$ groups or 1 to 3 —F groups, Ar is a $C_6$ monocyclic aromatic compound, which may be unsubstituted or substituted with one or more halogen atoms; —OH; —$NH_2$; —$C_1$-$C_6$ alkyl; —$O(C_1$-$C_6)$alkyl; —$C_3$-$C_6$ cycloalkenyl; —$NH(C_1$-$C_6$ alkyl); —$N(C_1$-$C_3$ alkyl)$_2$; —$CH_2N(C_1$-$C_3$ alkyl)$_2$; —$S(=O)_2$—$(C_1$-$C_3$ alkyl) or phenyl groups, wherein —$C_1$-$C_3$ alkyl; —$C_1$-$C_6$ alkyl and —$C_3$-$C_6$ cycloalkenyl may be each independently substituted with 1 to 5 —F or —$CH_3$ groups, and Het is a 4- to 6-membered heteroaromatic or non-aromatic ring compound containing 1 to 3 elements selected from the group consisting of N; O and S while having 0 to 3 double bonds, and may be unsubstituted or substituted with one or more halogen atoms; —$C_1$-$C_6$ alkyl; —$C(=O)$ ($C_1$-$C_3$ alkyl); —$S(=O)_2(C_1$-$C_3$ alkyl) or benzyl groups, wherein —$C_1$-$C_3$ alkyl and —$C_1$-$C_6$ alkyl may be each independently substituted with —OH; or 1 to 5 —F or —$CH_3$ groups.

In a preferred embodiment of the present invention, L, Q and X in formulas I, II and III may be defined as follows:

L is —$CH_2$-$L_1$-,
wherein
$L_1$ is $A_1$ and $A_2$ are each independently —N— or —$CR_3$—, provided that both $A_1$ and $A_2$ cannot be —N—, $R_3$ is hydrogen; —F or —OH, and $A_3$ is —NH— or —O—, Q is —$CH_2$—, —$C(=O)$— or —$S(=O)_2$—, and X may be selected from the group consisting of —$C_1$-$C_6$ alkyl; —($C_0$-$C_2$ alkyl)Ar; —($C_0$-$C_2$ alkyl)Het; —OAr; or following groups:

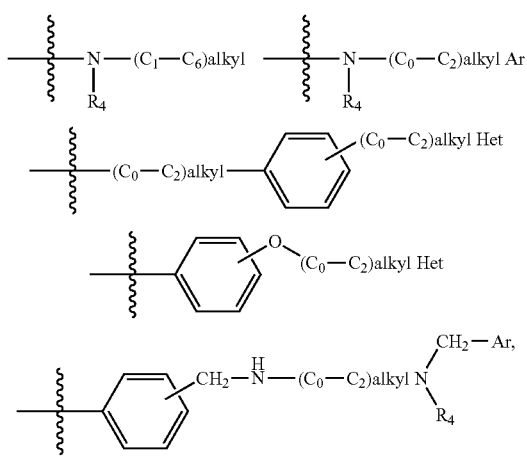

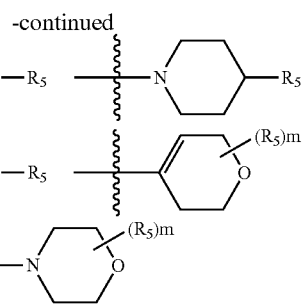

wherein $R_4$ is H or —$C_1$-$C_4$ alkyl,

—$C_0$-$C_2$ alkyl and —$C_1$-$C_6$ alkyl may be unsubstituted or substituted with 1 or 2 —$CH_3$ groups and/or 1 to 3 —F groups, and Ar and Het is each independently as defined in formula I to formula III.

In an embodiment of the present invention, the heterocyclic compound (Het) mentioned as X or a substituent in formula I to formula III above may have a structure selected from the following group:

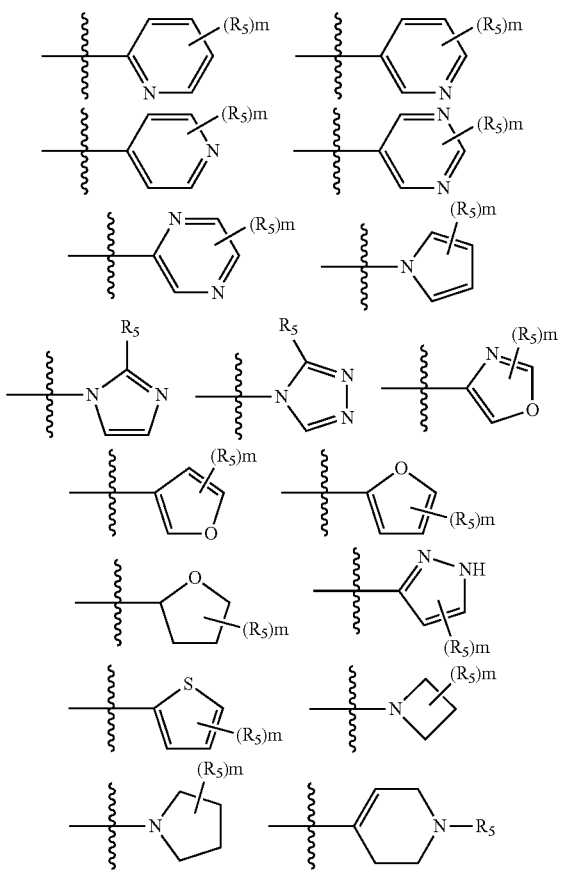

wherein $R_5$ are each independently hydrogen; —F; —Cl; —$C_1$-$C_6$ alkyl; —C(=O) ($C_1$-$C_3$ alkyl); —S(=O)$_2$($C_1$-$C_3$ alkyl) or benzyl, wherein —$C_1$-$C_3$ alkyl and —$C_1$-$C_6$ alkyl may be each independently substituted with —OH; 1 to 5 —F or —$CH_3$ groups, m is an integer of 0, 1, 2 or 3, and Het is unsubstituted when m is 0, and Het may be substituted with independent $R_5$ when m is 1, 2 or 3.

The compounds represented by formula I according to the present invention may be compounds represented by the following formula I-1:

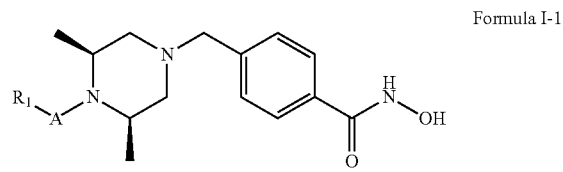

Formula I-1 wherein

A is —C(=O)—; —$CH_2$—; —NH(C=O)—; —C(=S)— or —S(=O)$_2$—, and $R_1$ is a straight or branched chain $C_1$-$C_4$ alkyl; a straight or branched chain $C_1$-$C_4$ alkenyl; a $C_3$-$C_5$ cycloalkyl; —$OC_6C_5$; —($C_0$-$C_2$ alkyl)$CF_3$; phenyl (which may be unsubstituted or substituted with $C_1$-$C_3$ alkyl; pyrrole; —$OCH_3$; —$CF_3$; —F; —Cl or —OH); pyridyl; furanyl; thiophenyl; benzyl (which may be unsubstituted or substituted with one or more $C_1$-$C_3$ alkyl; pyrrole; —$OCH_3$; —$CF_3$; —F; —Cl or —OH groups); phenethyl; naphthyl; oxazolyl; pyrimidinyl; pyrazolyl or pyrazinyl.

The compounds represented by formula I-1 are preferably compounds 82, 83, 84, 98, 99, 100, 120, 121, 122, 123, 125, 126, 127, 128, 145, 146, 147, 148, 149, 159, 160, 161, 177, 184, 188, 204, 211, 212, 213, 214, 222, 223, 224, 225, 232, 255, 265, 266, 267, 270, 272, 275, 290, 291, 292, 293, 294, 295, 296, 297, 354, 355, 403, 404 and 405 as disclosed herein.

The compounds represented by formula I may be compounds represented by the following formula I-2:

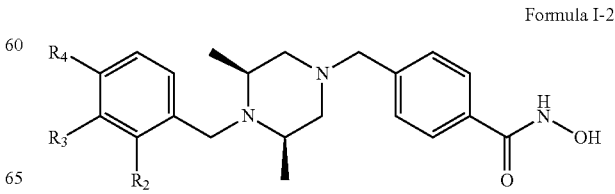

Formula I-2 wherein $R_2$, $R_3$ or $R_4$ may be each independently hydrogen or any one selected from the following group:

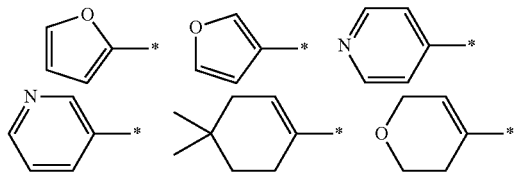

The compounds represented by formula I-2 are preferably compounds 309, 327, 328, 329, 330, 331, 332, 342, 343, 344, 345, 346 and 347 as disclosed herein.

The compounds represented by formula I according to the present invention may be compounds represented by the following formula I-3:

Formula I-3

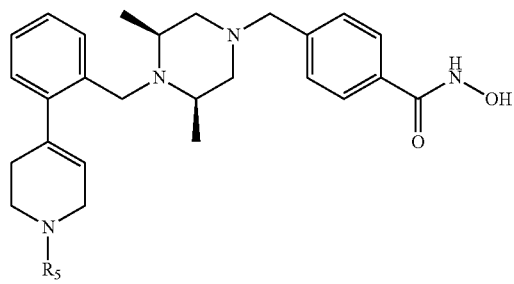

wherein $R_5$ may be selected from the group consisting of a straight or branched chain $C_1$-$C_4$ alkyl; —$COCH_3$; —$CH_2CF_3$ and —$SO_2CH_3$.

The compounds represented by formula I-3 are preferably compounds 481, 482, 483, 484 and 485 as disclosed herein.

The compounds represented by formula I according to the present invention may be compounds represented by formula I-4:

Formula I-4

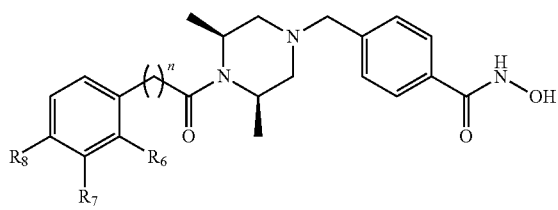

wherein n is an integer of 0, 1 or 2, and $R_6$, $R_7$ or $R_8$ may be each independently hydrogen or any one selected from the group consisting of the following group:

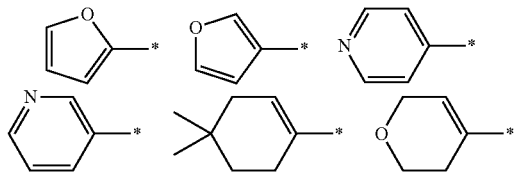

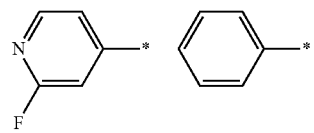

The compounds represented by formula I-4 are preferably compounds 234, 242, 243, 244, 245, 246, 247, 283, 284, 285, 286, 288, 326 and 340 as disclosed herein.

The compounds represented by formula I according to the present invention may be compounds represented by formula I-5:

Formula I-5

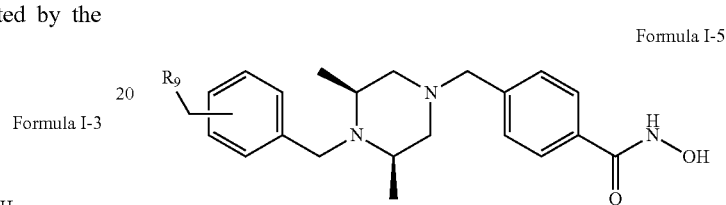

wherein $R_9$ may be selected from among morpholine; piperidine; pyrrolidine; azetidine; piperazine; —$C_1$-$C_2$ primary or secondary alkylamine;

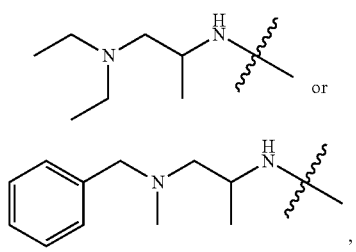

wherein pyrrolidine may be unsubstituted or substituted with one or more —F or —Cl groups, azeditine may be unsubstituted or substituted with one or more —F or —Cl groups, and piperazine may be unsubstituted or substituted with one or more straight or branched chain $C_1$-$C_5$ alkyl; benzyl; —$COCH_3$; —$CH_2CF_3$ or —$SO_2CH_3$ groups.

The compounds represented by formula I-5 are preferably compounds 356, 376, 382, 383, 384, 385, 411, 412, 413, 426, 427, 428, 429, 430, 431, 452, 453, 454, 455, 456, 457, 466, 467, 468 and 486 as disclosed herein.

The compounds represented by formula I according to the present invention may be compounds represented by the following formula I-$6_A$ or formula I-$6_B$:

Formula I-$6_A$

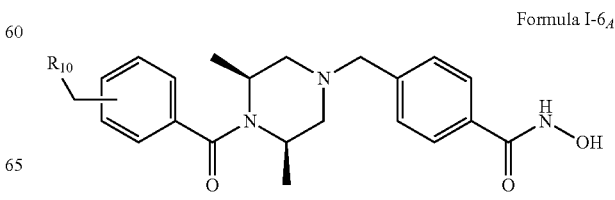

-continued

Formula I-6$_B$

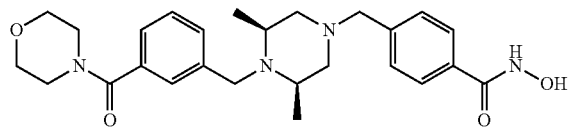

wherein R$_{10}$ may be selected from among pyrrolidine; piperidine; C$_1$-C$_2$ primary or secondary alkylamine; piperazine; morpholine;

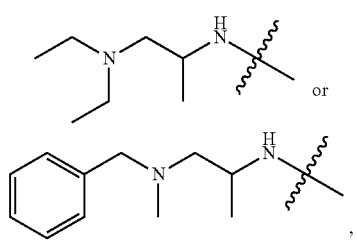

or

, wherein pyrrolidine may be unsubstituted or substituted with one or more —F or —Cl groups, and piperazine may be unsubstituted or substituted with one or more straight or branched chain C$_1$-C$_5$ alkyl; —COCH$_3$; —CH$_2$CF$_3$ or —SO$_2$CH$_3$ groups.

The compounds represented by formula I-6$_A$ are preferably compounds 423, 424, 425, 432, 433, 434, 435, 439, 440, 441, 442, 443, 444, 458, 459, 460, 461, 462 and 463 as disclosed herein. Furthermore, the compounds represented by formula I-6$_B$ are preferably compound 446 as disclosed herein.

The compounds represented by formula I according to the present invention may be compounds represented by the following formula I-7:

Formula I-7

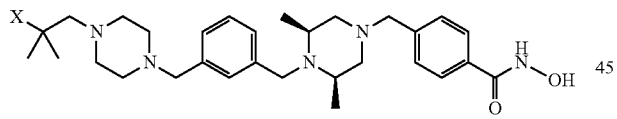

wherein X may be selected from —OH; —F; —Cl or —Br.

The compounds represented by formula I-7 are preferably compounds 386 and 387 as disclosed herein.

The compounds represented by formula I according to the present invention may be compounds represented by the following formula I-8:

Formula I-8

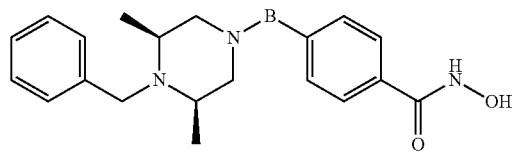

wherein B may be selected from among

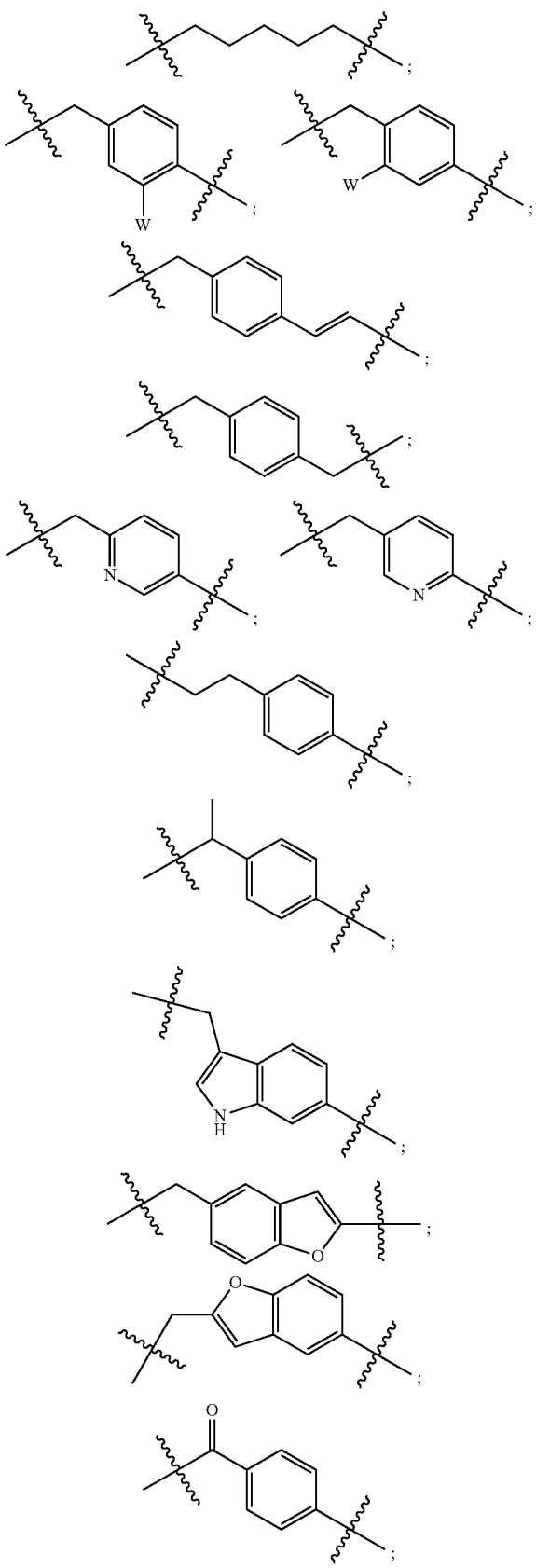

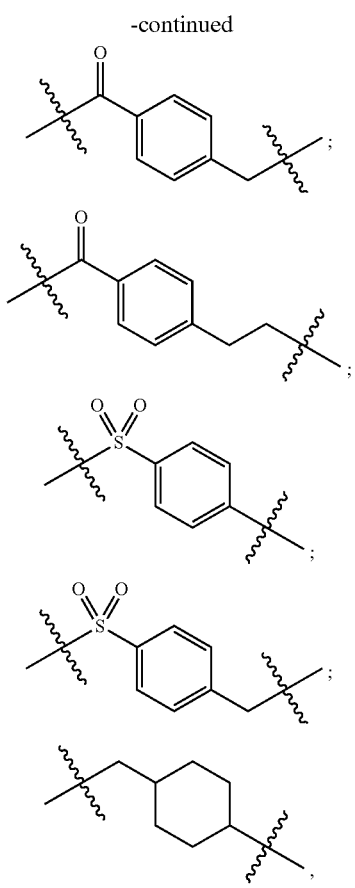

wherein w is hydrogen or may be substituted with —F; —Cl or —OH.

The compounds represented by formula I-8 are preferably compounds 154, 171, 172, 173, 194, 218, 219, 520, 571, 574, 652, 812, 813, 814, 818, 820, 822, 823 and 824 as disclosed herein.

The compounds represented by formula I according to the present invention may be compounds represented by the following formula I-9:

Formula I-9

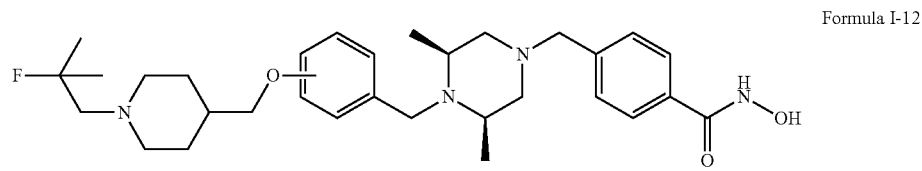

wherein A is —C(=O)—; —CH$_2$—; —NH(C=O)—; —C(=S)— or —S(=O)$_2$—, and $R_{11}$ may be selected from among furanyl; benzyl; pyrrole-substituted phenyl or pyrrole-substituted anilinyl.

The compounds represented by formula I-9 are preferably compounds 321, 322 and 323 as disclosed herein.

The compounds represented by formula I according to the present invention may be compounds represented by the following formula I-10:

Formula I-10

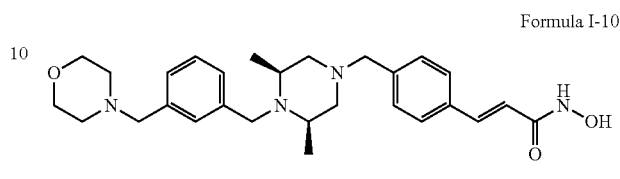

The compounds represented by formula I-10 are preferably compound 472 as disclosed herein.

The compounds represented by formula I according to the present invention may be compounds represented by the following formula I-11:

Formula I-11

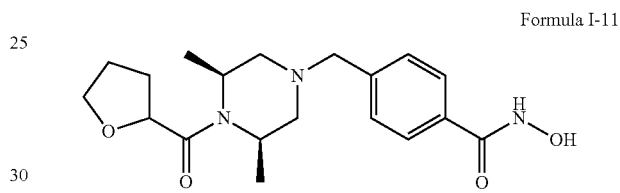

The compounds represented by formula I-11 are preferably compound 402 as disclosed herein.

The compounds represented by formula I according to the present invention may be compounds represented by the following formula I-12:

Formula I-12

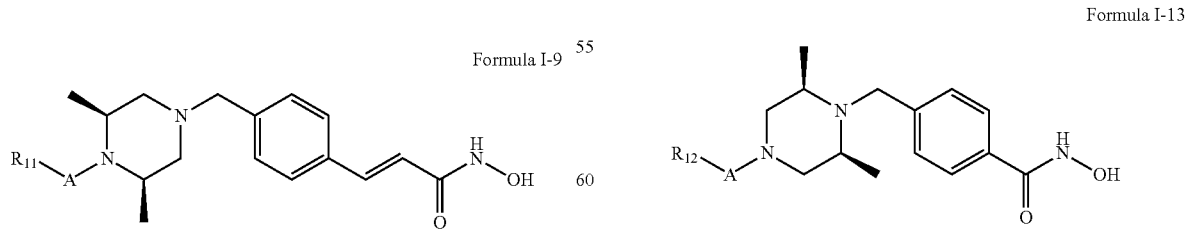

The compounds represented by formula I-12 are preferably compounds 380 and 388 as disclosed herein.

The compounds represented by formula I according to the present invention may be compounds represented by the following formula I-13:

Formula I-13 wherein A is —C(=O)—; —CH$_2$—; —CH(CH$_3$)—; —NH(C=O)—; —NCH$_3$(C=O)—; —C(=S)— or —S(=O)$_2$—, and $R_{12}$ may be selected from among straight or branched C$_1$-C$_4$ alkyl; phenyl (which may be unsubstituted or substituted with one or more straight or branched chain $C_1$-$C_3$ alkyl; —F; —Cl; $CF_3$; —$OCH_3$; —$C_1$-$C_2$ primary or secondary alkylamine; —$SO_2CH_3$; thiophenyl; pyrrole; pyrazole; furanyl; triazolyl or imidazolyl); pyridinyl; thiophenyl; furanyl; benzyl (which may be unsubstituted or substituted with —F, —Cl or —$OCH_3$); indole (which may be unsubstituted or substituted with one or more straight or branched chain $C_1$-$C_3$alkyl groups), dihydrobenzofuranyl; phenylamine (which may be unsubstituted or substituted with straight or branched chain $C_1$-$C_3$ alkyl); indoline or naphthyl.

The compounds represented by formula I-13 are preferably compounds 80, 81, 103, 104, 105, 106, 107, 108, 109, 110, 111, 112, 113, 114, 115, 118, 162, 163, 164, 165, 166, 167, 168, 183, 185, 186, 187, 189, 196, 197, 215, 220, 230, 231, 233, 256, 268, 271, 273, 274, 298, 299, 300, 301, 302, 303, 304 and 305 as disclosed herein.

The compounds represented by formula I according to the present invention may be compounds represented by the following formula I-14:

Formula I-14

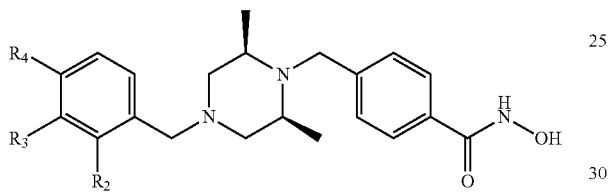

wherein $R_2$, $R_3$ and $R_4$ may be each independently hydrogen or any one selected from the following group:

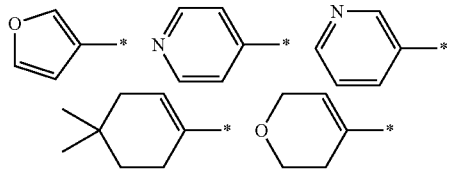

The compounds represented by formula I-14 are preferably compounds 348, 349, 350, 351, 352, 396, 400 and 401 as disclosed herein.

The compounds represented by formula I according to the present invention may be compounds represented by the following formula I-15:

Formula I-15

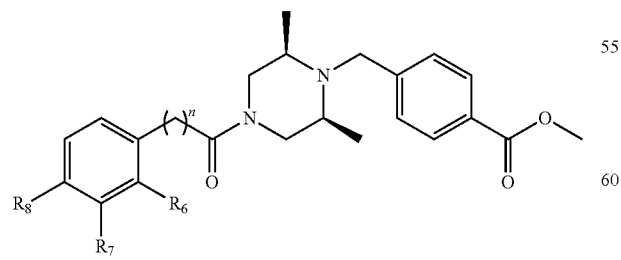

wherein n is an integer of 0, 1 or 2, and $R_6$, $R_7$ and $R_8$ may be each independently hydrogen or any one selected from the following group:

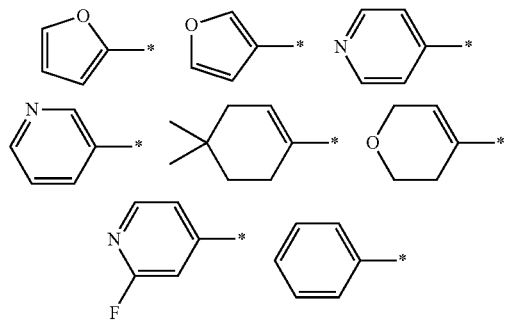

The compounds represented by formula I-15 are preferably compounds 250, 251, 252, 253, 257, 258, 259, 260, 261, 262, 263, 276, 277, 278, 279 and 280 as disclosed herein.

The compounds represented by formula I according to the present invention may be compounds represented by the following formula I-16:

Formula I-16

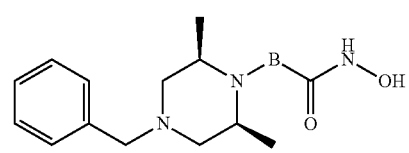

wherein B may be selected from among

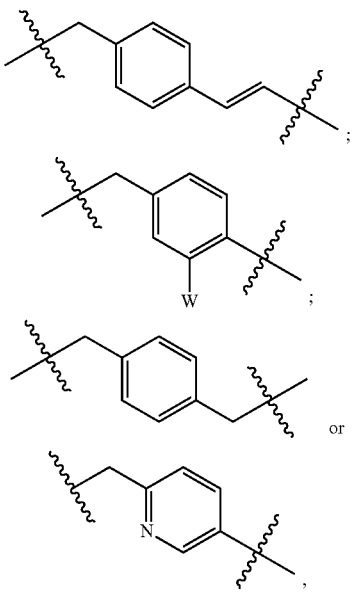

wherein w may be substituted with —F or —Cl.

The compounds represented by formula I-16 are preferably compounds 174, 175, 176 and 195 as disclosed herein.

The compounds represented by formula I according to the present invention may be compounds represented by the following formula I-17:

Formula I-17

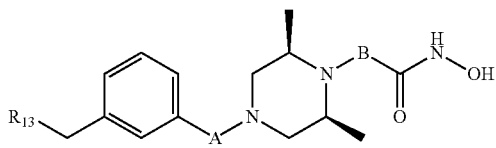

wherein A is —C(=O)—; —CH$_2$—; —NH(C=O)—; —C(=S)— or —S(=O)$_2$—, and B may be selected from among

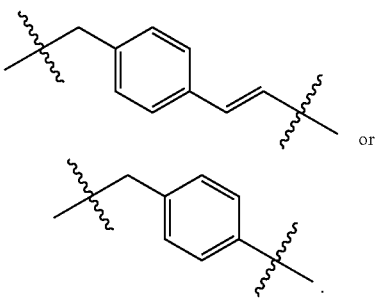

Also, R$_{13}$ may be selected from among pyrrolidine and —C$_1$-C$_2$ primary or secondary alkylamine.

The compounds represented by formula I-17 are preferably compounds 475, 476, 478, 479, 480 and 487 as disclosed herein.

The compounds represented by formula I according to the present invention may be compounds represented by the following formula I-18:

Formula I-18

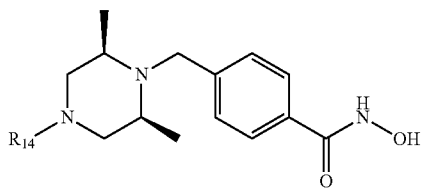

The compounds represented by formula I-18 are preferably compound 477 as disclosed herein.

The compounds represented by formula I according to the present invention may be compounds represented by the following formula I-19:

Formula I-19

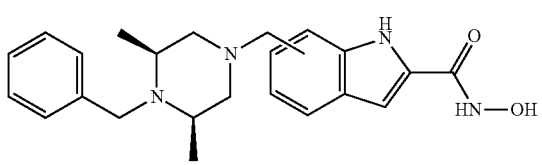

wherein R$_{14}$ may be selected from among

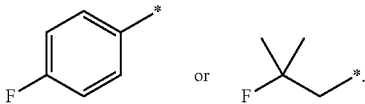

The compounds represented by formula I-19 are preferably compounds 119 and 193 as disclosed herein.

The compounds represented by formula I according to the present invention may be compounds represented by the following formula I-20:

Formula I-20

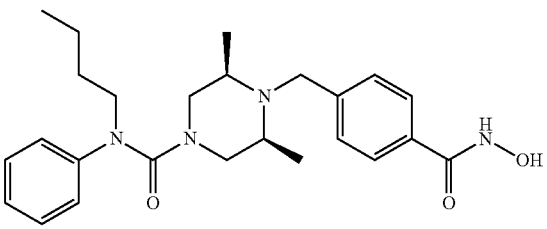

The compounds represented by formula I-20 are preferably compound 198 as disclosed herein.

The compounds represented by formula I according to the present invention may be compounds represented by the following formula I-21:

Formula I-21

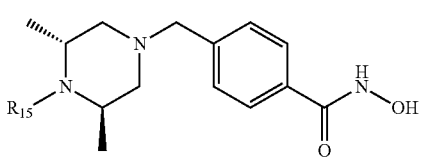

wherein R$_{15}$ may be selected from among

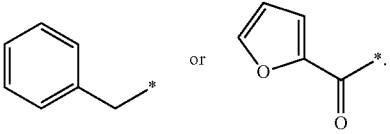

The compounds represented by formula I-21 are preferably compounds 248 and 249 as disclosed herein.

The compounds represented by formula I according to the present invention may be compounds represented by the following formula I-22:

Formula I-22

The compounds represented by formula I-22 are preferably compounds 569 and 573 as disclosed herein.

The compounds represented by formula I according to the present invention may be compounds represented by the following formula I-23:

Formula I-23

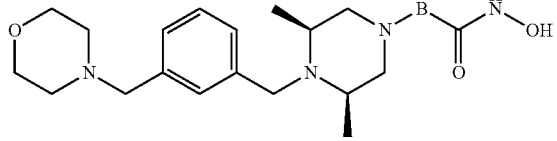

wherein B may be selected from among

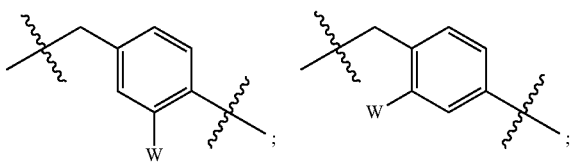

-continued

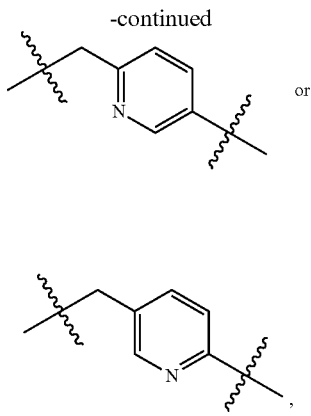

wherein w is hydrogen; —F; —Cl or —OH.

The compounds represented by formula I-23 are preferably compounds 609, 653 and 696 as disclosed herein.

The compounds represented by formula I, formula II, formula III and formulas I-1 to I-23 are shown in Table 1 below.

TABLE 1

Names of dimethylpiperazine derivative compounds

| No. | Name of Compound |
|---|---|
| 080 | 4-(((2S,6R)-4-benzoyl-2,6-dimethylpiperazin-1-yl)methyl)-N-hydroxybenzamide |
| 081 | 4-(((2S,6R)-4-benzyl-2,6-dimethylpiperazin-1-yl)methyl)-N-hydroxybenzamide |
| 082 | 4-(((3R,5S)-4-acetyl-3,5-dimethylpiperazin-1-yl)methyl)-N-hydroxybenzamide |
| 083 | 4-(((3R,5S)-4-benzoyl-3,5-dimethylpiperazin-1-yl)methyl)-N-hydroxybenzamide |
| 084 | 4-(((3R,5S)-4-benzyl-3,5-dimethylpiperazin-1-yl)methyl)-N-hydroxybenzamide |
| 098 | (2S,6R)-4-(4-(hydroxycarbamoyl)benzyl)-N-isopropyl-2,6-dimethylpiperazine-1-carboxamide |
| 099 | (2S,6R)-N-(3-chlorophenyl)-4-(4-(hydroxycarbamoyl)benzyl)-2,6-dimethylpiperazine-1-carboxamide |
| 100 | 4-(((3R,5S)-3,5-dimethyl-4-(phenylsulfonyl)piperazin-1-yl)methyl)-N-hydroxybenzamide |
| 103 | (3R,5S)-4-(4-(hydroxycarbamoyl)benzyl)-N-isopropyl-3,5-dimethylpiperazine-1-carboxamide |
| 104 | (3R,5S)-N-(3-chlorophenyl)-4-(4-(hydroxycarbamoyl)benzyl)-3,5-dimethylpiperazine-1-carboxamide |
| 105 | 4-(((2S,6R)-2,6-dimethyl-4-(phenylsulfonyl)piperazin-1-yl)methyl)-N-hydroxybenzamide |
| 106 | 4-(((2S,6R)-4-(4-chlorobenzoyl)-2,6-dimethylpiperazin-1-yl)methyl)-N-hydroxybenzamide |
| 107 | 4-(((2S,6R)-4-(3-chlorobenzoyl)-2,6-dimethylpiperazin-1-yl)methyl)-N-hydroxybenzamide |
| 108 | 4-(((2S,6R)-4-(2-chlorobenzoyl)-2,6-dimethylpiperazin-1-yl)methyl)-N-hydroxybenzamide |
| 109 | 4-(((2S,6R)-4-((4-chlorophenyl)sulfonyl)-2,6-dimethylpiperazin-1-yl)methyl)-N-hydroxybenzamide |
| 110 | 4-(((2S,6R)-4-((2-chlorophenyl)sulfonyl)-2,6-dimethylpiperazin-1-yl)methyl)-N-hydroxybenzamide |
| 111 | 4-(((2S,6R)-2,6-dimethyl-4-picolinoylpiperazin-1-yl)methyl)-N-hydroxybenzamide |
| 112 | 4-(((2S,6R)-2,6-dimethyl-4-nicotinoylpiperazin-1-yl)methyl)-N-hydroxybenzamide |
| 113 | 4-(((2S,6R)-2,6-dimethyl-4-(pyridin-3-ylsulfonyl)piperazin-1-yl)methyl)-N-hydroxybenzamide |
| 114 | 4-(((2S,6R)-2,6-dimethyl-4-(thiophene-2-carbonyl)piperazin-1-yl)methyl)-N-hydroxybenzamide |
| 115 | 4-(((2S,6R)-4-(furan-2-carbonyl)-2,6-dimethylpiperazin-1-yl)methyl)-N-hydroxybenzamide |
| 118 | 4-(((2S,6R)-4-(2-chlorobenzyl)-2,6-dimethylpiperazin-1-yl)methyl)-N-hydroxybenzamide |

TABLE 1-continued

Names of dimethylpiperazine derivative compounds

| No. | Name of Compound |
|---|---|
| 119 | 4-(((2R,6S)-4-(4-fluorophenyl)-2,6-dimethylpiperazin-1-yl)methyl)-N-hydroxybenzamide |
| 120 | 4-(((3R,5S)-4-(2-chlorobenzoyl)-3,5-dimethylpiperazin-1-yl)methyl)-N-hydroxybenzamide |
| 121 | 4-(((3R,5S)-4-(3-chlorobenzoyl)-3,5-dimethylpiperazin-1-yl)methyl)-N-hydroxybenzamide |
| 122 | 4-(((3R,5S)-4-(4-chlorobenzoyl)-3,5-dimethylpiperazin-1-yl)methyl)-N-hydroxybenzamide |
| 123 | 4-(((3R,5S)-3,5-dimethyl-4-picolinoylpiperazin-1-yl)methyl)-N-hydroxybenzamide |
| 125 | 4-(((3R,5S)-4-(furan-2-carbonyl)-3,5-dimethylpiperazin-1-yl)methyl)-N-hydroxybenzamide |
| 126 | 4-(((3R,5S)-3,5-dimethyl-4-(thiophene-2-carbonyl)piperazin-1-yl)methyl)-N-hydroxybenzamide |
| 127 | 4-(((3R,5S)-4-(2-chlorobenzyl)-3,5-dimethylpiperazin-1-yl)methyl)-N-hydroxybenzamide |
| 128 | 4-(((3R,5S)-4-(3-chlorobenzyl)-3,5-dimethylpiperazin-1-yl)methyl)-N-hydroxybenzamide |
| 145 | 4-(((3R,5S)-4-(furan-2-ylmethyl)-3,5-dimethylpiperazin-1-yl)methyl)-N-hydroxybenzamide |
| 146 | 4-(((3R,5S)-3,5-dimethyl-4-(2-phenylacetyl)piperazin-1-yl)methyl)-N-hydroxybenzamide |
| 147 | 4-(((3R,5S)-4-ethyl-3,5-dimethylpiperazin-1-yl)methyl)-N-hydroxybenzamide |
| 148 | 4-(((3R,5S)-3,5-dimethyl-4-propylpiperazin-1-yl)methyl)-N-hydroxybenzamide |
| 149 | 4-(((3R,5S)-3,5-dimethyl-4-(2,2,2-trifluoroethyl)piperazin-1-yl)methyl)-N-hydroxybenzamide |
| 154 | 6-((3R,5S)-4-benzyl-3,5-dimethylpiperazin-1-yl)-N-hydroxyhexanamide |
| 159 | (2S,6R)-4-(4-(hydroxycarbamoyl)benzyl)-2,6-dimethyl-N-phenylpiperazine-1-carboxamide |
| 160 | (2S,6R)-4-(4-(hydroxycarbamoyl)benzyl)-2,6-dimethyl-N-(o-tolyl)piperazine-1-carboxamide |
| 161 | (2S,6R)-N-benzyl-4-(4-(hydroxycarbamoyl)benzyl)-2,6-dimethylpiperazine-1-carboxamide |
| 162 | (3R,5S)-4-(4-(hydroxycarbamoyl)benzyl)-3,5-dimethyl-N-phenylpiperazine-1-carboxamide |
| 163 | (3R,5S)-4-(4-(hydroxycarbamoyl)benzyl)-N-(2-methoxyphenyl)-3,5-dimethylpiperazine-1-carboxamide |
| 164 | (3R,5S)-4-(4-(hydroxycarbamoyl)benzyl)-N-(3-methoxyphenyl)-3,5-dimethylpiperazine-1-carboxamide |
| 165 | (3R,5S)-4-(4-(hydroxycarbamoyl)benzyl)-N-(4-methoxyphenyl)-3,5-dimethylpiperazine-1-carboxamide |
| 166 | (3R,5S)-4-(4-(hydroxycarbamoyl)benzyl)-3,5-dimethyl-N-(o-tolyl)piperazine-1-carboxamide |
| 167 | (3R,5S)-4-(4-(hydroxycarbamoyl)benzyl)-3,5-dimethyl-N-(m-tolyl)piperazine-1-carboxamide |
| 168 | (3R,5S)-N-benzyl-4-(4-(hydroxycarbamoyl)benzyl)-3,5-dimethylpiperazine-1-carboxamide |
| 171 | 4-(((3R,5S)-4-benzyl-3,5-dimethylpiperazin-1-yl)methyl)-2-fluoro-N-hydroxybenzamide |
| 172 | (E)-3-(4-(((3R,5S)-4-benzyl-3,5-dimethylpiperazin-1-yl)methyl)phenyl)-N-hydroxyacrylamide |
| 173 | 2-(4-(((3R,5S)-4-benzyl-3,5-dimethylpiperazin-1-yl)methyl)phenyl)-N-hydroxyacetamide |
| 174 | 4-(((2S,6R)-4-benzyl-2,6-dimethylpiperazin-1-yl)methyl)-2-fluoro-N-hydroxybenzamide |
| 175 | (E)-3-(4-(((2S,6R)-4-benzyl-2,6-dimethylpiperazin-1-yl)methyl)phenyl)-N-hydroxyacrylamide |
| 176 | 2-(4-(((2S,6R)-4-benzyl-2,6-dimethylpiperazin-1-yl)methyl)phenyl)-N-hydroxyacetamide |
| 177 | phenyl (2S,6R)-4-(4-(hydroxycarbamoyl)benzyl)-2,6-dimethylpiperazine-1-carboxylate |
| 183 | 4-(((2S,6R)-2,6-dimethyl-4-phenethylpiperazin-1-yl)methyl)-N-hydroxybenzamide |
| 184 | 4-(((3R,5S)-3,5-dimethyl-4-phenethylpiperazin-1-yl)methyl)-N-hydroxybenzamide |
| 185 | (3R,5S)-4-(4-(hydroxycarbamoyl)benzyl)-3,5-dimethyl-N-(1-methyl-1H-indol-5-yl)piperazine-1-carboxamide |
| 186 | (3R,5S)-N-(3-(1H-pyrrol-1-yl)phenyl)-4-(4-(hydroxycarbamoyl)benzyl)-3,5-dimethylpiperazine-1-carboxamide |
| 187 | (3R,5S)-N-(2,3-dihydrobenzofuran-5-yl)-4-(4-(hydroxycarbamoyl)benzyl)-3,5-dimethylpiperazine-1-carboxamide |

TABLE 1-continued

Names of dimethylpiperazine derivative compounds

| No. | Name of Compound |
|---|---|
| 188 | 4-(((3R,5S)-3,5-dimethyl-4-(3-phenylpropanoyl)piperazin-1-yl)methyl)-N-hydroxybenzamide |
| 189 | 4-(((2S,6R)-2,6-dimethyl-4-(m-tolylcarbamothioyl)piperazin-1-yl)methyl)-N-hydroxybenzamide |
| 193 | 4-(((2S,6R)-4-(2-fluoro-2-methylpropyl)-2,6-dimethylpiperazin-1-yl)methyl)-N-hydroxybenzamide |
| 194 | 6-(((3R,5S)-4-benzyl-3,5-dimethylpiperazin-1-yl)methyl)-N-hydroxynicotinamide |
| 195 | 6-(((2S,6R)-4-benzyl-2,6-dimethylpiperazin-1-yl)methyl)-N-hydroxynicotinamide |
| 196 | (3R,5S)-4-(4-(hydroxycarbamoyl)benzyl)-N,3,5-trimethyl-N-phenylpiperazine-1-carboxamide |
| 197 | N-hydroxy-4-(((2S,6R)-4-(indoline-1-carbonyl)-2,6-dimethylpiperazin-1-yl)methyl)benzamide |
| 198 | (3R,5S)-N-butyl-4-(4-(hydroxycarbamoyl)benzyl)-3,5-dimethyl-N-phenylpiperazine-1-carboxamide |
| 204 | 4-(((3R,5S)-3,5-dimethyl-4-(4,4,4-trifluorobutyl)piperazin-1-yl)methyl)-N-hydroxybenzamide |
| 211 | 4-(((3R,5S)-4-(2-fluorobenzyl)-3,5-dimethylpiperazin-1-yl)methyl)-N-hydroxybenzamide |
| 212 | 4-(((3R,5S)-4-(2,5-difluorobenzyl)-3,5-dimethylpiperazin-1-yl)methyl)-N-hydroxybenzamide |
| 213 | 4-(((3R,5S)-3,5-dimethyl-4-(2,4,5-trifluorobenzyl)piperazin-1-yl)methyl)-N-hydroxybenzamide |
| 214 | 4-(((3R,5S)-4-(3,5-bis(trifluoromethyl)benzyl)-3,5-dimethylpiperazin-1-yl)methyl)-N-hydroxybenzamide |
| 215 | 4-(((2S,6R)-2,6-dimethyl-4-(2,4,5-trifluorobenzyl)piperazin-1-yl)methyl)-N-hydroxybenzamide |
| 218 | 4-(2-((3R,5S)-4-benzyl-3,5-dimethylpiperazin-1-yl)ethyl)-N-hydroxybenzamide |
| 219 | 4-(1-((3R,5S)-4-benzyl-3,5-dimethylpiperazin-1-yl)ethyl)-N-hydroxybenzamide |
| 220 | 4-(((2S,6R)-2,6-dimethyl-4-(1-phenylethyl)piperazin-1-yl)methyl)-N-hydroxybenzamide |
| 222 | 4-(((3R,5S)-4-(2-(3-fluorophenyl)acetyl)-3,5-dimethylpiperazin-1-yl)methyl)-N-hydroxybenzamide |
| 223 | 4-(((3R,5S)-3,5-dimethyl-4-(2-(3-(trifluoromethyl)phenyl)acetyl)piperazin-1-yl)methyl)-N-hydroxybenzamide |
| 224 | 4-(((3R,5S)-4-(2-(3-chlorophenyl)acetyl)-3,5-dimethylpiperazin-1-yl)methyl)-N-hydroxybenzamide |
| 225 | 4-(((3R,5S)-4-(3-fluorobenzyl)-3,5-dimethylpiperazin-1-yl)methyl)-N-hydroxybenzamide |
| 230 | (3R,5S)-4-(4-(hydroxycarbamoyl)benzyl)-N-(3-methoxybenzyl)-3,5-dimethylpiperazine-1-carboxamide (Trifluoroacetic acid salt) |
| 231 | (3R,5S)-N-(3-fluorobenzyl)-4-(4-(hydroxycarbamoyl)benzyl)-3,5-dimethylpiperazine-1-carboxamide |
| 232 | (2S,6R)-N-(3-fluorobenzyl)-4-(4-(hydroxycarbamoyl)benzyl)-2,6-dimethylpiperazine-1-carboxamide |
| 233 | 4-(((2S,6R)-4-(2-(3-chlorophenyl)acetyl)-2,6-dimethylpiperazin-1-yl)methyl)-N-hydroxybenzamide |
| 234 | 4-(((3R,5S)-4-(2-([1,1'-biphenyl]-3-yl)acetyl)-3,5-dimethylpiperazin-1-yl)methyl)-N-hydroxybenzamide |
| 242 | 4-(((3R,5S)-4-(3-(furan-2-yl)benzoyl)-3,5-dimethylpiperazin-1-yl)methyl)-N-hydroxybenzamide |
| 243 | 4-(((3R,5S)-4-(3-(furan-3-yl)benzoyl)-3,5-dimethylpiperazin-1-yl)methyl)-N-hydroxybenzamide |
| 244 | 4-(((3R,5S)-4-(3-(3,6-dihydro-2H-pyran-4-yl)benzoyl)-3,5-dimethylpiperazin-1-yl)methyl)-N-hydroxybenzamide |
| 245 | 4-(((3R,5S)-3,5-dimethyl-4-(3-(pyridin-4-yl)benzoyl)piperazin-1-yl)methyl)-N-hydroxybenzamide (Trifluoroacetic acid salt) |
| 246 | 4-(((3R,5S)-3,5-dimethyl-4-(3-(pyridin-3-yl)benzoyl)piperazin-1-yl)methyl)-N-hydroxybenzamide |
| 247 | 4-(((3R,5S)-4-(4',4'-dimethyl-2',3',4',5'-tetrahydro-[1,1'-biphenyl]-3-carbonyl)-3,5-dimethylpiperazin-1-yl)methyl)-N-hydroxybenzamide |
| 248 | 4-(((3R,5R)-4-benzyl-3,5-dimethylpiperazin-1-yl)methyl)-N-hydroxybenzamide |
| 249 | 4-(((3R,5R)-4-(furan-2-carbonyl)-3,5-dimethylpiperazin-1-yl)methyl)-N-hydroxybenzamide |
| 250 | 4-(((2S,6R)-4-(2-([1,1'-biphenyl]-3-yl)acetyl)-2,6-dimethylpiperazin-1-yl)methyl)-N-hydroxybenzamide (Trifluoroacetic acid salt) |

TABLE 1-continued

Names of dimethylpiperazine derivative compounds

| No. | Name of Compound |
|---|---|
| 251 | 4-(((2S,6R)-2,6-dimethyl-4-(2-(3-(pyridin-4-yl)phenyl)acetyl)piperazin-1-yl)methyl)-N-hydroxybenzamide (Trifluoroacetic acid salt) |
| 252 | 4-(((2S,6R)-4-(2-(3-(3,6-dihydro-2H-pyran-4-yl)phenyl)acetyl)-2,6-dimethylpiperazin-1-yl)methyl)-N-hydroxybenzamide |
| 253 | 4-(((2S,6R)-4-(2-(4',4'-dimethyl-2',3',4',5'-tetrahydro-[1,1'-biphenyl]-3-yl)acetyl)-2,6-dimethylpiperazin-1-yl)methyl)-N-hydroxybenzamide (Trifluoroacetic acid salt) |
| 255 | 4-(((3R,5S)-4-(3-(1H-pyrrol-1-yl)benzyl)-3,5-dimethylpiperazin-1-yl)methyl)-N-hydroxybenzamide |
| 256 | 4-(((2S,6R)-4-(3-(1H-pyrrol-1-yl)benzyl)-2,6-dimethylpiperazin-1-yl)methyl)-N-hydroxybenzamide |
| 257 | 4-(((2S,6R)-4-(3-(furan-2-yl)benzoyl)-2,6-dimethyl piperazin-1-yl)methyl)-N-hydroxybenzamide |
| 258 | 4-(((2S,6R)-4-(3-(furan-3-yl)benzoyl)-2,6-dimethyl piperazin-1-yl)methyl)-N-hydroxybenzamide |
| 259 | 4-(((2S,6R)-4-(3-(3,6-dihydro-2H-pyran-4-yl)benzoyl)-2,6-dimethylpiperazin-1-yl)methyl)-N-hydroxybenzamide |
| 260 | 4-(((2S,6R)-2,6-dimethyl-4-(3-(pyridin-4-yl)benzoyl)piperazin-1-yl)methyl)-N-hydroxybenzamide |
| 261 | 4-(((2S,6R)-2,6-dimethyl-4-(3-(pyridin-3-yl)benzoyl)piperazin-1-yl)methyl)-N-hydroxybenzamide |
| 262 | 4-(((2S,6R)-4-(3-(2-fluoropyridin-4-yl)benzoyl)-2,6-dimethylpiperazin-1-yl)methyl)-N-hydroxybenzamide |
| 263 | 4-(((2S,6R)-4-(4',4'-dimethyl-2',3',4',5'-tetrahydro-[1,1'-biphenyl]-3-carbonyl)-2,6-dimethylpiperazin-1-yl)methyl)-N-hydroxybenzamide |
| 265 | 4-(((3R,5S)-3,5-dimethyl-4-(naphthalen-2-ylmethyl)piperazin-1-yl)methyl)-N-hydroxybenzamide |
| 266 | 4-(((3R,5S)-3,5-dimethyl-4-(pyridin-4-ylmethyl)piperazin-1-yl)methyl)-N-hydroxybenzamide (Trifluoroacetic acid salt) |
| 267 | 4-(((3R,5S)-4-(3-chloro-2-(trifluoromethyl)benzyl)-3,5-dimethylpiperazin-1-yl)methyl)-N-hydroxybenzamide |
| 268 | 4-(((2S,6R)-2,6-dimethyl-4-(naphthalen-2-ylmethyl)piperazin-1-yl)methyl)-N-hydroxybenzamide |
| 270 | N-hydroxy-4-(((3R,5S)-4-isopentyl-3,5-dimethylpiperazin-1-yl)methyl)benzamide (Trifluoroacetic acid salt) |
| 271 | N-hydroxy-4-(((2S,6R)-4-isopentyl-2,6-dimethylpiperazin-1-yl)methyl)benzamide (Trifluoroacetic acid salt) |
| 272 | 4-(((3R,5S)-3,5-dimethyl-4-(3-methylbut-2-en-1-yl)piperazin-1-yl)methyl)-N-hydroxybenzamide |
| 273 | N-hydroxy-4-(((2S,6R)-4-isopropyl-2,6-dimethylpiperazin-1-yl)methyl)benzamide (Trifluoroacetic acid salt) |
| 274 | 4-(((2S,6R)-4-butyl-2,6-dimethylpiperazin-1-yl)methyl)-N-hydroxybenzamide (Trifluoroacetic acid salt) |
| 275 | 4-(((3R,5S)-4-butyl-3,5-dimethylpiperazin-1-yl)methyl)-N-hydroxybenzamide (Trifluoroacetic acid salt) |
| 276 | 4-(((2S,6R)-4-(2-(furan-2-yl)benzoyl)-2,6-dimethyl piperazin-1-yl)methyl)-N-hydroxybenzamide |
| 277 | 4-(((2S,6R)-4-(2-(furan-3-yl)benzoyl)-2,6-dimethyl piperazin-1-yl)methyl)-N-hydroxybenzamide |
| 278 | 4-(((2S,6R)-4-(2-(3,6-dihydro-2H-pyran-4-yl)benzoyl)-2,6-dimethylpiperazin-1-yl)methyl)-N-hydroxybenzamide |
| 279 | 4-(((2S,6R)-2,6-dimethyl-4-(2-(pyridin-3-yl)benzoyl)piperazin-1-yl)methyl)-N-hydroxybenzamide |
| 280 | 4-(((2S,6R)-4-(4',4'-dimethyl-2',3',4',5'-tetrahydro-[1,1'-biphenyl]-2-carbonyl)-2,6-dimethylpiperazin-1-yl)methyl)-N-hydroxybenzamide |
| 283 | 4-(((3R,5S)-4-(2-(furan-2-yl)benzoyl)-3,5-dimethyl piperazin-1-yl)methyl)-N-hydroxybenzamide |
| 284 | 4-(((3R,5S)-4-(2-(furan-3-yl)benzoyl)-3,5-dimethyl piperazin-1-yl)methyl)-N-hydroxybenzamide |
| 285 | 4-(((3R,5S)-3,5-dimethyl-4-(2-(pyridin-4-yl)benzoyl)piperazin-1-yl)methyl)-N-hydroxybenzamide |
| 286 | 4-(((3R,5S)-3,5-dimethyl-4-(2-(pyridin-3-yl)benzoyl)piperazin-1-yl)methyl)-N-hydroxybenzamide |
| 288 | 4-(((3R,5S)-4-(4',4'-dimethyl-2',3',4',5'-tetrahydro-[1,1'-biphenyl]-2-carbonyl)-3,5-dimethylpiperazin-1-yl)methyl)-N-hydroxybenzamide |

TABLE 1-continued

Names of dimethylpiperazine derivative compounds

| No. | Name of Compound |
|---|---|
| 290 | 4-(((3R,5S)-3,5-dimethyl-4-(4-methylbenzoyl)piperazin-1-yl)methyl)-N-hydroxybenzamide (Trifluoroacetic acid salt) |
| 291 | N-hydroxy-4-(((3R,5S)-4-(4-methoxybenzoyl)-3,5-dimethylpiperazin-1-yl)methyl)benzamide (Trifluoroacetic acid salt) |
| 292 | 4-(((3R,5S)-3,5-dimethyl-4-pivaloylpiperazin-1-yl)methyl)-N-hydroxybenzamide (Trifluoroacetic acid salt) |
| 293 | 4-(((3R,5S)-3,5-dimethyl-4-propionylpiperazin-1-yl)methyl)-N-hydroxybenzamide (Trifluoroacetic acid salt) |
| 294 | 4-(((3R,5S)-4-butyryl-3,5-dimethylpiperazin-1-yl)methyl)-N-hydroxybenzamide (Trifluoroacetic acid salt) |
| 295 | 4-(((3R,5S)-4-(cyclopropanecarbonyl)-3,5-dimethylpiperazin-1-yl)methyl)-N-hydroxybenzamide (Trifluoroacetic acid salt) |
| 296 | N-hydroxy-4-(((3R,5S)-4-isobutyryl-3,5-dimethylpiperazin-1-yl)methyl)benzamide (Trifluoroacetic acid salt) |
| 297 | 4-(((3R,5S)-3,5-dimethyl-4-(3-methylbutanoyl)piperazin-1-yl)methyl)-N-hydroxybenzamide (Trifluoroacetic acid salt) |
| 298 | 4-(((2S,6R)-2,6-dimethyl-4-(3-(trifluoromethyl)benzyl)piperazin-1-yl)methyl)-N-hydroxybenzamide |
| 299 | 4-(((2S,6R)-4-(4-(dimethylamino)benzyl)-2,6-dimethylpiperazin-1-yl)methyl)-N-hydroxybenzamide |
| 300 | 4-(((2S,6R)-2,6-dimethyl-4-(4-(methylsulfonyl)benzyl)piperazin-1-yl)methyl)-N-hydroxybenzamide |
| 301 | 4-(((2S,6R)-4-(4-(1H-imidazol-1-yl)benzyl)-2,6-dimethylpiperazin-1-yl)methyl)-N-hydroxybenzamide |
| 302 | 4-(((2S,6R)-2,6-dimethyl-4-(4-(thiophen-2-yl)benzyl)piperazin-1-yl)methyl)-N-hydroxybenzamide |
| 303 | 4-(((2S,6R)-4-(4-(furan-2-yl)benzyl)-2,6-dimethylpiperazin-1-yl)methyl)-N-hydroxybenzamide |
| 304 | 4-(((2S,6R)-4-(4-(4H-1,2,4-triazol-4-yl)benzyl)-2,6-dimethylpiperazin-1-yl)methyl)-N-hydroxybenzamide |
| 305 | 4-(((2S,6R)-2,6-dimethyl-4-(2-(2-methyl-1H-imidazol-1-yl)benzyl)piperazin-1-yl)methyl)-N-hydroxybenzamide |
| 309 | 4-(((3R,5S)-4-(4-(furan-3-yl)benzyl)-3,5-dimethylpiperazin-1-yl)methyl)-N-hydroxybenzamide |
| 321 | (2S,6R)-N-(3-(1H-pyrrol-1-yl)phenyl)-4-(4-((E)-3-(hydroxyamino)-3-oxoprop-1-en-1-yl)benzyl)-2,6-dimethylpiperazine-1-carboxamide |
| 322 | (E)-3-(4-(((3R,5S)-4-(furan-2-carbonyl)-3,5-dimethylpiperazin-1-yl)methyl)phenyl)-N-hydroxyacrylamide |
| 323 | (E)-3-(4-(((3R,5S)-3,5-dimethyl-4-(2-phenylacetyl)piperazin-1-yl)methyl)phenyl)-N-hydroxyacrylamide |
| 326 | 4-(((3R,5S)-4-(2-(3,6-dihydro-2H-pyran-4-yl)benzoyl)-3,5-dimethylpiperazin-1-yl)methyl)-N-hydroxybenzamide |
| 327 | 4-(((3R,5S)-4-(2-(furan-2-yl)benzyl)-3,5-dimethylpiperazin-1-yl)methyl)-N-hydroxybenzamide |
| 328 | 4-(((3R,5S)-4-(2-(furan-3-yl)benzyl)-3,5-dimethylpiperazin-1-yl)methyl)-N-hydroxybenzamide |
| 329 | 4-(((3R,5S)-3,5-dimethyl-4-(2-(pyridin-4-yl)benzyl)piperazin-1-yl)methyl)-N-hydroxybenzamide |
| 330 | 4-(((3R,5S)-3,5-dimethyl-4-(2-(pyridin-3-yl)benzyl)piperazin-1-yl)methyl)-N-hydroxybenzamide |
| 331 | 4-(((3R,5S)-4-((4',4'-dimethyl-2',3',4',5'-tetrahydro-[1,1'-biphenyl]-2-yl)methyl)-3,5-dimethylpiperazin-1-yl)methyl)-N-hydroxybenzamide |
| 332 | 4-(((3R,5S)-4-(2-(3,6-dihydro-2H-pyran-4-yl)benzyl)-3,5-dimethylpiperazin-1-yl)methyl)-N-hydroxybenzamide |
| 340 | 4-(((3R,5S)-4-(4-(furan-2-yl)benzoyl)-3,5-dimethylpiperazin-1-yl)methyl)-N-hydroxybenzamide |
| 342 | 4-(((3R,5S)-4-(3-(furan-2-yl)benzyl)-3,5-dimethylpiperazin-1-yl)methyl)-N-hydroxybenzamide |
| 343 | 4-(((3R,5S)-4-(3-(furan-3-yl)benzyl)-3,5-dimethylpiperazin-1-yl)methyl)-N-hydroxybenzamide |
| 344 | 4-(((3R,5S)-3,5-dimethyl-4-(3-(pyridin-3-yl)benzyl)piperazin-1-yl)methyl)-N-hydroxybenzamide |
| 345 | 4-(((3R,5S)-3,5-dimethyl-4-(3-(pyridin-4-yl)benzyl)piperazin-1-yl)methyl)-N-hydroxybenzamide |
| 346 | 4-(((3R,5S)-4-(3-(3,6-dihydro-2H-pyran-4-yl)benzyl)-3,5-dimethylpiperazin-1-yl)methyl)-N-hydroxybenzamide |
| 347 | 4-(((3R,5S)-4-((4',4'-dimethyl-2',3',4',5'-tetrahydro-[1,1'-biphenyl]-3-yl)methyl)-3,5-dimethylpiperazin-1-yl)methyl)-N-hydroxybenzamide |
| 348 | 4-(((2S,6R)-4-(2-(furan-3-yl)benzyl)-2,6-dimethylpiperazin-1-yl)methyl)-N-hydroxybenzamide |
| 349 | 4-(((2S,6R)-2,6-dimethyl-4-(2-(pyridin-3-yl)benzyl)piperazin-1-yl)methyl)-N-hydroxybenzamide |

TABLE 1-continued

Names of dimethylpiperazine derivative compounds

| No. | Name of Compound |
|---|---|
| 350 | 4-(((2S,6R)-2,6-dimethyl-4-(2-(pyridin-4-yl)benzyl)piperazin-1-yl)methyl)-N-hydroxybenzamide |
| 351 | 4-(((2S,6R)-4-(2-(3,6-dihydro-2H-pyran-4-yl)benzyl)-2,6-dimethylpiperazin-1-yl)methyl)-N-hydroxybenzamide |
| 352 | 4-(((2S,6R)-4-((4',4'-dimethyl-2',3',4',5'-tetrahydro-[1,1'-biphenyl]-2-yl)methyl)-2,6-dimethylpiperazin-1-yl)methyl)-N-hydroxybenzamide |
| 354 | 4-(((3R,5S)-3,5-dimethyl-4-(oxazol-4-ylmethyl)piperazin-1-yl)methyl)-N-hydroxybenzamide |
| 355 | 4-(((3R,5S)-3,5-dimethyl-4-(pyrimidin-5-ylmethyl)piperazin-1-yl)methyl)-N-hydroxybenzamide |
| 356 | 4-(((3R,5S)-3,5-dimethyl-4-(3-(morpholinomethyl)benzyl)piperazin-1-yl)methyl)-N-hydroxybenzamide |
| 376 | 4-(((3R,5S)-3,5-dimethyl-4-(4-(morpholinomethyl)benzyl)piperazin-1-yl)methyl)-N-hydroxybenzamide |
| 380 | 4-(((3R,5S)-4-(3-((1-(2-fluoro-2-methylpropyl)piperidin-4-yl)methoxy)benzyl)-3,5-dimethylpiperazin-1-yl)methyl)-N-hydroxybenzamide |
| 382 | 4-(((3R,5S)-3,5-dimethyl-4-(3-(piperidin-1-ylmethyl)benzyl)piperazin-1-yl)methyl)-N-hydroxybenzamide |
| 383 | 4-(((3R,5S)-4-(3-(((R)-3-fluoropyrrolidin-1-yl)methyl)benzyl)-3,5-dimethylpiperazin-1-yl)methyl)-N-hydroxybenzamide |
| 384 | 4-(((3R,5S)-4-(3-((3,3-difluoroazetidin-1-yl)methyl)benzyl)-3,5-dimethylpiperazin-1-yl)methyl)-N-hydroxybenzamide |
| 385 | 4-(((3R,5S)-4-(3-((4-benzylpiperazin-1-yl)methyl)benzyl)-3,5-dimethylpiperazin-1-yl)methyl)-N-hydroxybenzamide |
| 386 | N-hydroxy-4-(((3R,5S)-4-(3-((4-(2-hydroxy-2-methyl propyl)piperazin-1-yl)methyl)benzyl)-3,5-dimethylpiperazin-1-yl)methyl)benzamide |
| 387 | 4-(((3R,5S)-4-(3-((4-(2-fluoro-2-methylpropyl)piperazin-1-yl)methyl)benzyl)-3,5-dimethylpiperazin-1-yl)methyl)-N-hydroxybenzamide |
| 388 | 4-(((3R,5S)-4-(4-((1-(2-fluoro-2-methylpropyl)piperidin-4-yl)methoxy)benzyl)-3,5-dimethylpiperazin-1-yl)methyl)-N-hydroxybenzamide |
| 396 | 4-(((2S,6R)-4-(3-(furan-3-yl)benzyl)-2,6-dimethylpiperazin-1-yl)methyl)-N-hydroxybenzamide |
| 400 | 4-(((2S,6R)-4-((4',4'-dimethyl-2',3',4',5'-tetrahydro-[1,1'-biphenyl]-4-yl)methyl)-2,6-dimethylpiperazin-1-yl)methyl)-N-hydroxybenzamide |
| 401 | 4-(((2S,6R)-4-(4-(3,6-dihydro-2H-pyran-4-yl)benzyl)-2,6-dimethylpiperazin-1-yl)methyl)-N-hydroxybenzamide |
| 402 | 4-(((3R,5S)-3,5-dimethyl-4-(tetrahydrofuran-2-carbonyl)piperazin-1-yl)methyl)-N-hydroxybenzamide |
| 403 | 4-(((3R,5S)-3,5-dimethyl-4-(1H-pyrazole-3-carbonyl)piperazin-1-yl)methyl)-N-hydroxybenzamide |
| 404 | 4-(((3R,5S)-3,5-dimethyl-4-(pyrazine-2-carbonyl)piperazin-1-yl)methyl)-N-hydroxybenzamide |
| 405 | N-hydroxy-4-(((3R,5S)-4-isonicotinoyl-3,5-dimethyl piperazin-1-yl)methyl)benzamide |
| 411 | 4-(((3R,5S)-4-(4-(((R)-3-fluoropyrrolidin-1-yl)methyl)benzyl)-3,5-dimethylpiperazin-1-yl)methyl)-N-hydroxybenzamide |
| 412 | 4-(((3R,5S)-4-(4-((3,3-difluoroazetidin-1-yl)methyl)benzyl)-3,5-dimethylpiperazin-1-yl)methyl)-N-hydroxybenzamide |
| 413 | 4-(((3R,5S)-4-(4-((4-benzylpiperazin-1-yl)methyl)benzyl)-3,5-dimethylpiperazin-1-yl)methyl)-N-hydroxybenzamide |
| 423 | 4-(((3R,5S)-3,5-dimethyl-4-(3-(pyrrolidin-1-ylmethyl)benzoyl)piperazin-1-yl)methyl)-N-hydroxybenzamide |
| 424 | 4-(((3R,5S)-3,5-dimethyl-4-(3-(piperidin-1-ylmethyl)benzoyl)piperazin-1-yl)methyl)-N-hydroxybenzamide |
| 425 | 4-(((3R,5S)-4-(3-((diethylamino)methyl)benzoyl)-3,5-dimethylpiperazin-1-yl)methyl)-N-hydroxybenzamide |
| 426 | 4-(((3R,5S)-4-(3-((diethylamino)methyl)benzyl)-3,5-dimethylpiperazin-1-yl)methyl)-N-hydroxybenzamide |
| 427 | 4-(((3R,5S)-3,5-dimethyl-4-(3-(pyrrolidin-1-ylmethyl)benzyl)piperazin-1-yl)methyl)-N-hydroxybenzamide |
| 428 | 4-(((3R,5S)-3,5-dimethyl-4-(3-((4-methylpiperazin-1-yl)methyl)benzyl)piperazin-1-yl)methyl)-N-hydroxybenzamide |
| 429 | 4-(((3R,5S)-4-(3-((4-ethylpiperazin-1-yl)methyl)benzyl)-3,5-dimethylpiperazin-1-yl)methyl)-N-hydroxybenzamide |

TABLE 1-continued

Names of dimethylpiperazine derivative compounds

| No. | Name of Compound |
|---|---|
| 430 | N-hydroxy-4-(((3R,5S)-4-(3-((4-isopropylpiperazin-1-yl)methyl)benzyl)-3,5-dimethylpiperazin-1-yl)methyl)benzamide |
| 431 | 4-(((3R,5S)-4-(3-((4-acetylpiperazin-1-yl)methyl)benzyl)-3,5-dimethylpiperazin-1-yl)methyl)-N-hydroxybenzamide |
| 432 | 4-(((3R,5S)-3,5-dimethyl-4-(3-((4-methylpiperazin-1-yl)methyl)benzoyl)piperazin-1-yl)methyl)-N-hydroxybenzamide |
| 433 | 4-(((3R,5S)-4-(3-((4-ethylpiperazin-1-yl)methyl)benzoyl)-3,5-dimethylpiperazin-1-yl)methyl)-N-hydroxybenzamide |
| 434 | N-hydroxy-4-(((3R,5S)-4-(3-((4-isopropylpiperazin-1-yl)methyl)benzoyl)-3,5-dimethylpiperazin-1-yl)methyl)benzamide |
| 435 | 4-(((3R,5S)-4-(3-((4-acetylpiperazin-1-yl)methyl)benzoyl)-3,5-dimethylpiperazin-1-yl)methyl)-N-hydroxybenzamide |
| 439 | 4-(((3R,5S)-3,5-dimethyl-4-(3-(morpholinomethyl)benzoyl)piperazin-1-yl)methyl)-N-hydroxybenzamide |
| 440 | 4-(((3R,5S)-4-(3-(((1-(diethylamino)propan-2-yl)amino)methyl)benzoyl)-3,5-dimethylpiperazin-1-yl)methyl)-N-hydroxybenzamide |
| 441 | 4-(((3R,5S)-4-(3-(((1-(benzyl(methyl)amino)propan-2-yl)amino)methyl)benzoyl)-3,5-dimethylpiperazin-1-yl)methyl)-N-hydroxybenzamide |
| 442 | N-hydroxy-4-(((3R,5S)-4-(3-((4-isopentylpiperazin-1-yl)methyl)benzoyl)-3,5-dimethylpiperazin-1-yl)methyl)benzamide |
| 443 | 4-(((3R,5S)-3,5-dimethyl-4-(3-((4-(2,2,2-trifluoroethyl)piperazin-1-yl)methyl)benzoyl)piperazin-1-yl)methyl)-N-hydroxybenzamide |
| 444 | 4-(((3R,5S)-3,5-dimethyl-4-(3-((4-(methylsulfonyl) piperazin-1-yl)methyl)benzoyl)piperazin-1-yl)methyl)-N-hydroxybenzamide |
| 446 | 4-(((3R,5S)-3,5-dimethyl-4-(3-(morpholine-4-carbonyl)benzyl)piperazin-1-yl)methyl)-N-hydroxybenzamide |
| 452 | 4-(((3R,5S)-3,5-dimethyl-4-(3-((4-(methylsulfonyl) piperazin-1-yl)methyl)benzyl)piperazin-1-yl)methyl)-N-hydroxybenzamide |
| 453 | 4-(((3R,5S)-3,5-dimethyl-4-(3-((4-(2,2,2-trifluoroethyl)piperazin-1-yl)methyl)benzyl)piperazin-1-yl)methyl)-N-hydroxybenzamide |
| 454 | N-hydroxy-4-(((3R,5S)-4-(3-((4-isopentylpiperazin-1-yl)methyl)benzyl)-3,5-dimethylpiperazin-1-yl)methyl)benzamide |
| 455 | 4-(((3R,5S)-4-(3-(((1-(diethylamino)propan-2-yl)amino)methyl)benzyl)-3,5-dimethylpiperazin-1-yl)methyl)-N-hydroxybenzamide |
| 456 | 4-(((3R,5S)-4-(3-(((1-(benzyl(methyl)amino)propan-2-yl)amino)benzyl)-3,5-dimethylpiperazin-1-yl) methyl)-N-hydroxybenzamide |
| 457 | 4-(((3R,5S)-3,5-dimethyl-4-(2-(morpholinomethyl)benzyl)piperazin-1-yl)methyl)-N-hydroxybenzamide |
| 458 | 4-(((3R,5S)-3,5-dimethyl-4-(4-(morpholinomethyl)benzoyl)piperazin-1-yl)methyl)-N-hydroxybenzamide |
| 459 | 4-(((3R,5S)-3,5-dimethyl-4-(4-(piperidin-1-ylmethyl)benzoyl)piperazin-1-yl)methyl)-N-hydroxybenzamide |
| 460 | 4-(((3R,5S)-4-(4-(((R)-3-fluoropyrrolidin-1-yl)methyl)benzoyl)-3,5-dimethylpiperazin-1-yl)methyl)-N-hydroxybenzamide |
| 461 | 4-(((3R,5S)-3,5-dimethyl-4-(4-(pyrrolidin-1-ylmethyl)benzoyl)piperazin-1-yl)methyl)-N-hydroxybenzamide |
| 462 | 4-(((3R,5S)-3,5-dimethyl-4-(4-((4-methylpiperazin-1-yl)methyl)benzoyl)piperazin-1-yl)methyl)-N-hydroxybenzamide |
| 463 | 4-(((3R,5S)-3,5-dimethyl-4-(4-((4-(methylsulfonyl) piperazin-1-yl)methyl)benzoyl)piperazin-1-yl)methyl)-N-hydroxybenzamide |
| 466 | 4-(((3R,5S)-3,5-dimethyl-4-(4-(pyrrolidin-1-ylmethyl)benzyl)piperazin-1-yl)methyl)-N-hydroxybenzamide |
| 467 | 4-(((3R,5S)-3,5-dimethyl-4-(4-(piperidin-1-ylmethyl)benzyl)piperazin-1-yl)methyl)-N-hydroxybenzamide |
| 468 | 4-(((3R,5S)-3,5-dimethyl-4-(4-((4-methylpiperazin-1-yl)methyl)benzyl)piperazin-1-yl)methyl)-N-hydroxybenzamide |
| 472 | (E)-3-(4-(((3R,5S)-3,5-dimethyl-4-(3-(morpholinomethyl)benzyl)piperazin-1-yl)methyl)phenyl)-N-hydroxyacrylamide |
| 475 | (E)-3-(4-(((2S,6R)-2,6-dimethyl-4-(3-(pyrrolidin-1-ylmethyl)benzyl)piperazin-1-yl)methyl)phenyl)-N-hydroxyacrylamide |
| 476 | (E)-3-(4-(((2S,6R)-4-(3-((diethylamino)methyl)benzyl)-2,6-dimethylpiperazin-1-yl)methyl)phenyl)-N-hydroxyacrylamide |
| 477 | (E)-3-(4-(((2S,6R)-4-(4-(furan-2-yl)benzyl)-2,6-dimethylpiperazin-1-yl)methyl)phenyl)-N-hydroxyacrylamide |
| 478 | 4-(((2S,6R)-4-(3-((diethylamino)methyl)benzyl)-2,6-dimethylpiperazin-1-yl)methyl)-N-hydroxybenzamide (hydrochloride salt) |

TABLE 1-continued

Names of dimethylpiperazine derivative compounds

| No. | Name of Compound |
|---|---|
| 479 | 4-(((2S,6R)-2,6-dimethyl-4-(3-(pyrrolidin-1-ylmethyl)benzyl)piperazin-1-yl)methyl)-N-hydroxybenzamide |
| 480 | (E)-3-(4-(((2S,6R)-2,6-dimethyl-4-(3-(pyrrolidin-1-ylmethyl)benzoyl)piperazin-1-yl)methyl)phenyl)-N-hydroxyacrylamide |
| 481 | 4-(((3R,5S)-3,5-dimethyl-4-(2-(1-(methylsulfonyl)-1,2,3,6-tetrahydropyridin-4-yl)benzyl)piperazin-1-yl)methyl)-N-hydroxybenzamide |
| 482 | 4-(((3R,5S)-4-(2-(1-acetyl-1,2,3,6-tetrahydropyridin-4-yl)benzyl)-3,5-dimethylpiperazin-1-yl)methyl)-N-hydroxybenzamide |
| 483 | 4-(((3R,5S)-3,5-dimethyl-4-(2-(1-(2,2,2-trifluoroethyl)-1,2,3,6-tetrahydropyridin-4-yl)benzyl)piperazin-1-yl)methyl)-N-hydroxybenzamide |
| 484 | N-hydroxy-4-(((3R,5S)-4-(2-(1-isopropyl-1,2,3,6-tetrahydropyridin-4-yl)benzyl)-3,5-dimethylpiperazin-1-yl)methyl)benzamide |
| 485 | 4-(((3R,5S)-4-(2-(1-ethyl-1,2,3,6-tetrahydropyridin-4-yl)benzyl)-3,5-dimethylpiperazin-1-yl)methyl)-N-hydroxybenzamide |
| 486 | 4-(((3R,5S)-4-(4-((4-acetylpiperazin-1-yl)methyl)benzyl)-3,5-dimethylpiperazin-1-yl)methyl)-N-hydroxybenzamide (hydrochloride salt) |
| 487 | (E)-3-(4-(((2S,6R)-4-(3-((diethylamino)methyl)benzoyl)-2,6-dimethylpiperazin-1-yl)methyl)phenyl)-N-hydroxyacrylamide |
| 520 | 3-(((3R,5S)-4-benzyl-3,5-dimethylpiperazin-1-yl)methyl)-N-hydroxy-1H-indole-6-carboxamide |
| 569 | 5-(((3R,5S)-4-benzyl-3,5-dimethylpiperazin-1-yl)methyl)-N-hydroxy-1H-indole-2-carboxamide |
| 571 | 5-(((3R,5S)-4-benzyl-3,5-dimethylpiperazin-1-yl)methyl)-N-hydroxybenzofuran-2-carboxamide |
| 573 | 6-(((3R,5S)-4-benzyl-3,5-dimethylpiperazin-1-yl)methyl)-N-hydroxy-1H-indole-2-carboxamide |
| 574 | 2-(((3R,5S)-4-benzyl-3,5-dimethylpiperazin-1-yl)methyl)-N-hydroxybenzofuran-5-carboxamide |
| 609 | 5-(((3R,5S)-3,5-dimethyl-4-(3-(morpholinomethyl)benzyl)piperazin-1-yl)methyl)-N-hydroxypicolinamide |
| 652 | 4-(((3R,5S)-4-benzyl-3,5-dimethylpiperazin-1-yl)methyl)-N,2-dihydroxybenzamide |
| 653 | 4-(((3R,5S)-3,5-dimethyl-4-(3-(morpholinomethyl)benzyl)piperazin-1-yl)methyl)-N,2-dihydroxybenzamide |
| 696 | 4-(((3R,5S)-3,5-dimethyl-4-(3-(morpholinomethyl)benzyl)piperazin-1-yl)methyl)-3-fluoro-N-hydroxybenzamide |
| 812 | 5-(((3R,5S)-4-benzyl-3,5-dimethylpiperazin-1-yl)methyl)-N-hydroxypicolinamide |
| 813 | 4-(((3R,5S)-4-benzyl-3,5-dimethylpiperazin-1-yl)methyl)-3-fluoro-N-hydroxybenzamide |
| 814 | 4-((3R,5S)-4-benzyl-3,5-dimethylpiperazine-1-carbonyl)-N-hydroxybenzamide |
| 818 | 4-(((3R,5S)-4-benzyl-3,5-dimethylpiperazin-1-yl)sulfonyl)-N-hydroxybenzamide |
| 820 | 2-(4-(((3R,5S)-4-benzyl-3,5-dimethylpiperazin-1-yl)sulfonyl)phenyl)-N-hydroxyacetamide |
| 822 | 4-(((3R,5S)-4-benzyl-3,5-dimethylpiperazin-1-yl)methyl)-N-hydroxycyclohexane-1-carboxamide |
| 823 | 2-(4-((3R,5S)-4-benzyl-3,5-dimethylpiperazine-1-carbonyl)phenyl)-N-hydroxyacetamide |
| 824 | 3-(4-((3R,5S)-4-benzyl-3,5-dimethylpiperazine-1-carbonyl)phenyl)-N-hydroxypropanamide |

Preferably, the compounds represented by formula I or pharmaceutically acceptable salts thereof according to the present invention may be selected from the group consisting of compounds 081, 082, 083, 084, 098, 099, 100, 106, 107, 108, 109, 110, 112, 120, 121, 122, 123, 125, 126, 127, 128, 145, 146, 147, 148, 149, 159, 160, 161, 171, 173, 174, 175, 177, 186, 188, 193, 194, 195, 196, 198, 211, 214, 219, 248, 249, 250, 251, 252, 255, 265, 266, 267, 272, 283, 284, 285, 286, 292, 295, 297, 305, 326, 328, 329, 330, 332, 342, 343, 344, 345, 346, 349, 354, 356, 376, 380, 382, 383, 384, 385, 386, 387, 388, 403, 411, 413, 430, 431, 432, 433, 434, 435, 439, 440, 441, 442, 443, 444, 452, 453, 454, 455, 456, 467, 468, 481, 482, 483, 484, 485, 486, 569, 696, 813 and 823. More preferably, the compounds represented by formula I or pharmaceutically acceptable salts thereof according to the present invention may be selected from the group consisting of compounds 082, 083, 084, 098, 100, 120, 121, 122, 123, 125, 126, 127, 128, 145, 146, 148, 149, 159, 160, 161, 171, 174, 177, 194, 211, 249, 255, 283, 305, 326, 328, 329, 330, 332, 342, 343, 344, 345, 346, 349, 354, 356, 376, 382, 383, 387, 388, 411, 413, 431, 439, 441, 444, 452, 453, 454, 467, 468, 481, 482, 483, 484, 485, 696 and 813.

As used herein, the term "pharmaceutically acceptable salt" means any salt that is generally used in the pharmaceutical field. Examples of the pharmaceutically acceptable salt include, but are not limited to, salts with inorganic ions such as calcium, potassium, sodium or magnesium ions, salts with inorganic acids such as hydrochloric acid, nitric acid, phosphoric acid, bromic acid, iodic acid, perchloric acid, tartaric acid or sulfuric acid, salts with organic acids such as acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid or the like, salts with sulfonic acids such as methanesulfonic acid, ethanesulfonic acid, benzenesulfonic acid, p-toluenesulfonic acid or naphthalenesulfonic acid, salts with amino acids such as glycine, arginine or lysine, and salts with amines such as trimethylamine, triethylamine, ammonia, pyridine or picoline.

In the present invention, preferred salts include salts with hydrochloric acid, trifluoroacetic acid, citric acid, bromic acid, maleic acid, phosphoric acid, sulfuric acid, tartaric acid or the like, and preferred examples of such compounds include compounds 230, 245, 250, 251, 253, 266, 270, 271, 273, 274, 275, 290, 291, 292, 293, 294, 295, 296, 297, 478 and 486 as disclosed herein.

The compounds represented by formula I may contain one or more asymmetrical carbon atoms, and thus may exist in the form of racemates, racemic mixtures, single enantiomers, diastereomeric mixtures, and individual diastereomers. The compounds of formula I can be separated into such isomers by methods known in the art, for example, column chromatography or HPLC. Alternatively, stereoisomers of the compounds of formula I may be synthesized by stereospecific synthesis using optically pure starting materials and/or reagents of known configuration.

Methods for Preparation of Novel HDAC6 Inhibitors

The present invention provides methods for the preparation of the novel compounds of formula I, isomers thereof, or pharmaceutically acceptable salts thereof.

Preferred methods for the preparation of the novel compounds of formula I, isomers thereof, or pharmaceutically acceptable salts thereof are as shown in reaction schemes 1 to 23 below, and also include modifications obvious to those skilled in the art.

Reaction Scheme 1

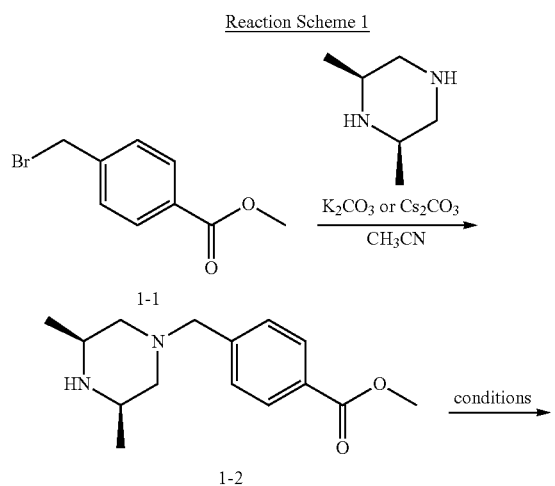

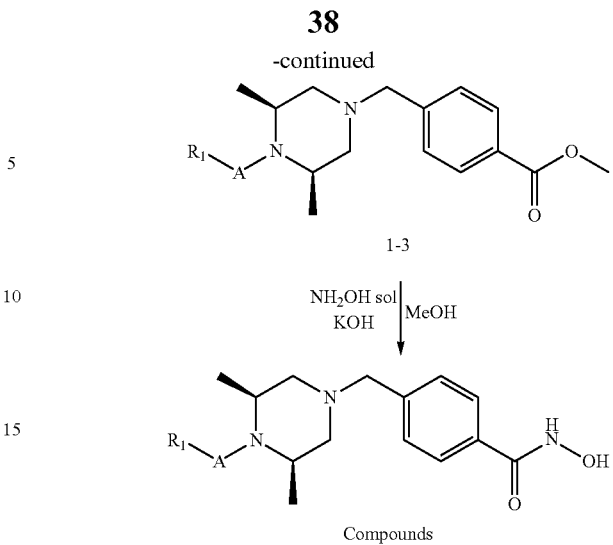

Conditions: a) $R_1$—$CH_2$—Br (or —I, —Cl, —OTf, —OMs), $K_2CO_3$ (or $Cs_2CO_3$/$CH_3CN$ (or DMF); b) $R_1$—CHO, Na(CN)BH$_3$, AcOH/THF; c) $R_1$—COCl, TEA/$CH_2Cl_2$; d) $R_1CO_2H$, HOBt, EDCI, DIPEA/$CH_2Cl_2$; e) $R_1$—NCO, TEA/$CH_2Cl_2$; f) 4-nitrophenyl 3-fluorobenzylcarbamate, TEA/DMF; g) $Ac_2O$, TEA/$CH_2Cl_2$; H) $R_1$—$SO_2Cl$, TEA/$CH_2Cl_2$; i) $R_1CO_2H$, HATU, DIPEA/DMF.

TABLE 2

| Compounds | A | $R_1$ | conditions |
|---|---|---|---|
| 82 | C=O | methyl | g |
| 83 | C=O | phenyl | c |
| 84 | $CH_2$ | phenyl | a |
| 98 | NH(C=O) | 2-propyl | e |
| 99 | NH(C=O) | 3-chlorophenyl | e |
| 100 | $SO_2$ | phenyl | h |
| 120 | C=O | 2-chlorophenyl | c |
| 121 | C=O | 3-chlorophenyl | c |
| 122 | C=O | 4-chlorophenyl | c |
| 123 | C=O | 2-pyridyl | c |
| 125 | C=O | 2-furanyl | c |
| 126 | C=O | 2-thiophenyl | c |
| 127 | $CH_2$ | 2-chlorophenyl | a |
| 128 | $CH_2$ | 3-chlorophenyl | a |
| 145 | $CH_2$ | furan-2-yl | b |
| 146 | C=O | benzyl | c |
| 147 | $CH_2$ | methyl | a |
| 148 | $CH_2$ | ethyl | a |
| 149 | $CH_2$ | 1,1,1-trifluoromethyl | a |
| 159 | NH(C=O) | phenyl | e |
| 160 | NH(C=O) | 2-methylphenyl | e |
| 161 | NH(C=O) | benzyl | e |
| 177 | C=O | phenol | c |
| 184 | $CH_2$ | benzyl | b |
| 188 | C=O | phenethyl | c |
| 204 | $CH_2$ | 1,1,1,-trifluoropropyl | a |
| 211 | $CH_2$ | 2-fluorophenyl | a |
| 212 | $CH_2$ | 2,5-difluorophenyl | a |
| 213 | $CH_2$ | 2,4,5-trifluorophenyl | a |
| 214 | $CH_2$ | 3,5-bis(trifluoromethyl)phenyl | a |
| 222 | C=O | 3-fluorobenzyl | d |

TABLE 2-continued

| Compounds | A | R₁ | conditions |
|---|---|---|---|
| 223 | C=O | 3-(trifluoromethyl)benzyl | d |
| 224 | C=O | 3-chlorobenzyl | d |
| 225 | CH₂ | 3-fluorophenyl | a |
| 232 | NH(C=O) | 3-fluorobenzyl | f |
| 255 | CH₂ | 3-(1H-pyrrol-1-yl)phenyl | a |
| 265 | CH₂ | naphthalen-2-yl | a |
| 266 | CH₂ | pyridin-4-yl | a |
| 267 | CH₂ | 3-chloro-2-(trifluoromethyl)phenyl | a |
| 270 | CH₂ | 4-isobutyl | a |
| 272 | CH₂ | 2-methylprop-1-en-1-yl | a |
| 275 | CH₂ | propyl | a |
| 290 | C=O | 4-methylphenyl | c |
| 291 | C=O | 4-methoxyphenyl | c |
| 292 | C=O | tert-butyl | c |
| 293 | C=O | ethyl | c |
| 294 | C=O | propyl | c |
| 295 | C=O | cyclopropyl | c |
| 296 | C=O | isopropyl | c |
| 297 | C=O | isobutyl | c |
| 354 | CH₂ | oxazol-4-yl | a |
| 355 | CH₂ | pyrimidin-5-yl | a |
| 403 | C=O | 1H-pyrazol-3-yl | i |
| 404 | C=O | 2-pyrazinyl | i |
| 405 | C=O | 4-pyridyl | c |

As shown in reaction scheme 1 above, an amine of (2S,6R)-2,6-dimethylpiperazine is subjected to an alkylation reaction with methyl (4-bromomethyl)benzoate to prepare compound 1-2, which is then subjected to an alkylation reaction, an acylation reaction or a reductive amination reaction under conditions a) to i), thereby preparing compounds 1-3. Finally, the prepared compounds 1-3 are reacted with an aqueous hydroxylamine solution and potassium hydroxide to prepare compounds 82, 83, 84, 98, 99, 100, 120, 121, 122, 123, 125, 126, 127, 128, 145, 146, 147, 148, 149, 159, 160, 161, 177, 184, 188, 204, 211, 212, 213, 214, 222, 223, 224, 225, 232, 255, 265, 266, 267, 270, 272, 275, 290, 291, 292, 293, 294, 295, 296, 297, 354, 355, 403, 404 and 405.

Reaction Scheme 2

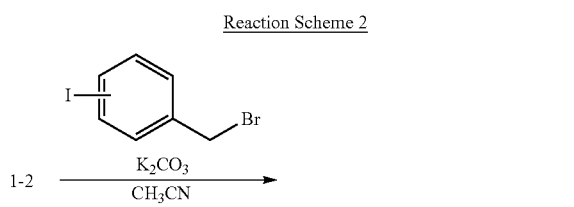

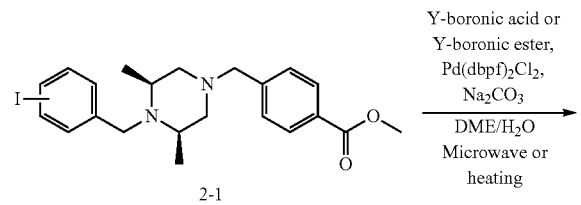

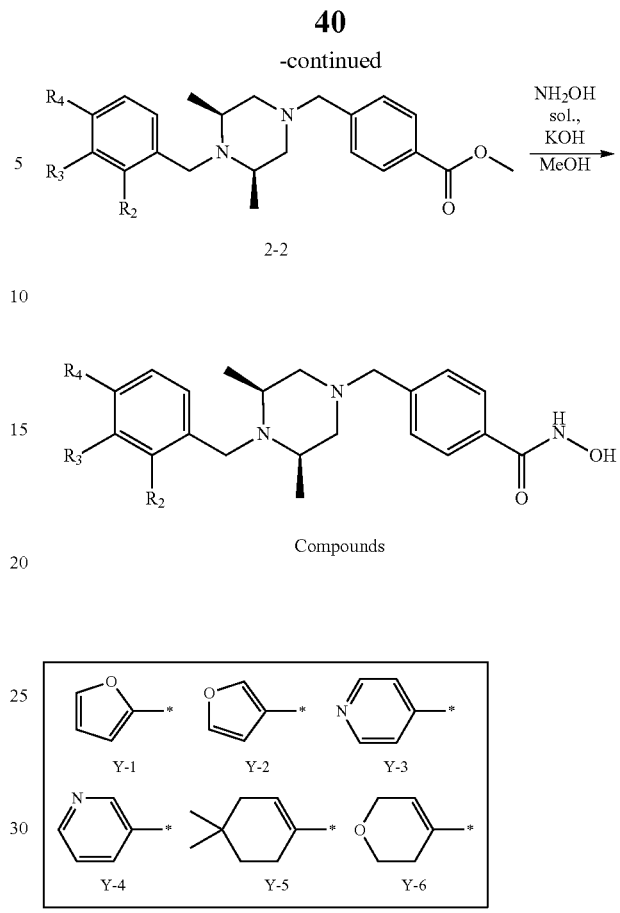

TABLE 3

| Compounds | R₂ | R₃ | R₄ |
|---|---|---|---|
| 309 | H | H | Y-2 |
| 327 | Y-1 | H | H |
| 328 | Y-2 | H | H |
| 329 | Y-3 | H | H |
| 330 | Y-4 | H | H |
| 331 | Y-5 | H | H |
| 332 | Y-6 | H | H |
| 342 | H | Y-1 | H |
| 343 | H | Y-2 | H |
| 344 | H | Y-4 | H |
| 345 | H | Y-3 | H |
| 346 | H | Y-6 | H |
| 347 | H | Y-5 | H |

As shown in reaction scheme 2 above, compound 1-2 is alkylated to prepare compound 2-1, which is then subjected to a Suzuki reaction with a boronic acid or boronic ester containing each of compounds Y-1 to Y-6, thereby preparing compounds 2-2. Finally, the prepared compounds 2-2 are reacted with an aqueous hydroxylamine solution and potassium hydroxide to prepare compounds 309, 327, 328, 329, 330, 331, 332, 342, 343, 344, 345, 346 and 347.

Reaction Scheme 3
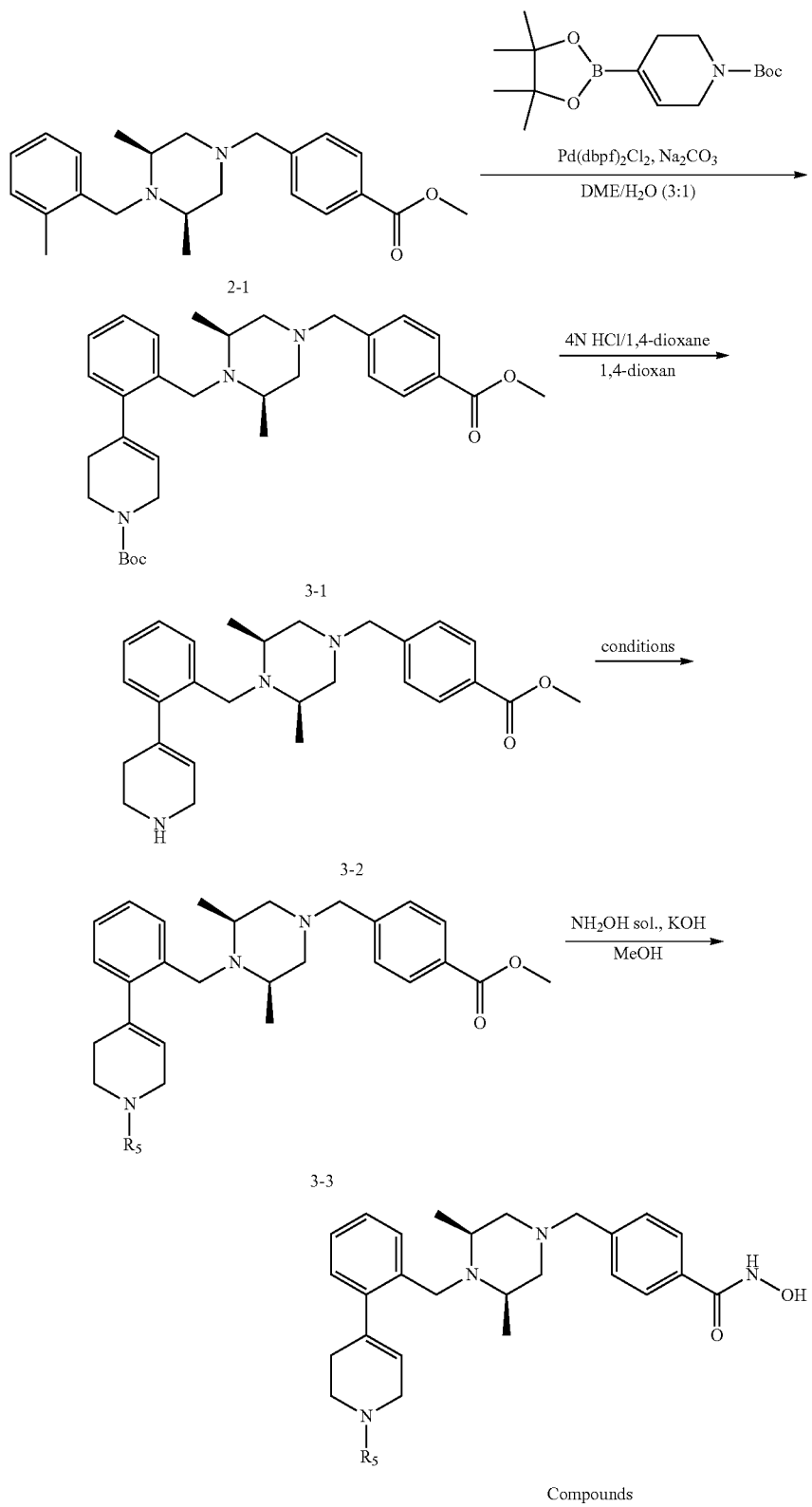
Compounds
Conditions:
a) MsCl, TEA/CH₂Cl₂; b) Ac₂O, TEA/CH₂Cl₂; c) R₅—OTf, K₂CO₃/CH₃CN; d) R₅—X, TEA/CH₂Cl₂.

TABLE 4

| Compounds | $R_5$ | conditions |
|---|---|---|
| 481 | methanesulfonyl | a |
| 482 | acetyl | b |
| 483 | 2,2,2-trifluoroethyl | c |
| 484 | isopropyl | d |
| 485 | ethyl | d |

As shown in reaction scheme 3 above, compound 2-1 is subjected to a Suzuki reaction with tert-butyl 4-(4,4,5,5-tetramethyl-1,3,2-dioxaborolan-2-yl)-5,6-dihydropyridine-1(2H)-carboxylate to prepare compound 3-1, which is then deprotected under an acidic condition, thereby preparing compound 3-2. The prepared compound 3-2 is subjected to substitution reactions under conditions a) to d) above to prepare compounds 3-3, which are then reacted with an aqueous hydroxylamine solution and potassium hydroxide, thereby preparing compounds 481, 482, 483, 484 and 485.

TABLE 5

| Compounds | n | $R_6$ | $R_7$ | $R_8$ | conditions |
|---|---|---|---|---|---|
| 234 | 1 | H | Y-8 | H | b |
| 242 | 0 | H | Y-1 | H | a |
| 243 | 0 | H | Y-2 | H | a |
| 244 | 0 | H | Y-6 | H | a |
| 245 | 0 | H | Y-3 | H | a |
| 246 | 0 | H | Y-4 | H | a |
| 247 | 0 | H | Y-5 | H | a |
| 283 | 0 | Y-1 | H | H | a |
| 284 | 0 | Y-2 | H | H | a |
| 285 | 0 | Y-3 | H | H | a |
| 286 | 0 | Y-4 | H | H | a |
| 288 | 0 | Y-5 | H | H | a |
| 326 | 0 | Y-6 | H | H | a |
| 340 | 0 | H | H | Y-1 | a |

As shown in reaction scheme 4 above, compound 1-2 is reacted with benzoyl chloride or benzoyl bromide to prepare compound 4-1, which is then subjected to a Suzuki reaction with a boronic acid or boronic ester containing each of Reaction Scheme 4

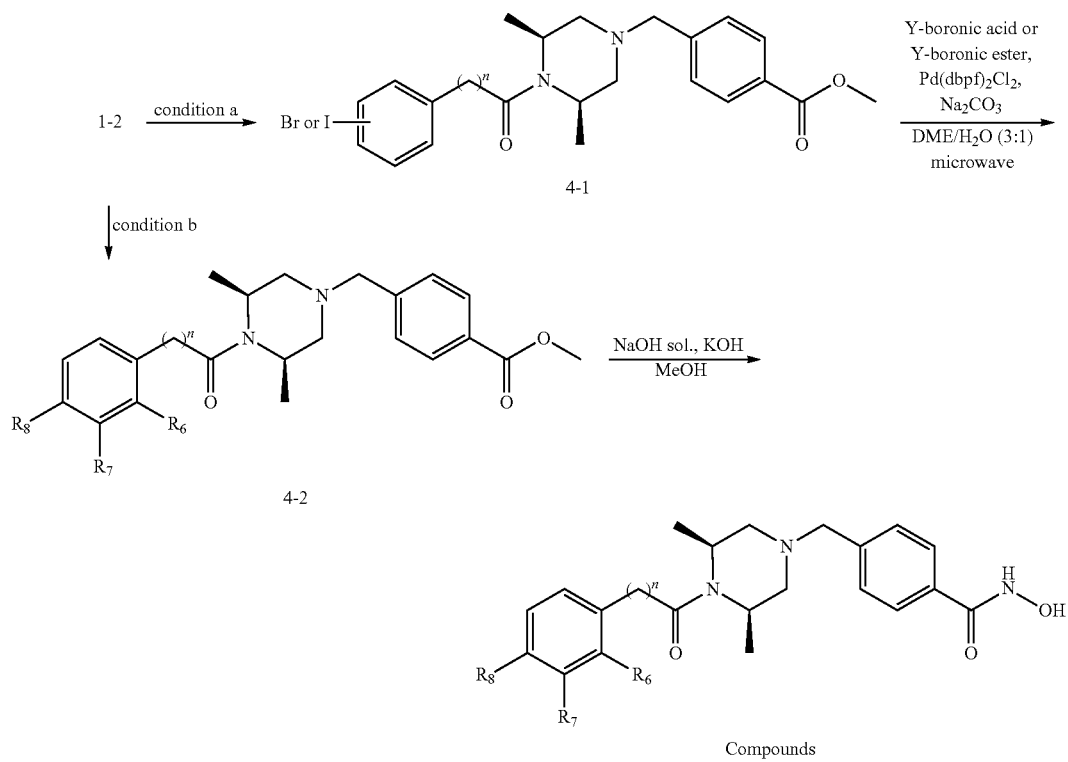

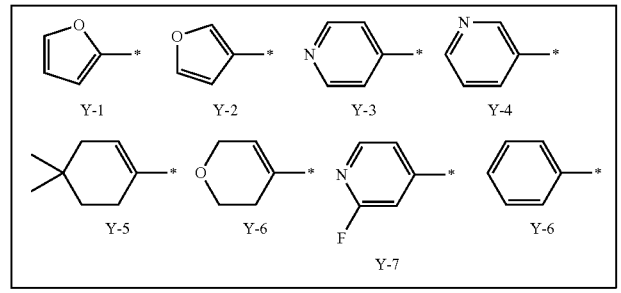

Conditions: a) iodo, chloro or bromo)benzoyl chloride, TEA/CH$_2$Cl$_2$; b) 2-([1,1'-biphenyl]-3-yl)acetic acid, HOBt, EDCI, DIPEA/CH$_2$Cl$_2$.

compounds Y-1 to Y-8, thereby preparing compounds 4-2. Alternatively, compound 1-2 is subjected to an amide coupling reaction with 2-([1,1'-biphenyl]-3-yl)acetic acid, thereby preparing compounds 4-2. The prepared compounds 4-2 are reacted with an aqueous hydroxylamine solution and potassium hydroxide, thereby preparing compounds 234, 242, 243, 244, 245, 246, 247, 283, 284, 285, 286, 288, 326 and 340.

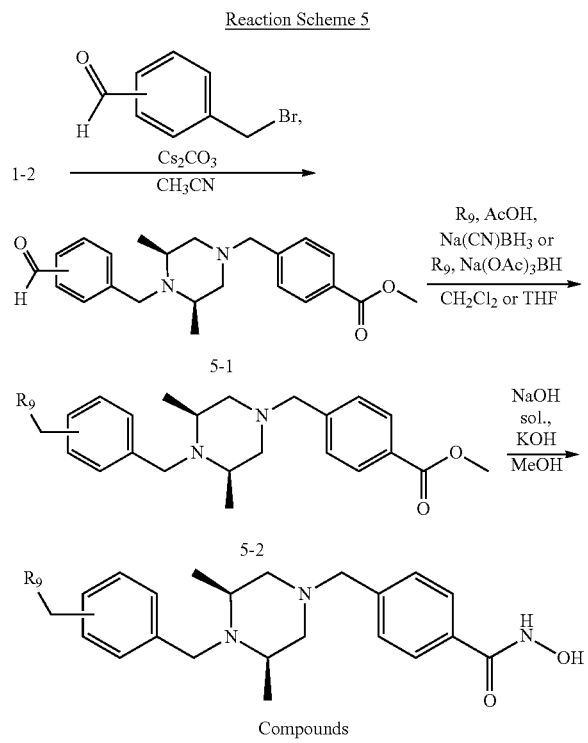

TABLE 6

| Compounds | Position | R$_9$ |
|---|---|---|
| 356 | meta | morpholine |
| 376 | para | morpholine |
| 382 | meta | piperidine |
| 383 | meta | (R)-3-fluoropyrrolidine |
| 384 | meta | 3,3-difluoroazetidine |
| 385 | meta | 4-benzylpiperazine |
| 411 | para | (R)-3-fluoropyrrolidine |
| 412 | para | 3,3-difluoroazetidine |
| 413 | para | 4-benzylpiperazine |
| 426 | meta | N,N-diethylamine |
| 427 | meta | pyrrolidine |
| 428 | meta | 4-methylpiperazine |
| 429 | meta | 4-ethylpiperazine |
| 430 | meta | 4-isopropylpiperazine |
| 431 | meta | 4-acetylpiperazine |
| 452 | meta | 4-methansulfonylpiperazine |
| 453 | meta | 4-(2,2,2-trifluoroethyl)piperazine |
| 454 | meta | 4-isopentylpiperazine |
| 455 | meta | N,N-diethylpropane-1,2-diamine |
| 456 | meta | N-benzyl-N-methylpropane-1,2-diamine |
| 457 | ortho | morpholine |
| 466 | para | pyrrolidine |
| 467 | para | piperidine |
| 468 | para | 4-methylpiperazine |
| 486 | para | 4-acetylpiperazine |

As shown in reaction scheme 5 above, compound 1-2 is subjected to a substitution reaction with ortho-, meta- or para-(bromomethyl)benzaldehyde to prepare compounds 5-1, which are then subjected to a reductive amination reaction with amine compounds, thereby preparing compounds 5-2. Finally, the prepared amine compounds 5-2 are reacted with an aqueous hydroxylamine solution and potassium hydroxide, thereby preparing compounds 356, 376, 382, 383, 384, 385, 411, 412, 413, 426, 427, 428, 429, 430, 431, 452, 453, 454, 455, 456, 457, 466, 467, 468 and 486.

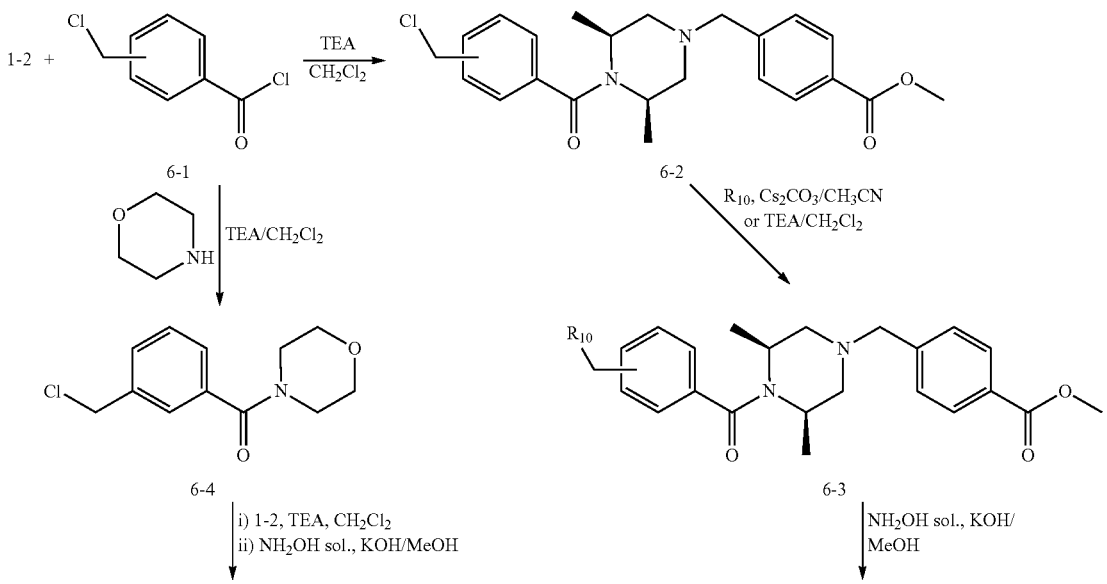

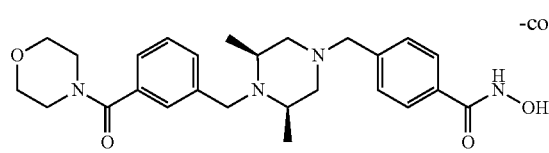

Compound 446

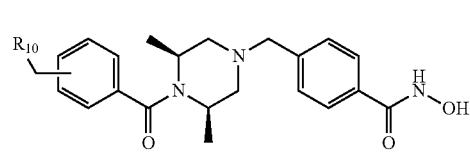

Compounds

TABLE 7

| Compounds | Position | R₁₀ |
|---|---|---|
| 423 | meta | pyrrolidine |
| 424 | meta | piperidine |
| 425 | meta | N,N-diethylamine |
| 432 | meta | 4-methylpiperazine |
| 433 | meta | 4-ethylpiperazine |
| 434 | meta | 4-isopropylpiperazine |
| 435 | meta | 4-acetylpiperazine |
| 439 | meta | morpholine |
| 440 | meta | N,N-diethylpropane-1,2-diamine |
| 441 | meta | N-benzyl-N-methylpropane-1,2-diamine |
| 442 | meta | 4-isopentylpiperazine |
| 443 | meta | 4-(2,2,2-trifluoroethyl)piperazine |
| 444 | meta | 4-methanesulfonylpiperazine |
| 458 | para | morpholine |
| 459 | para | piperidine |
| 460 | para | (R)-3-fluoropyrrolidine |
| 461 | para | pyrrolidine |

TABLE 7-continued

| Compounds | Position | R₁₀ |
|---|---|---|
| 462 | para | 4-methylpiperazine |
| 463 | para | 4-methaensulfonylpiperazine |

As shown in reaction scheme 6 above, compound 6-1 is prepared and subjected to an acylation reaction with compound 1-2 to prepare compound 6-2. The prepared compound 6-2 is subjected to a substitution reaction with amine compounds to prepare compounds 6-3, which are then reacted with an aqueous hydroxylamine solution and potassium hydroxide, thereby preparing compounds 423, 424, 425, 432, 433, 434, 435, 439, 440, 441, 442, 443, 444, 458, 459, 460, 461, 462 and 463.

Alternatively, compound 6-1 is reacted with morpholine to prepare compound 6-4. The prepared compound 6-4 and compound 1-2 are subjected to a substitution reaction, and then reacted with an aqueous hydroxylamine solution and potassium hydroxide, thereby preparing compound 446.

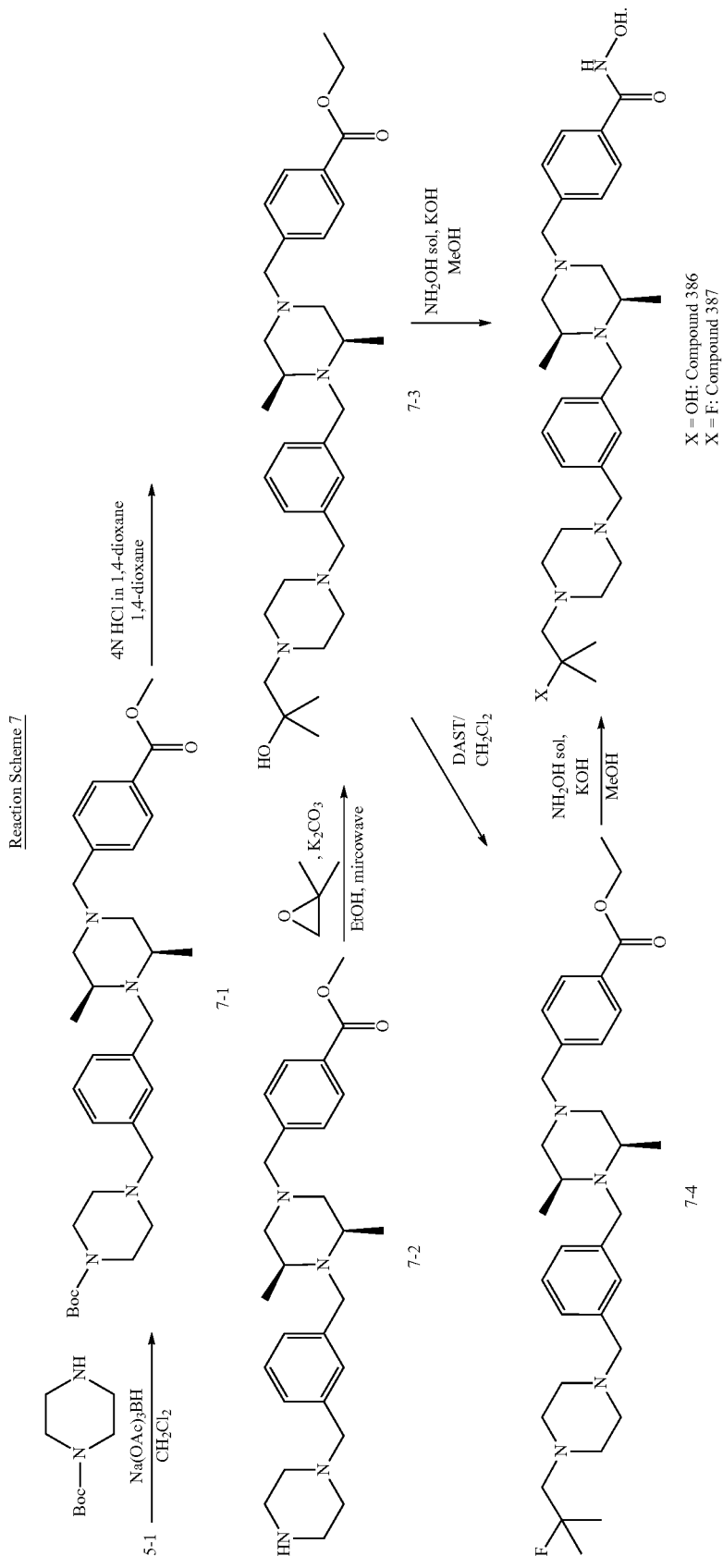

As shown in reaction scheme 7, compound 5-1 is subjected to a reductive amination reaction with 4-tert-butyl piperazine-1-carboxylate, and then deprotected under an acidic condition to prepare compound 7-2. The prepared compound 7-2 is reacted with 2,2-dimethyloxirane to prepare compound 7-3, which is then reacted with an aqueous hydroxylamine solution and potassium hydroxide, thereby preparing compound 386. Further, compound 7-3 is reacted with DAST to substitute the hydroxyl group with fluoride, thereby preparing compound 7-4. The prepared compound 7-4 is prepared with an aqueous hydroxylamine solution and potassium hydroxide, thereby preparing compound 387.

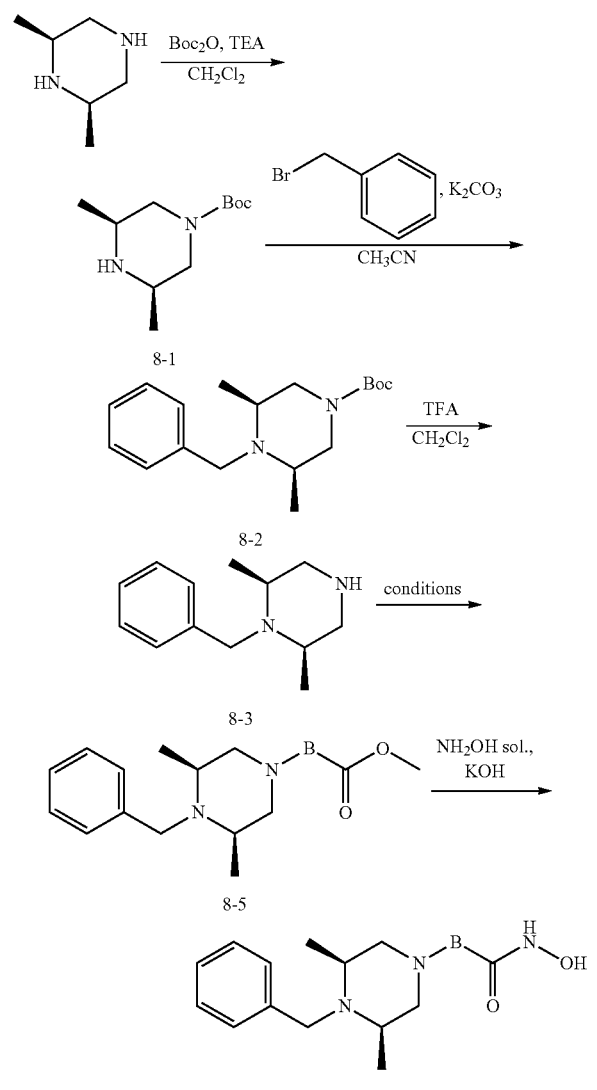

Reaction Scheme 8

TABLE 8

| Compound | B | Conditions |
|---|---|---|
| 154 | (straight chain alkyl linker) | a |
| 171 | (fluorobenzyl linker) | b |
| 172 | (styryl/vinyl phenyl linker) | b |
| 173 | (p-xylylene linker) | a |
| 194 | (methylpyridine linker) | a |
| 218 | (phenethyl linker) | a |
| 219 | (isopropyl phenyl linker) | a |
| 520 | (indole linker) | b (NaBH(OAc)₃) |
| 571 | (benzofuran linker) | a (DIPEA) |

TABLE 8-continued

| Compound | B | Conditions |
|---|---|---|
| 574 | benzofuran-2,5-diyl-CH2 | a (DIPEA) |
| 652 | 2-hydroxy-1,4-phenylene-CH2 | a (TEA) |
| 812 | pyridine-2,5-diyl-CH2 | b (NaBH(OAc)3) |
| 813 | 2-fluoro-1,4-phenylene-CH2 | a (K2CO3) |
| 814 | 4-(C=O)-phenylene | a (TEA) |
| 818 | 4-(SO2)-phenylene | a (TEA) |
| 820 | 4-(SO2)-phenylene-CH2 | a (TEA) |
| 822 | cyclohexane-1,4-diyl-CH2 | b (NaBH(OAc)3) |
| 823 | 4-(C=O)-phenylene-CH2 | c |
| 824 | 4-(C=O)-phenylene-CH2CH2 | c |

As shown in reaction scheme 8, (2S,6R)-2,6-dimethylpiperazine is protected with Boc and reacted with benzyl bromide, after which it is deprotected under an acidic condition, thereby preparing compound (8-3). The prepared compound 8-3 is subjected to an alkylation reaction or a reductive amination reaction with compound 8-4 shown in conditions a) to c), thereby preparing compounds 8-5. The prepared compounds 8-5 are reacted with an aqueous hydroxylamine solution and potassium hydroxide, thereby preparing compounds 154, 171, 172, 173, 194, 218, 219, 520, 571, 574, 652, 812, 813, 814, 818, 820, 822, 823 and 824.

Reaction Scheme 9

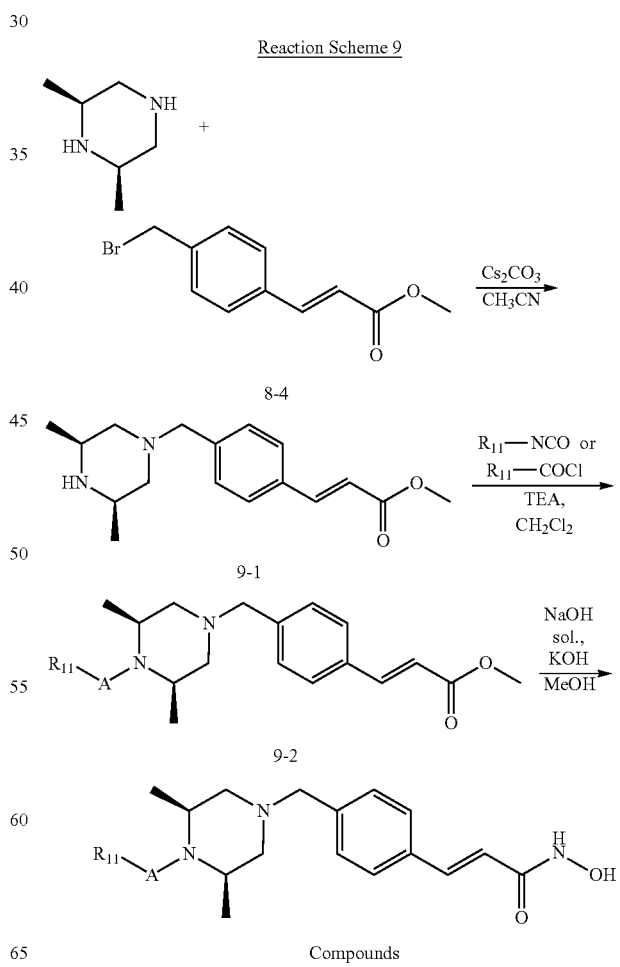

Compounds

TABLE 9

| Compounds | A | $R_{11}$ |
|---|---|---|
| 321 | NH(C=O) | 3-(1H-pyrrol-1-yl)phenyl |
| 322 | C=O | 2-furanyl |
| 323 | C=O | benzyl |

As shown in reaction scheme 9 above, compound 8-4 is reacted with (2S,6R)-2,6-dimethylpierazine to prepare compound 9-1, which is then subjected to a substitution reaction with an isocynate or carbonyl chloride containing substituents represented by $R_{11}$, thereby preparing compound 9-2. The prepared compounds 9-2 are reacted with an aqueous hydroxylamine solution and potassium hydroxide, thereby preparing compounds 321, 322 and 323.

Reaction Scheme 10

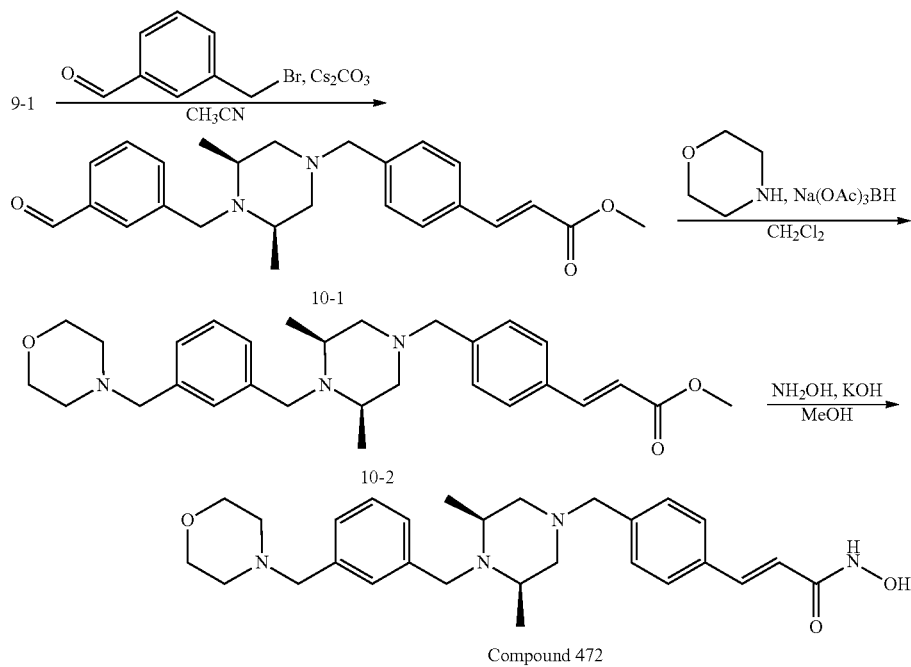

As shown in reaction scheme 10 above, compound 9-1 is subjected to an alkylation reaction with 3-(bromomethyl)benzaldehyde to prepare compound 10-1. The prepared compound 10-1 is subjected to a reductive amination reaction with morpholine to prepare compound 10-2, which is then reacted with an aqueous hydroxylamine solution and potassium hydroxide, thereby preparing compound 472.

Reaction Scheme 11

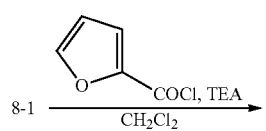

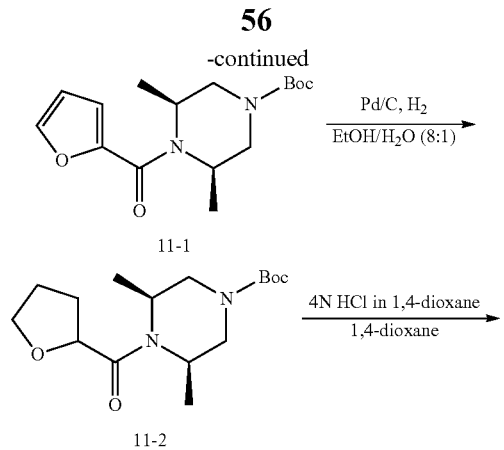

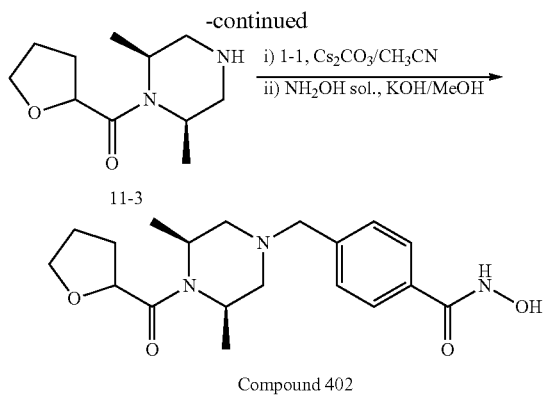

As shown in reaction scheme 11 above, compound 8-1 is reacted with furan-2-carbonyl chloride to prepare compound 11-1. The prepared compound 11-1 is hydrogenated to prepare compound 11-2, which is then Boc deprotected under an acidic condition to prepare compound 11-3. The prepared compound 11-3 is reacted with compound 1-1, and then reacted with an aqueous hydroxylamine solution and potassium hydroxide, thereby preparing compound 402.

pounds 12-2, which are then reacted with MsCl to prepare compounds 12-3. Compounds 12-3 are reacted with compound 1-2 to prepare compounds 12-4, which are deprotected under an acidic condition and reacted with 2,2-dimethyloxirane to prepare compounds 12-6. The prepared

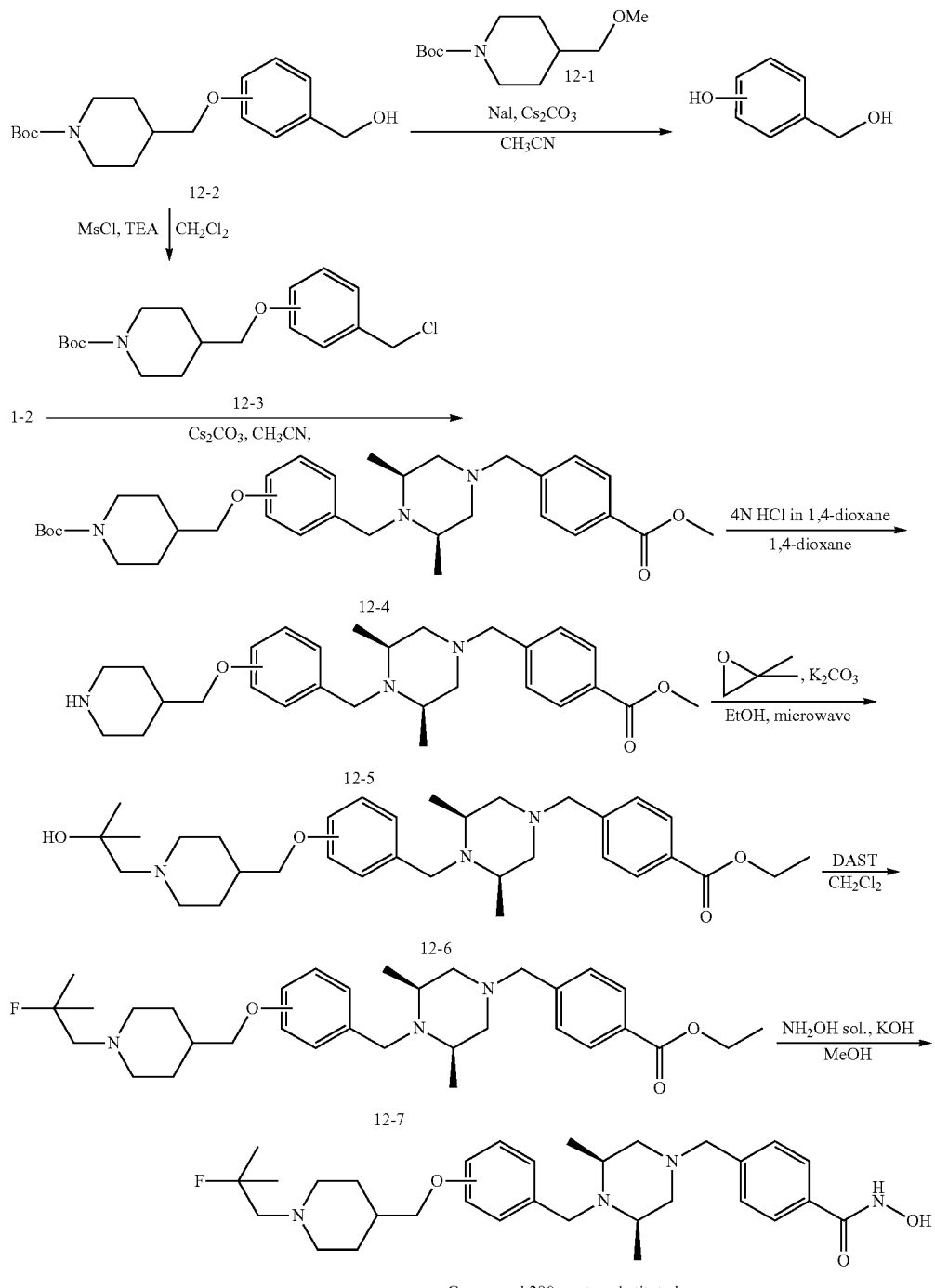

As shown in reaction scheme 12 above, 3-hydroxybenzylalcohol and 4-hydroxybenzyl alcohol are subjected to a substitution reaction with compound 12-1 to prepare compounds 12-6 are reacted with DAST to substitute the hydroxyl group with fluoride to thereby prepare compounds 12-7. Finally, the prepared compounds 12-7 are reacted with an aqueous hydroxylamine solution and potassium hydroxide, thereby preparing compounds 380 and 388.

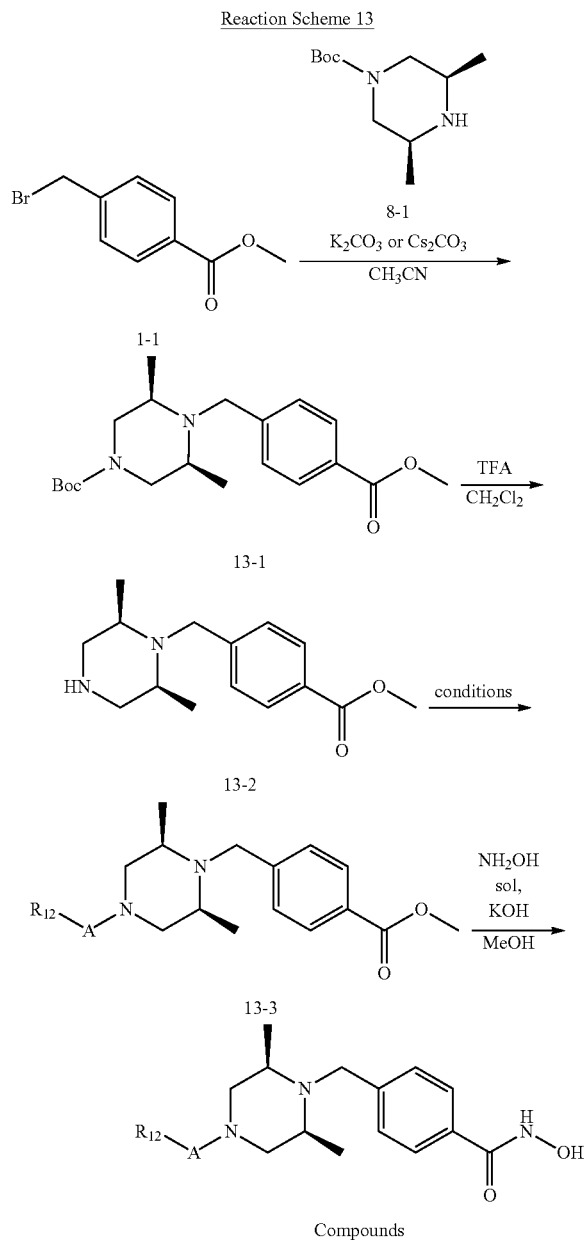

Reaction Scheme 13

Conditions:
a) R$_{12}$—CH$_2$—Br (I or —Cl), K$_2$CO$_3$ K$_2$CO$_3$ (or Cs$_2$CO$_3$)/CH$_3$CN (or DMF); b) R$_{12}$—CHO, NaCNBH$_3$, AcOH/THF or AcOH/CH$_2$ClCH$_2$Cl; c) R$_{12}$—COX, TEA/CH$_2$Cl$_2$; d) R$_{12}$CO$_2$H, HOBt, EDCI, DIPEA/CH$_2$Cl$_2$; e) R$_{12}$—NCO, TEA/CH$_2$Cl$_2$; f) R$_{12}$—NCS, TEA/CH$_2$Cl$_2$;

g) 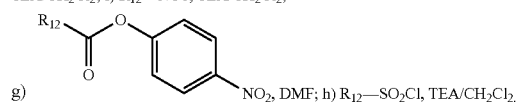 NO$_2$, DMF; h) R$_{12}$—SO$_2$Cl, TEA/CH$_2$Cl$_2$.

TABLE 10

| Compounds | A | R$_{12}$ | conditions |
|---|---|---|---|
| 80 | C=O | phenyl | c |
| 81 | CH$_2$ | phenyl | a |

TABLE 10-continued

| Compounds | A | R$_{12}$ | conditions |
|---|---|---|---|
| 103 | NH(C=O) | 2-propyl | e |
| 104 | NH(C=O) | 3-chlorophenyl | e |
| 105 | SO$_2$ | phenyl | h |
| 106 | C=O | 4-chlorophenyl | c |
| 107 | C=O | 3-chlorophenyl | c |
| 108 | C=O | 2-chlorophenyl | c |
| 109 | SO$_2$ | 4-chlorophenyl | h |
| 110 | SO$_2$ | 2-chlorophenyl | h |
| 111 | C=O | 2-pyridinyl | c |
| 112 | C=O | 3-pyridinyl | c |
| 113 | SO$_2$ | 3-pyridinyl | h |
| 114 | C=O | 2-thiophenyl | c |
| 115 | C=O | 2-furanyl | c |
| 118 | CH$_2$ | 2-chlorophenyl | a |
| 162 | NH(C=O) | phenyl | e |
| 163 | NH(C=O) | 2-methoxyphenyl | e |
| 164 | NH(C=O) | 3-methoxyphenyl | e |
| 165 | NH(C=O) | 4-methoxyphenyl | e |
| 166 | NH(C=O) | 2-methylphenyl | e |
| 167 | NH(C=O) | 3-methylphenyl | e |
| 168 | NH(C=O) | benzyl | e |
| 183 | CH$_2$ | benzyl | b |
| 185 | NH(C=O) | 1-methyl-1H-indole | e |
| 186 | NH(C=O) | 3-(1H-pyrrol-1-yl)phenyl | e |
| 187 | NH(C=O) | 2,3-dihydrobenzofuran-5-yl | e |
| 189 | C=S | 3-methylphenylamine | f |
| 196 | NCH$_3$(C=O) | phenyl | g |
| 197 | C=O | indoline | g |
| 215 | CH$_2$ | 2,4,5-trifluorophenyl | a |
| 220 | CH(CH$_3$) | phenyl | a |
| 230 | NH(C=O) | 3-methoxybenzyl | g |
| 231 | NH(C=O) | 3-fluorobenzyl | g |
| 233 | C=O | 3-chlorobenzyl | d |
| 256 | CH$_2$ | (3-pyrrole)phenyl | a |
| 268 | CH$_2$ | naphthalen-2-yl | a |
| 271 | CH$_2$ | isobutyl | a |
| 273 | CH(CH$_3$) | methyl | a |
| 274 | CH$_2$ | propyl | a |
| 298 | CH$_2$ | 3-trifluoromethylphenyl | b |
| 299 | CH$_2$ | 4-(N,N-dimethylamino)phenyl | b |
| 300 | CH$_2$ | 4-(methylsulfonyl)phenyl | b |
| 301 | CH$_2$ | 4-(1H-imidazol-1-yl)phenyl | b |
| 302 | CH$_2$ | 4-(thiophen-2-yl)phenyl | b |
| 303 | CH$_2$ | 4-(furan-2-yl)phenyl | b |
| 304 | CH$_2$ | 4-(4H-1,2,4-triazol-4-yl)phenyl | b |
| 305 | CH$_2$ | 2-(2-methyl-1H-imidazol-1-yl)phenyl | b |

As shown in reaction scheme 13 above, compound 8-1 and compound 1-1 are subjected to an alkylation reaction to prepare compound 13-1, which is then deprotected under an acidic condition to prepare compound 13-2. The prepared compound 13-2 is subjected to an alkylation reaction, an acylation reaction or a reductive amination reaction under conditions a) to h), thereby preparing compounds 13-3. Finally, the prepared compounds 13-3 are reacted with an aqueous hydroxylamine solution and potassium hydroxide, thereby preparing compounds 80, 81, 103, 104, 105, 106, 107, 108, 109, 110, 111, 112, 113, 114, 115, 118, 162, 163, 164, 165, 166, 167, 168, 183, 185, 186, 187, 189, 196, 197, 215, 220, 230, 231, 233, 256, 268, 271, 273, 274, 298, 299, 300, 301, 302, 303, 304 and 305.

Reaction Scheme 14

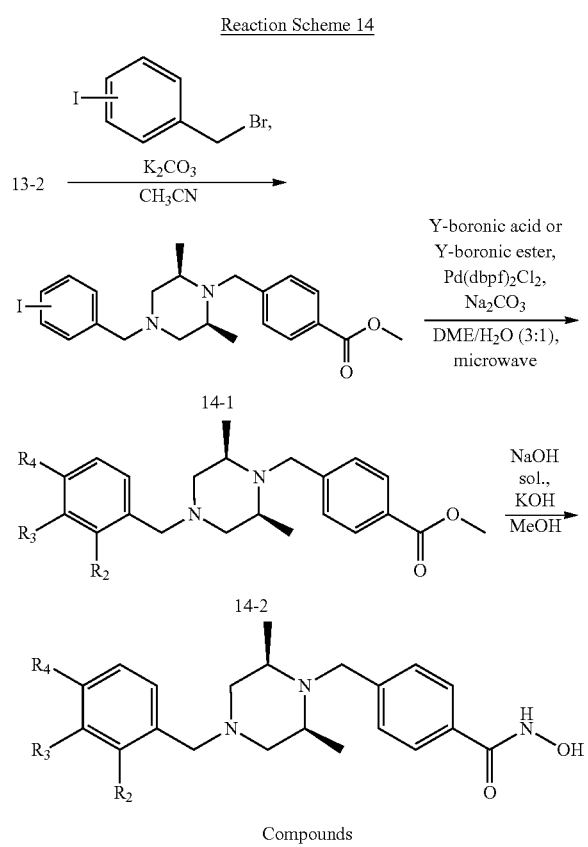

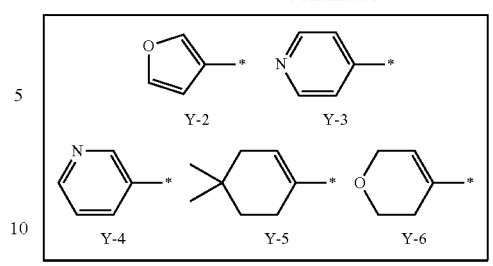

TABLE 11

| Compounds | $R_2$ | $R_3$ | $R_4$ |
|---|---|---|---|
| 348 | Y-2 | H | H |
| 349 | Y-4 | H | H |
| 350 | Y-3 | H | H |
| 351 | Y-6 | H | H |
| 352 | Y-5 | H | H |
| 396 | H | Y-2 | H |
| 400 | H | H | Y-5 |
| 401 | H | H | Y-6 |

As shown in reaction scheme 14 above, compound 13-2 is subjected to an alkylation reaction to prepare compound 14-1, which is then subjected to a Suzuki reaction with a boronic acid boronic ester containing each of Y-2 to Y-6, thereby preparing compounds 14-2. Finally, the prepared compounds 14-2 are reacted with an aqueous hydroxylamine solution and potassium hydroxide, thereby preparing compounds 348, 349, 350, 351, 352, 396, 400 and 401.

Reaction Scheme 15

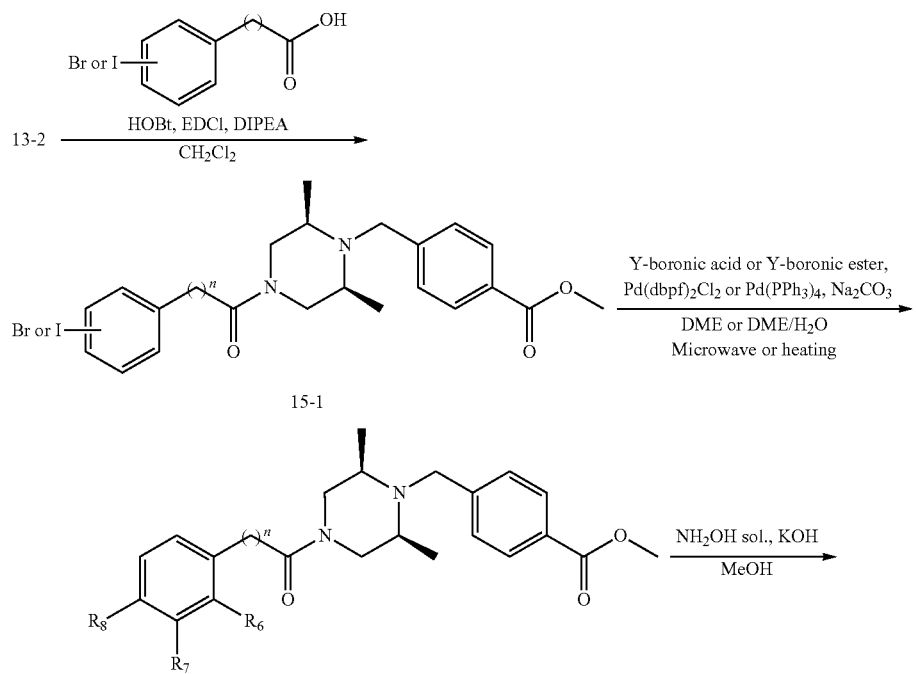

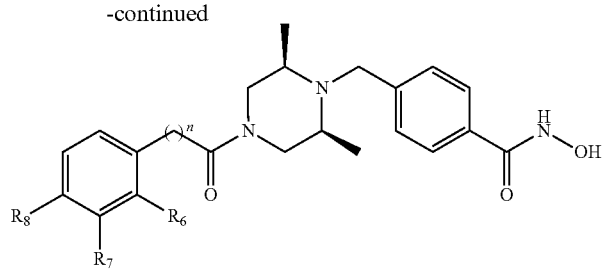

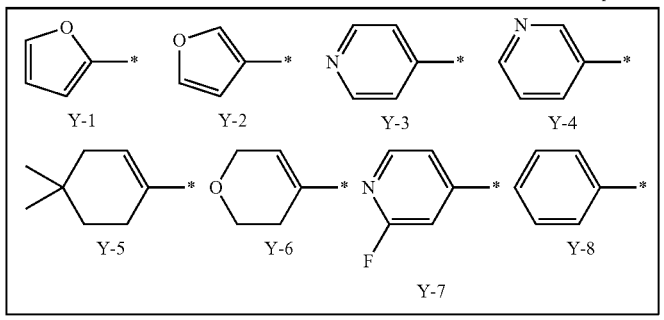

TABLE 12

| Compounds | n | R$_6$ | R$_7$ | R$_8$ |
|---|---|---|---|---|
| 250 | 1 | H | Y-8 | H |
| 251 | 1 | H | Y-3 | H |
| 252 | 1 | H | Y-6 | H |
| 253 | 1 | H | Y-5 | H |
| 257 | 0 | H | Y-1 | H |
| 258 | 0 | H | Y-2 | H |
| 259 | 0 | H | Y-6 | H |
| 260 | 0 | H | Y-3 | H |
| 261 | 0 | H | Y-4 | H |
| 262 | 0 | H | Y-7 | H |
| 263 | 0 | H | Y-5 | H |
| 276 | 0 | Y-1 | H | H |
| 277 | 0 | Y-2 | H | H |
| 278 | 0 | Y-6 | H | H |
| 279 | 0 | Y-4 | H | H |
| 280 | 0 | Y-5 | H | H |

As shown in reaction scheme 15 above, compound 13-2 is subjected to an amide coupling reaction with 2-, 3-, 4-iodobenzoic acid or 2-(3-bromophenyl)acetic acid to prepare compound 15-1, which is then subjected to a Suzuki reaction with a boronic acid or boronic ester containing each of Y-1 to Y-8, thereby preparing compounds 15-2. Finally, the prepared compounds 15-2 are reacted with an aqueous hydroxylamine solution and potassium hydroxide, thereby preparing compounds 250, 251, 252, 253, 257, 258, 259, 260, 261, 262, 263, 276, 277, 278, 279 and 280.

Reaction Scheme 16

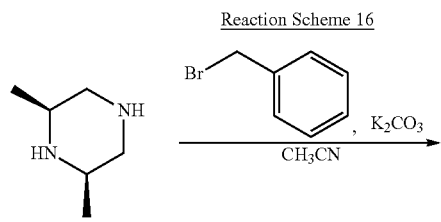

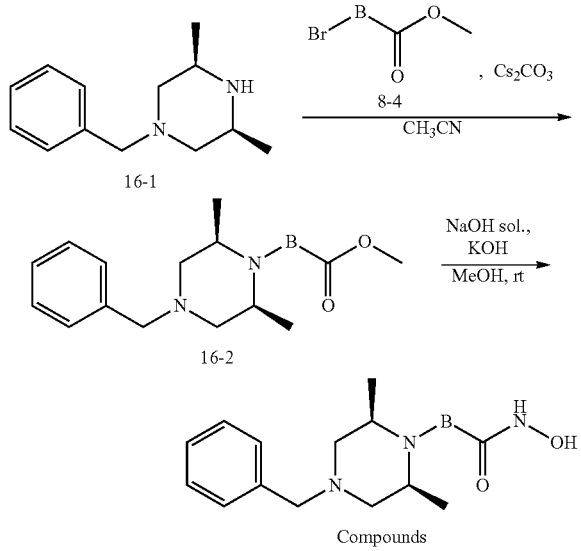

TABLE 13

| Compounds | B |
|---|---|
| 174 | |
| 175 | |

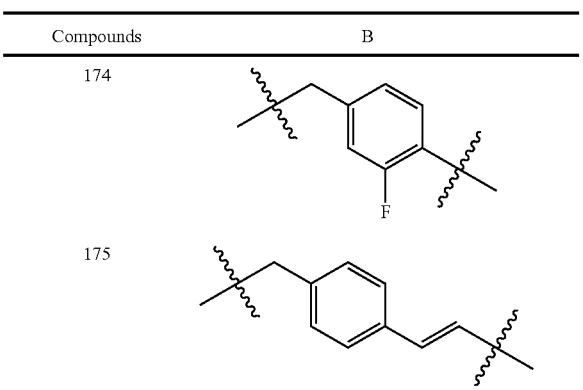

TABLE 13-continued

| Compounds | B |
|---|---|
| 176 | 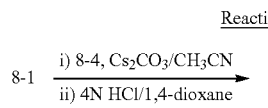 |
| 195 | (pyridine linker structure) |

As shown in reaction scheme 16 above, (2S,6R)-2,6-dimethylpiperazine is reacted with benzyl bromide to introduce a benzyl group therein to thereby prepare compound 16-1, which is then subjected to an alkylation reaction with compound 8-4, thereby preparing compounds 16-2. Finally, the prepared compounds 16-2 are reacted with an aqueous hydroxylamine solution and potassium hydroxide, thereby preparing compounds 174, 175, 176 and 195.

Reaction Scheme 17

8-1 $\xrightarrow{\text{i) 8-4, Cs}_2\text{CO}_3\text{/CH}_3\text{CN}}_{\text{ii) 4N HCl/1,4-dioxane}}$

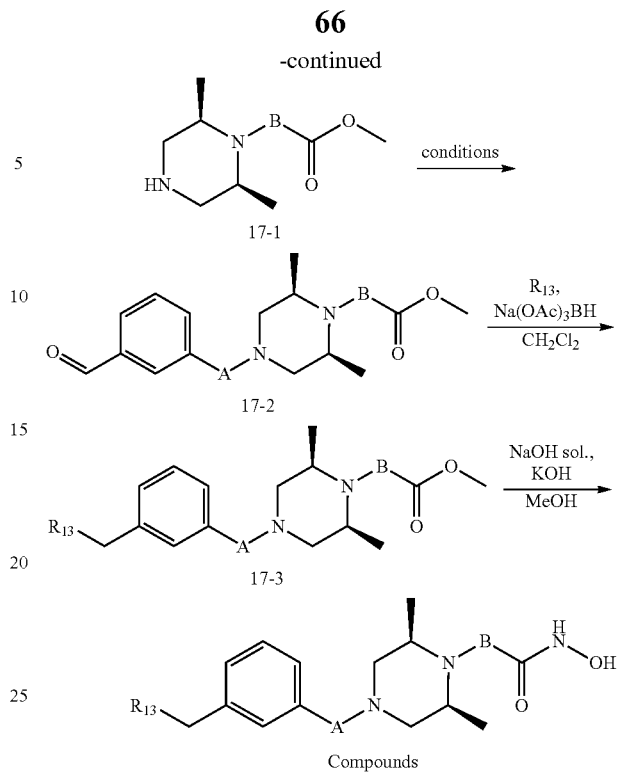

Conditions: a) (3-bromomethyl)benzaldehyde, $Cs_2CO_3/CH_3CN$; b) 3-formylbenzoic acid, HOBt, EDCI, DIPEA/$CH_2Cl_2$.

TABLE 14

| Compounds | A | B | $R_{13}$ | conditions |
|---|---|---|---|---|
| 475 | $CH_2$ | (4-substituted phenyl with vinyl) | pyrrolidine | a |
| 476 | $CH_2$ | (4-substituted phenyl with vinyl) | diethylamine | a |
| 478 | $CH_2$ | (4-substituted phenyl) | diethylamine | a |
| 479 | $CH_2$ | (4-substituted phenyl) | pyrrolidine | a |

TABLE 14-continued

| Compounds | A | B | R13 | conditions |
|---|---|---|---|---|
| 480 | C=O | (benzyl-styryl linker) | pyrrolidine | b |
| 487 | C=O | (benzyl-styryl linker) | diethylamine | b |

As shown in reaction scheme 17 above, compound 8-1 is subjected to an alkylation reaction with compound 8-4 and deprotected under an acidic condition, thereby preparing compound 17-1. The prepared compound 17-1 is subjected to an alkylation reaction or an amide coupling reaction under conditions a) or b) to prepare compounds 17-2, which are then subjected to a reductive amination reaction with pyrrolidine or diethylamine, thereby preparing compounds 17-3. Finally, the prepared compounds 17-3 are reacted with an aqueous hydroxylamine solution and potassium hydroxide, thereby preparing compounds 475, 476, 478, 479, 480 and 487.

Reaction Scheme 18

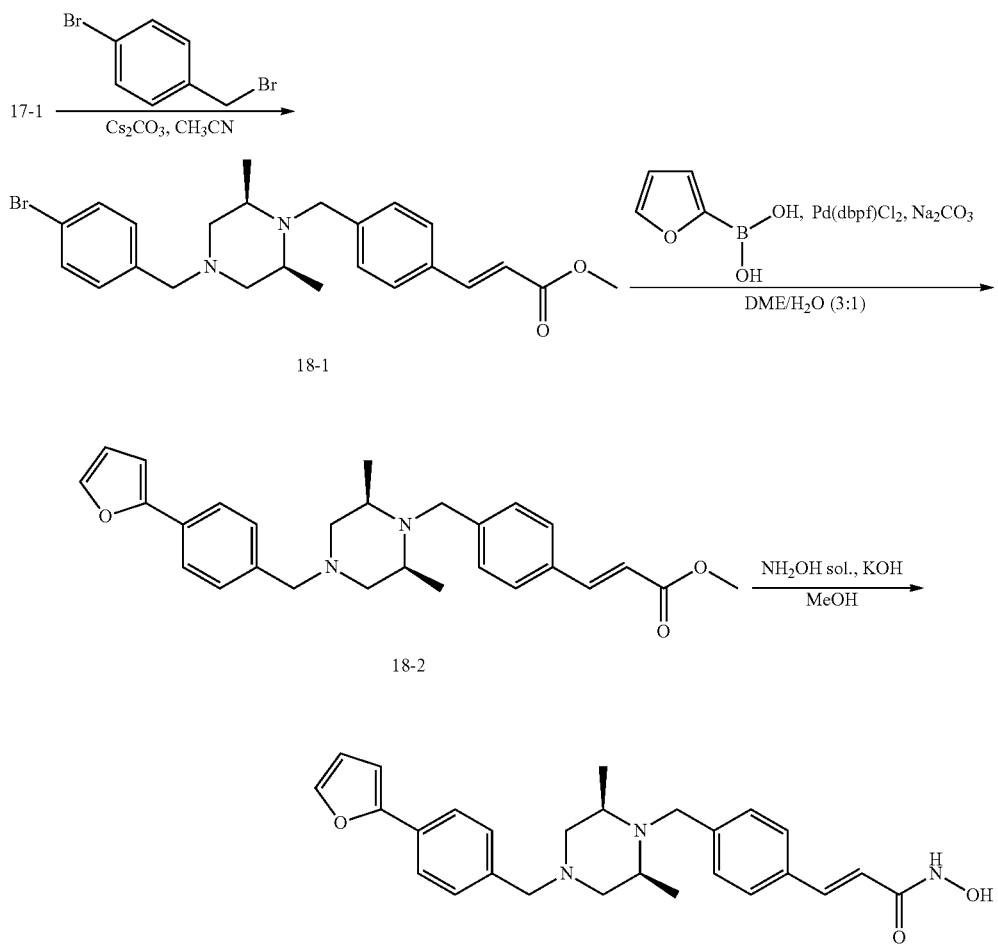

Compound 477

As shown in reaction scheme 18 above, compound 17-1 is subjected to an alkylation reaction with 4-bromobenzyl bromide to prepare compound 18-1, which is then subjected to a Suzuki reaction with furan-2-yl bornic acid, thereby preparing compound 18-2. Finally, the prepared compound 18-2 is reacted with an aqueous hydroxylamine solution and potassium hydroxide, thereby preparing compound 477.

Reaction Scheme 19

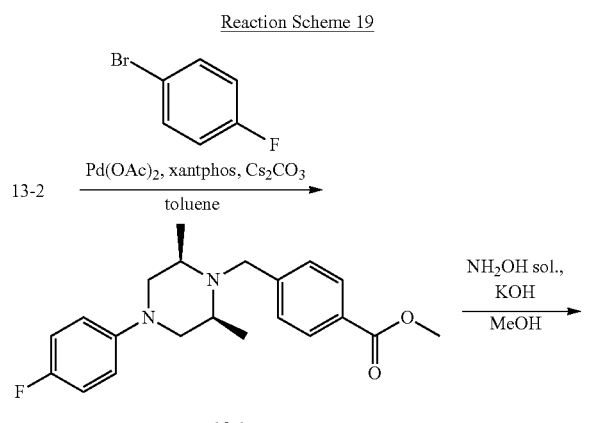

Compound 119

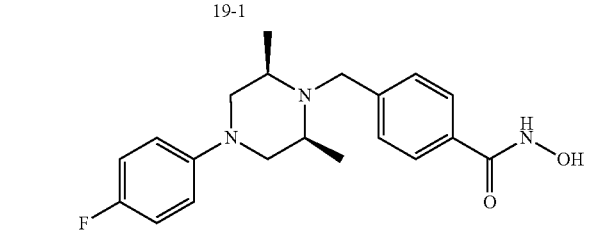

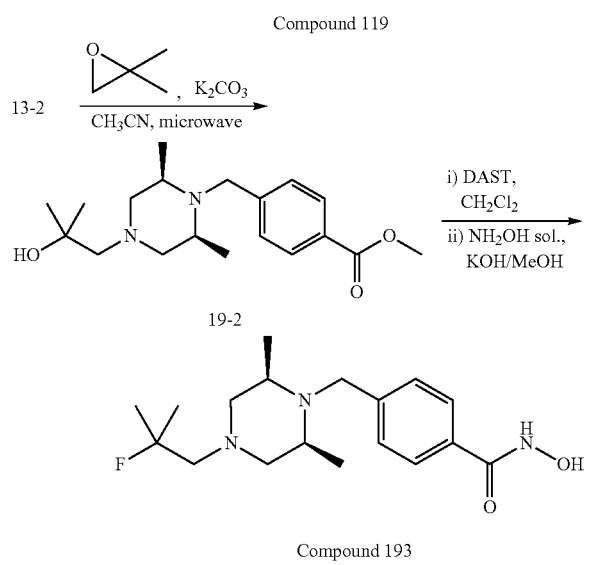

Compound 193

As shown in reaction scheme 19 above, compound 13-2 is subjected to a Buchwald reaction with 1-bromo-4-fluorobenzene to prepare compound 19-1, which is then reacted with an aqueous hydroxylamine solution and potassium hydroxide, thereby preparing compound 119.

Alternatively, compound 13-2 is reacted with 2,2-dimethyloxirane to prepare compound 19-2, which is then reacted with DAST to substitute the hydroxyl group with fluoride and then reacted with an aqueous hydroxylamine solution and potassium hydroxide, thereby preparing compound 193.

Reaction Scheme 20

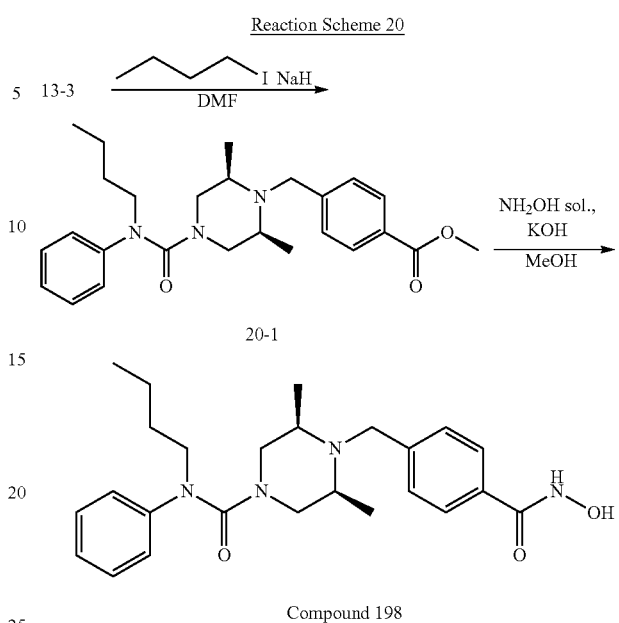

Compound 198

As shown in reaction scheme 20 above, compound 13-3 is subjected to an alkylation reaction with butyl iodide to prepare compound 20-1, which is then reacted with an aqueous hydroxylamine solution and potassium hydroxide, thereby preparing compound 198.

Reaction Scheme 21

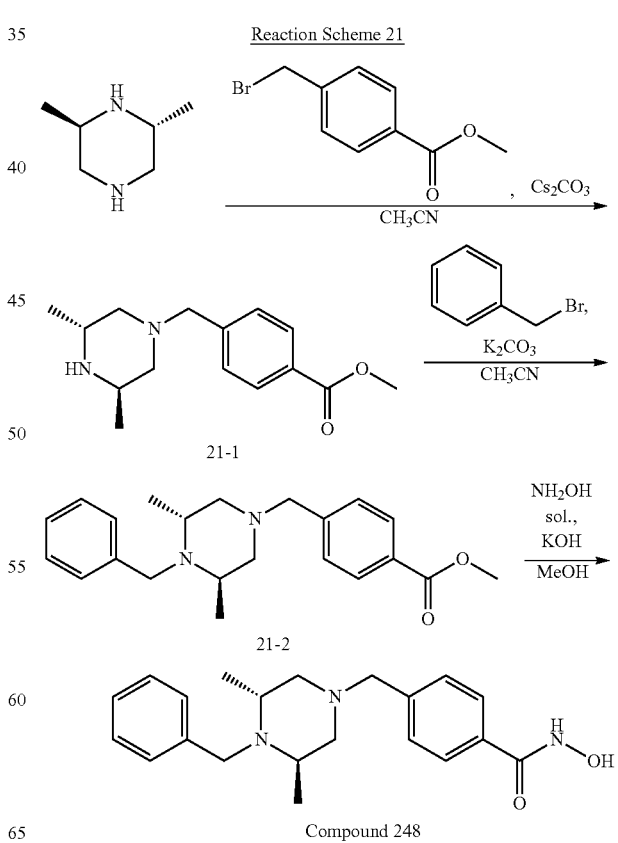

Compound 248

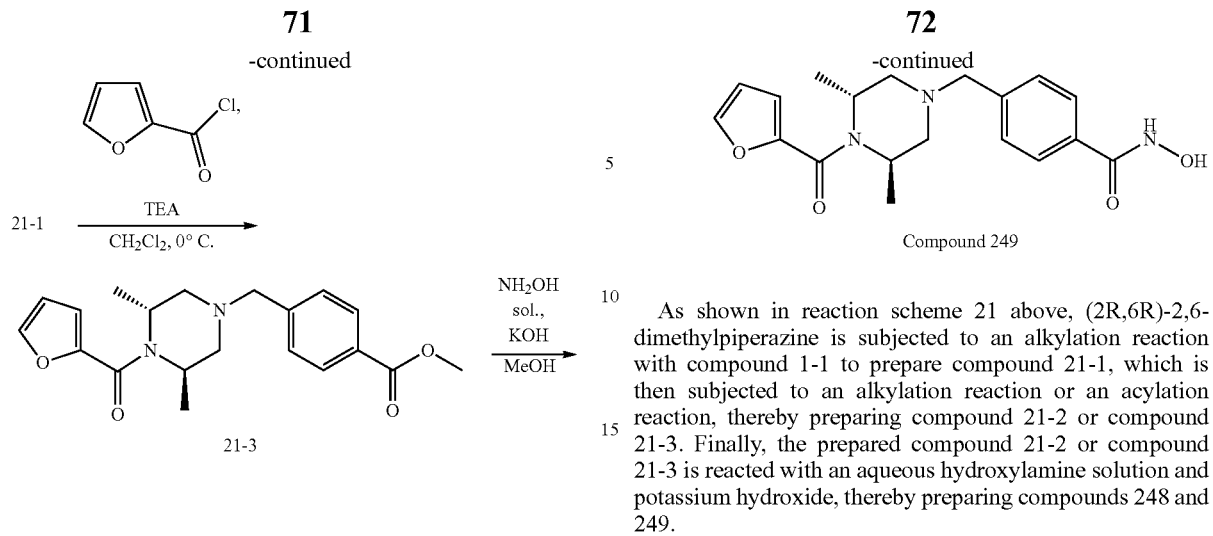

As shown in reaction scheme 21 above, (2R,6R)-2,6-dimethylpiperazine is subjected to an alkylation reaction with compound 1-1 to prepare compound 21-1, which is then subjected to an alkylation reaction or an acylation reaction, thereby preparing compound 21-2 or compound 21-3. Finally, the prepared compound 21-2 or compound 21-3 is reacted with an aqueous hydroxylamine solution and potassium hydroxide, thereby preparing compounds 248 and 249.

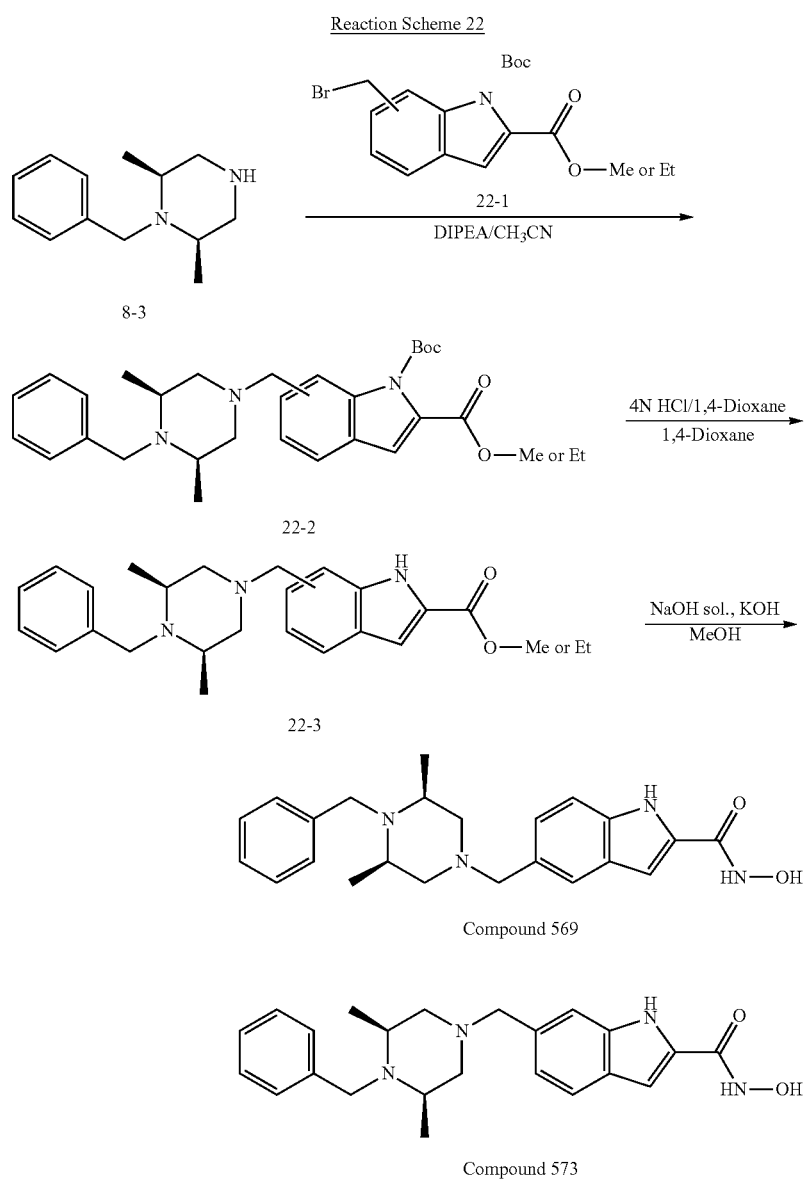

As shown in reaction scheme 22 above, (2S,6R)-1-benzyl-2,6-dimethylpiperazine is subjected to an alkylation reaction with compound 8-3 and compound 22-1 to prepare compounds 22-2, which are then deprotected to remove the tert-butyloxycarbonyl group, thereby preparing compounds 22-3. Finally, compounds 22-3 are reacted with an aqueous hydroxylamine solution and potassium hydroxide, thereby preparing compounds 569 and 573.

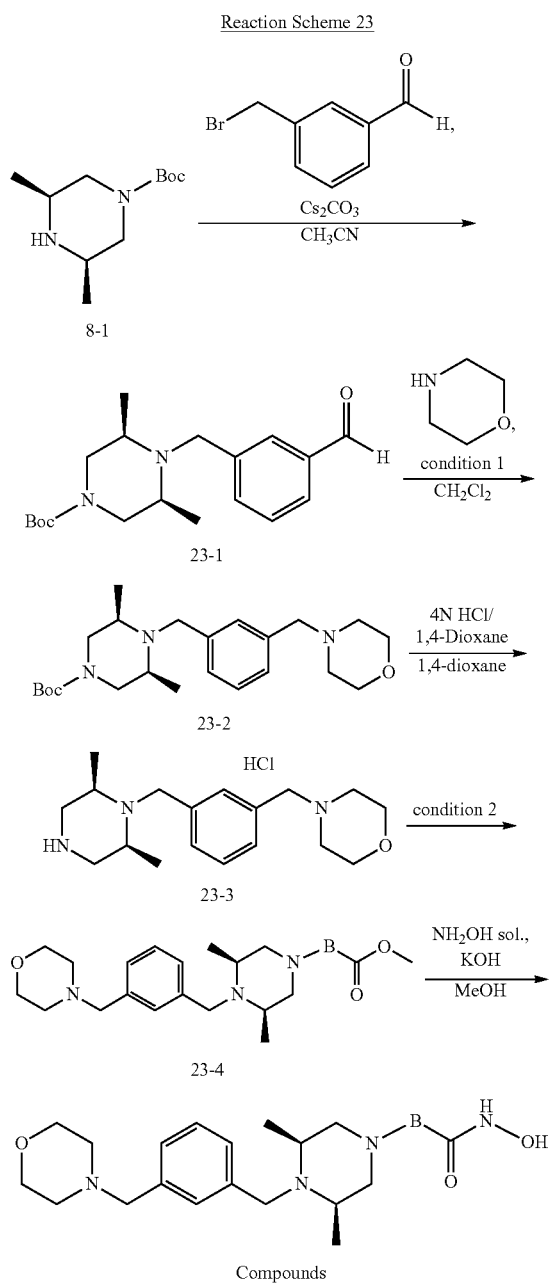

Conditions:
a) Br-B-C(=O)-O- (8-4), TEA/CH₃CN; b) OHC-B-C(=O)-O- (8-4), reducing agent/CH₂Cl₂.

TABLE 15

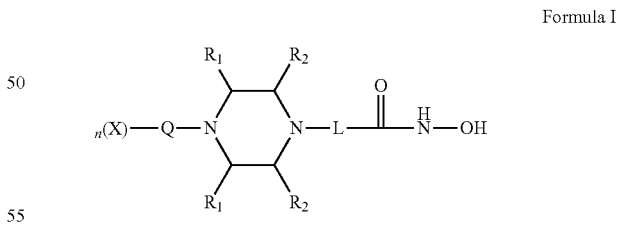

| Compounds | B | Condition 1 | Condition 2 |
|---|---|---|---|
| 609 | (pyridyl linker) | NaCNBH₃/AcOH | b (NaCNBH₃) |
| 653 | (hydroxyphenyl linker) | NaBH(OAc)₃ | a |
| 696 | (fluorophenyl linker) | NaBH(OAc)₃ | a |

As shown in reaction scheme 23 above, compound 8-1 is subjected to an alkylation reaction to prepare compound 23-1, which is then subjected to a reductive amination reaction with morpholine to prepare compound 23-2, which is then deprotected to remove the tert-butyloxycarbonyl group, thereby preparing compound 23-3. Compound 23-3 is subjected to an alkylation reaction with compound 8-4 to prepare compounds 23-4. Finally, the prepared compounds 23-4 are reacted with an aqueous hydroxylamine solution and potassium hydroxide, thereby preparing compounds 609, 653 and 696.

Compositions Comprising Novel Compounds Having HDAC6 Inhibitory Activity, the Use Thereof and the Method of Treating Diseases The present invention provides a pharmaceutical composition for preventing or treating histone deacetylase 6 (HDAC6) activity-associated diseases, which contains, as an active ingredient, a compound represented by the following formula I, an isomer thereof or a pharmaceutically acceptable salt thereof:

Formula I $n(X)-Q-N(R_1)(R_2)-N-L-C(=O)-N(H)-OH$ (piperazine ring with $R_1, R_2$ substituents)

wherein L, $R_1$, $R_2$, Q, X and n are as defined above.

The pharmaceutical composition according to the present invention exhibits a remarkable effect on the prevention or treatment of histone deacetylase 6 (HDAC6) activity-associated diseases by selectively inhibiting histone deacetylase 6 (HDAC6).

Histone deacetylase 6 (HDAC6) activity-associated diseases include cancer, inflammatory diseases, autoimmune diseases, neurological diseases and neurodegenerative disorders. Specifically, these histone deacetylase 6 (HDAC6) activity-associated diseases include lung cancer, colon cancer, breast cancer, prostate cancer, liver cancer, brain cancer, ovarian cancer, stomach cancer, skin cancer, pancreatic cancer, glioma, glioblastoma, leukaemia, lymphoma, multiple myeloma, solid cancer, Wilson's disease, Spinocerebellar ataxia, prion disease, Parkinson's disease, Huntington's disease, amyotrophic lateral sclerosis, amyloidosis, Alzheimer's disease, alcoholic liver disease, spinal muscular atrophy, rheumatoid arthritis, and osteoarthritis, as well as disorders or diseases associated with the abnormal function of histone deacetylase.

In an embodiment, the compound represented by formula I according to the present invention may be a compound represented by formula II or formula III. In another embodiment, the compound represented by formula I according to the present invention may be any one of the compounds represented by formula I-1 to I-23. In still another embodiment, the compound represented by formula I according to the present invention may be any one of compounds 080 to 824.

The pharmaceutically acceptable salt is as described above with respect to a pharmaceutically acceptable salt of the compound represented by formula I according to the present invention.

For administration, the pharmaceutical composition according to the present invention may further contain at least one pharmaceutically acceptable carrier in addition to the compound of formula I, an isomer thereof or a pharmaceutically acceptable salt thereof. The pharmaceutically acceptable carrier that is used in the present invention may be at least one of physiological saline, sterile water, Ringer solution, buffered saline, dextrose solution, maltodextrin solution, glycerol, ethanol, and a mixture of two or more thereof. If necessary, the composition may contain other conventional additives such as an antioxidant, a buffer or a bacteriostatic agent. In addition, the composition can be formulated into injectable formulations such as solutions, suspensions, turbid fluid, etc, pills, capsules, granules and tablets using a diluent, a dispersing agent, a surfactant, a binder and a lubricant. Thus, the composition of the present invention may be in the form of patches, liquids, pills, capsules, granules, tablets, suppositories, etc. These formulations can be prepared either by conventional methods that are used for formulation in the art or by the method disclosed in Remington's Pharmaceutical Science (the latest edition), Mack Publishing Company, Easton Pa. In addition, the composition of the present invention can be prepared as various formulations depending on diseases or components.

The composition of the present invention may be administered orally or parenterally (e.g., intravenously, subcutaneously, intraperitoneally or topically) depending on the intended use. The dose of the pharmaceutical composition varies depending on the patient's weight, age, sex, health conditions, diet, the time of administration, the mode of administration, excretion rate, the severity of the disease, and the like.

The pharmaceutical composition of the present invention may further contain, in addition to the compound represented by formula I, an isomer thereof or a pharmaceutically acceptable salt thereof, one or more active ingredients that exhibit medical efficacy identical or similar thereto.

The present invention provides a method for preventing or treating histone deacetylase 6 activity-associated diseases, which comprises administering a therapeutically effective amount of the compound represented by formula I, an isomer thereof or a pharmaceutically acceptable salt thereof.

As used herein, the term "therapeutically effective amount" refers to the amount of the compound represented by formula I, which is effective for the prevention or treatment of histone deacetylase 6 activity-associated diseases.

The present invention also provides a method of selectively inhibiting HDAC6, which comprises administering the compound of formula I, an isomer thereof or a pharmaceutically acceptable salt thereof to mammals including humans.

The method of preventing or treating histone deacetylase 6 activity-associated disease according to the present invention includes inhibiting or averting the disease as well as addressing the disease itself, prior to the onset of symptoms by administering the compound represented by formula I. In the management of diseases, the magnitude of a prophylactic or therapeutic dose of a particular active ingredient will vary with the nature and severity of the disease or condition, and may also vary according to the route by which the active ingredient is administered. The dose and the dose frequency will also vary according to the age, body weight, and response of the individual patient. Suitable dosing regimens can be readily selected by those skilled in the art with due consideration of such factors. In addition, the method of preventing or treating histone deacetylase 6 activity-associated disease according to the present invention may further comprise administering a therapeutically effective amount of an additional active agent helpful for the treatment of the disease together with the compound represented by formula I, in which the additional active agent can exhibit a synergistic effect with the compound of formula I or an assistant effect.

The present invention is also intended to provide the use of the compound represented by formula I, an isomer thereof or a pharmaceutically acceptable salt thereof, for the preparation of a medicament for treating histone deacetylase 6 activity-associated disease. For the preparation of the medicament, the compound represented by formula I may be mixed with a pharmaceutically acceptable adjuvant, diluent, carrier or the like, and combined with other active agents such that the active ingredients can have synergistic effects.

The particulars mentioned in the use, composition and treatment method of the present invention may be appropriately combined unless contradictory to one another.

Advantageous Effects

The compounds represented by formula I, isomers thereof or pharmaceutically acceptable salts thereof can selectively inhibit HDAC6, and thus exhibit excellent effects on the prevention or treatment of histone deacetylase 6 activity-associated diseases.

MODE FOR INVENTION

Hereinafter, the present invention will be described in further detail with reference to Examples, Preparation Examples and Experimental Examples. It is to be understood, however, that these examples are for illustrative purposes only and are not intended to limit the scope of the present invention.

Preparation of Novel Dimethylpiperazine Derivative Compounds

Specific methods for preparing the compounds of formula I are as follows.

Example 1

Synthesis of Compound 80

(4-(((2S,6R)-4-benzoyl-2,6-dimethylpiperazin-1-yl)methyl)-N-hydroxybenzamide)

Step 1: Synthesis of Methyl 4-(((2S,6R)-4-benzoyl-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol) was dissolved in methylene chloride (3 mL), and then benzoyl chloride (0.049 mL, 0.420 mmol) and TEA (0.106 mL, 0.763 mmol) were added thereto. The mixture was stirred at 0° C. for 1 hour, and saturated sodium hydrogen carbonate was added to the reaction mixture, followed by extraction with methylene chloride. The organic layer was separated and concentrated under reduced pressure. The concentrate was purified by column chromatography (silicon dioxide; methanol/methylene chloride=5%) and concentrated to afford the desired compound (0.124 g, 88.7%) as a pale yellow oil.

Step 2: Synthesis of Compound 80

Methyl 4-(((2S,6R)-4-benzoyl-2,6-dimethylpiperazin-1-yl)methyl)benzoate (formula 13-3, 0.060 g, 0.164 mmol) was dissolved in methanol (1 mL), and then hydroxylamine (0.2 mL, 3.275 mmol, 50.00% aqueous solution) and potassium hydroxide (0.091 g, 1.637 mmol) were added thereto. The mixture was stirred at room temperature for 20 minutes, and saturated sodium hydrogen carbonate was added to the reaction mixture, followed by extraction with ethyl acetate. The organic layer was concentrated under reduced pressure to afford compound 80 (0.045 g, 74.8%) as a white solid.

$^1$H NMR (400 MHz, DMSO-$d_6$) δ 7.68 (d, 2 H, J=8.2 Hz), 7.46-7.39 (m, 5 H), 7.34 (d, 2 H, J=8.8 Hz), 3.67 (s, 2 H), 3.17 (s, 2 H), 2.69-2.61 (m, 2 H), 2.60-2.57 (m, 2 H), 1.82-1.76 (m, 2 H), 0.83 (d, 6 H, J=6.12 Hz); LRMS (ES) m/z 368.0 (M$^+$+1).

Example 2

Synthesis of Compound 81

(4-(((2S,6R)-4-benzyl-2,6-dimethylpiperazin-1-yl)methyl)-N-hydroxybenzamide)

Step 1: Synthesis of Methyl 4-(((2S,6R)-4-benzyl-2,6-dimethylpiperazin-1-yl)methyl)benzoate Methyl 4-(((2S,6R)-2,6-dimethylpiperazin-1-yl)methyl)benzoate (formula 13-2, 0.050 g, 0.191 mmol) was dissolved in acetonitrile (2 mL), and then benzyl bromide (0.023 mL, 0.210 mmol) and K$_2$CO$_3$ (0.053 g, 0.381 mmol) were added thereto. The mixture was heated and stirred at 80° C. for 1 hour, and then concentrated under reduced pressure. The concentrate was purified by column chromatography (silicon dioxide; ethyl acetate/hexane=30%) and concentrated to afford the desired compound (0.022 g, 32.8%) as a colorless oil.

Step 2: Synthesis of Compound 81

Methyl 4-(((2S,6R)-4-benzyl-2,6-dimethylpiperazin-1-yl)methyl)benzoate (formula 13-3, 0.022 g, 0.062 mmol) was dissolved in methanol (2 mL), and then hydroxylamine (0.023 mL, 0.210 mmol, 50.00% aqueous solution) and potassium hydroxide (0.053 g, 0.381 mmol) were added thereto. The mixture was stirred at room temperature for 20 minutes, and water was added to the reaction mixture, followed by extraction with ethyl acetate. The organic layer was washed with a saturated aqueous solution of sodium chloride, dried with anhydrous sodium sulfate, and then concentrated under reduced pressure. Compound 81 (0.003 g, 13.6%) was obtained as a white solid.

$^1$H NMR (400 MHz, DMSO-$d_6$) δ 7.65 (d, 2 H, J=8.1 Hz), 7.34-7.23 (m, 7 H), 3.73 (s, 2 H), 3.39 (s, 2 H), 2.64 (d, 2 H, J=10.4 Hz), 2.56-2.54 (m, 2 H), 1.79 (t, 2 H, J=10.6 Hz), 0.88 (d, 6 H, J=6.1 Hz); LRMS (ES) m/z 354.2 (M$^+$+1).

Example 3

Synthesis of Compound 82

(4-(((3R,5S)-4-acetyl-3,5-dimethylpiperazin-1-yl)methyl)-N-hydroxybenzamide)

Step 1: Synthesis of Methyl 4-(((3R,5S)-4-acetyl-3,5-dimethylpiperazin-1-yl)methyl)benzoate Methyl 4-(((3R,5S)-3,5-dimethylpiperazin-1-yl)methyl)benzoate (formula 1-2, 0.100 g, 0.381 mmol) was dissolved in methylene chloride (2 mL), and then acetic anhydride (0.072 mL, 0.763 mmol) and TEA (0.266 mL, 1.907 mmol) were added thereto. The mixture was stirred at 0° C. for 1 hour, and saturated sodium hydrogen carbonate was added thereto, followed by extraction with methylene chloride. The organic layer was dried with anhydrous magnesium sulfate, and then concentrated under reduced pressure to afford the desired compound (0.115 g, 99.1%) as a white solid.

Step 2: Synthesis of Compound 82

Methyl 4-(((3R,5S)-4-acetyl-3,5-dimethylpiperazin-1-yl)methyl)benzoate (formula 1-3, 0.052 g, 0.171 mmol) was dissolved in methanol (0.5 mL), and then hydroxylamine (0.209 mL, 3.417 mmol, 50.00% aqueous solution) and potassium hydroxide (0.096 g, 1.708 mmol) were added thereto. The mixture was stirred at room temperature for 20 minutes, and then concentrated under reduced pressure. Saturated sodium hydrogen carbonate was added to the concentrate, followed by extraction with ethyl acetate. The organic layer was dried with anhydrous sodium sulfate, and then concentrated under reduced pressure. The concentrate was purified by PTLC (100% ethylacetate) to afford the desired compound 82 (0.016 g, 30.7%) as a white solid.

$^1$H NMR (400 MHz, CD$_3$OD) δ 7.73 (d, 2 H, J=8.3 Hz), 7.50 (d, 2 H, J=8.3 Hz), 4.51-4.50 (m, 1 H), 4.11-4.10 (m, 1 H), 3.57 (s, 2 H), 2.71 (d, 2 H, J=11.5 Hz), 2.21-2.20 (m, 2 H), 2.11 (s, 3 H), 1.40-1.38 (m, 6 H); LRMS (ES) m/z 306.2 (M$^+$+1).

Example 4

Synthesis of Compound 83

(4-(((3R,5S)-4-benzoyl-3,5-dimethylpiperazin-1-yl)methyl)-N-hydroxybenzamide)

Step 1: Synthesis of Methyl 4-(((3R,5S)-4-benzoyl-3,5-dimethylpiperazin-1-yl)methyl)benzoate Methyl 4-(((3R,5S)-3,5-dimethylpiperazin-1-yl)methyl)benzoate (formula 1-2, 0.100 g, 0.381 mmol) was dissolved in methylene chloride (3 mL), and then benzoyl chloride (0.049 mL, 0.420 mmol) and TEA (0.106 mL, 0.763 mmol) were added thereto. The mixture was stirred at 0° C. for 1 hour, and saturated sodium hydrogen carbonate was added to the reaction mixture, followed by methylene chloride. The organic layer was separated and concentrated under reduced pressure. The concentrate was purified by column chromatography (silicon dioxide; ethyl acetate/hexane=30%) and concentrated to afford the desired compound (0.124 g, 88.7%) as a pale yellow oil.

Step 2: Synthesis of Compound 83

Methyl 4-(((3R,5S)-4-benzoyl-3,5-dimethylpiperazin-1-yl)methyl)benzoate (formula 1-3, 0.060 g, 0.164 mmol) was dissolved in methanol (1 mL), and then hydroxylamine (0.2 mL, 3.275 mmol, 50.00% aqueous solution) and potassium hydroxide (0.091 g, 1.637 mmol) were added thereto. The mixture was stirred at room temperature for 20 minutes, and saturated sodium hydrogen carbonate was added to the reaction mixture, followed by extraction with ethyl acetate. The organic layer was concentrated under reduced pressure to yield compound 83 (0.045 g, 74.8%) as a white solid.
$^1$H NMR (400 MHz, CD$_3$OD) δ 7.72 (d, 2 H, J=8.3 Hz), 7.49 (d, 2 H, J=8.2 Hz), 7.46-7.44 (m, 3 H), 7.36-7.34 (m, 2 H), 3.59 (s, 2 H), 2.71 (d, 2 H, J=10.7 Hz), 2.26 (dd, 2 H, J=10.2, 3.6 Hz), 1.39 (d, 6 H, J=6.7 Hz).

Example 5

Synthesis of Compound 84

(4-(((3R,5S)-4-benzyl-3,5-dimethylpiperazin-1-yl)methyl)-N-hydroxybenzamide)

Step 1: Synthesis of Methyl 4-(((3R,5S)-3,5-dimethylpiperazin-1-yl)methyl)benzoate (2S,6R)-2,6-dimethylpiperazine (50.000 g, 437.867 mmol) and Cs$_2$CO$_3$ (171.199 g, 525.440 mmol) were dissolved in acetonitrile (200 mL) at 0° C., and methyl 4-(bromomethyl)benzoate (formula 1-1, 80.242 g, 350.293 mmol) was added to the solution, followed by stirring at room temperature for 5 hours. The reaction mixture was filtered through a glass filter to remove solids, and the filtrate was concentrated under reduced pressure to remove the solvent. Water was added to the concentrate, followed by extraction with ethyl acetate. The organic layer was washed with a saturated aqueous solution of sodium chloride, dried with anhydrous magnesium sulfate, filtered, and concentrated under reduced pressure. Hexane (100 mL) was added to the concentrate and stirred, and the precipitated solid was filtered, washed with hexane, and dried to yield the desired compound (85.200 g, 74.2%) as a white solid.

Step 2: Synthesis of Methyl 4-(((3R,5S)-4-benzyl-3,5-dimethylpiperazin-1-yl)methyl)benzoate Methyl 4-(((3R,5S)-3,5-dimethylpiperazin-1-yl)methyl)benzoate (formula 1-2, 30.000 g, 114.351 mmol), benzyl bromide (14.961 mL, 125.786 mmol) and K$_2$CO$_3$ (23.707 g, 171.527 mmol) were dissolved in acetonitrile (150 mL) at room temperature, and the solution was stirred at the same temperature for 17 hours. The reaction mixture was filtered through a glass filter to remove solids, and the filtrate was concentrated under reduced pressure to remove the solvent. Water was added to the concentrate, followed by extraction with ethyl acetate. The organic layer was washed with a saturated aqueous solution of sodium chloride, dried with anhydrous magnesium sulfate, filtered, and concentrated under reduced pressure. The concentrate was purified by column chromatography (silicon dioxide; 120 g cartridge; ethyl acetate/hexane=from 0% to 30%) and concentrated to afford the desired compound (22.400 g, 55.6%) as a white solid.

Step 3: Synthesis of Compound 84

Methyl 4-(((3R,5S)-4-benzyl-3,5-dimethylpiperazin-1-yl)methyl)benzoate (formula 1-3, 15.000 g, 42.557 mmol), hydroxylamine (52.061 mL, 851.136 mmol, 50.00% aqueous solution) and potassium hydroxide (23.879 g, 425.568 mmol) were dissolved in methanol (300 mL) at 0° C., and the solution was stirred at the same temperature for 1 hour. The reaction mixture was concentrated under reduced pressure to remove the solvent, and a saturated aqueous solution of sodium hydrogen carbonate was added to the concentrate, followed by extraction with methylene chloride. The organic layer was washed with a saturated aqueous solution of sodium chloride, dried with anhydrous magnesium sulfate, filtered, and concentrated under reduced pressure. The concentrate was purified by column chromatography (silicon dioxide; 120 g cartridge; methanol/methylene chloride=from 0% to 20%) and concentrated, and then the obtained material was crystallized from diethyl ether (200 mL) and methylene chloride (50 mL) at 25° C. and filtered. The resulting solid was washed with diethyl ether and dried to yield compound 84 (12.580 g, 83.6%) as a white solid.
$^1$H NMR (400 MHz, DMSO-d$_6$) δ 11.18 (brs, 1 H), 9.03 (brs, 1 H ), 7.70 (d, 2 H, J=8.2 Hz), 7.36-7.33 (m, 4 H), 7.28 (dd, 2 H, J=7.5, 7.5 Hz), 7.18 (dd, 1 H, J=7.2, 7.2 Hz), 3.73 (s, 2 H), 3.44 (s, 2 H), 2.64 (d, 2 H, J=10.6 Hz), 2.61-2.53 (m, 2 H), 1.81 (t, 2 H, J=10.5 Hz), 0.90 (d, 6 H, J=6.1 Hz); LRMS (ES) m/z 354.2 (M$^+$+1).

Example 6

Synthesis of Compound 98

((2S,6R)-4-(4-(hydroxycarbamoyl)benzyl)-N-isopropyl-2,6-dimethylpiperazine-1-carboxamide)

Step 1: Synthesis of Methyl 4-(((3R,5S)-4-isopropylcarbamoyl-3,5-dimethylpiperazin-1-yl)methyl)benzoate Methyl 4-(((3R,5S)-3,5-dimethylpiperazin-1-yl)methyl)benzoate (formula 1-2, 0.100 g, 0.381 mmol) was dissolved in methylene chloride (3 mL), and then 2-isocyanatopropane (0.041 mL, 0.419 mmol) and TEA (0.080 mL, 0.572 mmol) were added thereto. The mixture was stirred at 0° C. for 2 hours, and water was added to the reaction mixture, followed by extraction with methylene chloride. The organic layer was concentrated under reduced pressure to yield the desired compound (0.120 g, 90.6%) as a yellow solid.

Step 2: Synthesis of Compound 98

Methyl 4-(((3R,5S)-4-isopropylcarbamoyl-3,5-dimethylpiperazin-1-yl)methyl)benzoate (formula 1-3, 0.060 g, 0.173 mmol) was dissolved in methanol (1 mL), and then hydroxylamine (0.211 mL, 3.454 mmol, 50.00% aqueous solution) and potassium hydroxide (0.097 g, 1.727 mmol) were added thereto. The mixture was stirred at room temperature for 1 hour, and saturated sodium hydrogen carbonate was added thereto, followed by extraction with ethyl acetate. The organic layer was dried with anhydrous sodium sulfate, and then concentrated under reduced pressure. Compound 98 (0.040 g, 66.5%) was obtained as a white solid.

$^1$H NMR (400 MHz, CD$_3$OD) δ 7.72 (d, 2 H, J=8.3 Hz), 7.46 (d, 2 H, J=8.2 Hz), 4.06-4.03 (m, 2 H), 3.96-3.93 (m, 1 H), 3.54 (s, 2 H), 2.68 (d, 2 H, J=11.1 Hz), 2.15 (dd, 2 H, J=10.2, 3.6 Hz), 1.29 (d, 6 H, J=6.8 Hz), 1.14 (d, 6 H, J=6.6 Hz); LRMS (ES) m/z 349.1 (M$^+$+1).

Example 7

Synthesis of Compound 99

((2S,6R)-N-(3-chlorophenyl)-4-(4-(hydroxycarbamoyl)benzyl)-2,6-dimethylpiperazine-1-carboxamide)

Step 1: Synthesis of Methyl 4-((4-(3-chlorophenylcarbamoyl-3,5-dimethylpiperazin-1-yl)methyl)benzoate Methyl 4-(((3R,5S)-3,5-dimethylpiperazin-1-yl)methyl)benzoate (formula 1-2, 0.100 g, 0.381 mmol) was dissolved in methylene chloride (3 mL), and then 3-chlorophenylisocynate (0.051 mL, 0.419 mmol) and TEA (0.080 mL, 0.572 mmol) were added thereto. The mixture was stirred at 0° C. for 2 hours, and water was added to the reaction mixture, followed by extraction with methylene chloride. The organic layer was concentrated under reduced pressure to yield the desired compound (0.018 g, 68.1%) as a white solid.

Step 2: Synthesis of Compound 99

Methyl 4-((4-(3-chlorophenylcarbamoyl-3,5-dimethylpiperazin-1-yl)methyl)benzoate (formula 1-3, 0.050 g, 0.120 mmol) was dissolved in methanol (1 mL), and then hydroxylamine (0.147 mL, 2.404 mmol, 50.00% aqueous solution) and potassium hydroxide (0.067 g, 1.202 mmol) were added thereto. The mixture was stirred at room temperature for 1 hour, and the reaction mixture was concentrated under reduced pressure. Saturated sodium hydrogen carbonate was added to the concentrate, followed by stirring. The precipitated solid was filtered and dried to yield compound 99 (0.040 g, 66.5%) as a white solid.

$^1$H NMR (400 MHz, CD$_3$OD) δ 7.74 (d, 2 H, J=8.0 Hz), 7.53-7.52 (m, 1 H), 7.45 (d, 2 H, J=8.1 Hz), 7.29-7.28 (m, 1 H), 7.24-7.22 (m, 1 H), 7.01 (d, 1 H, J=7.8 Hz), 4.21-4.20 (m, 2 H), 3.56 (s, 2 H), 2.74 (d, 2 H, J=11.4 Hz), 2.22 (dd, 2 H, J=10.2, 3.6 Hz), 1.25 (d, 6 H, J=6.5 Hz).

Example 8

Synthesis of Compound 100

(4-(((3R,5S)-3,5-dimethyl-4-(phenylsulfonyl)piperazin-1-yl)methyl)-N-hydroxybenzamide)

Step 1: Synthesis of Methyl 4-(((3R,5S)-3,5-dimethylpiperazine-4-(phenylsulfonyl-1-yl)methyl)benzoate Methyl 4-(((3R,5S)-3,5-dimethylpiperazin-1-yl)methyl)benzoate (formula 1-2, 0.100 g, 0.381 mmol) was dissolved in methylene chloride (3 mL), and then benzenesulfonyl chloride (0.054 mL, 0.419 mmol) and TEA (0.080 mL, 0.572 mmol) were added thereto. The mixture was stirred at 0° C. for 2 hours, and then stirred at room temperature for 3 hours. Water was added to the reaction mixture, followed by extraction with methylene chloride. The organic layer was concentrated under reduced pressure. The concentrate was purified by column chromatography (silicon dioxide; ethyl acetate/hexane=25%) and concentrated to afford the desired compound (0.048 g, 31.3%) as a pale yellow solid.

Step 2: Synthesis of Compound 100

Methyl 4-(((3R,5S)-3,5-dimethylpiperazine-4-(phenylsulfonyl-1-yl)methyl)benzoate (formula 1-3, 0.048 g, 0.119 mmol) was dissolved in methanol (1 mL), and then hydroxylamine (0.146 mL, 2.385 mmol, 50.00% aqueous solution) and potassium hydroxide (0.067 g, 1.193 mmol) were added thereto. The mixture was stirred at room temperature for 1 hour, and saturated sodium hydrogen carbonate was added to the reaction mixture, followed by extraction with ethyl acetate. The organic layer was dried with anhydrous sodium sulfate, and then concentrated under reduced pressure to yield compound 100 (0.034 g, 70.7%) as a white solid.

$^1$H NMR (400 MHz, CD$_3$OD) δ 7.84 (d, 2 H, J=8.1 Hz), 7.68 (d, 2 H, J=8.3 Hz), 7.63-7.61 (m, 1 H), 7.58-7.54 (m, 2 H), 7.41 (d, 2 H, J=8.3 Hz), 4.06-4.03 (m, 2 H), 3.41 (s, 2 H), 2.53 (d, 2 H, J=11.3 Hz), 1.85-1.81 (m, 2 H), 1.43 (d, 6 H, J=6.9 Hz); LRMS (ES) m/z 404.1 (M$^+$+1).

Example 9

Synthesis of Compound 103

((3R,5S)-4-(4-(hydroxycarbamoyl)benzyl)-N-isopropyl-3,5-dimethylpiperazine-1-carboxamide)

Step 1: Synthesis of Methyl 4-(((2S,6R)-4-(isopropylcarbamoyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol) was dissolved in methylene chloride (3 mL), and then 2-isocyanatopropane (0.041 mL, 0.419 mmol) and TEA (0.079 mL, 0.572 mmol) were added thereto. The mixture was stirred for 2 hours while elevating the temperature from 0° C. to room temperature, and then water was added to the reaction mixture, followed by extraction with methylene chloride. The organic layer was dried with anhydrous magnesium sulfate, and then concentrated under reduced pressure to yield the desired compound (0.094 g, 70.1%).

Step 2: Synthesis of Compound 103

Methyl 4-(((2S,6R)-4-(isopropylcarbamoyl)-2,6-dimethylpiperazin-1-yl)methyl)benzoate (formula 13-3, 0.045 g, 0.130 mmol) was dissolved in methanol (0.5 mL), and then hydroxylamine (0.158 mL, 2.590 mmol, 50.00% aqueous solution) and potassium hydroxide (0.073 g, 1.295 mmol) were added thereto. The mixture was stirred at room temperature for 1 hour, and saturated sodium hydrogen carbonate was added to the reaction mixture, followed by extraction with ethyl acetate. The organic layer was dried with anhydrous sodium sulfate, and then concentrated under reduced pressure. Compound 103 (0.020 g, 44.3%) was obtained as a white solid.

$^1$H NMR (400 MHz, CD$_3$OD) δ 7.69 (d, 2 H, J=8.2 Hz), 7.50 (d, 2 H, J=8.2 Hz), 3.91-3.82 (m, 5 H), 2.67-2.61 (m,

2 H), 2.55-2.50 (m, 2 H), 1.13 (d, 6 H, J=6.6 Hz), 1.03 (d, 6 H, J=6.0 Hz); LRMS (ES) m/z 349.2 (M$^+$+1).

Example 10

Synthesis of Compound 104

((3R,5S)-N-(3-chlorophenyl)-4-(4-(hydroxycarbamoyl)benzyl)-3,5-dimethylpiperazine-1-carboxamide)

Step 1: Synthesis of Methyl 4-(((2S,6R)-4-(3-chlorophenylcarbamoyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol) was dissolved in methylene chloride (3 mL), and then 3-chlorophenyl isocyanate (0.051 mL, 0.419 mmol) and TEA (0.079 mL, 0.572 mmol) were added thereto. The mixture was stirred for 2 hours while elevating the temperature from 0° C. to room temperature, and then water was added to the reaction mixture, followed by extraction with methylene chloride. The organic layer was dried with anhydrous magnesium sulfate, and then concentrated under reduced pressure to yield the desired compound (0.094 g, 70.1%).

Step 2: Synthesis of Compound 104

Methyl 4-(((2S,6R)-4-(3-chlorophenylcarbamoyl)-2,6-dimethylpiperazin-1-yl)methyl)benzoate (formula 13-3, 0.065 g, 0.156 mmol) was dissolved in methanol (0.5 mL), and then hydroxylamine (0.191 mL, 3.126 mmol, 50.00% aqueous solution) and potassium hydroxide (0.088 g, 1.563 mmol) were added thereto. The mixture was stirred at room temperature for 1 hour, and the reaction mixture was concentrated under reduced pressure. Saturated sodium hydrogen carbonate was added to the concentrate, which was then stirred. The precipitated solid was filtered and dried to yield compound 104 (0.035 g, 53.7%) as a white solid.

$^1$H NMR (400 MHz, DMSO-d$_6$) δ 8.67 (s, 1 H), 7.67 (d, 2 H, J=8.2 Hz), 7.63-7.62 (m, 1 H), 7.41-7.38 (m, 3 H), 7.24 (dd, 1 H, J=10.2, 3.6 Hz), 7.46 (dd, 1 H, J=10.2, 3.6 Hz), 3.95 (d, 2 H, J=12.8 Hz), 3.77 (s, 2 H), 2.68-2.65 (m, 2 H), 2.53-2.52 (m, 2 H), 0.97 (d, 6 H, J=6.1 Hz).

Example 11

Synthesis of Compound 105

(4-(((2S,6R)-2,6-dimethyl-4-(phenylsulfonyl)piperazin-1-yl)methyl)-N-hydroxybenzamide)

Step 1: Synthesis of Methyl 4-(((2S,6R)-2,6-dimethyl-4-(phenylsulfonyl)piperazin-1-yl)methyl)benzoate Methyl 4-(((2S,6R)-2,6-dimethylpiperazin-1-yl)methyl)benzoate (formula 13-2, 0.100 g, 0.381 mmol) was dissolved in methylene chloride (3 mL), and then phenylsulfonyl chloride (0.065 g, 0.306 mmol) and TEA (0.116 mL, 0.835 mmol) were added thereto. The mixture was stirred at room temperature for 1 hour, and water was added to the reaction mixture, followed by extraction with methylene chloride. The organic layer was concentrated under reduced pressure. The concentrate was purified by column chromatography (silicon dioxide; ethyl acetate/hexane=25%) and concentrated to afford the desired compound (0.108 g, 88.8%) as a colorless oil.

Step 2: Synthesis of Compound 105

Methyl 4-(((2S,6R)-2,6-dimethyl-4-(phenylsulfonyl)piperazin-1-yl)methyl)benzoate (formula 13-3, 0.045 g, 0.115 mmol) was dissolved in methanol (0.5 mL), and then hydroxylamine (0.137 mL, 2.236 mmol, 50.00% aqueous solution) and potassium hydroxide (0.063 g, 1.118 mmol) were added thereto. The mixture was stirred at room temperature for 1 hour, and the reaction mixture was concentrated under reduced pressure. Saturated sodium hydrogen carbonate was added to the concentrated, followed by stirring. The precipitated solid was filtered and dried to yield compound 105 (0.027 g, 59.9%) as a white solid.

$^1$H NMR (400 MHz, DMSO-d$_6$) δ 7.76-7.74 (m, 3 H), 7.69-7.68 (m, 2 H), 7.61 (d, 2 H, J=8.3 Hz), 7.28 (d, 2 H, J=8.1 Hz), 3.71 (s, 2 H), 3.44 (d, 2 H, J=10.5 Hz), 2.65-2.64 (m, 2 H), 2.02 (t, 2 H, J=10.8 Hz), 0.91 (d, 6 H, J=6.2 Hz); LRMS (ES) m/z 404.1 (M$^+$+1)

Example 12

Synthesis of Compound 106

(4-(((2S,6R)-4-(4-chlorobenzoyl)-2,6-dimethylpiperazin-1-yl)methyl)-N-hydroxybenzamide)

Step 1: Synthesis of Methyl 4-((4-(4-chlorobenzoyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol) was dissolved in methylene chloride (3 mL), and then 4-chlorobenzoyl chloride (0.054 mL, 0.419 mmol) and TEA (0.159 mL, 1.144 mmol) were added thereto. The mixture was stirred at room temperature for 1 hour, and water was added to the reaction mixture, followed by extraction with methylene chloride. The organic layer was concentrated under reduced pressure. The concentrate was purified by column chromatography (silicon dioxide; ethyl acetate/hexane=30%) and concentrated to afford the desired compound (0.142 g, 92.9%) as a brown oil.

Step 2: Synthesis of Compound 106

Methyl 4-((4-(4-chlorobenzoyl)-2,6-dimethylpiperazin-1-yl)methyl)benzoate (formula 13-3, 0.070 g, 0.175 mmol) was dissolved in methanol (1 mL), and then hydroxylamine (0.214 mL, 3.492 mmol, 50.00% aqueous solution) and potassium hydroxide (0.098 g, 1.746 mmol) were added thereto. The mixture was stirred at room temperature for 30 minutes, and saturated sodium hydrogen carbonate was added to the reaction mixture, followed by extraction with ethyl acetate. The organic layer was concentrated under reduced pressure to yield compound 106 (0.028 g, 39.9%) as a white solid.

$^1$H NMR (400 MHz, DMSO-d$_6$) δ 7.69 (d, 2 H, J=8.3 Hz), 7.51 (d, 2 H, J=8.4 Hz), 7.48 (d, 2 H, J=8.3 Hz), 7.41 (d, 2 H, J=8.4 Hz), 4.38-4.37 (m, 1 H), 3.88 (s, 2 H), 3.51-3.50 (m, 1 H), 3.06-3.05 (m, 1 H), 2.82-2.80 (m, 1 H), 2.67-2.58 (m, 2 H ), 1.10 (s, 3 H), 0.92-0.88 (m, 3 H); LRMS (ES) m/z 402.1 (M$^+$+1).

Example 13

Synthesis of Compound 107

(4-(((2S,6R)-4-(3-chlorobenzoyl)-2,6-dimethylpiperazin-1-yl)methyl)-N-hydroxybenzamide)

Step 1: Synthesis of Methyl 4-((4-(3-chlorobenzoyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.278 mmol) was dissolved in methylene chloride (3 mL), and then 3-chlorobenzoyl chloride (0.039 mL, 0.306 mmol) and TEA (0.116 mL, 0.835 mmol) were added thereto. The mixture was stirred at room temperature for 1 hour, and water was added to the reaction mixture, followed by extraction with methylene chloride. The organic layer was concentrated under reduced pressure. The concentrate was purified by column chromatography (silicon dioxide; ethyl acetate/hexane=30%) and concentrated to afford the desired compound (0.100 g, 89.6%) as a yellow oil.

Step 2: Synthesis of Compound 107

Methyl 4-((4-(3-chlorobenzoyl)-2,6-dimethylpiperazin-1-yl)methyl)benzoate (formula 13-3, 0.050 g, 0.125 mmol) was dissolved in methanol (1 mL), and then hydroxylamine (0.153 mL, 2.494 mmol, 50.00% aqueous solution) and potassium hydroxide (0.070 g, 1.247 mmol) were added thereto. The mixture was stirred at room temperature for 30 minutes, and then saturated sodium hydrogen carbonate was added to the reaction mixture, followed by extraction with ethyl acetate. The organic layer was concentrated under reduced pressure to yield compound 107 (0.025 g, 49.9%) as a white solid.

$^1$H NMR (400 MHz, DMSO-$d_6$) δ 7.68 (d, 2 H, J=8.2 Hz), 7.54 (d, 1 H, J=7.9 Hz), 7.52-7.46 (m, 2 H), 7.42 (d, 2 H, J=8.0 Hz), 7.36 (d, 1 H, J=7.5 Hz), 4.25 (d, 1 H, J=9.4 Hz), 3.78 (s, 2H), 2.98-2.96 (m, 2 H), 2.71-2.68 (m, 3 ), 1.02 (s, 3 H), 0.84 (s, 3 H); LRMS (ES) m/z 402.1 (M$^+$+1).

Example 14

Synthesis of Compound 108

(4-(((2S,6R)-4-(2-chlorobenzoyl)-2,6-dimethylpiperazin-1-yl)methyl)-N-hydroxybenzamide)

Step 1: Synthesis of Methyl 4-((4-(2-chlorobenzoyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.278 mmol) was dissolved in methylene chloride (3 mL), and then 2-chlorobenzoyl chloride (0.039 mL, 0.306 mmol) and TEA (0.116 mL, 0.835 mmol) were added thereto. The mixture was stirred at room temperature for 1 H our, and then water was added to the reaction mixture, followed by extraction with methylene chloride. The organic layer was concentrated under reduced pressure to yield the desired compound (0.110 g, 98.6%) as a yellow oil.

Step 2: Synthesis of Compound 108

Methyl 4-((4-(2-chlorobenzoyl)-2,6-dimethylpiperazin-1-yl)methyl)benzoate (formula 13-3, 0.055 g, 0.137 mmol) was dissolved in methanol (1 mL), and then hydroxylamine (0.168 mL, 2.744 mmol, 50.00% aqueous solution) and potassium hydroxide (0.077 g, 1.372 mmol) were added thereto. The mixture was stirred at room temperature for 30 minutes, and then saturated sodium hydrogen carbonate was added to the reaction mixture, followed by extraction with ethyl acetate. The organic layer was concentrated under reduced pressure to yield compound 108 (0.025 g, 45.3%) as a white solid.

$^1$H NMR (400 MHz, CD$_3$OD) δ 11.13 (s, 1 H), 8.97 (s, 1 H), 7.68 (d, 2 H, J=8.0 Hz), 7.53 (d, 1 H, J=7.2 Hz), 7.44-7.35 (m, 5 H), 4.28 (d, 2 H, J=11.9 Hz), 3.78 (s, 2 H), 3.06 (d, 1 H, J=12.8 Hz), 2.92-2.89 (m, 1 H), 2.74-2.61 (m, 3 H), 1.02 (d, 3 H, J=5.9 Hz), 0.81-0.78 (m, 3 H); LRMS (ES) m/z 402.1 (M$^+$+1).

Example 15

Synthesis of Compound 109

(4-(((2S,6R)-4-((4-chlorophenyl)sulfonyl)-2,6-dimethylpiperazin-1-yl)methyl)-N-hydroxybenzamide)

Step 1: Synthesis of Methyl 4-(((2S,6R)-4-((4-chlorophenyl)sulfonyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol) was dissolved in methylene chloride (3 mL), and then 4-chlorobenzene-1-sulfonyl chloride (0.065 g, 0.306 mmol) and TEA (0.116 mL, 0.835 mmol) were added thereto. The mixture was stirred at room temperature for 1 hour, and then water was added to the reaction mixture, followed by extraction with methylene chloride. The organic layer was concentrated under reduced pressure. The concentrate was purified by column chromatography (silicon dioxide; ethyl acetate/hexane=30%) and concentrated to afford the desired compound (0.108 g, 88.8%) as a colorless oil.

Step 2: Synthesis of Compound 109

Methyl 4-(((2S,6R)-4-((4-chlorophenyl)sulfonyl)-2,6-dimethylpiperazin-1-yl)methyl)benzoate (formula 13-3, 0.05 g, 0.114 mmol) was dissolved in methanol (1 mL), and then hydroxylamine (0.140 mL, 2.289 mmol, 50.00% aqueous solution) and potassium hydroxide (0.064 g, 1.144 mmol) were added thereto. The mixture was stirred at room temperature for 30 minutes, and then saturated sodium hydrogen carbonate was added to the reaction mixture, followed by extraction with ethyl acetate. The organic layer was dried with anhydrous sodium sulfate, and then concentrated under reduced pressure to yield compound 109 (0.035 g, 69.8%) as a white solid.

$^1$H NMR (400 MHz, CD$_3$OD) δ 7.78 (d, 2 H, J=8.4 Hz), 7.66 (d, 4 H, J=7.2 Hz), 7.43 (d, 2 H, J=7.9 Hz), 3.83 (s, 2 H), 3.52 (d, 2 H, J=11.3 Hz), 2.21-2.20 (m, 2 H), 3.52 (d, 2 H, J=11.3 Hz), 1.01 (d, 6 H, J=6.1 Hz); LRMS (ES) m/z 438.0 (M$^+$+1)

Example 16

Synthesis of Compound 110

(4-(((2S,6R)-4-((2-chlorophenyl)sulfonyl)-2,6-dimethylpiperazin-1-yl)methyl)-N-hydroxybenzamide)

Step 1: Synthesis of Methyl 4-(((2S,6R)-4-((2-chlorophenyl)sulfonyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol) was dissolved in methylene chloride (3 mL), and then 2-chlorobenzene-1-sulfonyl chloride (0.042 mL, 0.306 mmol) and TEA (0.116 mL, 0.835 mmol) were added thereto. The mixture was stirred at room temperature for 1 hour, and then water was added to the reaction mixture, followed by extraction with methylene chloride. The organic layer was concentrated under reduced pressure. The concentrate was purified by column chromatography (silicon dioxide; ethyl acetate/hexane=30%) and concentrated to afford the desired compound (0.105 g, 68.3%) as a colorless oil.

Step 2: Synthesis of Compound 110

Methyl 4-(((2S,6R)-4-((2-chlorophenyl)sulfonyl)-2,6-dimethylpiperazin-1-yl)methyl)benzoate (formula 13-3, 0.060 g, 0.137 mmol) was dissolved in methanol (1 mL), and then hydroxylamine (0.168 mL, 2.746 mmol, 50.00% aqueous solution) and potassium hydroxide (0.077 g, 1.373 mmol) were added thereto. The mixture was stirred at room temperature for 30 minutes, and then saturated sodium hydrogen carbonate was added to the reaction mixture, followed by extraction with ethyl acetate. The organic layer was dried with anhydrous sodium sulfate, and then concentrated under reduced pressure. Compound 110 (0.037 g, 61.5%) was obtained as a white solid.

$^1$H NMR (400 MHz, DMSO-$d_6$) δ 11.10 (s, 1 H), 9.00 (s, 1 H), 7.98 (d, 1 H, J=7.3 Hz), 7.71-7.64 (m, 4 H), 7.60-7.52 (m, 1 H), 7.37 (d, 2 H, J=8.1 Hz), 3.75 (s, 2 H), 3.52 (d, 2 H, J=11.3 Hz), 2.60-2.56 (m, 4 H), 0.93 (d, 6 H, J=5.8 Hz); LRMS (ES) m/z 438.1 (M$^+$+1)

Example 17

Synthesis of Compound 111

(4-(((2S,6R)-2,6-dimethyl-4-picolinoylpiperazin-1-yl)methyl)-N-hydroxybenzamide)

Step 1: Synthesis of Methyl 4-(((2S,6R)-2,6-dimethyl-4-picolinoylpiperazin-1-yl)methyl)benzoate Methyl 4-(((2S,6R)-2,6-dimethylpiperazin-1-yl)methyl)benzoate (formula 13-2, 0.100 g, 0.381 mmol) was dissolved in methylene chloride (3 mL), and then picolinoyl chloride (0.075 g, 0.419 mmol) and TEA (0.159 mL, 1.144 mmol) were added thereto. The mixture was stirred at room temperature for 1 hour, and then water was added to the reaction mixture, followed by extraction with methylene chloride. The organic layer was concentrated under reduced pressure. The concentrate was purified by column chromatography (silicon dioxide; ethyl acetate=100%) and concentrated to afford the desired compound (0.046 g, 32.8%) as a yellow oil.

Step 2: Synthesis of Compound 111

Methyl 4-(((2S,6R)-2,6-dimethyl-4-picolinoylpiperazin-1-yl)methyl)benzoate (formula 13-3, 0.02 g, 0.054 mmol) was dissolved in methanol (1 mL), and then hydroxylamine (0.067 mL, 1.089 mmol, 50.00% aqueous solution) and potassium hydroxide (0.03 g, 0.544 mmol) were added thereto. The mixture was stirred at room temperature for 30 minutes, and then saturated sodium hydrogen carbonate was added to the reaction mixture, followed by extraction with ethyl acetate. The organic layer was concentrated under reduced pressure to yield compound 111 (0.001 g, 5.0%) as a colorless oil.

$^1$H NMR (400 MHz, DMSO-$d_6$) δ 8.65 (dd, 1 H, J=10.2, 3.6 Hz), 8.62 (d, 1 H, J=3.0 Hz), 7.90 (dd, 1 H, J=10.2, 3.6 Hz), 7.70 (d, 2 H, J=8.4 Hz), 7.55-7.51 (m, 3 H), 4.42 (d, 1 H, J=12.3 Hz), 3.89 (s, 2 H), 3.49 (d, 1 H, J=12.7 Hz), 3.12-3.11 (m, 1 H), 2.85-2.84 (m, 1 H), 2.72-2.63 (m, 2 H), 1.12 (d, 3 H, J=3.6 Hz), 0.92 (d, 3 H, J=5.2 Hz).

Example 18

Synthesis of Compound 112

(4-(((2S,6R)-2,6-dimethyl-4-nicotinoylpiperazin-1-yl)methyl)-N-hydroxybenzamide)

Step 1: Synthesis of methyl (((2S,6R)-2,6-dimethyl-4-nicotinoylpiperazin-1-yl)methyl)benzoate Methyl 4-(((2S,6R)-2,6-dimethylpiperazin-1-yl)methyl)benzoate (formula 13-2, 0.100 g, 0.381 mmol) was dissolved in methylene chloride (3 mL), and then nicotinoyl chloride (0.075 g, 0.419 mmol) and TEA (0.159 mL, 1.144 mmol) were added thereto. The mixture was stirred at room temperature for 1 hour, and then water was added to the reaction mixture, followed by extraction with methylene chloride. The organic layer was concentrated under reduced pressure. The concentrate was purified by column chromatography (silicon dioxide; methanol/methylene chloride=5%) and concentrated to afford the desired compound (0.119 g, 85.0%) as a yellow oil.

Step 2: Synthesis of Compound 112

Methyl (((2S,6R)-2,6-dimethyl-4-nicotinoylpiperazin-1-yl)methyl)benzoate (formula 13-3, 0.060 g, 0.163 mmol) was dissolved in methanol (1 mL), and then hydroxylamine (0.200 mL, 3.266 mmol, 50.00% aqueous solution) and potassium hydroxide (0.092 g, 1.633 mmol) were added thereto. The mixture was stirred at room temperature for 30 minutes, and then saturated sodium hydrogen carbonate was added to the reaction mixture, followed by extraction with ethyl acetate. The organic layer was concentrated under reduced pressure and extracted with ethyl acetate and water. The organic layer was concentrated under reduced pressure to yield compound 112 (0.001 g, 1.7%) as a colorless oil.

$^1$H NMR (400 MHz, DMSO-$d_6$) δ 8.65 (dd, 1 H, J=10.2, 3.6 Hz), 8.62 (d, 1 H, J=3.0 Hz), 7.90 (dd, 1 H, J=10.2, 3.6 Hz), 7.70 (d, 2 H, J=8.4 Hz), 7.55-7.51 (m, 3 H), 4.42 (d, 1 H, J=12.3 Hz), 3.89 (s, 2 H), 3.49 (d, 1 H, J=12.7 Hz), 3.12-3.11 (m, 1 H), 2.85-2.84 (m, 1 H), 2.72-2.63 (m, 2 H), 1.12 (d, 3 H, J=3.6 Hz), 0.92 (d, 3 H, J=5.2 Hz); LRMS (ES) m/z 369.2 (M$^+$+1).

Example 19

Synthesis of Compound 113

(4-(((2S,6R)-2,6-dimethyl-4-(pyridin-3-ylsulfonyl) piperazin-1-yl)methyl)-N-hydroxybenzamide)

Step 1: Synthesis of methyl 4-(((2S,6R)-2,6-dimethyl-4-(pyridin-3-ylsulfonyl)piperazin-1-yl)methyl)benzoate Methyl 4-(((2S,6R)-2,6-dimethylpiperazin-1-yl)methyl) benzoate (formula 13-2, 0.100 g, 0.381 mmol) was dissolved in methylene chloride (3 mL), and then pyridine-3-sulfonyl chloride (0.090 g, 0.419 mmol) and TEA (0.159 mL, 1.144 mmol) were added thereto. The mixture was stirred at room temperature for 1 hour, and then water was added to the reaction mixture, followed by extraction with methylene chloride. The organic layer was concentrated under reduced pressure. The concentrate was purified by column chromatography (silicon dioxide; methanol/methylene chloride=5%) and concentrated to afford the desired compound (0.105 g, 68.3%) as a white solid.

Step 2: Synthesis of Compound 113

Methyl 4-(((2S,6R)-2,6-dimethyl-4-(pyridin-3-ylsulfonyl)piperazin-1-yl)methyl)benzoate (formula 13-3, 0.600 g, 0.149 mmol) was dissolved in methanol (1 mL), and then hydroxylamine (0.182 mL, 2.974 mmol, 50.00% aqueous solution) and potassium hydroxide (0.830 g, 1.487 mmol) were added thereto. The mixture was stirred at room temperature for 30 minutes, and then saturated sodium hydrogen carbonate was added to the reaction mixture, followed by extraction with ethyl acetate. The organic layer was dried with anhydrous sodium sulfate, and then concentrated under reduced pressure. Compound 113 (0.033 g, 54.9%) was obtained as a white solid.

$^1$H NMR (400 MHz, CD$_3$OD) δ 8.93 (d, 1 H, J=2.3 Hz), 8.84 (dd, 1 H, J=10.2, 3.6 Hz), 8.22-8.20 (m, 1 H), 7.66-7.65 (m, 1 H), 7.65 (d, 2 H, J=8.3 Hz), 7.42 (d, 2 H, J=8.2 Hz), 3.83 (s, 2 H), 3.58 (d, 2 H, J=11.5 Hz), 2.74-2.72 (m, 2 H), 2.24 (t, 2 H, J=10.8 Hz), 1.01 (d, 6 H, J=6.2 Hz); LRMS (ES) m/z 405.1 (M$^+$+1).

Example 20

Synthesis of Compound 114

(4-(((2S,6R)-2,6-dimethyl-4-(thiophene-2-carbonyl) piperazin-1-yl)methyl)-N-hydroxybenzamide)

Step 1: Synthesis of Methyl 4-(((2S,6R)-2,6-dimethyl-4-(thiophene-2-carbonyl)piperazin-1-yl) methyl)benzoate Methyl 4-(((2S,6R)-2,6-dimethylpiperazin-1-yl)methyl) benzoate (formula 13-2, 0.100 g, 0.381 mmol) was dissolved in methylene chloride (3 mL), and then thiophene-2-carbonyl chloride (0.046 mL, 0.419 mmol) and TEA (0.159 mL, 1.144 mmol) were added thereto. The mixture was stirred at room temperature for 1 hour, and then water was added to the reaction mixture, followed by extraction with methylene chloride. The organic layer was concentrated under reduced pressure. The concentrate was purified by column chromatography (silicon dioxide; ethyl acetate/hexane=30%) and concentrated to afford the desired compound (0.127 g, 89.5%) as a yellow oil.

Step 2: Synthesis of Compound 114

Methyl 4-(((2S,6R)-2,6-dimethyl-4-(thiophene-2-carbonyl)piperazin-1-yl)methyl)benzoate (formula 13-3, 0.070 g, 0.188 mmol) was dissolved in methanol (1 mL), and then hydroxylamine (0.230 mL, 3.759 mmol, 50.00% aqueous solution) and potassium hydroxide (0.105 g, 1.879 mmol) were added thereto. The mixture was stirred at room temperature for 30 minutes, and then saturated sodium hydrogen carbonate was added to the reaction mixture, followed by extraction with ethyl acetate. The organic layer was concentrated under reduced pressure to yield compound 114 (0.013 g, 18.5%) as a white solid.

$^1$H NMR (400 MHz, CD$_3$OD) δ 7.70 (d, 2 H, J=8.4 Hz), 7.65 (dd, 1 H, J=10.2, 3.6 Hz), 7.52 (d, 2 H, J=8.4 Hz), 7.40 (dd, 1 H, J=10.2, 3.6 Hz), 7.12 (dd, 1 H, J=10.2, 3.6 Hz), 4.20-4.19 (m, 2 H), 3.89 (s, 2 H), 3.03-2.97 (m, 2 H), 2.70-2.62 (m, 2 H), 1.05 (d, 6 H, J=5.6 Hz); LRMS (ES) m/z 374.1 (M$^+$+1).

Example 21

Synthesis of Compound 115

(4-(((2S,6R)-4-(furan-2-carbonyl)-2,6-dimethylpiperazin-1-yl)methyl)-N-hydroxybenzamide)

Step 1: Synthesis of Methyl 4-(((2S,6R)-4-(furan-2-carbonyl)-2,6-dimethylpiperazin-1-yl)methyl)benzoate Methyl 4-(((2S,6R)-2,6-dimethylpiperazin-1-yl)methyl) benzoate (formula 13-2, 0.100 g, 0.381 mmol) was dissolved in methylene chloride (3 mL), and furan-2-carbonyl chloride (0.040 mL, 0.419 mmol) and TEA (0.159 mL, 1.144 mmol) were added thereto. The mixture was stirred at room temperature for 1 hour, and then water was added to the reaction mixture, followed by extraction with methylene chloride. The organic layer was concentrated under reduced pressure. The concentrate was purified by column chromatography (silicon dioxide; ethyl acetate/hexane=30%) and concentrated to afford the desired compound (0.115 g, 84.7%) as a pale yellow oil.

Step 2: Synthesis of Compound 115

Methyl 4-(((2S,6R)-4-(furan-2-carbonyl)-2,6-dimethylpiperazin-1-yl)methyl)benzoate (formula 13-3, 0.060 g, 0.168 mmol) was dissolved in methanol (1 mL), and then hydroxylamine (0.206 mL, 3.367 mmol, 50.00% aqueous solution) and potassium hydroxide (0.095 g, 1.683 mmol) were added thereto. The mixture was stirred at room temperature for 30 minutes, and then saturated sodium hydrogen carbonate was added to the reaction mixture, followed by extraction with ethyl acetate. The organic layer was concentrated under reduced pressure to yield compound 115 (0.007 g, 11.6%) as a pale yellow solid.

$^1$H NMR (400 MHz, CD$_3$OD) δ 7.71-7.69 (m, 3 H), 7.53 (d, 2 H, J=8.4 Hz), 7.04 (dd, 1 H, J=10.2, 3.6 Hz), 6.59 (dd, 1 H, J=10.2, 3.6 Hz), 4.31 (d, 2 H, J=13.1 Hz), 3.90 (s, 2 H), 2.85-2.82 (m, 2 H), 2.69-2.65 (m, 2 H), 1.08 (d, 6 H, J=5.4 Hz); LRMS (ES) m/z 358.1 (M$^+$+1).

Example 22

Synthesis of Compound 118

(4-(((2S,6R)-4-(2-chlorobenzyl)-2,6-dimethylpiperazin-1-yl)methyl)-N-hydroxybenzamide)

Step 1: Synthesis of Methyl 4-(((2S,6R)-4-(2-chlorobenzyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.278 mmol) was dissolved in acetonitrile (2 mL), and then 2-chlorobenzyl bromide (0.038 mL, 0.292 mmol) and K$_2$CO$_3$ (0.096 g, 0.696 mmol) were added thereto. The mixture was stirred at room temperature for 2 hours, and then the reaction mixture was concentrated under reduced pressure. The concentrate was purified by column chromatography (silicon dioxide; ethyl acetate/hexane=25%) and concentrated to afford the desired compound (0.080 g, 74.3%) as a pale yellow oil.

Step 2: Synthesis of Compound 118

Methyl 4-(((2S,6R)-4-(2-chlorobenzyl)-2,6-dimethylpiperazin-1-yl)methyl)benzoate (formula 13-3, 0.040 g, 0.103 mmol) was dissolved in methanol (1 mL), and then hydroxylamine (0.126 mL, 2.068 mmol, 50.00% aqueous solution) and potassium hydroxide (0.058 g, 1.034 mmol) were added thereto. The mixture was stirred at room temperature for 30 minutes, and then the reaction mixture was concentrated under reduced pressure. Saturated sodium hydrogen carbonate was added to the concentrate, followed by stirring. The precipitated solid was filtered and dried to yield compound 118 (0.018 g, 43.3%) as a white solid.
$^1$H NMR (400 MHz, DMSO-d$_6$) δ 7.65 (d, 2 H, J=8.2 Hz), 7.37-7.33 (m, 4 H), 7.33-7.31 (m, 2 H), 3.74 (s, 2 H), 3.41 (s, 2 H ), 2.65-2.62 (m, 2 H), 2.55-2.51 (m, 2 H), 1.83-1.82 (m, 2 H), 0.88 (d, 6 H, J=6.1 Hz); LRMS (ES) m/z 388.1 (M$^+$+1).

Example 23

Synthesis of Compound 119

(4-(((2S,6R)-4-(4-fluorophenyl)-2,6-dimethylpiperazin-1-yl)methyl)-N-hydroxybenzamide)

Step 1: Synthesis of Methyl 4-(((2S,6R)-4-(4-fluorophenyl)-2,6-dimethylpiperazin-1-yl)methyl)benzoate Pd(OAc)$_2$ (0.006 g, 0.028 mmol) and xantphos (0.003 g, 0.006 mmol) were dissolved in toluene, and then 1-bromo-4-fluorobenzene (0.049 g, 0.278 mmol), methyl 4-(((2S,6R)-2,6-dimethylpiperazin-1-yl)methyl)benzoate (formula 13-2, 0.100 g, 0.278 mmol) and Cs$_2$CO$_3$ (0.227 g, 0.696 mmol) were added thereto. The mixture was heated and stirred at 100° C. for 17 hours. Water was added to the reaction mixture, followed by extraction with ethyl acetate. The organic layer was concentrated under reduced pressure. The concentrate was purified by column chromatography (silicon dioxide; ethyl acetate/hexane=15%) and concentrated to afford the desired compound (0.007 g, 7.1%) as a white solid.

Step 2: Synthesis of Compound 119

Methyl 4-(((2S,6R)4-(4-fluorophenyl)-2,6-dimethylpiperazin-1-yl)methyl)benzoate (formula 19-1, 0.007 g, 0.020 mmol) was dissolved in methanol (1 mL), and then hydroxylamine (0.024 mL, 0.393 mmol, 50.00% aqueous solution) and potassium hydroxide (0.011 g, 0.196 mmol) were added thereto. The mixture was stirred at room temperature for 30 minutes, and then the reaction mixture was concentrated under reduced pressure to remove the solvent. Saturated sodium hydrogen carbonate was added to the concentrate, followed by extraction with ethyl acetate. The organic layer was concentrated under reduced pressure to yield compound 119 (0.003 g, 58.0%) as a pale brown solid.
$^1$H NMR (400 MHz, CD$_3$OD) δ 7.71 (d, 2 H, J=8.2 Hz), 7.53 (d, 2 H, J=8.2 Hz), 6.98-6.95 (m, 4 H), 4.12 (s, 2 H), 3.41 (d, 2 H, J=11.4 Hz), 2.81-2.78 (m, 2 H), 2.51 (t, 2 H, J=11.1 Hz), 1.12 (d, 6 H, J=6.1 Hz); LRMS (ES) m/z 358.1 (M$^+$+1).

Example 24

Synthesis of Compound 120

(4-(((3R,5S)-4-(2-chlorobenzoyl)-3,5-dimethylpiperazin-1-yl)methyl)-N-hydroxybenzamide)

Step 1: Synthesis of Methyl 4-(((3R,5S)-4-(2-chlorobenzoyl)-3,5-dimethylpiperazin-1-yl)methyl)benzoate Methyl 4-(((3R,5S)-3,5-dimethylpiperazin-1-yl)methyl)benzoate (formula I-2, 0.100 g, 0.381 mmol) was dissolved in methylene chloride (1 mL), and then 2-chlorobenzoyl chloride (0.058 mL, 0.801 mmol) and TEA (0.106 mL, 0.762 mmol) were added thereto. The mixture was stirred at room temperature for 2 hours, and then water was added to the reaction mixture, followed by extraction with ethyl acetate. The organic layer was separated and concentrated under reduced pressure. The concentrate was purified by column chromatography (silicon dioxide; methanol/methylene chloride=5%) and concentrated to afford the desired compound (0.076 g, 49.7%) as a yellow oil.

Step 2: Synthesis of Compound 120

Methyl 4-(((3R,5S)-4-(2-chlorobenzoyl)-3,5-dimethylpiperazin-1-yl)methyl)benzoate (formula 1-3, 0.070 g, 0.175 mmol) was dissolved in methanol (1 mL), and then hydroxylamine (0.214 mL, 3.492 mmol, 50.00% aqueous solution) and potassium hydroxide (0.098 g, 1.746 mmol) were added thereto. The mixture was stirred at room temperature for 1 hour, and then saturated sodium hydrogen carbonate was added to the reaction mixture, followed by extraction with ethyl acetate. The organic layer was concentrated under reduced pressure to yield compound 120 (0.029 g, 41.3%) as a pale yellow solid.
$^1$H NMR (400 MHz, DMSO-d$_6$) δ 7.69 (d, 2 H, J=8.1 Hz), 7.41-7.40 (m, 3 H), 7.33 (d, 2 H, J=8.0 Hz), 3.51 (s, 2 H ), 2.79-2.61 (m, 4 H), 2.14-2.13 (m, 2 H), 1.36 (d, 3 H , J=6.8 Hz), 1.24-1.18 (m, 3 H).

Example 25

Synthesis of Compound 121

(4-(((3R,5S)-4-(3-chlorobenzoyl)-3,5-dimethylpiperazin-1-yl)methyl)-N-hydroxybenzamide)

Step 1: Synthesis of Methyl 4-(((3R,5S)-4-(3-chlorobenzoyl)-3,5-dimethylpiperazin-1-yl)methyl)benzoate Methyl 4-(((3R,5S)-3,5-dimethylpiperazin-1-yl)methyl)benzoate (formula I-2, 0.100 g, 0.381 mmol) was dissolved in methylene chloride (1 mL), and then 3-chlorobenzoyl chloride (0.080 g, 0.457 mmol) and TEA (0.106 mL, 0.762 mmol) were added thereto. The mixture was stirred at room temperature for 2 hours, and then water was added to the reaction mixture, followed by extraction with ethyl acetate. The organic layer was separated and concentrated under reduced pressure. The concentrate was purified by column chromatography (silicon dioxide; methanol/methylene chloride=5%) and concentrated to afford the desired compound (0.062 g, 40.6%) as a pale yellow oil.

Step 2: Synthesis of Compound 121

Methyl 4-(((3R,5S)-4-(3-chlorobenzoyl)-3,5-dimethylpiperazin-1-yl)methyl)benzoate (formula 1-3, 0.050 g, 0.125 mmol) was dissolved in methanol (1 mL), and then hydroxylamine (0.153 mL, 2.494 mmol, 50.00% aqueous solution) and potassium hydroxide (0.070 g, 1.247 mmol) were added thereto. The mixture was stirred at room temperature for 1 hour, and then saturated sodium hydrogen carbonate was added to the reaction mixture, followed by extraction with ethyl acetate. The organic layer was concentrated under reduced pressure to yield compound 121 (0.021 g, 41.9%) as a pale yellow solid.

$^1$H NMR (400 MHz, DMSO-$d_6$) δ 7.68 (d, 2 H, J=8.0 Hz), 7.47-7.41 (m, 3 H), 7.32 (d, 2 H, J=8.0 Hz), 7.29 (s, 1 H), 3.49 (s, 2 H), 2.61-2.50 (m, 4 H), 2.16-2.12 (m, 2 H), 1.28 (d, 6 H, J=5.6 Hz).

Example 26

Synthesis of Compound 122

(4-(((3R,5S)-4-(4-chlorobenzoyl)-3,5-dimethylpiperazin-1-yl)methyl)-N-hydroxybenzamide)

Step 1: Synthesis of Methyl 4-(((3R,5S)-4-(4-chlorobenzoyl)-3,5-dimethylpiperazin-1-yl)methyl)benzoate Methyl 4-(((3R,5S)-3,5-dimethylpiperazin-1-yl)methyl)benzoate (formula 1-2, 0.100 g, 0.381 mmol) was dissolved in methylene chloride (1 mL), and then 4-chlorobenzoyl chloride (0.080 g, 0.457 mmol) and TEA (0.106 mL, 0.762 mmol) were added thereto. The mixture was stirred at room temperature for 2 hours, and then water was added to the reaction mixture, followed by extraction with ethyl acetate. The organic layer was separated and concentrated under reduced pressure. The concentrate was purified by column chromatography (silicon dioxide; methanol/methylene chloride=5%) and concentrated to afford the desired compound (0.059 g, 38.6%) as a pale yellow oil.

Step 2: Synthesis of Compound 122

Methyl 4-(((3R,5S)-4-(4-chlorobenzoyl)-3,5-dimethylpiperazin-1-yl)methyl)benzoate (formula 1-3, 0.050 g, 0.125 mmol) was dissolved in methanol (1 mL), and then hydroxylamine (0.153 mL, 2.494 mmol, 50.00% aqueous solution) and potassium hydroxide (0.070 g, 1.247 mmol) were added thereto. The mixture was stirred at room temperature for 1 hour, and then saturated sodium hydrogen carbonate was added to the reaction mixture, followed by extraction with ethyl acetate. The organic layer was concentrated under reduced pressure to yield compound 122 (0.014 g, 27.9%) as a pale yellow solid.

$^1$H NMR (400 MHz, DMSO-$d_6$) δ 11.10 (brs, 1 H), 9.05 (brs, 1 H), 7.72 (d, 2 H, J=8.1 Hz), 7.50 (d, 2 H, J=8.3 Hz), 7.43 (d, 2 H, J=8.1 Hz), 7.38 (d, 2 H, J=8.4 Hz), 4.10 (brs, 2 H), 3.54 (s, 2 H), 2.63 (d, 2 H, J=11.1 Hz), 2.15 (dd, 2 H, J=11.3, 4.1 Hz), 1.29 (d, 6 H, J=6.1 Hz); LRMS (ES) m/z 402.8 (M$^+$+1).

Example 27

Synthesis of Compound 123

(4-(((3R,5S)-3,5-dimethyl-4-picolinoylpiperazin-1-yl)methyl)-N-hydroxybenzamide)

Step 1: Synthesis of Methyl 4-(((3R,5S)-3,5-dimethyl-4-picolinoylpiperazin-1-yl)methyl)benzoate Methyl 4-(((3R,5S)-3,5-dimethylpiperazin-1-yl)methyl)benzoate (formula I-2, 0.100 g, 0.381 mmol) was dissolved in methylene chloride (1 mL), and then picolinoyl chloride (0.065 g, 0.457 mmol) and TEA (0.106 mL, 0.762 mmol) were added thereto. The mixture was stirred at room temperature for 2 hours, and then water was added to the reaction mixture, followed by extraction with ethyl acetate. The organic layer was separated and concentrated under reduced pressure. The concentrate was purified by column chromatography (silicon dioxide; methanol/methylene chloride=5%) and concentrated to afford the desired compound (0.042 g, 30.0%) as a white solid.

Step 2: Synthesis of Compound 123

Methyl 4-(((3R,5S)-3,5-dimethyl-4-picolinoylpiperazin-1-yl)methyl)benzoate (formula 1-3, 0.035 g, 0.095 mmol) was dissolved in methanol (1 mL), and then hydroxylamine (0.117 mL, 1.905 mmol, 50.00% aqueous solution) and potassium hydroxide (0.053 g, 0.953 mmol) were added thereto. The mixture was stirred at room temperature for 1 hour, and then saturated sodium hydrogen carbonate was added to the reaction mixture, followed by extraction with ethyl acetate. The organic layer was concentrated under reduced pressure to yield compound 123 (0.011 g, 31.3%) as a pale yellow solid.

$^1$H NMR (400 MHz, DMSO-$d_6$) δ 8.56-8.55 (m, 1 H), 7.82 (d, 2 H, J=8.0 Hz), 3.71 (s, 2 H), 2.96 (brs, 2 H), 2.56 (brs, 2 H), 1.02 (brs, 3 H), 0.88 (brs, 3 H); LRMS (ES) m/z 369.4 (M$^+$+1).

Example 28

Synthesis of Compound 125

(4-(((3R,5S)-4-(furan-2-carbonyl)-3,5-dimethylpiperazin-1-yl)methyl)-N-hydroxybenzamide)

Step 1: Synthesis of Methyl 4-(((3R,5S)-4-(furan-2-carbonyl)-3,5-dimethylpiperazin-1-yl)methyl)benzoate Methyl 4-(((3R,5S)-3,5-dimethylpiperazin-1-yl)methyl)benzoate (formula 1-2, 6.000 g, 22.870 mmol) and TEA (4.781 mL, 34.305 mmol) were dissolved in methylene chloride (120 mL) at 0° C., and furan-2-carbonyl chloride (2.488 mL, 25.157 mmol) was added to the solution, which was then stirred at the same temperature for 1 hour. A saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and concentrated under reduced pressure. The concentrate was purified by column chromatography (silicon dioxide; 80 g cartridge; ethyl acetate/hexane=from 0% to 30%) and concentrated to afford the desired compound (7.440 g, 91.3%) as a white solid.

Step 2: Synthesis of Compound 125

Methyl 4-(((3R,5S)-4-(furan-2-carbonyl)-3,5-dimethylpiperazin-1-yl)methyl)benzoate (formula 1-3, 7.440 g, 20.874 mmol), hydroxylamine (25.536 mL, 417.485 mmol, 50.00% aqueous solution) and potassium hydroxide (11.713 g, 208.742 mmol) were dissolved in methanol (150 mL) at 0° C., and the solution was stirred at the same temperature for 1 hour. The reaction mixture was concentrated under reduced pressure to remove the solvent, and a saturated aqueous solution of sodium hydrogen carbonate was added to the concentrate, followed by extraction with methylene chloride. The organic layer was washed with a saturated aqueous solution of sodium chloride, dried with anhydrous magnesium sulfate, filtered, and then concentrated under reduced pressure to afford compound 125 (5.330 g, 71.4%) as an apricot solid.

$^1$H NMR (400 MHz, DMSO-d$_6$) δ 11.23 (brs, 1 H), 9.06 (brs, 1 H), 7.81 (s, 1 H), 7.74 (d, 2 H, J=7.6 Hz), 7.42 (d, 2 H, J=5.8 Hz), 6.95 (d, 1 H, J=3.3 Hz), 6.61-6.60 (m, 1 H), 4.49 (brs, 2 H), 3.54 (s, 2 H), 2.68 (d, 2 H, J=11.0 Hz), 2.14 (d, 2 H, J=8.2 Hz), 1.25 (d, 6 H, J=5.6 Hz); LRMS (ES) m/z 358.2 (M$^+$+1).

Example 29

Synthesis of Compound 126

(4-(((3R,5S)-3,5-dimethyl-4-(thiophene-2-carbonyl)piperazin-1-yl)methyl)-N-hydroxybenzamide)

Step 1: Synthesis of Methyl 4-(((3R,5S)-3,5-dimethyl-4-(thiophene-2-carbonyl)piperazin-1-yl)methyl)benzoate Methyl 4-(((3R,5S)-3,5-dimethylpiperazin-1-yl)methyl)benzoate (formula I-2, 0.100 g, 0.381 mmol) was dissolved in methylene chloride (1 mL), and then thiophene-2-carbonyl chloride (0.067 g, 0.457 mmol) and TEA (0.106 mL, 0.762 mmol) were added thereto. The mixture was stirred at room temperature for 2 hours, and then water was added to the reaction mixture, followed by extraction with ethyl acetate. The organic layer was separated and concentrated under reduced pressure. The concentrate was purified by column chromatography (silicon dioxide; methanol/methylene chloride=5%) and concentrated to afford the desired compound (0.061 g, 43.0%) as a pale yellow oil.

Step 2: Synthesis of Compound 126

Methyl 4-(((3R,5S)-3,5-dimethyl-4-(thiophene-2-carbonyl)piperazin-1-yl)methyl)benzoate (formula 1-3, 0.050 g, 0.134 mmol) was dissolved in methanol (1 mL), and then hydroxylamine (0.164 mL, 2.685 mmol, 50.00% aqueous solution) and potassium hydroxide (0.075 g, 1.342 mmol) were added thereto. The mixture was stirred at room temperature for 1 hour, and then saturated sodium hydrogen carbonate was added to the reaction mixture, followed by extraction with ethyl acetate. The organic layer was concentrated under reduced pressure to yield compound 126 (0.019 g, 37.9%) as a pale yellow solid.

$^1$H NMR (400 MHz, DMSO-d$_6$) δ 7.72-7.71 (m, 3 H), 7.41-7.36 (m, 3 H), 7.10 (brs, 1 H), 4.43 (brs, 2 H), 3.52 (s, 2 H), 2.67-2.64 (m, 2 H), 2.14-2.12 (m, 2 H), 1.36 (d, 6 H, J=5.5 Hz).

Example 30

Synthesis of Compound 127

(4-(((3R,5S)-4-(2-chlorobenzyl)-3,5-dimethylpiperazin-1-yl)methyl)-N-hydroxybenzamide)

Step 1: Synthesis of Methyl 4-(((3R,5S)-4-(2-chlorobenzyl)-3,5-dimethylpiperazin-1-yl)methyl)benzoate Methyl 4-(((3R,5S)-3,5-dimethylpiperazin-1-yl)methyl)benzoate (formula I-2, 0.100 g, 0.381 mmol) was dissolved in acetonitrile (2 mL), and then 1-(bromomethyl)-2-chlorobenzene (0.094 g, 0.457 mmol) and K$_2$CO$_3$ (0.105 g, 0.762 mmol) were added thereto. The mixture was stirred at room temperature for 16 hours, and then water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.035 g, 23.7%) as a white oil.

Step 2: Synthesis of Compound 127

Methyl 4-(((3R,5S)-4-(2-chlorobenzyl)-3,5-dimethylpiperazin-1-yl)methyl)benzoate (formula 1-3, 0.030 g, 0.078 mmol) was dissolved in methanol (0.5 mL), and then hydroxylamine (0.095 mL, 1.551 mmol, 50.00% aqueous solution) and potassium hydroxide (0.044 g, 0.775 mmol) were added thereto. The mixture was stirred at room temperature for 1 hour, and then water was added to the reaction mixture, followed by extraction with ethyl acetate. The organic layer was washed with a saturated aqueous solution of sodium chloride, dried with anhydrous magnesium sulfate, and then concentrated under reduced pressure. Compound 127 (0.011 g, 36.6%) was obtained as a pale yellow solid.

$^1$H NMR (400 MHz, DMSO-d$_6$) δ 7.78-7.68 (m, 3 H), 7.32-7.19 (m, 6 H), 3.68 (s, 2 H), 3.44 (s, 2 H), 2.69-2.66 (m, 4 H), 1.86-1.83 (m, 2 H), 0.78 (brs, 6 H).

Example 31

Synthesis of Compound 128

(4-(((3R,5S)-4-(3-chlorobenzyl)-3,5-dimethylpiperazin-1-yl)methyl)-N-hydroxybenzamide)

Step 1: Synthesis of Methyl 4-(((3R,5S)-4-(3-chlorobenzyl)-3,5-dimethylpiperazin-1-yl)methyl)benzoate Methyl 4-(((3R,5S)-3,5-dimethylpiperazin-1-yl)methyl)benzoate (formula 1-2, 0.100 g, 0.381 mmol) was dissolved in acetonitrile (2 mL), and then 1-(bromomethyl)-3-chlorobenzene (0.094 g, 0.457 mmol) and $K_2CO_3$ (0.105 g, 0.762 mmol) were added thereto. The mixture was stirred at room temperature for 16 hours, and then water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.041 g, 27.8%) as a white oil.

Step 2: Synthesis of Compound 128

Methyl 4-(((3R,5S)-4-(3-chlorobenzyl)-3,5-dimethylpiperazin-1-yl)methyl)benzoate (formula 1-3, 0.035 g, 0.090 mmol) was dissolved in methanol (0.5 mL), and then hydroxylamine (0.111 mL, 1.809 mmol, 50.00% aqueous solution) and potassium hydroxide (0.051 g, 0.905 mmol) were added thereto. The mixture was stirred at room temperature for 1 hour, and then water was added to the reaction mixture, followed by extraction with ethyl acetate. The organic layer was washed with a saturated aqueous solution of sodium chloride, dried with anhydrous magnesium sulfate, and then concentrated under reduced pressure. Compound 128 (0.015 g, 42.7%) was obtained as a pale yellow solid.

$^1$H NMR (400 MHz, DMSO-$d_6$) δ 7.68 (d, 2 H, J=9.6 Hz), 7.38 (s, 1 H), 7.30 (d, 2 H, J=4.0 Hz), 7.27-7.20 (m, 3 H), 3.69 (s, 2 H), 3.40 (s, 2 H), 2.64-2.54 (m, 4 H), 1.82-1.75 (m, 2 H), 0.84 (d, 6 H, J=8.0 Hz).

Example 32

Synthesis of Compound 145

(4-(((3R,5S)-4-(furan-2-ylmethyl)-3,5-dimethylpiperazin-1-yl)methyl)-N-hydroxybenzamide)

Step 1: Synthesis of Methyl 4-(((3R,5S)-4-(furan-2-ylmethyl)-3,5-dimethylpiperazin-1-yl)methyl)benzoate Methyl 4-(((3R,5S)-3,5-dimethylpiperazin-1-yl)methyl)benzoate (formula 1-2, 0.300 g, 1.144 mmol) and 2-furaldehyde (0.104 mL, 1.258 mmol) were dissolved in methylene chloride (5 mL), and acetic acid (0.069 mL, 1.144 mmol) was added thereto at 40° C., followed by stirring for 1 hour. Na(CN)BH$_3$ (0.072 g, 1.144 mmol) was added to the reaction mixture, followed by stirring at the same temperature for 3 days. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=25%) and concentrated to afford the desired compound (0.028 g, 7.2%) as a pale yellow oil.

Step 2: Synthesis of Compound 145

Methyl 4-(((3R,5S)-4-(furan-2-ylmethyl)-3,5-dimethylpiperazin-1-yl)methyl)benzoate (formula 1-3, 0.028 g, 0.082 mmol) was dissolved in methanol (1 mL), and then hydroxylamine (0.100 mL, 1.635 mmol, 50.00% aqueous solution) and potassium hydroxide (0.046 g, 0.818 mmol) were added thereto. The mixture was stirred at room temperature for 30 minutes, and then the reaction mixture was concentrated under reduced pressure to remove the solvent. A saturated aqueous solution of sodium hydrogen carbonate was added to the concentrate, followed by extraction with methylene chloride. The organic layer was washed with a saturated aqueous solution of sodium chloride, dried with anhydrous sodium sulfate, and then concentrated under reduced pressure. Compound 145 (0.013 g, 46.3%) was obtained as a white solid.

$^1$H NMR (400 MHz, DMSO-$d_6$) δ 11.10 (brs, 1 H), 9.00 (brs, 1 H), 7.67 (d, 2 H, J=8.1 Hz), 7.59 (d, 1 H, J=2.4 Hz), 7.30 (d, 2 H, J=8.1 Hz), 6.41-6.40 (m, 1 H), 6.28-6.27 (m, 1 H), 3.86 (s, 2 H), 3.38 (s, 2 H), 2.60 (d, 2 H, J=10.0 Hz), 2.44-2.40 (m, 2 H), 1.74 (t, 2 H, J=10.6 Hz), 0.87 (d, 6 H, J=6.4 Hz).

Example 33

Synthesis of Compound 146

(4-(((3R,5S)-3,5-dimethyl-4-(2-phenylacetyl)piperazin-1-yl)methyl)-N-hydroxybenzamide)

Step 1: Synthesis of Methyl 4-(((3R,5S)-3,5-dimethyl-4-(2-phenylacetyl)piperazin-1-yl)methyl)benzoate Methyl 4-(((3R,5S)-3,5-dimethylpiperazin-1-yl)methyl)benzoate (formula 1-2, 0.100 g, 0.381 mmol) was dissolved in methylene chloride (1 mL), and then 2-phenylacetyl chloride (0.065 g, 0.419 mmol) and TEA (0.106 mL, 0.762 mmol) were added thereto. The mixture was stirred at room temperature for 15 hours, and then water was added to the reaction mixture, followed by extraction with ethyl acetate. The organic layer was separated and concentrated under reduced pressure. The concentrate was purified by column chromatography (silicon dioxide; methanol/methylene chloride=5%) and concentrated to afford the desired compound (0.042 g, 29.0%) as a white solid.

Step 2: Synthesis of Compound 146

Methyl 4-(((3R,5S)-3,5-dimethyl-4-(2-phenylacetyl)piperazin-1-yl)methyl)benzoate (formula 1-3, 0.030 g, 0.079 mmol) was dissolved in methanol (0.5 mL), and hydroxylamine (0.096 mL, 1.577 mmol, 50.00% aqueous solution) and potassium hydroxide (0.044 g, 0.788 mmol) were added thereto. The mixture was stirred at room temperature for 1 hour, and then saturated sodium hydrogen carbonate was added to the reaction mixture, followed by extraction with ethyl acetate. The organic layer was concentrated under reduced pressure to yield compound 146 (0.014 g, 46.5%) as a pale yellow solid.

$^1$H NMR (400 MHz, DMSO-$d_6$) 57.69 (d, 2 H, J=8.0 Hz), 7.34 (d, 2 H, J=8.0 Hz), 7.31-7.27 (m, 2 H), 7.22-7.20 (m, 3 H), 4.41 (brs, 1 H), 4.12 (brs, 1 H), 3.47-3.33 (m, 2 H), 3.31 (s, 2 H), 2.62-2.59 (m, 2 H), 2.02-2.01 (m, 2 H), 1.22 (brs, 6 H).

Example 34

Synthesis of Compound 147

(4-(((3R,5S)-4-ethyl-3,5-dimethylpiperazin-1-yl)methyl)-N-hydroxybenzamide)

Step 1: Synthesis of Methyl 4-(((3R,5S)-4-ethyl-3,5-dimethylpiperazin-1-yl)methyl)benzoate Methyl 4-(((3R,5S)-3,5-dimethylpiperazin-1-yl)methyl)benzoate (formula 1-2, 0.100 g, 0.381 mmol), iodoethane (0.037 mL, 0.457 mmol) and $K_2CO_3$ (0.105 g, 0.762 mmol) were dissolved in acetonitrile (1 mL) and stirred at room temperature for 7 hours. Water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.059 g, 53.3%) as a pale yellow solid.

Step 2: Synthesis of Compound 147

Methyl 4-(((3R,5S)-3,5-dimethylpiperazin-1-yl)methyl)benzoate (formula 1-3, 0.040 g, 0.174 mmol) was dissolved in methanol (0.5 mL), and then hydroxylamine (0.213 mL, 3.487 mmol, 50.00% aqueous solution) and potassium hydroxide (0.098 g, 1.744 mmol) were added thereto. The mixture was stirred at room temperature for 1 hour, and then the reaction mixture was concentrated under reduced pressure to remove the solvent. A saturated aqueous solution of sodium hydrogen carbonate was added to the concentrate, followed by extraction with ethylacetate. The organic layer was washed with a saturated aqueous solution of sodium chloride, dried with anhydrous sodium sulfate, and then concentrated under reduced pressure. Compound 147 (0.010 g, 19.7%) was obtained as a brown solid.

$^1$H NMR (400 MHz, DMSO-$d_6$) δ 7.65 (d, 2 H, J=7.8 Hz), 7.20 (d, 2 H, J=7.9 Hz), 2.73 (q, 2 H, J=7.6 Hz), 2.61-2.55 (m, 4 H), 1.70-1.66 (m, 2 H), 0.90 (d, 6 H, J=5.9 Hz), 0.81 (t, 3 H, J 5=7.0 Hz).

Compound 35: Synthesis of Compound 148 (4-(((3R,5S)-3,5-dimethyl-4-propylpiperazin-1-yl)methyl)-N-hydroxybenzamide)

Step 1: Synthesis of Methyl 4-(((3R,5S)-3,5-dimethyl-4-propylpiperazin-1-yl)methyl)benzoate Methyl 4-(((3R,5S)-3,5-dimethylpiperazin-1-yl)methyl)benzoate (formula 1-2, 0.100 g, 0.381 mmol), iodopropane (0.045 mL, 0.457 mmol) and $K_2CO_3$ (0.105 g, 0.762 mmol) were dissolved in acetonitrile (1 mL) and stirred at room temperature for 7 hours. Water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.054 g, 46.5%) as a white solid.

Step 2: Synthesis of Compound 148

Methyl 4-(((3R,5S)-3,5-dimethyl-4-propylpiperazin-1-yl)methyl)benzoate (formula 1-3, 0.040 g, 0.131 mmol) was dissolved in methanol (0.5 mL), and then hydroxylamine (0.161 mL, 3.487 mmol, 50.00% aqueous solution) and potassium hydroxide (0.074 g, 1.314 mmol) were added thereto. The mixture was stirred at room temperature for 1 hour, and then the reaction mixture was concentrated under reduced pressure to remove the solvent. A saturated aqueous solution of sodium hydrogen carbonate was added to the concentrate, followed by extraction with ethyl acetate. The organic layer was washed with a saturated aqueous solution of sodium chloride, dried with anhydrous sodium sulfate, and then concentrated under reduced pressure. Compound 148 (0.017 g, 42.4%) was obtained as a brown solid.

$^1$H NMR (400 MHz, DMSO-$d_6$) δ 7.66 (d, 2 H, J=8.0 Hz), 7.21 (d, 2 H, J=8.0 Hz), 3.35 (s, 2 H), 2.60-2.52 (m, 6 H), 1.68 (t, 2 H, J=10.4 Hz), 1.32-1.30 (m, 2 H), 0.90 (d, 6 H, J=6.0 Hz), 0.76 (t, 3 H, J=7.4 Hz).

Example 36

Synthesis of Compound 149

(4-(((3R,5S)-3,5-dimethyl-4-(2,2,2-trifluoroethyl)piperazin-1-yl)methyl)-N-hydroxybenzamide)

Step 1: Synthesis of Methyl 4-(((3R,5S)-3,5-dimethyl-4-(2,2,2-trifluoroethyl)piperazin-1-yl)methyl)benzoate Methyl 4-(((3R,5S)-3,5-dimethylpiperazin-1-yl)methyl)benzoate (formula 1-2, 0.100 g, 0.381 mmol), 2,2,2-trifluoroethyl trifluoromethane sulfonate (0.066 mL, 0.457 mmol) and $K_2CO_3$ (0.105 g, 0.762 mmol) were dissolved in acetonitrile (1 mL) and stirred at room temperature for 12 hours. Water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.062 g, 47.2%) as a white oil.

Step 2: Synthesis of Compound 149

Methyl 4-(((3R,5S)-3,5-dimethyl-4-(2,2,2-trifluoroethyl)piperazin-1-yl)methyl)benzoate (formula 1-3, 0.030 g, 0.087 mmol) was dissolved in methanol (0.5 mL), and then hydroxylamine (0.107 mL, 1.742 mmol, 50.00% aqueous solution) and potassium hydroxide (0.049 g, 1.744 mmol) were added thereto. The mixture was stirred at room temperature for 1 hour, and then the reaction mixture was concentrated under reduced pressure to remove the solvent. A saturated aqueous solution of sodium hydrogen carbonate was added to the concentrate, followed by extraction with methylene chloride. The organic layer was washed with a saturated aqueous solution of sodium chloride, dried with anhydrous sodium sulfate, and then concentrated under reduced pressure. Compound 149 (0.011 g, 36.6%) was obtained as a brown solid.

$^1$H NMR (400 MHz, DMSO-$d_6$) δ 7.68 (d, 2 H, J=7.9 Hz), 7.31 (d, 2 H, J=8.0 Hz), 3.41 (s, 2 H), 3.28 (s, 2 H), 2.70-2.63 (m, 2 H), 2.60-2.49 (m, 2 H), 1.73 (t, 2 H, J=10.5 Hz), 0.96 (d, 6 H, J=6.2 Hz).

Example 37

Synthesis of Compound 154

(6-((3R,5S)-4-benzyl-3,5-dimethylpiperazin-1-yl)-N-hydroxyhexanamide)

Step 1: Synthesis of Ethyl 6-((3R,5S)-4-benzyl-3,5-dimethylpiperazin-1-yl)hexanoate (2S,6R)-1-benzyl-2,6-dimethylpiperazin (formula 8-3, 0.100 g, 0.489 mmol) was dissolved in acetonitrile (1 mL), and then ethyl 6-bromohexanoate (formula 8-4, 0.131 g, 0.587 mmol) and $Cs_2CO_3$ (0.319 g, 0.979 mmol) were added thereto. The mixture was stirred at room temperature for 20 hours, and then water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=20%) and concentrated to afford the desired compound (0.090 g, 53.1%) as a white oil.

Step 2: Synthesis of Compound 154

Ethyl 6-((3R,5S)-4-benzyl-3,5-dimethylpiperazin-1-yl)hexanoate (formula 8-5, 0.040 g, 0.115 mmol) was dissolved in methanol (0.5 mL), and hydroxylamine (0.141 mL, 2.309 mmol, 50.00% aqueous solution) and potassium hydroxide (0.065 g, 1.154 mmol) were added thereto. The mixture was stirred at room temperature for 1 hour, and then the reaction mixture was concentrated under reduced pressure to remove the solvent. Saturated sodium hydrogen carbonate was added to the concentrate, followed by extraction with methylene chloride. The organic layer was washed with a saturated aqueous solution of sodium chloride, dried with anhydrous sodium sulfate, and then concentrated under reduced pressure to yield compound 154 (0.021 g, 54.6%) as a white solid.

$^1$H NMR (400 MHz, DMSO-$d_6$) δ 7.33-7.24 (m, 4 H), 7.17-7.15 (m, 1 H), 3.69 (s, 2 H), 2.68-2.53 (m, 4 H), 2.13 (t, 2 H, J=7.2 Hz), 1.86 (t, 2 H, J=7.4 Hz), 1.66 (t, 2 H, J=10.6 Hz), 1.45-1.34 (m, 4 H), 1.20-1.18 (m, 2 H), 0.84 (d, 6 H, J=8.0 Hz).

Example 38

Synthesis of Compound 159

((2S,6R)-4-(4-(hydroxycarbamoyl)benzyl)-2,6-dimethyl-N-phenylpiperazine-1-carboxamide)

Step 1: Synthesis of Methyl 4-(((3R,5S)-3,5-dimethyl-4-(phenylcarbamoyl)piperazin-1-yl)methyl)benzoate Methyl 4-(((3R,5S)-3,5-dimethylpiperazin-1-yl)methyl)benzoate (compound 1-2, 0.150 g, 0.572 mmol) was dissolved in methylene chloride (2 mL), and then phenyl isocyanate (0.069 mL, 0.629 mmol) and TEA (0.119 mL, 0.858 mmol) were added thereto. The mixture was stirred at 0° C. for 2 hours, and then stirred at room temperature for 2 hours. Water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=30%) and concentrated to afford the desired compound (0.171 g, 78.4%) as a white solid.

Step 2: Synthesis of Compound 159

Methyl 4-(((3R,5S)-3,5-dimethyl-4-(phenylcarbamoyl)piperazin-1-yl)methyl)benzoate (formula 1-3, 0.100 g, 0.262 mmol) was dissolved in methanol (2 mL), and then hydroxylamine (0.321 mL, 5.243 mmol, 50.00% aqueous solution) and potassium hydroxide (0.147 g, 2.621 mmol) were added thereto. The mixture was stirred at room temperature for 30 minutes, and then the reaction mixture was concentrated under reduced pressure to remove the solvent. Saturated sodium hydrogen carbonate was added to the concentrate, followed by extraction with methylene chloride. The organic layer was washed with a saturated aqueous solution of sodium chloride, dried with anhydrous sodium sulfate, and then concentrated under reduced pressure to yield compound 159 (0.030 g, 29.9%) as a white solid.

$^1$H NMR (400 MHz, $CD_3OD$) δ 8.22 (s, 1 H), 7.69 (d, 2 H, J=8.1 Hz), 7.44 (d, 2 H, J=7.4 Hz), 7.34-7.32 (m, 2 H), 6.92-6.89 (m, 1 H), 4.20-4.17 (m, 2 H), 7.50 (s, 2 H), 2.64 (d, 2 H, J=11.1 Hz), 2.12-2.08 (m, 2 H), 1.26 (d, 6 H, J=6.7 Hz); LRMS (ES) m/z 383.2 ($M^+$+1).

Example 39

Synthesis of Compound 160

((2S,6R)-4-(4-(hydroxycarbamoyl)benzyl)-2,6-dimethyl-N-o-tolylpiperazine-1-carboxamide)

Step 1: Synthesis of Methyl 4-(((3R,5S)-3,5-dimethyl-4-(o-tolylcarbamoyl)piperazin-1-yl)methyl)benzoate Methyl 4-(((3R,5S)-3,5-dimethylpiperazin-1-yl)methyl)benzoate (formula 1-2, 0.200 g, 0.762 mmol) was dissolved in methylene chloride (3 mL), and then o-tolyl isocyanate (0.103 mL, 0.839 mmol) and TEA (0.159 mL, 1.144 mmol) were added thereto. The mixture was stirred at 0° C. for 2 hours, and then stirred at room temperature for 1 hour. Water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.030 g, 10.0%) as a white solid.

Step 2: Synthesis of Compound 160

Methyl 4-(((3R,5S)-3,5-dimethyl-4-(o-tolylcarbamoyl)piperazin-1-yl)methyl)benzoate (formula 1-3, 0.030 g, 0.076 mmol) was dissolved in methanol (2 mL), and hydroxylamine (0.093 mL, 1.517 mmol, 50.00% aqueous solution) and potassium hydroxide (0.043 g, 0.759 mmol) were added thereto. The mixture was stirred at room temperature for 30 minutes, and then the reaction mixture was concentrated under reduced pressure to remove the solvent. Saturated sodium hydrogen carbonate was added to the concentrate, followed by extraction with methylene chloride. The organic layer was washed with a saturated aqueous solution of sodium chloride, dried with anhydrous sodium sulfate, and then concentrated under reduced pressure to yield compound 160 (0.010 g, 33.3%) as a white solid.

$^1$H NMR (400 MHz, DMSO-d$_6$) δ 11.10 (s, 1 H), 9.00 (s, 1 H), 7.85 (s, 1 H), 7.72 (d, 2 H, J=8.2 Hz), 7.43 (d, 2 H, J=8.0 Hz), 7.17-7.10 (m, 3 H), 7.03 (dd, 1 H, J=10.2, 3.6 Hz), 3.54 (s, 2 H), 2.65 (d, 2 H, J=11.2 Hz), 2.16 (s, 3 H), 2.12-2.13 (m, 1 H). 1.30 (d, 6 H, J=6.6 Hz); LRMS (ES) m/z 397.2 (M$^+$+1).

Example 40

Synthesis of Compound 161

((2S,6R)-N-benzyl-4-(4-(hydroxycarbamoyl)benzyl)-2,6-dimethylpiperazine-1-carboxamide)

Step 1: Synthesis of Methyl 4-(((3R,5S)-4-(benzylcarbamoyl)-3,5-dimethylpiperazin-1-yl)methyl)benzoate Methyl 4-(((3R,5S)-3,5-dimethylpiperazin-1-yl)methyl)benzoate (formula 1-2, 0.150 g, 0.572 mmol) was dissolved in methylene chloride (2 mL), and then benzyl isocyanate (0.078 mL, 0.629 mmol) and TEA (0.119 mL, 0.858 mmol) were added thereto at 0° C. The mixture was stirred at room temperature for 1 hour. Water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=30%) and concentrated to afford the desired compound (0.517 g, 69.4%) as a white solid.

Step 2: Synthesis of Compound 161

Methyl 4-(((3R,5S)-4-(benzylcarbamoyl)-3,5-dimethylpiperazin-1-yl)methyl)benzoate (formula 1-3, 0.100 g, 0.253 mmol) was dissolved in methanol (2 mL), and hydroxylamine (0.309 mL, 5.057 mmol, 50.00% aqueous solution) and potassium hydroxide (0.114 g, 2.529 mmol) were added thereto. The mixture was stirred at room temperature for 30 minutes, and then the reaction mixture was concentrated under reduced pressure to remove the solvent. Saturated sodium hydrogen carbonate was added to the concentrate, followed by extraction with methylene chloride. The organic layer was washed with a saturated aqueous solution of sodium chloride, dried with anhydrous sodium sulfate, and then concentrated under reduced pressure to yield compound 161 (0.062 g, 61.8%) as a white solid.

$^1$H NMR (400 MHz, DMSO-d$_6$) δ 11.10 (s, 1 H), 9.10 (s, 1 H), 7.71 (d, 2 H, J=8.0 Hz), 7.41 (d, 2 H, J=7.9 Hz), 7.31-7.27 (m, 2 H), 7.24-7.18 (m, 3 H), 6.91-6.90 (m, 1 H), 4.25 (d, 2 H, J=5.5 Hz), 4.04-4.03 (m, 2 H), 3.51 (s, 2 H), 2.60 (d, 2 H, J=11.0 Hz), 2.08-2.05 (m, 2 H), 1.22 (d, 6 , J=6.6 Hz).

Example 41

Synthesis of Compound 162

((3R,5S)-4-(4-(hydroxycarbamoyl)benzyl)-3,5-dimethyl-N-phenylpiperazine-1-carboxamide)

Step 1: Synthesis of 4-(((2S,6R)-2,6-dimethyl-4-(phenylcarbamoyl)piperazin-1-yl)methyl)benzoate Methyl 4-(((2S,6R)-2,6-dimethylpiperazin-1-yl)methyl)benzoate (formula 13-2, 0.150 g, 0.572 mmol) was dissolved in methylene chloride (4 mL), and then phenyl isocyanate (0.069 mL, 0.629 mmol) and TEA (0.119 mL, 0.858 mmol) were added thereto. The mixture was stirred at room temperature for 1 hour, and then water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=25%) and concentrated to afford the desired compound (0.217 g, 99.5%) as a pale yellow oil.

Step 2: Synthesis of Compound 162

Methyl 4-(((2S,6R)-2,6-dimethyl-4-(phenylcarbonyl)piperazin-1-yl)methyl)benzoate (formula 13-3, 0.107 g, 0.280 mmol) was dissolved in methanol (3 mL), and then hydroxylamine (0.343 mL, 5.610 mmol, 50.00% aqueous solution) and potassium hydroxide (0.157 g, 2.805 mmol) were added thereto. The mixture was stirred at room temperature for 30 minutes, and then the reaction mixture was concentrated under reduced pressure. Saturated sodium hydrogen carbonate was added to the concentrate, followed by stirring. The precipitated solid was filtered and dried to yield compound 162 (0.041 g, 38.2%) as a white solid.

$^1$H NMR (400 MHz, DMSO-d$_6$) δ 11.20 (s, 1 H), 9.00 (s, 1 H), 8.48 (s, 1 H), 7.68 (d, 2 H, J=8.0 Hz), 7.45-7.42 (m, 4 H), 7.22 (dd, 2 H, J=10.2, 3.6 Hz), 6.93-6.91 (m, 1 H), 3.97 (d, 2 H, J=13.3 Hz), 3.78 (s, 2 H), 2.63-2.60 (m, 1 H), 0.97 (d, 6 H, J=6.0 Hz); LRMS (ES) m/z 383.2 (M$^+$+1).

Example 42

Synthesis of Compound 163

((3R,5S)-4-(4-(hydroxycarbamoyl)benzyl)-N-(2-methoxyphenyl)-3,5-dimethylpiperazine-1-carboxamide)

Step 1: Synthesis of Methyl 4-(((2S,6R)-4-(2-methoxyphenylcarbamoyl)-2,6-dimethylpiperazin-1-yl)methyl)benzoate Methyl 4-(((2S,6R)-2,6-dimethylpiperazin-1-yl)methyl)benzoate (formula 13-2, 0.150 g, 0.572 mmol) was dissolved in methylene chloride (4 mL), and then 2-methoxyphenyl isocyanate (0.094 g, 0.629 mmol) and TEA (0.119 mL, 0.858 mmol) were added thereto. The mixture was stirred at room temperature for 1 hour, and then water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=25%) and concentrated to afford the desired compound (0.169 g, 71.8%) as a pale yellow oil.

Step 2: Synthesis of Compound 163

Methyl 4-(((2S,6R)-4-(2-methoxyphenylcarbamoyl)-2,6-dimethylpiperazin-1-yl)methyl)benzoate (formula 13-3, 0.100 g, 0.243 mmol) was dissolved in methanol (3 mL), and then hydroxylamine (0.297 mL, 4.860 mmol, 50.00% aqueous solution) and potassium hydroxide (0.136 g, 2.430 mmol) were added thereto. The mixture was stirred at room temperature for 30 minutes, and then saturated sodium hydrogen carbonate was added to the reaction mixture, followed by extraction with methylene chloride. The organic layer was washed with a saturated aqueous solution of sodium chloride, dried with anhydrous sodium sulfate, and then concentrated under reduced pressure. Compound 163 (0.060 g, 59.9%) was obtained as a white solid.

$^1$H NMR (400 MHz, DMSO-$d_6$) δ 7.68-7.65 (m, 3 H), 7.56 (d, 1 H, J=8.0 Hz), 7.39 (d, 2 H, J=8.2 Hz), 7.00-6.98 (m, 2 H), 6.87-6.85 (m, 1 H), 3.88 (d, 2 H, J=11.6 Hz), 3.78 (s, 3 H), 3.76 (s, 2 H), 2.69-2.63 (m, 2 H), 2.55-2.52 (m, 2 H), 0.96 (d, 6 H, J=6.0 Hz); LRMS (ES) m/z 413.2 (M$^+$+1).

Example 43

Synthesis of Compound 164

((3R,5S)-4-(4-(hydroxycarbamoyl)benzyl)-N-(3-methoxyphenyl)-3,5-dimethylpiperazine-1-carboxamide)

Step 1: Synthesis of Methyl 4-(((2S,6R)-4-(3-methoxyphenylcarbamoyl)-2,6-dimethylpiperazin-1-yl)methyl)benzoate Methyl 4-(((2S,6R)-2,6-dimethylpiperazin-1-yl)methyl)benzoate (formula 13-2, 0.150 g, 0.572 mmol) was dissolved in methylene chloride (4 mL), and then 3-methoxyphenyl isocyanate (0.094 g, 0.629 mmol) and TEA (0.119 mL, 0.858 mmol) were added thereto. The mixture was stirred at room temperature for 1 hour, and then water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=25%) and concentrated to afford the desired compound (0.210 g, 89.3%) as a pale yellow oil.

Step 2: Synthesis of Compound 164

Methyl 4-(((2S,6R)-4-(3-methoxyphenylcarbamoyl)-2,6-dimethylpiperazin-1-yl)methyl)benzoate (formula 13-3, 0.100 g, 0.243 mmol) was dissolved in methanol (3 mL), and then hydroxylamine (0.297 mL, 4.860 mmol, 50.00% aqueous solution) and potassium hydroxide (0.136 g, 2.430 mmol) were added thereto. The mixture was stirred at room temperature for 30 minutes, and then saturated sodium hydrogen carbonate was added to the reaction mixture, followed by extraction with methylene chloride. The organic layer was washed with a saturated aqueous solution of sodium chloride, dried with anhydrous sodium sulfate, and then concentrated under reduced pressure. Compound 164 (0.025 g, 24.9%) was obtained as a white solid.

$^1$H NMR (400 MHz, DMSO-$d_6$) δ 11.10 (s, 1 H), 9.00 (s, 1 H), 8.46 (s, 1 H), 7.67 (d, 2 H, J=8.2 Hz), 7.43 (d, 2 H, J=8.2 Hz), 7.14-7.11 (m, 1 H), 7.09-7.02 (m, 1 H), 6.57 (dd, 1 H, J=10.2, 3.6 Hz), 3.95 (d, 2 H, J=12.8 Hz), 3.77 (s, 2 H), 3.69 (s, 3 H), 2.35-2.54 (m, 2 H), 2.50-2.48 (m, 2 H), 0.96 (d, 6 H , J=6.0 Hz); LRMS (ES) m/z 413.2 (M$^+$+1).

EXAMPLE 44

Synthesis of Compound 165

((3R,5S)-4-(4-(hydroxycarbamoyl)benzyl)-N-(4-methoxyphenyl)-3,5-dimethylpiperazine-1-carboxamide)

Step 1: Synthesis of Methyl 4-(((2S,6R)-4-(4-methoxyphenylcarbamoyl)-2,6-dimethylpiperazin-1-yl)methyl)benzoate Methyl 4-(((2S,6R)-2,6-dimethylpiperazin-1-yl)methyl)benzoate (formula 13-2, 0.150 g, 0.572 mmol) was dissolved in methylene chloride (4 mL), and then 4-methoxyphenyl isocyanate (0.094 g, 0.629 mmol) and TEA (0.119 mL, 0.858 mmol) were added thereto. The mixture was stirred at room temperature for 1 hour, and then water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=30%) and concentrated to afford the desired compound (0.022 g, 9.4%) as a pale yellow oil.

Step 2: Synthesis of Compound 165

Methyl 4-(((2S,6R)-4-(4-methoxyphenylcarbamoyl)-2,6-dimethylpiperazin-1-yl)methyl)benzoate (formula 13-3, 0.022 g, 0.053 mmol) was dissolved in methanol (3 mL), and then hydroxylamine (0.065 mL, 1.069 mmol, 50.00% aqueous solution) and potassium hydroxide (0.03 g, 0.535 mmol) were added thereto. The mixture was stirred at room temperature for 30 minutes, and then the reaction mixture was concentrated under reduced pressure. Saturated sodium hydrogen carbonate was added to the concentrate, followed by stirring. The precipitated solid was filtered and dried to yield compound 165 (0.008 g, 36.3%) as a white solid.

$^1$H NMR (400 MHz, DMSO-$d_6$) δ 8.31 (s, 1 H), 7.67 (d, 2 H, J=8.2 Hz), 7.40 (d, 2 H, J=8.2 Hz), 7.31 (d, 2 H, J=9.1 Hz), 6.80 (d, 2 H, J=9.1 Hz), 6.80 (d, 2 H, J=9.1 Hz), 3.94 (d, 2 H, J=12.3 Hz), 3.76 (s, 2 H), 3.69 (s, 3 ), 2.66-2.25 (m, 4 H), 0.96 (d, 6 H, J=6.0 Hz); LRMS (ES) m/z 413.2 (M$^+$+1).

Example 45

Synthesis of Compound 166

((3R,5S)-4-(4-(hydroxycarbamoyl)benzyl)-3,5-dimethyl-N-o-tolylpiperazine-1-carboxamide)

Step 1: Synthesis of Methyl 4-(((2S,6R)-2,6-dimethyl-4-(o-tolylcarbamoyl)piperazin-1-yl)methyl) benzoate Methyl 4-(((2S,6R)-2,6-dimethylpiperazin-1-yl)methyl)benzoate (formula 13-2, 0.150 g, 0.572 mmol) was dissolved in methylene chloride (4 mL), and then o-tolyl isocyanate (0.078 mL, 0.629 mmol) and TEA (0.119 mL, 0.858 mmol) were added thereto at 0° C. The mixture was stirred at room temperature for 1 hour, and then water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=30%) and concentrated to afford the desired compound (0.182 g, 80.5%) as a white solid.

Step 2: Synthesis of Compound 166

Methyl 4-(((2S,6R)-2,6-dimethyl-4-(o-tolylcarbamoyl)piperazin-1-yl)methyl)benzoate (formula 13-3, 0.082 g, 0.207 mmol) was dissolved in methanol (3 mL), and then hydroxylamine (0.254 mL, 4.147 mmol, 50.00% aqueous solution) and potassium hydroxide (0.116 g, 2.073 mmol) were added thereto. The mixture was stirred at room temperature for 30 minutes, and then the reaction mixture was concentrated under reduced pressure. Saturated sodium hydrogen carbonate was added to the concentrate, followed by stirring. The precipitated solid was filtered and dried to yield compound 166 (0.010 g, 12.2%) as a white solid.

$^1$H NMR (400 MHz, DMSO-$d_6$) δ 8.04 (s, 1 H), 7.66 (d, 2 H, J=8.1 Hz), 7.34 (d, 2 H, J=8.1 Hz), 7.16-7.10 (m, 3 H), 7.04-7.02 (m, 1 H), 3.90 (d, 2 H, J=13.6 Hz), 3.76 (s, 2 H), 2.69-2.63 (m, 2 H), 2.54-2.50 (m, 2 H), 2.12 (s, 3 H), 0.97 (d, 6, J=6.0 Hz); LRMS (ES) m/z 397.2 (M$^+$+1).

Example 46

Synthesis of Compound 167

((3R,5S)-4-(4-(hydroxycarbamoyl)benzyl)-3,5-dimethyl-N-m-tolylpiperazine-1-carboxamide)

Step 1: Synthesis of Methyl 4-(((2S,6R)-2,6-dimethyl-4-(m-tolylcarbamoyl)piperazin-1-yl)methyl)benzoate Methyl 4-(((2S,6R)-2,6-dimethylpiperazin-1-yl)methyl)benzoate (formula 13-2, 0.150 g, 0.572 mmol) was dissolved in methylene chloride (4 mL), and then m-tolyl isocyanate (0.084 mL, 0.629 mmol) and TEA (0.119 mL, 0.858 mmol) were added thereto at 0° C. The mixture was stirred at room temperature for 1 hour, and then water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=30%) and concentrated to afford the desired compound (0.170 g, 75.2%) as a white solid.

Step 2: Synthesis of Compound 167

Methyl 4-(((2S,6R)-2,6-dimethyl-4-(m-tolylcarbamoyl)piperazin-1-yl)methyl)benzoate (formula 13-3, 0.070 g, 0.177 mmol) was dissolved in methanol (3 mL), and then hydroxylamine (0.217 mL, 3.540 mmol, 50.00% aqueous solution) and potassium hydroxide (0.099 g, 1.770 mmol) were added thereto. The mixture was stirred at room temperature for 30 minutes, and then the reaction mixture was concentrated under reduced pressure. Saturated sodium hydrogen carbonate was added to the concentrate, followed by stirring. The precipitated solid was filtered and dried to yield compound 167 (0.008 g, 36.3%) as a white solid.

$^1$H NMR (400 MHz, DMSO-$d_6$) δ 8.40 (s, 1 H), 7.68 (d, 2 H, J=8.2 Hz), 7.41 (d, 2 H, J=8.2 Hz), 7.26-7.24 (m, 2 H), 7.11 (dd, 1 H, J=10.2, 3.6 Hz), 6.74 (d, 2 H, J=7.2 Hz), 3.96 (d, 2 H, J=13.0 Hz), 3.77 (s, 2 H), 2.65-2.59 (m, 4 H), 2.24 (s, 3 H), 0.96 (d, 6 H, J=6.0 Hz); LRMS (ES) m/z 397.2 (M$^+$+1).

Example 47

Synthesis of Compound 168

((3R,5S)-N-benzyl-4-(4-(hydroxycarbamoyl)benzyl)-3,5-dimethylpiperazine-1-carboxamide)

Step 1: Synthesis of Methyl 4-(((2S,6R)-4-(benzylcarbamoyl)-2,6-dimethylpiperazin-1-yl)methyl)benzoate Methyl 4-(((2S,6R)-2,6-dimethylpiperazin-1-yl)methyl)benzoate (formula 13-2, 0.150 g, 0.572 mmol) was dissolved in methylene chloride (4 mL), and then benzyl isocyanate (0.078 mL, 0.629 mmol) and TEA (0.119 mL, 0.858 mmol) were added thereto at 0° C. The mixture was stirred at room temperature for 1 hour, and then water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=30%) and concentrated to afford the desired compound (0.115 g, 50.9%) as a pale yellow solid.

Step 2: Synthesis of Compound 168

Methyl 4-(((2S,6R)-4-(benzylcarbamoyl)-2,6-dimethylpiperazin-1-yl)methyl)benzoate (formula 13-3, 0.060 g, 0.152 mmol) was dissolved in methanol (3 mL), and then hydroxylamine (0.186 mL, 3.034 mmol, 50.00% aqueous solution) and potassium hydroxide (0.085 g, 1.517 mmol) were added thereto. The mixture was stirred at room temperature for 30 minutes, and then the reaction mixture was concentrated under reduced pressure. Saturated sodium hydrogen carbonate was added to the concentrate, followed by stirring. The precipitated solid was filtered and dried to yield compound 168 (0.045 g, 74.8%) as a white solid.

$^1$H NMR (400 MHz, DMSO-$d_6$) δ 11.05 (s, 1 H), 9.00 (s, 1 H), 7.67 (d, 2 H, J=8.2 Hz), 7.42 (d, 2 H, J=8.2 Hz), 7.30-7.19 (m, 5 H), 7.04-7.06 (m, 1 H), 4.22 (d, 2 H, J=5.8 Hz), 3.83 (d, 2 H, J=12.1 Hz), 3.75 (s, 2 H), 2.56-2.54 (m, 2 H), 2.45-2.43 (m, 2 H), 0.92 (d, 6 H, J=6.0 Hz); LRMS (ES) m/z 397.2 (M$^+$+1).

Example 48

Synthesis of Compound 171

(4-(((3R,5S)-4-benzyl-3,5-dimethylpiperazin-1-yl)methyl)-2-fluoro-N-hydroxybenzamide)

Step 1: Synthesis of Methyl 4-(((3R,5S)-4-benzyl-3,5-dimethylpiperazin-1-yl)methyl)-2-fluorobenzoate (2S,6R)-1-benzyl-2,6-dimethylpiperazin (formula 8-3, 0.200 g, 0.979 mmol) and methyl 4-formyl-2-fluorobenzoate (formula 8-4, 0.178 g, 0.979 mmol) were dissolved in tetrahydrofuran (5 mL), and acetic acid (0.028 mL, 0.979 mmol) was added thereto at room temperature, followed by stirring for 1 hour. Next, Na(CN)BH$_3$ (0.062 g, 0.979 mmol) was added to the reaction mixture, followed by stirring at the same temperature for 2 hours. Then, water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=25%) and concentrated to afford the desired compound (0.028 g, 7.2%) as a pale yellow oil.

Step 2: Synthesis of Compound 171

Methyl 4-(((3R,5S)-4-benzyl-3,5-dimethylpiperazin-1-yl)methyl)-2-fluorobenzoate (formula 8-5, 0.100 g, 0.264 mmol) was dissolved in methanol (3 mL), and then hydroxylamine (0.323 mL, 5.284 mmol, 50.00% aqueous solution) and potassium hydroxide (0.148 g, 2.642 mmol) were added thereto. The mixture was stirred at room temperature for 1 H our and 40 minutes, and then the reaction mixture was concentrated under reduced pressure to remove the solvent. A saturated aqueous solution of sodium hydrogen carbonate was added to the concentrate, followed by extraction with methylene chloride. The organic layer was washed with a saturated aqueous solution of sodium chloride, dried with anhydrous sodium sulfate, and then concentrated under reduced pressure. Compound 171 (0.034 g, 33.9%) was obtained as a pale orange solid.

$^1$H NMR (400 MHz, DMSO-$d_6$) δ 11.00 (brs, 1 H), 9.10 (brs, 1 H ), 7.47 (dd, 1 H, J=7.5, 7.5 Hz), 7.32 (d, 2 H , J=7.6 Hz), 7.26 (dd, 2 H, J=7.5, 7.5 Hz), 7.17-7.13 (m, 2 H), 3.71 (s, 2 H), 3.42 (s, 2 H), 2.63-2.53 (m, 4 H), 1.81 (t, 2 H, J=10.4 Hz), 0.88 (d, 6 H, J=6.0 Hz); LRMS (ES) m/z 372.2 ($M^+$+1).

Example 49

Synthesis of Compound 172

((E)-3-(4-(((3R,5S)-4-benzyl-3,5-dimethylpiperazin-1-yl)methyl)phenyl)-N-hydroxyacrylamide)

Step 1: Synthesis of (E)-Methyl 3-(4-(dimethoxymethyl)phenyl)acrylate (E)-3-(4-formylphenyl)acrylic acid (1.000 g, 5.676 mmol) was dissolved in methanol (10 mL), and SOCl$_2$ (0.824 mL, 11.353 mmol) was added thereto at 0° C., followed by stirring at room temperature for 3 hours. The reaction mixture was concentrated under reduced pressure to remove the solvent. Water was added to the concentrate, followed by extraction with methylene chloride. The organic layer was washed with a saturated aqueous solution of sodium chloride, dried with anhydrous magnesium sulfate, and then concentrated under reduced pressure to yield the desired compound (0.870 g, 64.9%) as a pale yellow solid.

Step 2: Synthesis of (E)-methyl 3-(4-formylphenyl)acrylate (E)-methyl 3-(4-(dimethoxymethyl)phenyl)acrylate (0.870 g, 3.682 mmol) was dissolved in methanol (15 mL) at room temperature, and HCl (15 mL, 1N methanol solution) was added thereto at the same temperature, followed by stirring for 2 hours and 30 minutes. The reaction mixture was concentrated under reduced pressure. A saturated aqueous solution of sodium hydrogen carbonate was added to the concentrate. The precipitated solid was filtered and dried to yield the desired compound (0.695 g, 99.2%) as a pale yellow solid.

Step 3: Synthesis of (E)-methyl 3-(4-(((3R,5S)-4-benzyl-3,5-dimethylpiperazin-1-yl)methyl)phenyl) acrylate (2S,6R)-1-benzyl-2,6-dimethylpiperazine (formula 8-3, 0.050 g, 0.245 mmol) and (E)-methyl 3-(4-formylphenyl) acrylate (0.047 g, 0.245 mmol) were dissolved in tetrahydrofuran (1 mL), and acetic acid (0.007 mL, 0.245 mmol) was added thereto at room temperature, followed by stirring for 1 hour. Na(CN)BH$_3$ (0.015 g, 0.245 mmol) was added to the reaction mixture, followed by stirring at the same temperature for 2 hours. Water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=25%) and concentrated to afford the desired compound (0.012 g, 13.0%) as a white solid.

Step 4: Synthesis of Compound 172

(E)-methyl 3-(4-(((3R,5S)-4-benzyl-3,5-dimethylpiperazin-1-yl)methyl)phenyl)acrylate (formula 8-5, 0.050 g, 0.135 mmol) was dissolved in methanol (3 mL), and then hydroxylamine (0.165 mL, 2.699 mmol, 50.00% aqueous solution) and potassium hydroxide (0.076 g, 1.350 mmol) were added thereto. The mixture was stirred at room temperature for 1 hour, and then the reaction mixture was concentrated under reduced pressure to remove the solvent. Saturated sodium hydrogen carbonate was added to the concentrate, followed by extraction with methylene chloride. The organic layer was washed with a saturated aqueous solution of sodium chloride, dried with anhydrous sodium sulfate, and then concentrated under reduced pressure to yield compound 172 (0.024 g, 47.9%) as a white solid.

$^1$H NMR (400 MHz, DMSO-$d_6$) δ 9.60 (brs, 1 H), 7.44 (d, 2 H, J=8.0 Hz), 7.32-7.24 (m, 7 H), 7.15 (dd, 1 H, J=7.1, 7.1 Hz), 6.39 (d, 1 H, J=15.8 Hz), 3.70 (s, 2 H), 3.37 (s, 2 H), 2.62 (d, 2 H, J=10.7 Hz), 2.56-2.52 (m, 2 H), 1.77 (t, 2 H, J=10.5 Hz), 0.87 (d, 6 H, J=6.1 Hz); LRMS (ES) m/z 380.5 ($M^+$+1).

Example 50

Synthesis of Compound 173

(2-(4-(((3R,5S)-4-benzyl-3,5-dimethylpiperazin-1-yl)methyl)phenyl)-N-hydroxyacetamide)

Step 1: Synthesis of Methyl 2-(4-(bromomethyl)phenyl)acetate 2-(4-(bromomethyl)phenyl)acetic acid (3.000 g, 13.096 mmol) was dissolved in methanol (30 mL), and SOCl$_2$ (1.900 mL, 26.193 mmol) was added thereto at 0° C., followed by stirring at the same temperature for 1 hour. Then, the reaction mixture was concentrated under reduced pressure to remove the solvent. A saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, and then concentrated under reduced pressure to yield the desired compound (3.140 g, 98.6%) as a colorless oil.

Step 2: Synthesis of methyl 2-(4-(((3R,5S)-4-benzyl-3,5-dimethylpiperazin-1-yl)methyl)phenyl)acetate (2S,6R)-1-benzyl-2,6-dimethylpiperazine (formula 8-3, 0.200 g, 0.979 mmol), methyl 2-(4-(bromomethyl)phenyl)acetate (formula 8-4, 0.238 g, 0.979 mmol) and $Cs_2CO_3$ (0.478 g, 1.468 mmol) were dissolved in acetonitrile (5 mL) at room temperature. The reaction solution was stirred at the same temperature for 2 hours, and then the reaction mixture was concentrated under reduced pressure to remove the solvent. Water was added to the concentrate, followed by extraction with ethylacetate. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=25%) and concentrated to afford the desired compound (0.273 g, 76.1%) as a pale yellow oil.

Step 3: Synthesis of Compound 173

Methyl 2-(4-(((3R,5S)-4-benzyl-3,5-dimethylpiperazin-1-yl)methyl)phenyl)acetate (formula 8-5, 0.173 g, 0.472 mmol) was dissolved in methanol (3 mL), and then hydroxylamine (0.577 mL, 9.441 mmol, 50.00% aqueous solution) and potassium hydroxide (0.265 g, 4.720 mmol) were added thereto. The mixture was stirred at room temperature for 1 hour, and then the reaction mixture was concentrated under reduced pressure to remove the solvent. Saturated sodium hydrogen carbonate (20 mL) was added to the concentrate, followed by stirring. The precipitated solid was filtered and dried to yield compound 173 (0.140 g, 80.7%) as a white solid.

$^1$H NMR (400 MHz, DMSO-$d_6$) δ 10.60 (brs, 1 H), 8.80 (brs, 1 H ), 7.31 (d, 2 H, J=7.3 Hz), 7.27-7.24 (m, 2 H), 7.17-7.15 (m, 5 H), 3.69 (s, 2 H), 3.33 (s, 2 H), 3.22 (s, 2 H), 2.61 (d, 2 H, J=10.1 Hz), 2.53-2.49 (m, 2 H), 1.75 (t, 2 H, J=10.5 Hz), 0.87 (d, 6 H, J=6.1 Hz); LRMS (ES) m/z 368.4 ($M^+$+1).

Example 51

Synthesis of Compound 174

(4-(((2S,6R)-4-benzyl-2,6-dimethylpiperazin-1-yl)methyl)-2-fluoro-N-hydroxybenzamide)

Step 1: Synthesis of Methyl 4-(((2S,6R)-4-benzyl-2,6-dimethylpiperazin-1-yl)methyl)-2-fluorobenzoate (3R,5S)-1-benzyl-3,5-dimethylpiperazine (formula 16-1, 0.200 g, 0.979 mmol) was dissolved in acetonitrile (3 mL), and then methyl 4-(bromomethyl)-2-fluorobenzoate (formula 8-4, 0.254 g, 1.028 mmol) and $Cs_2CO_3$ (0.478 g, 1.468 mmol) were added thereto. The mixture was stirred at 80° C. for 2 hours, and then water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=15%) and concentrated to afford the desired compound (0.211 g, 58.2%) as a pale yellow oil.

Step 2: Synthesis of Compound 174

Methyl 4-(((2S,6R)-4-benzyl-2,6-dimethylpiperazin-1-yl)methyl)-2-fluorobenzoate (formula 16-2, 0.100 g, 0.270 mmol) was dissolved in methanol (3 mL), and then hydroxylamine (0.330 mL, 5.339 mmol, 50.00% aqueous solution) and potassium hydroxide (0.151 g, 2.699 mmol) were added thereto. The mixture was stirred at room temperature for 30 minutes, and then the reaction mixture was concentrated under reduced pressure to remove the solvent. Saturated sodium hydrogen carbonate was added to the concentrate, followed by extraction with methylene chloride. The organic layer was washed with a saturated aqueous solution of sodium chloride, dried with anhydrous magnesium sulfate, and then concentrated under reduced pressure to yield compound 174 (0.058 g, 57.8%) as a white solid.

$^1$H NMR (400 MHz, DMSO-$d_6$) δ 7.46-7.44 (m, 1 H), 7.31-7.23 (m, 5 H), 7.20-7.16 (m, 2 H), 3.72 (s, 2 H), 3.40 (s, 2 H), 2.65 (d, 2 H, J=10.4 Hz), 2.56-2.54 (m, 2 H), 1.82-1.80 (m, 2 H), 0.85 (d, 6 H, J=6.1 Hz); LRMS (ES) m/z 372.4 ($M^+$+1).

Example 52

Synthesis of Compound 175

((E)-3-(4-(((2S,6R)-4-benzyl-2,6-dimethylpiperazin-1-yl)methyl)phenyl)-N-hydroxyacrylamide)

Step 1: Synthesis of (3R,5S)-1-benzyl-3,5-dimethylpiperazine (2S,6R)-2,6-dimethylpiperazine (1.000 g, 8.757 mmol) and $K_2CO_3$ (1.724 g, 13.136 mmol) were dissolved in acetonitrile (50 mL), and benzylbromide (1.092 mL, 9.195 mmol) was added thereto at 0° C., and the mixture was stirred at the same temperature for 1 hour and 30 minutes. Water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (1.170 g, 65.4%) as a yellow oil.

Step 2: Synthesis of (E)-Methyl 3-(4-(hydroxymethyl)phenyl)acrylate (E)-3-(4-(hydroxymethyl)phenyl)acrylic acid (0.300 g, 1.577 mmol) was dissolved in methanol (5 mL), and $NaBH_4$ (0.063 g, 1.656 mmol) was added thereto at room temperature, followed by stirring at the same temperature for 50 minutes. Water was added to the reaction mixture, followed by extraction with ethyl acetate. The organic layer was washed with a saturated aqueous solution of sodium chloride, dried with anhydrous magnesium sulfate, and then concentrated under reduced pressure to yield the desired compound (0.284 g, 93.7%) as a white solid.

Step 3: Synthesis of (E)-Methyl 3-(4-(bromomethyl))phenyl)acrylate (E)-methyl 3-(4-(hydroxymethyl)phenyl)acrylate (0.284 g, 1.478 mmol) was dissolved in toluene (10 mL), and $PBr_3$ (0.042 mL, 0.443 mmol) was added thereto at 0° C., followed by stirring at the room temperature for 30 minutes. Water was added to the reaction mixture, followed by extraction with ethyl acetate. The organic layer was washed with a saturated aqueous solution of sodium chloride, dried with anhydrous magnesium sulfate, and then concentrated under reduced pressure to yield the desired compound (0.260 g, 69.0%) as a white solid.

Step 4: Synthesis of (E)-Methyl 3-(4-(((2S,6R)-4-benzyl-2,6-dimethylpiperazin-1-yl)methyl)phenyl) acrylate (3R,5S)-1-benzyl-3,5-dimethylpiperazine (formula 16-1, 0.200 g, 0.979 mmol), (E)-methyl 3-(4-(bromomethyl))phenyl)acrylate (formula 8-4, 0.250 g, 0.979 mmol) and $Cs_2CO_3$ (0.478 g, 1.468 mmol) were dissolved in acetonitrile (5 mL) at 80° C., and the reaction solution was stirred at the same temperature for 1 hour and 40 minutes. Then, water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=15%) and concentrated to afford the desired compound (0.078 g, 21.1%) as a yellow oil.

Step 5: Synthesis of Compound 175

(E)-methyl 3-(4-(((2S,6R)-4-benzyl-2,6-dimethylpiperazin-1-yl)methyl)phen yl)acrylate (formula 16-2, 0.078 g, 0.206 mmol) was dissolved in methanol (1.5 mL), and then hydroxylamine (0.252 mL, 4.121 mmol, 50.00% aqueous solution) and potassium hydroxide (0.116 g, 2.061 mmol) were added thereto. The mixture was stirred at room temperature for 1 hour, and then the reaction mixture was concentrated under reduced pressure to remove the solvent. Saturated sodium hydrogen carbonate was added to the resulting concentrate, followed by extraction with methylene chloride. The organic layer was washed with a saturated aqueous solution of sodium chloride, dried with anhydrous magnesium sulfate, and then concentrated under reduced pressure to yield compound 175 (0.040 g, 51.1%) as an orange solid.
$^1$H NMR (400 MHz, DMSO-$d_6$) δ 10.00 (s, 2 H), 7.45 (d, 2 H, J=8.0 Hz), 7.36-7.21 (m, 8 H), 6.40 (d, 1 H, J=15.7 Hz), 3.71 (s, 2 H), 3.39 (s, 2 H), 2.64 (d, 2 H, J=10.6 Hz), 2.59-2.54 (m, 2 H), 1.81-1.76 (m, 2 H), 0.87 (d, 6 H, J=6.0 Hz); LRMS (ES) m/z 380.4 (M$^+$+1).

Example 53

Synthesis of Compound 176

(2-(4-(((2S,6R)-4-benzyl-2,6-dimethylpiperazin-1-yl)methyl)phenyl)-N-hydroxyacetamide)

Step 1: Synthesis of Methyl 2-(4-(((2S,6R)-4-benzyl-2,6-dimethylpiperazin-1-yl)methyl)phenyl)acetate (3R,5S)-1-benzyl-3,5-dimethylpiperazine (formula 16-1, 0.200 g, 0.979 mmol), methyl 2-(4-(bromomethyl)phenyl) acetate (formula 8-4, 0.238 g, 0.979 mmol) and $Cs_2CO_3$ (0.478 g, 1.468 mmol) were dissolved in acetonitrile (5 mL) at room temperature. The reaction solution was stirred at the same temperature for 5 hours, and then the reaction mixture was concentrated under reduced pressure to remove the solvent. Water was added to the resulting concentrate, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=30%) and concentrated to yield the desired compound (0.274 g, 76.4%) as a pale yellow oil.

Step 2: Synthesis of Compound 176

Methyl 2-(4-(((2S,6R)-4-benzyl-2,6-dimethylpiperazin-1-yl)methyl)phen yl)acetate (formula 16-2, 0.143 g, 0.390 mmol) was dissolved in methanol (3 mL), and then hydroxylamine (0.477 mL, 7.804 mmol, 50.00% aqueous solution) and potassium hydroxide (0.219 g, 3.9902 mmol) were added thereto. The mixture was stirred at room temperature for 1 hour, and then the reaction mixture was concentrated under reduced pressure. Saturated sodium hydrogen carbonate (5 mL) was added to the concentrate, followed by stirring. The precipitated solid was filtered and dried to yield compound 176 (0.105 g, 73.2%) as a white solid.
$^1$H NMR (400 MHz, DMSO-$d_6$) δ 10.50 (s, 1 H), 9.00 (s, 1 H), 7.32-7.21 (m, 1 H), 7.16 (d, 2 H, J=7.9 Hz), 3.69 (s, 2 H), 3.37 (s, 2 H), 3.22 (s, 2 H), 2.62 (d, 2 H, J=10.8 Hz), 2.56-2.52 (m, 1 H), 1.80-1.75 (m, 1 H), 0.88 (d, 6 H, J=6.0 Hz); LRMS (ES) m/z 368.5 (M$^+$+1).

Example 54

Synthesis of Compound 177

(phenyl(2S,6R)-4-(4-(hydroxycarbamoyl)benzyl)-2,6-dimethylpiperazine-1-carboxylate)

Step 1: Synthesis of Phenyl (2S,6R)-4-(4-(methoxycarbonyl)benzyl)-2,6-dimethylpiperzine-1-carboxylate Methyl 4-(((3R,5S)-3,5-dimethylpiperazin-1-yl)methyl) benzoate (formula 1-2, 0.200 g, 0.762 mmol) was dissolved in methylene chloride (5 mL), and then phenylchloroformate (0.105 mL, 0.839 mmol) and TEA (0.211 mL, 1.525 mmol) were added thereto. The mixture was stirred at 0° C. for 2 hours, and then water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=25%) and concentrated to afford the desired compound (0.066 g, 22.6%) as a colorless oil.

Step 2: Synthesis of Compound 177

Phenyl (2S,6R)-4-(4-(methoxycarbonyl)benzyl)-2,6-dimethylpiperzine-1-carboxylate (formula 1-3, 0.066 g, 0.173 mmol) was dissolved in methanol (3 mL), and then hydroxylamine (0.211 mL, 3.451 mmol, 50.00% aqueous solution) and potassium hydroxide (0.097 g, 1.726 mmol) were added thereto. The mixture was stirred at room temperature for 10 minutes, and then the reaction mixture was concentrated under reduced pressure to remove the solvent. Saturated sodium hydrogen carbonate was added to the resulting concentrate, followed by extraction with methylene chloride. The organic layer was washed with a saturated aqueous solution of sodium chloride, dried with anhydrous sodium sulfate, and then concentrated under reduced pressure to yield 177 (0.062 g, 61.8%) as a pale orange solid.

$^1$H NMR (400 MHz, DMSO-$d_6$) δ 11.00 (s, 1 H), 9.00 (s, 1 H), 7.72 (d, 2 H, J=8.0 Hz), 7.43 (d, 2 H , J=8.0 Hz), 7.39-7.36 (m, 1 H), 7.22 (dd, 1 H, J=10.2, 3.6 Hz), 7.10 (d, 2 H, J=7.6 Hz), 4.15-4.13 (m, 1 H), 3.56 (s, 2 H), 2.66 (d, 2 H, J=11.4 Hz), 2.21-2.17 (m, 1 H), 1.35 (d, 6 H, J=6.7 Hz); LRMS (ES) m/z 384.2 (M$^+$+1).

Example 55

Synthesis of Compound 183

(4-(((2S,6R)-2,6-dimethyl-4-phenethylpiperazin-1-yl)methyl)-N-hydroxybenzamide)

Step 1: Synthesis of Methyl 4-(((2S,6R)-2,6-dimethyl-4-phenethylpiperazin-1-yl)methyl)benzoate Methyl 4-(((2S,6R)-2,6-dimethylpiperazin-1-yl)methyl) benzoate (formula 13-2, 0.100 g, 0.381 mmol) and phenylacetaldehyde (0.049 mL, 0.419 mmol) were dissolved in tetrahydrofuran (2 mL), and acetic acid (0.021 mL, 0.381 mmol) was added thereto at room temperature, followed by stirring for 1 hour. Na(CN)BH$_3$ (0.024 g, 0.381 mmol) was added to the reaction mixture, followed by stirring at the same temperature for 17 hours. A saturated aqueous solution of sodium hydrogen carbonate was added to the reaction mixture, followed by extraction with ethyl acetate. The organic layer was washed with a saturated aqueous solution of sodium chloride, and then concentrated under reduced pressure. The concentrate was purified by column chromatography (silicon dioxide; 4 g cartridge, ethyl acetate/hexane=30%) and concentrated to afford the desired compound (0.040 g, 28.6%) as a pale yellow oil.

Step 2: Synthesis of Compound 183

Methyl 4-(((2S,6R)-2,6-dimethyl-4-phenethylpiperazin-1-yl)methyl)benzoate (formula 13-3, 0.045 g, 0.123 mmol) was dissolved in methanol (3 mL), and then hydroxylamine (0.150 mL, 2.456 mmol, 50.00% aqueous solution) and potassium hydroxide (0.069 g, 1.228 mmol) were added thereto. The mixture was stirred at room temperature for 30 minutes, and then the reaction mixture was concentrated under reduced pressure to remove the solvent. Saturated sodium hydrogen carbonate was added to the resulting concentrate, followed by extraction with methylene chloride. The organic layer was dried with an hydrous sodium sulfate, and then concentrated under reduced pressure to yield compound 183 (0.040 g, 88.7%) as a white solid.

$^1$H NMR (400 MHz, DMSO-$d_6$) δ 7.66 (d, 2 H, J=8.0 Hz), 7.38 (d, 2 H, J=8.0 Hz), 7.26-7.17 (m, 5 H), 3.73 (s, 2 H), 2.80 (d, 2 H, J=10.1 Hz), 2.71 (t, 2 H, J=7.8 Hz), 2.55-2.53 (m, 2 H), 2.42 (t, 2 H, J=7.8 Hz), 1.83-1.80 (m, 2 H), 0.91 (d, 6 H, J=6.1 Hz).

Example 56

Synthesis of Compound 184

(4-(((3R,5S)-3,5-dimethyl-4-phenethylpiperazin-1-yl)methyl)-N-hydroxybenzamide)

Step 1: Synthesis of Methyl 4-(((3R,5S)-3,5-dimethyl-4-phenethylpiperazin-1-yl)methyl)benzoate Methyl 4-(((3R,5S)-3,5-dimethylpiperazin-1-yl)methyl) benzoate (formula 1-2, 0.100 g, 0.381 mmol) and phenylacetaldehyde (0.049 mL, 0.419 mmol) were dissolved in tetrahydrofuran (2 mL), and acetic acid (0.021 mL, 0.381 mmol) was added thereto at room temperature, followed by stirring for 1 hour. Na(CN)BH$_3$ (0.024 g, 0.381 mmol) was added to the mixture, which was then stirred at the same temperature for 17 hours. The reaction mixture was washed with an aqueous solution of sodium chloride, and then concentrated under reduced pressure. The concentrate was purified by column chromatography (silicon dioxide; ethyl acetate/hexane=30%) and concentrated to afford the desired compound (0.010 g, 7.2%) as a colorless oil.

Step 2: Synthesis of Compound 184

Methyl 4-(((3R,5S)-3,5-dimethyl-4-phenethylpiperazin-1-yl)methyl)benzoate (formula 1-3, 0.010 g, 0.027 mmol) was dissolved in methanol (1 mL), and then hydroxylamine (0.033 mL, 0.546 mmol, 50.00% aqueous solution) and potassium hydroxide (0.015 g, 0.273 mmol) were added thereto. The mixture was stirred at room temperature for 30 minutes, and then the reaction mixture was concentrated under reduced pressure to remove the solvent. Saturated sodium hydrogen carbonate was added to the resulting concentrate, followed by extraction with methylene chloride. The organic layer was dried with anhydrous magnesium sulfate, and then concentrated under reduced pressure to yield compound 184 (0.007 g, 69.8%) as a white solid.

$^1$H NMR (400 MHz, DMSO-$d_6$) δ 11.50 (s, 1 H), 9.00 (s, 1 H), 7.70 (d, 2 H, J=8.2 Hz), 7.35 (d, 2 H, J=8.0 Hz), 7.28 (d, 2 H, J=8.0 Hz), 7.18 (d, 2 H, J=8.2 Hz), 3.43 (s, 1 H), 2.83-2.79 (m, 2 H), 2.72-2.59 (m, 6 H), 1.77-1.72 (m, 2 H), 1.00 (d, 6 H , J=6.1 Hz).

Example 57

Synthesis of Compound 185

((3R,5S)-4-(4-(hydroxycarbamoyl)benzyl)-3,5-dimethyl-N-(1-methyl-1 H -indol-5-yl)piperazine-1-carboxamide)

Step 1: Synthesis of Methyl 4-(((2S,6R)-2,6-dimethyl-4-(1-methyl-1 H-indol-5-ylcarbamoyl)piperazin-1-yl)methyl)benzoate Methyl 4-(((2S,6R)-2,6-dimethylpiperazin-1-yl)methyl) benzoate (formula 13-2, 0.100 g, 0.381 mmol), 5-isocyanato-1-methyl-1 H-indole (0.079 g, 0.457 mmol) and TEA (0.106 mL, 0.762 mmol) were dissolved in methylene chloride (1 mL), and then stirred at room temperature for 3 hours. Water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.061 g, 36.8%) as a white solid.

Step 2: Synthesis of Compound 185

Methyl 4-(((2S,6R)-2,6-dimethyl-4-(1-methyl-1 H-indol-5-ylcarbamoyl)piperazin-1-yl)methyl)benzoate (formula 13-3, 0.040 g, 0.092 mmol) was dissolved in methanol (0.5 mL), and then hydroxylamine (0.113 mL, 1.841 mmol, 50.00% aqueous solution) and potassium hydroxide (0.052 g, 0.921 mmol) were added thereto. The mixture was stirred at room temperature for 1 hour, and then the reaction mixture was concentrated under reduced pressure to remove the solvent. Saturated sodium hydrogen carbonate was added to the resulting concentrate, followed by extraction with methylene chloride. The organic layer was washed with a saturated aqueous solution of sodium chloride, dried with anhydrous sodium sulfate, and then concentrated under reduced pressure to yield compound 185 (0.018 g, 44.9%) as a pale yellow solid.

$^1$H NMR (400 MHz, DMSO-d$_6$) δ 8.30 (s, 1 H), 7.67 (d, 2 H, J=8.2 Hz), 7.57 (d, 1 H, J=1.7 Hz), 7.38 (d, 2 H, J=8.2 Hz), 7.27 (d, 1 H, J=8.8 Hz), 7.23-7.22 (m, 1 H), 7.17 (dd, 1 H, J=10.2, 3.6 Hz), 6.29 (dd, 1 H, J=10.2, 3.6 Hz), 3.99-3.96 (m, 2 H), 3.77 (s, 2 H), 3.73 (s, 3 H), 2.62-2.52 (m, 4 ), 0.97 (d, 6 H, J=6.0 Hz).

Example 58

Synthesis of Compound 186

((3R,5S)-N-(3-(1 H-pyrrol-1-yl)phenyl)-4-(4-(hydroxycarbamoyl)benzyl)-3,5-dimethylpiperazine-1-carboxamide)

Step 1: Synthesis of Methyl 4-(((2S,6R)-4-(3-(1 H-pyrrol-1-yl)phenylcarbamoyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol), 1-(3-isocyanatophenyl)-1 H-pyrrole (0.084 g, 0.457 mmol) and TEA (0.106 mL, 0.762 mmol) were dissolved in methylene chloride (1 mL), and then stirred at room temperature for 3 hours. Water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.059 g, 34.7%) as a white solid.

Step 2: Synthesis of Compound 186

Methyl 4-(((2S,6R)-4-(3-(1 H-pyrrol-1-yl)phenylcarbamoyl)-2,6-dimethyl piperazin-1-yl)methyl)benzoate (formula 13-3, 0.040 g, 0.090 mmol) was dissolved in methanol (0.5 mL), and then hydroxylamine (0.110 mL, 1.792 mmol, 50.00% aqueous solution) and potassium hydroxide (0.050 g, 0.896 mmol) were added thereto. The mixture was stirred at room temperature for 1 hour, and then the reaction mixture was concentrated under reduced pressure to remove the solvent. Saturated sodium hydrogen carbonate was added to the concentrate, followed by extraction with methylene chloride. The organic layer was washed with a saturated aqueous solution of sodium chloride, dried with anhydrous sodium sulfate, and then concentrated under reduced pressure to yield compound 186 (0.013 g, 32.4%) as a white solid.

$^1$H NMR (400 MHz, DMSO-d$_6$) δ 8.67 (brs, 1 H), 7.78-7.76 (m, 3H), 7.36-7.22 (m, 6 H), 7.09 (d, 2 H, J=8.0 Hz), 6.23 (s, 2 H), 3.97 (d, 2 H, J=12.0 Hz), 3.75 (s, 2 H), 2.67-2.61 (m, 4 H), 0.84 (d, 6 H, J=4.8 Hz).

Example 59

Synthesis of Compound 187

((3R,5S)-N-(2,3-dihydrobenzofuran-5-yl)-4-(4-(hydroxycarbamoyl)benzyl)-3,5-dimethylpiperazine-1-carboxamide)

Step 1: Synthesis of Methyl 4-(((2S,6R)-4-(2,3-dihydrobenzofuran-5-ylcarbamoyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol), 5-isocyanato-2,3-dihydrobenzofuran (0.074 g, 0.457 mmol) and TEA (0.106 mL, 0.762 mmol) were dissolved in methylene chloride (1 mL), and then stirred at room temperature for 3 hours. Water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.070 g, 43.4%) as a white solid.

Step 2: Synthesis of Compound 187

Methyl 4-(((2S,6R)-4-(2,3-dihydrobenzofuran-5-ylcarbamoyl)-2,6-dimethylpiperazin-1-yl)methyl)benzoate (formula 13-3, 0.040 g, 0.094 mmol) was dissolved in methanol (0.5 mL), and then hydroxylamine (0.116 mL, 1.889 mmol, 50.00% aqueous solution) and potassium hydroxide (0.053 g, 0.945 mmol) were added thereto. The mixture was stirred at room temperature for 1 hour, and then the reaction mixture was concentrated under reduced pressure to remove the solvent. Saturated sodium hydrogen carbonate was added to the resulting concentrate, followed by extraction with methylene chloride. The organic layer was washed with a saturated aqueous solution of sodium chloride, dried with anhydrous sodium sulfate, and then concentrated under reduced pressure to yield compound 187 (0.020 g, 49.9%) as a white solid.

$^1$H NMR (400 MHz, DMSO-d$_6$) δ 8.27 (s, 1 H), 7.66 (d, 2 H, J=8.1 Hz), 7.37 (d, 2 H, J=20.0 Hz), 7.29 (d, 1 H, J=1.2 Hz), 7.04-7.02 (m, 1 H), 6.60 (d, 1 H, J=8.0 Hz), 4.45 (t, 2 H, J=8.7 Hz), 3.92 (d, 2 H, J=12.0 Hz), 3.74 (s, 2 H), 3.11 (t, 2 H, J=8.6 Hz), 2.61-2.56 (m, 4 H), 0.96 (d, 6 H, J=6.0 Hz).

Example 60

Synthesis of Compound 188

(4-(((3R,5S)-3,5-dimethyl-4-(3-phenylpropanoyl) piperazin-1-yl) methyl)-N-hydroxybenzamide)

Step 1: Synthesis of Methyl 4-(((3R,5S)-3,5-dimethyl-4-(3-phenylpropanoyl)piperazin-1-yl)methyl) benzoate Methyl 4-(((3R,5S)-3,5-dimethylpiperazin-1-yl)methyl)benzoate (formula 1-2, 0.070 g, 0.267 mmol) was dissolved in methylene chloride (1 mL), and then 3-phenylpropanoyl chloride (0.054 g, 0.320 mmol) and TEA (0.074 mL, 0.534 mmol) were added thereto. The mixture was stirred at room temperature for 3 hours, and then water was added to the reaction mixture, followed by extraction with methylene chloride. The organic layer was separated and concentrated under reduced pressure. The concentrate was purified by column chromatography (silicon dioxide; methanol/methylene chloride=5%) and concentrated to afford the desired compound (0.097 g, 92.2%) as a white oil.

Step 2: Synthesis of Compound 188

Methyl 4-(((3R,5S)-3,5-dimethyl-4-(3-phenylpropanoyl)piperazin-1-yl)methyl)benzoate (formula 1-3, 0.040 g, 0.101 mmol) was dissolved in methanol (0.5 mL), and then hydroxylamine (0.124 mL, 2.028 mmol, 50.00% aqueous solution) and potassium hydroxide (0.057 g, 1.014 mmol) were added thereto. The mixture was stirred at room temperature for 1 hour, and then saturated sodium hydrogen carbonate was added to the concentrate, followed by extraction with methylene chloride. The organic layer was concentrated under reduced pressure to yield compound 188 (0.019 g, 47.4%) as a white solid.

$^1$H NMR (400 MHz, DMSO-$d_6$) δ 7.70 (d, 2 H, J=8.4 Hz), 7.38 (d, 2 H, J=8.0 Hz), 7.27-7.14 (m, 5 H), 4.39 (brs, 1 H), 4.00 (brs, 1 H), 3.48 (s, 2 H), 2.80-2.78 (m, 2 H), 2.69-2.66 (m, 2 H), 2.58-2.57 (m, 2 H), 2.01-1.98 (m, 2 H), 1.19 (brs, 6 H).

Example 61

Synthesis of Compound 189

(4-(((2S,6R)-2,6-dimethyl-4-(m-tolylcarbamothioyl)piperazin-1-yl)methyl)-N-hydroxybenzamide)

Step 1: Synthesis of Methyl 4-(((2S,6R)-2,6-dimethyl-4-(m-tolylcarbamothioyl)piperazin-1-yl)methyl)benzoate Methyl 4-(((2S,6R)-2,6-dimethylpiperazin-1-yl)methyl)benzoate (compound 13-2, 0.070 g, 0.267 mmol), 1-isothiocyanate-3-methylbenzene (0.048 g, 0.320 mmol) and TEA (0.106 mL, 0.762 mmol) were dissolved in methylene chloride (1 mL), and then stirred at the room temperature for 6 hours. Water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.092 g, 83.8%) as a yellow solid.

Step 2: Synthesis of Compound 189

Methyl 4-(((2S,6R)-2,6-dimethyl-4-(m-tolylcarbamothioyl)piperazin-1-yl)methyl)benzoate (formula 13-3, 0.040 g, 0.097 mmol) was dissolved in methanol (0.5 mL), and then hydroxylamine (0.119 mL, 1.944 mmol, 50.00% aqueous solution) and potassium hydroxide (0.055 g, 0.972 mmol) were added thereto. The mixture was stirred at room temperature for 1 hour, and then the reaction mixture was concentrated under reduced pressure to remove the solvent. Saturated sodium hydrogen carbonate was added to the resulting concentrate, followed by extraction with methylene chloride. The organic layer was washed with a saturated aqueous solution of sodium chloride, dried with anhydrous sodium sulfate, and then concentrated under reduced pressure to yield compound 189 (0.021 g, 52.4%) as a white solid.

$^1$H NMR (400 MHz, DMSO-$d_6$) δ 7.65 (d, 2 H, J=8.0 Hz), 7.30 (d, 2 H, J=8.0 Hz), 7.14 (t, 1 H, J=8.0 Hz), 7.05-7.04 (m, 1 H ), 6.88 (d, 1 H, J=8.0 Hz), 4.55 (d, 2 H, J=12.0 Hz), 3.75 (s, 2 H), 2.91-2.85 (m, 2 H), 2.55-2.51 (m, 2 H), 2.48 (s, 3 H ), 0.98 (d, 6 H, J=6.1 Hz).

Example 62

Synthesis of Compound 193

(4-(((2S,6R)-4-(2-fluoro-2-methylpropyl)-2,6-dimethylpiperazin-1-yl)methyl)-N-hydroxybenzamide)

Step 1: Synthesis of Methyl 4-(((2S,6R)-4-(2-hydroxy-2-methylpropyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol) was dissolved in acetonitrile (2 mL), and 2,2-dimethyloxirane (0.041 g, 0.572 mmol) and K$_2$CO$_3$ (0.105 g, 0.762 mmol) were added thereto. The mixture was stirred at 80° C. for 48 hours, and then water was added to the reaction mixture, followed by extraction with ethyl acetate. The organic layer was dried with anhydrous magnesium sulfate, and then concentrated under reduced pressure. The concentrate was purified by column chromatography (silicon dioxide; ethyl acetate/hexane=50%) and concentrated to afford the desired compound (0.040 g, 31.4%) as a brown oil.

Step 2: Synthesis of methyl 4-(((2S,6R)-4-(2-fluoro-2-methylpropyl)-2,6-dimethylpiperazin-1-yl)methyl)benzoate Methyl 4-(((2S,6R)-4-(2-hydroxy-2-methylpropyl)-2,6-dimethylpiperazin-1-yl)methyl)benzoate (formula 19-2, 0.080 g, 0.239 mmol) was dissolved in methylene chloride (4 mL), and DAST (0.042 g, 0.263 mmol) was added thereto at 0° C., followed by stirring at room temperature for 40 minutes. Then, water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=50%) and concentrated to afford the desired compound (0.065 g, 80.8%) as a yellow oil.

Step 3: Synthesis of Compound 193

Methyl 4-(((2S,6R)-4-(2-fluoro-2-methylpropyl)-2,6-dimethylpiperazin-1-yl)methyl)benzoate (0.065 g, 0.193 mmol) was dissolved in methanol (2 mL), and then hydroxylamine (0.236 mL, 3.864 mmol, 50.00% aqueous solution) and potassium hydroxide (0.108 g, 1.932 mmol) were added thereto. The mixture was stirred at room temperature for 30 minutes, and then the reaction mixture was concentrated under reduced pressure to remove the solvent. Saturated sodium hydrogen carbonate was added to the resulting concentrate, followed by extraction with methylene chloride. The organic layer was washed with a saturated aqueous solution of sodium chloride, dried with anhydrous magnesium sulfate, and then concentrated under reduced pressure to yield compound 193 (0.030 g, 46.0%) as a pale orange solid.

$^1$H NMR (400 MHz, DMSO-d$_6$) δ 7.65 (d, 2 H, J=8.2 Hz), 7.35 (d, 2 H, J=8.2 Hz), 3.72 (s, 2 H), 2.74 (d, 2 H, J=10.0 Hz), 2.57-2.53 (m, 2 H), 2.35 (d, 2 H, J=22.1 Hz), 1.95-1.93 (m, 2 H), 1.29 (d, 6 H, J=22.1 Hz), 0.89 (d, 6 H, J=6.1 Hz); LRMS (ES) m/z 338.2 (M$^+$+1).

Example 63

Synthesis of Compound 194

(6-(((3R,5S)-4-benzyl-3,5-dimethylpiperazin-1-yl)methyl)-N-hydroxynicotinamide)

Step 1: Synthesis of Methyl 6-(((3R,5S)-4-benzyl-3,5-dimethylpiperazin-1-yl)methyl)nicotinate (2S,6R)-1-benzyl-2,6-dimethylpiperazine (formula 8-3, 0.200 g, 0.831 mmol) was dissolved in acetonitrile (4 mL), and then methyl 6-(bromomethyl)nicotinate (formula 8-4, 0.191 g, 0.831 mmol) and Cs$_2$CO$_3$ (0.541 g, 1.661 mmol) were added thereto. The mixture was stirred at room temperature for 17 hours, and then water was added to the reaction mixture, followed by extraction with ethyl acetate. The organic layer was dried with anhydrous magnesium sulfate, and then concentrated under reduced pressure. The concentrate was purified by column chromatography (silicon dioxide; ethyl acetate/hexane=25%) and concentrated to afford the desired compound (0.183 g, 62.3%) as a pale yellow solid.

Step 2: Synthesis of Compound 194

Methyl 6-(((3R,5S)-4-benzyl-3,5-dimethylpiperazin-1-yl)methyl)nicotinate (formula 8-5, 0.100 g, 0.283 mmol) was dissolved in methanol (2 mL), and then hydroxylamine (0.346 mL, 5.658 mmol, 50.00% aqueous solution) and potassium hydroxide (0.159 g, 2.829 mmol) were added thereto. The mixture was stirred at room temperature for 30 minutes, and then the reaction mixture was concentrated under reduced pressure to remove the solvent. A saturated aqueous solution of sodium hydrogen carbonate was added to the resulting concentrate, followed by extraction with methylene chloride. The organic layer was dried with anhydrous sodium sulfate, and then concentrated under reduced pressure. Compound 194 (0.032 g, 31.9%) was obtained as a pale orange solid.

$^1$H NMR (400 MHz, DMSO-d$_6$) δ 8.75 (d, 1 H, J=1.4 Hz), 7.94 (dd, 1 H, J=10.2, 3.6 Hz), 7.35-7.33 (m, 2 H), 7.30-7.24 (m, 3 H), 7.17-7.15 (m, 1 H), 3.73 (s, 2 H), 3.48 (s, 2 H), 2.67 (d, 2 H, J=9.9 Hz), 2.58-2.54 (m, 2 H), 1.88-1.83 (m, 2 H), 0.90 (d, 6 H, J=6.1 Hz); LRMS (ES) m/z 355.2 (M$^+$+1).

Example 64

Synthesis of Compound 195

(6-(((2S,6R)-4-benzyl-2,6-dimethylpiperazin-1-yl)methyl)-N-hydroxynicotinamide)

Step 1: Synthesis of Methyl 6-(((2S,6R)-4-benzyl-2,6-dimethylpiperazin-1-yl)methyl)nicotinate (3R,5S)-1-benzyl-3,5-dimethylpiperazine (formula 16-1, 0.150 g, 0.734 mmol) was dissolved in acetonitrile (4 mL), and then methyl 4-(bromomethyl)nicotinate (formula 8-4, 0.169 g, 0.734 mmol) and Cs$_2$CO$_3$ (0.718 g, 2.203 mmol) were added thereto. The mixture was stirred at room temperature for 17 hours, and then water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=25%) and concentrated to afford the desired compound (0.108 g, 41.6%) as a yellow solid.

Step 2: Synthesis of Compound 195

Methyl 6-(((2S,6R)-4-benzyl-2,6-dimethylpiperazin-1-yl)methyl)nicotinate (formula 16-2, 0.050 g, 0.141 mmol) was dissolved in methanol (2 mL), and then hydroxylamine (0.173 mL, 2.829 mmol, 50.00% aqueous solution) and potassium hydroxide (0.079 g, 1.415 mmol) were added thereto. The mixture was stirred at room temperature for 20 minutes, and then the reaction mixture was concentrated under reduced pressure to remove the solvent. Saturated sodium hydrogen carbonate was added to the concentrate, followed by extraction with methylene chloride. The organic layer was washed with a saturated aqueous solution of sodium chloride, dried with anhydrous magnesium sulfate, and then concentrated under reduced pressure to yield compound 195 (0.022 g, 43.9%) as a white solid.

$^1$H NMR (400 MHz, DMSO-d$_6$) δ 8.75 (s, 1 H), 7.99 (d, 1 H , J=8.2 Hz), 7.50 (d, 1 H, J=8.2 Hz), 7.35-7.21 (m, 5 H), 3.82 (s, 2 H), 3.44 (s, 2 H), 2.73-2.60 (m, 4 H ), 1.78 (t, 2 H , J=9.9 Hz), 0.88 (d, 6 H, J=6.1 Hz); LRMS (ES) m/z 355.2 (M$^+$+1).

Example 65

Synthesis of Compound 196

((3R,5S)-4-(4-(hydroxycarbamoyl)benzyl)-N,3,5-trimethyl-N-phenylpiperazine-1-carboxamide)

Step 1: Synthesis of 4-nitrophenyl methyl(phenyl)carbamate

N-methylaniline (0.300 g, 2.800 mmol) and TEA (0.776 mL, 5.600 mmol) were dissolved in methylene chloride (5 mL), and 4-nitrophenyl chloroformate (0.621 g, 3.080 mmol) was added thereto at 0° C., followed by stirring at the same temperature for 2 hours. Then, water was added to the reaction mixture, followed by extraction with ethyl acetate. The organic layer was washed with a saturated aqueous solution of sodium chloride, dried with anhydrous magnesium sulfate, and then concentrated under reduced pressure to yield the desired compound (0.709 g, 93.0%) as a yellow oil.

Step 2: Synthesis of Methyl 4-(((2S,6R)-2,6-dimethyl-4-(methyl(phenyl)carbamoyl)piperazin-1-yl)methyl)benzoate 4-nitrophenyl methyl(phenyl)carbamate (0.500 g, 1.836 mmol), methyl 4-(((2S,6R)-2,6-dimethylpiperazin-1-yl)methyl)benzoate (formula 13-2, 0.549 g, 1.836 mmol) and TEA (0.382 mL, 2.755 mmol) were dissolved in N,N-dimethylformamide (20 mL). The reaction solution was stirred at 100° C. for 17 hours, and then water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=50%) and concentrated to afford the desired compound (0.373 g, 51.4%) as a brown oil.

Step 3: Synthesis of Compound 196

Methyl 4-(((2S,6R)-2,6-dimethyl-4-(methyl(phenyl)carbamoyl)piperazin-1-yl)methyl)benzoate (formula 13-3, 0.110 g, 0.278 mmol) was dissolved in methanol (2 mL), and then hydroxylamine (0.340 mL, 5.563 mmol, 50.00% aqueous solution) and potassium hydroxide (0.156 g, 2.781 mmol) were added thereto. The mixture was stirred at room temperature for 1 hour, and then a saturated aqueous solution of sodium hydrogen carbonate was added to the reaction mixture, followed by extraction with methylene chloride. The organic layer was washed with a saturated aqueous solution of sodium chloride, dried with anhydrous sodium sulfate, and then concentrated under reduced pressure to yield compound 196 (0.092 g, 83.4%) as a white solid.

$^1$H NMR (400 MHz, DMSO-$d_6$) δ 10.90 (s, 1 H), 9.10 (s, 1 H), 7.64 (d, 2 H, J=8.3 Hz), 7.35-7.30 (m, 4 H), 7.12-7.08 (m, 3 H), 3.65 (s, 2 H), 3.47 (d, 2 H, J=12.8 Hz), 3.07 (s, 3 H), 2.41 (t, 1 H, J=11.5 Hz), 2.33-2.28 (m, 2 H), 0.86 (d, 6 H, J=6.4 Hz); LRMS (ES) m/z 397.2 (M$^+$+1).

Example 66

Synthesis of Compound 197

(N-hydroxy-4-(((2S,6R)-4-(indoline-1-carbonyl)-2,6-dimethylpiperazin-1-yl)methyl)benzamide)

Step 1: Synthesis of 4-nitrophenyl indoline-1-carboxylate

Indoline (0.300 g, 2.518 mmol) and TEA (0.698 mL, 5.035 mmol) were dissolved in methylene chloride (5 mL), and 4-nitrophenyl chloroformate (0.558 g, 2.769 mmol) was added thereto at 0° C., followed by stirring at the same temperature for 30 minutes. Water was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=25%) and concentrated to afford the desired compound (0.668 g, 93.3%) as a pale brown solid.

Step 2: Synthesis of Methyl 4-(((2S,6R)-4-(indoline-1-carbonyl)-2,6-dimethylpiperazin-1-yl)methyl)benzoate 4-Nitrophenyl indoline-1-carboxylate (0.300 g, 1.055 mmol), methyl 4-(((2S,6R)-2,6-dimethylpiperazin-1-yl)methyl)benzoate (formula 13-2, 0.315 g, 1.055 mmol) and TEA (0.439 mL, 3.166 mmol) were dissolved in N,N-dimethylformamide (6 mL) at 100° C., and then stirred at the same temperature for 17 hours. Then, water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=50%) and concentrated to afford the desired compound (0.282 g, 65.6%) as a brown solid.

Step 3: Synthesis of Compound 197

Methyl 4-(((2S,6R)-4-(indoline-1-carbonyl)-2,6-dimethylpiperazin-1-yl)methyl)benzoate (formula 13-3, 0.100 g, 0.245 mmol) was dissolved in methanol (2 mL), and then hydroxylamine (0.300 mL, 4.908 mmol, 50.00% aqueous solution) and potassium hydroxide (0.138 g, 2.454 mmol) were added thereto. The mixture was stirred at room temperature for 1 hour, and then a saturated aqueous solution of sodium hydrogen carbonate was added to the reaction mixture, followed by extraction with methylene chloride. The organic layer was washed with a saturated aqueous solution of sodium chloride, dried with anhydrous sodium sulfate, and then concentrated under reduced pressure to yield compound 197 (0.068 g, 67.8%) as a white solid.

$^1$H NMR (400 MHz, DMSO-$d_6$) δ 7.67 (d, 2 H, J=8.3 Hz), 7.41 (d, 2 H, J=8.1 Hz), 7.18 (d, 1 H, J=7.3 Hz), 7.10-7.08 (m, 1 H), 7.00 (d, 1 H, J=7.8 Hz), 6.87-6.85 (m, 1 H), 3.83-3.78 (m, 4 H), 3.54 (d, 2 H, J=12.6 Hz), 2.98 (t, 2 H, J=8.2 Hz), 2.73 (t, 2 H, J=11.7 Hz), 2.61-2.59 (m, 2 H), 0.92 (d, 6 H, J=6.0 Hz); LRMS (ES) m/z 409.2 (M$^+$+1).

Example 67

Synthesis of Compound 198

((3R,5S)-N-butyl-4-(4-(hydroxycarbamoyl)benzyl)-3,5-dimethyl-N-phenylpiperazine-1-carboxamide)

Step 1: Synthesis of Methyl 4-(((3R,5S)-4-(butylphenylcarbamoyl)-3,5-dimethylpiperazin-1-yl)methyl)benzoate Methyl 4-(((2S,6R)-2,6-dimethyl-4-(phenylcarbamoyl)piperazin-1-yl)methyl)benzoate (formula 13-3, 0.500 g, 1.311 mmol) and NaH (0.033 g, 1.376 mmol) were dissolved in N,N-dimethylformamide (10 mL) and stirred at room temperature for 1 H our. Then, 1-iodobutane (0.164 mL, 1.442 mmol) was added to the reaction mixture, followed by stirring at the same temperature for 3 hours. Next, water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=50%) and concentrated to afford the desired compound (0.115 g, 20.1%) as a pale yellow oil.

Step 2

Synthesis of Compound 198

Methyl 4-(((3R,5S)-4-(butylphenylcarbamoyl)-3,5-dimethylpiperazin-1-yl)methyl)benzoate (formula 20-1, 0.060 g, 0.137 mmol) was dissolved in methanol (2 mL), and then hydroxylamine (0.168 mL, 2.742 mmol, 50.00% aqueous solution) and potassium hydroxide (0.077 g, 1.371 mmol) were added thereto. The mixture was stirred at room temperature for 20 minutes, and a saturated aqueous solution of sodium hydrogen carbonate was added to the reaction mixture, followed by extraction with methylene chloride. The extract was passed through a plastic filter to remove solid residue and an aqueous layer, and the organic layer was concentrated under reduced pressure to yield compound 198 (0.038 g, 63.2%) as a white solid.

$^1$H NMR (400 MHz, DMSO-$d_6$) δ 8.95 (s, 1 H), 7.62 (d, 2 H, J=8.2 Hz), 7.35-7.30 (m, 4 H), 7.12-7.06 (m, 3 H ), 3.63 (s, 2 H), 3.52-3.48 (m, 2 ), 3.43 (d, 2 H, J=13.1 Hz), 2.39-2.37 (m, 2 H), 2.33-2.26 (m, 2 H), 1.43-1.37 (m, 2 H), 1.28-1.20 (m, 2 H), 0.92-0.90 (m, 3 H), 0.89-0.87 (m, 6 ); LRMS (ES) m/z 439.3 (M$^+$+1).

Example 68

Synthesis of Compound 204

(4-(((3R,5S)-3,5-dimethyl-4-(4,4,4-trifluorobutyl) piperazin-1-yl)methyl)-N-hydroxybenzamide)

Step 1: Synthesis of Methyl 4-(((3R,5S)-3,5-dimethyl-4-(4,4,4-trifluorobutyl)piperazin-1-yl)methyl) benzoate Methyl 4-(((3R,5S)-3,5-dimethylpiperazin-1-yl)methyl) benzoate (formula 1-2, 0.300 g, 1.004 mmol) was dissolved in acetonitrile (5 mL), and then 1,1,1,-trifluoro-4-iodobutane (0.129 mL, 1.004 mmol) and Cs$_2$CO$_3$ (0.318 g, 2.510 mmol) were added thereto. The mixture was heated under reflux for 17 hours, and then cooled to room temperature. The reaction mixture was filtered through a glass filter to remove solids, and the filtrate was concentrated under reduced pressure. The concentrate was purified by column chromatography (silicon dioxide; ethyl acetate/hexane=50%) and concentrated to yield the desired compound (0.115 g, 30.8%) as a pale yellow oil.

Step 2

Synthesis of Compound 204

Methyl 4-(((3R,5S)-3,5-dimethyl-4-(4,4,4-trifluorobutyl) piperazin-1-yl)methyl)benzoate (formula 1-3, 0.065 g, 0.175 mmol) was dissolved in methanol (2 mL), and then hydroxylamine (0.214 mL, 3.491 mmol, 50.00% aqueous solution) and potassium hydroxide (0.098 g, 1.745 mmol) were added thereto. The mixture was stirred at room temperature for 40 minutes, and then the reaction mixture was concentrated under reduced pressure to remove the solvent. A saturated aqueous solution of sodium hydrogen carbonate was added to the resulting concentrate, followed by extraction with methylene chloride. The extract was passed through a plastic filter to remove solid residue and an aqueous layer, and the organic layer was concentrated under reduced pressure. Compound 204 (0.023 g, 35.3%) was obtained as a white solid.

$^1$H NMR (400 MHz, DMSO-$d_6$) δ 11.20 (s, 1 H), 9.00 (s, 1 H), 7.70 (d, 2 H, J=7.2 Hz), 7.34 (d, 2 H, J=7.6 Hz), 3.42 (s, 2 H), 2.62-2.59 (m, 6 H), 2.34-2.33 (m, 2 H), 2.72-1.66 (m, 2 H), 1.25-1.24 (m, 2 H), 0.94 (d, 6 , J=5.1 Hz); LRMS (ES) m/z 374.2 (M$^+$+1).

Example 69

Synthesis of Compound 211

(4-(((3R,5S)-4-(2-fluorobenzyl)-3,5-dimethylpiperazin-1-yl)methyl)-N-hydroxybenzamide)

Step 1: Synthesis of Methyl 4-(((3R,5S)-4-(2-fluorobenzyl)-3,5-dimethylpiperazin-1-yl)methyl)benzoate Methyl 4-(((3R,5S)-3,5-dimethylpiperazin-1-yl)methyl) benzoate (formula 1-2, 0.100 g, 0.381 mmol), 1-(bromomethyl)-2-fluorobenzene (0.055 mL, 0.457 mmol) and K$_2$CO$_3$ (0.105 g, 0.762 mmol) were dissolved in acetonitrile (1 mL) and stirred at room temperature for 7 hours. Water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.067 g, 47.4%) as a white oil.

Step 2: Synthesis of Compound 211

Methyl 4-(((3R,5S)-4-(2-fluorobenzyl)-3,5-dimethylpiperazin-1-yl)methyl)benzoate (formula 1-3, 0.050 g, 0.135 mmol) was dissolved in methanol (1 mL), and then hydroxylamine (0.165 mL, 2.699 mmol, 50.00% aqueous solution) and potassium hydroxide (0.076 g, 1.350 mmol) were added thereto. The mixture was stirred at room temperature for 1 h our, and then the reaction mixture was concentrated under reduced pressure to remove the solvent. A saturated aqueous solution of sodium hydrogen carbonate was added to the concentrate, followed by extraction with methylene chloride. The organic layer was washed with a saturated aqueous solution of sodium chloride, dried with anhydrous sodium sulfate, and then concentrated under reduced pressure. Compound 211 (0.031 g, 61.8%) was obtained as a yellow solid.

$^1$H NMR (400 MHz, DMSO-$d_6$) δ 7.69 (d, 2 H, J=7.3 Hz), 7.63-7.60 (m, 1 H), 7.30 (d, 2 H, J=7.8 Hz), 3.79 (s, 2 H), 3.43 (s, 2 H), 2.68-2.56 (m, 4 H), 1.81 (t, 2 H, J=10.4 Hz), 0.87 (d, 6 H, J=6.0 Hz).

Example 70

Synthesis of Compound 212

(4-(((3R,5S)-4-(2,5-difluorobenzyl)-3,5-dimethylpiperazin-1-yl)methyl)-N-hydroxybenzamide)

Step 1: Synthesis of Methyl 4-(((3R,5S)-4-(2,5-difluorobenzyl)-3,5-dimethylpiperazin-1-yl)methyl) benzoate Methyl 4-(((3R,5S)-3,5-dimethylpiperazin-1-yl)methyl) benzoate (formula 1-2, 0.100 g, 0.381 mmol), 2-(bromomethyl)-1,4-difluorobenzene (0.059 mL, 0.457 mmol) andK$_2$CO$_3$ (0.105 g, 0.762 mmol) were dissolved in acetonitrile (1 mL) and stirred at room temperature for 7 hours. Water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.057 g, 38.5%) as a white solid.

Step 2: Synthesis of Compound 212

Methyl 4-(((3R,5S)-4-(2,5-difluorobenzyl)-3,5-dimethylpiperazin-1-yl)methyl)benzoate (formula 1-3, 0.050 g, 0.129 mmol) was dissolved in methanol (1 mL), and then hydroxylamine (0.157 mL, 2.574 mmol, 50.00% aqueous solution) and potassium hydroxide (0.072 g, 1.287 mmol) were added thereto. The mixture was stirred at room temperature for 1 hour, and then the reaction mixture was concentrated under reduced pressure to remove the solvent. A saturated aqueous solution of sodium hydrogen carbonate was added to the concentrate, followed by extraction with methylene chloride. The organic layer was washed with a saturated aqueous solution of sodium chloride, dried with anhydrous sodium sulfate, and then concentrated under reduced pressure. Compound 212 (0.025 g, 49.9%) was obtained as a pale yellow solid.

$^1$H NMR (400 MHz, DMSO-d$_6$) δ 7.69 (d, 2 H, J=7.8 Hz), 7.39-7.35 (m, 1 H), 7.30 (d, 2 H, J=7.9 Hz), 7.18-7.15 (m, 1 H), 3.70 (s, 2 H), 3.44 (s, 2 H), 2.69-2.60 (m, 4 H), 1.83 (t, 2 H, J=10.4 Hz), 0.84 (d, 6 H, J=6.0 Hz).

Example 71

Synthesis of Compound 213

(4-(((3R,5S)-3,5-dimethyl-4-(2,4,5-trifluorobenzyl)piperazin-1-yl)methyl)-N-hydroxybenzamide)

Step 1: Synthesis of Methyl 4-(((3R,5S)-3,5-dimethyl-4-(2,4,5-trifluorobenzyl)piperazin-1-yl)methyl)benzoate Methyl 4-(((3R,5S)-3,5-dimethylpiperazin-1-yl)methyl)benzoate (formula 1-2, 0.100 g, 0.381 mmol), 1-(bromomethyl)-2,4,5-trifluorobenzene (0.103 g, 0.457 mmol) and K$_2$CO$_3$ (0.105 g, 0.762 mmol) were dissolved in acetonitrile (1 mL) and stirred at room temperature for 7 hours. Water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.071 g, 45.8%) as a white solid.

Step 2: Synthesis of Compound 213

Methyl 4-(((3R,5S)-3,5-dimethyl-4-(2,4,5-trifluorobenzyl)piperazin-1-yl)methyl)benzoate (formula 1-3, 0.050 g, 0.123 mmol) was dissolved in methanol (1 mL), and then hydroxylamine (0.150 mL, 2.460 mmol, 50.00% aqueous solution) and potassium hydroxide (0.069 g, 1.230 mmol) were added thereto. The mixture was stirred at room temperature for 1 hour, and then the reaction mixture was concentrated under reduced pressure to remove the solvent. A saturated aqueous solution of sodium hydrogen carbonate was added to the resulting concentrate, followed by extraction with methylene chloride. The organic layer was washed with a saturated aqueous solution of sodium chloride, dried with anhydrous sodium sulfate, and then concentrated under reduced pressure. Compound 213 (0.024 g, 47.9%) was obtained as a white solid.

$^1$H NMR (400 MHz, DMSO-d$_6$) δ 7.64 (d, 2 H, J=8.0 Hz), 7.60-7.58 (m, 1 H), 7.48-7.46 (m, 1 H), 7.11 (d, 2 H, J=8.0 Hz), 3.37 (s, 2 H), 3.22 (s, 2 H), 2.69-2.55 (m, 4 H), 1.79 (t, 2 H, J=10.2 Hz), 0.84 (d, 6 H, J=6.1 Hz).

Example 72

Synthesis of Compound 214

(4-(((3R,5S)-4-(3,5-bis(trifluoromethyl)benzyl)-3,5-dimethylpiperazin-1-yl)methyl)-N-hydroxybenzamide)

Step 1: Synthesis of Methyl 4-(((3R,5S)-4-(3,5-bis(trifluoromethyl)benzyl)-3,5-dimethylpiperazin-1-yl)methyl)benzoate Methyl 4-(((3R,5S)-3,5-dimethylpiperazin-1-yl)methyl)benzoate (formula 1-2, 0.100 g, 0.381 mmol), 1-(bromomethyl)-3,5-bis(trifluoromethyl)benzene (0.084 ml, 0.457 mmol) and K$_2$CO$_3$ (0.105 g, 0.762 mmol) were dissolved in acetonitrile (1 mL) and stirred at room temperature for 7 hours. Water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; methanol/methylene chloride=5%) and concentrated to afford the desired compound (0.075 g, 40.3%) as a white oil.

Step 2: Synthesis of Compound 214

Methyl 4-(((3R,5S)-4-(3,5-bis(trifluoromethyl)benzyl)-3,5-dimethylpiperazin-1-yl)methyl)benzoate (formula 1-3, 0.050 g, 0.102 mmol) was dissolved in methanol (1 mL), and then hydroxylamine (0.125 mL, 2.047 mmol, 50.00% aqueous solution) and potassium hydroxide (0.057 g, 1.024 mmol) were added thereto. The mixture was stirred at room temperature for 1 hour, and then the reaction mixture was concentrated under reduced pressure to remove the solvent. A saturated aqueous solution of sodium hydrogen carbonate was added to the resulting concentrate, followed by extraction with methylene chloride. The organic layer was washed with a saturated aqueous solution of sodium chloride, dried with anhydrous sodium sulfate, and then concentrated under reduced pressure. Compound 214 (0.021 g, 41.9%) was obtained as a white solid.

$^1$H NMR (400 MHz, DMSO-d$_6$) δ 8.06 (s, 2 H), 7.91 (s, 2 H), 7.67 (d, 2 H, J=6.7 Hz), 7.22 (d, 2 H, J=7.3 Hz), 3.89 (s, 2 H), 3.41 (s, 2 H), 2.70-2.55 (m, 4 H), 1.83 (t, 2 H, J=10.1 Hz), 0.82 (d, 6 H, J=5.9 Hz).

Example 73

Synthesis of Compound 215

(4-(((2S,6R)-2,6-dimethyl-4-(2,4,5-trifluorobenzyl)piperazin-1-yl)methyl)-N-hydroxybenzamide)

Step 1: Synthesis of Methyl 4-(((2S,6R)-2,6-dimethyl-4-(2,4,5-trifluorobenzyl)piperazin-1-yl)methyl)benzoate Methyl 4-(((2S,6R)-2,6-dimethylpiperazin-1-yl)methyl)benzoate (formula 13-2, 0.100 g, 0.381 mmol), 1-(bromomethyl)-2,4,5-trifluorobenzene (0.103 g, 0.457 mmol) and K₂CO₃ (0.105 g, 0.762 mmol) were dissolved in acetonitrile (1 ml) at 25° C., and the reaction solution was stirred at the same temperature for 7 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; 4 g cartridge; methanol/methylene chloride=from 0% to 5%) and concentrated to afford the desired compound (0.071 g, 45.8%) as a white solid.

Step 2: Synthesis of Compound 215

Methyl 4-(((2S,6R)-2,6-dimethyl-4-(2,4,5-trifluorobenzyl)piperazin-1-yl)methyl)benzoate (formula 13-3, 0.050 g, 0.123 mmol), hydroxylamine (0.150 mL, 2.460 mmol, 50.00% aqueous solution) and potassium hydroxide (0.069 g, 1.230 mmol) were dissolved in methanol (1 ml) at 25° C., and the reaction solution was stirred at the same temperature for 1 hour. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield compound 215 (0.024 g, 47.9%) as a white solid.

¹H NMR (400 MHz, DMSO-d₆) δ 7.64 (d, 2 H, J=8.04 Hz), 7.60-7.46 (m, 3 H), 7.11 (d, 2 H, J=8.04 Hz), 3.67 (s, 2 H), 3.17 (s, 2 H), 2.69-2.61 (m, 2 H), 2.60-2.57 (m, 2 H), 1.82-1.76 (m, 2 H), 0.83 (d, 6 H, J=6.12 Hz).

Example 74

Synthesis of Compound 218

(4-(2-((3R,5S)-4-benzyl-3,5-dimethylpiperazin-1-yl)ethyl)-N-hydroxybenzamide)

Step 1: Synthesis of Methyl 4-(2-((3R,5S)-4-benzyl-3,5-dimethylpiperazin-1-yl)ethyl)benzoate (2S,6R)-1-benzyl-2,6-dimethylpiperazine (formula 8-3, 0.200 g, 0.831 mmol) and DIPEA (0.363 mL, 2.077 mmol) were dissolved in acetonitrile (5 mL), and methyl 4-(2-bromoethyl)benzoate (formula 8-4, 0.404 g, 1.661 mmol) was added thereto at room temperature. The mixture was stirred at 60° C. for 17 hours, and then water was added to the reaction mixture, followed by extraction with methylene chloride. The extract was passed through a plastic filter to remove solid residue and an aqueous layer, and the organic layer was concentrated under reduced pressure. The concentrate was concentrated by column chromatography (silicon dioxide; ethyl acetate/hexane=25%) and concentrated to afford the desired compound (0.075 g, 24.6%) as a pale yellow oil.

Step 2: Synthesis of Compound 218

Methyl 4-(2-((3R,5S)-4-benzyl-3,5-dimethylpiperazin-1-yl)ethyl)benzoate (formula 8-5, 0.075 g, 0.205 mmol) was dissolved in methanol (3 mL), and then hydroxylamine (0.125 mL, 0.2046 mmol, 50.00% aqueous solution) and potassium hydroxide (0.266 g, 4.093 mmol) were added thereto. The mixture was stirred at room temperature for 30 minutes, and then the reaction mixture was concentrated under reduced pressure. Saturated sodium hydrogen carbonate was added to the concentrate, followed by stirring. The precipitated solid was filtered and dried to yield compound 218 (0.058 g, 77.1%) as a white solid.

¹H NMR (400 MHz, DMSO-d₆) δ 7.64 (d, 2 H, J=8.2 Hz), 7.35 (d, 2 H, J=7.4 Hz), 7.31-7.27 (m, 2 H), 7.17-7.16 (m, 1 H), 3.72 (s, 2 H), 2.80 (d, 2 H, J=10.0 Hz), 2.74-2.71 (m, 2 H), 2.46-2.42 (m, 2 H), 1.82-1.80 (m, 2 H), 0.93 (d, 6 H, J=6.1 Hz).

Example 75

Synthesis of Compound 219

(4-(1-((3R,5S)-4-benzyl-3,5-dimethylpiperazin-1-yl)ethyl)-N-hydroxybenzamide)

Step 1: Synthesis of Methyl 4-(1-bromoethyl)benzoate

Methyl 4-(1-hydroxyethyl)benzoate (0.500 g, 2.775 mmol) was dissolved in toluene (10 mL), and PBr₃ (0.079 mL, 0.832 mmol) was added thereto at 0° C. The mixture was stirred at the same temperature for 1 hour and 20 minutes, and the reaction mixture was concentrated under reduced pressure to yield the desired compound (0.410 g, 60.8%) as a purple oil.

Step 2: Synthesis of Methyl 4-(1-((3R,5S)-4-benzyl-3,5-dimethylpiperazin-1-yl)ethyl)benzoate (3R,5S)-1-benzyl-3,5-dimethylpiperazine (formula 8-3, 0.200 g, 0.831 mmol), methyl 4-(1-bromoethyl)benzoate (formula 8-4, 0.222 g, 0.914 mmol) and Cs₂CO₃ (0.812 g, 2.492 mmol) were dissolved in N,N-dimethylformamide (4 mL) at room temperature, and the reaction solution was stirred at 50° C. for 17 hours. The reaction mixture was filtered through a glass filter to remove solids, and water was added to the filtrate, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=25%) and concentrated to afford the desired compound (0.168 g, 55.2%) as a pale yellow oil.

Step 3: Synthesis of Compound 219

Methyl 4-(1-((3R,5S)-4-benzyl-3,5-dimethylpiperazin-1-yl)ethyl)benzoate (formula 8-5, 0.080 g, 0.218 mmol) was dissolved in methanol (3 mL), and then hydroxylamine (0.134 mL, 2.183 mmol, 50.00% aqueous solution) and potassium hydroxide (0.284 g, 4.366 mmol) were added thereto. The mixture was stirred at room temperature for 30 minutes, and the reaction mixture was concentrated under reduced pressure to remove the solvent. A saturated aqueous solution of sodium hydrogen carbonate was added to the resulting concentrate, followed by extraction with methylene chloride. The extract was passed through a plastic filter to remove solid residue and an aqueous layer, and the organic layer was concentrated under reduced pressure to yield compound 219 (0.051 g, 63.6%) as a white solid.

¹H NMR (400 MHz, DMSO-d₆) δ 11.10 (s, 1 H), 9.10 (s, 1 H), 7.67 (d, 2 H, J=6.9 Hz), 7.31-7.23 (m, 6 H), 7.16-7.14 (m, 1 H), 3.68 (s, 2 H), 2.82 (d, 2 H, J=11.0 Hz), 2.53-2.82 (m, 3 H), 1.74 (t, 1 H, J=10.2 Hz), 1.64 (t, 1 H, J=10.5 Hz), 1.24 (d, 3 H, J=6.7 Hz), 0.90 (d, 3 H, J=6.0 Hz), 0.86-0.84 (m, 1 H), 0.81 (d, 3 H, J=6.7 Hz).

Example 76

Synthesis of Compound 220

(4-(((2S,6R)-2,6-dimethyl-4-(1-phenylethyl)piperazin-1-yl)methyl)-N-hydroxybenzamide)

Step 1: Synthesis of (1-bromoethyl)benzene (1-hydroxyethyl)benzene (1.000 g, 8.186 mmol) and $PBr_3$ (0.233 mL, 2.456 mmol) were dissolved in toluene (10 mL) at 0° C., and the reaction solution was stirred at the same temperature for 1 hour. A saturated aqueous solution of sodium hydrogen carbonate was added to the reaction mixture, followed by extraction with methylene chloride. The extract was passed through a plastic filter to remove solid residue and an aqueous layer, and the organic layer was concentrated under reduced pressure to yield the desired compound (0.900 g, 59.4%) as a pale brown oil.

Step 2: Synthesis of Methyl 4-(((2S,6R)-2,6-dimethyl-4-(1-phenylethyl)piperazin-1-yl)methyl)benzoate Methyl 4-(((2S,6R)-2,6-dimethylpiperazin-1-yl)methyl) benzoate (formula 13-2, 0.200 g, 0.669 mmol), (1-bromoethyl)benzene (0.136 g, 0.736 mmol) and $Cs_2CO_3$ (0.654 g, 2.008 mmol) were dissolved in N,N-dimethylformamide (4 mL) at room temperature, and the reaction solution was stirred at 50° C. for 17 hours. Then, water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (silicon dioxide; ethyl acetate/hexane=25%) and concentrated to afford the desired compound (0.22 g, 89.7%) as a colorless oil.

Step 3: Synthesis of Compound 220

Methyl 4-(((2S,6R)-2,6-dimethyl-4-(1-phenylethyl)piperazin-1-yl)methyl)benzoate (formula 13-3, 0.110 g, 0.300 mmol) was dissolved in methanol (3 mL), and then hydroxylamine (0.184 mL, 3.001 mmol, 50.00% aqueous solution) and potassium hydroxide (0.391 g, 6.003 mmol) were added thereto. The mixture was stirred at room temperature for 20 minutes, and then the reaction mixture was concentrated under reduced pressure to remove the solvent. A saturated aqueous solution of sodium hydrogen carbonate was added to the resulting concentrate, followed by extraction with methylene chloride. The extract was passed through a plastic filter to remove solid residue and an aqueous layer, and the organic layer was concentrated under reduced pressure to yield compound 220 (0.063 g, 57.1%) as a white solid.

$^1$H NMR (400 MHz, DMSO-$d_6$) δ 7.63 (d, 2 H, J=8.3 Hz), 7.35-7.33 (m, 2 H), 7.30-7.26 (m, 4 H), 7.24-7.21 (m, 1 H), 3.69 (s, 2 H), 2.85-2.83 (m, 1 H), 2.55-2.50 (m, 3 H), 1.75-1.74 (m, 1 H), 1.63-1.62 (m, 1 H), 1.25 (d, 3 H, J=6.8 Hz), 0.91-0.90 (m, 1 H), 0.88 (d, 3 H, J=4.9 Hz), 0.78 (d, 3 H, J=6.1 Hz).

Example 77

Synthesis of Compound 222

(4-(((3R,5S)-4-(2-(3-fluorophenyl)acetyl)-3,5-dimethylpiperazin-1-yl)methyl)-N-hydroxybenzamide)

Step 1: Synthesis of Methyl 4-(((3R,5S)-4-(2-(3-fluorophenyl)acetyl)-3,5-dimethylpiperazin-1-yl) methyl)benzoate Methyl 4-(((3R,5S)-3,5-dimethylpiperazin-1-yl)methyl) benzoate (formula 1-2, 0.100 g, 0.381 mmol), 2-(3-fluorophenyl)acetic acid (0.088 g, 0.572 mmol), HOBt (0.077 g, 0.572 mmol), EDCI (0.110 g, 0.572 mmol) and DIPEA (0.133 mL, 0.762 mmol) were dissolved in methylene chloride (2 ml) at 25° C., and the reaction solution was stirred at the same temperature for 20 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; 4 g cartridge; methanol/methylene chloride=from 0% to 5%) and concentrated to afford the desired compound (0.047 g, 30.9%) as a pale yellow solid.

Step 2: Synthesis of Compound 222

Methyl 4-(((3R,5S)-4-(2-(3-fluorophenyl)acetyl)-3,5-dimethylpiperazin-1-yl)methyl)benzoate (formula 1-3, 0.040 g, 0.100 mmol), hydroxylamine (0.123 mL, 2.008 mmol, 50.00% aqueous solution) and potassium hydroxide (0.056 g, 1.004 mmol) were dissolved in methanol (1 ml) at 25° C., and the reaction solution was stirred at the same temperature for 1 hour. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield compound 222 (0.019 g, 47.4%) as an orange solid.

$^1$H NMR (400 MHz, DMSO-$d_6$) δ 7.64 (d, 2 H, J=8.0 Hz), 7.32-7.27 (m, 1 H), 7.24 (d, 2 H, J=8.0 Hz), 7.04-7.01 (m, 3 H), 4.35 (brs, 1 H), 4.07 (brs, 1 H), 3.75-3.62 (m, 2 H), 3.46 (s, 2 H), 2.63-2.52 (m, 2 H), 1.99-1.73 (m, 2 H), 1.20 (d, 6 H, J=17.2 Hz).

Example 78

Synthesis of Compound 223

(4-(((3R,5S)-3,5-dimethyl-4-(2-(3-(trifluoromethyl) phenyl)acetyl)piperazin-1-yl)methyl)-N-hydroxybenzamide)

Step 1: Synthesis of Methyl 4-(((3R,5S)-3,5-dimethyl-4-(2-(3-(trifluoromethyl)phenyl)acetyl)piperazin-1-yl)methyl)benzoate Methyl 4-(((3R,5S)-3,5-dimethylpiperazin-1-yl)methyl) benzoate (formula 1-2, 0.100 g, 0.381 mmol), 2-(3-(trifluoromethyl)phenyl)acetic acid (0.117 g, 0.572 mmol), HOBt (0.077 g, 0.572 mmol), EDCI (0.110 g, 0.572 mmol) and DIPEA (0.133 mL, 0.762 mmol) were dissolved in methylene chloride (2 ml) at 25° C., and the reaction solution was stirred at the same temperature for 20 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; 12 g cartridge; methanol/methylene chloride=from 0% to 5%) and concentrated to afford the desired compound (0.037 g, 21.6%) as a colorless oil.

Step 2: Synthesis of Compound 223

Methyl 4-(((3R,5S)-3,5-dimethyl-4-(2-(3-(trifluoromethyl)phenyl)acetyl)piperazin-1-yl)methyl)benzoate (formula 1-3, 0.030 g, 0.067 mmol), hydroxylamine (0.082 mL, 1.338 mmol, 50.00% aqueous solution) and potassium hydroxide (0.038 g, 0.669 mmol) were dissolved in methanol (1 ml) at 25° C., and the reaction solution was stirred at the same temperature for 1 hour. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield compound 223 (0.013 g, 43.2%) as a pale yellow solid.
$^1$H NMR (400 MHz, DMSO-d$_6$) δ 7.64 (d, 2 H, J=8.0 Hz), 7.56-7.48 (m, 4 H), 7.20 (d, 2 H, J=8.4 Hz), 4.36 (brs, 1 H), 4.12 (brs, 1 H), 3.92-3.67 (brs, 1 H), 3.48 (s, 2 H), 2.61 (d, 2 H, J=11.2 Hz), 2.05-2.00 (m, 2 H), 1.23 (d, 6 H, J=31.6 Hz).

Example 79

Synthesis of Compound 224

(4-(((3R,5S)-4-(2-(3-chlorophenyl)acetyl)-3,5-dimethylpiperazin-1-yl)methyl)-N-hydroxybenzamide)

Step 1: Synthesis of Methyl 4-(((3R,5S)-4-(2-(3-chlorophenyl)acetyl)-3,5-dimethylpiperazin-1-yl)methyl)benzoate Methyl 4-(((3R,5S)-3,5-dimethylpiperazin-1-yl)methyl)benzoate (formula 1-2, 0.100 g, 0.381 mmol), 2-(3-chlorophenyl)acetic acid (0.098 g, 0.572 mmol), HOBt (0.077 g, 0.572 mmol), EDCI (0.110 g, 0.572 mmol) and DIPEA (0.133 mL, 0.762 mmol) were dissolved in methylene chloride (2 ml) at 25° C., and the reaction solution was stirred at the same temperature for 20 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide; 4 g cartridge; methanol/methylene chloride=from 0% to 5%) and concentrated to afford the desired compound (0.042 g, 26.6%) as a colorless oil.

Step 2: Synthesis of Compound 224

Methyl 4-(((3R,5S)-4-(2-(3-chlorophenyl)acetyl)-3,5-dimethylpiperazin-1-yl)methyl)benzoate (formula 1-3, 0.035 g, 0.084 mmol), hydroxylamine (0.103 mL, 1.687 mmol, 50.00% aqueous solution) and potassium hydroxide (0.047 g, 0.844 mmol) were dissolved in methanol (1 ml) at 25° C., and the reaction solution was stirred at the same temperature for 1 hour. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield compound 224 (0.020 g, 57.0%) as a white solid.
$^1$H NMR (400 MHz, DMSO-d$_6$) δ 7.62 (d, 2 H, J=7.6 Hz), 7.31-7.23 (m, 4 H), 7.15 (d, 2 H, J=6.4 Hz), 4.35 (brs, 1 H), 4.07 (brs, 1 H), 3.76-3.47 (m, 2 H), 3.30 (s, 2 H), 2.62 (d, 2 H, J=10.8 Hz), 1.98 (brs, 2 H), 1.23 (d, 6 H, J=25.2 Hz).

Example 80

Synthesis of Compound 225

(4-(((3R,5S)-4-(3-fluorobenzyl)-3,5-dimethylpiperazin-1-yl)methyl)-N-hydroxybenzamide)

Step 1: Synthesis of Methyl 4-(((3R,5S)-4-(3-fluorobenzyl)-3,5-dimethylpiperazin-1-yl)methyl)benzoate Methyl 4-(((3R,5S)-3,5-dimethylpiperazin-1-yl)methyl)benzoate (compound 1-2, 0.150 g, 0.572 mmol), 3-fluorobenzyl bromide (0.077 mL, 0.629 mmol) and K$_2$CO$_3$ (0.119 g, 0.858 mmol) were dissolved in acetonitrile (4 mL) at room temperature, and the reaction solution was stirred at the same temperature for 17 hours. Then, water was added to the reaction mixture, followed by extraction with ethyl acetate. The extract was passed through a plastic filter to remove solid residue and an aqueous layer, and the organic layer was concentrated under reduced pressure. The concentrate was purified by column chromatography (silicon dioxide; 4 g cartridge; ethyl acetate/hexane=from 0% to 40%) and concentrated to afford the desired compound (0.110 g, 51.9%) as a white solid.

Step 2: Synthesis of Compound 225

Methyl 4-(((3R,5S)-4-(3-fluorobenzyl)-3,5-dimethylpiperazin-1-yl)methyl)benzoate (compound 1-3, 0.060 g, 0.162 mmol), hydroxylamine (0.099 mL, 1.620 mmol, 50.00% aqueous solution) and potassium hydroxide (0.211 g, 3.239 mmol) were dissolved in methanol (3 mL) at room temperature, and the reaction solution was stirred at the same temperature for 1 hour, and then concentrated under reduced pressure to remove the solvent. A saturated aqueous solution of sodium hydrogen carbonate was added to the resulting concentrate, followed by extraction with methylene chloride. The extract was passed through a plastic filter to remove solid residue and an aqueous layer, and the organic layer was concentrated under reduced pressure to yield compound 225 (0.044 g, 73.1%) as a white solid.
$^1$H NMR (400 MHz, DMSO-d$_6$) δ 7.65 (d, 2 H, J=8.0 Hz), 7.31-7.27 (m, 1 H), 7.22 (d, 2 H, J=8.0 Hz), 7.17-7.13 (m, 2 H), 6.97-6.96 (m, 1 H), 3.70 (s, 2 H), 3.43 (s, 2 H), 2.64 (d, 2 H, J=11.2 Hz), 2.57-2.56 (m, 2 H), 1.78 (t, 2 H, J=10.6 Hz), 0.84 (d, 6 H, J=6.0 Hz); LRMS (ES) m/z 372.2 (M$^+$+1).

Example 81

Synthesis of Compound 230

((3R,5S)-4-(4-(hydroxycarbamoyl)benzyl)-N-(3-methoxybenzyl)-3,5-dimethylpiperazine-1-carboxamide (Trifluoroacetic acid salt))

Step 1: Synthesis of 4-nitrophenyl 3-methoxybenzyl carbamate 3-methoxybenzyl amine (0.100 g, 0.729 mmol) and TEA (0.152 mL, 1.093 mmol) were dissolved in methylene chloride (2 mL), and 4-nitrophenyl chloroformate (0.162 g, 0.802 mmol) was added thereto at 0° C., followed by stirring at the same temperature for 2 hours. Then, water was added to the reaction mixture, followed by extraction with methylene chloride. The extract was passed through a plastic filter to solid residue and an aqueous layer, and the organic layer was concentrated under reduced pressure. The obtained product was used without additional purification (0.200 g, 90.8%, yellow oil).

Step 2: Synthesis of Methyl 4-(((2S,6R)-4-((3-methoxybenzyl)carbamoyl)-2,6-dimethylpiperazin-1-yl)methyl)benzoate 4-Nitrophenyl 3-methoxybenzyl carbamate (0.130 g, 0.430 mmol), methyl 4-(((2S,6R)-2,6-dimethylpiperazin-1-yl)methyl)benzoate (formula 13-2, 0.129 g, 0.430 mmol) and TEA (0.179 mL, 1.290 mmol) were dissolved in N,N-dimethylformamide (4 mL) at room temperature, and the reaction solution was stirred at 100° C. for 3 hours. Then, the reaction mixture was concentrated under reduced pressure. The obtained product was used without additional purification (0.180 g, 98.4%, brown oil).

Step 3: Synthesis of Compound 230

Methyl 4-(((2S,6R)-4-((3-methoxybenzyl)carbamoyl)-2,6-dimethylpiperazin-1-yl)methyl)benzoate (formula 13-3, 0.180 g, 0.423 mmol), hydroxylamine (0.517 mL, 8.460 mmol, 50.00% aqueous solution) and potassium hydroxide (0.237 g, 4.230 mmol) were dissolved in methanol (2 mL) at room temperature, and the reaction solution was stirred at the same temperature for 17 hours. The concentrate was purified by column chromatography (Waters, $C_{18}$, 19*100 mm column, 0.1% trifluoroacetic acid/acetonitrile=from 5% to 80%) and concentrated to afford compound 230 (0.033 g, 18.3%) as a white solid.
$^1$H NMR (400 MHz, DMSO-$d_6$) δ 11.11 (brs, 1 H), 8.95 (brs, 1 H), 7.64 (d, 2 H, J=8.4 Hz), 7.39 (d, 2 H, J=8.0 Hz), 7.17 (dd, 1 H, J=7.0, 7.0 Hz), 7.03 (dd, 1 H, J=6.0, 6.0 Hz), 6.75-6.72 (m, 2 H), 4.16 (d, 2 H, J=5.6 Hz), 3.80 (d, 2 H, J=12.4 Hz), 3.72 (s, 2 H), 3.68 (s, 3 H), 2.53 (d, 2 H, J=10.4 Hz), 2.42-2.38 (m, 2 H), 0.89 (d, 6 H, J=6.0 Hz); LRMS (ES) m/z 427.3 (M$^+$+1)

Example 82

Synthesis of Compound 231

((3R,5S)-N-(3-fluorobenzyl)-4-(4-(hydroxycarbamoyl)benzyl)-3,5-dimethylpiperazine-1-carboxamide)

Step 1: Synthesis of 4-nitrophenyl 3-fluorobenzylcarbamate (3-fluorophenyl)methylamine (0.200 g, 1.598 mmol) and TEA (0.243 g, 2.397 mmol) were dissolved in methylene chloride (2 mL), and 4-nitrophenyl chloroformate (0.354 g, 1.758 mmol) was added thereto at 0° C., followed by stirring at the same temperature for 1 hour. Then, water was added to the reaction mixture, followed by extraction with methylene chloride. The extract was passed through a plastic filter to solid residue and an aqueous layer, and the organic layer was concentrated under reduced pressure. The obtained product was used without additional purification (0.410 g, 88.4%, yellow solid).

Step 2: Synthesis of Methyl 4-(((2S,6R)-4-((3-fluorobenzyl)carbamoyl)-2,6-dimethylpiperazin-1-yl)methyl)benzoate 4-Nitrophenyl 3-fluorobenzylcarbamate (0.200 g, 0.689 mmol), methyl 4-(((2S,6R)-2,6-dimethylpiperazin-1-yl)methyl)benzoate (formula 13-2, 0.216 g, 0.724 mmol) and TEA (0.287 mL, 2.067 mmol) were dissolved in N,N-dimethylformamide (3 mL) at room temperature, and the reaction solution was stirred at 100° C. for 2 hours and 30 minutes. Then, the reaction mixture was concentrated under reduced pressure using V10. The concentrate was purified by column chromatography (silicon dioxide, 4 g cartridge; ethyl acetate/hexane=from 0% to 50%) and concentrated to afford the desired compound (0.178 g, 62.5%) as a pale brown oil.

Step 3: Synthesis of Compound 231

Methyl 4-(((2S,6R)-4-((3-fluorobenzyl)carbamoyl)-2,6-dimethylpiperazin-1-yl)methyl)benzoate (formula 13-3, 0.100 g, 0.242 mmol), hydroxylamine (0.296 mL, 4.837 mmol, 50.00% aqueous solution) and potassium hydroxide (0.136 g, 2.418 mmol) were dissolved in methanol (3 mL) at room temperature, and the reaction solution was stirred at the same temperature for 30 minutes. Then, the reaction mixture was concentrated under reduced pressure. A saturated aqueous solution of sodium hydrogen carbonate (10 mL) was added to the concentrate, followed by stirring. The precipitated solid was filtered and dried to yield compound 231 (0.055 g, 54.9%) as a white solid.
$^1$H NMR (400 MHz, DMSO-$d_6$) δ 7.64 (d, 2 H, J=8.0 Hz), 7.38 (d, 2 H, J=8.0 Hz), 7.33-7.27 (m, 1 H), 7.10 (t, 1 H, J=5.8 Hz), 7.06-6.98 (m, 3 H), 4.20 (d, 2 H, J=5.6 Hz), 3.79 (d, 2 H, J=12.8 Hz), 3.72 (s, 2 H), 2.52 (t, 2 H, J=11.6 Hz), 2.42-2.38 (m, 2 H), 0.89 (d, 6 H, J=6.0 Hz); LRMS (ES) m/z 415.2 (M$^+$+1).

Example 83

Synthesis of Compound 232

((2S,6R)-N-(3-fluorobenzyl)-4-(4-(hydroxycarbamoyl)benzyl)-2,6-dimethylpiperazine-1-carboxamide)

Step 1: Synthesis of Methyl 4-(((3R,5S)-4-((3-fluorobenzyl)carbamoyl)-3,5-dimethylpiperazin-1-yl)methyl)benzoate 4-Nitrophenyl 3-fluorobenzylcarbamate (0.220 g, 0.758 mmol), methyl 4-(((3R,5S)-3,5-dimethylpiperazin-1-yl)methyl)benzoate (formula 1-2, 0.209 g, 0.796 mmol) and TEA (0.315 mL, 2.274 mmol) were dissolved in N,N-dimethylformamide (3 mL) at room temperature, and the reaction solution was stirred at 100° C. for 2 hours and 30 minutes. Then, the reaction mixture was concentrated under reduced pressure. The concentrate was purified by column chromatography (silicon dioxide, 4 g cartridge; ethyl acetate/hexane=from 0% to 50%) and concentrated to afford the desired compound (0.185 g, 59.0%) as a colorless oil.

Step 2: Synthesis of Compound 232

Methyl 4-(((3R,5S)-4-((3-fluorobenzyl)carbamoyl)-3,5-dimethylpiperazin-1-yl)methyl)benzoate (formula 1-3, 0.100 g, 0.242 mmol), hydroxylamine (0.296 mL, 4.837 mmol, 50.00% aqueous solution) and potassium hydroxide (0.136 g, 2.418 mmol) were dissolved in methanol (3 mL) at room temperature, and the reaction solution was stirred at the same temperature for 30 minutes. The reaction mixture was concentrated under reduced pressure to remove the solvent. A saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure to yield compound 232 (0.026 g, 25.9%) as a white solid.

$^1$H NMR (400 MHz, DMSO-$d_6$) δ 7.70 (d, 2 H, J=8.0 Hz), 7.48 (d, 2 H, J=8.4 Hz), 7.31-7.25 (m, 1 H), 7.06 (d, 1 H, J=7.6 Hz), 6.98 (d, 1 H, J=10.0 Hz), 6.93-6.88 (m, 1 H), 4.35 (s, 2 H), 4.07-4.04 (m, 2 H), 3.54 (s, 2 H), 2.67 (d, 2 H, J=11.2 Hz), 2.17 (dd, 2 H, J=10.2, 3.6 Hz), 1.31 (d, 6 H, J=6.8 Hz).

Example 84

Synthesis of Compound 233

(4-(((2S,6R)-4-(2-(3-chlorophenyl)acetyl)-2,6-dimethylpiperazin-1-yl)methyl)-N-hydroxybenzamide)

Step 1: Synthesis of Methyl 4-(((2S,6R)-4-(2-(3-chlorophenyl)acetyl)-2,6-dimethylpiperazin-1-yl)methyl)benzoate 2-(3-chlorophenyl)acetic acid (0.200 g, 0.669 mmol), methyl 4-(((2S,6R)-2,6-dimethylpiperazin-1-yl)methyl)benzoate (formula 13-2, 0.126 g, 0.736 mmol), EDCI (0.257 g, 1.339 mmol), HOBt (0.205 g, 1.339 mmol) and DIPEA (0.584 mL, 3.347 mmol) were dissolved in methylene chloride (5 mL) at room temperature, and the reaction solution was stirred at the same temperature for 17 hours. Then, a saturated aqueous solution of sodium hydrogen carbonate was added to the reaction mixture, followed by extraction with methylene chloride. The extract was passed through a plastic filter to remove solid residue and an aqueous solution, and the organic layer was concentrated under reduced pressure. The concentrate was purified by column chromatography (silicon dioxide, 4 g cartridge; ethyl acetate/hexane=from 10% to 70%) and concentrated to afford the desired compound (0.187 g, 67.3%) as a colorless oil.

Step 2: Synthesis of Compound 233

Methyl 4-(((2S,6R)-4-(2-(3-chlorophenyl)acetyl)-2,6-dimethylpiperazin-1-yl)methyl)benzoate (formula 13-3, 0.100 g, 0.241 mmol), hydroxylamine (50.00% aqueous solution, 0.295 mL, 4.820 mmol) and potassium hydroxide (0.135 g, 2.410 mmol) were dissolved in methanol (3 mL) at room temperature, and the reaction solution was stirred at the same temperature for 30 minutes. Then, a saturated aqueous solution of sodium hydrogen carbonate was added to the reaction mixture, followed by extraction with methylene chloride. The extract was passed through a plastic filter to remove solid residue and an aqueous solution, and the organic layer was concentrated under reduced pressure. Diethyl ether (3 mL) was added to the concentrate, followed by stirring. The precipitated solid was filtered and dried to yield compound 233 (0.053 g, 52.9%) as a white solid.

$^1$H NMR (400 MHz, DMSO-$d_6$) δ 7.63 (d, 2 H, J=8.4 Hz), 7.33 (d, 2 H, J=8.4 Hz), 7.27-7.24 (m, 3 H), 7.16-7.14 (m, 1 H), 4.10 (d, 1 H, J=12.4 Hz), 3.81 (d, 1 H, J=13.2 Hz), 3.76-3.65 (m, 4 H), 2.86-2.52 (m, 1 H), 2.43 (d, 1 H, J=12.4 Hz), 2.38-2.28 (m, 2 H), 0.90 (t, 6 H, J=5.4 Hz); LRMS (ES) m/z 416.1 (M$^+$+1).

Example 85

Synthesis of Compound 234

(4-(((3R,5S)-4-(2-([1,1'-biphenyl]-3-yl)acetyl)-3,5-dimethylpiperazin-1-yl)methyl)-N-hydroxybenzamide)

Step 1: Synthesis of Methyl 4-(((3R,5S)-4-(2-([1,1'-biphenyl]-3-yl)acetyl)-3,5-dimethylpiperazin-1-yl)methyl)benzoate Methyl 4-(((3R,5S)-3,5-dimethylpiperazin-1-yl)methyl)benzoate (formula 1-2, 0.100 g, 0.381 mmol), 2-([1,1'-biphenyl]-3-yl)acetic acid (0.097 g, 0.457 mmol), HOBt (0.077 g, 0.572 mmol), EDCI (0.110 g, 0.572 mmol) and DIPEA (0.099 g, 0.762 mmol) were dissolved in methylene chloride (2 ml) at 25° C., and the reaction solution was stirred at the same temperature for 7 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide, 12 g cartridge; methanol/methylene chloride=from 0% to 5%) and concentrated to afford the desired compound (0.114 g, 65.5%) as a yellow solid.

Step 2: Synthesis of Compound 234

Methyl 4-(((3R,5S)-4-(2-([1,1'-biphenyl]-3-yl)acetyl)-3,5-dimethylpiperazin-1-yl)methyl)benzoate (formula 4-2, 0.050 g, 0.110 mmol), hydroxylamine (0.134 mL, 2.190 mmol, 50.00% aqueous solution) and potassium hydroxide (0.061 g, 1.095 mmol) were dissolved in methanol (1 ml) at 25° C., and the reaction solution was stirred at the same temperature for 1 hour. Saturated sodium hydrogen carbonate was added to the reaction mixture, followed by extraction with methylene chloride. The organic layer was washed with a saturated aqueous solution of sodium chloride, dried with anhydrous sodium sulfate, and then concentrated under reduced pressure to yield compound 234 (0.027 g, 53.9%) as a pale yellow solid.

$^1$H NMR (400 MHz, DMSO-$d_6$) δ 7.70 (d, 2 H, J=7.6 Hz), 7.68 (d, 2 H, J=8.0 Hz), 7.58-7.30 (m, 8 H), 7.21 (m, 1 H), 4.39 (brs, 1 H), 4.14 (brs, 1 H) 3.83-3.64 (m, 2 H), 3.48 (s, 2 H), 2.62 (d, 2 H, J=10.8 Hz), 2.29 (brs, 2 H), 1.22 (d, 6 H, J=20 Hz).

Example 86

Synthesis of Compound 242

(4-(((3R,5S)-4-(3-(furan-2-yl)benzoyl)-3,5-dimethylpiperazin-1-yl)methyl)-N-hydroxybenzamide)

Step 1: Synthesis of 3-iodobenzoyl chloride 3-iodobenzoic acid (0.200 g, 0.806 mmol) was dissolved in SOCl$_2$ (1.170 mL, 16.128 mmol) and stirred at 100° C. for 2 hours, and the reaction mixture was concentrated under reduced pressure. The obtained product was used without additional purification (0.215 g, 100.0%, brown oil).

Step 2: Methyl 4-(((3R,5S)-4-(3-iodobenzoyl)-3,5-dimethylpiperazin-1-yl)methyl)benzoate Methyl 4-(((3R,5S)-3,5-dimethylpiperazin-1-yl)methyl) benzoate (formula 1-2, 0.215 g, 0.807 mmol), 3-iodobenzoyl chloride (0.233 mL, 0.887 mmol) and TEA (0.224 mL, 1.613 mmol) were dissolved in methylene chloride (5 mL) at 0° C., and the reaction solution was stirred at the same temperature for 2 hours. Then, water was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 30% to 50%) and concentrated to afford the desired compound (0.365 g, 91.8%) as a colorless oil.

Step 3: Methyl 4-(((3R,5S)-4-(3-(furan-2-yl)benzoyl)-3,5-dimethylpiperazin-1-yl)methyl)benzoate 1,2-Dimethoxyethane/water (v/v=3/1) (1 mL) were added to a mixture of methyl 4-(((3R,5S)-4-(3-iodobenzoyl)-3,5-dimethylpiperazin-1-yl)methyl)benzoate (formula 4-1, 0.346 g, 0.703 mmol), furan-2-ylboronic acid (0.118 g, 1.054 mmol), Pd(dppf)Cl$_2$ (0.029 g, 0.035 mmol) and Na$_2$CO$_3$ (0.223 g, 2.108 mmol), and heated by microwave irradiation at 120° C. for 30 minutes, followed by cooling to room temperature. Then, a 1N aqueous solution of hydrochloric acid was added to the reaction mixture, followed by extraction with ethyl acetate. The organic layer was washed with water, dried with anhydrous magnesium sulfate, and then concentrated under reduced pressure. The concentrate was purified by column chromatography (silicon dioxide; ethyl acetate/hexane=from 10% to 25%) and concentrated to afford the desired compound (0.301 g, 99.0%) as a brown oil.

Step 4: Synthesis of Compound 242

Methyl 4-(((3R,5S)-4-(3-(furan-2-yl)benzoyl)-3,5-dimethylpiperazin-1-yl)methyl)benzoate (formula 4-2, 0.050 g, 0.116 mmol), hydroxylamine (0.141 mL, 2.312 mmol, 50.00% aqueous solution) and potassium hydroxide (0.065 g, 1.156 mmol) were dissolved in methanol (2 mL) at room temperature, and the reaction solution was stirred at the same temperature for 30 minutes. Then, the reaction mixture was concentrated under reduced pressure. A saturated aqueous solution of sodium hydrogen carbonate was added to the concentrate, and the precipitated solid was filtered and dried to yield compound 242 (0.034 g, 67.6%) as a white solid.
$^1$H NMR (400 MHz, DMSO-d$_6$) δ 7.79 (s, 1 H), 7.78-7.70 (m, 3 H), 7.64 (s, 1 H), 7.48 (t, 1 H, J=7.7 Hz), 7.37 (d, 2 H, J=8.0 Hz), 7.24 (d, 1 H, J=7.6 Hz), 7.08 (d, 1 H, J=3.4 Hz), 6.63-6.61 (m, 1 H), 3.53 (s, 2 H), 2.63 (brs, 2 H), 2.18-2.14 (m, 2 H), 1.31 (brs, 6 H).

Example 87

Synthesis of Compound 243

(4-(((3R,5S)-4-(3-(furan-3-yl)benzoyl)-3,5-dimethyl-piperazin-1-yl)methyl)-N-hydroxybenzamide)

Step 1: Synthesis of Methyl 4-(((3R,5S)-4-(3-(furan-3-yl)benzoyl)-3,5-dimethylpiperazin-1-yl) methyl)benzoate 1,2-Dimethoxyethane/water (v/v=3/1) (1 mL) were added to a mixture of methyl 4-(((3R,5S)-4-(3-iodobenzoyl)-3,5-dimethylpiperazin-1-yl)methyl)benzoate (formula 4-1, 0.120 g, 0.244 mmol), furan-3-ylboronic acid (0.041 g, 0.366 mmol), Pd(dbpf)Cl$_2$ (0.008 g, 0.012 mmol) and Na$_2$CO$_3$ (0.077 g, 0.731 mmol), and heated by microwave irradiation at 120° C. for 30 minutes, followed by cooling to room temperature. Then, a 1N aqueous solution of hydrochloric acid was added to the reaction mixture, followed by extraction with ethyl acetate. The organic layer was washed with water, dried with anhydrous magnesium sulfate, and then concentrated under reduced pressure. The concentrate was purified by column chromatography (silicon dioxide; ethyl acetate/hexane=from 10% to 30%) and concentrated to afford the desired compound (0.050 g, 47.0%) as a brown solid.

Step 2: Synthesis of Compound 243

4-(((3R,5S)-4-(3-(furan-3-yl)benzoyl)-3,5-dimethylpiperazin-1-yl)methyl)benzoate (formula 4-2, 0.050 g, 0.114 mmol), hydroxylamine (0.140 mL, 2.289 mmol, 50.00% aqueous solution) and potassium hydroxide (0.064 g, 1.144 mmol) were dissolved in methanol (2 mL) at room temperature, and the reaction solution was stirred at the same temperature for 30 minutes. Then, the reaction mixture was concentrated under reduced pressure. A saturated aqueous solution of sodium hydrogen carbonate was added to the concentrate, and the precipitated solid was filtered and dried to yield compound 243 (0.029 g, 57.4%) as a white solid.
$^1$H NMR (400 MHz, DMSO-d$_6$) δ 8.29 (s, 1 H), 7.76-7.70 (m, 3 H), 7.66 (d, 1 H, J=8.0 Hz), 7.46-7.38 (m, 3 H), 7.20 (d, 1 H, J=7.6 Hz), 7.05-7.04 (m, 1 H), 3.54 (s, 2 H), 2.68-2.64 (m, 2 H), 2.19-2.15 (m, 2 H), 1.32 (brs, 6 H).

Example 88

Synthesis of Compound 244

(4-(((3R,5S)-4-(3-(3,6-dihydro-2H-pyran-4-yl)benzoyl)-3,5-dimethylpiperazin-1-yl)methyl)-N-hydroxybenzamide)

Step 1: Synthesis of Methyl 4-(((3R,5S)-4-(3-(3,6-dihydro-2H-pyran-4-yl)benzoyl)-3,5-dimethylpiperazin-1-yl)methyl)benzoate 1,2-Dimethoxyethane/water (v/v=3/1) (1 mL) were added to a mixture of methyl 4-(((3R,5S)-4-(3-iodobenzoyl)-3,5-dimethylpiperazin-1-yl)methyl)benzoate (formula 4-1, 0.120 g, 0.244 mmol), 2-(3,6-dihydro-2H-pyran-4-yl)-4,4,5,5-tetramethyl-1,3,2-dioxaborolane (0.077 g, 0.366 mmol), Pd(dbpf)Cl$_2$ (0.008 g, 0.012 mmol) and Na$_2$CO$_3$ (0.077 g, 0.731 mmol), and heated by microwave irradiation at 120° C. for 30 minutes, followed by cooling to room temperature. Then, a 1N aqueous solution of hydrochloric acid was added to the reaction mixture, followed by extraction with ethyl acetate. The organic layer was washed with water, dried with anhydrous magnesium sulfate, and then concentrated under reduced pressure. The concentrate was purified by column chromatography (silicon dioxide; ethyl acetate/hexane=from 10% to 50%) and concentrated to afford the desired compound (0.049 g, 44.8%) as a brown oil.

Step 2: Synthesis of Compound 244

Methyl 4-(((3R,5S)-4-(3-(3,6-dihydro-2H-pyran-4-yl) benzoyl)-3,5-dimethylpiperazin-1-yl)methyl)benzoate (formula 4-2, 0.049 g, 0.113 mmol), hydroxylamine (0.139 mL, 2.266 mmol, 50.00% aqueous solution) and potassium hydroxide (0.064 g, 1.133 mmol) were dissolved in methanol (2 mL) at room temperature, and the reaction solution was stirred at the same temperature for 30 minutes. Then, the reaction mixture was concentrated under reduced pressure. A saturated aqueous solution of sodium hydrogen carbonate was added to the concentrate, and the precipitated solid was filtered and dried to yield compound 244 (0.013 g, 24.7%) as a white solid.

$^1$H NMR (400 MHz, DMSO-$d_6$) δ 7.72 (d, 2 H, J=8.0 Hz), 7.50 (d, 1 H, J=7.7 Hz), 7.45-7.37 (m, 4 H), 7.22 (d, 1 H, J=7.4 Hz), 6.33 (s, 1 H), 4.23-4.22 (m, 2 H), 3.82 (t, 2 H, J=5.3 Hz), 3.53 (s, 2 H), 2.68-2.63 (m, 2 H), 2.18-2.14 (m, 2 H), 1.30 (brs, 6 H).

Example 89

Synthesis of Compound 245

(4-(((3R,5S)-3,5-dimethyl-4-(3-(pyridin-4-yl)benzoyl)piperazin-1-yl)methyl)-N-hydroxybenzamide (Trifluoroacetic acid salt))

Step 1: Synthesis of Methyl 4-(((3R,5S)-3,5-dimethyl-4-(3-(pyridin-4-yl)benzoyl)piperazin-1-yl)methyl)benzoate 1,2-Dimethoxyethane/water (v/v=3/1) (1 mL) were added to a mixture of methyl 4-(((3R,5S)-4-(3-iodobenzoyl)-3,5-dimethylpiperazin-1-yl)methyl)benzoate (formula 4-1, 0.200 g, 0.406 mmol), pyridine-4-boronic acid hydrate (0.086 g, 0.609 mmol), Pd(dbpf)Cl$_2$ (0.013 g, 0.020 mmol) and Na$_2$CO$_3$ (0.129 g, 1.219 mmol), and heated by microwave irradiation at 120° C. for 20 minutes, followed by cooling to room temperature. Then, a saturated aqueous solution of sodium hydrogen carbonate was added to the reaction mixture, followed by extraction with ethyl acetate. The organic layer was washed with water, dried with anhydrous magnesium sulfate, and then concentrated under reduced pressure. The concentrate was purified by column chromatography (silicon dioxide; methanol/methylene chloride=from 0% to 5%) and concentrated to afford the desired compound (0.167 g, 92.8%) as a brown oil.

Step 2: Synthesis of Compound 245

Methyl 4-(((3R,5S)-3,5-dimethyl-4-(3-(pyridin-4-yl)benzoyl)piperazin-1-yl)methyl)benzoate (formula 4-2, 0.105 g, 0.236 mmol), hydroxylamine (0.288 mL, 4.712 mmol, 50.00% aqueous solution) and potassium hydroxide (0.132 g, 2.356 mmol) were dissolved in methanol (2 mL) at room temperature, and the reaction solution was stirred at the same temperature for 30 minutes. Then, a saturated aqueous solution of sodium hydrogen carbonate was added to the reaction mixture, followed by extraction with methylene chloride. The organic layer was dried with anhydrous sodium sulfate, and then concentrated under reduced pressure. Then, the concentrate was purified by column chromatography (Waters, C$_{18}$, 19*100 mm column, 0.1% trifluoroacetic acid aqueous solution/acetonitrile=from 5% to 80%) and concentrated to afford compound 245 (0.072 g, 54.6%) as a white solid.

$^1$H NMR (400 MHz, DMSO-$d_6$) δ 8.91 (d, 2 H, J=6.6 Hz), 8.24 (d, 2 H, J=6.0 Hz), 8.05 (d, 1 H, J=7.9 Hz), 7.98 (s, 1 H), 7.81 (d, 2 H, J=7.9 Hz), 7.68 (t, 1 H, J=7.7 Hz), 7.61-7.56 (m, 3 H), 4.78 (brs, 1 H), 4.24-4.00 (m, 3 H), 3.23-3.10 (m, 2 H), 1.36 (brs, 6 H).

Example 90

Synthesis of Compound 246

(4-(((3R,5S)-3,5-dimethyl-4-(3-(pyridin-3-yl)benzoyl)piperazin-1-yl)methyl)-N-hydroxybenzamide)

Step 1: Synthesis of 4-(((3R,5S)-3,5-dimethyl-4-(3-(pyridin-3-yl)benzoyl)piperazin-1-yl)methyl)benzoate 1,2-Dimethoxyethane/water (v/v=3/1) (1.2 mL) were added to a mixture of methyl 4-(((3R,5S)-4-(3-iodobenzoyl)-3,5-dimethylpiperazin-1-yl)methyl)benzoate (formula 4-1, 0.100 g, 0.203 mmol), pyridine-3-ylboronic acid (0.050 g, 0.406 mmol), Na$_2$CO$_3$ (0.065 g, 0.609 mmol) and Pd(dbpf)Cl$_2$ (0.007 g, 0.010 mmol), and heated by microwave irradiation at 120° C. for 20 minutes, followed by cooling to room temperature. Then, water was added to the reaction mixture, followed by extraction with ethyl acetate. The organic layer was dried with anhydrous magnesium sulfate, and then concentrated under reduced pressure. The concentrate was purified by column chromatography (silicon dioxide, 4 g cartridge; ethylacetate/hexane=from 0% to 80%) and concentrated to afford the desired compound (0.080 g, 88.8%) as a yellow solid.

Step 2: Synthesis of Compound 246

Methyl 4-(((3R,5S)-3,5-dimethyl-4-(3-(pyridin-3-yl)benzoyl)piperazin-1-yl)methyl)benzoate (formula 4-2, 0.065 g, 0.147 mmol), hydroxylamine (0.090 mL, 1.465 mmol, 50.00% aqueous solution) and potassium hydroxide (0.191 g, 2.931 mmol) were dissolved in methanol (3 mL) at room temperature, and the reaction solution was stirred at the same temperature for 2 hours, and then concentrated. The concentrate was washed with a saturated aqueous solution of sodium hydrogen carbonate and distilled water, thereby obtaining compound 246 (0.035 g, 53.7%) as a yellow solid.

$^1$H NMR (400 MHz, CDCl$_3$): 8.93 (d, 1 H, J=2.3 Hz), 8.60 (m, 1H), 7.06 (dd, 1 H, J=8.0, 1.6 Hz), 7.82-7.77 (m, 1 H), 7.72-7.69 (m, 3 H), 7.58-7.48 (m, 2 H), 7.39-7.35 (m, 3 H), 3.37-3.28 (m, 2 H), 2.63 (m, 2 H), 2.19 (dd, 2 H, J=11.4, 4.0 Hz), 1.32 (s, 6 H).

Example 91

Synthesis of Compound 247

((4-(((3R,5S)-4-(4',4'-dimethyl-2',3',4',5'-tetrahydro-[1,1'-biphenyl]-3-carbonyl)-3,5-dimethylpiperazin-1-yl)methyl)-N-hydroxybenzamide)

Step 1: Synthesis of Methyl 4-(((3R,5S)-4-(3-(4,4-dimethylcyclohexe-1-enyl)benzoyl)-3,5-dimethylpiperazin-1-yl)methyl)benzoate 1,2-Dimethoxyethane (0.9 mL)/water (0.3 mL) were added to a mixture of methyl 4-(((3R,5S)-4-(3-iodobenzoyl)-3,5-dimethylpiperazin-1-yl)methyl)benzoate (formula 4-1, 0.100 g, 0.203 mmol), 2-(4,4-dimethylcyclohexe-1-enyl)-4,4,5,5-tetramethyl-1,3,2-dioxaborolane (0.096 g, 0.406 mmol), Na$_2$CO$_3$ (0.065 g, 0.609 mmol) and Pd(dbpf)Cl$_2$ (0.007 g, 0.010 mmol), and heated by microwave irradiation at 120° C. for 20 minutes, followed by cooling to room temperature. Then, water was added to the reaction mixture, followed by extraction with ethyl acetate. The organic layer was dried with anhydrous magnesium sulfate, and then concentrated under reduced pressure. The concentrate was purified by column chromatography (silicon dioxide, 4 g cartridge; ethyl acetate/hexane=from 0% to 40%) and concentrated to afford the desired compound (0.030 g, 31.1%) as a yellow solid.

Step 2: Synthesis of Compound 247

Methyl 4-(((3R,5S)-4-(3-(4,4-dimethylcyclohexe-1-enyl) benzoyl)-3,5-dimethylpiperazin-1-yl)methyl)benzoate (formula 4-2, 0.030 g, 0.063 mmol), hydroxylamine (0.039 mL, 0.632 mmol, 50.00% aqueous solution) and potassium hydroxide (0.082 g, 1.264 mmol) were dissolved in methanol (3 mL) at room temperature, and the reaction solution was stirred at the same temperature for 2 hours. Then, the reaction mixture was concentrated. The concentrate was washed with a saturated aqueous solution of sodium hydrogen carbonate and distilled water, thereby obtaining the desired compound 247 (0.021 g, 69.9%) as a yellow solid.

$^1$H NMR (400 MHz, CDCl$_3$): 7.71 (d, 1 H, J=8.0 Hz), 7.47-7.45 (m, 1 H), 7.38-7.32 (m, 4 H), 7.18 (d, 1 H, J=7.6 Hz), 6.16 (s, 1 H), 3.51 (m, 2 H), 2.62 (m, 2 H), 2.38 (m, 2 H), 2.15 (m, 2 H), 1.98 (m, 2 H), 1.50-1.46 (m, 2 H), 2.29 (m, 6 H), 0.94 (s, 6 H).

Example 92

Synthesis of Compound 248

(4-(((3R,5R)-4-benzyl-3,5-dimethylpiperazin-1-yl) methyl)-N-hydroxybenzamide)

Step 1: Synthesis of Methyl 4-(((3R,5R)-4-benzyl-3,5-dimethylpiperazin-1-yl)methyl)benzoate Methyl 4-(((3R,5R)-3,5-dimethylpiperazin-1-yl)methyl) benzoate (formula 21-1, 0.050 g, 0.191 mmol), benzyl bromide (0.023 mL, 0.191 mmol) and K$_2$CO$_3$ (0.040 g, 0.286 mmol) were dissolved in acetonitrile (2 mL) at room temperature, and the reaction solution was stirred at the same temperature for 17 hours. Then, the reaction mixture was filtered through a plastic filter to remove solids, and the filtrate was concentrated under reduced pressure. The concentrate was purified by column chromatography (silicon dioxide, 4 g cartridge; ethyl acetate/hexane=from 0% to 30%) and concentrated to afford the desired compound (0.038 g, 56.6%) as a colorless oil.

Step 2: Synthesis of Compound 248

Methyl 4-(((3R,5R)-4-benzyl-3,5-dimethylpiperazin-1-yl)methyl)benzoate (formula 21-2, 0.038 g, 0.108 mmol), hydroxylamine (0.132 mL, 2.156 mmol, 50.00% aqueous solution) and potassium hydroxide (0.060 g, 1.078 mmol) were dissolved in methanol (2 mL) at room temperature, and the reaction solution was stirred at the same temperature for 30 minutes. Then, the reaction mixture was concentrated under reduced pressure to remove the solvent. A saturated aqueous solution of sodium hydrogen carbonate was added to the resulting concentrate, followed by extraction with methylene chloride. The extract was passed through a plastic filter to remove solid residue and an aqueous layer, and the organic layer was concentrated under reduced pressure to yield compound 248 (0.018 g, 47.2%) as a white solid.

$^1$H NMR (400 MHz, DMSO-d$_6$) δ 7.71 (d, 2 H, J=8.2 Hz), 7.44 (d, 2 H, J=8.2 Hz), 7.38 (d, 2 H, J=7.3 Hz), 7.29 (dd, 1 H, J=7.4, 7.4 Hz), 7.23-7.22 (m, 1 H), 4.02 (d, 1 H, J=13.4 Hz), 3.58 (d, 1 H, J=13.5 Hz), 3.43-3.42 (m, 2 H), 2.92-2.88 (m, 2 H), 2.49-2.47 (m, 2 H), 2.25-2.25 (m, 2 H), 1.09 (d, 6 H, J=6.4 Hz); LRMS (ES) m/z 354.2 (M$^+$+1).

Example 93

Synthesis of Compound 249

(4-(((3R,5R)-4-(furan-2-carbonyl)-3,5-dimethylpiperazin-1-yl)methyl)-N-hydroxybenzamide)

Step 1: Synthesis of Methyl 4-(((3R,5R)-4-(furan-2-carbonyl)-3,5-dimethylpiperazin-1-yl)methyl)benzoate Methyl 4-(((3R,5R)-3,5-dimethylpiperazin-1-yl)methyl) benzoate (formula 21-1, 0.050 g, 0.191 mmol) and TEA (0.053 mL, 0.381 mmol) were dissolved in methylene chloride (2 mL), and 2-furoyl chloride (0.019 mL, 0.191 mmol) was added thereto at 0° C., followed by stirring at the same temperature for 3 hours. Then, a saturated aqueous solution of sodium hydrogen carbonate was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 0% to 40%) and concentrated to afford the desired compound (0.033 g, 48.6%) as a yellow oil.

Step 2: Synthesis of Compound 249

Methyl 4-(((3R,5R)-4-(furan-2-carbonyl)-3,5-dimethylpiperazin-1-yl)methyl)benzoate (formula 21-3, 0.033 g, 0.093 mmol), hydroxylamine (0.113 mL, 1.852 mmol, 50.00% aqueous solution) and potassium hydroxide (0.052 g, 0.926 mmol) were dissolved in methanol (2 mL) at room temperature, and the reaction solution was stirred at the same temperature for 30 minutes. Then, the reaction mixture was concentrated under reduced pressure to remove the solvent. A saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure to yield compound 249 (0.019 g, 57.4%) as a white solid.

$^1$H NMR (400 MHz, DMSO-d$_6$) δ 7.73 (d, 2 H, J=7.9 Hz), 7.66 (s, 1 H), 7.48 (d, 2 H, J=7.9 Hz), 7.01 (d, 1 H, J=3.3 Hz), 6.58 (s, 1 H), 4.17-4.13 (m, 2 H), 3.67 (d, 1 H, J=13.5 Hz), 3.53 (d, 1 H, J=13.8 Hz), 2.68-2.65 (m, 2 H), 2.42-2.38 (m, 2 H), 1.35 (d, 6 H, J=6.4 Hz); LRMS (ES) m/z 358.1 (M$^+$+1).

Example 94

Synthesis of Compound 250

(4-(((2S,6R)-4-(2-([1,1'-biphenyl]-3-yl)acetyl)-2,6-dimethylpiperazin-1-yl)methyl)-N-hydroxybenzamide (Trifluoroacetic acid salt))

Step 1: Synthesis of Methyl 4-(((2S,6R)-4-(2-(3-bromophenyl)acetyl)-2,6-dimethylpiperazin-1-yl)methyl)benzoate Methyl 4-(((2S,6R)-2,6-dimethylpiperazin-1-yl)methyl)benzoate (formula 13-2, 2.000 g, 6.693 mmol), 2-(3-bromophenyl)acetic acid (1.583 g, 7.363 mmol), EDCI (2.566 g, 13.386 mmol), HOBt (2.050 g, 13.386 mmol) and DIPEA (5.845 mL, 33.466 mmol) were dissolved in methylene chloride (5 mL) at room temperature, and the reaction solution was stirred at the same temperature for 17 hours. Then, a saturated aqueous solution of sodium hydrogen carbonate was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 12 g cartridge; ethyl acetate/hexane=from 40% to 70%) and concentrated to afford the desired compound (2.230 g, 72.5%) as a colorless oil.

Step 2: Synthesis of Methyl 4-(((2S,6R)-4-(2-(3-bromophenyl)acetyl)-2,6-dimethylpiperazin-1-yl)methyl)benzoate 1,2-Dimethoxyethane (2 mL) was added to a mixture of methyl 4-(((2S,6R)-4-(2-(3-bromophenyl)acetyl)-2,6-dimethylpiperazin-1-yl)methyl)benzoate (formula 15-1, 0.100 g, 0.218 mmol), phenylboronic acid (0.029 g, 0.239 mmol), Pd(PPh$_3$)$_4$ (0.013 g, 0.011 mmol) and Na$_2$CO$_3$ (0.069 g, 0.653 mmol) at room temperature, and the reaction solution was stirred at 100° C. for 17 hours. Then, a saturated aqueous solution of sodium hydrogen carbonate was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 0% to 40%) and concentrated to afford the desired compound (0.043 g, 43.3%) as a colorless oil.

Step 3: Synthesis of Compound 250

Methyl 4-(((2S,6R)-4-(2-([1,1'-biphenyl]-3-yl)acetyl)-2,6-dimethylpiperazin-1-yl)methyl)benzoate (formula 15-2, 0.043 g, 0.094 mmol), hydroxylamine (0.115 mL, 1.884 mmol, 50.00% aqueous solution) and potassium hydroxide (0.053 g, 0.942 mmol) were dissolved in methanol (2 mL) at room temperature, and the reaction solution was stirred at the same temperature for 30 minutes. Then, water was added to the reaction mixture, followed by extraction with methylene chloride. The extract was passed through a plastic filter to remove solid residue and an aqueous solution, and the organic layer was concentrated under reduced pressure. The concentrate was purified by column chromatography (Waters, C$_{18}$, 19*100 mm column, 0.1% trifluoroacetic acid/acetonitrile=from 5% to 80%) and concentrated to afford compound 250 (0.015 g, 34.8%) as a white solid.

$^1$H NMR (400 MHz, DMSO-d$_6$) δ 7.55-7.37 (m, 9 H), 7.30 (d, 2 H, J=7.7 Hz), 7.22 (dd, 1 H, J=7.2, 7.2 Hz), 7.12 (d, 2 H, J=7.0 Hz), 4.55-4.48 (m, 2 H), 4.38 (d, 1 H, J=14.7 Hz), 4.15 (d, 1 H, J=15.0 Hz), 3.91 (d, 1 H, J=15.0 Hz), 3.68 (d, 1 H, J=6.5 Hz), 3.67 (d, 1 H, J=14.5 Hz), 3.35-3.27 (m, 1 H), 2.97-2.91 (m, 3 H), 1.54 (d, 3 H, J=5.7 Hz), 1.31 (d, 3 H, J=6.4 Hz).

Example 95

Synthesis of Compound 251

(4-(((2S,6R)-2,6-dimethyl-4-(2-(3-(pyridin-4-yl)phenyl)acetyl)piperazin-1-yl)methyl)-N-hydroxybenzamide (Trifluoroacetic acid salt))

Step 1: Synthesis of Methyl 4-(((2S,6R)-2,6-dimethyl-4-(2-(3-(pyridin-4-yl)phenyl)acetyl)piperazin-1-yl)methyl)benzoate 1,2-Dimethoxyethane (4 mL)/water (1 mL) were added to a mixture of methyl 4-(((2S,6R)-4-(2-(3-bromophenyl)acetyl)-2,6-dimethylpiperazin-1-yl)methyl)benzoate (formula 15-1, 0.200 g, 0.435 mmol), pyridin-4-ylboronic acid (0.059 g, 0.479 mmol), Pd(PPh$_3$)$_4$ (0.025 g, 0.022 mmol) and Na$_2$CO$_3$ (0.138 g, 1.306 mmol) at room temperature and the reaction mixture was heated under reflux for 17 hours, and then cooled to room temperature. Then, a saturated aqueous solution of sodium hydrogen carbonate was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; methanol/methylene chloride=from 0% to 10%) and concentrated to afford the desired compound (0.123 g, 61.7%) as a yellow oil.

Step 2: Synthesis of Compound 251

Methyl 4-(((2S,6R)-2,6-dimethyl-4-(2-(3-(pyridin-4-yl)phenyl)acetyl)piperazin-1-yl)methyl)benzoate (formula 15-2, 0.100 g, 0.219 mmol), hydroxylamine (0.267 mL, 4.371 mmol, 50.00% aqueous solution) and potassium hydroxide (0.123 g, 2.186 mmol) were dissolved in methanol (2 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was passed through a plastic filter to remove solid residue and an aqueous solution, and the organic layer was concentrated under reduced pressure. The concentrate was purified by column chromatography (Waters, C$_{18}$, 19*100 mm column, 0.1% trifluoroacetic acid/acetonitrile=from 5% to 80%) and concentrated to afford compound 251 (0.006 g, 6.0%) as a white solid.

$^1$H NMR (400 MHz, DMSO-d$_6$) δ 8.65 (d, 2 H, J=5.9 Hz), 7.69-7.64 (m, 5 H), 7.45 (dd, 1 H, J=7.7, 7.7 Hz), 7.34 (d, 3 H, J=8.3 Hz), 4.16 (d, 1 H, J=12.8 Hz), 3.91 (d, 1 H, J=13.1 Hz), 3.82 (d, 2 H, J=8.0 Hz), 3.71 (s, 2 H), 2.90 (dd, 1 H, J=10.4, 13.3 Hz), 2.41-2.32 (m, 2 H), 0.96-0.85 (m, 6 H).

Example 96

Synthesis of Compound 252

(4-(((2S,6R)-4-(2-(3-(3,6-dihydro-2H-pyran-4-yl)phenyl)acetyl)-2,6-dimethylpiperazin-1-yl)methyl)-N-hydroxybenzamide)

Step 1: Synthesis of Methyl 4-(((2S,6R)-4-(2-(3-(3,6-dihydro-2H-pyran-4-yl)phenyl)acetyl)-2,6-dimethylpiperazin-1-yl)methyl)benzoate 1,2-Dimethoxyethane (4 mL)/water (1 mL) were added to a mixture of methyl 4-(((2S,6R)-4-(2-(3-bromophenyl)acetyl)-2,6-dimethylpiperazin-1-yl)methyl)benzoate (formula 15-1, 0.200 g, 0.435 mmol), 2-(3,6-dihydro-2H-pyran-4-yl)-4,4,5,5-tetramethyl-1,3,2-dioxaborolane (0.101 g, 0.479 mmol), Pd(PPh$_3$)$_4$ (0.025 g, 0.022 mmol) and Na$_2$CO$_3$ (0.138 g, 1.306 mmol) at room temperature and the reaction mixture was heated under reflux for 17 hours, and then cooled to room temperature. Then, a saturated aqueous solution of sodium hydrogen carbonate was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 30% to 100%) and concentrated to afford the desired compound (0.084 g, 41.7%) as a white solid.

Step 2: Synthesis of Compound 252

Methyl 4-(((2S,6R)-4-(2-(3-(3,6-dihydro-2H-pyran-4-yl)phenyl)acetyl)-2,6-dimethylpiperazin-1-yl)methyl)benzoate (formula 15-2, 0.050 g, 0.108 mmol), hydroxylamine (0.132 mL, 2.162 mmol, 50.00% aqueous solution) and potassium hydroxide (0.061 g, 1.081 mmol) were dissolved in methanol (2 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was passed through aplastic filter to remove solid residue and an aqueous solution, and the organic layer was concentrated under reduced pressure to yield compound 252 (0.016 g, 31.9%) as a white solid.
$^1$H NMR (400 MHz, CH$_3$OD) δ 7.70-7.69 (m, 2 H), 7.43 (d, 2 H, J=8.3 Hz), 7.34 (d, 2 H, J=5.8 Hz), 7.30-7.28 (m, 1 H), 7.16-7.16 (m, 1 H), 6.20-6.19 (m, 1 H), 4.32-4.30 (m, 3 H), 3.94 (t, 2 H, J=5.5 Hz), 3.86-3.77 (m, 5 H), 2.85 (dd, 1 H, J=11.3, 11.3 Hz), 2.59-2.56 (m, 1 H), 2.52-2.50 (m, 3 H), 2.19-2.18 (m, 1 H), 1.06 (d, 3 H, J=6.1 Hz), 0.95 (d, 3 H, J=6.2 Hz); LRMS (ES) m/z 464.2 (M$^+$+1).

Example 97

Synthesis of Compound 253

(4-(((2S,6R)-4-(2-(4',4'-dimethyl-2',3',4',5'-tetrahydro-[1,1'-biphenyl]-3-yl)acetyl)-2,6-dimethylpiperazin-1-yl)methyl)-N-hydroxybenzamide (Trifluoroacetic acid salt))

Step 1: Synthesis of Methyl 4-(((2S,6R)-4-(2-(4',4'-dimethyl-2',3',4',5'-tetrahydro-[1,1'-biphenyl]-3-yl)acetyl)-2,6-dimethylpiperazin-1-yl)methyl)benzoate 1,2-Dimethoxyethane (4 mL)/water (1 mL) were added to a mixture of methyl 4-(((2S,6R)-4-(2-(3-bromophenyl)acetyl)-2,6-dimethylpiperazin-1-yl)methyl)benzoate (formula 15-1, 0.150 g, 0.327 mmol), 2-(4,4-dimethylcyclo-1-hexenyl)-4,4,5,5-tetramethyl-1,3,2-dioxaborolane (0.085 g, 0.359 mmol), Pd(PPh$_3$)$_4$ (0.019 g, 0.016 mmol) and Na$_2$CO$_3$ (0.104 g, 0.980 mmol) at room temperature and the reaction mixture was heated under reflux for 17 hours, and then cooled to room temperature. Then, a saturated aqueous solution of sodium hydrogen carbonate was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 0% to 20%) and concentrated to afford the desired compound (0.089 g, 55.8%) as a pale yellow oil.

Step 2: Synthesis of Compound 253

Methyl 4-(((2S,6R)-4-(2-(4',4'-dimethyl-2',3',4',5'-tetrahydro-[1,1'-biphenyl]-3-yl)acetyl)-2,6-dimethylpiperazin-1-yl)methyl)benzoate (formula 15-2, 0.050 g, 0.102 mmol), hydroxylamine (0.125 mL, 2.046 mmol, 50.00% aqueous solution) and potassium hydroxide (0.057 g, 1.023 mmol) were dissolved in methanol (2 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was passed through a plastic filter to remove solid residue and an aqueous solution, and the organic layer was concentrated under reduced pressure. The concentrate was purified by column chromatography (Waters, C$_{18}$, 19*100 mm column, 0.1% trifluoroacetic acid/acetonitrile=from 5% to 80%) and concentrated to yield compound 253 (0.015 g, 29.9%) as a white solid.
$^1$H NMR (400 MHz, DMSO-d$_6$) δ 7.65 (d, 2 H, J=8.2 Hz), 7.33-7.26 (m, 4 H), 7.23 (dd, 1 H, J=7.6, 7.6 Hz), 7.07 (d, 1 H, J=6.9 Hz), 6.07 (s, 1 H), 4.15 (d, 1 H, J=11.0 Hz), 3.85 (d, 1 H, J=13.2 Hz), 3.76-3.65 (m, 4 H), 2.85 (dd, 1 H, J=11.3, 11.3 Hz), 2.47-2.44 (m, 1 H), 2.37 (s, 3 H), 2.25 (s, 1 H), 1.98 (s, 1 H), 1.49 (t, 2 H, J=6.3 Hz), 0.94 (s, 9 H), 0.89 (d, 3 H, J=5.8 Hz); LRMS (ES) m/z 490.3 (M$^+$+1).

Example 98

Synthesis of Compound 255

(4-(((3R,5S)-4-(3-(1H-pyrrol-1-yl)benzyl)-3,5-dimethylpiperazin-1-yl)methyl)-N-hydroxybenzamide)

Step 1: Synthesis of Methyl 4-(((3R,5S)-4-(3-(1H-pyrrol-1-yl)benzyl)-3,5-dimethylpiperazin-1-yl)methyl)benzoate Methyl 4-(((3R,5S)-3,5-dimethylpiperazin-1-yl)methyl)benzoate (formula 1-2, 0.200 g, 0.762 mmol), 1-(3-(bromomethyl)phenyl)-1H-pyrrole (0.198 g, 0.839 mmol) and K$_2$CO$_3$ (0.211 g, 1.525 mmol) were dissolved in acetonitrile (2 ml) at 25° C., and the reaction solution was stirred at the same temperature for 8 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide, 12 g cartridge; methanol/methylene chloride=from 0% to 5%) and concentrated to afford the desired compound (0.164 g, 51.5%) as a colorless oil.

Step 2: Synthesis of Compound 255

Methyl 4-(((3R,5S)-4-(3-(1H-pyrrol-1-yl)benzyl)-3,5-dimethylpiperazin-1-yl)methyl)benzoate (formula 1-3, 0.050 g, 0.120 mmol), hydroxylamine (0.146 mL, 2.395 mmol, 50.00% aqueous solution) and potassium hydroxide (0.067 g, 1.197 mmol) were dissolved in methanol (1 ml) at 25° C., and the solution was stirred at the same temperature for 1 hour. Then, saturated sodium hydrogen carbonate was added to the reaction mixture, followed by extraction with methylene chloride. The organic layer was washed with a saturated aqueous solution of sodium chloride, dried with an anhydrous magnesium sulfate, and then concentrated under reduced pressure to yield compound 255 (0.024 g, 47.9%) as a white solid.

$^1$H NMR (400 MHz, DMSO-$d_6$) δ 7.61 (d, 2 H, J=8.4 Hz), 7.45-7.42 (m, 1 H), 7.32 (d, 2 H, J=5.2 Hz), 7.26 (d, 2 H, J=2.4 Hz), 7.22-7.21 (m, 1 H), 7.13-7.11 (m, 2 H) 6.22-6.21 (m, 2 H), 3.80 (s, 2 H), 3.33 (s, 2 H), 2.63-2.57 (m, 4 H), 1.79-1.72 (m, 2 H), 0.85 (d, 6 H, J=16.8 Hz).

Example 99

Synthesis of Compound 256

(4-(((2S,6R)-4-(3-(1H-pyrrol-1-yl)benzyl)-2,6-dimethylpiperazin-1-yl)methyl)-N-hydroxybenzamide)

Step 1: Synthesis of Methyl 4-(((2S,6R)-4-(3-(1H-pyrrol-1-yl)benzyl)-2,6-dimethylpiperazin-1-yl) methyl)benzoate Methyl 4-(((2S,6R)-2,6-dimethylpiperazin-1-yl)methyl) benzoate (formula 13-2, 0.200 g, 0.762 mmol), 1-(3-(bromomethyl)phenyl)-1H-pyrrole (0.198 g, 0.839 mmol) and $K_2CO_3$ (0.211 g, 1.525 mmol) were dissolved in acetonitrile (2 ml) at 25° C., and the reaction solution was stirred at the same temperature for 8 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (silicon dioxide, 12 g cartridge; methanol/methylene chloride=from 0% to 5%) and concentrated to afford the desired compound (0.177 g, 55.6%) as a white solid.

Step 2: Synthesis of Compound 256

Methyl 4-(((2S,6R)-4-(3-(1H-pyrrol-1-yl)benzyl)-2,6-dimethylpiperazin-1-yl)methyl)benzoate (formula 13-3, 0.050 g, 0.120 mmol), hydroxylamine (0.146 mL, 2.395 mmol, 50.00% aqueous solution) and potassium hydroxide (0.067 g, 1.197 mmol) were dissolved in methanol (1 ml) at 25° C., and the reaction solution was stirred at the same temperature for 1 hour. Then, saturated sodium hydrogen carbonate was added to the reaction mixture, followed by extraction with methylene chloride. The organic layer was washed with a saturated aqueous solution of sodium chloride, dried with an anhydrous magnesium sulfate, and then concentrated under reduced pressure to yield compound 256 (0.031 g, 61.9%) as a white solid.

$^1$H NMR (400 MHz, DMSO-$d_6$) δ 7.61 (d, 2 H, J=8.4 Hz), 7.41-7.30 (m, 7 H), 7.14 (d, 2 H, J=7.2 Hz), 6.22-6.21 (m, 2 H, J=2.4 Hz), 3.70 (s, 2 H), 3.42 (s, 2 H), 2.66 (d, 2 H, J=10 Hz), 2.57-2.52 (m, 2 H), 1.83-1.77 (m, 2 H), 0.85 (d, 6 H, J=10.4 Hz).

Example 100

Synthesis of Compound 257

(4-(((2S,6R)-4-(3-(furan-2-yl)benzoyl)-2,6-dimethylpiperazin-1-yl)methyl)-N-hydroxybenzamide)

Step 1: Synthesis of Methyl 4-(((2S,6R)-4-(3-iodobenzoyl)-2,6-dimethylpiperazin-1-yl)methyl)benzoate Methyl 4-(((2S,6R)-2,6-dimethylpiperazin-1-yl)methyl) benzoate (formula 13-2, 7.000 g, 28.224 mmol), 3-iodobenzoic acid (8.145 g, 31.046 mmol), EDCI (10.821 g, 56.447 mmol), HOBt (7.628 g, 56.447 mmol) and N,N-diisopropylethylamine (18.238 g, 141.118 mmol) were dissolved in methylene chloride (150 mL) at room temperature, and the reaction solution was stirred overnight at the same temperature. Then, water was added to the reaction mixture, followed by extraction with methylene chloride. The organic layer was dried with anhydrous sodium sulfate, and then concentrated under reduced pressure. The concentrate was purified by column chromatography (silicon dioxide; ethyl acetate/hexane=from 30% to 50%) and concentrated to afford the desired compound (10.737 g, 77.3%) as a white solid.

Step 2: Synthesis of Methyl 4-(((2S,6R)-4-(3-(furan-2-yl)benzoyl)-2,6-dimethylpiperazin-1-yl) methyl)benzoate 1,2-Dimethoxyethane/water (v/v=3/1) (3 mL) were added to a mixture of methyl 4-(((2S,6R)-4-(3-iodobenzoyl)-2,6-dimethylpiperazin-1-yl)methyl)benzoate (formula 15-1, 0.400 g, 0.812 mmol), furan-2-ylboronic acid (0.136 g, 1.219 mmol), Pd(dbpf)Cl$_2$ (0.026 g, 0.041 mmol) and Na$_2$CO$_3$ (0.258 g, 2.437 mmol), and heated by microwave irradiation at 120° C. for 30 minutes, followed by cooling to room temperature. Then, a 1N aqueous solution of hydrochloric acid was added to the reaction mixture, followed by extraction with methylene chloride. The organic layer was washed with water, dried with anhydrous magnesium sulfate, and then concentrated under reduced pressure. The concentrate was purified by column chromatography (silicon dioxide; ethyl acetate/hexane=from 10% to 50%) and concentrated to afford the desired compound (0.030 g, 8.5%) as a yellow oil.

Step 3: Synthesis of Compound 257

Methyl 4-(((2S,6R)-4-(3-(furan-2-yl)benzoyl)-2,6-dimethylpiperazin-1-yl)methyl)benzoate (formula 15-2, 0.030 g, 0.069 mmol), hydroxylamine (0.084 mL, 1.378 mmol, 50% aqueous solution) and potassium hydroxide (0.039 g, 0.689 mmol) were dissolved in methanol (1 mL) at room temperature, and the reaction solution was stirred at the same temperature for 30 minutes. Then, the reaction mixture was concentrated under reduced pressure. A saturated aqueous solution of sodium hydrogen carbonate was added to the concentrate, and the precipitated solid was filtered and dried to yield compound 257 (0.012 g, 41.2%) as a white solid.

¹H NMR (400 MHz, DMSO-d₆) δ 7.79-7.79 (m, 2 H), 7.77-7.68 (m, 3 H), 7.50 (t, 1 H, J=7.7 Hz), 7.41 (d, 2 H, J=7.9 Hz), 7.29 (d, 1 H, J=7.6 Hz), 7.07 (d, 1 H, J=3.3 Hz), 6.63-6.62 (m, 1 H), 4.30-4.27 (m, 1 H), 3.78 (s, 2 H), 3.01-2.99 (m, 1 H), 2.73-2.71 (m, 1 H), 2.56-2.51 (m, 3 H), 1.03 (s, 3 H), 0.82 (s, 3 H).

Example 101

Synthesis of Compound 258

(4-(((2S,6R)-4-(3-(furan-3-yl)benzoyl)-2,6-dimethylpiperazin-1-yl)methyl)-N-hydroxybenzamide)

Step 1: Synthesis of Methyl 4-(((2S,6R)-4-(3-(furan-3-yl)benzoyl)-2,6-dimethylpiperazin-1-yl)methyl)benzoate 1,2-Dimethoxyethane/water (v/v=3/1) (3 mL) were added to a mixture of methyl 4-(((2S,6R)-4-(3-iodobenzoyl)-2,6-dimethylpiperazin-1-yl)methyl)benzoate (formula 15-1, 0.400 g, 0.812 mmol), furan-3-ylboronic acid (0.136 g, 1.219 mmol), Pd(dbpf)Cl₂ (0.026 g, 0.041 mmol) and Na₂CO₃ (0.258 g, 2.437 mmol), and heated by microwave irradiation at 120° C. for 30 minutes, followed by cooling to room temperature. Then, a 1N aqueous solution of hydrochloric acid was added to the reaction mixture, followed by extraction with methylene chloride. The organic layer was washed with water, dried with anhydrous magnesium sulfate, and then concentrated under reduced pressure. The concentrate was purified by column chromatography (silicon dioxide; ethyl acetate/hexane=from 10% to 50%) and concentrated to afford the desired compound (0.061 g, 17.4%) as a yellow oil.

Step 2: Synthesis of Compound 258

Methyl 4-(((2S,6R)-4-(3-(furan-3-yl)benzoyl)-2,6-dimethylpiperazin-1-yl)methyl)benzoate (formula 15-2, 0.061 g, 0.141 mmol), hydroxylamine (0.173 mL, 2.830 mmol, 50% aqueous solution) and potassium hydroxide (0.079 g, 1.415 mmol) were dissolved in methanol (2 mL) at room temperature, and the reaction solution was stirred at the same temperature for 30 minutes. Then, the reaction mixture was concentrated under reduced pressure. A saturated aqueous solution of sodium hydrogen carbonate was added to the concentrate, and the precipitated solid was filtered and dried to yield compound 258 (0.016 g, 25.9%) as a white solid.
¹H NMR (400 MHz, DMSO-d₆) δ 8.29 (s, 1 H), 7.77 (s, 1 H), 7.72-7.68 (m, 3 H), 7.64 (s, 1 H), 7.47-7.41 (m, 3 H), 7.25 (d, 1 H, J=7.6 Hz), 7.03 (s, 1 H), 4.31-4.28 (m, 1 H), 3.79 (s, 2 H), 3.00-2.98 (m, 1 H), 2.71-2.68 (m, 1 H), 2.56-2.51 (m, 3 H), 1.03 (s, 3 H), 0.82 (s, 3 H).

Example 102

Synthesis of Compound 259

(4-(((2S,6R)-4-(3-(3,6-dihydro-2H-pyran-4-yl)benzoyl)-2,6-dimethylpiperazin-1-yl)methyl)-N-hydroxybenzamide)

Step 1: Synthesis of Methyl 4-(((2S,6R)-4-(3-(3,6-dihydro-2H-pyran-4-yl)benzoyl)-2,6-dimethylpiperazin-1-yl)methyl)benzoate 1,2-Dimethoxyethane/water (v/v=3/1) (3 mL) were added to a mixture of methyl 4-(((2S,6R)-4-(3-iodobenzoyl)-2,6-dimethylpiperazin-1-yl)methyl)benzoate (formula 15-1, 0.400 g, 0.812 mmol), 2-(3,6-dihydro-2H-pyran-4-yl)-4,4,5,5-tetramethyl-1,3,2-dioxaborolane (0.256 g, 1.219 mmol), Pd(dbpf)Cl₂ (0.026 g, 0.041 mmol) and Na₂CO₃ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with ethyl acetate. The organic layer was dried with anhydrous magnesium sulfate, and then concentrated under reduced pressure. The concentrate was purified by column chromatography (silicon dioxide; ethyl acetate/hexane=from 20% to 65%) and concentrated to afford the desired compound (0.290 g, 79.6%) as a brown solid.

Step 2: Synthesis of Compound 259

Methyl 4-(((2S,6R)-4-(3-(3,6-dihydro-2H-pyran-4-yl)benzoyl)-2,6-dimethylpiperazin-1-yl)methyl)benzoate (formula 15-2, 0.060 g, 0.134 mmol), hydroxylamine (0.164 mL, 2.675 mmol, 50.00% aqueous solution) and potassium hydroxide (0.075 g, 1.338 mmol) were dissolved in methanol (2 mL) at room temperature, and the reaction solution was stirred at the same temperature for 30 minutes. Then, the reaction mixture was concentrated under reduced pressure. A saturated aqueous solution of sodium hydrogen carbonate was added to the concentrate, and the precipitated solid was filtered and dried to yield compound 259 (0.010 g, 16.6%) as a white solid.
¹H NMR (400 MHz, DMSO-d₆) δ 7.69 (d, 2 H, J=8.0 Hz), 7.54 (d, 1 H, J=7.9 Hz), 7.44-7.41 (m, 4 H), 7.28 (d, 1 H, J=7.7 Hz), 6.33 (s, 1 H), 4.24-4.23 (m, 3 H), 3.83 (t, 2 H, J=5.4 Hz), 3.78 (s, 2 H), 2.98-2.96 (m, 1 H), 2.70-2.68 (m, 1 H), 2.55-2.51 (m, 3 H), 2.46 (s, 2 H), 1.02 (s, 3 H), 0.82 (s, 3 H).

Example 103

Synthesis of Compound 260

(4-(((2S,6R)-2,6-dimethyl-4-(3-(pyridin-4-yl)benzoyl)piperazin-1-yl)methyl)-N-hydroxybenzamide)

Step 1: Synthesis of Methyl 4-(((2S,6R)-2,6-dimethyl-4-(3-(pyridin-4-yl)benzoyl)piperazin-1-yl)methyl)benzoate 1,2-Dimethoxyethane/water (v/v=3/1) (3 mL) were added to a mixture of methyl 4-(((2S,6R)-4-(3-iodobenzoyl)-2,6-dimethylpiperazin-1-yl)methyl)benzoate (formula 15-1, 0.400 g, 0.812 mmol), pyridine-4-boronic acid hydrate (0.172 g, 1.219 mmol), Pd(dbpf)Cl₂ (0.026 g, 0.041 mmol) and Na₂CO₃ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 50% to 65%) and concentrated to afford the desired compound (0.354 g, 98.3%) as a brown oil.

Step 2: Synthesis of Compound 260

Methyl 4-(((2S,6R)-2,6-dimethyl-4-(3-(pyridin-4-yl)benzoyl)piperazin-1-yl)methyl)benzoate (formula 15-2, 0.060 g, 0.135 mmol), hydroxylamine (0.165 mL, 2.706 mmol, 50.00% aqueous solution) and potassium hydroxide (0.076 g, 1.353 mmol) were dissolved in methanol (2 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 260 (0.003 g, 5.5%) as a pale brown solid.

$^1$H NMR (400 MHz, DMSO-$d_6$) δ 8.67-8.66 (m, 2 H), 7.91 (d, 1 H, J=7.9 Hz), 7.81 (s, 1 H), 7.77-7.75 (m, 2 H), 7.68 (d, 2 H, J=8.2 Hz), 7.61 (t, 1 H, J=7.7 Hz), 7.49 (d, 1 H, J=7.6 Hz), 7.43-7.41 (m, 2 H), 4.31-4.29 (m, 1 H), 3.79 (s, 2 H), 3.02-3.02 (m, 1 H), 2.73-2.68 (m, 1 H), 2.67-2.55 (m, 3 H), 1.04 (s, 3 H), 0.86 (s, 3 H).

Example 104

Synthesis of Compound 261

(4-(((2S,6R)-2,6-dimethyl-4-(3-(pyridin-3-yl)benzoyl)piperazin-1-yl)methyl)-N-hydroxybenzamide)

Step 1: Synthesis of Methyl 4-(((2S,6R)-2,6-dimethyl-4-(3-(pyridin-3-yl)benzoyl)piperazin-1-yl)methyl)benzoate 1,2-Dimethoxyethane/water (v/v=3/1) (3 mL) were added to a mixture of methyl 4-(((2S,6R)-4-(3-iodobenzoyl)-2,6-dimethylpiperazin-1-yl)methyl)benzoate (formula 15-1, 0.328 g, 0.665 mmol), pyridin-3-ylboronic acid (0.090 g, 0.732 mmol), Pd(dbpf)Cl$_2$ (0.022 g, 0.033 mmol) and Na$_2$CO$_3$ (0.155 g, 1.464 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 50% to 65%) and concentrated to afford the desired compound (0.244 g, 82.8%) as a brown solid.

Step 2: Synthesis of Compound 261

Methyl 4-(((2S,6R)-2,6-dimethyl-4-(3-(pyridin-3-yl)benzoyl)piperazin-1-yl)methyl)benzoate (formula 15-2, 0.060 g, 0.135 mmol), hydroxylamine (0.165 mL, 2.706 mmol, 50.00% aqueous solution) and potassium hydroxide (0.076 g, 1.353 mmol) were dissolved in methanol (2 mL) at room temperature, and the solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 261 (0.014 g, 23.3%) as a pale brown solid.

$^1$H NMR (400 MHz, DMSO-$d_6$) δ 8.91-8.90 (m, 1 H), 8.59-8.58 (m, 1 H), 8.12-8.09 (m, 1 H), 7.81 (d, 1 H, J=7.8 Hz), 7.72 (s, 1 H), 7.67 (d, 2 H, J=8.1 Hz), 7.56 (t, 1 H, J=7.7 Hz), 7.51-7.47 (m, 1 H), 7.43-7.39 (m, 3 H), 4.29-4.26 (m, 1 H), 3.77 (s, 2 H), 3.44-3.42 (m, 1 H), 3.01-2.99 (m, 1 H), 2.71-2.66 (m, 1 H), 2.58 (brs, 2 H), 1.01 (s, 3 H), 0.81 (s, 3 H).

Example 105

Synthesis of Compound 262

(4-(((2S,6R)-4-(3-(2-fluoropyridin-4-yl)benzoyl)-2,6-dimethylpiperazin-1-yl)methyl)-N-hydroxybenzamide)

Step 1: Synthesis of Methyl 4-(((2S,6R)-4-(3-(2-fluoropyridin-4-yl)benzoyl)-2,6-dimethylpiperazin-1-yl)methyl)benzoate 1,2-Dimethoxyethane/water (v/v=3/1) (3 mL) were added to a mixture of methyl 4-(((2S,6R)-4-(3-iodobenzoyl)-2,6-dimethylpiperazin-1-yl)methyl)benzoate (formula 15-1, 0.400 g, 0.812 mmol), (2-fluoropyridin-4-yl)boronic acid (0.172 g, 1.219 mmol), Pd(dbpf)Cl$_2$ (0.026 g, 0.041 mmol) and Na$_2$CO$_3$ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 10% to 50%) and concentrated to afford the desired compound (0.366 g, 97.5%) as a brown oil.

Step 2: Synthesis of Compound 262

Methyl 4-(((2S,6R)-4-(3-(2-fluoropyridin-4-yl)benzoyl)-2,6-dimethylpiperazin-1-yl)methyl)benzoate (formula 15-2, 0.060 g, 0.130 mmol), hydroxylamine (0.159 mL, 2.600 mmol, 50.00% aqueous solution) and potassium hydroxide (0.073 g, 1.300 mmol) were dissolved in methanol (2 mL) at room temperature, and the solution was stirred at the same temperature for 30 minutes. Then, the reaction mixture was concentrated under reduced pressure. A saturated aqueous solution of sodium hydrogen carbonate was added to the concentrate, and the precipitated solid was filtered and dried to yield compound 262 (0.009 g, 14.1%) as a pale brown solid.

$^1$H NMR (400 MHz, DMSO-$d_6$) δ 7.77 (d, 1 H, J=8.0 Hz), 7.67-7.65 (m, 3 H), 7.54 (t, 1 H, J=7.7 Hz), 7.47-7.44 (m, 2 H), 7.38 (d, 2 H, J=8.1 Hz), 6.60-6.59 (m, 1 H), 6.51 (dd, 1 H, J=6.8, 1.6 Hz), 4.26-4.24 (m, 1 H), 3.77 (s, 2 H), 2.99-2.97 (m, 1 H), 2.72-2.70 (m, 1 H), 2.66-2.54 (m, 3 H), 1.01 (s, 3 H), 0.81 (s, 3 H).

Example 106

Synthesis of Compound 263

(4-(((2S,6R)-4-(4',4'-dimethyl-2',3',4',5'-tetrahydro-[1,1'-biphenyl]-3-carbonyl)-2,6-dimethylpiperazin-1-yl)methyl)-N-hydroxybenzamide)

Step 1: Synthesis of Methyl 4-(((2S,6R)-4-(4',4'-dimethyl-2',3',4',5'-tetrahydro-[1,1'-biphenyl]-3-carbonyl)-2,6-dimethylpiperazin-1-yl)methyl)benzoate 1,2-Dimethoxyethane/water (v/v=3/1) (3 mL) were added to a mixture of methyl 4-(((2S,6R)-4-(3-iodobenzoyl)-2,6-dimethylpiperazin-1-yl)methyl)benzoate (formula 15-1, 0.400 g, 0.812 mmol), 2-(4,4-dimethylcyclohex-1-en-1-yl)-4,4,5,5-tetramethyl-1,3,2-dioxaborolane (0.288 g, 1.219 mmol), Pd(dbpf)Cl$_2$ (0.026 g, 0.041 mmol) and Na$_2$CO$_3$ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 10% to 20%) and concentrated to afford the desired compound (0.065 g, 16.8%) as a brown oil.

Step 2: Synthesis of Compound 263

Methyl 4-(((2S,6R)-4-(4',4'-dimethyl-2',3',4',5'-tetrahydro-[1,1'-biphenyl]-3-carbonyl)-2,6-dimethylpiperazin-1-yl)methyl)benzoate (formula 15-2, 0.065 g, 0.137 mmol), hydroxylamine (0.167 mL, 2.735 mmol, 50.00% aqueous solution) and potassium hydroxide (0.077 g, 1.367 mmol) were dissolved in methanol (2 mL) at room temperature, and the reaction solution was stirred at the same temperature for 30 minutes. Then, the reaction mixture was concentrated under reduced pressure. A saturated aqueous solution of sodium hydrogen carbonate was added to the concentrate, and the precipitated solid was filtered and dried to yield compound 263 (0.044 g, 68.3%) as a white solid.

$^1$H NMR (400 MHz, DMSO-d$_6$) δ 7.66 (d, 2 H, J=8.1 Hz), 7.49 (d, 1 H, J=8.0 Hz), 7.38-7.34 (m, 4 H), 7.21 (d, 1 H, J=7.6 Hz), 6.15-6.13 (m, 1 H), 4.24-4.22 (m, 1 H), 3.76 (s, 2 H), 2.95-2.93 (m, 1 H), 2.67-2.50 (m, 4 H), 2.37 (s, 2 H), 1.96 (s, 2 H), 1.47 (t, 2 H, J=6.3 Hz), 1.05 (s, 3 H), 0.92 (s, 6 H), 0.80 (s, 3 H).

Example 107

Synthesis of Compound 265

(4-(((3R,5S)-3,5-dimethyl-4-(naphthalen-2-ylmethyl)piperazin-1-yl)methyl)-N-hydroxybenzamide)

Step 1: Synthesis of Methyl 4-(((3R,5S)-3,5-dimethyl-4-(naphthalene-2-ylmethyl)piperazin-1-yl)methyl)benzoate Methyl 4-(((3R,5S)-3,5-dimethylpiperazin-1-yl)methyl)benzoate (formula 1-2, 0.150 g, 0.572 mmol), Cs$_2$CO$_3$ (0.279 g, 0.858 mmol) and 2-(bromomethyl)naphthalene (0.126 g, 0.572 mmol) were dissolved in acetonitrile (3 mL) at room temperature, and the reaction solution was stirred at the same temperature for 48 hours. Then, water was added to the reaction mixture, followed by extraction with methylene chloride. The extract was passed through a plastic filter to remove solid residue and an aqueous layer, and the organic layer was concentrated under reduced pressure. The obtained product was used without additional purification (0.230 g, 99.9%)

Step 2: Synthesis of Compound 265

Methyl 4-(((3R,5S)-3,5-dimethyl-4-(naphthalene-2-ylmethyl)piperazin-1-yl)methyl)benzoate (formula 1-3, 0.230 g, 0.571 mmol), hydroxylamine (0.699 mL, 11.428 mmol, 50.00% aqueous solution) and potassium hydroxide (0.321 g, 5.714 mmol) were dissolved in methanol (3 mL)/tetrahydrofuran (1 mL) at room temperature, and the reaction solution was stirred at the same temperature for 30 minutes. The reaction mixture was concentrated under reduced pressure to remove the solvent, a saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure. The concentrate was crystallized from methanol (5 mL) to yield compound 265 (0.042 g, 18.2%) as a white solid.

$^1$H NMR (400 MHz, DMSO-d$_6$) δ 7.87-7.82 (m, 4 H), 7.66 (d, 2 H, J=8.0 Hz), 7.50 (d, 1 H, J=9.0 Hz), 7.47-7.44 (m, 2 H), 7.23 (d, 2 H, J=8.0 Hz), 3.88 (s, 2 H), 3.41 (s, 2 H), 2.67-2.61 (m, 4 H), 1.84 (t, 2 H, J=10.1 Hz), 0.93 (d, 6 H, J=6.0 Hz); LRMS (ES) m/z 404.2 (M$^+$+1).

Example 108

Synthesis of Compound 266

(4-(((3R,5S)-3,5-dimethyl-4-(pyridin-4-ylmethyl)piperazin-1-yl)methyl)-N-hydroxybenzamide (Trifluoroacetic acid salt))

Step 1: Synthesis of Methyl 4-(((3R,5S)-3,5-dimethyl-4-(pyridin-4-ylmethyl)piperazin-1-yl)methyl)benzoate Methyl 4-(((3R,5S)-3,5-dimethylpiperazin-1-yl)methyl)benzoate (formula 1-2, 0.150 g, 0.572 mmol), Cs$_2$CO$_3$ (0.279 g, 0.858 mmol) and 4-(bromomethyl)pyridine (0.098 g, 0.572 mmol) were dissolved in acetonitrile (3 mL) at room temperature, and the reaction solution was stirred at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The product was used without additional purification (0.200 g, 99.0%)

Step 2: Synthesis of Compound 266

Methyl 4-(((3R,5S)-3,5-dimethyl-4-(pyridin-4-ylmethyl) piperazin-1-yl) methyl)benzoate (formula 1-3, 0.200 g, 0.566 mmol), hydroxylamine (0.692 mL, 11.317 mmol, 50.00% aqueous solution) and potassium hydroxide (0.317 g, 5.658 mmol) were dissolved in methanol (3 mL) at room temperature, and the solution was stirred at the same temperature for 30 minutes. The reaction mixture was concentrated under reduced pressure to remove the solvent, and a saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure. The concentrate was purified by column chromatography (Waters, C$_{18}$, 19*100 mm column, 0.1% trifluoroacetic acid/acetonitrile=from 5% to 80%) and concentrated to afford the desired compound 266 (0.019 g, 9.5%) as a white solid.

$^1$H NMR (400 MHz, CH$_3$OD) δ 8.77 (d, 2 H, J=6.7 Hz), 8.17 (d, 2 H, J=6.7 Hz), 7.90 (d, 2 H, J=8.3 Hz), 7.67 (d, 2 H, J=8.3 Hz), 4.45 (s, 2 H), 4.18 (s, 2 H), 3.41 (d, 2 H, J=11.4 Hz), 3.03-3.00 (m, 4 H), 1.04 (d, 6 H, J=6.0 Hz).

Example 109

Synthesis of Compound 267

(4-(((3R,5S)-4-(3-chloro-2-(trifluoromethyl)benzyl)-3,5-dimethylpiperazin-1-yl)methyl)-N-hydroxybenzamide)

Step 1: Synthesis of Methyl 4-(((3R,5S)-4-(3-chloro-2-(trifluoromethyl)benzyl)-3,5-dimethylpiperazin-1-yl)methyl)benzoate Methyl 4-(((3R,5S)-3,5-dimethylpiperazin-1-yl)methyl)benzoate (formula 1-2, 0.150 g, 0.572 mmol), $Cs_2CO_3$ (0.279 g, 0.858 mmol) and 1-(bromomethyl)-3-chloro-2-(trifluoromethyl)benzene (0.156 g, 0.572 mmol) were dissolved in acetonitrile (3 mL) at room temperature, and the reaction solution was stirred at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 0% to 30%) and concentrated to afford the desired compound (0.203 g, 78.0%).

Step 2: Synthesis of Compound 267

Methyl 4-(((3R,5S)-4-(3-chloro-2-(trifluoromethyl)benzyl)-3,5-dimethylpiperazin-1-yl)methyl)benzoate (formula 1-3, 0.100 g, 0.220 mmol), hydroxylamine (0.269 mL, 4.396 mmol, 50.00% aqueous solution) and potassium hydroxide (0.123 g, 2.198 mmol) were dissolved in methanol (3 mL) at room temperature, and the reaction solution was stirred at the same temperature for 30 minutes. The reaction mixture was concentrated under reduced pressure to remove the solvent, and a saturated aqueous solution of sodium hydrogen carbonate was added to the resulting concentrate, followed by extraction with methylene chloride. The extract was passed through a plastic filter to remove solid residue and an aqueous layer, and the organic layer was concentrated under reduced pressure to yield compound 267 (0.044 g, 43.9%) as a white solid.

$^1$H NMR (400 MHz, $CDCl_3$) δ 9.80 (brs, 2 H), 7.82 (s, 1 H), 7.71-7.65 (m, 4 H), 7.33 (d, 2 H, J=3.9 Hz), 4.58 (s, 2 H), 3.44-3.35 (m, 3 H), 2.67 (d, 2 H, J=10.3 Hz), 2.60 (s, 2 H), 1.82 (t, 2 H, J=9.4 Hz), 0.83 (s, 6 H); LRMS (ES) m/z 456.1 ($M^+$+1).

Example 110

Synthesis of Compound 268

(4-(((2S,6R)-2,6-dimethyl-4-(naphthalen-2-ylmethyl)piperazin-1-yl)methyl)-N-hydroxybenzamide)

Step 1: Synthesis of Methyl 4-(((2S,6R)-2,6-dimethyl-4-(naphthalene-2-ylmethyl)piperazin-1-yl)methyl)benzoate Methyl 4-(((2S,6R)-2,6-dimethylpiperazin-1-yl)methyl)benzoate (formula 13-2, 0.150 g, 0.502 mmol), $Cs_2CO_3$ (0.245 g, 0.753 mmol) and 2-(bromomethyl)naphthalene (0.111 g, 0.502 mmol) were dissolved in acetonitrile (3 mL) at room temperature, and the reaction solution was stirred at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The product was used without additional purification (0.200 g, 99.0%).

Step 2: Synthesis of Compound 268

Methyl 4-(((2S,6R)-2,6-dimethyl-4-(naphthalene-2-ylmethyl)piperazin-1-yl)methyl)benzoate (formula 13-3, 0.200 g, 0.497 mmol), hydroxylamine (0.608 mL, 9.937 mmol) and potassium hydroxide (0.279 g, 4.969 mmol) were dissolved in methanol (3 mL) at room temperature, and the reaction solution was stirred at the same temperature for 30 minutes. Then, the reaction mixture was concentrated under reduced pressure. A saturated aqueous solution of sodium hydrogen carbonate (3 mL) was added to the concentrate, followed by stirring. The precipitated solid was filtered and dried, and the resulting product was purified by column chromatography (silicon dioxide, 4 g cartridge; methanol/methylene chloride=from 0% to 10%) and concentrated to afford compound 268 (0.075 g, 37.4%) as a white solid.

$^1$H NMR (400 MHz, DMSO-$d_6$) δ 11.13 (s, 1 H), 8.99 (s, 1 H), 7.90-7.86 (m, 3 H), 7.78 (s, 1 H), 7.67 (d, 2 H, J=7.2 Hz), 7.50-7.47 (m, 3 H), 7.42 (d, 2 H, J=7.8 Hz), 3.76 (s, 2 H), 3.57 (s, 2 H), 2.71 (d, 2 H, J=10.6 Hz), 2.60-2.56 (m, 2 H), 1.86 (t, 2 H, J=10.5 Hz), 0.88 (d, 6 H, J=6.0 Hz); LRMS (ES) m/z 404.2 ($M^+$+1).

Example 111

Synthesis of Compound 270

(N-hydroxy-4-(((3R,5S)-4-isopentyl-3,5-dimethylpiperazin-1-yl)methyl)benzamide (Trifluoroacetic acid salt))

Step 1: Synthesis of Methyl 4-(((3R,5S)-4-isopentyl-3,5-dimethylpiperazin-1-yl)methyl)benzoate Methyl 4-(((3R,5S)-3,5-dimethylpiperazin-1-yl)methyl)benzoate (formula 1-2, 0.150 g, 0.572 mmol), $Cs_2CO_3$ (0.279 g, 0.858 mmol) and 1-bromo-3-methylbutane (0.086 mL, 0.720 mmol) were dissolved in N,N-dimethylformamide (100 ml) at room temperature, and the reaction solution was stirred at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The product was used without additional purification (0.190 g, 99.9%)

Step 2: Synthesis of Compound 270

Methyl 4-(((3R,5S)-4-isopentyl-3,5-dimethylpiperazin-1-yl)methyl)benzoate (formula 1-3, 0.190 g, 0.571 mmol), hydroxylamine (0.699 mL, 11.429 mmol, 50.00% aqueous solution) and potassium hydroxide (0.321 g, 5.715 mmol) were dissolved in methanol (3 mL) at room temperature, and the solution was stirred at the same temperature for 30 minutes. The reaction mixture was concentrated under reduced pressure to remove the solvent, and a saturated aqueous solution of sodium hydrogen carbonate was added to the resulting concentrate, followed by extraction with methylene chloride. The extract was passed through a plastic filter to remove solid residue and an aqueous layer, and the organic layer was concentrated under reduced pressure. The concentrate was purified by column chromatography (Waters, $C_{18}$, 19*100 mm column, 0.1% trifluoroacetic acid/acetonitrile=from 5% to 80%) and concentrated to afford compound 270 (0.025 g, 13.1%) as a white solid.

$^1$H NMR (400 MHz, DMSO-$d_6$) δ 11.23 (brs, 1 H), 9.10 (brs, 1 H), 7.75 (d, 2 H, J=8.2 Hz), 7.42 (d, 2 H, J=8.1 Hz), 3.71 (s, 2 H), 3.45-3.45 (m, 2 H), 3.18-3.18 (m, 2 H), 3.01 (d, 2 H, J=11.3 Hz), 2.28 (t, 2 H, J=11.3 Hz), 1.67-1.60 (m, 1 H), 1.52-1.48 (m, 2 H), 1.22 (d, 6 H, J=6.3 Hz), 0.93 (d, 6 H, J=6.6 Hz); LRMS (ES) m/z 334.2 (M$^+$+1).

Example 112

Synthesis of Compound 271

(N-hydroxy-4-(((2S,6R)-4-isopentyl-2,6-dimethylpiperazin-1-yl)methyl)benzamide (Trifluoroacetic acid salt))

Step 1: Synthesis of Methyl 4-(((2S,6R)-4-isopentyl-2,6-dimethylpiperazin-1-yl)methyl)benzoate Methyl 4-(((2S,6R)-2,6-dimethylpiperazin-1-yl)methyl)benzoate (formula 13-2, 0.150 g, 0.502 mmol), Cs$_2$CO$_3$ (0.245 g, 0.753 mmol) and 1-bromo-3-methylbutane (0.060 mL, 0.502 mmol) were dissolved in acetonitrile (3 mL) at room temperature, and the reaction solution was stirred at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The product was used without additional purification (0.170 g, 101.9%).

Step 2: Synthesis of Compound 271

Methyl 4-(((2S,6R)-4-isopentyl-2,6-dimethylpiperazin-1-yl)methyl)benzoate (formula 13-3, 0.170 g, 0.511 mmol), hydroxylamine (0.626 mL, 10.226 mmol, 50.00% aqueous solution) and potassium hydroxide (0.287 g, 5.113 mmol) were dissolved in methanol (3 mL) at room temperature, and the solution was stirred at the same temperature for 30 minutes. Then, the concentrate was purified by column chromatography (Waters, $C_{18}$, 19*100 mm column, 0.1% trifluoroacetic acid/acetonitrile=from 5% to 80%) and concentrated to afford compound 271 (0.097 g, 56.9%) as a white solid.

$^1$H NMR (400 MHz, DMSO-$d_6$) δ 11.18 (brs, 1 H), 9.00 (brs, 1 H), 7.67 (d, 2 H, J=8.3 Hz), 7.41 (d, 2 H, J=8.2 Hz), 3.74 (s, 2 H), 2.70 (d, 2 H, J=10.8 Hz), 2.56-2.53 (m, 2 H), 2.19 (t, 2 H, J=7.6 Hz), 1.70 (t, 2 H, J=10.6 Hz), 1.57-1.54 (m, 1 H), 1.32-1.26 (m, 2 H), 0.89 (d, 6 H, J=6.2 Hz), 0.86 (d, 6 H, J=6.6 Hz); LRMS (ES) m/z 334.2 (M$^+$+1).

Example 113

Synthesis of Compound 272

(4-(((3R,5S)-3,5-dimethyl-4-(3-methylbut-2-en-1-yl)piperazin-1-yl)methyl)-N-hydroxybenzamide)

Step 1: Synthesis of Methyl 4-(((3R,5S)-3,5-dimethyl-4-(3-methylbut-2-en-1-yl)piperazin-1-yl)methyl)benzoate Methyl 4-(((3R,5S)-3,5-dimethylpiperazin-1-yl)methyl)benzoate (formula 1-2, 0.150 g, 0.572 mmol), Cs$_2$CO$_3$ (0.279 g, 0.858 mmol) and 1-bromo-3-methyl-2-butene (0.067 mL, 0.572 mmol) were dissolved in N,N-dimethylformamide (3 mL) at room temperature, and the reaction solution was stirred at 100° C. for 17 hours. Then, a saturated aqueous solution of sodium hydrogen carbonate was added to the reaction mixture, followed by extraction with methylene chloride. The extract was passed through a plastic filter to remove solid residue and an aqueous solution, and the organic layer was concentrated under reduced pressure. The concentrate was purified by column chromatography (silicon dioxide, 4 g cartridge; methanol/methylene chloride=from 0% to 10%) and concentrated to afford the desired compound (0.123 g, 65.1%) as crude.

Step 2: Synthesis of Compound 272

Methyl 4-(((3R,5S)-3,5-dimethyl-4-(3-methylbut-2-en-1-yl)piperazin-1-yl)methyl)benzoate (formula 1-3, 0.070 g, 0.212 mmol), hydroxylamine (0.259 mL, 4.237 mmol, 50.00% aqueous solution) and potassium hydroxide (0.119 g, 2.118 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was passed through a plastic filter to remove solid residue and an aqueous layer, and the organic layer was concentrated under reduced pressure to yield compound 272 (0.030 g, 42.7%) as a white solid.

$^1$H NMR (400 MHz, DMSO-$d_6$) δ 11.10 (brs, 1 H), 9.00 (brs, 1 H), 7.69 (d, 2 H, J=8.0 Hz), 7.33 (d, 2 H, J=8.0 Hz), 5.30 (s, 1 H), 3.40 (s, 2 H), 3.35 (s, 2 H), 3.29 (d, 2 H, J=6.1 Hz), 2.62-2.60 (m, 4 H), 1.74-1.72 (m, 2 H), 1.69 (s, 3 H), 1.60 (s, 3 H), 0.92 (d, 6 H, J=7.0 Hz); LRMS (ES) m/z 332.2 (M$^+$+1).

Example 114

Synthesis of Compound 273

(N-hydroxy-4-(((2S,6R)-4-isopropyl-2,6-dimethylpiperazin-1-yl)methyl)benzamide (Trifluoroacetic acid salt))

Step 1: Synthesis of Methyl 4-(((2S,6R)-4-isopropyl-2,6-dimethylpiperazin-1-yl)methyl)benzoate Methyl 4-(((2S,6R)-2,6-dimethylpiperazin-1-yl)methyl)benzoate (formula 13-2, 0.150 g, 0.502 mmol), Cs$_2$CO$_3$ (0.245 g, 0.753 mmol) and 2-iodopropane (0.050 mL, 0.502 mmol) were dissolved in acetonitrile (3 mL) at room temperature, and the reaction solution was stirred at the same temperature for 17 hours. Then, water was added to the reaction mixture, followed by extraction with methylene chloride. The extract was passed through a plastic filter to remove solid residue and an aqueous solution, and the organic layer was concentrated under reduced pressure. The product was used without additional purification (0.150 g, 98.2%).

Step 2: Synthesis of Compound 273

Methyl 4-(((2S,6R)-4-isopropyl-2,6-dimethylpiperazin-1-yl)methyl)benzoate (formula 13-3, 0.150 g, 0.493 mmol), hydroxylamine (0.603 mL, 10.226 mmol, 50.00% aqueous solution) and potassium hydroxide (0.276 g, 4.927 mmol) were dissolved in methanol (3 mL) at room temperature, and the solution was stirred at the same temperature for 30 minutes. Then, the concentrate was purified by column chromatography (Waters, $C_{18}$, 19*100 mm column, 0.1% trifluoroacetic acid/acetonitrile=from 5% to 80%) and concentrated to afford compound 273 (0.097 g, 64.5%) as a white solid.

$^1$H NMR (400 MHz, DMSO-$d_6$) δ 11.20 (s, 1 H), 9.36 (s, 1 H), 7.72 (d, 2 H, J=8.2 Hz), 7.46 (d, 2 H, J=8.2 Hz), 3.93 (s, 2 H), 3.44-3.41 (m, 1 H), 3.35 (d, 2 H, J=11.6 Hz), 2.92-2.90 (m, 2 H), 2.77-2.74 (m, 2 H), 1.25 (d, 6 H, J=6.6 Hz), 1.08 (d, 6 H, J=4.8 Hz); LRMS (ES) m/z 306.2 (M$^+$+1)

Example 115

Synthesis of Compound 274

(4-(((2S,6R)-4-butyl-2,6-dimethylpiperazin-1-yl) methyl)-N-hydroxybenzamide (Trifluoroacetic acid salt))

Step 1: Synthesis of Methyl 4-(((2S,6R)-4-butyl-2, 6-dimethylpiperazin-1-yl)methyl)benzoate Methyl 4-(((2S,6R)-2,6-dimethylpiperazin-1-yl)methyl) benzoate (formula 13-2, 0.150 g, 0.502 mmol), $Cs_2CO_3$ (0.245 g, 0.753 mmol) and 1-iodobutane (0.057 mL, 0.502 mmol) were dissolved in acetonitrile (3 mL) at room temperature, and the reaction solution was stirred at the same temperature for 17 hours. Then, water was added to the reaction mixture, followed by extraction with methylene chloride. The extract was passed through a plastic filter to remove solid residue and an aqueous solution, and the organic layer was concentrated under reduced pressure. The product was used without additional purification (0.160 g, 100.1%).

Step 2: Synthesis of Compound 274

Methyl 4-(((2S,6R)-4-butyl-2,6-dimethylpiperazin-1-yl) methyl)benzoate (formula 13-3, 0.160 g, 0.502 mmol), hydroxylamine (0.615 mL, 10.049 mmol, 50.00% aqueous solution) and potassium hydroxide (0.282 g, 5.024 mmol) were dissolved in methanol (3 mL) at room temperature, and the solution was stirred at the same temperature for 30 minutes. Then, the concentrate was purified by column chromatography (Waters, $C_{18}$, 19*100 mm column, 0.1% trifluoroacetic acid/acetonitrile=from 5% to 80%) and concentrated to afford compound 274 (0.087 g, 54.2%) as a white solid.

$^1$H NMR (400 MHz, $D_2O$) δ 7.66 (d, 2 H, J=8.3 Hz), 7.51 (d, 2 H, J=8.4 Hz), 4.40 (s, 2 H), 3.58 (d, 2 H, J=12.4 Hz), 3.37-3.36 (m, 2 H), 3.07-2.97 (m, 4 H), 1.57-1.54 (m, 2 H), 1.39 (d, 6 H, J=6.3 Hz), 1.26-1.20 (m, 2 H), 0.79 (t, 3 H, J=7.4 Hz); LRMS (ES) m/z 320.2 (M$^+$+1).

Example 116

Synthesis of Compound 275

(4-(((3R,5S)-4-butyl-3,5-dimethylpiperazin-1-yl) methyl)-N-hydroxybenzamide (Trifluoroacetic acid salt))

Step 1: Synthesis of Methyl 4-(((3R,5S)-4-butyl-3, 5-dimethylpiperazin-1-yl)methyl)benzoate Methyl 4-(((3R,5S)-3,5-dimethylpiperazin-1-yl)methyl) benzoate (formula 1-2, 0.150 g, 0.502 mmol), $Cs_2CO_3$ (0.245 g, 0.753 mmol) and 1-iodobutane (0.057 mL, 0.502 mmol) were dissolved in acetonitrile (3 mL), and the reaction mixture was heated under reflux for 17 hours, and then cooled to room temperature. Then, water was added to the reaction mixture, followed by extraction with methylene chloride. The extract was passed through a plastic filter to remove solid residue and an aqueous solution, and the organic layer was concentrated under reduced pressure. The product was used without additional purification (0.120 g, 98.9%)

Step 2: Synthesis of Compound 275

Methyl 4-(((3R,5S)-4-butyl-3,5-dimethylpiperazin-1-yl) methyl)benzoate (formula 1-3, 0.120 g, 0.377 mmol), hydroxylamine (0.461 mL, 7.537 mmol, 50.00% aqueous solution) and potassium hydroxide (0.211 g, 3.768 mmol) were dissolved in methanol (3 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was passed through a plastic filter to remove solid residue and an aqueous layer, and the organic layer was concentrated under reduced pressure. The concentrate was purified by column chromatography (Waters, $C_{18}$, 19*100 mm column, 0.1% trifluoroacetic acid/acetonitrile=from 5% to 80%) and concentrated to afford the desired compound 275 (0.088 g, 73.1%) as a white solid.

$^1$H NMR (400 MHz, $D_2O$) δ 7.66 (d, 2 H, J=8.3 Hz), 7.47 (d, 2 H, J=8.2 Hz), 4.15-4.15 (m, 2 H), 3.57-3.56 (m, 2 H), 3.44 (d, 2 H, J=13.2 Hz), 3.22 (t, 2 H, J=8.5 Hz), 2.91-2.90 (m, 2 H), 1.58-1.54 (m, 2 H), 1.28 (d, 6 H, J=6.4 Hz), 0.82 (t, 3 H, J=7.4 Hz); LRMS (ES) m/z 320.2 (M$^+$+1)

Example 117

Synthesis of Compound 276

(4-(((2S,6R)-4-(2-(furan-2-yl)benzoyl)-2,6-dimethyl-piperazin-1-yl)methyl)-N-hydroxybenzamide)

Step 1: Synthesis of Methyl 4-(((2S,6R)-4-(2-iodo-benzoyl)-2,6-dimethylpiperazin-1-yl)methyl)benzoate Methyl 4-(((2S,6R)-2,6-dimethylpiperazin-1-yl)methyl) benzoate (formula 13-2, 4.000 g, 16.128 mmol), 2-iodobenzoic acid (4.654 g, 17.741 mmol), EDCI (6.183 g, 32.255 mmol), HOBt (4.359 g, 32.255 mmol) and N,N-diisopropylethylamine (10.422 g, 80.639 mmol) were dissolved in methylene chloride (100 mL) at room temperature, and the solution was stirred overnight at the same temperature. Then, water was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 30% to 50%) and concentrated to afford the desired compound (7.630 g, 96.1%) as a white solid.

Step 2: Synthesis of Methyl 4-(((2S,6R)-4-(2-(furan-2-yl)benzoyl)-2,6-dimethylpiperazin-1-yl) methyl)benzoate 1,2-Dimethoxyethane/water (v/v=3/1) (3 mL) were added to a mixture of methyl 4-(((2S,6R)-4-(2-iodobenzoyl)-2,6- dimethylpiperazin-1-yl)methyl)benzoate (formula 15-1, 0.400 g, 0.812 mmol), furan-2-ylboronic acid (0.136 g, 1.219 mmol), Pd(dbpf)Cl$_2$ (0.026 g, 0.041 mmol) and Na$_2$CO$_3$ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 10% to 30%) and concentrated to afford the desired compound (0.211 g, 60.1%) as a white solid.

Step 3: Synthesis of Compound 276

Methyl 4-(((2S,6R)-4-(2-(furan-2-yl)benzoyl)-2,6-dimethylpiperazin-1-yl)methyl)benzoate (formula 15-2, 0.060 g, 0.139 mmol), hydroxylamine (0.170 mL, 2.775 mmol, 50.00% aqueous solution) and potassium hydroxide (0.078 g, 1.387 mmol) were dissolved in methanol (1 mL) at room temperature, and the reaction solution was stirred at the same temperature for 30 minutes. Then, the reaction mixture was concentrated under reduced pressure. A saturated aqueous solution of sodium hydrogen carbonate was added to the concentrate, and the precipitated solid was filtered and dried to yield compound 276 (0.017 g, 27.9%) as a white solid.
$^1$H NMR (400 MHz, DMSO-d$_6$) δ 7.80-7.65 (m, 4 H), 7.50-7.47 (m, 1 H), 7.40-7.30 (m, 3 H), 7.26 (t, 1 H, J=6.8 Hz), 6.69 (dd, 1 H, J=27.4, 9.3 Hz), 6.61-6.51 (m, 1 H), 4.36-4.33 (m, 1 H), 3.76-3.61 (m, 2 H), 3.09-2.99 (m, 1 H), 2.83-2.77 (m, 1 H), 2.69-2.55 (m, 3 H), 1.03 (d, 3 H, J=5.9 Hz), 0.70 (m, 3 H).

Example 118

Synthesis of Compound 277

(4-(((2S,6R)-4-(2-(furan-3-yl)benzoyl)-2,6-dimethylpiperazin-1-yl)methyl)-N-hydroxybenzamide)

Step 1: Synthesis of Methyl 4-(((2S,6R)-4-(2-(furan-3-yl)benzoyl)-2,6-dimethylpiperazin-1-yl)methyl)benzoate 1,2-Dimethoxyethane/water (v/v=3/1) (3 mL) were added to a mixture of methyl 4-(((2S,6R)-4-(2-iodobenzoyl)-2,6-dimethylpiperazin-1-yl)methyl)benzoate (formula 15-1, 0.400 g, 0.812 mmol), furan-3-ylboronic acid (0.136 g, 1.219 mmol), Pd(dbpf)Cl$_2$ (0.026 g, 0.041 mmol) and Na$_2$CO$_3$ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 10% to 30%) and concentrated to afford the desired compound (0.186 g, 52.8%) as a brown solid.

Step 2: Synthesis of Compound 277

Methyl 4-(((2S,6R)-4-(2-(furan-3-yl)benzoyl)-2,6-dimethylpiperazin-1-yl)methyl)benzoate (formula 15-2, 0.060 g, 0.139 mmol), hydroxylamine (0.170 mL, 2.775 mmol, 50.00% aqueous solution) and potassium hydroxide (0.078 g, 1.387 mmol) were dissolved in methanol (1 mL) at room temperature, and the solution was stirred at the same temperature for 30 minutes. Then, the reaction mixture was concentrated under reduced pressure. A saturated aqueous solution of sodium hydrogen carbonate was added to the concentrate, and the precipitated solid was filtered and dried to yield compound 277 (0.023 g, 37.6%) as a white solid.
$^1$H NMR (400 MHz, DMSO-d$_6$) δ 7.82 (s, 1 H), 7.77-7.64 (m, 3 H), 7.58-7.52 (m, 1 H), 7.46 (t, 1 H, J=7.5 Hz), 7.36 (q, 2 H, J=8.1 Hz), 7.29-7.25 (m, 2 H), 6.67-6.66 (m, 1 H), 4.31 (d, 1 H, J=10.5 Hz), 3.74 (s, 1 H), 3.62 (q, 2 H, J=18.9 Hz), 2.90 (m, 1 H), 2.76-2.68 (m, 1 H), 2.62-2.56 (m, 2 H), 1.00-0.98 (m, 3 H), 0.66 (m, 3 H).

Example 119

Synthesis of Compound 278

(4-(((2S,6R)-4-(2-(3,6-dihydro-2H-pyran-4-yl)benzoyl)-2,6-dimethylpiperazin-1-yl)methyl)-N-hydroxybenzamide)

Step 1: Synthesis of Methyl 4-(((2S,6R)-4-(2-(3,6-dihydro-2H-pyran-4-yl)benzoyl)-2,6-dimethylpiperazin-1-yl)methyl)benzoate Methyl 4-(((2S,6R)-4-(2-iodobenzoyl)-2,6-dimethylpiperazin-1-yl)methyl)benzoate (formula 15-1, 0.400 g, 0.812 mmol), 2-(3,6-dihydro-2H-pyran-4-yl)-4,4,5,5-tetramethyl-1,3,2-dioxaborolane (0.256 g, 1.219 mmol), Pd(dbpf)Cl$_2$ (0.026 g, 0.041 mmol) and Na$_2$CO$_3$ (0.258 g, 2.437 mmol) were dissolved in 1,2-dimethoxyethane/water (v/v=3/1) (3 mL) at room temperature, and the reaction solution was stirred overnight at 100° C. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 10% to 50%) and concentrated to afford the desired compound (0.272 g, 74.6%) as a brown solid.

Step 2: Synthesis of Compound 278

Methyl 4-(((2S,6R)-4-(2-(3,6-dihydro-2H-pyran-4-yl)benzoyl)-2,6-dimethylpiperazin-1-yl)methyl)benzoate (formula 15-2, 0.060 g, 0.134 mmol), hydroxylamine (0.164 mL, 2.675 mmol, 50.00% aqueous solution) and potassium hydroxide (0.075 g, 1.338 mmol) were dissolved in methanol (1 mL) at room temperature, and the solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 278 (0.049 g, 81.8%) as a white solid.
$^1$H NMR (400 MHz, DMSO-d$_6$) δ 7.68 (d, 2 H, J=8.0 Hz), 7.45-7.39 (m, 3 H), 7.31 (t, 2 H, J=7.5 Hz), 7.23-7.18 (m, 1 H), 5.83-5.76 (m, 1 H), 4.32-4.29 (m, 1 H), 4.15-4.10 (m, 2 H), 3.78-3.73 (m, 4 H), 3.06 (d, 1 H, J=12.6 Hz), 2.78 (q, 1 H, J=10.9 Hz), 2.67-2.56 (m, 2 H), 2.24-2.10 (m, 1 H), 1.03-1.02 (m, 3 H), 0.80-0.78 (m, 3 H).

Example 120

Synthesis of Compound 279

(4-(((2S,6R)-2,6-dimethyl-4-(2-(pyridin-3-yl)benzoyl)piperazin-1-yl)methyl)-N-hydroxybenzamide)

Step 1: Synthesis of Methyl 4-(((2S,6R)-2,6-dimethyl-4-(2-(pyridin-3-yl)benzoyl)piperazin-1-yl)methyl)benzoate Methyl 4-(((2S,6R)-4-(2-iodobenzoyl)-2,6-dimethylpiperazin-1-yl)methyl)benzoate (formula 15-1, 0.400 g, 0.812 mmol), pyridin-3-ylboronic acid (0.150 g, 1.219 mmol), Pd(dbpf)Cl$_2$ (0.026 g, 0.041 mmol) and Na$_2$CO$_3$ (0.258 g, 2.437 mmol) were dissolved in 1,2-dimethoxyethane/water (v/v=3/1) (3 mL) at room temperature, and the reaction solution was stirred overnight at 100° C. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 50% to 60%) and concentrated to afford the desired compound (0.348 g, 96.7%) as a brown oil.

Step 2: Synthesis of Compound 279

Methyl 4-(((2S,6R)-2,6-dimethyl-4-(2-(pyridin-3-yl)benzoyl)piperazin-1-yl)methyl)benzoate (formula 15-2, 0.070 g, 0.158 mmol), hydroxylamine (0.193 mL, 3.156 mmol, 50.00% aqueous solution) and potassium hydroxide (0.089 g, 1.578 mmol) were dissolved in methanol (1 mL) at room temperature, and the solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 279 (0.062 g, 88.4%) as a white solid.

$^1$H NMR (400 MHz, DMSO-d$_6$) δ 8.62-8.53 (m, 2 H), 7.82-7.76 (m, 1 H), 7.67 (d, 2 H, J=8.0 Hz), 7.60-7.43 (m, 4 H), 7.34 (dd, 3 H, J=36.4, 7.5 Hz), 4.20 (d, 1 H, J=12.5 Hz), 3.72-3.60 (m, 1 H), 3.55-3.41 (m, 1 H), 3.06-2.86 (m, 1 H), 2.66-2.63 (m, 1 H), 2.28-2.22 (m, 1 H), 1.99 (brs, 1 H), 1.06 (brs, 1 H), 0.92-0.91 (m, 3 H), 0.68-0.62 (m, 3 H).

Example 121

Synthesis of Compound 280

(4-(((2S,6R)-4-(4',4'-dimethyl-2',3',4',5'-tetrahydro-[1,1'-biphenyl]-2-carbonyl)-2,6-dimethylpiperazin-1-yl)methyl)-N-hydroxybenzamide)

Step 1: Synthesis of Methyl 4-(((2S,6R)-4-(4',4'-dimethyl-2',3',4',5'-tetrahydro-[1,1'-biphenyl]-2-carbonyl)-2,6-dimethylpiperazin-1-yl)methyl)benzoate Methyl 4-(((2S,6R)-4-(2-iodobenzoyl)-2,6-dimethylpiperazin-1-yl)methyl)benzoate (formula 15-1, 0.400 g, 0.812 mmol), 2-(4,4-dimethylcyclohex-1-en-1-yl)-4,4,5,5-tetramethyl-1,3,2-dioxaborolane (0.288 g, 1.219 mmol), Pd(dbpf)Cl$_2$ (0.026 g, 0.041 mmol) and Na$_2$CO$_3$ (0.258 g, 2.437 mmol) were dissolved in 1,2-dimethoxyethane/water (v/v=3/1) (3 mL) at room temperature, and the reaction solution was stirred overnight at 100° C. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 10% to 20%) and concentrated to afford the desired compound (0.274 g, 71.1%) as a brown solid.

Step 2: Synthesis of Compound 280

Methyl 4-(((2S,6R)-4-(4',4'-dimethyl-2',3',4',5'-tetrahydro-[1,1'-biphenyl]-2-carbonyl)-2,6-dimethylpiperazin-1-yl)methyl)benzoate (formula 15-2, 0.060 g, 0.135 mmol), hydroxylamine (0.165 mL, 2.706 mmol, 50.00% aqueous solution) and potassium hydroxide (0.076 g, 1.353 mmol) were dissolved in methanol (1 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 280 (0.049 g, 75.7%) as a white solid.

$^1$H NMR (400 MHz, DMSO-d$_6$) δ 7.69-7.67 (m, 2 H), 7.38-7.34 (m, 3 H), 7.31-7.24 (m, 2 H), 7.16 (t, 1 H, J=8.7 Hz), 5.56 (s, 1 H), 4.29 (dd, 1 H, J=31.1, 13.2 Hz), 3.81-3.71 (m, 2 H), 3.09 (t, 1 H, J=14.5 Hz), 2.84-2.62 (m, 2 H), 2.46-2.33 (m, 3 H), 2.10 (brs, 1 H), 1.88-1.73 (m, 2 H), 1.44-1.38 (m, 2 H), 1.05-1.00 (m, 3 H), 0.95-0.89 (m, 6 H), 0.81-0.67 (m, 3 H).

Example 122

Synthesis of Compound 283

(4-(((3R,5S)-4-(2-(furan-2-yl)benzoyl)-3,5-dimethylpiperazin-1-yl)methyl)-N-hydroxybenzamide)

Step 1: Synthesis of 2-iodobenzoyl chloride

2-Iodobenzoic acid (4.000 g, 16.128 mmol) and SOCl$_2$ (23.399 mL, 322.555 mmol) were stirred overnight at 100° C., and then the reaction mixture was concentrated under reduced pressure. The product was used without additional purification (4.295 g, 99.9%, brown oil).

Step 2: Synthesis of Methyl 4-(((3R,5S)-4-(2-iodobenzoyl)-3,5-dimethylpiperazin-1-yl)methyl)benzoate Methyl 4-(((3R,5S)-3,5-dimethylpiperazin-1-yl)methyl)benzoate (formula 1-2, 4.295 g, 16.119 mmol), 2-iodobenzoyl chloride (4.652 g, 17.731 mmol) and TEA (4.469 mL, 32.237 mmol) were dissolved in methylene chloride (70 mL) at room temperature, and the reaction solution was stirred at the same temperature for 1 hour. Then, water was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 30% to 50%) and concentrated to afford the desired compound (7.120 g, 89.7%) as a white solid.

Step 3: Synthesis of Methyl 4-(((3R,5S)-4-(2-(furan-2-yl)benzoyl)-3,5-dimethylpiperazin-1-yl)methyl)benzoate 1,2-Dimethoxyethane/water (v/v=3/1) (3 mL) were added to a mixture of methyl 4-(((3R,5S)-4-(2-iodobenzoyl)-3,5- dimethylpiperazin-1-yl)methyl)benzoate (formula 4-1, 0.400 g, 0.812 mmol), furan-2-ylboronic acid (0.136 g, 1.219 mmol), Pd(dbpf)Cl$_2$ (0.026 g, 0.041 mmol) and Na$_2$CO$_3$ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 0% to 15%) and concentrated to afford the desired compound (0.040 g, 11.4%) as a colorless oil.

Step 4: Synthesis of Compound 283

Methyl 4-(((3R,5S)-4-(2-(furan-2-yl)benzoyl)-3,5-dimethylpiperazin-1-yl)methyl)benzoate (formula 4-2, 0.040 g, 0.092 mmol), hydroxylamine (0.113 mL, 1.850 mmol, 50.00% aqueous solution) and potassium hydroxide (0.052 g, 0.925 mmol) were dissolved in methanol (2 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 283 (0.016 g, 39.4%) as a white solid.

$^1$H NMR (400 MHz, DMSO-d$_6$) δ 7.78-7.68 (m, 4 H), 7.46 (t, 1 H, J=7.6 Hz), 7.41-7.21 (m, 4 H), 6.73 (dd, 1 H, J=33.6, 3.4 Hz), 6.61-6.59 (m, 1 H), 4.70-4.65 (m, 1 H), 3.56-3.41 (m, 3 H), 2.72-2.66 (m, 1 H), 2.41-2.33 (m, 1 H), 2.18-2.03 (m, 1 H), 1.63-1.60 (m, 1 H), 1.33 (t, 3 H, J=9.8 Hz), 1.16 (d, 1 H, J=6.8 Hz), 0.86 (d, 1 H, J=6.8 Hz).

Example 123

Synthesis of Compound 284

(4-(((3R,5S)-4-(2-(furan-3-yl)benzoyl)-3,5-dimethylpiperazin-1-yl)methyl)-N-hydroxybenzamide)

Step 1: Synthesis of Methyl 4-(((3R,5S)-4-(2-(furan-3-yl)benzoyl)-3,5-dimethylpiperazin-1-yl)methyl)benzoate 1,2-Dimethoxyethane/water (v/v=3/1) (3 mL) were added to a mixture of methyl 4-(((3R,5S)-4-(2-iodobenzoyl)-3,5-dimethylpiperazin-1-yl)methyl)benzoate (formula 4-1, 0.400 g, 0.812 mmol), furan-3-ylboronic acid (0.136 g, 1.219 mmol), Pd(dbpf)Cl$_2$ (0.026 g, 0.041 mmol) and Na$_2$CO$_3$ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 0% to 10%) and concentrated to afford the desired compound (0.128 g, 36.5%) as a colorless oil.

Step 2: Synthesis of Compound 284

Methyl 4-(((3R,5S)-4-(2-(furan-3-yl)benzoyl)-3,5-dimethylpiperazin-1-yl)methyl)benzoate (formula 4-2, 0.128 g, 0.296 mmol), hydroxylamine (0.362 mL, 5.919 mmol, 50.00% aqueous solution) and potassium hydroxide (0.166 g, 2.959 mmol) were dissolved in methanol (3 mL) at room temperature, and the solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 284 (0.038 g, 29.5%) as a white solid.

$^1$H NMR (400 MHz, DMSO-d$_6$) δ 7.85-7.75 (m, 2 H), 7.68 (d, 2 H, J=8.2 Hz), 7.60-7.51 (m, 1 H), 7.46-7.35 (m, 2 H), 7.33-7.21 (m, 3 H), 6.82-6.66 (m, 1 H), 4.69-4.54 (m, 1 H), 3.52-3.49 (m, 1 H), 3.27-3.25 (m, 1 H), 2.70-2.56 (m, 1 H), 2.37-2.34 (m, 1 H), 2.16-2.04 (m, 1 H), 1.86-1.82 (m, 1 H), 1.39-1.21 (m, 4 H), 1.12 (d, 2 H, J=6.8 Hz), 0.82 (d, 1 H, J=6.8 Hz).

Example 124

Synthesis of Compound 285

(4-(((3R,5S)-3,5-dimethyl-4-(2-(pyridin-4-yl)benzoyl)piperazin-1-yl)methyl)-N-hydroxybenzamide)

Step 1: Synthesis of Methyl 4-(((3R,5S)-3,5-dimethyl-4-(2-(pyridin-4-yl)benzoyl)piperazin-1-yl)methyl)benzoate 1,2-Dimethoxyethane/water (v/v=3/1) (3 mL) were added to a mixture of methyl 4-(((3R,5S)-4-(2-iodobenzoyl)-3,5-dimethylpiperazin-1-yl)methyl)benzoate (formula 4-1, 0.400 g, 0.812 mmol), pyridine-4-boronic acid hydrate (0.172 g, 1.219 mmol), Pd(dbpf)Cl$_2$ (0.026 g, 0.041 mmol) and Na$_2$CO$_3$ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure.

The concentrate was purified by column chromatography (silicon dioxide; ethyl acetate/hexane=from 50% to 60%) and concentrated to afford the desired compound (0.129 g, 35.9%) as a pale yellow solid.

Step 2: Synthesis of Compound 285

Methyl 4-(((3R,5S)-3,5-dimethyl-4-(2-(pyridin-4-yl)benzoyl)piperazin-1-yl)methyl)benzoate (formula 4-2, 0.060 g, 0.135 mmol), hydroxylamine (0.165 mL, 2.706 mmol, 50.00% aqueous solution) and potassium hydroxide (0.076 g, 1.353 mmol) were dissolved in methanol (3 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 285 (0.016 g, 26.9%) as a white solid.

$^1$H NMR (400 MHz, DMSO-d$_6$) δ 8.64 (d, 2 H, J=5.8 Hz), 7.67 (d, 2 H, J=8.0 Hz), 7.61-7.41 (m, 6 H), 7.30 (d, 1 H, J=8.0 Hz), 4.34 (brs, 1 H), 3.24-3.17 (m, 3 H), 2.24 (d, 1 H, J=11.0 Hz), 1.44-1.40 (m, 1 H), 1.29 (d, 3 H, J=6.7 Hz), 1.07 (d, 3 H, J=6.6 Hz).

Example 125

Synthesis of Compound 286

(4-(((3R,5S)-3,5-dimethyl-4-(2-(pyridin-3-yl)benzoyl)piperazin-1-yl)methyl)-N-hydroxybenzamide)

Step 1: Synthesis of Methyl ((3R,5S)-3,5-dimethyl-4-(2-(pyridin-3-yl)benzoyl)piperazin-1-yl)methyl)benzoate 1,2-Dimethoxyethane/water (v/v=3/1) (3 mL) were added to a mixture of methyl 4-(((3R,5S)-4-(2-iodobenzoyl)-3,5-dimethylpiperazin-1-yl)methyl)benzoate (formula 4-1, 0.400 g, 0.812 mmol), pyridin-3-ylboronic acid (0.150 g, 1.219 mmol), Pd(dbpf)Cl$_2$ (0.026 g, 0.041 mmol) and Na$_2$CO$_3$ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=50%) and concentrated to afford the desired compound (0.292 g, 81.1%) as a yellow solid.

Step 2: Synthesis of Compound 286

Methyl ((3R,5S)-3,5-dimethyl-4-(2-(pyridin-3-yl)benzoyl)piperazin-1-yl)methyl)benzoate (formula 4-2, 0.060 g, 0.135 mmol), hydroxylamine (0.165 mL, 2.706 mmol, 50.00% aqueous solution) and potassium hydroxide (0.076 g, 1.353 mmol) were dissolved in methanol (3 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 286 (0.050 g, 83.8%) as a white solid.

$^1$H NMR (400 MHz, DMSO-d$_6$) δ 8.58-8.57 (m, 2 H), 7.78 (d, 1 H, J=7.9 Hz), 7.68 (d, 2 H, J=8.1 Hz), 7.57-7.43 (m, 5 H), 7.30 (d, 2 H, J=7.9 Hz), 4.31-4.29 (m, 1 H), 3.26-3.18 (m, 3 H), 2.23 (d, 1 H, J=11.2 Hz), 1.37-1.35 (m, 1 H), 1.28 (d, 3 H, J=6.7 Hz), 1.07 (d, 3 H, J=6.7 Hz).

Example 126

Synthesis of Compound 288

(4-(((3R,5S)-4-(4',4'-dimethyl-2',3',4',5'-tetrahydro-[1,1'-biphenyl]-2-carbonyl)-3,5-dimethylpiperazin-1-yl)methyl)-N-hydroxybenzamide)

Step 1: Synthesis of Methyl 4-(((3R,5S)-4-(4',4'-dimethyl-2',3',4',5'-tetrahydro-[1,1'-biphenyl]-2-carbonyl)-3,5-dimethylpiperazin-1-yl)methyl)benzoate 1,2-Dimethoxyethane/water (v/v=3/1) (3 mL) were added to a mixture of methyl 4-(((3R,5S)-4-(2-iodobenzoyl)-3,5-dimethylpiperazin-1-yl)methyl)benzoate (formula 4-1, 0.400 g, 0.812 mmol), 2-(4,4-dimethylcyclohex-1-en-1-yl)-4,4,5,5-tetramethyl-1,3,2-dioxaborolane (0.288 g, 1.219 mmol), Pd(dbpf)Cl$_2$ (0.026 g, 0.041 mmol) and Na$_2$CO$_3$ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 0% to 10%) and concentrated to afford the desired compound (0.143 g, 37.0%) as a brown solid.

Step 2: Synthesis of Compound 288

Methyl 4-(((3R,5S)-4-(4',4'-dimethyl-2',3',4',5'-tetrahydro-[1,1'-biphenyl]-2-carbonyl)-3,5-dimethylpiperazin-1-yl)methyl)benzoate (formula 4-3, 0.060 g, 0.126 mmol), hydroxylamine (0.155 mL, 2.528 mmol, 50.00% aqueous solution) and potassium hydroxide (0.071 g, 1.264 mmol) were dissolved in methanol (3 mL) at room temperature, and the solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 288 (0.047 g, 78.0%) as a white solid.

$^1$H NMR (400 MHz, DMSO-d$_6$) δ 7.71 (d, 2 H, J=8.0 Hz), 7.36-7.26 (m, 4 H), 7.21-7.19 (m, 2 H), 5.55 (s, 1 H), 4.48 (brs, 1 H), 3.50-3.47 (m, 2 H), 2.69 (d, 1 H, J=11.0 Hz), 2.40-2.37 (m, 1 H), 2.12-1.98 (m, 3 H), 1.86-1.81 (m, 2 H), 1.41-1.38 (m, 2 H), 1.34 (d, 3 H, J=6.6 Hz), 1.17 (d, 3 H, J=6.6 Hz), 0.93-0.91 (m, 6 H).

Example 127

Synthesis of Compound 290

(4-(((3R,5S)-3,5-dimethyl-4-(4-methylbenzoyl)piperazin-1-yl)methyl)-N-hydroxybenzamide (Trifluoroacetic acid salt))

Step 1: Synthesis of Methyl 4-(((3R,5S)-3,5-dimethyl-4-(4-methylbenzoyl)piperazin-1-yl)methyl)benzoate Methyl 4-(((3R,5S)-3,5-dimethylpiperazin-1-yl)methyl)benzoate (formula 1-2, 0.100 g, 0.381 mmol), 4-methylbenzoyl chloride (0.060 mL, 0.457 mmol) and TEA (0.077 g, 0.762 mmol) were dissolved in methylene chloride (1 ml) at 25° C., and the reaction solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield the desired compound (0.078 g, 53.8%) as a pale yellow solid.

Step 2: Synthesis of Compound 290

Methyl 4-(((3R,5S)-3,5-dimethyl-4-(4-methylbenzoyl)piperazin-1-yl)methyl)benzoate (formula 1-3, 0.050 g, 0.131 mmol), hydroxylamine (0.161 mL, 2.628 mmol, 50.00% aqueous solution) and potassium hydroxide (0.074 g, 1.314 mmol) were dissolved in methanol (0.5 ml) at 25° C., and the reaction solution was stirred at the same temperature for 1 hour. Then, a saturated solution of sodium hydrogen carbonate was added to the reaction solution, followed by extraction with methylene chloride. The organic layer was washed with a saturated aqueous solution of sodium chloride, dried with anhydrous magnesium sulfate, and then concentrated under reduced pressure. The concentrate was purified by column chromatography (Waters, $C_{18}$, acetonitrile/0.1% trifluoroacetic acid aqueous solution=from 5% to 70%) and concentrated to afford compound 290 (0.019 g, 37.9%) as a white solid.

$^1$H NMR (400 MHz, $D_2O$) δ 7.67 (d, 2 H, J=8.4 Hz), 7.53 (d, 2 H, J=8.3 Hz), 7.21 (d, 2 H, J=7.8 Hz), 7.17 (d, 2 H, J=8.2 Hz), 4.38 (s, 2 H), 3.20 (m, 4 H), 2.24 (s, 3 H), 1.29 (brs, 6 H).

Example 128

Synthesis of Compound 291

(N-hydroxy-4-(((3R,5S)-4-(4-methoxybenzoyl)-3,5-dimethylpiperazin-1-yl)methyl)benzamide (Trifluoroacetic acid salt))

Step 1: Synthesis of Methyl 4-(((3R,5S)-4-(4-methoxybenzoyl)-3,5-dimethylpiperazin-1-yl)methyl)benzoate Methyl 4-(((3R,5S)-3,5-dimethylpiperazin-1-yl)methyl)benzoate (formula 1-2, 0.100 g, 0.381 mmol), 4-methoxybenzoyl chloride (0.062 mL, 0.457 mmol) and TEA (0.077 g, 0.762 mmol) were dissolved in methylene chloride (1 ml) at 25° C., and the reaction solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield the desired compound (0.088 g, 58.2%) as a pale yellow solid.

Step 2: Synthesis of Compound 291

Methyl 4-(((3R,5S)-4-(4-methoxybenzoyl)-3,5-dimethylpiperazin-1-yl)methyl)benzoate (formula 1-3, 0.050 g, 0.126 mmol), hydroxylamine (0.154 mL, 2.522 mmol, 50.00% aqueous solution) and potassium hydroxide (0.071 g, 1.261 mmol) were dissolved in methanol (0.5 ml) at 25° C., and the reaction solution was stirred at the same temperature for 1 hour. Then, a saturated solution of sodium hydrogen carbonate was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (Waters, $C_{18}$, acetonitrile/0.1% trifluoroacetic acid aqueous solution=from 5% to 70%) and concentrated to afford compound 291 (0.023 g, 45.9%) as a white solid.

$^1$H NMR (400 MHz, $D_2O$) δ 7.67 (d, 2 H, J=8.4 Hz), 7.52 (d, 2 H, J=8.3 Hz), 7.24 (d, 2 H, J=8.8 Hz), 6.93 (d, 2 H, J=8.8 Hz), 4.38 (s, 2 H), 3.73 (s, 3 H), 3.36-3.20 (m, 4 H), 1.29 (brs, 6 H).

Example 129

Synthesis of Compound 292

(4-(((3R,5S)-3,5-dimethyl-4-pivaloylpiperazin-1-yl)methyl)-N-hydroxybenzamide (Trifluoroacetic acid salt))

Step 1: Synthesis of Methyl 4-(((3R,5S)-3,5-dimethyl-4-pivaloylpiperazin-1-yl)methyl)benzoate Methyl 4-(((3R,5S)-3,5-dimethylpiperazin-1-yl)methyl)benzoate (formula 1-2, 0.100 g, 0.381 mmol), pivaloyl chloride (0.055 g, 0.457 mmol) and TEA (0.077 g, 0.762 mmol) were dissolved in methylene chloride (1 ml) at 25° C., and the reaction solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield the desired compound (0.105 g, 79.5%) as a yellow oil.

Step 2: Synthesis of Compound 292

Methyl 4-(((3R,5S)-3,5-dimethyl-4-pivaloylpiperazin-1-yl)methyl)benzoate (formula 1-3, 0.050 g, 0.144 mmol), hydroxylamine (0.177 mL, 2.886 mmol) and potassium hydroxide (0.081 g, 1.443 mmol) were dissolved in methanol (0.5 ml) at 25° C., and the reaction solution was stirred at the same temperature for 1 hour. Then, a saturated solution of sodium hydrogen carbonate was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (Waters, $C_{18}$, acetonitrile/0.1% trifluoroacetic acid aqueous solution=from 5% to 70%) and concentrated to afford the desired compound 292 (0.018 g, 35.9%) as a white solid.

$^1$H NMR (400 MHz, $D_2O$) δ 7.66 (d, 2 H, J=8.3 Hz), 7.52 (d, 2 H, J=8.2 Hz), 4.75-4.73 (m, 2 H), 4.35 (s, 2 H), 3.34 (m, 2 H), 3.13 (m, 2 H), 1.31 (brs, 6 H), 1.12 (s, 9 H).

Example 130

Synthesis of Compound 293

(4-(((3R,5S)-3,5-dimethyl-4-propionylpiperazin-1-yl)methyl)-N-hydroxybenzamide (Trifluoroacetic acid salt))

Step 1: Synthesis of Methyl 4-(((3R,5S)-3,5-dimethyl-4-propionylpiperazin-1-yl)methyl)benzoate Methyl 4-(((3R,5S)-3,5-dimethylpiperazin-1-yl)methyl)benzoate (formula 1-2, 0.100 g, 0.381 mmol), propionyl chloride (0.042 g, 0.457 mmol) and TEA (0.077 g, 0.762 mmol) were dissolved in methylene chloride (1 ml) at 25° C., and the reaction solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield the desired compound (0.113 g, 93.1%) as a yellow oil.

Step 2: Synthesis of Compound 293

Methyl 4-(((3R,5S)-3,5-dimethyl-4-propionylpiperazin-1-yl)methyl)benzoate (formula 1-3, 0.050 g, 0.157 mmol), hydroxylamine (0.192 mL, 3.141 mmol, 50.00% aqueous solution) and potassium hydroxide (0.088 g, 1.570 mmol) were dissolved in methanol (0.5 ml) at 25° C., and the reaction solution was stirred at the same temperature for 1 hour. Then, a saturated solution of sodium hydrogen carbonate was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (Waters, $C_{18}$, acetonitrile/0.1% trifluoroacetic acid aqueous solution=from 5% to 70%) and concentrated to afford compound 293 (0.027 g, 53.8%) as a white solid.

$^1$H NMR (400 MHz, $D_2O$) δ 7.66 (d, 2 H, J=7.9 Hz), 7.52 (d, 2 H, J=8.0 Hz), 4.75-4.73 (m, 2 H), 4.37 (s, 2 H), 3.40-3.37 (m, 2 H), 3.12-3.08 (m, 2 H), 2.42-2.27 (m, 2 H), 1.31 (brs, 6 H), 0.95 (t, 3 H, J=11.6 Hz).

Example 131

Synthesis of Compound 294

(4-(((3R,5S)-4-butyryl-3,5-dimethylpiperazin-1-yl) methyl)-N-hydroxybenzamide (Trifluoroacetic acid salt))

Step 1: Synthesis of Methyl 4-(((3R,5S)-4-butyryl-3,5-dimethylpiperazin-1-yl)methyl)benzoate Methyl 4-(((3R,5S)-3,5-dimethylpiperazin-1-yl)methyl) benzoate (formula 1-2, 0.100 g, 0.381 mmol), butyryl chloride (0.049 g, 0.457 mmol) and TEA (0.077 g, 0.762 mmol) were dissolved in methylene chloride (1 ml) at 25° C., and the reaction solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield the desired compound (0.077 g, 60.8%) as a pale yellow oil.

Step 2: Synthesis of Compound 294

Methyl 4-(((3R,5S)-4-butyryl-3,5-dimethylpiperazin-1-yl)methyl)benzoate (formula 1-3, 0.050 g, 0.150 mmol), hydroxylamine (0.184 mL, 3.008 mmol) and potassium hydroxide (0.084 g, 1.504 mmol) were dissolved in methanol (0.5 ml) at 25° C., and the reaction solution was stirred at the same temperature for 1 hour. Then, a saturated solution of sodium hydrogen carbonate was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (Waters, $C_{18}$, acetonitrile/0.1% trifluoroacetic acid aqueous solution=from 5% to 70%) and concentrated to afford compound 294 (0.024 g, 47.9%) as a white solid.

$^1$H NMR (400 MHz, $D_2O$) δ 7.67 (d, 2 H, J=6.5 Hz), 7.52 (d, 2 H, J=6.1 Hz), 4.74-4.71 (m, 2 H), 4.35 (s, 2 H), 3.40-3.37 (m, 2 H), 3.11-3.09 (m, 2 H), 2.35-2.23 (m, 2 H), 1.44 (q, 6 H, J=14.8, 7.4 Hz), 1.33 (brs, 3 H), 1.22 (brs, 3 H), 0.77 (t, 3 H, J=7.4 Hz).

Example 132

Synthesis of Compound 295

(4-(((3R,5S)-4-(cyclopropanecarbonyl)-3,5-dimethylpiperazin-1-yl)methyl)-N-hydroxybenzamide (Trifluoroacetic acid salt))

Step 1: Synthesis of Methyl 4-(((3R,5S)-4-(cyclopropanecarbonyl)-3,5-dimethylpiperazin-1-yl) methyl)benzoate Methyl 4-(((3R,5S)-3,5-dimethylpiperazin-1-yl)methyl) benzoate (formula 1-2, 0.100 g, 0.381 mmol), cyclopropanecarbonyl chloride (0.042 mL, 0.457 mmol) and TEA (0.077 g, 0.762 mmol) were dissolved in methylene chloride (1 ml) at 25° C., and the reaction solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield the desired compound (0.105 g, 83.4%) as a yellow oil.

Step 2: Synthesis of Compound 295

Methyl 4-(((3R,5S)-4-(cyclopropanecarbonyl)-3,5-dimethylpiperazin-1-yl)methyl)benzoate (formula 1-3, 0.050 g, 0.151 mmol), hydroxylamine (0.185 mL, 3.026 mmol, 50.00% aqueous solution) and potassium hydroxide (0.085 g, 1.513 mmol) were dissolved in methanol (0.5 ml) at 25° C., and the reaction solution was stirred at the same temperature for 1 hour. Then, a saturated solution of sodium hydrogen carbonate was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (Waters, $C_{18}$, acetonitrile/0.1% trifluoroacetic acid aqueous solution=from 5% to 70%) and concentrated to afford compound 295 (0.021 g, 41.9%) as a white solid.

$^1$H NMR (400 MHz, $D_2O$) δ 7.66 (d, 2 H, J=8.2 Hz), 7.53 (d, 2 H, J=8.2 Hz), 4.73-4.71 (m, 2 H), 4.38 (s, 2 H), 3.43-3.40 (m, 2 H), 3.14-3.12 (m, 2 H), 1.83-1.25 (m, 1 H), 1.28 (brs, 6 H), 0.79-0.75 (m, 4 H).

Example 133

Synthesis of Compound 296

(N-hydroxy-4-(((3R,5S)-4-isobutyryl-3,5-dimethylpiperazin-1-yl)methyl)benzamide (Trifluoroacetic acid salt))

Step 1: Synthesis of Methyl 4-(((3R,5S)-4-isobutyryl-3,5-dimethylpiperazin-1-yl)methyl)benzoate Methyl 4-(((3R,5S)-3,5-dimethylpiperazin-1-yl)methyl) benzoate (formula 1-2, 0.100 g, 0.381 mmol), isobutyryl chloride (0.048 mL, 0.457 mmol) and TEA (0.077 g, 0.762 mmol) were dissolved in methylene chloride (1 ml) at 25° C., and the reaction solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield the desired compound (0.097 g, 76.5%) as a yellow oil.

Step 2: Synthesis of Compound 296

Methyl 4-(((3R,5S)-4-isobutyryl-3,5-dimethylpiperazin-1-yl)methyl)benzoate (formula 1-3, 0.050 g, 0.150 mmol), hydroxylamine (0.184 mL, 3.008 mmol, 50.00% aqueous solution) and potassium hydroxide (0.084 g, 1.504 mmol) were dissolved in methanol (0.5 ml) at 25° C., and the reaction solution was stirred at the same temperature for 1 hour. Then, a saturated solution of sodium hydrogen carbonate was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (Waters, $C_{18}$, acetonitrile/0.1% trifluoroacetic acid aqueous solution=from 5% to 70%) and concentrated to afford compound 296 (0.025 g, 49.9%) as a white solid.

$^1$H NMR (400 MHz, $D_2O$) δ 7.67 (d, 2 H, J=8.2 Hz), 7.52 (d, 2 H, J=8.2 Hz), 4.73 (m, 1 H), 4.49 (m, 1 H), 4.37 (s, 2 H), 3.41-3.38 (m, 2 H), 3.13-3.09 (m, 2 H), 2.83-2.79 (m, 1 H), 1.33 (brs, 3 H), 1.22 (brs, 3 H), 0.95-0.93 (m, 6 H).

Example 134

Synthesis of Compound 297

(4-(((3R,5S)-3,5-dimethyl-4-(3-methylbutanoyl) piperazin-1-yl)methyl)-N-hydroxybenzamide (Trifluoroacetic acid salt))

Step 1: Synthesis of Methyl 4-(((3R,5S)-3,5-dimethyl-4-(3-methylbutanoyl)piperazin-1-yl)methyl) benzoate Methyl 4-(((3R,5S)-3,5-dimethylpiperazin-1-yl)methyl)benzoate (formula 1-2, 0.100 g, 0.381 mmol), 3-methylbutanoyl chloride (55 mg, 0.457 mmol) and TEA (0.077 g, 0.762 mmol) were dissolved in methylene chloride (1 ml) at 25° C., and the reaction solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure to yield the desired compound (0.078 g, 59.1%) as a yellow oil.

Step 2: Synthesis of Compound 297

Methyl 4-(((3R,5S)-3,5-dimethyl-4-(3-methylbutanoyl) piperazin-1-yl)methyl)benzoate (formula 1-3, 0.050 g, 0.144 mmol), hydroxylamine (0.177 mL, 2.886 mmol, 50.00% aqueous solution) and potassium hydroxide (0.081 g, 1.443 mmol) were dissolved in methanol (0.5 ml) at 25° C., and the reaction solution was stirred at the same temperature for 1 hour. Then, a saturated solution of sodium hydrogen carbonate was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (Waters, $C_{18}$, acetonitrile/0.1% trifluoroacetic acid aqueous solution=from 5% to 70%) and concentrated to afford the desired compound 297 (0.021 g, 41.9%) as a white solid.

$^1$H NMR (400 MHz, $D_2O$) δ 7.66 (d, 2 H, J=8.3 Hz), 7.52 (d, 2 H, J=8.3 Hz), 4.78-4.75 (m, 1 H), 4.44-4.43 (m, 1 H), 4.37 (s, 2 H), 3.40-3.38 (m, 2 H), 3.10-3.09 (m, 2 H), 2.32-2.08 (m, 2 H), 1.91-1.84 (m, 1 H), 1.32 (brs, 3 H), 1.25 (brs, 1 H), 0.82-0.72 (m, 6 H).

Example 135

Synthesis of Compound 298

(4-(((2S,6R)-2,6-dimethyl-4-(3-(trifluoromethyl) benzyl)piperazin-1-yl)methyl)-N-hydroxybenzamide)

Step 1: Synthesis of Methyl 4-(((2S,6R)-2,6-dimethyl-4-(3-(trifluoromethyl)benzyl)piperazin-1-yl) methyl)benzoate Methyl 4-(((2S,6R)-2,6-dimethylpiperazin-1-yl)methyl) benzoate (formula 13-2, 0.200 g, 0.762 mmol), 3-(trifluoromethyl)benzaldehyde (0.133 g, 0.762 mmol) and acetic acid (0.022 mL, 0.762 mmol) were dissolved in 1,2-ethylene chloride (4 mL), and stirred at room temperature for 2 hours, and then $Na(CN)BH_3$ (0.048 g, 0.762 mmol) was added thereto, followed by stirring at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 0% to 20%) and concentrated to afford the desired compound (0.246 g, 76.7%) as a colorless oil.

Step 2: Synthesis of Compound 298

Methyl 4-(((2S,6R)-2,6-dimethyl-4-(3-(trifluoromethyl) benzyl)piperazin-1-yl)methyl)benzoate (formula 13-3, 0.100 g, 0.238 mmol), hydroxylamine (0.291 mL, 4.757 mmol, 50.00% aqueous solution) and potassium hydroxide (0.133 g, 2.378 mmol) were dissolved in methanol (3 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was passed through a plastic filter to remove solid residue and an aqueous layer, and the organic layer was concentrated under reduced pressure to yield compound 298 (0.061 g, 60.9%) as a white solid.

$^1$H NMR (400 MHz, DMSO-$d_6$) δ 7.67-7.56 (m, 6 H), 7.28 (d, 2 H, J=8.2 Hz), 3.73 (s, 2 H), 3.50 (s, 2 H), 2.65-2.26 (m, 4 H), 1.85 (t, 2 H, J=10.4 Hz), 0.91 (d, 6 H, J=6.1 Hz); LRMS (ES) m/z 422.1 ($M^+$+1)

Example 136

Synthesis of Compound 299

(4-(((2S,6R)-4-(4-(dimethylamino)benzyl)-2,6-dimethylpiperazin-1-yl)methyl)-N-hydroxybenzamide)

Step 1: Synthesis of Methyl 4-(((2S,6R)-4-(4-(dimethylamino)benzyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol), 4-(dimethylamino)benzaldehyde (0.057 g, 0.381 mmol) and acetic acid (0.011 mL, 0.381 mmol) were dissolved in 1,2-ethylene chloride (4 mL), and stirred at room temperature for 2 hours, and then Na(CN)BH$_3$ (0.024 g, 0.381 mmol) was added thereto, followed by stirring at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 0% to 20%) and concentrated to afford the desired compound (0.062 g, 41.1%) as a colorless oil.

Step 2: Synthesis of Compound 299

Methyl 4-(((2S,6R)-4-(4-(dimethylamino)benzyl)-2,6-dimethylpiperazin-1-yl)methyl)benzoate (formula 13-3, 0.062 g, 0.157 mmol), hydroxylamine (0.192 mL, 3.135 mmol, 50.00% aqueous solution) and potassium hydroxide (0.088 g, 1.567 mmol) were dissolved in methanol (3 mL) at room temperature, and the reaction solution was stirred at the same temperature for 30 minutes. Then, the reaction mixture was concentrated under reduced pressure. A saturated aqueous solution of sodium hydrogen carbonate (5 mL) was added to the concentrate, followed by stirring. The precipitated solid was filtered and dried to yield compound 299 (0.041 g, 66.0%) as a white solid.

$^1$H NMR (400 MHz, DMSO-d$_6$) δ 7.65 (d, 2 H, J=8.2 Hz), 7.36 (d, 2 H, J=8.1 Hz), 7.07 (d, 2 H, J=8.6 Hz), 6.67 (d, 2 H, J=8.6 Hz), 3.72 (s, 2 H), 3.27 (s, 2 H), 2.63 (d, 2 H, J=10.5 Hz), 2.55-2.51 (m, 2 H), 1.73 (t, 2 H, J=10.6 Hz), 0.87 (d, 6 H, J=6.1 Hz); LRMS (ES) m/z 397.2 (M$^+$+1).

Example 137

Synthesis of Compound 300

(4-(((2S,6R)-2,6-dimethyl-4-(4-(methylsulfonyl)benzyl)piperazin-1-yl)methyl)-N-hydroxybenzamide)

Step 1: Synthesis of Methyl 4-(((2S,6R)-2,6-dimethyl-4-(4-(methylsulfonyl)benzyl)piperazin-1-yl)methyl)benzoate Methyl 4-(((2S,6R)-2,6-dimethylpiperazin-1-yl)methyl)benzoate (formula 13-2, 0.100 g, 0.381 mmol), 4-(methylsulfonyl)benzaldehyde (0.070 g, 0.381 mmol) and acetic acid (0.011 mL, 0.381 mmol) were dissolved in 1,2-ethylene chloride (4 mL), and stirred at room temperature for 2 hours, and then Na(CN)BH$_3$ (0.024 g, 0.381 mmol) was added thereto, followed by stirring at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 10% to 70%) and concentrated to afford the desired compound (0.058 g, 35.3%) as a yellow oil.

Step 2: Synthesis of Compound 300

Methyl 4-(((2S,6R)-2,6-dimethyl-4-(4-(methylsulfonyl)benzyl)piperazin-1-yl)methyl)benzoate (formula 13-3, 0.058 g, 0.135 mmol), hydroxylamine (0.165 mL, 2.694 mmol, 50.00% aqueous solution) and potassium hydroxide (0.076 g, 1.347 mmol) were dissolved in methanol (3 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure to yield compound 300 (0.015 g, 25.8%) as a white solid.

$^1$H NMR (400 MHz, DMSO-d$_6$) δ 7.87 (d, 2 H, J=8.2 Hz), 7.65 (d, 2 H, J=8.1 Hz), 7.57 (d, 2 H, J=8.1 Hz), 7.30 (d, 2 H, J=8.0 Hz), 3.74 (s, 2 H), 3.52 (s, 2 H), 3.21 (s, 3 H), 2.65 (d, 2 H, J=11.8 Hz), 2.60-2.56 (m, 2 H), 1.85 (t, 2 H, J=10.4 Hz), 0.93 (d, 6 H, J=6.8 Hz); LRMS (ES) m/z 432.2 (M$^+$+1).

Example 138

Synthesis of Compound 301

(4-(((2S,6R)-4-(4-(1H-imidazol-1-yl)benzyl)-2,6-dimethylpiperazin-1-yl)methyl)-N-hydroxybenzamide)

Step 1: Synthesis of Methyl 4-(((2S,6R)-4-(4-(1H-imidazol-1-yl)benzyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol), 4-(1H-imidazol-1-yl)benzaldehyde (0.066 g, 0.381 mmol) and acetic acid (0.011 mL, 0.381 mmol) were dissolved in 1,2-ethylene chloride (4 mL), and stirred at room temperature for 2 hours, and then Na(CN)BH$_3$ (0.024 g, 0.381 mmol) was added thereto, followed by stirring at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; methanol/methylene chloride=from 0% to 10%) and concentrated to afford the desired compound (0.065 g, 40.7%) as a pale yellow oil.

Step 2: Synthesis of Compound 301

Methyl 4-(((2S,6R)-4-(4-(1H-imidazol-1-yl)benzyl)-2,6-dimethylpiperazin-1-yl)methyl)benzoate (formula 13-3, 0.065 g, 0.155 mmol), hydroxylamine (0.190 mL, 3.106 mmol, 50.00% aqueous solution) and potassium hydroxide (0.087 g, 1.553 mmol) were dissolved in methanol (3 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure to yield compound 301 (0.037 g, 56.8%) as a white solid.

$^1$H NMR (400 MHz, DMSO-$d_6$) δ 11.18 (brs, 1 H), 9.00 (brs, 1 H), 8.24 (s, 1 H), 7.74 (s, 1 H), 7.67 (d, 2 H, J=8.0 Hz), 7.60 (d, 2 H, J=8.3 Hz), 7.42 (d, 4 H, J=8.0 Hz), 7.10 (s, 1 H), 3.86 (s, 2 H), 3.46 (s, 2 H), 2.68 (d, 2 H, J=10.6 Hz), 2.60-2.58 (m, 2 H), 1.83 (t, 2 H, J=10.6 Hz), 0.89 (d, 6 H, J=6.0 Hz); LRMS (ES) m/z 420.2 (M$^+$+1).

Example 139

Synthesis of Compound 302

(4-(((2S,6R)-2,6-dimethyl-4-(4-(thiophen-2-yl)benzyl)piperazin-1-yl)methyl)-N-hydroxybenzamide)

Step 1: Synthesis of Methyl 4-(((2S,6R)-2,6-dimethyl-4-(4-(thiophen-2-yl)benzyl)piperazin-1-yl)methyl)benzoate Methyl 4-(((2S,6R)-2,6-dimethylpiperazin-1-yl)methyl)benzoate (formula 13-2, 0.100 g, 0.381 mmol), 4-(thiophen-2-yl)benzaldehyde (0.072 g, 0.381 mmol) and acetic acid (0.011 mL, 0.381 mmol) were dissolved in 1,2-ethylene chloride (4 mL), and stirred at room temperature for 2 hours, and then Na(CN)BH$_3$ (0.024 g, 0.381 mmol) was added thereto, followed by stirring at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 0% to 20%) and concentrated to afford the desired compound (0.022 g, 13.3%) as a pale yellow oil.

Step 2: Synthesis of Compound 302

Methyl 4-(((2S,6R)-2,6-dimethyl-4-(4-(thiophen-2-yl)benzyl)piperazin-1-yl)methyl)benzoate (formula 13-3, 0.022 g, 0.051 mmol), hydroxylamine (0.062 mL, 1.012 mmol, 50.00% aqueous solution) and potassium hydroxide (0.028 g, 0.506 mmol) were dissolved in methanol (3 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure to yield compound 302 (0.019 g, 86.2%) as a white solid.

$^1$H NMR (400 MHz, DMSO-$d_6$) δ 7.65 (d, 2 H, J=8.1 Hz), 7.61 (d, 2 H, J=8.0 Hz), 7.53 (d, 1 H, J=5.0 Hz), 7.49 (d, 1 H, J=3.2 Hz), 7.33-7.31 (m, 4 H), 7.13 (dd, 1 H, J=4.4, 4.4 Hz), 3.74 (s, 2 H), 3.41 (s, 2 H), 2.67 (d, 2 H, J=9.5 Hz), 2.56-2.51 (m, 2 H), 1.82 (t, 2 H, J=10.6 Hz), 0.90 (d, 6 H, J=6.1 Hz); LRMS (ES) m/z 436.2 (M$^+$+1).

Example 140

Synthesis of Compound 303

(4-(((2S,6R)-4-(4-(furan-2-yl)benzyl)-2,6-dimethylpiperazin-1-yl)methyl)-N-hydroxybenzamide)

Step 1: Synthesis of Methyl 4-(((2S,6R)-4-(4-(furan-2-yl)benzyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol), 4-(furan-2-yl)benzaldehyde (0.066 g, 0.381 mmol) and acetic acid (0.011 mL, 0.381 mmol) were dissolved in 1,2-ethylene chloride (4 mL), and stirred at room temperature for 2 hours, and then Na(CN)BH$_3$ (0.024 g, 0.381 mmol) was added thereto, followed by stirring at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 0% to 20%) and concentrated to afford the desired compound (0.053 g, 33.2%) as a pale yellow oil.

Step 2: Synthesis of Compound 303

Methyl 4-(((2S,6R)-4-(4-(furan-2-yl)benzyl)-2,6-dimethylpiperazin-1-yl)methyl)benzoate (formula 13-3, 0.053 g, 0.127 mmol), hydroxylamine (0.155 mL, 2.533 mmol, 50.00% aqueous solution) and potassium hydroxide (0.071 g, 1.266 mmol) were dissolved in methanol (3 mL) at room temperature, and the reaction solution was stirred at the same temperature for 30 minutes. Then, the reaction mixture was concentrated under reduced pressure. A saturated aqueous solution of sodium hydrogen carbonate (5 mL) was added to the concentrate, followed by stirring. The precipitated solid was filtered and dried to yield compound 303 (0.045 g, 84.7%) as a white solid.

$^1$H NMR (400 MHz, DMSO-$d_6$) δ 7.74 (s, 1 H), 7.73-7.63 (m, 4 H), 7.33 (d, 2 H, J=8.2 Hz), 7.26 (d, 2 H, J=8.1 Hz), 6.91 (d, 1 H, J=3.1 Hz), 6.59 (dd, 1 H, J=3.4, 1.8 Hz), 3.72 (s, 2 H), 3.41 (s, 2 H), 2.65 (d, 2 H, J=10.8 Hz), 2.56-2.55 (m, 2 H), 1.81-1.79 (m, 2 H), 0.91 (d, 6 H, J=6.1 Hz); LRMS (ES) m/z 420.2 (M$^+$+1).

Example 141

Synthesis of Compound 304

(4-(((2S,6R)-4-(4-(4H-1,2,4-triazol-4-yl)benzyl)-2,6-dimethylpiperazin-1-yl)methyl)-N-hydroxybenzamide)

Step 1: Synthesis of Methyl 4-(((2S,6R)-4-(4-(4H-1,2,4-triazol-4-yl)benzyl)-2,6-dimethylpiperazin-1-yl)methyl)benzoate Methyl 4-(((2S,6R)-2,6-dimethylpiperazin-1-yl)methyl)benzoate (formula 13-2, 0.100 g, 0.381 mmol), 4-(4H-1,2, 4-triazol-4-yl)benzaldehyde (0.066 g, 0.381 mmol) and acetic acid (0.011 mL, 0.381 mmol) were dissolved in 1,2-ethylene chloride (4 mL), and stirred at room temperature for 2 hours, and then Na(CN)BH$_3$ (0.024 g, 0.381 mmol) was added thereto, followed by stirring at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; methanol/methylene chloride=from 0% to 10%) and concentrated to afford the desired compound (0.064 g, 40.0%) as a pale yellow oil.

Step 2: Synthesis of Compound 304

Methyl 4-(((2S,6R)-4-(4-(4H-1,2,4-triazol-4-yl)benzyl)-2,6-dimethylpiperazin-1-yl)methyl)benzoate (formula 13-3, 0.064 g, 0.153 mmol), hydroxylamine (0.187 mL, 3.051 mmol, 50.00% aqueous solution) and potassium hydroxide (0.086 g, 1.526 mmol) were dissolved in methanol (3 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure to yield compound 304 (0.016 g, 24.9%) as a white solid.

$^1$H NMR (400 MHz, DMSO-d$_6$) δ 11.18 (brs, 1 H), 9.28 (s, 1 H), 9.00 (brs, 1 H), 8.23 (s, 1 H), 7.81 (d, 2 H, J=8.5 Hz), 7.67 (d, 2 H, J=8.2 Hz), 7.47 (d, 2 H, J=8.5 Hz), 7.41 (d, 2 H, J=8.4 Hz), 3.75 (s, 2 H), 3.47 (s, 2 H), 2.68 (d, 2 H, J=10.2 Hz), 2.61-2.26 (m, 2 H), 1.84 (t, 2 H, J=10.6 Hz), 0.89 (d, 6 H, J=6.1 Hz); LRMS (ES) m/z 421.2 (M$^+$+1).

Example 142

Synthesis of Compound 305

(4-(((2S,6R)-2,6-dimethyl-4-(2-(2-methyl-1H-imidazol-1-yl)benzyl)piperazin-1-yl)methyl)-N-hydroxybenzamide)

Step 1: Synthesis of Methyl 4-(((2S,6R)-2,6-dimethyl-4-(2-(2-methyl-1H-imidazol-1-yl)benzyl)piperazin-1-yl)methyl)benzoate Methyl 4-(((2S,6R)-2,6-dimethylpiperazin-1-yl)methyl)benzoate (formula 13-2, 0.100 g, 0.381 mmol), 2-(2-methyl-1H-imidazol-1-yl)benzaldehyde (0.071 g, 0.381 mmol) and acetic acid (0.011 mL, 0.381 mmol) were dissolved in 1,2-ethylene chloride (4 mL), and stirred at room temperature for 2 hours, and then Na(CN)BH$_3$ (0.024 g, 0.381 mmol) was added thereto, followed by stirring at the same temperature for 17 hours. Then, water was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; methanol/methylene chloride=from 0% to 10%) and concentrated to afford the desired compound (0.066 g, 40.0%) as a pale yellow oil.

Step 2: Synthesis of Compound 305

Methyl 4-(((2S,6R)-2,6-dimethyl-4-(2-(2-methyl-1H-imidazol-1-yl)benzyl)piperazin-1-yl)methyl)benzoate (formula 13-3, 0.066 g, 0.153 mmol), hydroxylamine (0.187 mL, 3.052 mmol, 50.00% aqueous solution) and potassium hydroxide (0.086 g, 1.526 mmol) were dissolved in methanol (3 mL) at room temperature, and the reaction solution was stirred at the same temperature for 30 minutes. Then, the reaction mixture was concentrated under reduced pressure. A saturated aqueous solution of sodium hydrogen carbonate (5 mL) was added to the concentrate, followed by stirring. The precipitated solid was filtered and dried to yield compound 305 (0.036 g, 54.4%) as a white solid.

$^1$H NMR (400 MHz, DMSO-d$_6$) δ 7.66 (d, 2 H, J=8.2 Hz), 7.56 (dd, 1 H, J=7.6, 1.5 Hz), 7.49 (ddd, 1 H, J=7.5, 7.5, 1.4 Hz), 7.43 (dt, 1 H, J=7.5, 7.5, 1.7 Hz), 7.37 (d, 2 H, J=8.2 Hz), 7.31 (dd, 1 H, J=7.7, 1.2 Hz), 7.15 (d, 1 H, J=1.3 Hz), 6.91 (d, 1 H, J=1.2 Hz), 3.75 (s, 2 H), 3.12-3.04 (m, 2 H), 2.48-2.46 (m, 4 H), 2.05 (s, 3 H), 1.68 (t, 2 H, J=10.7 Hz), 0.85 (d, 6 H, J=7.0 Hz); LRMS (ES) m/z 434.2 (M$^+$+1).

Example 143

Synthesis of Compound 309

(4-(((3R,5S)-4-(4-(furan-3-yl)benzyl)-3,5-dimethylpiperazin-1-yl)methyl)-N-hydroxybenzamide)

Step 1: Synthesis of Methyl 4-(((3R,5S)-4-(4-(furan-3-yl)benzyl)-3,5-dimethylpiperazin-1-yl)methyl)benzoate 1,2-Dimethoxyethane (1 ml)/water (0.5 ml) were added to a mixture of methyl 4-(((3R,5S)-4-(4-iodobenzyl)-3,5-dimethylpiperazin-1-yl)methyl)benzoate (formula 2-1, 0.100 g, 0.209 mmol), furan-3-ylboronic acid (0.028 g, 0.251 mmol), Pd(dbpf)Cl$_2$ (0.007 g, 0.010 mmol) and Na$_2$CO$_3$ (0.066 g, 0.627 mmol) at room temperature, and heated by microwaves at 120° C. for 20 minutes. The reaction mixture was filtered through celite, and the filtrate was concentrated under reduced pressure. The concentrate was purified by column chromatography (silicon dioxide, 12 g cartridge; methanol/methylene chloride=from 0% to 5%) and concentrated to afford the desired compound (0.052 g, 59.4%) as a pale brown solid.

Step 2: Synthesis of Compound 309

Methyl 4-(((3R,5S)-4-(4-(furan-3-yl)benzyl)-3,5-dimethylpiperazin-1-yl)methyl)benzoate (formula 2-2, 0.030 g, 0.072 mmol), hydroxylamine (0.088 mL, 1.434 mmol, 50.00% aqueous solution) and potassium hydroxide (0.040 g, 0.717 mmol) were dissolved in methanol (0.5 mL) at room temperature, and the mixture was stirred at the same temperature for 1 hour. Then, water was added to the reaction mixture, followed by extraction with methylene chloride. The organic layer was washed with a saturated aqueous solution of sodium hydrogen carbonate, dried with anhydrous magnesium sulfate, and then concentrated under reduced pressure to yield compound 309 (0.021 g, 69.8%) as a pale orange solid.

$^1$H NMR (400 MHz, DMSO-d$_6$) δ 8.15 (s, 1 H), 7.73 (s, 1 H), 7.65 (d, 2 H, J=8.1 Hz), 7.55 (d, 2 H, J=8.1 Hz), 7.31-7.27 (m, 4 H), 3.72 (s, 1 H), 3.39 (s, 2 H), 2.67-2.64 (m, 2 H), 2.58-2.56 (m, 2 H), 1.83-1.73 (m, 2 H), 0.90 (s, 3 H), 0.88 (s, 3 H).

Example 144

Synthesis of Compound 321

((2S,6R)-N-(3-(1H-pyrrol-1-yl)phenyl)-4-(4-((E)-3-(hydroxyamino)-3-oxoprop-1-en-1-yl)benzyl)-2,6-dimethylpiperazine-1-carboxamide)

Step 1: Synthesis of (E)-Methyl 3-(4-(((3R,5S)-3,5-dimethylpiperazin-1-yl)methyl)phenyl)acrylate (2S,6R)-2,6-dimethylpiperazine (0.500 g, 4.379 mmol), (E)-methyl 3-(4-(bromomethyl)phenyl)acrylate (formula 8-4, 1.173 g, 4.598 mmol) and $Cs_2CO_3$ (2.140 g, 6.568 mmol) were dissolved in acetonitrile (10 mL) at room temperature, and the reaction solution was stirred at the same temperature for 5 hours. Then, the reaction mixture was filtered through a glass filter to remove solids, and the filtrate was concentrated under reduced pressure. The concentrate was purified by column chromatography (silicon dioxide, 12 g cartridge; methanol/methylene chloride=from 0% to 15%) and concentrated to afford the desired compound (1.090 g, 86.3%) as an orange solid.

Step 2: Synthesis of (E)-Methyl 3-(4-(((3R,5S)-4-((3-(1H-pyrrol-1-yl)phenyl)carbamoyl)-3,5-dimethylpiperazin-1-yl)methyl)phenyl)acrylate (E)-methyl 3-(4-(((3R,5S)-3,5-dimethylpiperazin-1-yl)methyl)phenyl)acrylate (formula 9-1, 0.050 g, 0.173 mmol) and TEA (0.036 mL, 0.260 mmol) were dissolved in methylene chloride (2 mL), and 1-(3-isocyanatophenyl)-1H-pyrrole (0.034 g, 0.182 mmol) was added thereto at 0° C., followed by stirring at the same temperature for 1 hour and 40 minutes. Then, the reaction mixture was filtered through a celite pad to remove solids, and water was added to the filtrate, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 0% to 40%) and concentrated to afford the desired compound (0.050 g, 61.0%) as a white solid.

Step 3: Synthesis of Compound 321

(E)-Methyl 3-(4-(((3R,5S)-4-((3-(1H-pyrrol-1-yl)phenyl)carbamoyl)-3,5-dimethylpiperazin-1-yl)methyl)phenyl) acrylate (formula 9-2, 0.050 g, 0.106 mmol), hydroxylamine (0.129 mL, 2.116 mmol, 50.00% aqueous solution) and potassium hydroxide (0.059 g, 1.058 mmol) were dissolved in methanol (3 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure to yield compound 321 (0.048 g, 95.8%) as a white solid.

$^1$H NMR (400 MHz, DMSO-$d_6$) δ 9.90 (brs, 1 H), 8.41 (s, 1 H), 7.73-7.72 (m, 1 H), 7.52 (d, 1 H, J=7.7 Hz), 7.42-7.28 (m, 6 H), 7.24 (dd, 2 H, J=2.1, 2.1 Hz), 7.12 (dd, 1 H, J=7.9, 1.3 Hz), 6.45 (d, 1 H, J=15.9 Hz), 6.26 (dd, 1 H, J=2.1, 2.1 Hz), 4.24 (t, 2 H, J=5.0 Hz), 3.53 (s, 2 H), 2.69 (d, 2 H, J=11.1 Hz), 2.14 (d, 2 H, J=7.4 Hz), 1.31 (d, 6 H, J=6.6 Hz); LRMS (ES) m/z 474.2 (M$^+$+1)

Example 145

Synthesis of Compound 322

((E)-3-(4-(((3R,5S)-4-(furan-2-carbonyl)-3,5-dimethylpiperazin-1-yl)methyl)phenyl)-N-hydroxyacrylamide)

Step 1: Synthesis of (E)-Methyl 3-(4-(((3R,5S)-4-(furan-2-carbonyl)-3,5-dimethylpiperazin-1-yl)methyl)phenyl)acrylate (E)-methyl 3-(4-(((3R,5S)-3,5-dimethylpiperazin-1-yl)methyl)phenyl)acrylate (formula 9-1, 0.050 g, 0.173 mmol) and TEA (0.036 mL, 0.260 mmol) were dissolved in methylene chloride (2 mL), and furan-2-carbonyl chloride (0.018 mL, 0.182 mmol) was added thereto at 0° C., followed by stirring at the same temperature for 1 hour and 30 minutes. Then, water was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 0% to 20%) and concentrated to afford the desired compound (0.053 g, 79.9%) as a colorless oil.

Step 2: Synthesis of Compound 322

(E)-methyl 3-(4-(((3R,5S)-4-(furan-2-carbonyl)-3,5-dimethylpiperazin-1-yl)methyl)phenyl)acrylate (formula 9-2, 0.053 g, 0.139 mmol), hydroxylamine (0.170 mL, 2.772 mmol, 50.00% aqueous solution) and potassium hydroxide (0.078 g, 1.386 mmol) were dissolved in methanol (3 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure to yield compound 322 (0.027 g, 50.8%) as a pale yellow solid.

$^1$H NMR (400 MHz, DMSO-$d_6$) δ 9.50 (brs, 1 H), 7.82 (s, 1 H), 7.46 (d, 2 H, J=7.8 Hz), 7.34 (d, 2 H, J=7.8 Hz), 7.10 (d, 1 H, J=15.7 Hz), 6.95 (s, 1 H), 6.61 (d, 1 H, J=1.5 Hz), 6.39 (d, 1 H, J=15.8 Hz), 4.49-4.48 (m, 2 H), 3.50 (s, 2 H), 2.70 (d, 2 H, J=11.0 Hz), 2.12 (d, 2 H, J=7.2 Hz), 1.37 (d, 6 H, J=6.2 Hz); LRMS (ES) m/z 384.1 (M$^+$+1).

Example 146

Synthesis of Compound 323

((E)-3-(4-(((3R,5S)-3,5-dimethyl-4-(2-phenylacetyl) piperazin-1-yl)methyl)phenyl)-N-hydroxyacrylamide)

Step 1: Synthesis of ((E)-Methyl 3-(4-(((3R,5S)-3, 5-dimethyl-4-(2-phenylacetyl)piperazin-1-yl)methyl) phenyl)acrylate (E)-methyl 3-(4-(((3R,5S)-3,5-dimethylpiperazin-1-yl) methyl)phenyl)acrylate (formula 9-1, 0.050 g, 0.173 mmol) and TEA (0.036 mL, 0.260 mmol) were dissolved in methylene chloride (2 mL), and 2-phenylacetyl chloride (0.024 mL, 0.182 mmol) was added thereto at 0° C., followed by stirring at the same temperature for 2 hours. Then, water was added to the reaction mixture, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; ethyl acetate/hexane=from 0% to 30%) and concentrated to afford the desired compound (0.037 g, 52.5%) as a colorless oil.

Step 2: Synthesis of Compound 323

(E)-methyl 3-(4-(((3R,5S)-3,5-dimethyl-4-(2-phenylacetyl)piperazin-1-yl)methyl)phenyl)acrylate (formula 9-2, 0.037 g, 0.091 mmol), hydroxylamine (0.111 mL, 1.820 mmol, 50.00% aqueous solution) and potassium hydroxide (0.051 g, 0.910 mmol) were dissolved in methanol (3 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure to yield compound 323 (0.021 g, 56.6%) as a pale yellow solid.

$^1$H NMR (400 MHz, D$_2$O) δ 9.90 (brs, 1 H), 7.48 (d, 2 H, J=8.0 Hz), 7.35 (d, 2 H, J=8.1 Hz), 7.32-7.28 (m, 2 H), 7.23-7.17 (m, 4 H), 6.41 (d, 1 H, J=15.8 Hz), 4.42 (s, 1 H), 4.11 (s, 1 H), 3.77 (d, 1 H, J=13.8 Hz), 3.62 (d, 1 H, J=15.9 Hz), 3.48 (s, 2 H), 2.68-2.62 (m, 2 H), 2.01 (d, 2 H, J=8.0 Hz), 0.88-0.85 (m, 6 H); LRMS (ES) m/z 408.2 (M$^+$+1).

Example 147

Synthesis of Compound 326

(4-(((3R,5S)-4-(2-(3,6-dihydro-2H-pyran-4-yl)benzoyl)-3,5-dimethylpiperazin-1-yl)methyl)-N-hydroxybenzamide)

Step 1: Synthesis of Methyl 4-(((3R,5S)-4-(2-(3,6-dihydro-2H-pyran-4-yl)benzoyl)-3,5-dimethylpiperazin-1-yl)methyl)benzoate 1,2-Dimethoxyethane/water (v/v=3/1) (3 mL) were added to a mixture of methyl 4-(((3R,5S)-4-(2-iodobenzoyl)-3,5-dimethylpiperazin-1-yl)methyl)benzoate (formula 4-1, 0.400 g, 0.812 mmol), 2-(3,6-dihydro-2H-pyran-4-yl)-4,4, 5,5-tetramethyl-1,3,2-dioxaborolane (0.256 g, 1.219 mmol), Pd(dbpf)Cl$_2$ (0.026 g, 0.041 mmol) and Na$_2$CO$_3$ (0.258 g, 2.437 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 0% to 20%) and concentrated to afford the desired compound (0.098 g, 26.8%) as a brown oil.

Step 2: Synthesis of Compound 326

Methyl 4-(((3R,5S)-4-(2-(3,6-dihydro-2H-pyran-4-yl) benzoyl)-3,5-dimethylpiperazin-1-yl)methyl)benzoate (formula 4-2, 0.098 g, 0.218 mmol), hydroxylamine (0.267 mL, 4.370 mmol, 50.00% aqueous solution) and potassium hydroxide (0.123 g, 2.185 mmol) were dissolved in methanol (3 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 326 (0.010 g, 9.7%) as a white solid.

$^1$H NMR (400 MHz, DMSO-d$_6$) δ 7.69 (d, 2 H, J=8.1 Hz), 7.41-7.23 (m, 6 H), 5.81 (s, 1 H), 4.49 (br, 1 H), 4.15-4.14 (m, 2 H), 3.78 (t, 2 H, J=5.4 Hz), 3.49 (s, 2 H), 2.71-2.68 (m, 2 H), 2.15-2.02 (m, 3 H), 1.34 (d, 3 H, J=6.7 Hz), 1.13 (d, 3 H, J=6.7 Hz).

Example 148

Synthesis of Compound 327

(4-(((3R,5S)-4-(2-(furan-2-yl)benzyl)-3,5-dimethylpiperazin-1-yl)methyl)-N-hydroxybenzamide)

Step 1: Synthesis of Methyl 4-(((3R,5S)-4-(2-(furan-2-yl)benzyl)-3,5-dimethylpiperazin-1-yl) methyl)benzoate 1,2-Dimethoxyethane/water (v/v=3/1) (2 mL) were added to a mixture of methyl 4-(((3R,5S)-4-(2-iodobenzyl)-3,5-dimethylpiperazin-1-yl)methyl)benzoate (formula 2-1, 0.250 g, 0.523 mmol), furan-2-ylboronic acid (0.088 g, 0.784 mmol), Pd(dbpf)Cl$_2$ (0.017 g, 0.026 mmol) and Na$_2$CO$_3$ (0.166 g, 1.568 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 0% to 10%) and concentrated to afford the desired compound (0.066 g, 30.0%) as a brown oil.

Step 2: Synthesis of Compound 327

Methyl 4-(((3R,5S)-4-(2-(furan-2-yl)benzyl)-3,5-dimethylpiperazin-1-yl)methyl)benzoate (formula 2-2, 0.066 g, 0.157 mmol), hydroxylamine (0.192 mL, 3.140 mmol, 50.00% aqueous solution) and potassium hydroxide (0.088 g, 1.570 mmol) were dissolved in methanol (2 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 327 (0.044 g, 66.5%) as a white solid.

$^1$H NMR (400 MHz, DMSO-$d_6$) δ 7.95 (d, 1 H, J=7.7 Hz), 7.80 (s, 1 H), 7.70 (d, 2 H, J=8.1 Hz), 7.56-7.54 (m, 1 H), 7.33-7.23 (m, 4 H), 6.71 (d, 1 H, J=3.3 Hz), 6.64-6.62 (m, 1 H), 3.79 (s, 2 H), 2.69-2.60 (m, 4 H), 1.85 (t, 2 H, J=10.4 Hz), 0.76 (d, 6 H, J=6.0 Hz).

Example 149

Synthesis of Compound 328

(4-(((3R,5S)-4-(2-(furan-3-yl)benzyl)-3,5-dimethylpiperazin-1-yl)methyl)-N-hydroxybenzamide)

Step 1: Synthesis of Methyl 4-(((3R,5S)-4-(2-(furan-3-yl)benzyl)-3,5-dimethylpiperazin-1-yl)methyl)benzoate 1,2-Dimethoxyethane/water (v/v=3/1) (2 mL) were added to a mixture of methyl 4-(((3R,5S)-4-(2-iodobenzyl)-3,5-dimethylpiperazin-1-yl)methyl)benzoate (formula 2-1, 0.250 g, 0.523 mmol), furan-3-ylboronic acid (0.088 g, 0.784 mmol), Pd(dbpf)Cl$_2$ (0.017 g, 0.026 mmol) and Na$_2$CO$_3$ (0.166 g, 1.568 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 0% to 5%) and concentrated to afford the desired compound (0.020 g, 9.3%) as a brown oil.

Step 2: Synthesis of Compound 328

Methyl 4-(((3R,5S)-4-(2-(furan-3-yl)benzyl)-3,5-dimethylpiperazin-1-yl)methyl)benzoate (formula 2-2, 0.020 g, 0.049 mmol), hydroxylamine (0.060 mL, 0.975 mmol, 50.00% aqueous solution) and potassium hydroxide (0.027 g, 0.487 mmol) were dissolved in methanol (1 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 328 (0.010 g, 50.9%) as a white solid.

$^1$H NMR (400 MHz, DMSO-$d_6$) δ 7.85-7.84 (m, 2 H), 7.76-7.76 (m, 1 H), 7.69 (d, 2 H, J=8.1 Hz), 7.28 (t, 4 H, J=8.0 Hz), 7.19 (t, 1 H, J=7.5 Hz), 6.76-6.75 (m, 1 H), 3.69 (s, 2 H), 2.65 (d, 2 H, J=10.3 Hz), 2.58-2.55 (m, 2 H), 1.84 (t, 2 H, J=10.5 Hz), 0.76 (d, 1 H, J=6.1 Hz).

Example 150

Synthesis of Compound 329

(4-(((3R,5S)-3,5-dimethyl-4-(2-(pyridin-4-yl)benzyl)piperazin-1-yl)methyl)-N-hydroxybenzamide)

Step 1: Synthesis of Methyl 4-(((3R,5S)-3,5-dimethyl-4-(2-(pyridin-4-yl)benzyl)piperazin-1-yl)methyl)benzoate 1,2-Dimethoxyethane/water (v/v=3/1) (2 mL) were added to a mixture of methyl 4-(((3R,5S)-4-(2-iodobenzyl)-3,5-dimethylpiperazin-1-yl)methyl)benzoate (formula 2-1, 0.250 g, 0.523 mmol), pyridine-4-boronic acid hydrate (0.110 g, 0.784 mmol), Pd(dbpf)Cl$_2$ (0.017 g, 0.026 mmol) and Na$_2$CO$_3$ (0.166 g, 1.568 mmol) at room temperature, and the reaction solution was stirred overnight at 100° C. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 20% to 60%) and concentrated to afford the desired compound (0.139 g, 62.1%) as a white solid.

Step 2: Synthesis of Compound 329

Methyl 4-(((3R,5S)-3,5-dimethyl-4-(2-(pyridin-4-yl)benzyl)piperazin-1-yl)methyl)benzoate (formula 2-2, 0.088 g, 0.204 mmol), hydroxylamine (0.250 mL, 4.083 mmol, 50.00% aqueous solution) and potassium hydroxide (0.115 g, 2.042 mmol) were dissolved in methanol (3 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 329 (0.076 g, 86.1%) as a white solid.

$^1$H NMR (400 MHz, DMSO-$d_6$) δ 8.65-8.63 (m, 2 H), 7.85 (d, 1 H, J=7.7 Hz), 7.69 (d, 2 H, J=8.2 Hz), 7.43-7.38 (m, 3 H), 7.32-7.27 (m, 3 H), 7.18-7.16 (m, 1 H), 3.58 (s, 2 H), 2.58 (d, 2 H, J=10.2 Hz), 2.44-2.43 (m, 2 H), 1.82 (t, 2 H, J=10.4 Hz), 0.75 (d, 6 H, J=6.2 Hz).

Example 151

Synthesis of Compound 330

(4-(((3R,5S)-3,5-dimethyl-4-(2-(pyridin-3-yl)benzyl)piperazin-1-yl)methyl)-N-hydroxybenzamide)

Step 1: Synthesis of Methyl 4-(((3R,5S)-3,5-dimethyl-4-(2-(pyridin-3-yl)benzyl)piperazin-1-yl)methyl)benzoate 1,2-Dimethoxyethane/water (v/v=3/1) (2 mL) were added to a mixture of methyl 4-(((3R,5S)-4-(2-iodobenzyl)-3,5-dimethylpiperazin-1-yl)methyl)benzoate (formula 2-1, 0.250 g, 0.523 mmol), pyridin-3-ylboronic acid (0.096 g, 0.784 mmol), Pd(dbpf)Cl$_2$ (0.017 g, 0.026 mmol) and Na$_2$CO$_3$ (0.166 g, 1.568 mmol) at room temperature, and the reaction solution was stirred overnight at 100° C. Then, a saturated aqueous solution of sodium hydrogen carbonate was added to the reaction solution, followed by extraction with methylene chloride. The organic layer was dried with anhydrous magnesium sulfate, and then concentrated under reduced pressure. The concentrate was purified by column chromatography (silicon dioxide; ethyl acetate/hexane=from 20% to 60%) and concentrated to afford the desired compound (0.083 g, 36.8%) as a yellow oil.

Step 2: Synthesis of Compound 330

Methyl 4-(((3R,5S)-3,5-dimethyl-4-(2-(pyridin-3-yl)benzyl)piperazin-1-yl)methyl)benzoate (formula 2-2, 0.083 g, 0.192 mmol), hydroxylamine (0.235 mL, 3.841 mmol, 50.00% aqueous solution) and potassium hydroxide (0.108 g, 1.921 mmol) were dissolved in methanol (3 mL) at room temperature, and the reaction solution was stirred at the same temperature for 1 hour. Then, the reaction solution was concentrated under reduced pressure. A saturated aqueous solution of sodium hydrogen carbonate was added to the concentrate, and the precipitated solid was filtered and dried. The resulting material was purified by column chromatography (Waters, $C_{18}$, C19*100 column, 0.1% trifluoroacetic acid aqueous solution/acetonitrile=from 5% to 80%), after which the compound was passed through a cartridge (PL-HCO$_3$ MP resin, methanol), and then concentrated to afford compound 330 (0.012 g, 14.5%) as a white solid.

$^1$H NMR (400 MHz, DMSO-d$_6$) δ 8.61-8.59 (m, 1 H), 8.55 (d, 1 H, J=2.1 Hz), 7.82 (dd, 2 H, J=13.4, 4.8 Hz), 7.68 (d, 2 H, J=8.1 Hz), 7.50-7.47 (m, 1 H), 7.40 (t, 1 H, J=7.0 Hz), 7.38-7.26 (m, 3 H), 7.18-7.16 (m, 1 H), 3.56 (s, 2 H), 2.58 (d, 2 H, J=10.0 Hz), 2.46-2.43 (m, 2 H), 1.82 (t, 2 H, J=10.4 Hz), 0.75 (d, 6 H, J=6.2 Hz).

Example 152

Synthesis of Compound 331

(4-(((3R,5S)-4-((4',4'-dimethyl-2',3',4',5'-tetrahydro-[1,1'-biphenyl]-2-yl)methyl)-3,5-dimethylpiperazin-1-yl)methyl)-N-hydroxybenzamide)

Step 1: Synthesis of Methyl 4-(((3R,5S)-4-((4',4'-dimethyl-2',3',4',5'-tetrahydro-[1,1'-biphenyl]-2-yl)methyl)-3,5-dimethylpiperazin-1-yl)methyl)benzoate 1,2-Dimethoxyethane/water (v/v=3/1) (2 mL) were added to a mixture of methyl 4-(((3R,5S)-4-(2-iodobenzyl)-3,5-dimethylpiperazin-1-yl)methyl)benzoate (formula 2-1, 0.250 g, 0.523 mmol), 2-(4,4-dimethylcyclohex-1-en-1-yl)-4,4,5,5-tetramethyl-1,3,2-dioxaborolane (0.185 g, 0.784 mmol), Pd(dbpf)Cl$_2$ (0.017 g, 0.026 mmol) and Na$_2$CO$_3$ (0.166 g, 1.568 mmol) at room temperature, and the reaction solution was heated by microwave irradiation at 120° C. for 30 minutes, followed by cooling to room temperature. Then, a saturated aqueous solution of sodium hydrogen carbonate was added to the reaction solution, followed by extraction with methylene chloride. The organic layer was dried with anhydrous magnesium sulfate, and then concentrated under reduced pressure. The concentrate was purified by column chromatography (silicon dioxide; ethyl acetate/hexane=from 0% to 5%) and concentrated to afford the desired compound (0.044 g, 18.4%) as a white solid.

Step 2: Synthesis of Compound 331

Methyl 4-(((3R,5S)-4-((4',4'-dimethyl-2',3',4',5'-tetrahydro-[1,1'-biphenyl]-2-yl)methyl)-3,5-dimethylpiperazin-1-yl)methyl)benzoate (formula 2-2, 0.044 g, 0.096 mmol), hydroxylamine (0.118 mL, 1.928 mmol, 50.00% aqueous solution) and potassium hydroxide (0.054 g, 0.964 mmol) were dissolved in methanol (2 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 331 (0.038 g, 85.9%) as a white solid.

$^1$H NMR (400 MHz, DMSO-d$_6$) δ 7.67 (d, 3 H, J=8.1 Hz), 7.22-7.20 (m, 3 H), 7.10 (t, 1 H, J=7.2 Hz), 5.40 (s, 1 H), 3.60 (s, 2 H), 2.64 (d, 2 H, J=10.4 Hz), 2.16 (s, 2 H), 1.94 (s, 2 H), 1.82 (t, 2 H, J=10.5 Hz), 1.47 (t, 2 H, J=6.2 Hz), 1.00 (s, 6 H), 0.78 (d, 6 H, J=6.1 Hz).

Example 153

Synthesis of Compound 332

(4-(((3R,5S)-4-(2-(3,6-dihydro-2H-pyran-4-yl)benzyl)-3,5-dimethylpiperazin-1-yl)methyl)-N-hydroxybenzamide)

Step 1: Synthesis of Methyl 4-(((3R,5S)-4-(2-(3,6-dihydro-2H-pyran-4-yl)benzyl)-3,5-dimethylpiperazin-1-yl)methyl)benzoate 1,2-Dimethoxyethane/water (v/v=3/1) (2 mL) were added to a mixture of methyl 4-(((3R,5S)-4-(2-iodobenzyl)-3,5-dimethylpiperazin-1-yl)methyl)benzoate (formula 2-1, 0.250 g, 0.523 mmol), 2-(3,6-dihydro-2H-pyran-4-yl)-4,4,5,5-tetramethyl-1,3,2-dioxaborolane (0.165 g, 0.784 mmol), Pd(dbpf)Cl$_2$ (0.017 g, 0.026 mmol) and Na$_2$CO$_3$ (0.166 g, 1.568 mmol) at room temperature, and the reaction solution was stirred overnight at 100° C. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 0% to 20%) and concentrated to afford the desired compound (0.108 g, 47.6%) as a pale brown solid.

Step 2: Synthesis of Compound 332

Methyl 4-(((3R,5S)-4-(2-(3,6-dihydro-2H-pyran-4-yl)benzyl)-3,5-dimethylpiperazin-1-yl)methyl)benzoate (formula 2-2, 0.108 g, 0.249 mmol), hydroxylamine (0.304 mL, 4.970 mmol, 50.00% aqueous solution) and potassium hydroxide (0.139 g, 2.485 mmol) were dissolved in methanol (2 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried. The resulting material was purified by column chromatography (Waters, $C_{18}$, C19*100 column, 0.1% trifluoroacetic acid aqueous solution/acetonitrile=from 5% to 80%), after which the compound was passed through a cartridge (PL-HCO$_3$ MP resin, methanol), and then concentrated to afford compound 332 (0.017 g, 15.3%) as a white solid.

$^1$H NMR (400 MHz, DMSO-d$_6$) δ 7.73-7.68 (m, 3 H), 7.29-7.20 (m, 3 H), 7.14 (t, 1 H, J=6.9 Hz), 7.04-7.02 (m, 1 H), 5.60 (s, 1 H), 4.19-4.19 (m, 2 H), 3.82 (t, 2 H, J=5.3 Hz), 3.64 (s, 2 H), 2.66-2.57 (m, 4 H), 2.26 (s, 2 H), 1.84 (t, 2 H, J=10.3 Hz), 0.79-0.78 (m, 6 H).

Example 154

Synthesis of Compound 340

(4-(((3R,5S)-4-(4-(furan-2-yl)benzoyl)-3,5-dimethyl-piperazin-1-yl)methyl)-N-hydroxybenzamide)

Step 1: Synthesis of Methyl 4-(((3R,5S)-4-(4-bromobenzoyl)-3,5-dimethylpiperazin-1-yl)methyl)benzoate 4-Bromobenzoyl chloride (1.000 g, 4.557 mmol), methyl 4-(((3R,5S)-3,5-dimethylpiperazin-1-yl)methyl)benzoate (formula 1-2, 1.315 g, 5.012 mmol) and TEA (1.263 mL, 9.113 mmol) were dissolved in methylene chloride (20 mL) at room temperature, and the reaction solution was stirred at the same temperature for 2 hours. Then, water was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 30% to 50%) and concentrated to afford the desired compound (2.007 g, 98.9%) as a white solid.

Step 2: Synthesis of Methyl 4-(((3R,5S)-4-(4-(furan-2-yl)benzoyl)-3,5-dimethylpiperazin-1-yl)methyl)benzoate 1,2-Dimethoxyethane/water (v/v=3/1) (4 mL) were added to a mixture of methyl 4-(((3R,5S)-4-(4-bromobenzoyl)-3,5-dimethylpiperazin-1-yl)methyl)benzoate (formula 4-1, 0.500 g, 1.123 mmol), furan-2-ylboronic acid (0.138 g, 1.235 mmol), Pd(dbpf)$_2$Cl$_2$ (0.037 g, 0.056 mmol) andNa$_2$CO$_3$ (0.262 g, 2.470 mmol), and heated by microwave irradiation at 120° C. for 30 minutes, followed by cooling to room temperature. Then, a saturated aqueous solution of sodium hydrogen carbonate was added to the reaction mixture, followed by extraction with methylene chloride. The organic layer was dried with anhydrous magnesium sulfate, and then concentrated under reduced pressure. The concentrate was purified by column chromatography (silicon dioxide; ethyl acetate/hexane=from 0% to 20%) and concentrated to afford the desired compound (0.163 g, 33.5%) as a white solid.

Step 3: Synthesis of Compound 340

Methyl 4-(((3R,5S)-4-(4-(furan-2-yl)benzoyl)-3,5-dimethylpiperazin-1-yl)methyl)benzoate (formula 4-2, 0.100 g, 0.231 mmol), hydroxylamine (0.283 mL, 4.624 mmol, 50.00% aqueous solution) and potassium hydroxide (0.130 g, 2.312 mmol) were dissolved in methanol (4 mL) at room temperature, and the reaction solution was stirred at the same temperature for 1 hour. Then, the reaction mixture was concentrated under reduced pressure. A saturated aqueous solution of sodium hydrogen carbonate was added to the concentrate, and the precipitated solid was filtered and dried to yield compound 340 (0.049 g, 48.7%) as a pale yellow solid.

$^1$H NMR (400 MHz, DMSO-d$_6$) δ 7.85 (d, 1 H, J=7.7 Hz), 7.76-7.71 (m, 4 H), 7.40-7.36 (m, 3 H), 7.24 (d, 1 H, J=7.9 Hz), 7.01 (d, 1 H, J=3.0 Hz), 6.60-6.59 (m, 1 H), 3.51-3.47 (m, 2 H), 2.62-2.60 (m, 2 H), 2.15-2.09 (m, 2 H), 1.27 (brs, 6 H).

Example 155

Synthesis of Compound 342

(4-(((3R,5S)-4-(3-(furan-2-yl)benzyl)-3,5-dimethyl-piperazin-1-yl)methyl)-N-hydroxybenzamide)

Step 1: Synthesis of Methyl 4-(((3R,5S)-4-(3-(furan-2-yl)benzyl)-3,5-dimethylpiperazin-1-yl)methyl)benzoate 1,2-Dimethoxyethane (4 mL)/water (1 mL) were added to a mixture of methyl 4-(((3R,5S)-4-(3-iodobenzyl)-3,5-dimethylpiperazin-1-yl)methyl)benzoate (formula 2-1, 0.100 g, 0.209 mmol), furan-2-ylboronic acid (0.047 g, 0.418 mmol), Pd(dbpf)$_2$Cl$_2$ (0.007 g, 0.010 mmol) and Na$_2$CO$_3$ (0.044 g, 0.418 mmol), and heated by microwave irradiation at 120° C. for 20 minutes, followed by cooling to room temperature. Then, a saturated aqueous solution of sodium hydrogen carbonate was added to the reaction mixture, followed by extraction with methylene chloride. The extract was passed through aplastic filter to remove solid residue and an aqueous layer, and the organic layer was concentrated under reduced pressure. The concentrate was purified by column chromatography (Waters, C$_{18}$, 19*100 mm column, 0.1% trifluoroacetic acid/acetonitrile=from 5% to 80%) and concentrated. The resulting material was dissolved in a solvent, and the compound was passed through a cartridge (PL-HCO$_3$ MP resin, methanol only), and then concentrated to afford the desired compound (0.064 g, 73.2%) as a brown oil.

Step 2: Synthesis of Compound 342

Methyl 4-(((3R,5S)-4-(3-(furan-2-yl)benzyl)-3,5-dimethylpiperazin-1-yl)methyl)benzoate (compound 2-2, 0.064 g, 0.153 mmol), hydroxylamine (0.094 mL, 1.529 mmol, 50.00% aqueous solution) and potassium hydroxide (0.172 g, 3.058 mmol) were dissolved in methanol (2 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure to yield compound 342 (0.031 g, 48.3%) as a white solid.

$^1$H NMR (400 MHz, DMSO-d$_6$) δ 11.10 (brs, 1 H), 9.00 (brs, 1 H), 7.75 (d, 1 H, J=1.3 Hz), 7.69 (d, 2 H, J=7.8 Hz), 7.66 (s, 1 H), 7.52 (d, 1 H, J=7.5 Hz), 7.35-7.31 (m, 3 H), 7.28 (d, 1 H, J=7.5 Hz), 6.90 (d, 1 H, J=3.0 Hz), 6.58 (dd, 1 H, J=3.4, 1.8 Hz), 3.75 (s, 2 H), 3.44 (s, 2 H), 2.66-2.57 (m, 4 H), 1.83 (t, 2 H, J=10.5 Hz), 0.91 (d, 6 H, J=6.1 Hz); LRMS (ES) m/z 420.2 (M$^+$+1).

Example 156

Synthesis of Compound 343

(4-(((3R,5S)-4-(3-(furan-3-yl)benzyl)-3,5-dimethyl-piperazin-1-yl)methyl)-N-hydroxybenzamide)

Step 1: Synthesis of Methyl 4-(((3R,5S)-4-(3-(furan-2-yl)benzyl)-3,5-dimethylpiperazin-1-yl)methyl)benzoate 1,2-Dimethoxyethane (4 mL)/water (1 mL) were added to a mixture of methyl 4-(((3R,5S)-4-(3-iodobenzyl)-3,5-dimethylpiperazin-1-yl)methyl)benzoate (formula 2-1, 0.100 g, 0.209 mmol), furan-3-ylboronic acid (0.047 g, 0.418 mmol), Pd(dbpf)$_2$Cl$_2$ (0.007 g, 0.010 mmol) and Na$_2$CO$_3$ (0.044 g, 0.418 mmol), and heated by microwave irradiation at 120° C. for 20 minutes, followed by cooling to room temperature. Then, a saturated aqueous solution of sodium hydrogen carbonate was added to the reaction mixture, followed by extraction with methylene chloride. The extract was passed through aplastic filter to remove solid residue and an aqueous layer, and the organic layer was concentrated under reduced pressure. The concentrate was purified by column chromatography (Waters, C$_{18}$, 19*100 mm column, 0.1% trifluoroacetic acid/acetonitrile=from 5% to 80%) and concentrated. The resulting material was dissolved in a solvent, and the compound was passed through a cartridge (PL-HCO$_3$ MP resin, methanol only), and then concentrated to afford the desired compound (0.061 g, 69.7%) as a brown oil.

Step 2: Synthesis of Compound 343

Methyl 4-(((3R,5S)-4-(3-(furan-3-yl)benzyl)-3,5-dimethylpiperazin-1-yl)methyl)benzoate (formula 2-2, 0.061 g, 0.146 mmol), hydroxylamine (0.089 mL, 1.457 mmol, 50.00% aqueous solution) and potassium hydroxide (0.164 g, 2.915 mmol) were dissolved in methanol (2 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was passed through a plastic filter to remove solid residue and an aqueous layer, and the organic layer was concentrated under reduced pressure. The concentrate was purified by column chromatography (silicon dioxide, 4 g cartridge; methanol/methylene chloride=from 0% to 100%) and concentrated to afford compound 343 (0.008 g, 13.1%) as a white solid.

$^1$H NMR (400 MHz, CH$_3$OD) δ 7.89-7.89 (m, 1 H), 7.72 (d, 2 H, J=8.2 Hz), 7.57 (dd, 1 H, J=1.6, 1.6 Hz), 7.54 (s, 1 H), 7.44 (d, 3 H, J=7.9 Hz), 7.33-7.30 (m, 2 H), 6.80-6.79 (m, 1 H), 3.95 (s, 2 H), 3.54 (s, 2 H), 2.77-2.17 (m, 4 H), 1.97 (t, 2 H, J=10.8 Hz), 1.13 (d, 6 H, J=6.0 Hz); LRMS (ES) m/z 420.2 (M$^+$+1).

Example 157

Synthesis of Compound 344

(4-(((3R,5S)-3,5-dimethyl-4-(3-(pyridin-3-yl)benzyl)piperazin-1-yl)methyl)-N-hydroxybenzamide)

Step 1: Synthesis of Methyl 4-(((3R,5S)-3,5-dimethyl-4-(3-(pyridin-3-yl)benzyl)piperazin-1-yl)methyl)benzoate 1,2-Dimethoxyethane (4 mL)/water (1 mL) were added to a mixture of methyl 4-(((3R,5S)-4-(3-iodobenzyl)-3,5-dimethylpiperazin-1-yl)methyl)benzoate (formula 2-1, 0.100 g, 0.209 mmol), pyridin-3-ylboronic acid (0.051 g, 0.418 mmol), Pd(dbpf)$_2$Cl$_2$ (0.007 g, 0.010 mmol) and Na$_2$CO$_3$ (0.044 g, 0.418 mmol), and heated by microwave irradiation at 120° C. for 20 minutes, followed by cooling to room temperature. Then, a saturated aqueous solution of sodium hydrogen carbonate was added to the reaction mixture, followed by extraction with methylene chloride. The extract was passed through aplastic filter to remove solid residue and an aqueous layer, and the organic layer was concentrated under reduced pressure. The concentrate was purified by column chromatography (Waters, C$_{18}$, 19*100 mm column, 0.1% trifluoroacetic acid/acetonitrile=from 5% to 80%) and concentrated. The resulting material was dissolved in a solvent, and the compound was passed through a cartridge (PL-HCO$_3$ MP resin, methanol only), and then concentrated to afford the desired compound (0.085 g, 94.7%) as a colorless oil.

Step 2: Synthesis of Compound 344

Methyl 4-(((3R,5S)-3,5-dimethyl-4-(3-(pyridin-3-yl)benzyl)piperazin-1-yl)methyl)benzoate (formula 2-2, 0.085 g, 0.198 mmol), hydroxylamine (0.121 mL, 1.979 mmol, 50.00% aqueous solution) and potassium hydroxide (0.222 g, 3.958 mmol) were dissolved in methanol (3 mL) at room temperature, and the reaction solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was filtered through a plastic filter equipped with an anhydrous sodium sulfate cartridge to remove solid residue and an aqueous layer, and the filtrate was concentrated under reduced pressure to yield compound 344 (0.055 g, 64.6%) as a white solid.

$^1$H NMR (400 MHz, CDCl$_3$) δ 8.86 (d, 1 H, J=1.9 Hz), 8.58 (d, 1 H, J=3.4 Hz), 8.04 (d, 1 H, J=7.8 Hz), 7.68 (d, 3 H, J=8.1 Hz), 7.54-7.48 (m, 2 H), 7.43 (d, 2 H, J=4.8 Hz), 7.26 (d, 2 H, J=8.0 Hz), 3.81 (s, 2 H), 3.41 (s, 2 H), 2.66 (d, 2 H, J=11.0 Hz), 2.63-2.59 (m, 2 H), 1.82 (t, 2 H, J=10.2 Hz), 0.93 (d, 6 H, J=6.0 Hz); LRMS (ES) m/z 431.2 (M$^+$+1)

Example 158

Synthesis of Compound 345

(4-(((3R,5S)-3,5-dimethyl-4-(3-(pyridin-4-yl)benzyl)piperazin-1-yl)methyl)-N-hydroxybenzamide)

Step 1: Synthesis of Methyl 4-(((3R,5S)-3,5-dimethyl-4-(3-(pyridin-4-yl)benzyl)piperazin-1-yl)methyl)benzoate 1,2-Dimethoxyethane (4 mL)/water (1 mL) were added to a mixture of methyl 4-(((3R,5S)-4-(3-iodobenzyl)-3,5-dimethylpiperazin-1-yl)methyl)benzoate (formula 2-1, 0.100 g, 0.209 mmol), pyridin-4-ylboronic acid (0.051 g, 0.418 mmol), Pd(dbpf)$_2$Cl$_2$ (0.007 g, 0.010 mmol) and Na$_2$CO$_3$ (0.044 g, 0.418 mmol), and heated by microwave irradiation at 120° C. for 20 minutes, followed by cooling to room temperature. Then, a saturated aqueous solution of sodium hydrogen carbonate was added to the reaction mixture, followed by extraction with methylene chloride. The extract was passed through aplastic filter to remove solid residue and an aqueous layer, and the organic layer was concentrated under reduced pressure. The concentrate was purified by column chromatography (Waters, $C_{18}$, 19*100 mm column, 0.1% trifluoroacetic acid/acetonitrile=from 5% to 80%) and concentrated. The resulting material was dissolved in a solvent, and the compound was passed through a cartridge (PL-$HCO_3$ MP resin, methanol only), and then concentrated to afford the desired compound (0.088 g, 98.0%) as a colorless oil.

Step 2: Synthesis of Compound 345

Methyl 4-(((3R,5S)-3,5-dimethyl-4-(3-(pyridin-4-yl)benzyl)piperazin-1-yl)methyl)benzoate (formula 4-2, 0.040 g, 0.093 mmol), hydroxylamine (0.031 g, 0.931 mmol) and potassium hydroxide (0.105 g, 1.862 mmol) were mixed in methanol (3 mL) at room temperature, and the mixture was stirred at the same temperature for 30 minutes. Then, a saturated aqueous solution of sodium hydrogen carbonate was added to the reaction mixture, followed by extraction with methylene chloride. The extract was filtered through a plastic filter to remove solid residue and an aqueous layer, and was then concentrated under reduced pressure. The concentrate was purified by column chromatography (silicon dioxide, 4 g cartridge; methanol/methylene chloride=from 0% to 10%) and concentrated to afford compound 345 (0.005 g, 12.5%) as a white solid.
$^1$H NMR (400 MHz, DMSO-$d_6$) δ 8.64 (d, 2 H, J=5.2 Hz), 7.74 (s, 1 H), 7.62-7.61 (m, 5 H), 7.47-7.45 (m, 2 H), 7.25 (d, 2 H, J=7.8 Hz), 3.82 (s, 2 H), 3.41 (s, 2 H), 2.68-2.61 (m, 4 H), 1.83 (t, 2 H, J=9.9 Hz), 0.92 (d, 6 H, J=5.8 Hz); LRMS (ES) m/z 431.2 ($M^+$+1).

Example 159

Synthesis of Compound 346

(4-(((3R,5S)-4-(3-(3,6-dihydro-2H-pyran-4-yl)benzyl)-3,5-dimethylpiperazin-1-yl)methyl)-N-hydroxybenzamide)

Step 1: Synthesis of Methyl 4-(((3R,5S)-4-(3-(3,6-dihydro-2H-pyran-4-yl)benzyl)-3,5-dimethylpiperazin-1-yl)methyl)benzoate 1,2-Dimethoxyethane (4 mL)/water (1 mL) were added to a mixture of methyl 4-(((3R,5S)-4-(3-iodobenzyl)-3,5-dimethylpiperazin-1-yl)methyl)benzoate (formula 2-1, 0.100 g, 0.209 mmol), 2-(3,6-dihydro-2H-pyran-4-yl)-4,4,5,5-tetramethyl-1,3,2-dioxaborolane (0.088 g, 0.418 mmol), Pd(dbpf)$_2$Cl$_2$ (0.007 g, 0.010 mmol) and Na$_2$CO$_3$ (0.044 g, 0.418 mmol), and heated by microwave irradiation at 120° C. for 20 minutes, followed by cooling to room temperature. Then, a saturated aqueous solution of sodium hydrogen carbonate was added to the reaction mixture, followed by extraction with methylene chloride. The extract was passed through aplastic filter to remove solid residue and an aqueous layer, and the organic layer was concentrated under reduced pressure. The concentrate was purified by column chromatography (Waters, $C_{18}$, 19*100 mm column, 0.1% trifluoroacetic acid/acetonitrile=from 5% to 80%) and concentrated. The resulting material was dissolved in a solvent, and the compound was passed through a cartridge (PL-HCO$_3$ MP resin, methanol only), and then concentrated to afford the desired compound (0.068 g, 74.9%) as a pale brown oil.

Step 2: Synthesis of Compound 346

Methyl 4-(((3R,5S)-4-(3-(3,6-dihydro-2H-pyran-4-yl)benzyl)-3,5-dimethylpiperazin-1-yl)methyl)benzoate (formula 2-2, 0.068 g, 0.156 mmol), hydroxylamine (0.096 mL, 1.565 mmol, 50.00% aqueous solution) and potassium hydroxide (0.176 g, 3.130 mmol) were mixed in methanol (3 mL) at room temperature, and the mixture was stirred at the same temperature for 30 minutes. Then, a saturated aqueous solution of sodium hydrogen carbonate was added to the reaction mixture, followed by extraction with methylene chloride. The extract was filtered through a plastic filter to remove solid residue and an aqueous layer, and was then concentrated under reduced pressure. The concentrate was purified by column chromatography (Waters, $C_{18}$, 19*100 mm column, 0.1% trifluoroacetic acid/acetonitrile=from 5% to 80%) and concentrated. The resulting material was dissolved in a solvent, and the compound was passed through a cartridge (PL-HCO$_3$ MP resin, 100% methanol), and then concentrated to afford compound 346 (0.005 g, 7.3%) as an apricot solid.
$^1$H NMR (400 MHz, CH$_3$OD) δ 7.72 (d, 2 H, J=8.2 Hz), 7.42 (d, 3 H, J=8.4 Hz), 7.31-7.28 (m, 3 H), 6.17 (t, 1 H, J=1.5 Hz), 4.32-4.30 (m, 2 H), 3.95-3.92 (m, 4 H), 3.52 (s, 2 H), 2.75-2.69 (m, 4 H), 2.39-2.52 (m, 2 H), 1.94 (t, 2 H, J=11.2 Hz), 1.11 (d, 6 H, J=6.1 Hz); LRMS (ES) m/z 436.2 ($M^+$+1).

Example 160

Synthesis of Compound 347

(4-(((3R,5S)-4-((4',4'-dimethyl-2',3',4',5'-tetrahydro-[1,1'-biphenyl]-3-yl)methyl)-3,5-dimethylpiperazin-1-yl)methyl)-N-hydroxybenzamide)

Step 1: Synthesis of Methyl 4-(((3R,5S)-4-((4',4'-dimethyl-2',3',4',5'-tetrahydro-[1,1'-biphenyl]-3-yl)methyl)-3,5-dimethylpiperazin-1-yl)methyl)benzoate 1,2-Dimethoxyethane (4 mL)/water (1 mL) were added to a mixture of methyl 4-(((3R,5S)-4-(3-iodobenzyl)-3,5-dimethylpiperazin-1-yl)methyl)benzoate (formula 2-1, 0.100 g, 0.209 mmol), 2-(4,4-dimethylcyclo-1-hexenyl)-4,4,5,5-tetramethyl-1,3,2-dioxaborolane (0.099 g, 0.418 mmol), Pd(dbpf)$_2$Cl$_2$ (0.007 g, 0.010 mmol) and Na$_2$CO$_3$ (0.044 g, 0.418 mmol), and heated by microwave irradiation at 120° C. for 20 minutes, followed by cooling to room temperature. Then, a saturated aqueous solution of sodium hydrogen carbonate was added to the reaction mixture, followed by extraction with methylene chloride. The extract was passed through aplastic filter to remove solid residue and an aqueous layer, and the organic layer was concentrated under reduced pressure. The concentrate was purified by column chromatography (Waters, $C_{18}$, 19*100 mm column, 0.1% trifluoroacetic acid/acetonitrile=from 5% to 80%) and concentrated. The resulting material was dissolved in a solvent, and the compound was passed through a cartridge (PL-HCO$_3$ MP resin, methanol only), and then concentrated to afford the desired compound (0.064 g, 66.5%) as a brown oil.

Step 2: Synthesis of Compound 347

Methyl 4-(((3R,5S)-4-((4',4'-dimethyl-2',3',4',5'-tetrahydro-[1,1'-biphenyl]-3-yl)methyl)-3,5-dimethylpiperazin-1-yl)methyl)benzoate (formula 2-2, 0.064 g, 0.139 mmol), hydroxylamine (0.085 mL, 1.389 mmol, 50.00% aqueous solution) and potassium hydroxide (0.156 g, 2.779 mmol) were mixed in methanol (3 mL) at room temperature, and the mixture was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 347 (0.020 g, 31.2%) as an orange solid.

$^1$H NMR (400 MHz, CH$_3$OD) δ 7.72 (d, 2 H, J=8.1 Hz), 7.43 (d, 2 H, J=8.0 Hz), 7.40 (s, 1 H), 7.28-7.23 (m, 3 H), 6.06 (s, 1 H), 3.93 (s, 2 H), 3.52 (s, 2 H), 2.76-2.69 (m, 4 H), 2.45-2.45 (m, 2 H), 2.03-2.02 (m, 2 H), 1.95 (t, 2 H, J=10.6 Hz), 1.57 (t, 2 H, J=6.4 Hz), 1.13 (d, 6 H, J=6.0 Hz), 1.00 (s, 6 H); LRMS (ES) m/z 462.3 (M$^+$+1).

Example 161

Synthesis of Compound 348

(4-(((2S,6R)-4-(2-(furan-3-yl)benzyl)-2,6-dimethyl-piperazin-1-yl)methyl)-N-hydroxybenzamide)

Step 1: Synthesis of Methyl 4-(((2S,6R)-4-(2-(furan-3-yl)benzyl)-2,6-dimethylpiperazin-1-yl)methyl)benzoate 1,2-Dimethoxyethane (4 mL)/water (1 mL) were added to a mixture of methyl 4-(((2S,6R)-4-(2-iodobenzyl)-2,6-dimethylpiperazin-1-yl)methyl)benzoate (formula 14-1, 0.100 g, 0.209 mmol), furan-3-ylboronic acid (0.047 g, 0.418 mmol), Pd(dbpf)$_2$Cl$_2$ (0.007 g, 0.010 mmol) and Na$_2$CO$_3$ (0.044 g, 0.418 mmol), and heated by microwave irradiation at 120° C. for 20 minutes, followed by cooling to room temperature. Then, a saturated aqueous solution of sodium hydrogen carbonate was added to the reaction mixture, followed by extraction with methylene chloride. The extract was passed through aplastic filter to remove solid residue and an aqueous layer, and was then concentrated under reduced pressure. The product was used without additional purification (0.090 g, 102.9%, crude).

Step 2: Synthesis of Compound 348

Methyl 4-(((2S,6R)-4-(2-(furan-3-yl)benzyl)-2,6-dimethylpiperazin-1-yl)methyl)benzoate (formula 14-2, 0.090 g, 0.215 mmol), hydroxylamine (0.132 mL, 2.150 mmol, 50.00% aqueous solution) and potassium hydroxide (0.241 g, 4.301 mmol) were mixed in methanol (3 mL) at room temperature, and the mixture was stirred at the same temperature for 30 minutes. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 15%) and concentrated to afford compound 348 (0.023 g, 25.5%) as a pale orange solid.

$^1$H NMR (400 MHz, DMSO-d$_6$) δ 11.13 (s, 1 H), 8.98 (s, 1 H), 8.99 (d, 1 H, J=1.6 Hz), 7.98-7.98 (m, 1 H), 7.76 (dd, 1 H, J=1.7, 1.7 Hz), 7.67 (d, 2 H, J=8.6 Hz), 7.44-7.39 (m, 4 H), 7.33-7.29 (m, 2 H), 6.84 (dd, 1 H, J=1.8, 0.7 Hz), 3.75 (s, 2 H), 3.37 (s, 2 H), 2.68 (d, 2 H, J=10.7 Hz), 1.85-1.84 (m, 2 H), 0.89 (d, 6 H, J=6.1 Hz).

Example 162

Synthesis of Compound 349

(4-(((2S,6R)-2,6-dimethyl-4-(2-(pyridin-3-yl)benzyl)piperazin-1-yl)methyl)-N-hydroxybenzamide)

Step 1: Synthesis of Methyl 4-(((2S,6R)-2,6-dimethyl-4-(2-(pyridin-3-yl)benzyl)piperazin-1-yl)methyl)benzoate 1,2-Dimethoxyethane (4 mL)/water (1 mL) were added to a mixture of methyl 4-(((2S,6R)-4-(2-iodobenzyl)-2,6-dimethylpiperazin-1-yl)methyl)benzoate (formula 14-1, 0.100 g, 0.209 mmol), pyridin-3-ylboronic acid (0.051 g, 0.418 mmol), Pd(dbpf)$_2$Cl$_2$ (0.007 g, 0.010 mmol) and Na$_2$CO$_3$ (0.044 g, 0.418 mmol), and heated by microwave irradiation at 120° C. for 20 minutes, followed by cooling to room temperature. Then, a saturated aqueous solution of sodium hydrogen carbonate was added to the reaction mixture, followed by extraction with methylene chloride. The extract was passed through aplastic filter to remove solid residue and an aqueous layer, and was then concentrated under reduced pressure. The product was used without additional purification (0.090 g, 100.2%).

Step 2: Synthesis of Compound 349

Methyl 4-(((2S,6R)-2,6-dimethyl-4-(2-(pyridin-3-yl)benzyl)piperazin-1-yl)methyl)benzoate (formula 14-2, 0.090 g, 0.210 mmol), hydroxylamine (0.128 mL, 2.095 mmol, 50.00% aqueous solution) and potassium hydroxide (0.235 g, 4.190 mmol) were mixed in methanol (3 mL) at room temperature, and the mixture was stirred at the same temperature for 1 hour. Then, the reaction mixture was concentrated under reduced pressure. A saturated aqueous solution of sodium hydrogen carbonate (20 mL) was added to the concentrate, and the precipitated solid was filtered and dried to yield compound 349 (0.041 g, 45.5%) as an apricot solid.

$^1$H NMR (400 MHz, DMSO-d$_6$) δ 8.60-8.56 (m, 2 H), 7.86 (d, 1 H, J=7.6 Hz), 7.65 (d, 2 H, J=7.6 Hz), 7.49-7.38 (m, 4 H), 7.35 (d, 2 H, J=7.9 Hz), 7.28 (d, 1 H, J=6.5 Hz), 3.70 (s, 2 H), 3.30 (s, 2 H), 2.50-2.48 (m, 4 H), 1.72 (t, 2 H, J=10.2 Hz), 0.83 (d, 6 H, J=5.9 Hz); LRMS (ES) m/z 431.2 (M$^+$+1).

Example 163

Synthesis of Compound 350

(4-(((2S,6R)-2,6-dimethyl-4-(2-(pyridin-4-yl)benzyl)piperazin-1-yl)methyl)-N-hydroxybenzamide)

Step 1: Synthesis of Methyl 4-(((2S,6R)-2,6-dimethyl-4-(2-(pyridine-4-yl)benzyl)piperazin-1-yl)methyl)benzoate 1,2-Dimethoxyethane (3 mL)/water (1 mL) were added to a mixture of methyl 4-(((2S,6R)-4-(2-iodobenzyl)-2,6-dimethylpiperazin-1-yl)methyl)benzoate (formula 14-1, 0.100 g, 0.209 mmol), pyridin-4-ylboronic acid (0.051 g, 0.418 mmol), Pd(dbpf)$_2$Cl$_2$ (0.007 g, 0.010 mmol) and Na$_2$CO$_3$ (0.044 g, 0.418 mmol), and heated by microwave irradiation at 120° C. for 20 minutes, followed by cooling to room temperature. Then, a saturated aqueous solution of sodium hydrogen carbonate was added to the reaction mixture, followed by extraction with methylene chloride. The extract was passed through aplastic filter to remove solid residue and an aqueous layer, and was then concentrated under reduced pressure. The product was used without additional purification (0.090 g, 100.2%).

Step 2: Synthesis of Compound 350

Methyl 4-(((2S,6R)-2,6-dimethyl-4-(2-(pyridine-4-yl)benzyl)piperazin-1-yl)methyl)benzoate (formula 14-2, 0.090 g, 0.210 mmol), hydroxylamine (0.128 mL, 2.095 mmol, 50.00% aqueous solution) and potassium hydroxide (0.235 g, 4.190 mmol) were mixed in methanol (3 mL) at room temperature, and the mixture was stirred at the same temperature for 1 hour. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 15%) and concentrated to afford compound 350 (0.026 g, 28.8%) as a pale orange solid.

$^1$H NMR (400 MHz, DMSO-$d_6$) δ 8.52 (d, 2 H, J=6.1 Hz), 7.70 (d, 2 H, J=8.2 Hz), 7.49 (d, 2 H, J=6.4 Hz), 7.50-7.47 (m, 5 H), 7.42-7.40 (m, 2 H), 7.29-7.27 (m, 1 H), 3.85 (s, 2 H), 3.42 (s, 2 H), 2.56 (d, 2 H, J=10.6 Hz), 2.47-2.46 (m, 2 H), 1.79 (t, 2 H, J=10.7 Hz), 0.97 (d, 6 H, J=6.2 Hz).

Example 164

Synthesis of Compound 351

(4-(((2S,6R)-4-(2-(3,6-dihydro-2H-pyran-4-yl)benzyl)-2,6-dimethylpiperazin-1-yl)methyl)-N-hydroxybenzamide)

Step 1: Synthesis of Methyl 4-(((2S,6R)-4-(2-(3,6-dihydro-2H-pyran-4-yl)benzyl)-2,6-dimethylpiperazin-1-yl)methyl)benzoate 1,2-Dimethoxyethane (3 mL)/water (1 mL) were added to a mixture of methyl 4-(((2S,6R)-4-(2-iodobenzyl)-2,6-dimethylpiperazin-1-yl)methyl)benzoate (formula 14-1, 0.100 g, 0.209 mmol), 2-(3,6-dihydro-2H-pyran-4-yl)-4,4,5,5-tetramethyl-1,3,2-dioxaborolane (0.088 g, 0.418 mmol), Pd(dbpf)$_2$Cl$_2$ (0.007 g, 0.010 mmol) and Na$_2$CO$_3$ (0.044 g, 0.418 mmol), and heated by microwave irradiation at 120° C. for 20 minutes, followed by cooling to room temperature. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 0% to 60%) and concentrated to afford the desired compound (0.017 g, 18.7%) as a pale yellow oil.

Step 2: Synthesis of Compound 351

Methyl 4-(((2S,6R)-4-(2-(3,6-dihydro-2H-pyran-4-yl)benzyl)-2,6-dimethylpiperazin-1-yl)methyl)benzoate (formula 14-2, 0.017 g, 0.039 mmol), hydroxylamine (0.024 mL, 0.391 mmol, 50.00% aqueous solution) and potassium hydroxide (0.044 g, 0.782 mmol) were mixed in methanol (1 mL) at room temperature, and the mixture was stirred at the same temperature for 30 minutes. Then, a saturated aqueous solution of sodium hydrogen carbonate was added to the reaction mixture, followed by extraction with methylene chloride. The extract was filtered through a plastic filter equipped with an anhydrous sodium sulfate cartridge to remove solid residue and an aqueous layer, and was then concentrated under reduced pressure to yield compound 351 (0.012 g, 70.4%) as a white solid.

$^1$H-NMR (400 MHz, CD$_3$OD) δ 7.71 (d, 2 H, J=8.3 Hz), 7.49 (d, 2 H, J=8.3 Hz), 7.38-7.37 (m, 1 H), 7.24-7.22 (m, 2 H), 7.12-7.11 (m, 1 H), 5.61 (s, 1 H), 4.26-4.24 (m, 2 H), 3.90-3.87 (m, 4 H), 3.48 (s, 2 H), 2.70 (d, 2 H, J=11.0 Hz), 2.69-2.64 (m, 2 H), 2.36-2.35 (m, 2 H), 1.90 (t, 2 H, J=10.9 Hz), 1.03 (d, 6 H, J=6.1 Hz); LRMS (ES) m/z 436.2 (M$^+$+1).

Example 165

Synthesis of Compound 352

(4-(((2S,6R)-4-((4',4'-dimethyl-2',3',4',5'-tetrahydro-[1,1'-biphenyl]-2-yl)methyl)-2, 6-dimethylpiperazin-1-yl)methyl)-N-hydroxybenzamide)

Step 1: Synthesis of Methyl 4-(((2S,6R)-4-((4',4'-dimethyl-2',3',4',5'-tetrahydro-[1,1'-biphenyl]-2-yl)methyl)-2,6-dimethylpiperazin-1-yl)methyl)benzoate 1,2-dimethoxyethane (3 mL)/water (1 mL) were added to a mixture of methyl 4-(((2S,6R)-4-(2-iodobenzyl)-2,6-dimethylpiperazin-1-yl)methyl)benzoate (formula 14-1, 0.100 g, 0.209 mmol), 2-(4,4-dimethylcyclo-1-hexenyl)-4,4,5,5-tetramethyl-1,3,2-dioxaborolane (0.099 g, 0.418 mmol), Pd(dbpf)$_2$Cl$_2$ (0.007 g, 0.010 mmol) and Na$_2$CO$_3$ (0.044 g, 0.418 mmol), and heated by microwave irradiation at 120° C. for 20 minutes, followed by cooling to room temperature. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 0% to 10%) and concentrated to afford the desired compound (0.013 g, 13.5%) as a pale yellow oil.

Step 2: Synthesis of Compound 352

Methyl 4-(((2S,6R)-4-((4',4'-dimethyl-2',3',4',5'-tetrahydro-[1,1'-biphenyl]-2-yl)methyl)-2,6-dimethylpiperazin-1-yl)methyl)benzoate (formula 14-2, 0.013 g, 0.028 mmol), hydroxylamine (50.00% aqueous solution, 0.017 mL, 0.282 mmol) and potassium hydroxide (0.032 g, 0.564 mmol) were mixed in methanol (1 mL) at room temperature, and the mixture was stirred at the same temperature for 30 minutes. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by PTLC (silicon dioxide; 100% ethyl acetate) and concentrated to afford compound 352 (0.007 g, 53.7%) as an orange solid.

$^1$H-NMR (400 MHz, CD$_3$OD) δ 7.71 (d, 2 H, J=7.1 Hz), 7.49 (d, 2 H, J=6.9 Hz), 7.37-7.36 (m, 1 H), 7.20-7.18 (m, 2 H), 7.07-7.04 (m, 1 H), 5.43 (s, 1 H), 3.91 (s, 2 H), 3.48 (s, 2 H), 2.72-2.66 (m, 4 H), 2.24 (s, 2 H), 1.96 (s, 2 H), 1.88

(t, 2 H, J=10.4 Hz), 1.50 (t, 2 H, J=6.2 Hz), 1.03 (d, 12 H, J=3.9 Hz); LRMS (ES) m/z 462.2 (M$^+$+1).

Example 166

Synthesis of Compound 354

(4-(((3R,5S)-3,5-dimethyl-4-(oxazol-4-ylmethyl) piperazin-1-yl)methyl)-N-hydroxybenzamide)

Step 1: Synthesis of oxazol-4-ylmethyl methanesulfonate

Oxazol-4-ylmethanol (0.300 g, 3.028 mmol) and TEA (0.633 mL, 4.541 mmol) were mixed in methylene chloride (5 mL) at 0° C., and MsCl (0.258 mL, 3.330 mmol) was added to the mixture, followed by stirring at the same temperature. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 0% to 50%) and concentrated to afford the desired compound (0.119 g, 22.2%) as an orange oil.

Step 2: Synthesis of Methyl 4-(((3R,5S)-3,5-dimethyl-4-(oxazol-4-ylmethyl)piperazin-1-yl)methyl) benzoate Methyl 4-(((3R,5S)-3,5-dimethylpiperazin-1-yl)methyl) benzoate (formula 1-2, 0.150 g, 0.572 mmol), oxazol-4-ylmethyl methanesulfonate (0.111 g, 0.629 mmol) and Cs$_2$CO$_3$ (0.279 g, 0.858 mmol) were added to N,N-dimethylformamide (3 mL) at 80° C., and the mixture was stirred at the same temperature for 17 hours. Then, the reaction mixture was concentrated under reduced pressure. The concentrate was purified by column chromatography (silicon dioxide, 4 g cartridge; methanol/methylene chloride=from 0% to 15%) and concentrated to afford the desired compound (0.054 g, 27.5%) as a pale yellow oil.

Step 3: Synthesis of Compound 354

Methyl 4-(((3R,5S)-3,5-dimethyl-4-(oxazol-4-ylmethyl) piperazin-1-yl)methyl)benzoate (formula 1-3, 0.054 g, 0.157 mmol), hydroxylamine (0.096 mL, 1.572 mmol, 50.00% aqueous solution) and potassium hydroxide (0.176 g, 3.145 mmol) were mixed in methanol (1 mL) at room temperature, and the mixture was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter equipped with an anhydrous sodium sulfate cartridge to remove solid residue and an aqueous layer, and was then concentrated under reduced pressure to afford compound 354 (0.003 g, 5.5%) as a yellow solid.

$^1$H NMR (400 MHz, DMSO-d$_6$) δ 8.16 (s, 1 H), 7.92 (s, 1 H), 7.72 (d, 2 H, J=8.1 Hz), 7.41 (d, 2 H, J=8.0 Hz), 3.98 (s, 2 H), 3.51 (s, 2 H), 2.73 (d, 2 H, J=11.8 Hz), 2.70-2.66 (m, 2 H), 1.93 (t, 2 H, J=10.8 Hz), 1.19 (d, 6 H, J=6.1 Hz); LRMS (ES) m/z 345.2 (M$^+$+1).

Example 167

Synthesis of Compound 355

(4-(((3R,5S)-3,5-dimethyl-4-(pyrimidin-5-ylmethyl) piperazin-1-yl)methyl)-N-hydroxybenzamide)

Step 1: Synthesis of Methyl 4-(((3R,5S)-3,5-dimethyl-4-(pyrimidin-5-ylmethyl)piperazin-1-yl) methyl)benzoate Methyl 4-(((3R,5S)-3,5-dimethylpiperazin-1-yl)methyl) benzoate (formula 1-2, 0.200 g, 0.762 mmol), 5-(chloromethyl)pyrimidine (0.108 g, 0.839 mmol) and Cs$_2$CO$_3$ (0.373 g, 1.144 mmol) were added to N,N-dimethylformamide (3 mL) at room temperature, and the mixture was stirred at 120° C. for 48 hours. Then, the reaction mixture was concentrated under reduced pressure to remove the solvent, and water was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 15%) and concentrated to afford the desired compound (0.027 g, 10.0%) as a yellow solid.

Step 2: Synthesis of Compound 355

Methyl 4-(((3R,5S)-3,5-dimethyl-4-(pyrimidin-5-ylmethyl)piperazin-1-yl)methyl)benzoate (formula 1-3, 0.027 g, 0.076 mmol), hydroxylamine (0.047 mL, 0.762 mmol, 50.00% aqueous solution) and potassium hydroxide (0.085 g, 1.523 mmol) were mixed in methanol (1 mL) at room temperature, and the mixture was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter equipped with an anhydrous sodium sulfate cartridge to remove solid residue and an aqueous layer, and was then concentrated under reduced pressure to afford compound 355 (0.003 g, 11.1%) as a pale yellow solid.

$^1$H NMR (400 MHz, CH$_3$OD) δ 9.03 (s, 1 H), 8.83 (s, 1 H), 7.74 (d, 2 H, J=8.3 Hz), 7.46 (d, 2 H, J=8.3 Hz), 3.92 (s, 2 H), 3.56 (s, 2 H), 2.78 (d, 2 H, J=10.7 Hz), 2.72-2.68 (m, 2 H), 1.97 (t, 2 H, J=10.8 Hz), 0.93 (d, 6 H, J=6.6 Hz); LRMS (ES) m/z 356.1 (M$^+$+1).

Example 168

Synthesis of Compound 356

(4-(((3R,5S)-3,5-dimethyl-4-(3-(morpholinomethyl) benzyl)piperazin-1-yl)methyl)-N-hydroxybenzamide)

Step 1: Synthesis of Methyl 4-(((3R,5S)-4-(3-formylbenzyl)-3,5-dimethylpiperazin-1-yl)methyl)benzoate Methyl 4-(((3R,5S)-3,5-dimethylpiperazin-1-yl)methyl) benzoate (formula 1-2, 0.500 g, 1.906 mmol), 3-(bromomethyl)benzaldehyde (0.417 g, 2.096 mmol) and Cs$_2$CO$_3$ (0.931 g, 2.859 mmol) were mixed in acetonitrile (20 mL) at room temperature, and the mixture was stirred at the same temperature for 17 hours. Then, the reaction mixture was concentrated under reduced pressure to remove the solvent, and water was added to the resulting concentrate, followed by extraction with ethyl acetate. The extract was filtered through a plastic filter to remove solid residue and an aqueous layer, and then concentrated under reduced pressure. The concentrate was purified by column chromatography (silicon dioxide; 12 g cartridge; ethyl acetate/hexane=from 0% to 60%) and concentrated to afford the desired compound (0.530 g, 73.1%) as a pale brown oil.

Step 2: Synthesis of Methyl 4-(((3R,5S)-3,5-dimethyl-4-(3-(morpholinomethyl)benzyl)piperazin-1-yl)methyl)benzoate Methyl 4-(((3R,5S)-4-(3-formylbenzyl)-3,5-dimethylpiperazin-1-yl)methyl)benzoate (formula 5-1, 0.200 g, 0.526 mmol), morpholine (0.050 mL, 0.578 mmol) and acetic acid (0.015 mL, 0.526 mmol) were mixed in tetrahydrofuran (5 mL) at room temperature and the mixture was stirred. Then, Na(CN)BH$_3$ (0.033 g, 0.526 mmol) was added to the mixture, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide; 4 g cartridge; ethyl acetate/hexane=from 20% to 100%) and concentrated to afford the desired compound (0.109 g, 45.9%) as a colorless oil.

Step 3: Synthesis of Compound 356

Methyl 4-(((3R,5S)-3,5-dimethyl-4-(3-(morpholinomethyl)benzyl)piperazin-1-yl)methyl)benzoate (formula 5-2, 0.050 g, 0.111 mmol), hydroxylamine (0.135 mL, 2.214 mmol, 50.00% aqueous solution) and potassium hydroxide (0.072 g, 1.107 mmol) were mixed in methanol (2 mL) at room temperature, and the mixture was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter equipped with an anhydrous sodium sulfate cartridge to remove solid residue and an aqueous layer, and was then concentrated under reduced pressure to afford compound 356 (0.034 g, 67.9%) as a white solid.
$^1$H NMR (400 MHz, DMSO-d$_6$) δ 7.66 (d, 2 H, J=8.0 Hz), 7.27-7.22 (m, 5 H), 7.10 (s, 1 H), 3.71 (s, 2 H), 3.55 (s, 4 H), 3.44 (s, 2 H), 3.39 (s, 2 H), 2.63 (d, 2 H, J=10.5 Hz), 2.57-2.55 (m, 2 H), 2.32 (s, 4 H), 1.78 (t, 2 H, J=10.5 Hz), 0.89 (d, 6 H, J=6.0 Hz); LRMS (ES) m/z 453.2 (M$^+$+1).

Example 169

Synthesis of Compound 376

(4-(((3R,5S)-3,5-dimethyl-4-(4-(morpholinomethyl)benzyl)piperazin-1-yl)methyl)-N-hydroxybenzamide)

Step 1: Synthesis of Methyl 4-(((3R,5S)-4-(4-formylbenzyl)-3,5-dimethylpiperazin-1-yl)methyl)benzoate Methyl 4-(((3R,5S)-3,5-dimethylpiperazin-1-yl)methyl)benzoate (formula 1-2, 0.200 g, 0.762 mmol), 4-(bromomethyl)benzaldehyde (0.167 g, 0.839 mmol) and Cs$_2$CO$_3$ (0.373 g, 1.144 mmol) were mixed in acetonitrile (5 mL) at room temperature, and the mixture was stirred at the same temperature for 17 hours. Then, water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 5% to 70%) and concentrated to afford the desired compound (0.131 g, 45.2%) as a pale yellow oil.

Step 2: Synthesis of Methyl 4-(((3R,5S)-3,5-dimethyl-4-(4-(morpholinomethyl)benzyl)piperazin-1-yl)methyl)benzoate Methyl 4-(((3R,5S)-4-(4-formylbenzyl)-3,5-dimethylpiperazin-1-yl)methyl)benzoate (formula 5-1, 0.131 g, 0.344 mmol) and morpholine (0.033 g, 0.379 mmol) were mixed in methylene chloride (4 mL) at room temperature, and the mixture was stirred for 30 minutes. Then, Na(OAc)$_3$BH (0.109 g, 0.516 mmol) was added thereto, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.134 g, 86.2%) as a pale yellow oil.

Step 3: Synthesis of Compound 376

Methyl 4-(((3R,5S)-3,5-dimethyl-4-(4-(morpholinomethyl)benzyl)piperazin-1-yl)methyl)benzoate (formula 5-2, 0.134 g, 0.297 mmol), hydroxylamine (0.181 mL, 2.967 mmol, 50.00% aqueous solution) and potassium hydroxide (0.386 g, 5.934 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 376 (0.030 g, 22.3%) as a white solid.
$^1$H NMR (400 MHz, DMSO-d$_6$) δ 11.18 (brs, 1 H), 9.04 (brs, 1 H), 7.70 (d, 2 H, J=8.2 Hz), 7.35 (d, 2 H, J=8.1 Hz), 7.28 (d, 2 H, J=8.0 Hz), 7.21 (d, 2 H, J=8.0 Hz), 3.71 (s, 2 H), 3.56 (t, 4 H, J=4.4 Hz), 3.43 (s, 2 H), 3.41 (s, 2 H), 2.63 (d, 2 H, J=10.4 Hz), 2.58-2.53 (m, 2 H), 2.32 (s, 4 H), 1.80 (t, 2 H, J=10.4 Hz), 0.90 (d, 6 H, J=6.1 Hz); LRMS (ES) m/z 453.2 (M$^+$+1).

Example 170

Synthesis of Compound 380

(4-(((3R,5S)-4-(3-((1-(2-fluoro-2-methylpropyl)piperidin-4-yl)methoxy)benzyl)-3,5-dimethylpiperazin-1-yl)methyl)-N-hydroxybenzamide)

Step 1: Synthesis of Tert-Butyl 4-((3-(hydroxymethyl)phenoxy)methyl)piperidine-1-carboxylate 3-(hydroxymethyl)phenol (0.500 g, 4.028 mmol), tert-butyl 4-((methylsulfonyloxy)methyl)piperidine-1-carboxylate (formula 12-1, 1.300 g, 4.430 mmol), $Cs_2CO_3$ (1.968 g, 6.042 mmol) and NaI (0.030 g, 0.201 mmol) were mixed in acetonitrile (50 mL) at room temperature, and the mixture was heated under reflux for 5 hours, and then cooled to room temperature. Water was added to the reaction mixture, followed by extraction with ethyl acetate. The organic layer was washed with a saturated aqueous solution of NaCl, dried with anhydrous magnesium sulfate, and then concentrated under reduced pressure. The concentrate was purified by column chromatography (silicon dioxide, 12 g cartridge; ethyl acetate/hexane=from 10% to 60%) and concentrated to afford the desired compound (0.790 g, 61.0%) as a colorless oil.

Step 2: Synthesis of Tert-Butyl 4-((3-(hydroxymethyl)phenoxy)methyl)piperidine-1-carboxylate Tert-butyl 4-((3-(hydroxymethyl)phenoxy)methyl)piperidine-1-carboxylate (formula 12-2, 0.500 g, 1.556 mmol) and TEA (0.434 mL, 3.111 mmol) were mixed in methylene chloride (50 mL) at 0° C., and MsCl (0.132 mL, 1.711 mmol) was added to the mixture. Next, the mixture was stirred at the same temperature for 1 hour, and then stirred at room temperature for 1 hour. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethylacetate/hexane=from 0% to 40%) and concentrated to afford the desired compound (0.204 g, 38.6%) as a colorless oil.

Step 3: Synthesis of Tert-Butyl 4-((3-(((2S,6R)-4-(4-(methoxycarbonyl)benzyl)-2,6-dimethylpiperazin-1-yl)methyl)phenoxy)methyl)piperidine-1-carboxylate Methyl 4-(((3R,5S)-3,5-dimethylpiperazin-1-yl)methyl)benzoate (formula 1-2, 0.150 g, 0.572 mmol), tert-butyl 4-((3-(chloromethyl)phenoxy)methyl)piperidine-1-carboxylate (formula 12-3, 0.194 g, 0.572 mmol) and $Cs_2CO_3$ (0.279 g, 0.858 mmol) were mixed in acetonitrile (10 mL) at room temperature, and the mixture was heated under reflux for 5 hours, and then cooled to room temperature. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 10% to 70%) and concentrated to afford the desired compound (0.181 g, 56.0%) as a pale yellow oil.

Step 4: Synthesis of Methyl 4-(((3R,5S)-3,5-dimethyl-4-(3-(piperidin-4-ylmethoxy)benzyl)piperazin-1-yl)methyl)benzoate Tert-butyl 4-((3-(((2S,6R)-4-(4-(methoxycarbonyl)benzyl)-2,6-dimethylpiperazin-1-yl)methyl)phenoxy)methyl)piperidine-1-carboxylate (formula 12-4, 0.180 g, 0.318 mmol) was added to 1,4-dioxane (5 mL) at room temperature, and HCl (4.00 M 1,4-dioxane solution, 0.795 mL, 3.182 mmol) was added to the mixture, which was then stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The product was used without additional purification (0.141 g, 95.2%, pale yellow oil).

Step 5: Synthesis of Ethyl 4-(((3R,5S)-4-(3-((1-(2-hydroxy-2-methylpropyl)piperidin-4-yl)methoxy)benzyl)-3,5-dimethylpiperazin-1-yl)methyl)benzoate Ethanol (4 mL) were added to mixture of methyl 4-(((3R,5S)-3,5-dimethyl-4-(3-(piperidin-4-ylmethoxy)benzyl)piperazin-1-yl)methyl)benzoate (formula 12-5, 0.150 g, 0.322 mmol), 2,2-dimethyloxirane (0.044 mL, 0.483 mmol) and $K_2CO_3$ (0.089 g, 0.644 mmol), and heated by microwave irradiation at 110° C. for 20 minutes, followed by cooling to room temperature. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.091 g, 52.5%) as a colorless oil.

Step 6: Synthesis of Ethyl 4-(((3R,5S)-4-(3-((1-(2-fluoro-2-methylpropyl)piperidin-4-yl)methoxy)benzyl)-3,5-dimethylpiperazin-1-yl)methyl)benzoate Ethyl 4-(((3R,5S)-4-(3-((1-(2-hydroxy-2-methylpropyl)piperidin-4-yl)methoxy)benzyl)-3,5-dimethylpiperazin-1-yl)methyl)benzoate (formula 12-6, 0.090 g, 0.163 mmol) was dissolved in methylene chloride (5 mL), and DAST (0.029 g, 0.179 mmol) was added thereto at 0° C. The mixture was stirred at the same temperature for 30 minutes, and then stirred at room temperature for 1 hour. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 8 g cartridge; ethyl acetate/hexane=from 0% to 50%) and concentrated to afford the desired compound (0.088 g, 97.4%) as a pale brown oil.

Step 7: Synthesis of Compound 380

Ethyl 4-(((3R,5S)-4-(3-((1-(2-fluoro-2-methylpropyl)piperidin-4-yl)methoxy)benzyl)-3,5-dimethylpiperazin-1-yl)methyl)benzoate (formula 12-7, 0.088 g, 0.159 mmol), hydroxylamine (0.097 mL, 1.589 mmol, 50.00% aqueous solution) and potassium hydroxide (0.207 g, 3.178 mmol) were dissolved in methanol (10 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 380 (0.027 g, 31.4%) as a white solid.

$^1$H NMR (400 MHz, DMSO-$d_6$) δ 7.70 (d, 2 H, J=8.1 Hz), 7.34 (d, 2 H, J=8.1 Hz), 7.18 (dd, 1 H, J=8.0, 8.0 Hz), 6.91-6.89 (m, 2 H), 6.73 (d, 1 H, J=8.5 Hz), 3.78 (d, 2 H, J=5.4 Hz), 3.68 (s, 2 H), 3.51 (s, 2 H), 2.91 (d, 2 H, J=11.3 Hz), 2.64 (d, 2 H, J=10.8 Hz), 2.58-2.56 (m, 2 H), 2.41 (d, 2 H, J=22.9 Hz), 2.07 (t, 2 H, J=10.8 Hz), 1.81 (t, 2 H, J=10.6 Hz), 1.71 (d, 3 H, J=11.5 Hz), 1.33 (s, 3 H), 1.28-1.24 (m, 5 H), 0.89 (d, 6 H, J=6.0 Hz); LRMS (ES) m/z 541.3 (M$^+$+1).

Example 171

Synthesis of Compound 382

(4-(((3R,5S)-3,5-dimethyl-4-(3-(piperidin-1-ylmethyl)benzyl)piperazin-1-yl)methyl)-N-hydroxybenzamide)

Step 1: Synthesis of Methyl 4-(((3R,5S)-3,5-dimethyl-4-(3-(piperidin-1-ylmethyl)benzyl)piperazin-1-yl)methyl)benzoate Methyl 4-(((3R,5S)-4-(3-formylbenzyl)-3,5-dimethylpiperazin-1-yl)methyl)benzoate (formula 5-1, 0.150 g, 0.394 mmol) and piperidine (0.038 mL, 0.434 mmol) were dissolved in methylene chloride (10 mL), and the solution was stirred at room temperature for 30 minutes. Na(OAc)$_3$BH (0.125 g, 0.591 mmol) was added to the reaction solution, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.095 g, 53.6%) as a pale yellow oil.

Step 2: Synthesis of Compound 382

Methyl 4-(((3R,5S)-3,5-dimethyl-4-(3-(piperidin-1-ylmethyl)benzyl)piperazin-1-yl)methyl)benzoate (formula 5-2, 0.044 g, 0.098 mmol), hydroxylamine (0.060 mL, 0.979 mmol, 50.00% aqueous solution) and potassium hydroxide (0.127 g, 1.957 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was filtered through a plastic filter to remove solid residue and an aqueous layer, and then concentrated under reduced pressure to afford compound 382 (0.037 g, 83.9%) as a white solid.

$^1$H NMR (400 MHz, DMSO-d$_6$) δ 7.68 (d, 2 H, J=8.2 Hz), 7.30-7.28 (m, 3 H), 7.22-7.20 (m, 2 H), 7.08 (d, 1 H, J=6.2 Hz), 3.72 (s, 2 H), 3.41 (s, 2 H), 3.40 (s, 2 H), 2.65-2.62 (m, 2 H), 2.58-2.53 (m, 2 H), 2.29 (s, 4 H), 1.80 (t, 2 H, J=10.7 Hz), 1.49-1.46 (m, 4 H), 1.40-1.38 (m, 2 H), 0.90 (d, 6 H, J=6.1 Hz); LRMS (ES) m/z 451.2 (M$^+$+1).

Example 172

Synthesis of Compound 383

(4-(((3R,5S)-4-(3-(((R)-3-fluoropyrrolidin-1-yl)methyl)benzyl)-3,5-dimethylpiperazin-1-yl)methyl)-N-hydroxybenzamide)

Step 1: Synthesis of Methyl 4-(((3R,5S)-4-(3-(((R)-3-fluoropyrrolidin-1-yl)methyl)benzyl)-3,5-dimethylpiperazin-1-yl)methyl)benzoate Methyl 4-(((3R,5S)-4-(3-formylbenzyl)-3,5-dimethylpiperazin-1-yl)methyl)benzoate (formula 5-1, 0.150 g, 0.394 mmol) and (R)-3-fluoropyrrolidine hydrochloride (0.054 g, 0.434 mmol) were dissolved in methylene chloride (10 mL), and the solution was stirred at room temperature for 30 minutes. Na(OAc)$_3$BH (0.125 g, 0.591 mmol) was added to the reaction solution, which was then stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.120 g, 67.1%) as a pale yellow oil.

Step 2: Synthesis of Compound 383

Methyl 4-(((3R,5S)-4-(3-(((R)-3-fluoropyrrolidin-1-yl)methyl)benzyl)-3,5-dimethylpiperazin-1-yl)methyl)benzoate (formula 5-2, 0.060 g, 0.132 mmol), hydroxylamine (0.081 mL, 1.323 mmol, 50.00% aqueous solution) and potassium hydroxide (0.172 g, 2.646 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 383 (0.048 g, 79.8%) as a white solid.

$^1$H NMR (400 MHz, DMSO-d$_6$) δ 9.58 (brs, 1 H), 7.67 (d, 2 H, J=8.0 Hz), 7.28-7.17 (m, 5 H), 7.11 (s, 1 H), 5.18 (d, 1 H, J=55.7 Hz), 3.72 (s, 2 H), 3.39 (s, 2 H), 2.80-2.71 (m, 2 H), 2.64 (d, 2 H, J=10.5 Hz), 2.60-2.55 (m, 2 H), 2.31-2.27 (m, 1 H), 2.17-1.89 (m, 2 H), 1.79 (t, 2 H, J=10.4 Hz), 0.89 (d, 6 H, J=5.9 Hz).

Example 173

Synthesis of Compound 384

(4-(((3R,5S)-4-(3-((3,3-difluoroazetidin-1-yl)methyl)benzyl)-3,5-dimethylpiperazin-1-yl)methyl)-N-hydroxybenzamide)

Step 1: Synthesis of Methyl 4-(((3R,5S)-4-(3-((3,3-difluoroazetidin-1-yl)methyl)benzyl)-3,5-dimethylpiperazin-1-yl)methyl)benzoate Methyl 4-(((3R,5S)-4-(3-formylbenzyl)-3,5-dimethylpiperazin-1-yl)methyl)benzoate (formula 5-1, 0.150 g, 0.394 mmol) and 3,3-difluoroazetidine hydrochloride (0.056 g, 0.434 mmol) were dissolved in methylene chloride (4 mL), and the solution was stirred at room temperature for 30 minutes. Na(OAc)$_3$BH (0.125 g, 0.591 mmol) was added to the reaction solution, which was then stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.131 g, 72.6%) as a pale yellow oil.

Step 2: Synthesis of Compound 384

Methyl 4-(((3R,5S)-4-(3-((3,3-difluoroazetidin-1-yl)methyl)benzyl)-3,5-dimethylpiperazin-1-yl)methyl)benzoate (formula 5-2, 0.058 g, 0.127 mmol), hydroxylamine (0.078 mL, 1.268 mmol, 50.00% aqueous solution) and potassium hydroxide (0.165 g, 2.535 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with ethyl acetate. The extract was filtered through a plastic filter to remove solid residue and an aqueous layer, and then concentrated under reduced pressure to afford compound 384 (0.037 g, 63.7%) as a white solid.

$^1$H NMR (400 MHz, DMSO-d$_6$) δ 7.69 (d, 2 H, J=8.2 Hz), 7.32 (d, 2 H, J=8.2 Hz), 7.27-7.24 (m, 3 H), 7.11-7.10 (m, 1 H), 3.72 (s, 2 H), 3.70 (s, 2 H), 3.58 (t, 4 H, J=12.5 Hz), 3.43 (s, 2 H), 2.65-2.63 (m, 2 H), 2.59-2.53 (m, 2 H), 1.81 (t, 2 H, J=10.6 Hz), 0.89 (d, 6 H, J=6.1 Hz); LRMS (ES) m/z 459.2 (M$^+$+1).

Example 174

Synthesis of Compound 385

(4-(((3R,5S)-4-(3-((4-benzylpiperazin-1-yl)methyl)benzyl)-3,5-dimethylpiperazin-1-yl)methyl)-N-hydroxybenzamide)

Step 1: Synthesis of Methyl 4-(((3R,5S)-4-(3-((4-benzylpiperazin-1-yl)methyl)benzyl)-3,5-dimethylpiperazin-1-yl)methyl)benzoate Methyl 4-(((3R,5S)-4-(3-formylbenzyl)-3,5-dimethylpiperazin-1-yl)methyl)benzoate (formula 5-1, 0.150 g, 0.394 mmol) and 1-benzylpiperazine (0.076 g, 0.434 mmol) were dissolved in methylene chloride (4 mL), and the solution was stirred at room temperature for 30 minutes. Na(OAc)$_3$BH (0.125 g, 0.591 mmol) was added to the reaction solution, which was then stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.158 g, 74.1%) as a pale yellow oil.

Step 2: Synthesis of Compound 385

Methyl 4-(((3R,5S)-4-(3-((4-benzylpiperazin-1-yl)methyl)benzyl)-3,5-dimethylpiperazin-1-yl)methyl)benzoate (formula 5-2, 0.095 g, 0.176 mmol), hydroxylamine (0.107 mL, 1.757 mmol, 50.00% aqueous solution) and potassium hydroxide (0.229 g, 3.514 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 385 (0.084 g, 88.3%) as a white solid.

$^1$H NMR (400 MHz, DMSO-d$_6$) δ 7.67 (d, 2 H, J=8.2 Hz), 7.33-7.22 (m, 10 H), 7.09-7.07 (m, 1 H), 3.71 (s, 2 H), 3.45 (s, 2 H), 3.44 (s, 2 H), 3.40 (s, 2 H), 2.65-2.62 (m, 2 H), 2.56-2.52 (m, 2 H), 2.37-2.34 (m, 8 H), 1.79 (t, 2 H, J=10.5 Hz), 0.89 (d, 6 H, J=5.9 Hz); LRMS (ES) m/z 542.3 (M$^+$+1).

Example 175

Synthesis of Compound 386

(N-hydroxy-4-(((3R,5S)-4-(3-((4-(2-hydroxy-2-methylpropyl)piperazin-1-yl)methyl)benzyl)-3,5-dimethylpiperazin-1-yl)methyl)benzamide)

Step 1: Synthesis of Tert-Butyl 4-(3-(((2S,6R)-4-(4-(methoxycarbonyl)benzyl)-2,6-dimethylpiperazin-1-yl)methyl)benzyl)piperazine-1-carboxylate Methyl 4-(((3R,5S)-4-(3-formylbenzyl)-3,5-dimethylpiperazin-1-yl)methyl)benzoate (formula 5-1, 0.500 g, 1.314 mmol) and tert-butyl piperazine-1-carboxylate (0.269 g, 1.446 mmol) were dissolved in methylene chloride (10 mL), and the solution was stirred at room temperature for 30 minutes. Na(OAc)$_3$BH (0.418 g, 1.971 mmol) was added to the reaction solution, which was then stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.303 g, 41.9%) as a yellow oil.

Step 2: Synthesis of Methyl 4-(((3R,5S)-3,5-dimethyl-4-(3-(piperazin-1-ylmethyl)benzyl)piperazin-1-yl)methyl)benzoate Tert-butyl 4-(3-(((2S,6R)-4-(4-(methoxycarbonyl)benzyl)-2,6-dimethylpiperazin-1-yl)methyl)benzyl)piperazine-1-carboxylate (formula 7-1, 0.303 g, 0.550 mmol) was dissolved in 1,4-dioxane (5 mL) at room temperature, and HCl (4.00 M 1,4-dioxane solution, 1.375 mL, 5.502 mmol) was added to the solution, which was then stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The product was used without additional purification (0.235 g, 94.8%, yellow oil).

Step 3: Synthesis of Ethyl 4-(((3R,5S)-4-(3-((4-(2-hydroxy-2-methylpropyl)piperazin-1-yl)methyl)benzyl)-3,5-dimethylpiperazin-1-yl)methyl)benzoate Methyl 4-(((3R,5S)-3,5-dimethyl-4-(3-(piperazin-1-ylmethyl)benzyl)piperazin-1-yl)methyl)benzoate (formula 7-2, 0.190 g, 0.422 mmol), isobutylene oxide (0.380 mL, 4.216 mmol) and $K_2CO_3$ (0.583 g, 4.216 mmol) were added to ethanol (5 mL), and heated by microwave irradiation at 110° C. for 20 minutes, followed by cooling to room temperature to terminate the reaction. Then, a saturated aqueous solution of sodium hydrogen carbonate was added to the reaction mixture, followed by extraction with ethyl acetate. The organic layer was washed with a saturated aqueous solution of sodium chloride, dried with anhydrous magnesium sulfate, and then filtered and concentrated under reduced pressure. The product was used without additional purification (0.196 g, 84.2%, yellow oil).

Step 4: Synthesis of Compound 386

Ethyl 4-(((3R,5S)-4-(3-((4-(2-hydroxy-2-methylpropyl)piperazin-1-yl)methyl)benzyl)-3,5-dimethylpiperazin-1-yl)methyl)benzoate (formula 7-3, 0.050 g, 0.093 mmol), hydroxylamine (0.057 mL, 0.932 mmol, 50.00% aqueous solution) and potassium hydroxide (0.121 g, 1.863 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 386 (0.032 g, 65.6%) as a white solid.
$^1H$ NMR (400 MHz, DMSO-$d_6$) δ 11.17 (brs, 1 H) 9.01 (brs, 1 H) 7.70 (d, 2 H, J=8.0 Hz), 7.34 (d, 2 H, J=7.8 Hz), 7.27 (s, 1 H), 7.23-7.21 (m, 1 H), 7.09 (d, 1 H, J=6.6 Hz), 4.06 (brs, 1 H) 3.72 (s, 2 H), 3.43 (s, 2 H), 3.42 (s, 2 H), 2.65-2.62 (m, 2 H), 2.55-2.54 (m, 2 H).

Example 176

Synthesis of Compound 387

(4-(((3R,5S)-4-(3-((4-(2-fluoro-2-methylpropyl)piperazin-1-yl)methyl)benzyl)-3,5-dimethylpiperazin-1-yl)methyl)-N-hydroxybenzamide)

Step 1: Synthesis of Ethyl 4-(((3R,5S)-4-(3-((4-(2-hydroxy-2-methylpropyl)piperazin-1-yl)methyl)benzyl)-3,5-dimethylpiperazin-1-yl)methyl)benzoate Ethyl 4-(((3R,5S)-4-(3-((4-(2-hydroxy-2-methylpropyl)piperazin-1-yl)methyl)benzyl)-3,5-dimethylpiperazin-1-yl)methyl)benzoate (formula 7-3, 0.150 g, 0.287 mmol) was dissolved in methylene chloride (5 mL), and DAST (0.042 mL, 0.316 mmol) was added thereto at 0° C. The mixture was stirred at the same temperature for 30 minutes, and then stirred at room temperature for 1 hour. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 12 g cartridge; methanol/methylene chloride=from 0% to 5%) and concentrated to afford the desired compound (0.098 g, 63.4%) as a yellow oil.

Step 2: Synthesis of Compound 387

Ethyl 4-(((3R,5S)-4-(3-((4-(2-hydroxy-2-methylpropyl)piperazin-1-yl)methyl)benzyl)-3,5-dimethylpiperazin-1-yl)methyl)benzoate (formula 7-4, 0.098 g, 0.177 mmol), hydroxylamine (0.108 mL, 1.770 mmol, 50.00% aqueous solution) and potassium hydroxide (0.230 g, 3.540 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter equipped with an anhydrous sodium sulfate cartridge to remove solid residue and an aqueous layer, and then concentrated under reduced pressure to afford compound 387 (0.089 g, 93.0%) as an apricot solid.
$^1H$ NMR (400 MHz, DMSO-$d_6$) δ 7.68 (d, 2 H, J=7.9 Hz), 7.29 (d, 3 H, J=7.7 Hz), 7.23-7.21 (m, 2 H), 7.09-7.08 (m, 1 H), 3.72 (s, 2 H), 3.43 (s, 2 H), 3.41 (s, 2 H), 2.65-2.62 (m, 2 H), 2.56-2.54 (m, 2 H), 2.47-2.43 (m, 4 H), 2.40 (d, 2 H, J=23.3 Hz), 2.35-2.33 (m, 4 H), 1.80 (t, 2 H, J=10.4 Hz), 1.32 (s, 3 H), 1.26 (s, 3 H), 0.90 (d, 6 H, J=6.0 Hz); LRMS (ES) m/z 526.3 ($M^+$+1).

Example 177

Synthesis of Compound 388

(4-(((3R,5S)-4-(4-((1-(2-fluoro-2-methylpropyl)piperidin-4-yl)methoxy)benzyl)-3,5-dimethylpiperazin-1-yl)methyl)-N-hydroxybenzamide Step 1: Synthesis of Tert-Butyl 4-((4-(hydroxymethyl)phenoxy)methyl)piperidine-1-carboxylate 4-(hydroxymethyl)phenol (0.500 g, 4.028 mmol), tert-butyl 4-((methylsulfonyloxy)methyl)piperidine-1-carboxylate (formula 12-1, 1.300 g, 4.430 mmol), $Cs_2CO_3$ (1.968 g, 6.042 mmol) and NaI (0.030 g, 0.201 mmol) were mixed in acetonitrile (20 mL) at room temperature, and the mixture was heated under reflux for 17 hours. Then, water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 0% to 50%) and concentrated to afford the desired compound (0.552 g, 42.6%) as a colorless oil.

Step 2: Synthesis of Tert-Butyl 4-((4-(chloromethyl)phenoxy)methyl)piperidine-1-carboxylate Tert-butyl 4-((4-(hydroxymethyl)phenoxy)methyl)piperidine-1-carboxylate (formula 12-2, 0.500 g, 1.556 mmol) and TEA (0.434 mL, 3.111 mmol) were dissolved in methylene chloride (30 mL) at 0° C., and methanesulfonyl chloride (0.132 mL, 1.711 mmol) was added to the solution, followed by stirring at the same temperature for 2 hours. Then, water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 0% to 40%) and concentrated to afford the desired compound (0.136 g, 25.7%) as a white solid.

Step 3: Synthesis of Tert-Butyl 4-((4-(((2S,6R)-4-(4-(methoxycarbonyl)benzyl)-2,6-dimethylpiperazin-1-yl)methyl)phenoxy)methyl)piperidine-1-carboxylate Methyl 4-(((3R,5S)-3,5-dimethylpiperazin-1-yl)methyl)benzoate (formula 1-2, 0.100 g, 0.381 mmol), tert-butyl 4-((4-(chloromethyl)phenoxy)methyl)piperidine-1-carboxylate (formula 12-3, 0.130 g, 0.381 mmol), $Cs_2CO_3$ (0.186 g, 0.572 mmol) and NaI (0.003 g, 0.019 mmol) were mixed in acetonitrile (5 mL) at room temperature, and the mixture was heated under reflux for 3 hours, and then cooled to room temperature. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; ethyl acetate/hexane=from 10% to 60%) and concentrated to afford the desired compound (0.130 g, 60.3%) as a yellow oil.

Step 4: Synthesis of Methyl 4-(((3R,5S)-3,5-dimethyl-4-(4-(piperidin-4-ylmethoxy)benzyl)piperazin-1-yl)methyl)benzoate (hydrochloride salt)

Tert-butyl 4-((4-(((2S,6R)-4-(4-(methoxycarbonyl)benzyl)-2,6-dimethylpiperazin-1-yl)methyl)phenoxy)methyl)piperidine-1-carboxylate (formula 12-4, 0.150 g, 0.265 mmol) was dissolved in 1,4-dioxane (5 mL) at room temperature, and HCl (4.00 M solution in 1,4-dioxane, 1.326 mL, 5.303 mmol) was added to the solution, followed by stirring at the same temperature for 17 hours. The precipitated solid was washed with diethyl ether and dried to yield the desired compound (0.126 g, 94.6%) as a white solid.

Step 5: Synthesis of Ethyl 4-(((3R,5S)-4-(4-((1-(2-hydroxy-2-methylpropyl)piperidin-4-yl)methoxy)benzyl)-3,5-dimethylpiperazin-1-yl)methyl)benzoate Methyl 4-(((3R,5S)-3,5-dimethyl-4-(4-(piperidin-4-ylmethoxy)benzyl)piperazin-1-yl)methyl)benzoate hydrochloride (formula 12-5, 0.102 g, 0.203 mmol), 1,1-dimethyloxirane (0.073 g, 1.016 mmol) and $K_2CO_3$ (0.281 g, 2.032 mmol) were added to ethanol (3 mL), and heated by microwave irradiation at 110° C. for 20 minutes, followed by cooling to room temperature. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The product was used without additional purification (0.102 g, 93.4%, pale yellow oil).

Step 6: Synthesis of Ethyl 4-(((3R,5S)-4-(4-((1-(2-fluoro-2-methylpropyl)piperidin-4-yl)methoxy)benzyl)-3,5-dimethylpiperazin-1-yl)methyl)benzoate Ethyl 4-(((3R,5S)-4-(4-((1-(2-hydroxy-2-methylpropyl)piperidin-4-yl)methoxy)benzyl)-3,5-dimethylpiperazin-1-yl)methyl)benzoate (formula 12-6, 0.102 g, 0.185 mmol) was dissolved in methylene chloride (5 mL), and DAST (0.027 mL, 0.203 mmol) was added thereto at 0° C. The mixture was stirred at the same temperature for 30 minutes, and then stirred at room temperature for 1 hour. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The product was used without additional purification (0.083 g, 81.1%, pale brown oil).

Step 7: Synthesis of Compound 388

Ethyl 4-(((3R,5S)-4-(4-((1-(2-fluoro-2-methylpropyl)piperidin-4-yl)methoxy)benzyl)-3,5-dimethylpiperazin-1-yl)methyl)benzoate (formula 12-7, 0.083 g, 0.150 mmol), hydroxylamine (0.092 mL, 1.499 mmol, 50.00% aqueous solution) and potassium hydroxide (0.195 g, 2.998 mmol) were dissolved in methanol (5 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was filtered through a plastic filter to remove solid residue and an aqueous layer, and then concentrated under reduced pressure to afford compound 388 (0.073 g, 90.1%) as an apricot solid.

$^1$H NMR (400 MHz, DMSO-$d_6$) δ 7.68 (d, 2 H, J=8.2 Hz), 7.29 (d, 2 H, J=8.1 Hz), 7.21 (d, 2 H, J=8.6 Hz), 6.84 (d, 2 H, J=8.6 Hz), 3.77 (d, 2 H, J=5.9 Hz), 3.68 (s, 2 H), 3.40 (s, 2 H), 2.91 (d, 2 H, J=11.5 Hz), 2.62 (d, 2 H, J=9.8 Hz), 2.55-2.53 (m, 2 H), 2.41 (d, 2 H, J=22.9 Hz), 2.08 (t, 2 H, J=10.8 Hz), 1.81-1.69 (m, 6 H), 1.33 (s, 3 H), 1.29 (s, 4 H), 0.92 (d, 6 H, J=6.1 Hz); LRMS (ES) m/z 541.3 (M$^+$+1).

Example 178

Synthesis of Compound 396

(4-(((2S,6R)-4-(3-(furan-3-yl)benzyl)-2,6-dimethylpiperazin-1-yl)methyl)-N-hydroxybenzamide)

Step 1: Synthesis of Methyl 4-(((2S,6R)-4-(3-(furan-3-yl)benzyl)-2,6-dimethylpiperazin-1-yl)methyl)benzoate 1,2-dimethoxyethane (1 ml)/water (0.5 ml) were added to a mixture of methyl 4-(((2S,6R)-4-(3-iodobenzyl)-3,5-dimethylpiperazin-1-yl)methyl)benzoate (formula 14-1, 0.100 g, 0.209 mmol), furan-3-ylboronic acid (0.028 g, 0.251 mmol), Pd(dbpf)Cl$_2$ (0.007 g, 0.010 mmol) and Na$_2$CO$_3$ (0.066 g, 0.627 mmol), and the solution was heated by microwaves at 120° C. for 20 minutes, and then filtered through celite and concentrated under reduced pressure. The concentrate was purified by column chromatography (silicon dioxide, 12 g cartridge; methanol/methylene chloride=from 0% to 5%) and concentrated to afford the desired compound (0.051 g, 58.3%) as a white solid.

Step 2: Synthesis of Compound 396

Methyl 4-(((2S,6R)-4-(3-(furan-3-yl)benzyl)-2,6-dimethylpiperazin-1-yl)methyl)benzoate (formula 14-2, 0.030 g, 0.072 mmol), hydroxylamine (0.088 mL, 1.434 mmol, 50.00% aqueous solution) and potassium hydroxide (0.040 g, 0.717 mmol) were mixed in methanol (0.5 mL) at room temperature, and the mixture was stirred at the same temperature for 1 hours. Then, water was added to the reaction mixture, followed by extraction with methylene chloride. The organic layer was washed with a saturated aqueous solution of sodium hydrogen carbonate, dried with anhydrous magnesium sulfate, and then concentrated under reduced pressure to yield compound 396 (0.020 g, 66.5%) as a white solid.

$^1$H NMR (400 MHz, DMSO-$d_6$) δ 8.18 (s, 1 H), 7.73 (s, 1 H), 7.64 (d, 2 H, J=8.0 Hz), 7.49-7.47 (m, 2 H), 7.34-7.18 (m, 4 H), 6.94 (d, 1 H, J=0.96 Hz), 3.72 (s, 2 H), 3.41 (s, 2 H), 2.68-2.65 (m, 2 H), 2.55-2.51 (m, 2 H), 1.84-1.79 (m, 2 H), 0.91 (s, 3 H), 0.89 (s, 3 H).

Example 179

Synthesis of Compound 400

(4-(((2S,6R)-4-((4',4'-dimethyl-2',3',4',5'-tetrahydro-[1,1'-biphenyl]-4-yl)methyl)-2,6-dimethylpiperazin-1-yl)methyl)-N-hydroxybenzamide)

Step 1: Synthesis of Methyl 4-(((2S,6R)-4-((4',4'-dimethyl-2',3',4',5'-tetrahydro-[1,1'-biphenyl]-4-yl)methyl)-2,6-dimethylpiperazin-1-yl)methyl)benzoate 1,2-Dimethoxyethane (1 ml)/water (0.5 ml) were added to a mixture of methyl 4-(((2S,6R)-4-(4-iodobenzyl)-2,6-dimethylpiperazin-1-yl)methyl)benzoate (formula 14-1, 0.100 g, 0.209 mmol), (4,4-dimethylcyclohex-1-en-1-yl)boronic acid (0.038 g, 0.251 mmol), Pd(dbpf)Cl$_2$ (0.007 g, 0.010 mmol) and Na$_2$CO$_3$ (0.066 g, 0.627 mmol), and the solution was heated by microwaves at 120° C. for 20 minutes, after which it was filtered through celite, and then concentrated under reduced pressure. The concentrate was purified by column chromatography (silicon dioxide, 12 g cartridge; methanol/methylene chloride=from 0% to 5%) and concentrated to afford the desired compound (0.05 g, 51.9%) as a pale brown solid.

Step 2: Synthesis of Compound 400

Methyl 4-(((2S,6R)-4-((4',4'-dimethyl-2',3',4',5'-tetrahydro-[1,1'-biphenyl]-4-yl)methyl)-2,6-dimethylpiperazin-1-yl)methyl)benzoate (formula 14-3, 0.030 g, 0.065 mmol), hydroxylamine (0.080 mL, 1.303 mmol, 50.00% aqueous solution) and potassium hydroxide (0.037 g, 0.651 mmol) were mixed in methanol (0.5 mL) at room temperature, and the mixture was stirred at the same temperature for 1 hours. Then, water was added to the reaction mixture, followed by extraction with methylene chloride. The organic layer was washed with a saturated aqueous solution of sodium hydrogen carbonate, dried with anhydrous magnesium sulfate, and then concentrated under reduced pressure to yield compound 400 (0.023 g, 76.5%) as a pale yellow solid.

$^1$H NMR (400 MHz, DMSO-$d_6$) δ 7.64 (d, 2 H, J=7.9 Hz), 7.36 (d, 2 H, J=8.1 Hz), 7.24-7.20 (m, 4 H), 6.09 (brs, 1 H), 3.71 (s, 2 H), 2.64-2.51 (m, 4 H), 2.37 (brs, 2 H), 1.97 (brs, 2 H), 1.80-1.75 (m, 2 H), 1.49-1.46 (m, 2 H), 0.93-0.89 (m, 12 H).

Example 180

Synthesis of Compound 401

(4-(((2S,6R)-4-(4-(3,6-dihydro-2H-pyran-4-yl)benzyl)-2,6-dimethylpiperazin-1-yl)methyl)-N-hydroxybenzamide)

Step 1: Synthesis of Methyl 4-(((2S,6R)-4-(4-(3,6-dihydro-2H-pyran-4-yl)benzyl)-2,6-dimethylpiperazin-1-yl)methyl)benzoate 1,2-Dimethoxyethane (1 ml)/water (0.5 ml) were added to a mixture of methyl 4-(((2S,6R)-4-(4-iodobenzyl)-2,6-dimethylpiperazin-1-yl)methyl)benzoate (formula 14-1, 0.100 g, 0.209 mmol), (3,6-dihydro-2H-pyran-4-yl)boronic acid (0.032 g, 0.251 mmol), Pd(dbpf)Cl$_2$ (0.007 g, 0.010 mmol) and Na$_2$CO$_3$ (0.066 g, 0.627 mmol), and then heated by microwaves at 120° C. for 20 minutes. The reaction solution was filtered through celite, and the filtrate was concentrate under reduced pressure. The concentrate was purified by column chromatography (silicon dioxide, 12 g cartridge; methanol/methylene chloride=from 0% to 5%) and concentrated to afford the desired compound (0.029 g, 31.9%) as a pale brown solid.

Step 2: Synthesis of Compound 401

Methyl 4-(((2S,6R)-4-(4-(3,6-dihydro-2H-pyran-4-yl)benzyl)-2,6-dimethylpiperazin-1-yl)methyl)benzoate (formula 14-2, 0.025 g, 0.058 mmol), hydroxylamine (0.070 mL, 1.151 mmol, 50.00% aqueous solution) and potassium hydroxide (0.032 g, 0.575 mmol) were mixed in methanol (0.5 mL) at room temperature, and the mixture was stirred at the same temperature for 1 hours. Then, water was added to the reaction mixture, followed by extraction with methylene chloride. The organic layer was washed with a saturated aqueous solution of sodium hydrogen carbonate, dried with anhydrous magnesium sulfate, and then concentrated under reduced pressure to yield compound 401 (0.011 g, 43.9%) as a pale yellow solid.

$^1$H NMR (400 MHz, DMSO-$d_6$) δ 7.66 (d, 2 H, J=8.12 Hz), 7.40-7.36 (m, 4 H), 7.25 (d, 2 H, J=8.12 Hz), 6.23 (brs, 1 H), 4.21 (s, 2 H), 3.81 (t, 2 H, J=5.3 Hz), 3.73 (s, 2 H), 3.39 (s, 2 H), 2.66-2.54 (m, 4 H), 2.47-2.43 (m, 2 H), 1.82-1.76 (m, 2 H), 0.88 (s, 3H), 0.87 (s, 3 H).

Example 181

Synthesis of Compound 402

(4-(((3R,5S)-3,5-dimethyl-4-(tetrahydrofuran-2-carbonyl)piperazin-1-yl)methyl)-N-hydroxybenzamide)

Step 1: Synthesis of (3R,5S)-tert-butyl 4-(furan-2-carbonyl)-3,5-dimethylpiperazine-1-carboxylate (3R,5S)-tert-butyl 3,5-dimethylpiperazine-1-carboxylic acid (formula 8-1, 0.500 g, 2.333 mmol), furan-2-carbonyl chloride (0.276 mL, 2.800 mmol) and TEA (0.976 mL, 7.000 mmol) were dissolved in methylene chloride (10 mL) at 0° C., and the solution was stirred at the same temperature for 1 hour. Then, water was added to the reaction solution, followed by extraction with ethyl acetate. The organic layer was washed with a saturated aqueous solution of sodium hydrogen carbonate, dried with anhydrous magnesium sulfate, filtered, and then concentrated under reduced pressure. The concentrate was purified by column chromatography (silicon dioxide, 12 g cartridge; ethyl acetate/hexane=from 0% to 30%) and concentrated to afford the desired compound (0.620 g, 86.2%) as a colorless oil.

Step 2: Synthesis of (3R,5S)-tert-butyl 3,5-dimethyl-4-(tetrahydrofuran-2-carbonyl)piperazine-1-carboxylate (3R,5S)-tert-butyl 4-(furan-2-carbonyl)-3,5-dimethylpiperazine-1-carboxylate (formula 11-1, 0.100 g, 0.324 mmol) was dissolved in ethanol/water (8:1) (2 mL) at room temperature, and Pd/C (0.010 g) was slowly added thereto. Then, a hydrogen balloon was placed over the solution, followed by stirring at the same temperature for 2 hours. The reaction mixture was filtered through a celite pad to remove solids, and the filtrate was concentrated under reduced pressure to remove the solvent. The product was used without additional purification (0.100 g, 98.7%, colorless oil).

Step 3: Synthesis of ((2S,6R)-2,6-dimethylpiperazin-1-yl)(tetrahydrofuran-2-yl)methanone (hydrochloride salt)

(3R,5S)-tert-butyl 3,5-dimethyl-4-(tetrahydrofuran-2-carbonyl)piperazine-1-carboxylate (formula 11-2, 0.540 g, 1.729 mmol) and HCl (4.00 M 1,4-dioxane solution, 8.643 mL, 34.571 mmol) were dissolved in 1,4-dioxane (20 mL) at room temperature, and the solution was stirred at the same temperature for 17 hours. The reaction mixture was concentrated under reduced pressure to remove the solvent, and the product was used without additional purification (0.400 g, 109.0%, colorless oil).

Step 4: Synthesis of Methyl 4-(((3R,5S)-3,5-dimethyl-4-(tetrahydrofuran-2-carbonyl)piperazin-1-yl)methyl)benzoate ((2S,6R)-2,6-dimethylpiperazin-1-yl) (tetrahydrofuran-2-yl)methanone hydrochloride (formula 11-3, 0.400 g, 1.608 mmol), methyl 4-(bromomethyl)benzoate (formula 1-1, 0.368 g, 1.608 mmol) and $Cs_2CO_3$ (1.572 g, 4.824 mmol) were dissolved in acetonitrile (15 mL) at room temperature, and the solution was stirred at the same temperature for 17 hours. The reaction mixture was filtered through a glass filter to remove solids, and the filtrate was concentrated under reduced pressure. The concentrate was purified by column chromatography (silicon dioxide, 12 g cartridge; ethyl acetate/hexane=from 0% to 40%) and concentrated to afford the desired compound (0.196 g, 33.8%) as a colorless oil.

Step 5: Synthesis of Compound 402

Methyl 4-(((3R,5S)-3,5-dimethyl-4-(tetrahydrofuran-2-carbonyl)piperazin-1-yl)methyl)benzoate (0.140 g, 0.388 mmol), hydroxylamine (0.238 mL, 3.884 mmol, 50.00% aqueous solution) and potassium hydroxide (0.436 g, 7.768 mmol) were dissolved in methanol (4 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 402 (0.067 g, 47.7%) as an apricot solid.

$^1$H NMR (400 MHz, DMSO-$d_6$) δ 11.10 (brs, 1 H) 9.00 (brs, 1 H) 7.73 (d, 2 H, J=8.1 Hz), 7.43 (d, 2 H, J=8.0 Hz), 4.63-4.56 (m, 1 H), 4.37-4.35 (m, 2 H), 3.75-3.72 (m, 2 H), 3.35 (s, 2 H), 2.65-2.62 (m, 2 H), 2.11-2.09 (m, 3 H), 1.88-1.80 (m, 3 H), 1.35-1.21 (m, 6 H), 1.35-1.21 (m, 6 H); LRMS (ES) m/z 362.1 ($M^+$+1).

Example 182

Synthesis of Compound 403

(4-(((3R,5S)-3,5-dimethyl-4-(1H-pyrazole-3-carbonyl)piperazin-1-yl)methyl)-N-hydroxybenzamide)

Step 1: Synthesis of Methyl 4-(((3R,5S)-3,5-dimethyl-4-(1H-pyrazole-3-carbonyl)piperazin-1-yl)methyl)benzoate Methyl 4-(((3R,5S)-3,5-dimethylpiperazin-1-yl)methyl)benzoate (formula 1-2, 0.100 g, 0.381 mmol), 1H-pyrazole-3-carboxylic acid (0.047 g, 0.419 mmol), HATU (0.290 g, 0.762 mmol) and DIPEA (0.333 mL, 1.906 mmol) were dissolved in N,N-dimethylformamide (3 mL) at room temperature, and the solution was stirred at the same temperature for 17 hours. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure. The product was used without additional purification (0.150 g, 110.4%, yellow oil).

Step 2: Synthesis of Compound 403

Methyl 4-(((3R,5S)-3,5-dimethyl-4-(1H-pyrazole-3-carbonyl)piperazin-1-yl)methyl)benzoate (formula 1-3, 0.150 g, 0.421 mmol), hydroxylamine (0.257 mL, 4.209 mmol, 50.00% aqueous solution) and potassium hydroxide (0.472 g, 8.417 mmol) were dissolved in methanol (4 mL) at room temperature, and the solution was stirred at the same temperature for 1 hour. The reaction mixture was concentrated under reduced pressure to remove the solvent, and a saturated aqueous solution of sodium hydrogen carbonate (20 mL) and methylene chloride (10 mL) were added to the concentrate, followed by stirring. The precipitated solid was filtered, washed with water, and dried to yield compound 403 (0.046 g, 30.6%) as a white solid.

$^1$H-NMR (400 MHz, DMSO-$d_6$) δ 13.12 (brs, 1 H), 11.19 (brs, 1 H), 3.02 (brs 1 H),7.79 (s, 1 H), 7.73 (d, 2 H, J=8.2 Hz), 7.45 (d, 2 H, J=8.3 Hz), 6.54 (d, 1 H, J=2.0 Hz), 4.69 (brs, 1 H), 3.55 (s, 2 H), 2.68-2.65 (m, 2 H), 2.16-2.12 (m, 2 H), 1.35 (d, 6 H, J=6.7 Hz); LRMS (ES) m/z 358.2 ($M^+$+1).

Example 183

Synthesis of Compound 404

(4-(((3R,5S)-3,5-dimethyl-4-(pyrazine-2-carbonyl)piperazin-1-yl)methyl)-N-hydroxybenzamide)

Step 1: Synthesis of Methyl 4-(((3R,5S)-3,5-dimethyl-4-(pyrazine-2-carbonyl)piperazin-1-yl)methyl)benzoate Methyl 4-(((3R,5S)-3,5-dimethylpiperazin-1-yl)methyl)benzoate (formula 1-2, 0.100 g, 0.381 mmol), pyrazine-2-carboxylic acid (0.052 g, 0.419 mmol), HATU (0.290 g, 0.762 mmol) and DIPEA (0.333 mL, 1.906 mmol) were dissolved in N,N-dimethylformamide (3 mL) at room temperature, and the solution was stirred at the same temperature for 17 hours. Then, the reaction mixture was concentrated under reduced pressure to remove the solvent, and a saturated aqueous solution of sodium hydrogen carbonate was added to the concentrate, followed by extraction with methylene chloride. The extract was filtered through a plastic filter to remove solid residue and an aqueous layer, and then concentrated under reduced pressure. The product was used without additional purification (0.150 g, 106.8%, brown oil).

Step 2: Synthesis of Compound 404

Methyl 4-(((3R,5S)-3,5-dimethyl-4-(pyrazine-2-carbonyl)piperazin-1-yl)methyl)benzoate (formula 1-3, 0.150 g, 0.408 mmol), hydroxylamine (0.250 mL, 4.082 mmol, 50.00% aqueous solution) and potassium hydroxide (0.458 g, 8.165 mmol) were dissolved in methanol (4 mL) at room temperature, and the solution was stirred at the same temperature for 1 hour. Then, the reaction mixture was concentrated under reduced pressure to remove the solvent, and a saturated aqueous solution of sodium hydrogen carbonate was added to the concentrate, followed by extraction with methylene chloride. The extract was filtered through a plastic filter to remove solid residue and an aqueous layer, and then concentrated under reduced pressure. The concentrate was purified by column chromatography (Waters, $C_{18}$; 0.1% trifluoroacetic acid aqueous solution/acetonitrile=from 5% to 80%), after which it was passed through a SPE cartridge (PL-HCO$_3$ MP SPE) and concentrated to afford compound 404 (0.043 g, 28.6%) as a white solid.

$^1$H-NMR (400 MHz, CD$_3$OD) δ 8.85 (d, 1 H, J=1.5 Hz), 8.75 (d, 1 H, J=2.5 Hz), 8.65 (dd, 1 H, J=2.6, 1.6 Hz), 7.82 (d, 2 H, J=8.2 Hz), 7.60 (d, 2 H, J=8.2 Hz), 4.10 (brs, 2 H), 3.18 (brs, 2 H), 2.85 (brs, 2 H), 1.52 (d, 6 H, J=7.1 Hz); LRMS (ES) m/z 370.1 (M$^+$+1)

Example 184

Synthesis of Compound 405

(N-hydroxy-4-(((3R,5S)-4-isonicotinoyl-3,5-dimethylpiperazin-1-yl)methyl)benzamide)

Step 1: Synthesis of Methyl 4-(((3R,5S)-4-isonicotinoyl-3,5-dimethylpiperazin-1-yl)methyl) benzoate Methyl 4-(((3R,5S)-3,5-dimethylpiperazin-1-yl)methyl)benzoate (formula 1-2, 0.100 g, 0.381 mmol) and TEA (0.159 mL, 1.144 mmol) were dissolved in methylene chloride (4 mL) at room temperature, and isonicotinoyl chloride (0.081 g, 0.572 mmol) was added to the solution, followed by stirring at the same temperature for 1 hour. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, and then concentrated under reduced pressure. The product was used without additional purification (0.150 g, 107.1%, pale yellow oil).

Step 2: Synthesis of Compound 405

Methyl 4-(((3R,5S)-4-isonicotinoyl-3,5-dimethylpiperazin-1-yl)methyl)benzoate (formula 1-3, 0.150 g, 0.408 mmol), hydroxylamine (0.250 mL, 4.082 mmol, 50.00% aqueous solution) and potassium hydroxide (0.458 g, 8.165 mmol) were dissolved in methanol (4 mL) at room temperature, and the solution was stirred at the same temperature for 1 hour. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure. The concentrate was purified by column chromatography (Waters, $C_{18}$; 0.1% trifluoroacetic acid aqueous solution/acetonitrile=from 5% to 80%), after which it was passed through a SPE cartridge (PL-HCO$_3$ MP SPE) and concentrated to afford compound 405 (0.043 g, 28.6%) as a white solid.

$^1$H NMR (400 MHz, CD$_3$OD) δ 8.73 (d, 2 H, J=6.2 Hz), 7.79 (d, 2 H, J=8.2 Hz), 7.60-7.55 (m, 4 H), 3.89 (brs, 2 H), 2.96 (brs, 2 H), 2.61 (brs, 2 H), 1.45 (d, 6 H, J=6.0 Hz); LRMS (ES) m/z 369.1 (M$^+$+1).

Example 185

Synthesis of Compound 411

(4-(((3R,5S)-4-(4-(((R)-3-fluoropyrrolidin-1-yl)methyl)benzyl)-3,5-dimethylpiperazin-1-yl)methyl)-N-hydroxybenzamide)

Step 1: Synthesis of Methyl 4-(((3R,5S)-4-(4-(((R)-3-fluoropyrrolidin-1-yl)methyl)benzyl)-3,5-dimethylpiperazin-1-yl)methyl)benzoate Methyl 4-(((3R,5S)-4-(4-formylbenzyl)-3,5-dimethylpiperazin-1-yl)methyl)benzoate (formula 5-1, 0.100 g, 0.263 mmol) was dissolved in methylene chloride (1 mL) at room temperature, and (R)-3-fluoropyrrolidine (0.036 g, 0.289 mmol) was added to the mixture, followed by stirring for 30 minutes. Na(OAc)$_3$BH (0.061 g, 0.289 mmol) was added to the mixture, which was then stirred overnight at the same temperature. Then, water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 5%) and concentrated to afford the desired compound (0.059 g, 49.7%) as a pale brown solid.

Step 2: Synthesis of Compound 411

Methyl 4-(((3R,5S)-4-(4-(((R)-3-fluoropyrrolidin-1-yl)methyl)benzyl)-3,5-dimethylpiperazin-1-yl)methyl)benzoate (formula 5-2, 0.059 g, 0.130 mmol), hydroxylamine (0.159 mL, 2.601 mmol, 50.00% aqueous solution) and potassium hydroxide (0.073 g, 1.301 mmol) were dissolved in methanol (1 mL) at room temperature, and the solution was stirred at the same temperature for 2 hours. Then, the reaction mixture was concentrated under reduced pressure to remove the solvent, and a saturated aqueous solution of sodium hydrogen carbonate (10 mL) was added to the concentrate, followed by stirring. The precipitated solid was filtered, washed with water, and dried to yield compound 411 (0.011 g, 17.8%) as a white solid.

$^1$H NMR (400 MHz, DMSO-$d_6$) δ 7.67 (d, 1 H, J=11.2 Hz), 7.43-7.20 (m, 6 H), 5.25-5.11 (m, 1 H), 3.72 (s, 2 H), 3.55 (s, 2 H), 3.43 (s, 2 H), 2.81-2.53 (m, 7 H), 2.35-2.08 (m, 2 H), 1.90-1.78 (m, 3 H), 0.91-0.89 (m, 6 H).

Example 186

Synthesis of Compound 412

(4-(((3R,5S)-4-(4-((3,3-difluoroazetidin-1-yl)methyl)benzyl)-3,5-dimethylpiperazin-1-yl)methyl)-N-hydroxybenzamide)

Step 1: Synthesis of Methyl 4-(((3R,5S)-4-(4-((3,3-difluoroazetidin-1-yl)methyl)benzyl)-3,5-dimethyl-piperazin-1-yl)methyl)benzoate Methyl 4-(((3R,5S)-4-(4-formylbenzyl)-3,5-dimethylpiperazin-1-yl)methyl)benzoate (formula 5-1, 0.100 g, 0.263 mmol) was dissolved in methylene chloride (1 mL) at room temperature, and 3,3-difluoroazetidine (0.037 g, 0.289 mmol) was added to the mixture, followed by stirring for 30 minutes. Na(OAc)$_3$BH (0.061 g, 0.289 mmol) was added to the reaction mixture, which was stirred overnight at the same temperature. Then, water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 5%) and concentrated to afford the desired compound (0.073 g, 60.6%) as a white solid.

Step 2: Synthesis of Compound 412

Methyl 4-(((3R,5S)-4-(4-((3,3-difluoroazetidin-1-yl)methyl)benzyl)-3,5-dimethylpiperazin-1-yl)methyl)benzoate (formula 5-2, 0.073 g, 0.160 mmol), hydroxylamine (0.195 mL, 3.191 mmol, 50.00% aqueous solution) and potassium hydroxide (0.090 g, 1.595 mmol) were dissolved in methanol (1 mL) at room temperature, and the solution was stirred at the same temperature for 2 hours. Then, the reaction mixture was concentrated under reduced pressure to remove the solvent, and a saturated aqueous solution of sodium hydrogen carbonate (10 mL) was added to the concentrate, followed by stirring. The precipitated solid was filtered, washed with water, and dried to yield compound 412 (0.014 g, 18.9%) asa white solid.

$^1$H NMR (400 MHz, DMSO-$d_6$) δ 7.69 (d, 2 H, J=8.2 Hz), 7.30-7.19 (m, 6 H), 3.71-3.67 (m, 4 H), 3.59-3.52 (m, 5 H), 3.41 (m, 1 H), 2.64-2.62 (m, 4 H), 1.80 (t, 2 H, J=10.4 Hz), 0.90-0.88 (m, 6 H).

Example 187

Synthesis of Compound 413

(4-(((3R,5S)-4-(4-((4-benzylpiperazin-1-yl)methyl)benzyl)-3,5-dimethylpiperazin-1-yl)methyl)-N-hydroxybenzamide)

Step 1: Synthesis of Methyl 4-(((3R,5S)-4-(4-((4-benzylpiperazin-1-yl)methyl)benzyl)-3,5-dimethyl-piperazin-1-yl)methyl)benzoate Methyl 4-(((3R,5S)-4-(4-formylbenzyl)-3,5-dimethylpiperazin-1-yl)methyl)benzoate (formula 5-1, 0.100 g, 0.263 mmol) was dissolved in methylene chloride (1 mL), and 1-benzylpiperazine (0.049 mL, 0.289 mmol) was added to the mixture, followed by stirring for 30 minutes. Na(OAc)$_3$BH (0.061 g, 0.289 mmol) was added to the reaction mixture, which was then stirred overnight at the same temperature. Then, water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 5%) and concentrated to afford the desired compound (0.074 g, 51.8%) as a white solid.

Step 2: Synthesis of Compound 413

Methyl 4-(((3R,5S)-4-(4-((4-benzylpiperazin-1-yl)methyl)benzyl)-3,5-dimethylpiperazin-1-yl)methyl)benzoate (formula 5-2, 0.074 g, 0.137 mmol), hydroxylamine (0.168 mL, 2.742 mmol, 50.00% aqueous solution) and potassium hydroxide (0.077 g, 1.371 mmol) were dissolved in methanol (1 mL) at room temperature, and the solution was stirred at the same temperature for 2 hours. Then, the reaction mixture was concentrated under reduced pressure to remove the solvent, and a saturated aqueous solution of sodium hydrogen carbonate (10 mL) was added to the concentrate, followed by stirring. The precipitated solid was filtered, washed with water, and dried to yield compound 413 (0.053 g, 71.1%) as a white solid.

$^1$H NMR (400 MHz, DMSO-$d_6$) δ 7.67 (d, 2 H, J=8.0 Hz), 7.32-7.14 (m, 11 H), 3.70 (s, 2 H), 3.44 (m, 6 H), 3.22 (m, 2 H), 2.68-2.64 (m, 4 H), 2.35 (m, 6 H), 1.78 (t, 2 H, J=10.4 Hz), 0.90-0.88 (m, 6 H).

Example 188

Synthesis of Compound 423

(4-(((3R,5S)-3,5-dimethyl-4-(3-(pyrrolidin-1-ylmethyl)benzoyl)piperazin-1-yl)methyl)-N-hydroxybenzamide)

Step 1: Synthesis of 3-(chloromethyl)benzoyl chloride 3-(bromomethyl)benzoic acid (4.301 g, 20.000 mmol) and SOCl$_2$ (43.793 mL, 600.000 mmol) were mixed at 50° C., and the mixture was stirred overnight at the same temperature, followed by cooling to room temperature to terminate the reaction. The reaction mixture was concentrated under reduced pressure to remove the solvent, and the product was used without additional purification (3.778 g, 99.9%, brown liquid).

Step 2: Synthesis of Methyl 4-(((3R,5S)-4-(3-(chloromethyl)benzoyl)-3,5-dimethylpiperazin-1-yl)methyl)benzoate Methyl 4-(((3R,5S)-3,5-dimethylpiperazin-1-yl)methyl)benzoate (formula 1-2, 2.622 g, 9.993 mmol), 3-(chloromethyl)benzoyl chloride (formula 6-1, 3.778 g, 19.986 mmol) and TEA (2.770 mL, 19.986 mmol) were dissolved in methylene chloride (40 mL) at room temperature, and the solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 12 g cartridge; 100% methylene chloride) and concentrated to afford the desired compound (2.047 g, 49.4%) as a brown liquid.

Step 3: Synthesis of Methyl 4-(((3R,5S)-3,5-dimethyl-4-(3-(pyrrolidin-1-ylmethyl)benzoyl)piperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.178 g, 0.388 mmol), pyrrolidine (0.032 mL, 0.388 mmol) and TEA (0.108 mL, 0.777 mmol) were dissolved in methylene chloride (2 mL) at room temperature, and the solution was stirred overnight at the same temperature. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; methanol/methylene chloride=from 0% to 5%) and concentrated to afford the desired compound (0.155 g, 88.8%) as a pale yellow liquid.

Step 4: Synthesis of Compound 423

Methyl 4-(((3R,5S)-3,5-dimethyl-4-(3-(pyrrolidin-1-ylmethyl)benzoyl)piperazin-1-yl)methyl)benzoate (formula 6-3, 0.155 g, 0.345 mmol), hydroxylamine (0.422 mL, 6.895 mmol, 50.00% aqueous solution) and potassium hydroxide (0.193 g, 3.448 mmol) were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; methanol/methylene chloride=from 0% to 10%) and concentrated to afford compound 423 (0.070 g, 44.9%) as a white solid.

$^1$H NMR (400 MHz, DMSO-$d_6$) δ 11.2 (brs, 1 H), 9.03 (brs, 1 H), 7.72 (d, 2 H, J=8.6 Hz), 7.43 (d, 2 H, J=8.2 Hz), 7.38-7.32 (m, 2 H), 7.24 (s, 1 H), 7.20-7.17 (m, 2 H), 4.06 (brs, 2 H), 3.58-3.54 (m, 4 H), 2.68-2.61 (m, 2 H), 2.40 (s, 4 H), 2.16-2.12 (m, 2 H), 1.69-1.67 (m, 4 H), 1.21-1.28 (m, 6 H).

Example 189

Synthesis of Compound 424

(4-(((3R,5S)-3,5-dimethyl-4-(3-(piperidin-1-ylmethyl)benzoyl)piperazin-1-yl)methyl)-N-hydroxybenzamide)

Step 1: Synthesis of Methyl 4-(((3R,5S)-3,5-dimethyl-4-(3-(piperidin-1-ylmethyl)benzoyl)piperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.165 g, 0.359 mmol), piperidine (0.036 mL, 0.359 mmol) and Cs$_2$CO$_3$ (0.142 g, 0.431 mmol) were dissolved in acetonitrile (1.5 mL) at room temperature, and the solution was stirred overnight at the same temperature. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; methanol/methylene chloride=from 0% to 5%) and concentrated to afford the desired compound (0.127 g, 76.0%) as a colorless liquid.

Step 2: Synthesis of Compound 424

Methyl 4-(((3R,5S)-3,5-dimethyl-4-(3-(piperidin-1-ylmethyl)benzoyl)piperazin-1-yl)methyl)benzoate (formula 6-3, 0.127 g, 0.273 mmol), hydroxylamine (0.334 mL, 5.461 mmol, 50.00% aqueous solution) and potassium hydroxide (0.153 g, 2.731 mmol) were dissolved in methanol (1.5 mL) at room temperature, and the solution was stirred at the same temperature for 1 hour. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure to yield compound 424 (0.101 g, 79.4%) as a white solid.

$^1$H NMR (400 MHz, DMSO-$d_6$) δ 7.72 (d, 2 H, J=8.2 Hz), 7.43 (d, 2 H, J=8.1 Hz), 7.38-7.30 (m, 2 H), 7.23 (s, 1 H), 7.20-7.18 (m, 1 H), 3.54 (s, 2 H), 3.44 (s, 2 H), 2.63-2.61 (m, 2 H), 2.30 (m, 4 H), 2.16-2.12 (m, 2 H), 1.49-1.46 (m, 4 H), 1.38-1.37 (m, 2 H), 1.29 (s, 6 H).

Example 190

Synthesis of Compound 425

(4-(((3R,5S)-4-(3-((diethylamino)methyl)benzoyl)-3,5-dimethylpiperazin-1-yl)methyl)-N-hydroxybenzamide)

Step 1: Synthesis of Methyl 4-(((3R,5S)-4-(3-((diethylamino)methyl)benzoyl)-3,5-dimethylpiperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.165 g, 0.359 mmol), diethylamine hydrochloride (0.039 g, 0.359 mmol) and Cs$_2$CO$_3$ (0.142 g, 0.431 mmol) were dissolved in acetonitrile (1.5 mL) at room temperature, and the solution was stirred overnight at the same temperature. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; methanol/methylene chloride=from 0% to 5%) and concentrated to afford the desired compound (0.115 g, 71.1%) as a colorless liquid.

Step 2: Synthesis of Compound 425

Methyl 4-(((3R,5S)-4-(3-((diethylamino)methyl)benzoyl)-3,5-dimethylpiperazin-1-yl)methyl)benzoate (formula 6-3, 0.115 g, 0.255 mmol), hydroxylamine (0.312 mL, 5.106 mmol, 50.00% aqueous solution) and potassium hydroxide (0.143 g, 2.553 mmol) were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; methanol/methylene chloride=from 0% to 5%) and concentrated to afford compound 425 (0.061 g, 53.1%) as a white solid.

$^1$H NMR (400 MHz, DMSO-$d_6$) δ 11.2 (brs, 1 H), 9.03 (brs, 1 H), 7.72 (d, 2 H, J=8.2 Hz), 7.43 (d, 2 H, J=8.2 Hz), 7.36-7.34 (m, 2 H), 7.25 (s, 1 H), 7.18-7.16 (m, 1 H), 3.54 (s, 4 H), 2.63-2.61 (m, 2 H), 2.46-2.41 (m, 4 H), 2.16-2.12 (m, 2 H), 1.29 (m, 6 H), 0.98-0.94 (m, 6 H).

Example 191

Synthesis of Compound 426

(4-(((3R,5S)-4-(3-((diethylamino)methyl)benzyl)-3,5-dimethylpiperazin-1-yl)methyl)-N-hydroxybenzamide)

Step 1: Synthesis of Methyl 4-(((3R,5S)-4-(3-((diethylamino)methyl)benzyl)-3,5-dimethylpiperazin-1-yl)methyl)benzoate Methyl 4-(((3R,5S)-4-(3-formylbenzyl)-3,5-dimethylpiperazin-1-yl)methyl)benzoate (formula 5-1, 0.200 g, 0.526 mmol) and diethylamine hydrochloride (0.086 g, 0.788 mmol) were dissolved in methylene chloride (10 mL), and the solution was stirred at room temperature for 1 hour. Na(OAc)$_3$BH (0.223 g, 1.051 mmol) was added to the solution, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.026 g, 11.3%) as a pale yellow oil.

Step 2: Synthesis of Compound 426

Methyl 4-(((3R,5S)-4-(3-((diethylamino)methyl)benzyl)-3,5-dimethylpiperazin-1-yl)methyl)benzoate (formula 5-2, 0.026 g, 0.059 mmol), hydroxylamine (0.073 mL, 1.188 mmol, 50.00% aqueous solution) and potassium hydroxide (0.033 g, 0.594 mmol) were dissolved in methanol (4 mL) at room temperature, and the solution was stirred at the same temperature for 30 minutes. Then, the reaction solution was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 426 (0.019 g, 72.9%) as a white solid.

$^1$H-NMR (400 MHz, DMSO-$d_6$) δ 1.10 (brs, 1 H), 9.00 (brs, 1 H), 7.69 (d, 2 H, J=8.3 Hz), 7.33 (d, 2 H, J=8.1 Hz), 7.29 (s, 1 H), 7.24-7.18 (m, 2 H), 7.12-7.10 (m, 1 H), 3.72 (s, 2 H), 3.50 (s, 2 H), 3.43 (s, 2 H), 2.68-2.54 (m, 4 H), 2.43 (q, 4 H, J=7.1 Hz), 1.80 (t, 2 H, J=10.5 Hz), 0.96 (t, 6 H, J=7.1 Hz), 0.90 (d, 6 H, J=6.0 Hz); LRMS (ES) m/z 439.3 (M$^+$+1).

Example 192

Synthesis of Compound 427

(4-(((3R,5S)-3,5-dimethyl-4-(3-(pyrrolidin-1-ylmethyl)benzyl)piperazin-1-yl)methyl)-N-hydroxybenzamide)

Step 1: Synthesis of Methyl 4-(((3R,5S)-3,5-dimethyl-4-(3-(pyrrolidin-1-ylmethyl)benzyl)piperazin-1-yl)methyl)benzoate Methyl 4-(((3R,5S)-4-(3-formylbenzyl)-3,5-dimethylpiperazin-1-yl)methyl)benzoate (formula 5-1, 0.200 g, 0.526 mmol) and pyrrolidine (0.066 mL, 0.788 mmol) were dissolved in methylene chloride (4 mL), and the solution was stirred at room temperature for 1 hour. Na(OAc)$_3$BH (0.223 g, 1.051 mmol) was added to the solution, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.161 g, 70.3%) as a colorless oil.

Step 2: Synthesis of Compound 427

Methyl 4-(((3R,5S)-3,5-dimethyl-4-(3-(pyrrolidin-1-ylmethyl)benzyl)piperazin-1-yl)methyl)benzoate (formula 5-2, 0.086 g, 0.197 mmol), hydroxylamine (0.242 mL, 3.949 mmol, 50.00% aqueous solution) and potassium hydroxide (0.111 g, 1.974 mmol) were dissolved in methanol (4 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 427 (0.033 g, 38.3%) as a white solid.

$^1$H-NMR (400 MHz, DMSO-$d_6$) δ 11.10 (brs, 1 H), 9.00 (brs, 1 H), 7.70 (d, 2 H, J=8.2 Hz), 7.35 (d, 2 H, J=8.1 Hz), 7.26 (s, 1 H), 7.22-7.21 (m, 2 H), 7.11-7.09 (m, 1 H), 3.72 (s, 2 H), 3.54 (s, 2 H), 3.44 (s, 2 H), 2.65-2.55 (m, 4 H), 2.40 (s, 4 H), 1.81 (t, 2 H, J=10.5 Hz), 1.69 (s, 4 H), 0.90 (d, 6 H, J=6.1 Hz); LRMS (ES) m/z 437.3 (M$^+$+1).

Example 193

Synthesis of Compound 428

(4-(((3R,5S)-3,5-dimethyl-4-(3-((4-methylpiperazin-1-yl)methyl)benzyl)piperazin-1-yl)methyl)-N-hydroxybenzamide)

Step 1: Synthesis of Methyl 4-(((3R,5S)-3,5-dimethyl-4-(3-((4-methylpiperazin-1-yl)methyl)benzyl)piperazin-1-yl)methyl)benzoate Methyl 4-(((3R,5S)-4-(3-formylbenzyl)-3,5-dimethylpiperazin-1-yl)methyl)benzoate (formula 5-1, 0.200 g, 0.526 mmol) and 1-methylpiperazine (0.088 mL, 0.788 mmol) were dissolved in methylene chloride (4 mL), and the solution was stirred at room temperature for 1 hour. Na(OAc)$_3$BH (0.223 g, 1.051 mmol) was added to the solution, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.152 g, 62.2%) as a pale yellow oil.

Step 2: Synthesis of Compound 428

Methyl 4-(((3R,5S)-3,5-dimethyl-4-(3-((4-methylpiperazin-1-yl)methyl)benzyl)piperazin-1-yl)methyl)benzoate (formula 5-2, 0.075 g, 0.161 mmol), hydroxylamine (0.197 mL, 3.228 mmol, 50.00% aqueous solution) and potassium hydroxide (0.091 g, 1.614 mmol) were dissolved in methanol (4 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 428 (0.031 g, 41.2%) as a white solid.

$^1$H-NMR (400 MHz, DMSO-d$_6$) δ 7.69 (d, 2 H, J=8.2 Hz), 7.30 (d, 2 H, J=8.1 Hz), 7.27 (s, 1 H), 7.23-7.21 (m, 2 H), 7.09-7.08 (m, 1 H), 3.72 (s, 2 H), 3.43 (s, 2 H), 3.42 (s, 2 H), 2.63 (d, 2 H, J=10.2 Hz), 2.58-2.51 (m, 2 H), 2.36-2.33 (m, 8 H), 1.80 (t, 2 H, J=10.5 Hz), 0.90 (d, 6 H, J=6.1 Hz).

Example 194

Synthesis of Compound 429

(4-(((3R,5S)-4-(3-((4-ethylpiperazin-1-yl)methyl)benzyl)-3,5-dimethylpiperazin-1-yl)methyl)-N-hydroxybenzamide)

Step 1: Synthesis of Methyl 4-(((3R,5S)-4-(3-((4-ethylpiperazin-1-yl)methyl)benzyl)-3,5-dimethylpiperazin-1-yl)methyl)benzoate Methyl 4-(((3R,5S)-4-(3-formylbenzyl)-3,5-dimethylpiperazin-1-yl)methyl)benzoate (formula 5-1, 0.200 g, 0.526 mmol) and 1-ethylpiperazine (0.100 mL, 0.788 mmol) were dissolved in methylene chloride (4 mL), and the solution was stirred at room temperature for 1 hour. Na(OAc)$_3$BH (0.223 g, 1.051 mmol) was added to the solution, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.099 g, 39.3%) as a pale yellow oil.

Step 2: Synthesis of Compound 429

Methyl 4-(((3R,5S)-4-(3-((4-ethylpiperazin-1-yl)methyl)benzyl)-3,5-dimethylpiperazin-1-yl)methyl)benzoate (formula 5-2, 0.055 g, 0.115 mmol), hydroxylamine (0.141 mL, 2.298 mmol, 50.00% aqueous solution) and potassium hydroxide (0.064 g, 1.149 mmol) were dissolved in methanol (4 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 429 (0.031 g, 56.2%) as a white solid.

$^1$H-NMR (400 MHz, DMSO-d$_6$) δ 11.10 (brs, 1 H), 9.00 (brs, 1 H), 7.70 (d, 2 H, J=8.3 Hz), 7.34 (d, 2 H, J=8.2 Hz), 7.27 (s, 1 H), 7.23-7.21 (m, 2 H), 7.09-7.08 (m, 1 H), 3.72 (s, 2 H), 3.43 (s, 4 H), 2.63 (d, 2 H, J=10.2 Hz), 2.59-2.51 (m, 2 H), 2.36-2.33 (m, 8 H), 2.28 (q, 2 H, J=7.2 Hz), 1.81 (t, 2 H, J=10.5 Hz), 0.97 (t, 3 H, J=7.2 Hz), 0.90 (d, 6 H, J=6.1 Hz).

Example 195

Synthesis of Compound 430

(N-hydroxy-4-(((3R,5S)-4-(3-((4-isopropylpiperazin-1-yl)methyl)benzyl)-3,5-dimethylpiperazin-1-yl)methyl)benzamide)

Step 1: Synthesis of Methyl 4-(((3R,5S)-4-(3-((4-isopropylpiperazin-1-yl)methyl)benzyl)-3,5-dimethylpiperazin-1-yl)methyl)benzoate Methyl 4-(((3R,5S)-4-(3-formylbenzyl)-3,5-dimethylpiperazin-1-yl)methyl)benzoate (formula 5-1, 0.200 g, 0.526 mmol) and 1-isopropylpiperazine (0.113 mL, 0.788 mmol) were dissolved in methylene chloride (4 mL), and the solution was stirred at room temperature for 1 hour. Na(OAc)$_3$BH (0.223 g, 1.051 mmol) was added to the solution, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.225 g, 86.9%) as a pale brown oil.

Step 2: Synthesis of Compound 430

Methyl 4-(((3R,5S)-4-(3-((4-isopropylpiperazin-1-yl) methyl)benzyl)-3,5-dimethylpiperazin-1-yl)methyl)benzoate (formula 5-2, 0.100 g, 0.203 mmol), hydroxylamine (0.248 mL, 4.059 mmol, 50.00% aqueous solution) and potassium chloride (0.114 g, 2.030 mmol) were dissolved in methanol (4 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was filtered through a plastic filter to remove solid residue and an aqueous layer, and then concentrated under reduced pressure to afford compound 430 (0.055 g, 54.9%) as a white solid.

$^1$H-NMR (400 MHz, DMSO-$d_6$) δ 11.10 (brs, 1 H), 9.00 (brs, 1 H), 7.70 (d, 2 H, J=8.0 Hz), 7.35 (d, 2 H, J=8.0 Hz), 7.09-7.08 (m, 2 H), 3.72 (s, 2 H), 3.43 (s, 2 H), 3.42 (s, 2 H), 2.65-2.62 (m, 2 H), 2.59-2.51 (m, 3 H), 2.41-2.34 (m, 8 H), 1.81 (t, 2 H, J=10.3 Hz), 0.94 (d, 6 H, J=6.5 Hz), 0.90 (d, 6 H, J=6.0 Hz).

Example 196

Synthesis of Compound 431

(4-(((3R,5S)-4-(3-((4-acetylpiperazin-1-yl)methyl) benzyl)-3,5-dimethylpiperazin-1-yl)methyl)-N-hydroxybenzamide)

Step 1: Synthesis of Methyl 4-(((3R,5S)-4-(3-((4-acetylpiperazin-1-yl)methyl)benzyl)-3,5-dimethylpiperazin-1-yl)methyl)benzoate Methyl 4-(((3R,5S)-4-(3-formylbenzyl)-3,5-dimethylpiperazin-1-yl)methyl)benzoate (formula 5-1, 0.200 g, 0.526 mmol) and 1-acetylpiperazine (0.101 g, 0.788 mmol) were dissolved in methylene chloride (4 mL), and the solution was stirred at room temperature for 1 hour. Na(OAc)$_3$BH (0.223 g, 1.051 mmol) was added to the reaction solution, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.253 g, 97.7%) as a pale brown oil.

Step 2: Synthesis of Compound 431

Methyl 4-(((3R,5S)-4-(3-((4-acetylpiperazin-1-yl) methyl)benzyl)-3,5-dimethylpiperazin-1-yl)methyl)benzoate (formula 5-2, 0.070 g, 0.142 mmol), hydroxylamine (0.174 mL, 2.842 mmol, 50.00% aqueous solution) and potassium hydroxide (0.080 g, 1.421 mmol) were dissolved in methanol (4 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 431 (0.067 g, 95.5%) as a white solid.

$^1$H-NMR (400 MHz, DMSO-$d_6$) δ 7.69 (d, 2 H, J=8.1 Hz), 7.32 (d, 2 H, J=8.1 Hz), 7.28 (s, 1 H), 7.25-7.23 (m, 2 H), 7.12-7.11 (m, 1 H), 3.73 (s, 2 H), 3.43-3.39 (m, 6 H), 2.64 (d, 2 H, J=10.1 Hz), 2.59-2.53 (m, 2 H), 2.34 (t, 2 H, J=4.8 Hz), 2.28 (t, 2 H, J=5.0 Hz), 0.90 (d, 6 H, J=6.1 Hz).

Example 197

Synthesis of Compound 432

(4-(((3R,5S)-3,5-dimethyl-4-(3-((4-methylpiperazin-1-yl)methyl)benzoyl)piperazin-1-yl)methyl)-N-hydroxybenzamide)

Step 1: Synthesis of Methyl 4-(((3R,5S)-3,5-dimethyl-4-(3-((4-methylpiperazin-1-yl)methyl)benzoyl) piperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.200 g, 0.482 mmol), 1-methylpiperazine (0.059 mL, 0.530 mmol) and Cs$_2$CO$_3$ (0.188 g, 0.578 mmol) were dissolved in acetonitrile (2 mL) at room temperature, and the solution was stirred overnight at the same temperature. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; methanol/methylene chloride=from 0% to 5%) and concentrated to afford the desired compound (0.163 g, 70.5%) as a pale yellow liquid.

Step 2: Synthesis of Compound 432

Methyl 4-(((3R,5S)-3,5-dimethyl-4-(3-((4-methylpiperazin-1-yl)methyl)benzoyl)piperazin-1-yl)methyl)benzoate (formula 6-3, 0.163 g, 0.340 mmol), hydroxylamine (0.416 mL, 6.794 mmol, 50.00% aqueous solution) and potassium hydroxide (0.191 g, 3.397 mmol) were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure to yield compound 432 (0.095 g, 58.1%) as a white solid.

$^1$H NMR (400 MHz, DMSO-$d_6$) δ 7.72 (d, 2 H, J=8.2 Hz), 7.43 (d, 2 H, J=8.2 Hz), 7.38-7.30 (m, 2 H), 7.23-7.18 (m, 2 H), 3.54-3.47 (m, 6 H), 2.67-2.61 (m, 2 H), 2.33 (m, 8 H), 2.16-2.13 (m, 5 H), 1.28-1.23 (m, 6 H).

Example 198

Synthesis of Compound 433

(4-(((3R,5S)-4-(3-((4-ethylpiperazin-1-yl)methyl)benzoyl)-3,5-dimethylpiperazin-1-yl)methyl)-N-hydroxybenzamide)

Step 1: Synthesis of Methyl 4-(((3R,5S)-4-(3-((4-ethylpiperazin-1-yl)methyl)benzoyl)-3,5-dimethylpiperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.200 g, 0.482 mmol), 1-ethylpiperazine (0.067 mL, 0.530 mmol) and $Cs_2CO_3$ (0.188 g, 0.578 mmol) were dissolved in acetonitrile (2 mL) at room temperature, and the solution was stirred overnight at the same temperature. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; methanol/methylene chloride=from 0% to 5%) and concentrated to afford the desired compound (0.165 g, 69.4%) as a pale yellow liquid.

Step 2: Synthesis of Compound 433

Methyl 4-(((3R,5S)-4-(3-((4-ethylpiperazin-1-yl)methyl)benzoyl)-3,5-dimethylpiperazin-1-yl)methyl)benzoate (formula 6-3, 0.165 g, 0.334 mmol), hydroxylamine (50.00% aqueous solution, 0.409 mL, 6.686 mmol) and potassium hydroxide (0.188 g, 3.343 mmol) were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure to yield compound 433 (0.116 g, 70.0%) as a white solid.

$^1$H NMR (400 MHz, DMSO-$d_6$) δ 11.2 (brs, 1 H), 9.03 (brs, 1 H), 7.89 (d, 2 H, J=7.8 Hz), 7.72 (d, 2 H, J=8.2 Hz), 7.44-7.30 (m, 2 H), 7.23 (s, 1 H), 7.20-7.19 (m, 1 H), 4.51 (s, 4 H), 2.67-2.61 (m, 2 H), 2.34-2.25 (m, 8 H), 2.14 (dd, 2 H, J=11.3, 4.1 Hz), 1.28-1.23 (m, 6 H), 0.98-0.85 (m, 3 H).

Example 199

Synthesis of Compound 434

(N-hydroxy-4-(((3R,5S)-4-(3-((4-isopropylpiperazin-1-yl)methyl)benzoyl)-3,5-dimethylpiperazin-1-yl)methyl)benzamide)

Step 1: Synthesis of Methyl 4-(((3R,5S)-4-(3-((4-isopropylpiperazin-1-yl)methyl)benzoyl)-3,5-dimethylpiperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.200 g, 0.482 mmol), 1-isopropylpiperazine (0.076 mL, 0.530 mmol) and $Cs_2CO_3$ (0.188 g, 0.578 mmol) were dissolved in acetonitrile (2 mL) at room temperature, and the solution was stirred overnight at the same temperature. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; methanol/methylene chloride=from 0% to 5%) and concentrated to afford the desired compound (0.170 g, 69.5%) as a pale yellow liquid.

Step 2: Synthesis of Compound 434

Methyl 4-(((3R,5S)-4-(3-((4-isopropylpiperazin-1-yl)methyl)benzoyl)-3,5-dimethylpiperazin-1-yl)methyl)benzoate (formula 6-3, 0.170 g, 0.335 mmol), hydroxylamine (0.410 mL, 6.699 mmol, 50.00% aqueous solution) and potassium hydroxide (0.188 g, 3.349 mmol) were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure to yield compound 434 (0.128 g, 75.5%) as a white solid.

$^1$H NMR (400 MHz, DMSO-$d_6$) δ 11.2 (brs, 1 H), 9.02 (brs, 1 H), 7.72 (d, 2 H, J=8.2 Hz), 7.43 (d, 2 H, J=8.2 Hz), 7.39-7.30 (m, 2 H), 7.23-7.19 (s, 2 H), 3.54 (s, 2 H), 3.47 (s, 2 H), 2.67-2.60 (m, 3 H), 2.43-2.33 (m, 9 H), 2.15 (dd, 1 H, J=11.3, 4.0 Hz), 1.29-1.18 (m, 6 H), 0.96-0.94 (m, 6 H).

Example 200

Synthesis of Compound 435

(4-(((3R,5S)-4-(3-((4-acetylpiperazin-1-yl)methyl)benzoyl)-3,5-dimethylpiperazin-1-yl)methyl)-N-hydroxybenzamide)

Step 1: Synthesis of Methyl 4-(((3R,5S)-4-(3-((4-acetylpiperazin-1-yl)methyl)benzoyl)-3,5-dimethylpiperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.200 g, 0.482 mmol), 1-acetylpiperazine (0.068 g, 0.530 mmol) and $Cs_2CO_3$ (0.188 g, 0.578 mmol) were dissolved in acetonitrile (2 mL), and the solution was stirred overnight at the same temperature. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; methanol/methylene chloride=from 0% to 5%) and concentrated to afford the desired compound (0.186 g, 76.2%) as a pale yellow liquid.

Step 2: Synthesis of Compound 435

Methyl 4-((3R,5S)-4-(3-((4-acetylpiperazin-1-yl)methyl)benzoyl)-3,5-dimethylpiperazin-1-yl)methyl)benzoate (formula 6-3, 0.186 g, 0.367 mmol), hydroxylamine (0.449 mL, 7.346 mmol, 50.00% aqueous solution) and potassium hydroxide (0.206 g, 3.673 mmol) were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure to yield compound 435 (0.121 g, 64.7%) as a white solid.

$^1$H NMR (400 MHz, DMSO-$d_6$) δ 11.2 (brs, 1 H), 9.04 (brs, 1 H), 7.72 (d, 2 H, J=8.1 Hz), 7.42-7.33 (m, 4 H), 7.25-7.20 (s, 2 H), 4.52 (brs, 2 H), 3.53-3.52 (m, 4 H), 3.41-3.40 (m, 4 H), 2.67-2.62 (m, 2 H), 2.36-2.34 (m, 2 H), 2.29-2.27 (m, 2 H), 2.16-2.13 (m, 2 H), 1.97 (s, 3 H), 1.29 (s, 6 H).

Example 201

Synthesis of Compound 439

(4-(((3R,5S)-3,5-dimethyl-4-(3-(morpholinomethyl) benzoyl)piperazin-1-yl)methyl)-N-hydroxybenzamide)

Step 1: Synthesis of Methyl 4-(((3R,5S)-3,5-dimethyl-4-(3-(morpholinomethyl)benzoyl)piperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.200 g, 0.482 mmol), morpholine (0.069 g, 0.530 mmol) and Cs$_2$CO$_3$ (0.188 g, 0.578 mmol) were dissolved in acetonitrile (2 mL) at room temperature, and the solution was stirred overnight at the same temperature. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 0% to 10%) and concentrated to afford the desired compound (0.163 g, 66.6%) as a pale yellow liquid.

Step 2: Synthesis of Compound 439

Methyl 4-(((3R,5S)-3,5-dimethyl-4-(3-(morpholinomethyl)benzoyl)piperazin-1-yl)methyl)benzoate (formula 6-3, 0.163 g, 0.321 mmol), hydroxylamine (0.392 mL, 6.416 mmol, 50.00% aqueous solution) and potassium hydroxide (0.180 g, 3.208 mmol) were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure to afford compound 439 (0.105 g, 64.3%) as a white solid.

$^1$H NMR (400 MHz, DMSO-$d_6$) δ 7.71 (d, 2 H, J=8.2 Hz), 7.39-7.33 (m, 4 H), 7.22 (s, 1 H), 7.22-7.20 (m, 1 H), 4.41 (brs, 1 H) 3.57-3.55 (m, 4 H), 3.48 (s, 4 H), 2.65-2.61 (m, 2 H), 2.34 (s, 4 H), 2.15-2.11 (m, 2 H), 1.29-1.23 (m, 6 H).

Example 202

Synthesis of Compound 440

(4-(((3R,5S)-4-(3-(((1-(diethylamino)propan-2-yl) amino)methyl)benzoyl)-3,5-dimethylpiperazin-1-yl) methyl)-N-hydroxybenzamide Step 1: Synthesis of Methyl 4-(((3R,5S)-4-(3-(((1-(diethylamino)propan-2-yl)amino)methyl)benzoyl)-3,5-dimethylpiperazin-1-yl)methyl)benzoate Methyl 4-(((3R,5S)-4-(3-(chlorophenyl)benzoyl)-3,5-dimethylpiperazin-1-yl)methyl)benzoate (formula 6-2, 0.200 g, 0.482 mmol), N$_1$,N$_1$-diethylpropane-1,2-diamine (0.069 g, 0.530 mmol) and Cs$_2$CO$_3$ (0.188 g, 0.578 mmol) were dissolved in acetonitrile (2 mL) at room temperature, and the solution was stirred overnight at the same temperature. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethylacetate/hexane=from 0% to 10%) and concentrated to afford the desired compound (0.163 g, 66.6%) as a pale yellow liquid.

Step 2: Synthesis of Compound 440

Methyl 4-(((3R,5S)-4-(3-(((1-(diethylamino)propan-2-yl) amino)methyl)benzoyl)-3,5-dimethylpiperazin-1-yl) methyl)benzoate (formula 6-3, 0.163 g, 0.321 mmol), hydroxylamine (0.392 mL, 6.416 mmol, 50.00% aqueous solution) and potassium hydroxide (0.180 g, 3.208 mmol) were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure to afford compound 440 (0.105 g, 64.3%) as a white solid.

$^1$H NMR (400 MHz, DMSO-$d_6$) δ 7.71 (d, 2 H, J=8.2 Hz), 7.38-7.32 (m, 4 H), 7.25 (s, 1 H), 7.18-7.16 (m, 1 H), 4.37 (brs, 2 H), 3.83-3.80 (m, 1 H), 3.67-3.64 (m, 1 H), 3.52 (s, 2 H), 2.67-2.57 (m, 3 H), 2.45-2.37 (m, 2 H), 2.35-2.26 (m, 2 H), 2.25-2.11 (m, 5 H), 1.29 (s, 6 H), 0.93-0.86 (m, 9 H).

Example 203

Synthesis of Compound 441

(4-(((3R,5S)-4-(3-(((1-(benzyl(methyl)amino)propan-2-yl)amino)methyl)benzoyl)-3,5-dimethylpiperazin-1-yl)methyl)-N-hydroxybenzamide)

Step 1: Synthesis of Methyl 4-(((3R,5S)-4-(3-(((1-(benzyl(methyl)amino)propan-2-yl)amino)methyl) benzoyl)-3,5-dimethylpiperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.200 g, 0.482 mmol), N$_1$-benzyl-N$_1$-methylpropane-1,2-diamine (0.095 g, 0.530 mmol) and Cs$_2$CO$_3$ (0.188 g, 0.578 mmol) were dissolved in acetonitrile (2 mL) at room temperature, and the solution was stirred overnight at the same temperature. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 0% to 5%) and concentrated to afford the desired compound (0.167 g, 62.2%) as a pale yellow liquid.

Step 2: Synthesis of Compound 441

Methyl 4-(((3R,5S)-4-(3-(((1-(benzyl(methyl)amino)propan-2-yl)amino)methyl)benzoyl)-3,5-dimethylpiperazin-1-yl)methyl)benzoate (formula 6-3, 0.167 g, 0.300 mmol), hydroxylamine (0.367 mL, 5.999 mmol, 50.00% aqueous solution) and potassium hydroxide (0.168 g, 3.000 mmol) were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure to afford compound 441 (0.134 g, 80.3%) as a white solid.

$^1$H NMR (400 MHz, DMSO-d$_6$) δ 7.71 (d, 2 H, J=8.2 Hz), 7.37-7.30 (m, 4 H), 7.28-7.19 (m, 6 H), 7.18-7.16 (m, 1 H), 4.42 (brs, 2 H), 3.83-3.79 (m, 1 H), 3.67-3.64 (m, 1 H), 3.50 (s, 2 H), 3.46-3.43 (m, 1 H), 3.31 (s, 1 H), 2.74-2.69 (m, 1 H), 2.60 (m, 1 H), 2.33-2.28 (m, 2 H), 2.13-2.08 (m, 3 H), 1.27 (s, 6 H), 0.93-0.91 (m, 3 H); LRMS (ES) m/z 558.4 (M$^+$+1).

Example 204

Synthesis of Compound 442

(N-hydroxy-4-(((3R,5S)-4-(3-((4-isopentylpiperazin-1-yl)methyl)benzoyl)-3,5-dimethylpiperazin-1-yl)methyl)benzamide)

Step 1: Synthesis of Methyl 4-(((3R,5S)-4-(3-((4-isopentylpiperazin-1-yl)methyl)benzoyl)-3,5-dimethylpiperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.200 g, 0.482 mmol), 1-isobutylpiperazine trifluoroacetate (0.136 g, 0.530 mmol) and Cs$_2$CO$_3$ (0.188 g, 0.578 mmol) were dissolved in acetonitrile (2 mL) at room temperature, and the solution was stirred overnight at the same temperature. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 5%) and concentrated to afford the desired compound (0.162 g, 64.6%) as a pale yellow liquid.

Step 2: Synthesis of Compound 442

Methyl 4-(((3R,5S)-4-(3-((4-isopentylpiperazin-1-yl)methyl)benzoyl)-3,5-dimethylpiperazin-1-yl)methyl)benzoate (formula 6-3, 0.162 g, 0.311 mmol), hydroxylamine (0.381 mL, 6.226 mmol, 50.00% aqueous solution) and potassium hydroxide were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure to afford compound 442 (0.121 g, 74.6%) as a yellow solid.

$^1$H NMR (400 MHz, DMSO-d$_6$) δ 11.2 (brs, 1 H), 9.03 (brs, 1 H), 7.72 (d, 2 H, J=8.2 Hz), 7.43 (d, 2 H, J=8.1 Hz), 7.38-7.30 (m, 2 H), 7.23-7.19 (m, 2 H), 4.50 (brs, 2 H), 3.54-3.47 (m, 4 H), 2.62 (m, 2 H), 2.34 (m, 6 H), 2.26-2.22 (m, 3 H), 2.16-2.12 (m, 3 H), 1.56-1.53 (m, 1 H), 1.31-1.25 (m, 8 H), 0.86-0.84 (m, 6 H).

Example 205

Synthesis of Compound 443

(4-(((3R,5S)-3,5-dimethyl-4-(3-((4-(2,2,2-trifluoroethyl)piperazin-1-yl)methyl)benzoyl)piperazin-1-yl)methyl)-N-hydroxybenzamide)

Step 1: Synthesis of Methyl 4-(((3R,5S)-3,5-dimethyl-4-(3-((4-(2,2,2-trifluoroethyl)piperazin-1-yl)methyl)benzoyl)piperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.200 g, 0.482 mmol), 1-(2,2,2-trifluoroethyl)piperazine trifluoroacetate (0.141 g, 0.530 mmol) and Cs$_2$CO$_3$ (0.188 g, 0.578 mmol) were dissolved in acetonitrile (2 mL) at room temperature, and the solution was stirred overnight at the same temperature. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 5%) and concentrated to afford the desired compound (0.164 g, 62.3%) as a pale yellow liquid.

Step 2: Synthesis of Compound 443

Methyl 4-(((3R,5S)-3,5-dimethyl-4-(3-((4-(2,2,2-trifluoroethyl)piperazin-1-yl)methyl)benzoyl)piperazin-1-yl)methyl)benzoate (0.148 g, 0.270 mmol), hydroxylamine (0.331 mL, 5.408 mmol, 50.00% aqueous solution) and potassium hydroxide (0.152 g, 2.704 mmol) were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure to afford compound 443 (0.119 g, 80.5%) as a pale yellow solid.

$^1$H NMR (400 MHz, DMSO-d$_6$) δ 11.2 (brs, 1 H), 9.08 (brs, 1 H), 7.72 (d, 2 H, J=8.2 Hz), 7.39-7.19 (m, 6 H), 4.47 (brs, 2 H), 3.52-3.44 (m, 4 H), 3.17-3.10 (m, 2 H), 2.61 (s, 6 H), 2.36 (s, 4 H), 2.14-2.12 (m, 2 H), 1.29 (m, 6 H).

Example 206

Synthesis of Compound 444

(4-(((3R,5S)-3,5-dimethyl-4-(3-((4-(methylsulfonyl) piperazin-1-yl)methyl)benzoyl)piperazin-1-yl) methyl)-N-hydroxybenzamide)

Step 1: Synthesis of Methyl 4-(((3R,5S)-3,5-dimethyl-4-(3-((4-(methylsulfonyl)piperazin-1-yl) methyl)benzoyl)piperazin-1-yl)methyl)benzoate Methyl 4-(((3R,5S)-4-(3-(chloromethyl)benzoyl)-3,5-dimethylpiperazin-1-yl)methyl)benzoate (formula 6-2, 0.200 g, 0.482 mmol), 1-(methylsulfonyl)piperazine (0.087 g, 0.530 mmol) and $Cs_2CO_3$ (0.188 g, 0.578 mmol) were dissolved in acetonitrile (2 mL) at room temperature, and the solution was stirred overnight at the same temperature. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 5%) and concentrated to afford the desired compound (0.164 g, 62.8%) as a white solid.

Step 2: Synthesis of Compound 444

Methyl 4-(((3R,5S)-3,5-dimethyl-4-(3-((4-(methylsulfonyl)piperazin-1-yl)methyl)benzoyl)piperazin-1-yl)methyl) benzoate (formula 6-3, 0.059 g, 0.109 mmol), hydroxylamine (0.133 mL, 2.178 mmol, 50.00% aqueous solution) and potassium hydroxide (0.061 g, 1.089 mmol) were dissolved in methanol (1.5 mL) at room temperature, and the solution was stirred at the same temperature for 1 hour. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure to afford compound 444 (0.042 g, 71.6%) as a white solid.

$^1$H NMR (400 MHz, DMSO-$d_6$) δ 11.2 (brs, 1 H), 9.01 (brs, 1 H), 7.72 (d, 2 H, J=8.2 Hz), 7.42-7.33 (m, 4 H), 7.25-7.21 (m, 2 H), 4.47 (brs, 2 H), 3.55-3.53 (m, 4 H), 3.10 (m, 4 H), 2.87 (m, 3 H), 2.69-2.56 (m, 2 H), 2.45 (s, 4 H), 2.16-2.12 (m, 2 H), 1.29 (m, 6 H).

Example 207

Synthesis of Compound 446

(4-(((3R,5S)-3,5-dimethyl-4-(3-(morpholine-4-carbonyl)benzyl)piperazin-1-yl)methyl)-N-hydroxybenzamide)

Step 1: Synthesis of 3-(chloromethyl)benzoyl chloride

A mixture of 3-(bromomethyl)benzoic acid (1.000 g, 4.650 mmol) and $SOCl_2$ (10.120 mL, 139.509 mmol) was stirred at room temperature, and stirred at 70° C. for 16 hours, followed by cooling to room temperature to terminate the reaction. The reaction mixture was concentrated under reduced pressure, and the product was used without additional purification (0.879 g, 100.0%, brown oil).

Step 2: Synthesis of (3-(chloromethyl)phenyl) (morpholino)methanone 3-(Chloromethyl)benzoyl chloride (formula 6-1, 0.879 g, 4.650 mmol), morpholine (0.409 mL, 4.650 mmol) and TEA (1.289 mL, 9.300 mmol) were dissolved in methylene chloride (10 mL) at room temperature, and the solution was stirred at the same temperature for 30 minutes. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 12 g cartridge; ethyl acetate/hexane=from 15% to 40%) and concentrated to afford the desired compound (0.415 g, 37.2%) as a colorless oil.

Step 3: Synthesis of Methyl 4-(((3R,5S)-3,5-dimethyl-4-(3-(morpholine-4-carbonyl)benzyl)piperazin-1-yl)methyl)benzoate (3-(chloromethyl)phenyl) (morpholino)methanone (formula 6-4, 0.415 g, 1.730 mmol), methyl 4-(((3R,5S)-3,5-dimethylpiperazin-1-yl)methyl)benzoate (formula 1-2, 0.454 g, 1.730 mmol) and $Cs_2CO_3$ (1.127 g, 3.459 mmol) were dissolved in acetonitrile (2 mL), and the solution was stirred at room temperature for 16 hours, and then stirred at 100° C. for 6 hours, followed by cooling to room temperature to terminate the reaction. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 12 g cartridge; methanol/methylene chloride=from 0% to 10%) and concentrated to afford the desired compound (0.381 g, 47.3%) as a yellow oil.

Step 4: Synthesis of Compound 446

Methyl 4-(((3R,5S)-3,5-dimethyl-4-(3-(morpholine-4-carbonyl)benzyl)piperazin-1-yl)methyl)benzoate (0.095 g, 0.204 mmol), hydroxylamine (0.250 mL, 4.085 mmol, 50.00% aqueous solution) and potassium hydroxide (0.115 g, 2.043 mmol) were dissolved in methanol (2 mL) at room temperature, and the solution was stirred at the same temperature for 1 hour. Then, the reaction mixture was concentrated under reduced pressure. A saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure. Compound 446 was used without additional purification (0.064 g, 67.4%, white solid).

$^1$H-NMR (400 MHz, $CDCl_3$) δ 11.2 (brs, 1 H), 9.01 (brs, 1 H), 7.69 (d, 2 H, J=8.0 Hz), 7.48-7.34 (m, 5 H), 7.21 (d, 1 H, J=7.1 Hz), 3.75 (s, 2 H), 3.61 (brs, 7 H), 3.44 (s, 3 H), 2.66-2.63 (m, 4 H), 1.84-1.78 (m, 2 H), 0.87 (d, 6 H, J=6.0 Hz); LRMS (ES) m/z 467.2 ($M^+$+1).

Example 208

Synthesis of Compound 452

(4-(((3R,5S)-3,5-dimethyl-4-(3-((4-(methylsulfonyl)piperazin-1-yl)methyl)benzyl)piperazin-1-yl)methyl)-N-hydroxybenzamide)

Step 1: Synthesis of 1-benzyl-4-(methylsulfonyl)piperazine 1-benzylpiperazine (2.000 g, 11.347 mmol), MsCl (0.922 mL, 11.914 mmol) and TEA (2.372 mL, 17.020 mmol) were dissolved in methylene chloride (100 mL), and the solution was stirred at the same temperature for 3 hours. Water was added to the reaction mixture, followed by extraction with methylene chloride. The extract was filtered through a plastic filter to remove solid residue and an aqueous layer, and then concentrated under reduced pressure. The concentrate was crystallized from diethyl ether (20 mL) and hexane (5 mL) at room temperature and filtered, and the resulting solid was washed with hexane and dried to yield the desired compound (0.857 g, 29.7%) as a white solid.

Step 2: Synthesis of 1-(methylsulfonyl)piperazine 1-benzyl-4-(methylsulfonyl)piperazine (0.700 g, 2.752 mmol) was dissolved in methanol (30 mL) at room temperature, and Pd/C (0.075 g) was slowly added to the solution, and then a hydrogen balloon was placed over the solution, followed by stirring at the same temperature for 3 hours. The reaction mixture was filtered through a celite pad to remove solids, and the filtrate was concentrated under reduced pressure to remove the solvent. The product was used without additional purification (0.335 g, 74.1%, white solid).

Step 3: Methyl 4-(((3R,5S)-3,5-dimethyl-4-(3-((4-(methylsulfonyl)piperazin-1-yl)methyl)benzyl)piperazin-1-yl)methyl)benzoate Methyl 4-(((3R,5S)-4-(3-formylbenzyl)-3,5-dimethylpiperazin-1-yl)methyl)benzoate (formula 5-1, 0.200 g, 0.526 mmol) and 1-(methylsulfonyl)piperazine (0.129 g, 0.788 mmol) were dissolved in methylene chloride (5 mL), and the solution was stirred at room temperature for 1 hour. Na(OAc)$_3$BH (0.223 g, 1.051 mmol) was added to the reaction solution, which was then further stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.254 g, 91.4%) as a pale yellow oil.

Step 4: Synthesis of Compound 452

Methyl 4-(((3R,5S)-3,5-dimethyl-4-(3-((4-(methylsulfonyl)piperazin-1-yl)methyl)benzyl)piperazin-1-yl)methyl)benzoate (formula 5-2, 0.254 g, 0.480 mmol), hydroxylamine (0.588 mL, 9.608 mmol, 50.00% aqueous solution) and potassium hydroxide (0.270 g, 4.804 mmol) were dissolved in methanol (7 mL) at room temperature, and the solution was stirred at the same temperature for 1 hour. The reaction mixture was concentrated under reduced pressure to remove solids, and a saturated aqueous solution of sodium hydrogen carbonate was added to the resulting concentrate, followed by extraction with methylene chloride. The extract was filtered through a plastic filter equipped with an anhydrous sodium sulfate cartridge to remove solid residue and an aqueous layer, and was then concentrated under reduced pressure to afford compound 452 (0.115 g, 45.2%) as a white solid.

$^1$H-NMR (400 MHz, DMSO-d$_6$) δ 7.69 (d, 2 H, J=7.7 Hz), 7.31 (d, 2 H, J=7.8 Hz), 7.26-7.24 (m, 3 H), 7.12 (s, 1 H), 3.72 (s, 2 H), 3.51 (s, 2 H), 3.42 (s, 2 H), 3.10 (s, 4 H), 2.87 (s, 3 H), 2.64 (d, 2 H, J=10.7 Hz), 2.57-2.55 (m, 2 H), 2.44 (s, 4 H), 1.81 (t, 2 H, J=10.3 Hz), 0.90 (d, 6 H, J=5.8 Hz).

Example 209

Synthesis of Compound 453

(4-(((3R,5S)-3,5-dimethyl-4-(3-((4-(2,2,2-trifluoroethyl)piperazin-1-yl)methyl)benzyl)piperazin-1-yl)methyl)-N-hydroxybenzamide)

Step 1: Synthesis of Tert-Butyl 4-(2,2,2-trifluoroethyl)piperazine-1-carboxylate Tert-butyl piperazine-1-carboxylate (2.000 g, 10.738 mmol), 2,2,2-trifluoroethyl trifluoromethanesulfonate (1.625 mL, 11.275 mmol) and Cs$_2$CO$_3$ (4.198 g, 12.886 mmol) were dissolved in acetonitrile (100 mL) at room temperature, and the solution was stirred at the same temperature for 17 hours. The reaction mixture was filtered through a glass filter to remove solids, and the filtrate was concentrated under reduced pressure to remove the solvent. The concentrate was purified by column chromatography (silicon dioxide, 12 g cartridge; ethyl acetate/hexane=from 0% to 20%) and concentrated to afford the desired compound (2.150 g, 74.7%) as a colorless oil.

Step 2: Synthesis of 1-(2,2,2-trifluoroethyl)piperazine

Tert-butyl 4-(2,2,2-trifluoroethyl)piperazine-1-carboxylate (2.000 g, 7.455 mmol) was dissolved in methylene chloride (10 mL)/trifluoroacetic acid (5 mL) at room temperature, and the solution was stirred at the same temperature for 17 hours. The reaction mixture was concentrated under reduced pressure to remove the solvent, and the concentrate was crystallized from ethyl acetate (20 mL) at room temperature and filtered, and the resulting solid was washed with ethyl acetate and dried to afford the desired compound (0.457 g, 23.1%) as a white solid.

Step 3: Synthesis of Methyl 4-(((3R,5S)-3,5-dimethyl-4-(3-((4-(2,2,2-trifluoroethyl)piperazin-1-yl)methyl)benzyl)piperazin-1-yl)methyl)benzoate Methyl 4-(((3R,5S)-4-(3-formylbenzyl)-3,5-dimethylpiperazin-1-yl)methyl)benzoate (formula 5-1, 0.200 g, 0.526 mmol) and 1-(2,2,2-trifluoroethyl)piperazine (0.209 g, 0.788 mmol) were dissolved in methylene chloride (5 mL), and the solution was stirred at room temperature for 1 hour. Na(OAc)$_3$BH (0.223 g, 1.051 mmol) was added to the reaction solution, which was then further stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.115 g, 41.1%) as a pale yellow oil.

Step 4: Synthesis of Compound 453

Methyl 4-(((3R,5S)-3,5-dimethyl-4-(3-((4-(2,2,2-trifluoroethyl)piperazin-1-yl)methyl)benzyl)piperazin-1-yl)methyl)benzoate (formula 5-2, 0.115 g, 0.216 mmol), hydroxylamine (0.264 mL, 4.318 mmol, 50.00% aqueous solution) and potassium hydroxide (0.121 g, 2.159 mmol) were dissolved in methanol (5 mL) at room temperature, and the solution was stirred at the same temperature for 1 hour. The reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter equipped with an anhydrous sodium sulfate cartridge to remove solid residue and an aqueous layer, and was then concentrated under reduced pressure. The concentrate was purified by column chromatography (Waters, $C_{18}$; 0.1% trifluoroacetic acid aqueous solution/acetonitrile=from 0% to 30%), after which it was passed through a SPE cartridge (PL-HCO$_3$MP SPE) and concentrated to afford compound 453 (0.012 g, 10.4%) as a white solid.

$^1$H-NMR (400 MHz, DMSO-d$_6$) δ 11.17 (brs, 1 H), 9.01 (brs, 1 H), 7.70 (d, 2 H, J=8.3 Hz), 7.35 (d, 2 H, J=8.2 Hz), 7.27 (s, 1 H), 7.23-7.22 (m, 2 H), 7.10-7.09 (m, 1 H), 3.72 (s, 2 H), 3.44 (s, 4 H), 3.14 (q, 2 H, J=10.4 Hz), 2.68-2.65 (m, 2 H), 2.61-2.53 (m, 6 H), 2.37-2.33 (m, 4 H), 1.81 (t, 2 H, J=10.3 Hz), 0.90 (d, 6 H, J=6.0 Hz).

Example 210

Synthesis of Compound 454

(N-hydroxy-4-(((3R,5S)-4-(3-((4-isopentylpiperazin-1-yl)methyl)benzyl)-3,5-dimethylpiperazin-1-yl)methyl)benzamide)

Step 1: Synthesis of Tert-Butyl 4-isopentylpiperazine-1-carboxylate

Tert-butyl piperazine-1-carboxylate (2.000 g, 10.738 mmol), 1-bromo-3-methylbutane (1.352 mL, 11.275 mmol) and Cs$_2$CO$_3$ (4.198 g, 12.886 mmol) were dissolved in acetonitrile (150 mL) at room temperature, and the solution was stirred at the same temperature for 17 hours. The reaction mixture was filtered through a glass filter to remove solids, and the filtrate was concentrated under reduced pressure to remove the solvent. The concentrate was purified by column chromatography (silicon dioxide, 12 g cartridge; ethyl acetate/hexane=from 0% to 10%) and concentrated to afford the desired compound (1.220 g, 44.3%) as a colorless oil.

Step 2: Synthesis of 1-isopentylpiperazine trifluoroacetate

Tert-butyl 4-isopentylpiperazine-1-carboxylate (1.000 g, 3.900 mmol) was dissolved in methylene chloride (10 mL)/trifluoroacetic acid (5 mL) at room temperature, and the solution was stirred at the same temperature for 17 hours. The reaction mixture was concentrated under reduced pressure to remove the solvent, and the concentrate was crystallized from ethyl acetate (20 mL) at room temperature and filtered, and the resulting solid was washed with ethyl acetate and dried to afford the desired compound (0.929 g, 94.0%) as a white solid.

Step 3: Synthesis of Methyl 4-(((3R,5S)-4-(3-((4-isopentylpiperazin-1-yl)methyl)benzyl)-3,5-dimethylpiperazin-1-yl)methyl)benzoate Methyl 4-(((3R,5S)-4-(3-formylbenzyl)-3,5-dimethylpiperazin-1-yl)methyl)benzoate (formula 5-1, 0.220 g, 0.578 mmol) and 1-isopentylpiperazine trifluoroacetate (0.220 g, 0.867 mmol) were dissolved in methylene chloride (5 mL), and the solution was stirred at room temperature for 1 hour. Na(OAc)$_3$BH (0.245 g, 1.156 mmol) was added to the reaction solution, which was then further stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.232 g, 77.0%) as a pale yellow oil.

Step 4: Synthesis of Compound 454

Methyl 4-(((3R,5S)-4-(3-((4-isopentylpiperazin-1-yl)methyl)benzyl)-3,5-dimethylpiperazin-1-yl)methyl)benzoate (formula 5-2, 0.232 g, 0.446 mmol), hydroxylamine (0.545 mL, 8.910 mmol, 50.00% aqueous solution) and potassium hydroxide (0.250 g, 4.455 mmol) were dissolved in methanol (5 mL) at room temperature, and the solution was stirred at the same temperature for 30 minutes. The reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and was then concentrated under reduced pressure to afford compound 454 (0.067 g, 29.6%) as a white solid.

$^1$H-NMR (400 MHz, DMSO-d$_6$) δ 7.69 (d, 2 H, J=8.2 Hz), 7.30 (d, 2 H, J=8.1 Hz), 7.27 (s, 1 H), 7.23-7.21 (m, 2 H), 7.09-7.08 (m, 1 H), 3.72 (s, 2 H), 3.42 (s, 2 H), 3.41 (s, 2 H), 2.63 (d, 2 H, J=10.2 Hz), 2.58-2.53 (m, 2 H), 2.34-2.27 (m, 8 H), 2.24 (t, 2 H, J=7.6 Hz), 1.80 (t, 2 H, J=10.5 Hz), 1.57-1.53 (m, 1 H), 1.31-1.25 (m, 2 H), 0.89 (d, 6 H, J=6.1 Hz), 0.85 (d, 6 H, J=6.6 Hz).

Example 211

Synthesis of Compound 455

(4-(((3R,5S)-4-(3-(((1-(diethylamino)propan-2-yl)amino)methyl)benzyl)-3,5-dimethylpiperazin-1-yl)methyl)-N-hydroxybenzamide)

Step 1: Synthesis of Methyl 4-(((3R,5S)-4-(3-(((1-(diethylamino)propan-2-yl)amino)methyl)benzyl)-3,5-dimethylpiperazin-1-yl)methyl)benzoate Methyl 4-(((3R,5S)-4-(3-formylbenzyl)-3,5-dimethylpiperazin-1-yl)methyl)benzoate (formula 5-1, 0.200 g, 0.526 mmol) and N₁,N₁-diethylpropane-1,2-diamine (0.103 g, 0.788 mmol) were dissolved in methylene chloride (5 mL), and the solution was stirred at room temperature for 1 hour. Na(OAc)₃BH (0.223 g, 1.051 mmol) was added to the reaction solution, which was then further stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.149 g, 57.3%) as a pale yellow oil.

Step 2: Synthesis of Compound 455

Methyl 4-(((3R,5S)-4-(3-(((1-(diethylamino)propan-2-yl)amino)methyl)benzyl)-3,5-dimethylpiperazin-1-yl)methyl)benzoate (formula 5-2, 0.149 g, 0.301 mmol), hydroxylamine (0.368 mL, 6.024 mmol, 50.00% aqueous solution) and potassium hydroxide (0.169 g, 3.012 mmol) were dissolved in methanol (5 mL) at room temperature, and the solution was stirred at the same temperature for 30 minutes. The reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and was then concentrated under reduced pressure to afford compound 455 (0.064 g, 42.9%) as a white solid.

$^1$H-NMR (400 MHz, DMSO-d₆) δ 7.70 (d, 2 H, J=8.2 Hz), 7.34 (d, 2 H, J=8.0 Hz), 7.26 (s, 1 H), 7.24-7.18 (m, 2 H), 3.79-3.55 (m, 4 H), 3.43 (s, 2 H), 2.63 (d, 2 H, J=10.1 Hz), 2.59-2.54 (m, 2 H), 2.46-2.37 (m, 2 H), 2.34-2.25 (m, 2 H), 2.23-2.15 (m, 2 H), 1.81 (t, 2 H, J=10.4 Hz), 0.92-0.86 (m, 15 H).

Example 212

Synthesis of Compound 456

(4-(((3R,5S)-4-(3-(((1-(benzyl(methyl)amino)propan-2-yl)amino)methyl)benzyl)-3,5-dimethylpiperazin-1-yl)methyl)-N-hydroxybenzamide)

Step 1: Synthesis of Methyl 4-(((3R,5S)-4-(3-(((1-(benzyl(methyl)amino)propan-2-yl)amino)methyl)benzyl)-3,5-dimethylpiperazin-1-yl)methyl)benzoate Methyl 4-(((3R,5S)-4-(3-formylbenzyl)-3,5-dimethylpiperazin-1-yl)methyl)benzoate (formula 5-1, 0.200 g, 0.526 mmol) and N₁-benzyl-N₁-methylpropane-1,2-diamine (0.141 g, 0.788 mmol) were dissolved in methylene chloride (5 mL), and the solution was stirred at room temperature for 1 hour. Na(OAc)₃BH (0.223 g, 1.051 mmol) was added to the reaction solution, which was then further stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.252 g, 88.3%) as a pale yellow oil.

Step 2: Synthesis of Compound 456

Methyl 4-(((3R,5S)-4-(3-(((1-(benzyl(methyl)amino)propan-2-yl)amino)methyl)benzyl)-3,5-dimethylpiperazin-1-yl)methyl)benzoate (formula 5-2, 0.252 g, 0.464 mmol), hydroxylamine (0.568 mL, 9.286 mmol, 50.00% aqueous solution) and potassium hydroxide (0.261 g, 4.643 mmol) were dissolved in methanol (5 mL) at room temperature, and the solution was stirred at the same temperature for 30 minutes. The reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and was then concentrated under reduced pressure to afford compound 456 (0.196 g, 77.6%) as a white solid.

$^1$H-NMR (400 MHz, DMSO-d₆) δ 7.69 (d, 2 H, J=8.2 Hz), 7.33 (d, 2 H, J=8.2 Hz), 7.31-7.20 (m, 8 H), 7.12 (d, 1 H, J=6.5 Hz), 3.80-3.57 (m, 4 H), 3.39 (s, 2 H), 2.70-2.69 (m, 1 H), 2.61 (d, 2 H, J=10.8 Hz), 2.55-2.53 (m, 2 H), 2.34-2.29 (m, 1 H), 2.12-2.09 (m, 1 H), 1.79 (t, 2 H, J=10.4 Hz), 0.92 (d, 3 H, J=6.1 Hz), 0.88 (d, 6 H, J=6.0 Hz).

Example 213

Synthesis of Compound 457

(4-(((3R,5S)-3,5-dimethyl-4-(2-(morpholinomethyl)benzyl)piperazin-1-yl)methyl)-N-hydroxybenzamide)

Step 1: Synthesis of 2-(bromomethyl)benzaldehyde 2-(bromomethyl)benzonitrile (2.500 g, 12.752 mmol) was dissolved in methylene chloride (30 mL) at 0° C., and DIBAL-H (1.00 M solution, 13.390 mL, 13.390 mmol) was added to the solution, followed by stirring at the same temperature for 2 hours. Then, an aqueous solution of hydrochloric acid was added to the reaction mixture at 0° C., followed by stirring for 30 minutes. After completion of the reaction, water was added to the reaction mixture, which was then extracted with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 40 g cartridge; ethyl acetate/hexane=from 0% to 30%) and concentrated to afford the desired compound (0.400 g, 15.8%) as a brown oil.

Step 2: Synthesis of Methyl 4-(((3R,5S)-4-(2-formylbenzyl)-3,5-dimethylpiperazin-1-yl)methyl)benzoate Methyl 4-(((3R,5S)-3,5-dimethylpiperazin-1-yl)methyl)benzoate (formula 1-2, 0.500 g, 1.906 mmol), 2-(bromomethyl)benzaldehyde (0.379 g, 1.906 mmol) and Cs₂CO₃ (0.931 g, 2.859 mmol) were dissolved in acetonitrile (10 mL), and the solution was stirred at the same temperature for 17 hours. Water was added to the reaction mixture, which was then extracted with methylene chloride. The extract was filtered through a plastic filter to remove solid residue and an aqueous layer, and then concentrated under reduced pressure. The concentrate was purified by column chromatography (silicon dioxide, 12 g cartridge; ethyl acetate/hexane=from 0% to 40%) and concentrated to afford the desired compound (0.116 g, 16.0%) as a pale brown oil.

Step 3: Synthesis of Methyl 4-(((3R,5S)-3,5-dimethyl-4-(2-(morpholinomethyl)benzyl)piperazin-1-yl)methyl)benzoate Methyl 4-(((3R,5S)-4-(2-formylbenzyl)-3,5-dimethylpiperazin-1-yl)methyl)benzoate (formula 5-1, 0.116 g, 0.305 mmol) and morpholine (0.040 mL, 0.457 mmol) were dissolved in methylene chloride (10 mL), and the solution was stirred at room temperature for 30 minutes. Na(OAc) 3BH (0.129 g, 0.610 mmol) was added to the reaction solution, which was then further stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 0% to 30%) and concentrated to afford the desired compound (0.076 g, 55.2%) as a pale yellow oil.

Step 4: Synthesis of Compound 457

Methyl 4-(((3R,5S)-3,5-dimethyl-4-(2-(morpholinomethyl)benzyl)piperazin-1-yl)methyl)benzoate (formula 5-2, 0.076 g, 0.168 mmol), hydroxylamine (0.018 mL, 3.366 mmol, 50.00% aqueous solution) and potassium hydroxide (0.094 g, 1.683 mmol) were dissolved in methanol (5 mL) at room temperature, and the solution was stirred at the same temperature for 1 hour. The reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter equipped with an anhydrous sodium sulfate cartridge to remove solid residue and an aqueous layer, and was then concentrated under reduced pressure to afford compound 457 (0.060 g, 78.8%) as a pale yellow solid.
$^1$H-NMR (400 MHz, DMSO-$d_6$) δ 7.77 (d, 1 H, J=7.8 Hz), 7.71 (d, 2 H, J=8.1 Hz), 7.33 (d, 2 H, J=8.1 Hz), 7.22-7.21 (m, 1 H), 7.11-7.08 (m, 2 H), 3.86 (s, 2 H), 3.52 (s, 4 H), 3.46 (s, 2 H), 3.43 (s, 2 H), 2.68 (d, 2 H, J=10.8 Hz), 2.65-2.61 (m, 2 H), 2.33 (s, 4 H), 1.87 (t, 2 H, J=10.3 Hz), 0.80 (d, 6 H, J=6.0 Hz); LRMS (ES) m/z 453.2 (M$^+$+1).

Example 214

Synthesis of Compound 458

(4-(((3R,5S)-3,5-dimethyl-4-(4-(morpholinomethyl)benzoyl)piperazin-1-yl)methyl)-N-hydroxybenzamide)

Step 1: Synthesis of 4-(chloromethyl)benzoyl chloride

A mixture of 4-(bromomethyl)benzoic acid (5.000 g, 23.251 mmol) and SOCl$_2$ (8.444 mL, 116.257 mmol) was stirred at room temperature, and stirred at 50° C. for 17 hours, followed by cooling to room temperature to terminate the reaction. The reaction mixture was concentrated under reduced pressure to remove the solvent, and the product was used without additional purification (4.400 g, 100.1%, palet purple solid).

Step 2: Synthesis of Methyl 4-(((3R,5S)-4-(4-(chloromethyl)benzoyl)-3,5-dimethylpiperazin-1-yl)methyl)benzoate Methyl 4-(((3R,5S)-3,5-dimethylpiperazin-1-yl)methyl)benzoate (formula 1-2, 4.400 g, 23.275 mmol), 4-(chloromethyl)benzoyl chloride (formula 6-1, 3.053 g, 11.638 mmol) and TEA (6.488 mL, 46.551 mmol) were dissolved in methylene chloride (150 mL) at 0° C., and the solution was stirred at room temperature for 3 hours. Water was added to the reaction mixture, which was then extracted with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 40 g cartridge; ethyl acetate/hexane=from 5% to 70%) and concentrated, and then the resulting material was purified by column chromatography (silicon dioxide, 4 g cartridge; ethyl acetate/hexane=from 5% to 20%) and concentrated to afford the desired compound (1.720 g, 17.8%) as an orange solid.

Step 3: Synthesis of Methyl 4-(((3R,5S)-3,5-dimethyl-4-(4-(morpholinomethyl)benzoyl)piperazin-1-yl)methyl)benzoate Methyl 4-(((3R,5S)-4-(4-(chloromethyl)benzoyl)-3,5-dimethylpierazin-1-yl)methyl)benzoate (formula 6-2, 0.100 g, 0.241 mmol), morpholine (0.031 mL, 0.362 mmol) and Cs$_2$CO$_3$ (0.157 g, 0.482 mmol) were dissolved in acetonitrile (4 mL) at room temperature, and the solution was stirred at the same temperature for 17 hours. Then, the reaction mixture was concentrated under reduced pressure to remove the solvent, and water was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 5%) and concentrated to afford the desired compound (0.107 g, 95.4%) as a colorless oil.

Step 4: Synthesis of Compound 458

Methyl 4-(((3R,5S)-3,5-dimethyl-4-(4-(morpholinomethyl)benzoyl)piperazin-1-yl)methyl)benzoate (formula 6-3, 0.107 g, 0.230 mmol), hydroxylamine (0.281 mL, 4.596 mmol, 50.00% aqueous solution) and potassium hydroxide (0.129 g, 2.298 mmol) were dissolved in methanol (5 mL) at room temperature, and the solution was stirred at the same temperature for 1 hour. The reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter equipped with an anhydrous sodium sulfate cartridge to remove solid residue and an aqueous layer, and was then concentrated under reduced pressure to afford compound 458 (0.034 g, 31.6%) as a pale orange solid.

$^1$H-NMR (400 MHz, DMSO-d$_6$) δ 7.70 (d, 2 H, J=8.0 Hz), 7.36-7.34 (m, 4 H), 7.28 (d, 2 H, J=8.0 Hz), 4.12 (brs, 2 H), 3.57 (t, 4 H, J=4.4 Hz), 3.52 (s, 2 H), 3.48 (s, 2 H), 2.62-2.61 (m, 2 H), 2.35 (s, 4 H), 2.13 (dd, 2 H, J=11.2, 4.2 Hz), 1.28-1.25 (m, 6 H); LRMS (ES) m/z 467.2 (M$^+$+1).

Example 215

Synthesis of Compound 459

(4-(((3R,5S)-3,5-dimethyl-4-(4-(piperidin-1-ylmethyl)benzoyl)piperazin-1-yl)methyl)-N-hydroxybenzamide)

Step 1: Synthesis of Methyl 4-(((3R,5S)-3,5-dimethyl-4-(4-piperidine-1-ylmethyl)benzoyl)piperazin-1-yl)methyl)benzoate Methyl 4-(((3R,5S)-4-(4-(chloromethyl)benzoyl)-3,5-dimethylpiperazin-1-yl)methyl)benzoate (formula 6-2, 0.100 g, 0.241 mmol), piperidine (0.031 mL, 0.362 mmol) and Cs$_2$CO$_3$ (0.157 g, 0.482 mmol) were dissolved in acetonitrile (4 mL) at room temperature, and the solution was stirred at the same temperature for 17 hours. Then, the reaction mixture was concentrated under reduced pressure to remove the solvent, and water was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 5%) and concentrated to afford the desired compound (0.101 g, 90.4%) as a colorless oil.

Step 2: Synthesis of Compound 459

Methyl 4-(((3R,5S)-3,5-dimethyl-4-(4-piperidine-1-ylmethyl)benzoyl)piperazin-1-yl)methyl)benzoate (formula 6-3, 0.101 g, 0.218 mmol), hydroxylamine (0.267 mL, 4.357 mmol, 50.00% aqueous solution) and potassium hydroxide (0.122 g, 2.179 mmol) were dissolved in methanol (5 mL) at room temperature, and the solution was stirred at the same temperature for 1 hour. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 12 g cartridge; ethyl acetate/hexane=from 0% to 30%) and concentrated to afford compound 459 (0.073 g, 72.1%) as a white solid.

$^1$H-NMR (400 MHz, DMSO-d$_6$) δ 7.72 (d, 2 H, J=8.2 Hz), 7.42 (d, 2 H, J=8.2 Hz), 7.33 (d, 2 H, J=8.1 Hz), 7.27 (d, 2 H, J=8.1 Hz), 4.12 (brs, 1 H), 3.54 (s, 2 H), 3.43 (s, 2 H), 2.64-2.62 (m, 2 H), 2.31 (s, 4 H), 2.15 (dd, 2 H, J=11.4, 4.2 Hz), 1.52-1.46 (m, 4 H), 1.39-1.38 (m, 2 H), 1.29 (d, 6 H, J=6.1 Hz); LRMS (ES) m/z 465.2 (M$^+$+1).

Example 216

Synthesis of Compound 460

(4-(((3R,5S)-4-(4-(((R)-3-fluoropyrrolidin-1-yl)methyl)benzoyl)-3,5-dimethylpiperazin-1-yl)methyl)-N-hydroxybenzamide)

Step 1: Synthesis of Methyl 4-(((3R,5S)-4-(4-(((R)-3-fluoropyrrolidin-1-yl)methyl)benzoyl)-3,5-dimethylpiperazin-1-yl)methyl)benzoate Methyl 4-(((3R,5S)-4-(4-(chloromethyl)benzoyl)-3,5-dimethylpiperazin-1-yl)methyl)benzoate (formula 6-2, 0.100 g, 0.241 mmol), (R)-3-fluoropyrrolidine (0.045 g, 0.362 mmol) and Cs$_2$CO$_3$ (0.157 g, 0.482 mmol) were dissolved in acetonitrile (4 mL) at room temperature, and the solution was stirred at the same temperature for 17 hours. Then, the reaction mixture was concentrated under reduced pressure to remove the solvent, and water was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 5%) and concentrated to afford the desired compound (0.103 g, 91.4%) as a pale yellow oil.

Step 2: Synthesis of Compound 460

Methyl 4-(((3R,5S)-4-(4-(((R)-3-fluoropyrrolidin-1-yl)methyl)benzoyl)-3,5-dimethylpiperazin-1-yl)methyl)benzoate (formula 6-3, 0.103 g, 0.220 mmol), hydroxylamine (0.269 mL, 4.406 mmol, 50.00% aqueous solution) and potassium hydroxide (0.124 g, 2.203 mmol) were dissolved in methanol (5 mL) at room temperature, and the solution was stirred at the same temperature for 1 hour. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 12 g cartridge; ethyl acetate/hexane=from 0% to 30%) and concentrated to afford compound 460 (0.082 g, 79.4%) as a white solid.

$^1$H-NMR (400 MHz, DMSO-d$_6$) δ 11.19 (brs, 1 H), 9.04 (brs, 1 H), 7.72 (d, 2 H, J=8.2 Hz), 7.43 (d, 2 H, J=8.1 Hz), 7.36 (d, 2 H, J=8.1 Hz), 7.29 (d, 2 H, J=8.1 Hz), 5.20 (dt, 1 H, J=55.5, 5.8 Hz), 4.15 (brs, 2 H), 3.62 (s, 2 H), 3.55 (s, 2 H), 2.82-2.73 (m, 2 H), 2.68-2.61 (m, 3 H), 2.33-2.28 (m, 1 H), 2.17-2.13 (m, 3 H), 1.94-1.89 (m, 1 H), 1.29 (d, 6 H, J=5.3 Hz).

Example 217

Synthesis of Compound 461

(4-(((3R,5S)-3,5-dimethyl-4-(4-(pyrrolidin-1-ylmethyl)benzoyl)piperazin-1-yl)methyl)-N-hydroxybenzamide)

Step 1: Synthesis of Methyl 4-(((3R,5S)-3,5-dimethyl-4-(4-(pyrrolidin-1-ylmethyl)benzoyl)piperazin-1-yl)methyl)benzoate Methyl 4-(((3R,5S)-4-(4-(chloromethyl)benzoyl)-3,5-dimethylpiperazin-1-yl)methyl)benzoate (formula 6-2, 0.100 g, 0.241 mmol), pyrrolidine (0.030 mL, 0.362 mmol) and Cs$_2$CO$_3$ (0.157 g, 0.482 mmol) were dissolved in acetonitrile (4 mL) at room temperature, and the solution was stirred at the same temperature for 17 hours. Then, the reaction mixture was concentrated under reduced pressure to remove the solvent, and water was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 5%) and concentrated to afford the desired compound (0.102 g, 94.1%) as a pale yellow oil.

Step 2: Synthesis of Compound 461

Methyl 4-(((3R,5S)-3,5-dimethyl-4-(4-(pyrrolidin-1-ylmethyl)benzoyl)piperazin-1-yl)methyl)benzoate (formula 6-3, 0.102 g, 0.227 mmol), hydroxylamine (0.278 mL, 4.537 mmol, 50.00% aqueous solution) and potassium hydroxide (0.127 g, 2.269 mmol) were dissolved in methanol (5 mL) at room temperature, and the solution was stirred at the same temperature for 1 hour. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 12 g cartridge; ethyl acetate/hexane=from 0% to 30%) and concentrated to afford compound 461 (0.071 g, 69.5%) as a pale yellow solid.

$^1$H-NMR (400 MHz, DMSO-d$_6$) δ 11.18 (brs, 1 H), 9.04 (brs, 1 H), 7.72 (d, 2 H, J=8.2 Hz), 7.43 (d, 2 H, J=8.1 Hz), 7.35 (d, 2 H, J=8.0 Hz), 7.27 (d, 2 H, J=8.0 Hz), 4.19 (brs, 2 H), 3.58 (s, 2 H), 3.55 (s, 2 H), 2.63 (d, 2 H, J=10.0 Hz), 2.41 (s, 4 H), 2.15 (dd, 2 H, J=11.4, 4.2 Hz), 1.70-1.68 (m, 4 H), 1.29 (d, 6 H, J=6.1 Hz).

Example 218

Synthesis of Compound 462

(4-(((3R,5S)-3,5-dimethyl-4-(4-((4-methylpiperazin-1-yl)methyl)benzoyl)piperazin-1-yl)methyl)-N-hydroxybenzamide)

Step 1: Synthesis of Methyl 4-(((3R,5S)-3,5-dimethyl-4-(4-((4-methylpiperazin-1-yl)methyl)benzoyl)piperazin-1-yl)methyl)benzoate Methyl 4-(((3R,5S)-4-(4-(chloromethyl)benzoyl)-3,5-dimethylpiperazin-1-yl)methyl)benzoate (formula 6-2, 0.100 g, 0.241 mmol), 1-methylpiperazine (0.040 mL, 0.362 mmol) and Cs$_2$CO$_3$ (0.157 g, 0.482 mmol) were dissolved in acetonitrile (4 mL) at room temperature, and the solution was stirred at the same temperature for 17 hours. Then, the reaction mixture was concentrated under reduced pressure to remove the solvent, and water was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.102 g, 88.4%) as a colorless oil.

Step 2: Synthesis of Compound 462

Methyl 4-(((3R,5S)-3,5-dimethyl-4-(4-((4-methylpiperazin-1-yl)methyl)benzoyl)piperazin-1-yl)methyl)benzoate (formula 6-3, 0.102 g, 0.213 mmol), hydroxylamine (0.261 mL, 4.262 mmol, 50.00% aqueous solution) and potassium hydroxide (0.120 g, 2.131 mmol) were dissolved in methanol (5 mL) at room temperature, and the solution was stirred at the same temperature for 1 hour. The reaction mixture was concentrated under reduced pressure to remove the solvent, and a saturated aqueous solution of sodium hydrogen carbonate (20 mL) was added to the concentrate, followed by stirring. The precipitated solid was filtered, washed with water, and dried to yield compound 462 (0.057 g, 55.8%) as a white solid.

$^1$H-NMR (400 MHz, DMSO-d$_6$) δ 11.20 (brs, 1 H), 9.04 (brs, 1 H), 7.72 (d, 2 H, J=8.2 Hz), 7.43 (d, 2 H, J=8.1 Hz), 7.33 (d, 2 H, J=8.1 Hz), 7.27 (d, 2 H, J=7.8 Hz), 4.21 (brs, 2 H), 3.54 (s, 2 H), 3.47 (s, 2 H), 2.63 (d, 2 H, J=11.4 Hz), 2.33-2.32 (m, 8 H), 2.17-2.14 (m, 5 H), 1.30 (s, 6 H); LRMS (ES) m/z 480.2 (M$^+$+1).

Example 219

Synthesis of Compound 463

(4-(((3R,5S)-3,5-dimethyl-4-(4-((4-(methylsulfonyl)piperazin-1-yl)methyl)benzoyl)piperazin-1-yl)methyl)-N-hydroxybenzamide)

Step 1: Synthesis of Methyl 4-(((3R,5S)-3,5-dimethyl-4-(4-((4-(methylsulfonyl)piperazin-1-yl)methyl)benzoyl)piperazin-1-yl)methyl)benzoate Methyl 4-(((3R,5S)-4-(4-(chloromethyl)benzoyl)-3,5-dimethylpiperzin-1-yl)methyl)benzoate (formula 6-2, 0.100 g, 0.241 mmol), 1-(methylsulfonyl)piperazine (0.059 g, 0.362 mmol) and Cs$_2$CO$_3$ (0.157 g, 0.482 mmol) were dissolved in acetonitrile (4 mL) at room temperature, and the solution was stirred at the same temperature for 17 hours. Then, the reaction mixture was concentrated under reduced pressure to remove the solvent, and water was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.126 g, 96.3%) as a colorless oil.

Step 2: Synthesis of Compound 463

Methyl 4-(((3R,5S)-3,5-dimethyl-4-(4-((4-(methylsulfonyl)piperazin-1-yl)methyl)benzoyl)piperazin-1-yl)methyl)benzoate (formula 6-3, 0.126 g, 0.297 mmol), hydroxylamine (0.364 mL, 5.950 mmol, 50.00% aqueous solution) and potassium hydroxide (0.167 g, 2.975 mmol) were dissolved in methanol (5 mL) at room temperature, and the solution was stirred at the same temperature for 1 hour. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure. The concentrate was purified by column chromatography (silicon dioxide, 12 g cartridge; ethyl acetate/hexane=from 0% to 30%) and concentrated to afford compound 463 (0.065 g, 53.2%) as a white solid.

$^1$H-NMR (400 MHz, DMSO-d$_6$) δ 7.72 (d, 2 H, J=8.3 Hz), 7.42 (d, 2 H, J=8.1 Hz), 7.36 (d, 2 H, J=8.1 Hz), 7.30 (d, 2 H, J=8.2 Hz), 4.25 (brs, 2 H), 3.55 (s, 4 H), 3.11 (t, 4 H, J=4.5 Hz), 2.87 (s, 3 H), 2.63 (d, 2 H, J=10.3 Hz), 2.47 (s, 4 H), 2.15 (dd, 2 H, J=11.4, 4.1 Hz), 1.29-1.28 (m, 6 H).

Example 220

Synthesis of Compound 466

(4-(((3R,5S)-3,5-dimethyl-4-(4-(pyrrolidin-1-ylmethyl)benzyl)piperazin-1-yl)methyl)-N-hydroxybenzamide)

Step 1: Synthesis of Methyl 4-(((3R,5S)-4-(4-formylbenzyl)-3,5-dimethylpiperazin-1-yl)methyl)benzoate Methyl 4-(((3R,5S)-3,5-dimethylpiperazin-1-yl)methyl)benzoate (formula 1-2, 1.000 g, 3.812 mmol), 4-(bromomethyl)benzaldehyde (0.759 g, 3.812 mmol) and Cs$_2$CO$_3$ (2.484 g, 7.623 mmol) were dissolved in acetonitrile (25 mL) at room temperature, and the solution was stirred at the same temperature for 16 hours. The reaction mixture was filtered through a paper filter to remove solids, and the filtrate was concentrated under reduced pressure to remove the solvent. The concentrate was purified by column chromatography (silicon dioxide, 40 g cartridge; ethyl acetate/hexane=from 0% to 25%) and concentrated to afford the desired compound (0.934 g, 64.4%) as a white solid.

Step 2: Synthesis of Methyl 4-(((3R,5S)-3,5-dimethyl-4-(4-(pyrrolidin-1-ylmethyl)benzyl)piperazin-1-yl)methyl)benzoate Methyl 4-(((3R,5S)-4-(4-formylbenzyl)-3,5-dimethylpiperazin-1-yl)methyl)benzoate (formula 5-1, 0.180 g, 0.473 mmol) and pyrrolidine (0.044 mL, 0.520 mmol) were dissolved in methylene chloride (2 mL), and the solution was stirred at room temperature for 1 hour. Na(OAc)$_3$BH (0.150 g, 0.710 mmol) was added to the reaction solution, which was then further stirred at the same temperature for 16 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 30% to 100%) and concentrated to afford the desired compound (0.098 g, 47.5%) as a yellow solid.

Step 3: Synthesis of Compound 466

Methyl 4-(((3R,5S)-3,5-dimethyl-4-(4-(pyrrolidin-1-ylmethyl)benzyl)piperazin-1-yl)methyl)benzoate (formula 5-2, 0.098 g, 0.225 mmol) and hydroxylamine (0.275 mL, 4.490 mmol, 50.00% aqueous solution) were dissolved in methanol (3 mL) at room temperature, and potassium hydroxide (0.126 g, 2.245 mmol) was added to the solution, which was then stirred at the same temperature for 1 hour. Then, the reaction mixture was concentrated under reduced pressure to remove the solvent, and a saturated aqueous solution of sodium hydrogen carbonate was added to the resulting concentrate, followed by extraction with methylene chloride. The organic layer was washed with a saturated aqueous solution of sodium chloride, dried with anhydrous magnesium sulfate, filtered, and then concentrated under reduced pressure to afford compound 466 (0.055 g, 56.0%) as a white solid.

$^1$H-NMR (400 MHz, DMSO-d$_6$) δ 10.9 (brs, 1 H), 9.07 (brs, 1 H), 7.69 (d, 2 H, J=7.9 Hz), 7.34 (d, 2 H, J=7.8 Hz), 7.26 (d, 2 H, J=7.8 Hz), 7.20 (d, 2 H, J=7.8 Hz), 3.70 (s, 2 H), 3.51 (s, 2 H), 3.42 (s, 2 H), 2.66-2.64 (m, 2 H), 2.60-2.55 (m, 2 H), 2.39 (s, 4 H), 1.79 (t, 2 H, J=10.4 Hz), 1.66 (s, 4 H), 0.90 (d, 6 H, J=6.0 Hz); LRMS (ES) m/z 437.3 (M$^+$+1).

Example 221

Synthesis of Compound 467

(4-(((3R,5S)-3,5-dimethyl-4-(4-(piperidin-1-ylmethyl)benzyl)piperazin-1-yl)methyl)-N-hydroxybenzamide)

Step 1: Synthesis of Methyl 4-(((3R,5S)-3,5-dimethyl-4-(4-(piperidin-1-ylmethyl)benzyl)piperazin-1-yl)methyl)benzoate Methyl 4-(((3R,5S)-4-(4-formylbenzyl)-3,5-dimethylpiperazin-1-yl)methyl)benzoate (formula 5-1, 0.180 g, 0.473 mmol) and piperidine (0.052 mL, 0.520 mmol) were dissolved in methylene chloride (2 mL), and the solution was stirred at room temperature for 1 hour. Na(OAc)$_3$BH (0.150 g, 0.710 mmol) was added to the reaction solution, which was then further stirred at the same temperature for 16 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 30% to 100%) and concentrated to afford the desired compound (0.149 g, 70.1%) as a white solid.

Step 2: Synthesis of Compound 467

Methyl 4-(((3R,5S)-3,5-dimethyl-4-(4-(piperidin-1-ylmethyl)benzyl)piperazin-1-yl)methyl)benzoate (formula 5-2, 0.149 g, 0.332 mmol) and hydroxylamine (0.406 mL, 6.637 mmol, 50.00% aqueous solution) were dissolved in methanol (3 mL) at room temperature, and potassium hydroxide (0.186 g, 3.318 mmol) was added to the solution, which was then stirred at the same temperature for 1 hour. Then, the reaction mixture was concentrated under reduced pressure to remove the solvent, and a saturated aqueous solution of sodium hydrogen carbonate was added to the resulting concentrate, followed by extraction with methylene chloride. The organic layer was washed with a saturated aqueous solution of sodium chloride, dried with anhydrous magnesium sulfate, filtered, and then concentrated under reduced pressure to afford compound 467 (0.118 g, 78.8%) as a white solid.

$^1$H-NMR (400 MHz, DMSO-d$_6$) δ 11.2 (brs, 1 H), 9.04 (brs, 1 H), 7.69 (d, 2 H, J=7.7 Hz), 7.33 (d, 2 H, J=7.7 Hz), 7.26 (d, 2 H, J=7.7 Hz), 7.18 (d, 2 H, J=7.8 Hz), 3.70 (s, 2 H), 3.42 (s, 2 H), 2.62 (d, 2 H, J=10.4 Hz), 2.55 (m, 2 H), 2.27 (s, 4 H), 1.79 (t, 2 H, J=10.4 Hz), 1.48-1.45 (m, 4 H), 1.37-1.36 (m, 2 H), 0.90 (d, 6 H, J=5.9 Hz); LRMS (ES) m/z 451.2 (M$^+$+1).

Example 222

Synthesis of Compound 468

(4-(((3R,5S)-3,5-dimethyl-4-(4-((4-methylpiperazin-1-yl)methyl)benzyl)piperazin-1-yl)methyl)-N-hydroxybenzamide)

Step 1: Synthesis of Methyl 4-(((3R,5S)-3,5-dimethyl-4-(4-((4-methylpiperazin-1-yl)methyl)benzyl)piperazin-1-yl)methyl)benzoate Methyl 4-(((3R,5S)-4-(4-formylbenzyl)-3,5-dimethylpiperazin-1-yl)methyl)benzoate (formula 5-1, 0.180 g, 0.473 mmol) and 1-methylpiperazine (0.058 mL, 0.520 mmol) were dissolved in methylene chloride (2 mL), and the solution was stirred at room temperature for 1 hour. Na(OAc)$_3$BH (0.150 g, 0.710 mmol) was added to the reaction solution, which was then further stirred at the same temperature for 16 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 30% to 100%) and concentrated to afford the desired compound (0.193 g, 87.7%) as a white solid.

Step 2: Synthesis of Compound 468

Methyl 4-(((3R,5S)-3,5-dimethyl-4-(4-((4-methylpiperazin-1-yl)methyl)benzyl)piperazin-1-yl)methyl)benzoate (formula 5-2, 0.192 g, 0.413 mmol) and hydroxylamine (0.506 mL, 8.264 mmol, 50.00% aqueous solution) were dissolved in methanol (3 mL) at room temperature, and potassium hydroxide (0.232 g, 4.132 mmol) was added to the solution, which was then stirred at the same temperature for 1 hour. Then, the reaction mixture was concentrated under reduced pressure to remove the solvent, and a saturated aqueous solution of sodium hydrogen carbonate was added to the resulting concentrate, followed by extraction with methylene chloride. The organic layer was washed with a saturated aqueous solution of sodium chloride, dried with anhydrous magnesium sulfate, filtered, and then concentrated under reduced pressure to afford compound 468 (0.041 g, 21.5%) as a white solid.

$^1$H-NMR (400 MHz, DMSO-d$_6$) δ 11.1 (brs, 1 H), 9.06 (brs, 1 H), 7.68 (d, 2 H, J=8.1 Hz), 7.31 (d, 2 H, J=7.9 Hz), 7.27 (d, 2 H, J=8.0 Hz), 7.18 (d, 2 H, J=7.9 Hz), 3.70 (s, 2 H), 3.42 (s, 2 H), 3.39 (s, 2 H), 2.67-2.61 (m, 2 H), 2.59-2.54 (m, 2 H), 2.43-2.17 (m, 8 H), 2.13 (s, 3 H), 1.79 (t, 2 H, J=11.1 Hz), 0.89 (d, 6 H, J=6.0 Hz); LRMS (ES) m/z 466.3 (M$^+$+1).

Example 223

Synthesis of Compound 472

((E)-3-(4-(((3R,5S)-3,5-dimethyl-4-(3-(morpholinomethyl)benzyl)piperazin-1-yl)methyl)phenyl)-N-hydroxyacrylamide)

Step 1: Synthesis of (E)-Methyl 3-(4-(((3R,5S)-4-(3-formylbenzyl)-3,5-dimethylpiperazin-1-yl)methyl)phenyl)acrylate (E)-methyl 3-(4-(((3R,5S)-3,5-dimethylpiperazin-1-yl)methyl)phenyl)acrylate (formula 9-1, 0.300 g, 1.040 mmol), 3-(bromomethyl)benzaldehyde (0.207 g, 1.040 mmol) and Cs$_2$CO$_3$ (0.678 g, 2.081 mmol) were dissolved in acetonitrile (3 mL) at room temperature, and the solution was stirred at the same temperature for 16 hours. Water was added to the reaction mixture, followed by extraction with methylene chloride, and the extract was filtered through a plastic filter to remove solid residue and an aqueous layer, and then concentrated under reduced pressure. The concentrate was purified by column chromatography (silicon dioxide, 12 g cartridge; methanol/methylene chloride=from 0% to 10%) and concentrated to afford the desired compound (0.250 g, 59.2%) as a yellow oil.

Step 2: Synthesis of (E)-Methyl 3-(4-(((3R,5S)-3,5-dimethyl-4-(3-(morpholinomethyl)benzyl)piperazin-1-yl)methyl)phenyl)acrylate (E)-methyl 3-(4-(((3R,5S)-4-(3-formylbenzyl)-3,5-dimethylpiperazin-1-yl)methyl)phenyl)acrylate (formula 10-1, 0.250 g, 0.616 mmol) and morpholine (0.060 mL, 0.677 mmol) were dissolved in methylene chloride (3 mL), and the solution was stirred at room temperature for 1 hour. Na(OAc)$_3$BH (0.196 g, 0.924 mmol) was added to the reaction solution, which was then further stirred at the same temperature for 16 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 30% to 100%) and concentrated to afford the desired compound (0.186 g, 63.1%) as a yellow oil.

Step 3: Synthesis of Compound 472

(E)-Methyl 3-(4-(((3R,5S)-3,5-dimethyl-4-(3-(morpholinomethyl)benzyl)piperazin-1-yl)methyl)phenyl)acrylate (formula 10-2, 0.186 g, 0.389 mmol) and hydroxylamine (0.476 mL, 7.788 mmol, 50.00% aqueous solution) were dissolved in methanol (4 mL) at room temperature, and potassium hydroxide (0.219 g, 3.894 mmol) was added to the solution, which was then stirred at the same temperature for 1 hour. Then, the reaction mixture was concentrated under reduced pressure to remove the solvent, and a saturated aqueous solution of sodium hydrogen carbonate was added to the resulting concentrate, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (Waters, C$_{18}$; acetonitrile/0.1% trifluoroacetic acid=from 5% to 70%), after which it was passed through a SPE cartridge (PL-HCO₃ MP SPE) and concentrated to afford the desired compound 472 (0.142 g, 63.4%) as a white solid.

¹H-NMR (400 MHz, DMSO-d₆) δ 10.8 (brs, 1 H), 9.06 (brs, 1 H), 7.51-7.49 (m, 2 H), 7.45-7.41 (m, 1 H), 7.38-7.19 (m, 4 H), 7.17-7.11 (m, 2 H), 6.44-6.41 (m, 1 H), 3.71 (s, 2 H), 3.56 (s, 4 H), 3.43-3.41 (m, 4 H), 2.65-2.62 (m, 4 H), 2.33 (brs, 4 H), 1.82-1.72 (m, 2 H), 0.89 (d, 6 H, J=6.0 Hz); LRMS (ES) m/z 479.3 (M⁺+1).

Example 224

Synthesis of Compound 475

((E)-3-(4-(((2S,6R)-2,6-dimethyl-4-(3-(pyrrolidin-1-ylmethyl)benzyl)piperazin-1-yl)methyl)phenyl)-N-hydroxyacrylamide)

Step 1: Synthesis of (3R,5S)-tert-butyl 3,5-dimethylpiperazine-1-carboxylate (2S,6R)-2,6-dimethylpiperazine (10.000 g, 87.573 mmol) and TEA (24.278 mL, 175.147 mmol) were dissolved in methylene chloride (150 mL) at room temperature, and Boc₂O (20.119 mL, 87.573 mmol) was added to the solution, which was then stirred at the same temperature for 16 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 80 g cartridge; methanol/methylene chloride=from 0% to 5%) and concentrated to afford the desired compound (15.393 g, 82.0%) as a yellow solid.

Step 2: Synthesis of (3R,5S)-tert-butyl 4-(4-((E)-3-methoxy-3-oxoprop-1-en-1-yl)benzyl)-3,5-dimethylpiperazine-1-carboxylate (3R,5S)-tert-butyl 3,5-dimethylpiperazine-1-carboxylate (formula 8-1, 5.000 g, 23.332 mmol), methyl 3-(4-bromomethyl)cinamate (formula 8-4, 5.952 g, 23.332 mmol) and Cs₂CO₃ (15.204 g, 46.664 mmol) were mixed in acetonitrile (150 mL) at room temperature, and the mixture was heated under reflux, and then cooled to room temperature. The reaction mixture was filtered through a paper filter to remove solids, and the filtrate was concentrated under reduced pressure to remove the solvent. The concentrate was purified by column chromatography (silicon dioxide, 80 g cartridge; ethyl acetate/hexane=from 0% to 20%) and concentrated to afford the desired compound (6.800 g, 75.0%) as a yellow oil.

Step 3: Synthesis of (E)-Methyl 3-(4-(((2S,6R)-2,6-dimethylpiperazin-1-yl)methyl)phenyl)acrylate (3R,5S)-tert-butyl 4-(4-((E)-3-methoxy-3-oxoprop-1-en-1-yl)benzyl)-3,5-dimethylpiperazine-1-carboxylate (6.800 g, 17.503 mmol) and HCl (4.00M dioxane solution, 21.879 mL, 87.516 mmol) were dissolved in 1,4-dioxane (100 mL) at room temperature, and the solution was stirred at the same temperature for 16 hours. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The precipitated solid was filtered, washed with hexane and dried to afford the desired compound (2.970 g, 58.8%) as a brown solid.

Step 4: Synthesis of (E)-Methyl 3-(4-(((2S,6R)-4-(3-formylbenzyl)-2,6-dimethylpiperazin-1-yl)methyl)phenyl)acrylate (E)-methyl 3-(4-(((2S,6R)-2,6-dimethylpiperazin-1-yl)methyl)phenyl)acrylate (formula 17-1, 0.300 g, 1.040 mmol), 3-(bromomethyl)benzaldehyde (0.207 g, 1.040 mmol) and Cs₂CO₃ (0.678 g, 2.081 mmol) were dissolved in acetonitrile (3 mL) at room temperature, and the solution was stirred at the same temperature for 16 hours. The reaction mixture was filtered through a paper filter to remove solids, and the filtrate was concentrated under reduced pressure to remove the solvent. The concentrate was purified by column chromatography (silicon dioxide, 4 g cartridge; methanol/methylene chloride=from 0% to 10%) and concentrated to afford the desired compound (0.293 g, 69.3%) as a white solid.

Step 5: Synthesis of (E)-Methyl 3-(4-(((2S,6R)-2,6-dimethyl-4-(3-(pyrrolidin-1-ylmethyl)benzyl)piperazin-1-yl)methyl)phenyl)acrylate (E)-methyl 3-(4-(((2S,6R)-4-(3-formylbenzyl)-2,6-dimethylpiperazin-1-yl)methyl)phenyl)acrylate (formula 17-2, 0.130 g, 0.320 mmol) and pyrrolidine (0.029 mL, 0.352 mmol) were dissolved in methylene chloride (3 mL), and the solution was stirred at room temperature for 1 hour. Na(OAc)₃BH (0.102 g, 0.480 mmol) was added to the reaction solution, which was then further stirred at the same temperature for 16 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.062 g, 42.0%) as a yellow oil.

Step 6: Synthesis of Compound 475

(E)-Methyl 3-(4-(((2S,6R)-2,6-dimethyl-4-(3-(pyrrolidin-1-ylmethyl)benzyl)piperazin-1-yl)methyl)phenyl)acrylate (formula 17-3, 0.062 g, 0.133 mmol) and hydroxylamine (0.163 mL, 2.664 mmol, 50.00% aqueous solution) were dissolved in methanol (2 mL) at room temperature, and potassium hydroxide (0.075 g, 1.332 mmol) was added to the solution, which was then stirred at the same temperature for 1 hour. The reaction mixture was concentrated under reduced pressure to remove the solvent, and a saturated aqueous solution of sodium hydrogen carbonate (10 mL) was added to the concentrate, followed by stirring. The precipitated solid was filtered, washed with hexane, and dried to yield compound 475 (0.039 g, 63.8%) as a white solid.

¹H-NMR (400 MHz, DMSO-d₆) δ 9.58 (brs, 1 H), 7.45-7.40 (m, 2H), 7.33-7.31 (m, 2 H), 7.27-7.21 (m, 3 H), 7.18-7.12 (m, 2 H), 6.39-6.35 (m, 1 H), 3.71 (s, 2 H), 3.53 (s, 2 H), 2.65-2.63 (m, 3 H), 2.55-2.50 (m, 3 H), 2.39-2.33

(m, 4 H), 1.78 (t, 2 H, J=10.4 Hz), 1.67 (s, 4 H), 0.89 (d, 6 H, J=6.0 Hz); LRMS (ES) m/z 463.2 (M$^+$+1).

Example 225

Synthesis of Compound 476

((E)-3-(4-(((2S,6R)-4-(3-((diethylamino)methyl) benzyl)-2,6-dimethylpiperazin-1-yl)methyl)phenyl)-N-hydroxyacrylamide)

Step 1: Synthesis of (E)-Methyl 3-(4-(((2S,6R)-4-(3-((diethylamino)methyl)benzyl)-2,6-dimethylpiperazin-1-yl)methyl)phenyl)acrylate (E)-methyl 3-(4-(((2S,6R)-4-(3-formylbenzyl)-2,6-dimethylpiperazin-1-yl)methyl)phenyl)acrylate (formula 17-2, 0.130 g, 0.320 mmol) and diethylamine (0.039 g, 0.352 mmol) were dissolved in methylene chloride (3 mL), and the solution was stirred at room temperature for 1 hour. Na(OAc)$_3$BH (0.102 g, 0.480 mmol) was added to the reaction solution, which was then further stirred at the same temperature for 16 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 10%) and concentrated to afford the desired compound (0.061 g, 41.1%) as a yellow oil.

Step 2: Synthesis of Compound 476

(E)-methyl 3-(4-(((2S,6R)-4-(3-((diethylamino)methyl) benzyl)-2,6-dimethylpiperazin-1-yl)methyl)phenyl)acrylate (formula 17-3, 0.061 g, 0.134 mmol) and hydroxylamine (0.164 mL, 2.683 mmol, 50.00% aqueous solution) were dissolved in methanol (2 mL) at room temperature, and potassium hydroxide (0.075 g, 1.342 mmol) was added to the solution, which was then stirred at the same temperature for 1 hour. The reaction mixture was concentrated under reduced pressure to remove the solvent, and a saturated aqueous solution of sodium hydrogen carbonate was added to the resulting concentrate, followed by extraction with methylene chloride. The organic layer was washed with a saturated aqueous solution of sodium chloride, dried with anhydrous magnesium sulfate, filtered, and then concentrated under reduced pressure to afford compound 476 (0.026 g, 41.2%) as a white solid.

$^1$H-NMR (400 MHz, DMSO-d$_6$) δ 10.7 (brs, 1 H), 9.04 (brs, 1 H), 7.47-7.45 (m, 3 H), 7.37-7.36 (m, 2 H), 7.25-7.21 (m, 2 H), 7.16-7.11 (m, 2 H), 6.42-6.38 (m, 1 H), 3.72 (s, 2 H), 3.50 (s, 2 H), 3.37 (s, 2 H), 2.65-2.63 (m, 2 H), 2.62-2.50 (m, 2 H), 2.42 (q, 4 H, J=7.1 Hz), 1.78 (t, 2 H, J=10.4 Hz), 0.95 (t, 6 H, J=7.1 Hz), 0.87 (d, 6 H, J=6.0 Hz); LRMS (ES) m/z 465.3 (M$^+$+1).

Example 226

Synthesis of Compound 477

((E)-3-(4-(((2S,6R)-4-(4-(furan-2-yl)benzyl)-2,6-dimethylpiperazin-1-yl)methyl)phenyl)-N-hydroxyacrylamide)

Step 1: Synthesis of (E)-Methyl 3-(4-(((2S,6R)-4-(4-bromobenzyl)-2,6-dimethylpiperazin-1-yl) methyl)phenyl)acrylate (E)-methyl 3-(4-(((2S,6R)-2,6-dimethylpiperazin-1-yl) methyl)phenyl)acrylate (formula 17-1, 0.200 g, 0.694 mmol), 1-(bromomethyl)-4-bromobenzene (0.173 g, 0.694 mmol) and Cs$_2$CO$_3$ (0.452 g, 1.387 mmol) were dissolved in acetonitrile (3 mL) at room temperature, and the solution was stirred at the same temperature for 16 hours. The reaction mixture was filtered through a paper filter to remove solids, and the filtrate was concentrated under reduced pressure to remove the solvent. The concentrate was purified by column chromatography (silicon dioxide, 4 g cartridge; methanol/methylene chloride=from 0% to 10%) and concentrated to afford the desired compound (0.209 g, 65.9%) as a white solid.

Step 2: Synthesis of (E)-Methyl 3-(4-(((2S,6R)-4-(4-(furan-2-yl)benzyl)-2,6-dimethylpiperazin-1-yl) methyl)phenyl)acrylate 1,2-Dimethoxyethane (0.9 mL)/water (0.1 mL) were added to a mixture of (E)-methyl 3-(4-(((2S,6R)-4-(4-bromobenzyl)-2,6-dimethylpiperazin-1-yl)methyl)phenyl)acrylate (formula 18-1, 0.100 g, 0.219 mmol), furan-2-boronic acid (0.027 g, 0.240 mmol), Pd(dbpf)Cl$_2$ (0.007 g, 0.011 mmol) and Na$_2$CO$_3$ (0.070 g, 0.656 mmol) at room temperature, and the solution was stirred at 50° C. for 16 hours, and followed by cooling to room temperature to terminate the reaction. Water was added to the reaction mixture, which was then extracted with ethylacetate. The organic layer was washed with a saturated aqueous solution of sodium chloride, dried with anhydrous magnesium sulfate, filtered, and then concentrated under reduced pressure. The concentrate was purified by column chromatography (silicon dioxide; 4 g cartridge; methanol/methylene chloride=from 0% to 3%) and concentrated to afford the desired compound (0.080 g, 82.4%) as a white solid.

Step 3: Synthesis of Compound 477

(E)-Methyl 3-(4-(((2S,6R)-4-(4-(furan-2-yl)benzyl)-2,6-dimethylpiperazin-1-yl)methyl)phenyl)acrylate (formula 18-2, 0.077 g, 0.174 mmol), hydroxylamine (0.213 mL, 3.478 mmol, 50.00% aqueous solution) and potassium hydroxide (0.098 g, 1.739 mmol) were dissolved in methanol (3 mL) at room temperature, and the solution was stirred at the same temperature for 1 hour. The reaction mixture was concentrated under reduced pressure to remove the solvent, and a saturated aqueous solution of sodium hydrogen carbonate (20 mL) was added to the concentrate, followed by stirring. The precipitated solid was filtered, washed with hexane, and dried to yield compound 477 (0.075 g, 96.8%) as a brown solid.

$^1$H-NMR (400 MHz, DMSO-d$_6$) δ 9.23 (brs, 1 H), 7.73-7.72 (m, 1 H), 7.65-7.63 (m, 1 H), 7.50-7.48 (m, 1 H), 7.38-7.36 (m, 2 H), 7.33-7.27 (m, 3 H), 7.25-7.23 (m, 1 H), 7.06-7.02 (m, 1 H), 6.90 (d, 1 H, J=3.3 Hz), 6.59-6.57 (m, 1 H), 6.37-6.32 (m, 1 H), 3.70 (s, 2 H), 3.39 (s, 2 H), 2.66-2.53 (m, 4 H), 1.82-1.76 (m, 2 H), 0.90 (d, 6 H, J=5.9 Hz); LRMS (ES) m/z 446.2 (M$^+$+1)

Example 227

Synthesis of Compound 478

(4-(((2S,6R)-4-(3-((diethylamino)methyl)benzyl)-2, 6-dimethylpiperazin-1-yl)methyl)-N-hydroxybenzamide (hydrochloride salt))

Step 1: Synthesis of Methyl 4-(((2S,6R)-4-(3-((diethylamino)methyl)benzyl)-2,6-dimethylpiperazin-1-yl)methyl)benzoate Methyl 4-(((2S,6R)-4-(3-formylbenzyl)-2,6-dimethylpiperazin-1-yl)methyl)benzoate(formula 17-2, 0.150 g, 0.394 mmol) and diethylamine hydrochloride (0.065 g, 0.591 mmol) were dissolved in methylene chloride (4 mL), and the solution was stirred at room temperature for 1 hour. Na(OAc)$_3$BH (0.167 g, 0.788 mmol) was added to the reaction solution, which was then further stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 5% to 10%) and concentrated to afford the desired compound (0.054 g, 31.3%) as an orange oil.

Step 2: Synthesis of Compound 478 methyl 4-(((2S,6R)-4-(3-((diethylamino)methyl)benzyl)-2,6-dimethylpiperazin-1-yl)methyl)benzoate (formula 17-3, 0.054 g, 0.123 mmol), hydroxylamine (0.151 mL, 2.468 mmol, 50.00% aqueous solution) and potassium hydroxide (0.069 g, 1.234 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure. The product was used without additional purification (0.045 g, 83.1%, pale brown oil).

Step 3: Synthesis of Hydrochloride Salt of Compound 478

4-(((2S,6R)-4-(3-((diethylamino)methyl)benzyl)-2,6-dimethylpiperazin-1-yl)methyl)-N-hydroxybenzamide (0.048 g, 0.110 mmol) and HCl (4.00M dioxane solution, 0.137 mL, 0.548 mmol) were dissolved in 1,4-dioxane (3 mL) at room temperature, and the solution was stirred at the same temperature for 1 hour. The reaction mixture was concentrated under reduced pressure to remove the solvent, and ethyl acetate (20 mL) was added to the concentrate, followed by stirring. The precipitated solid was filtered, washed with ethyl acetate, and dried to yield compound 478 (0.039 g, 75.0%) as a white solid.

$^1$H-NMR (400 MHz, D$_2$O) δ 7.65 (d, 2 H, J=7.6 Hz), 7.51 (d, 2 H, J=8.4 Hz), 7.46-7.42 (m, 4 H), 4.52 (s, 2 H), 2.22 (s, 2 H), 2.20 (s, 2 H), 3.47-3.44 (m, 4 H), 3.08-3.05 (m, 6 H), 1.42 (d, 6 H, J=5.7 Hz), 1.17 (t, 6 H, J=7.0 Hz).

Example 228

Synthesis of Compound 479

(4-(((2S,6R)-2,6-dimethyl-4-(3-(pyrrolidin-1-ylmethyl)benzyl)piperazin-1-yl)methyl)-N-hydroxybenzamide)

Step 1: Synthesis of Methyl 4-(((2S,6R)-2,6-dimethyl-4-(3-(pyrrolidin-1-ylmethyl)benzyl)piperazin-1-yl)methyl)benzoate Methyl 4-(((2S,6R)-4-(3-formylbenzyl)-2,6-dimethylpiperazin-1-yl)methyl)benzoate (formula 17-2, 0.150 g, 0.394 mmol) and pyrrolidine (0.049 mL, 0.591 mmol) were dissolved in methylene chloride (4 mL), and the solution was stirred at room temperature for 1 hour. Na(OAc)$_3$BH (0.167 g, 0.788 mmol) was added to the reaction solution, which was then further stirred at the same temperature for 17 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 5% to 10%) and concentrated to afford the desired compound (0.122 g, 71.0%) as an orange oil.

Step 2: Synthesis of Compound 479

Methyl 4-(((2S,6R)-2,6-dimethyl-4-(3-(pyrrolidin-1-ylmethyl)benzyl)piperazin-1-yl)methyl)benzoate (formula 17-3, 0.122 g, 0.280 mmol), hydroxylamine (0.343 mL, 5.601 mmol, 50.00% aqueous solution) and potassium hydroxide (0.157 g, 2.801 mmol) were dissolved in methanol (5 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 479 (0.069 g, 56.4%) as a white solid.

$^1$H-NMR (400 MHz, DMSO-d$_6$) δ 11.11 (brs, 1 H), 9.05 (brs, 1 H), 7.66 (d, 2 H, J=8.1 Hz), 7.41 (d, 2 H, J=8.1 Hz), 7.26-7.22 (m, 2 H), 7.15 (dd, 2 H, J=7.3, 7.3 Hz), 3.74 (s, 2 H), 3.54 (s, 2 H), 3.39 (s, 2 H), 2.65 (d, 2 H, J=10.8 Hz), 2.56-2.55 (m, 2 H), 2.40 (s, 4 H), 1.79 (t, 2 H, J=10.6 Hz), 1.67 (s, 4 H), 0.87 (d, 6 H, J=6.1 Hz).

Example 229

Synthesis of Compound 480

((E)-3-(4-(((2S,6R)-2,6-dimethyl-4-(3-(pyrrolidin-1-ylmethyl)benzoyl)piperazin-1-yl)methyl)phenyl)-N-hydroxyacrylamide)

Step 1: Synthesis of (E)-Methyl 3-(4-(((2S,6R)-4-(3-formylbenzoyl)-2,6-dimethylpiperazin-1-yl)methyl)phenyl)acrylate (E)-methyl 3-(4-(((2S,6R)-2,6-dimethylpiperazin-1-yl)methyl)phenyl)acrylate (formula 17-1, 0.300 g, 1.040 mmol), 3-formylbenzoic acid (0.172 g, 1.144 mmol), EDCI (0.399 g, 2.081 mmol), HOBt (0.319 g, 2.081 mmol) and DIPEA (0.921 mL, 5.201 mmol) were dissolved in methylene chloride (3 mL) at room temperature, and the solution was stirred at the same temperature for 16 hours. The reaction mixture was concentrated under reduced pressure to remove the solvent, and the concentrate was purified by column chromatography (silicon dioxide, 4 g cartridge; ethyl acetate/hexane=from 30% to 40%) and concentrated to afford the desired compound (0.386 g, 88.2%) as a white solid.

Step 2: Synthesis of (E)-Methyl 3-(4-(((2S,6R)-2,6-dimethyl-4-(3-(pyrrolidin-1-ylmethyl)benzoyl)piperazin-1-yl)methyl)phenyl)acrylate (E)-methyl 3-(4-(((2S,6R)-4-(3-formylbenzoyl)-2,6-dimethylpiperazin-1-yl)methyl)phenyl)acrylate (formula 17-2, 0.190 g, 0.452 mmol) and pyrrolidine (0.035 g, 0.497 mmol) were dissolved in methylene chloride (3 mL), and the solution was stirred at room temperature for 1 hour. Na(OAc)$_3$BH (0.144 g, 0.678 mmol) was added to the reaction solution, which was then further stirred at the same temperature for 12 hours. Then, a saturated aqueous solution of sodium hydrogen carbonate was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; methanol/methylene chloride=from 0% to 10%) and concentrated to afford the desired compound (0.105 g, 49.0%) as a white solid.

Step 3: Synthesis of Compound 480

(E)-Methyl 3-(4-(((2S,6R)-2,6-dimethyl-4-(3-(pyrrolidin-1-ylmethyl)benzoyl)piperazin-1-yl)methyl)phenyl)acrylate (formula 17-3, 0.100 g, 0.210 mmol) and hydroxylamine (0.257 mL, 4.205 mmol, 50.00% aqueous solution) were dissolved in methanol (3 mL) at room temperature, and potassium hydroxide (0.118 g, 2.103 mmol) was added to the solution, which was then stirred at the same temperature for 1 hour. Then, the reaction mixture was concentrated under reduced pressure to remove the solvent, and a saturated aqueous solution of sodium hydrogen carbonate was added to the resulting concentrate, followed by extraction with ethyl acetate. The organic layer was washed with a saturated aqueous solution of sodium chloride, dried with anhydrous magnesium sulfate, filtered, and then concentrated under reduced pressure to afford compound 480 (0.049 g, 48.8%) as a white solid.

$^1$H-NMR (400 MHz, CD$_3$OD) δ 7.45-7.30 (m, 9 H), 6.51-6.46 (m, 1 H), 4.41-4.38 (m, 1 H), 3.85 (s, 2 H), 3.67 (s, 2 H), 3.54-3.48 (m, 1 H), 3.04-3.00 (m, 1 H), 2.79-2.76 (m, 1 H), 2.70-3.67 (m, 1 H), 2.54 (s, 6 H), 1.80 (s, 4 H), 1.14-1.08 (m, 3 H), 0.93-0.92 (m, 3 H); LRMS (ES) m/z 477.2 (M$^+$+1).

Example 230

Synthesis of Compound 481

(4-(((3R,5S)-3,5-dimethyl-4-(2-(1-(methylsulfonyl)-1,2,3,6-tetrahydropyridin-4-yl)benzyl)piperazin-1-yl)methyl)-N-hydroxybenzamide)

Step 1: Synthesis of Tert-Butyl 4-(2-(((2S,6R)-4-(4-(methoxycarbonyl)benzyl)-2,6-dimethylpiperazin-1-yl)methyl)phenyl)-5,6-dihydropyridine-1 (2 H)-carboxylate 1,2-Dimethoxyethane (15 mL)/water (5 mL) were added to a mixture of methyl 4-(((3R,5S)-4-(2-iodobenzyl)-3,5-dimethylpiperazin-1-yl)methyl)benzoate (formula 2-1, 1.600 g, 3.345 mmol), tert-butyl 4-(4,4,5,5-tetramethyl-1,3,2-dioxaboran-2-yl)-5,6-dihydropyridine-1(2 H)-carboxylate (2.068 g, 6.689 mmol), Pd(dbpf)$_2$Cl$_2$ (0.109 g, 0.167 mmol) and Na$_2$CO$_3$ (0.709 g, 6.689 mmol) at room temperature, and the solution was stirred at 50° C. for 17 hours, and followed by cooling to room temperature to terminate the reaction. A saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 12 g cartridge; ethyl acetate/hexane=from 5% to 50%) and concentrated to afford the desired compound (1.090 g, 61.1%) as a brown oil.

Step 2: Synthesis of Methyl 4-(((3R,5S)-3,5-dimethyl-4-(2-(1,2,3,6-tetrahydropyridin-4-yl)benzyl)piperazin-1-yl)methyl)benzoate Tert-Butyl 4-(2-(((2S,6R)-4-(4-(methoxycarbonyl)benzyl)-2,6-dimethylpiperazin-1-yl)methyl)phenyl)-5,6-dihydropyridine-1(2 H)-carboxylate (formula 3-1, 1.080 g, 2.024 mmol) was dissolved in 1,4-dioxane (15 mL) at room temperature, and HCl (4.00 M 1,4-dioxane solution, 5.059 mL, 20.236 mmol) was added to the solution, which was then stirred at the same temperature for 17 hours. The reaction mixture was concentrated under reduced pressure to remove the solvent, and ethyl acetate (200 mL) and methanol (10 mL) were added to the concentrate, followed by stirring. The precipitated solid was filtered, washed with ethyl acetate, and dried to yield the desired compound (0.851 g, 89.5%) as a pale yellow solid.

Step 3: Synthesis of Methyl 4-(((3R,5S)-3,5-dimethyl-4-(2-(1-(methylsulfonyl)-1,2,3,6-tetrahydropyridin-4-yl)benzyl)piperazin-1-yl)methyl)benzoate Methyl 4-(((3R,5S)-3,5-dimethyl-4-(2-(1,2,3,6-tetrahydropyridin-4-yl)benzyl)piperazin-1-yl)methyl)benzoate hydrochloride (formula 3-2, 0.060 g, 0.128 mmol) and TEA (0.053 mL, 0.383 mmol) were dissolved in methylene chloride (4 mL) at room temperature, and MsCl (0.015 mL, 0.191 mmol) was added to the solution, followed by stirring at the same temperature for 1 hour. The reaction mixture was concentrated under reduced pressure to remove the solvent, and the concentrate was purified by column chromatography (silicon dioxide, 4 g cartridge; methanol/methylene chloride=from 0% to 5%) and concentrated to afford the desired compound (0.055 g, 84.2%) as a pale yellow oil.

Step 4: Synthesis of Compound 481

Methyl 4-(((3R,5S)-3,5-dimethyl-4-(2-(1-(methylsulfonyl)-1,2,3,6-tetrahydropyridin-4-yl)benzyl)piperazin-1-yl)methyl)benzoate (formula 3-3, 0.055 g, 0.107 mmol), hydroxylamine (0.131 mL, 2.150 mmol, 50.00% aqueous solution) and potassium hydroxide (0.060 g, 1.075 mmol) were dissolved in methanol (2 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 481 (0.048 g, 87.1%) as a white solid.

$^1$H-NMR (400 MHz, DMSO-d$_6$) δ 7.72 (d, 1 H, J=8.2 Hz), 7.70 (d, 2 H, J=8.2 Hz), 7.32 (d, 2 H, J=8.1 Hz), 7.24 (dd, 1 H, J=7.5, 7.5 Hz), 7.15 (dd, 1 H, J=7.4, 7.4 Hz), 7.04 (d, 1 H, J=7.4 Hz), 5.59 (s, 1 H), 3.83 (d, 2 H, J=2.1 Hz), 3.62 (s, 2 H), 3.45 (s, 2 H), 3.40-3.38 (m, 2 H), 2.65 (d, 2 H, J=10.7 Hz), 2.61-2.57 (m, 2 H), 2.40 (s, 2 H), 1.85 (t, 2 H, J=10.3 Hz), 0.78 (d, 6 H, J=6.0 Hz).

Example 231

Synthesis of Compound 482

(4-(((3R,5S)-4-(2-(1-acetyl-1,2,3,6-tetrahydropyridin-4-yl)benzyl)-3,5-dimethylpiperazin-1-yl)methyl)-N-hydroxybenzamide)

Step 1: Synthesis of Methyl 4-(((3R,5S)-4-(2-(1-acetyl-1,2,3,6-tetrahydropyridin-4-yl)benzyl)-3,5-dimethylpiperazin-1-yl)methyl)benzoate Methyl 4-(((3R,5S)-3,5-dimethyl-4-(2-(1,2,3,6-tetrahydropyridin-4-yl)benzyl)piperazin-1-yl)methyl)benzoate hydrochloride (formula 3-2, 0.060 g, 0.128 mmol) and TEA (0.053 mL, 0.383 mmol) were dissolved in methylene chloride (4 mL) at room temperature, and acetic anhydride (0.020 g, 0.191 mmol) was added to the solution, followed by stirring at the same temperature for 1 hour. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 5%) and concentrated to afford the desired compound (0.046 g, 75.8%) as a pale yellow oil.

Step 2: Synthesis of Compound 482

Methyl 4-(((3R,5S)-4-(2-(1-acetyl-1,2,3,6-tetrahydropyridin-4-yl)benzyl)-3,5-dimethylpiperazin-1-yl)methyl)benzoate (formula 3-3, 0.046 g, 0.097 mmol), hydroxylamine (0.118 mL, 1.934 mmol, 50.00% aqueous solution) and potassium hydroxide (0.054 g, 0.967 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 482 (0.036 g, 78.1%) as a white solid.

$^1$H-NMR (400 MHz, DMSO-d$_6$) δ 11.05 (brs, 1 H), 9.12 (brs, 1 H), 7.71 (d, 3 H, J=7.9 Hz), 7.36 (d, 2 H, J=7.9 Hz), 7.23 (dd, 1 H, J=7.7, 7.7 Hz), 7.14 (dd, 1 H, J=7.4, 7.4 Hz), 7.03 (d, 1 H, J=7.5 Hz), 5.55 (s, 1 H), 4.08 (d, 2 H, J=21.4 Hz), 3.68-3.62 (m, 4 H), 3.46 (s, 2 H), 2.68-2.57 (m, 4 H), 2.35 (s, 1 H), 2.25 (s, 1 H), 2.07 (d, 3 H, J=8.5 Hz), 1.85 (t, 2 H, J=10.0 Hz), 0.78 (d, 6 H, J=5.9 Hz).

Example 232

Synthesis of Compound 483

(4-(((3R,5S)-3,5-dimethyl-4-(2-(1-(2,2,2-trifluoroethyl)-1,2,3,6-tetrahydropyridin-4-yl)benzyl)piperazin-1-yl)methyl)-N-hydroxybenzamide)

Step 1: Synthesis of Methyl 4-(((3R,5S)-3,5-dimethyl-4-(2-(1-(2,2,2-trifluoroethyl)-1,2,3,6-tetrahydropyridin-4-yl)benzyl)piperazin-1-yl)methyl)benzoate Methyl 4-(((3R,5S)-3,5-dimethyl-4-(2-(1,2,3,6-tetrahydropyridin-4-yl)benzyl)piperazin-1-yl)methyl)benzoate (0.050 g, 0.115 mmol), 2,2,2-trifluoroethyl trifluoromethanesulfonate (formula 3-2, 0.025 mL, 0.173 mmol) and K$_2$CO$_3$ (0.032 g, 0.231 mmol) were dissolved in acetonitrile (4 mL) at room temperature, and the solution was stirred at the same temperature for 4 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 12 g cartridge; ethyl acetate/hexane=from 0% to 30%) and concentrated to afford the desired compound (0.032 g, 53.9%) as a yellow oil.

Step 2: Synthesis of Compound 483

Methyl 4-(((3R,5S)-3,5-dimethyl-4-(2-(1-(2,2,2-trifluoroethyl)-1,2,3,6-tetrahydropyridin-4-yl)benzyl)piperazin-1-yl)methyl)benzoate (formula 3-3, 0.032 g, 0.062 mmol), hydroxylamine (0.076 mL, 1.241 mmol, 50.00% aqueous solution) and potassium hydroxide (0.035 g, 0.621 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure. The concentrate was purified by column chromatography (Waters, C$_{18}$; acetonitrile/0.1% trifluoroacetic acid aqueous solution=from 5% to 70%), after which it was passed through a SPE cartridge (PL-HCO$_3$ MPS PE) and concentrated to afford compound 483 (0.007 g, 21.8%) as a white solid.

$^1$H-NMR (400 MHz, DMSO-d$_6$) δ 9.03 (s, 1 H), 7.71-7.69 (m, 3 H), 7.39-7.38 (m, 2 H), 7.22 (dd, 1 H, J=7.3, 7.3 Hz), 7.13 (dd, 1 H, J=7.2, 7.2 Hz), 7.03 (d, 1 H, J=7.4 Hz), 5.49 (s, 1 H), 3.62 (s, 2 H), 3.47 (s, 2 H), 3.31-3.28 (m, 4 H), 2.88

(t, 2 H, J=5.0 Hz), 2.68-2.61 (m, 4 H), 2.33-2.30 (m, 2 H), 1.85-1.84 (m, 2 H), 0.79 (d, 6 H, J=5.7 Hz).

Example 233

Synthesis of Compound 484

(N-hydroxy-4-(((3R,5S)-4-(2-(1-isopropyl-1,2,3,6-tetrahydropyridin-4-yl)benzyl)-3,5-dimethylpiperazin-1-yl)methyl)benzamide)

Step 1: Synthesis of Methyl 4-(((3R,5S)-4-(2-(1-isopropyl-1,2,3,6-tetrahydropyridin-4-yl)benzyl)-3,5-dimethylpiperazin-1-yl)methyl)benzoate Methyl 4-(((3R,5S)-3,5-dimethyl-4-(2-(1,2,3,6-tetrahydropyridin-4-yl)benzyl)piperazin-1-yl)methyl)benzoate hydrochloride (formula 3-2, 0.150 g, 0.319 mmol) and TEA (0.222 mL, 1.596 mmol) were dissolved in methylene chloride (10 mL) at room temperature, and 2-iodopropane (0.075 g, 0.479 mmol) was added to the solution, which was then heated under reflux for 5 hours, followed by cooling to room temperature to terminate the reaction. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; ethyl acetate/hexane=from 0% to 20%) and concentrated, and then the resulting material was purified by chromatography (Waters, C$_{18}$; acetonitrile/0.1% trifluoroacetic acid aqueous solution=from 5% to 70%), after which it was passed through a SPE cartridge (PL-HCO$_3$ MP SPE) and concentrated to afford the desired compound (0.032 g, 21.1%) as a pale yellow oil.

Step 2: Synthesis of Compound 484

Methyl 4-(((3R,5S)-4-(2-(1-isopropyl-1,2,3,6-tetrahydropyridin-4-yl)benzyl)-3,5-dimethylpiperazin-1-yl)methyl)benzoate (formula 3-3, 0.032 g, 0.067 mmol), hydroxylamine (0.082 mL, 1.345 mmol, 50.00% aqueous solution) and potassium hydroxide (0.038 g, 0.673 mmol) were dissolved in methanol (3 mL) at room temperature, and the solution was stirred at the same temperature for 30 minutes. The reaction mixture was concentrated under reduced pressure to remove the solvent, and a saturated aqueous solution of sodium hydrogen carbonate (20 mL) was added to the concentrate, followed by stirring. The precipitated solid was filtered, washed with water, and dried to yield compound 484 (0.006 g, 18.7%) as a white solid.

$^1$H-NMR (400 MHz, CD$_3$OD) δ 7.78 (d, 1 H, J=6.7 Hz), 7.74 (d, 2 H, J=8.3 Hz), 7.47 (d, 2 H, J=8.1 Hz), 7.20 (dd, 1 H, J=6.5, 6.5 Hz), 7.13 (dd, 1 H, J=7.2, 7.2 Hz), 7.03 (d, 1 H, J=7.4 Hz), 5.55 (s, 1 H), 3.75 (s, 2 H), 3.57 (s, 2 H), 3.30 (s, 2 H), 2.87-2.81 (m, 3 H), 2.76-2.69 (m, 4 H), 2.42 (s, 2 H), 1.97 (t, 2 H, J=10.4 Hz), 1.19 (d, 6 H, J=6.5 Hz), 0.87 (d, 6 H, J=6.0 Hz).

Example 234

Synthesis of Compound 485

(4-(((3R,5S)-4-(2-(1-ethyl-1,2,3,6-tetrahydropyridin-4-yl)benzyl)-3,5-dimethylpiperazin-1-yl)methyl)-N-hydroxybenzamide)

Step 1: Synthesis of Methyl 4-(((3R,5S)-4-(2-(1-ethyl-1,2,3,6-tetrahydropyridin-4-yl)benzyl)-3,5-dimethylpiperazin-1-yl)methyl)benzoate Methyl 4-(((3R,5S)-3,5-dimethyl-4-(2-(1,2,3,6-tetrahydropyridin-4-yl)benzyl)piperazin-1-yl)methyl)benzoate hydrochloride (formula 3-2, 0.150 g, 0.319 mmol) and TEA (0.222 mL, 1.596 mmol) were dissolved in methylene chloride (4 mL) at room temperature, and 2-iodopropane (0.048 mL, 0.479 mmol) was added to the solution, which was then stirred at the same temperature for 3 hours. Water was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide, 4 g cartridge; methanol/methylene chloride=from 0% to 20%) and concentrated to afford the desired compound (0.048 g, 32.6%) as a yellow liquid.

Step 2: Synthesis of Compound 485

Methyl 4-(((3R,5S)-4-(2-(1-ethyl-1,2,3,6-tetrahydropyridin-4-yl)benzyl)-3,5-dimethylpiperazin-1-yl)methyl)benzoate (formula 3-3, 0.048 g, 0.104 mmol), hydroxylamine (0.127 mL, 2.080 mmol, 50.00% aqueous solution) and potassium hydroxide (0.058 g, 1.040 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the resulting concentrate, followed by extraction with methylene chloride. The extract was filtered through a plastic filter to remove solid residue and an aqueous layer, and then concentrated under reduced pressure to afford compound 485 (0.033 g, 68.6%) as a white solid.

$^1$H-NMR (400 MHz, DMSO-d$_6$) δ 7.70 (d, 3 H, J=8.2 Hz), 7.35 (d, 2 H, J=8.1 Hz), 7.20 (dd, 1 H, J=7.5, 7.5 Hz), 7.12 (dd, 1 H, J=7.5, 7.5 Hz), 7.00 (dd, 1 H, J=7.5, 1.3 Hz), 5.49 (s, 1 H), 3.62 (s, 2 H), 3.46 (s, 2 H), 3.03 (s, 2 H), 2.66-2.56 (m, 6 H), 2.45 (q, 2 H, J=7.2 Hz), 2.28 (brs, 2 H), 1.84 (t, 2 H, J=10.4 Hz), 1.07 (t, 3 H, J=7.2 Hz), 0.78 (d, 6 H, J=6.1 Hz).

Example 235

Synthesis of Compound 486

(4-(((3R,5S)-4-(4-((4-acetylpiperazin-1-yl)methyl)benzyl)-3,5-dimethylpiperazin-1-yl)methyl)-N-hydroxybenzamide (hydrochloride salt))

Step 1: Synthesis of Methyl 4-(((3R,5S)-4-(4-((4-acetylpiperazin-1-yl)methyl)benzyl)-3,5-dimethylpiperazin-1-yl)methyl)benzoate Methyl 4-(((3R,5S)-4-(4-formylbenzyl)-3,5-dimethylpiperazin-1-yl)methyl)benzoate (formula 5-1, 0.180 g, 0.473 mmol) and 1-(piperazin-1-yl)ethanone (0.067 g, 0.520 mmol) were dissolved in methylene chloride (2 mL), and the solution was stirred at room temperature for 1 hour. Na(OAc)$_3$BH (0.150 g, 0.710 mmol) was added to the reaction solution, which was then further stirred at the same temperature for 16 hours. Then, a saturated aqueous solution of sodium hydrogen carbonate was added to the reaction mixture, followed by extraction with methylene chloride. The extract was filtered through a plastic filter to remove solid residue and an aqueous layer, and then concentrated under reduced pressure. The concentrate was purified by column chromatography (silicon dioxide; 4 g cartridge; ethyl acetate/hexane=from 30% to 100%) and concentrated to afford the desired compound (0.112 g, 48.2%) as a white solid.

Step 2: Synthesis of Compound 486

Methyl 4-(((3R,5S)-4-(4-((4-acetylpiperazin-1-yl) methyl)benzyl)-3,5-dimethylpiperazin-1-yl)methyl)benzoate (formula 5-2, 0.112 g, 0.228 mmol) and hydroxylamine (0.279 mL, 4.563 mmol, 50.00% aqueous solution) were dissolved in methanol (3 mL) at room temperature, and potassium hydroxide (0.128 g, 2.282 mmol) were added to the solution, which was then stirred at the same temperature for 1 hour. Then, the reaction mixture was concentrated under reduced pressure to remove the solvent, and a saturated aqueous solution of sodium hydrogen carbonate was added to the resulting concentrate, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (Waters, C$_{18}$; acetonitrile/0.1% trifluoroacetic acid aqueous solution=from 5% to 70%), after which it was passed through a SPE cartridge (PL-HCO$_3$ MP SPE) and concentrated to afford compound 486 (0.049 g, 43.5%) as a white solid.

Step 3: Synthesis of Hydrochloride Salt of Compound 486

Compound 486 (0.049 g, 0.099 mmol) and HCl (4.00M dioxane solution, 0.124 mL, 0.496 mmol) were dissolved in 1,4-dioxane (1 mL) at room temperature, and the solution was stirred at the same temperature for 1 hour. The precipitated solid was filtered, washed with ethyl acetate, and dried to yield the desired compound (0.034 g, 63.9%) as a white solid.
$^1$H NMR (400 MHz, DMSO-d$_6$) δ 7.72 (d, 2 H, J=8.2 Hz), 7.61-7.55 (m, 4 H), 7.52 (d, 2 H, J=8.0 Hz), 4.59 (s, 2 H), 4.39 (s, 2 H), 4.23 (s, 2 H), 3.71-3.69 (m, 8 H), 3.56-3.46 (m, 6 H), 3.06 (m, 3 H), 2.11 (s, 3 H), 1.51-1.50 (m, 6 H); LRMS (ES) m/z 494.2 (M$^+$+1).

Example 236

Synthesis of Compound 487

((E)-3-(4-(((2S,6R)-4-(3-((diethylamino)methyl) benzoyl)-2,6-dimethylpiperazin-1-yl)methyl)phenyl)-N-hydroxyacrylamide)

Step 1: Synthesis of (E)-Methyl 3-(4-(((2S,6R)-4-(3-((diethylamino)methyl)benzoyl)-2,6-dimethylpiperazin-1-yl)methyl)phenyl)acrylate (E)-Methyl 3-(4-(((2S,6R)-4-(3-formylbenzoyl)-2,6-dimethylpiperazin-1-yl)methyl)phenyl)acrylate (formula 17-2, 0.190 g, 0.452 mmol) and diethylamine (0.054 g, 0.497 mmol) were dissolved in methylene chloride (3 mL), and the solution was stirred at room temperature for 1 hour. Na(OAc)$_3$BH (0.144 g, 0.678 mmol) was added to the reaction solution, which was then further stirred at the same temperature for 12 hours. Then, a saturated aqueous solution of sodium hydrogen carbonate was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; methanol/methylene chloride=from 0% to 10%) and concentrated to afford the desired compound (0.060 g, 27.8%) as a white solid.

Step 2: Synthesis of Compound 487

(E)-Methyl 3-(4-(((2S,6R)-4-(3-((diethylamino)methyl) benzoyl)-2,6-dimethylpiperazin-1-yl)methyl)phenyl)acrylate (formula 17-3, 0.060 g, 0.126 mmol) and hydroxylamine (0.154 mL, 2.512 mmol, 50.00% aqueous solution) were dissolved in methanol (2 mL) at room temperature, and potassium hydroxide (0.070 g, 1.256 mmol) was added to the solution, which was then stirred at the same temperature for 1 hour. Then, the reaction mixture was concentrated under reduced pressure to remove the solvent, and a saturated aqueous solution of sodium hydrogen carbonate was added to the resulting concentrate, followed by extraction with ethyl acetate. The organic layer was washed with a saturated aqueous solution of sodium chloride, dried with anhydrous magnesium sulfate, filtered, and then concentrated under reduced pressure to afford compound 487 (0.006 g, 9.3%) as a white solid.
$^1$H NMR (400 MHz, DMSO-d$_6$) δ 7.57-7.53 (m, 1 H), 7.51-7.46 (m, 3 H), 7.45-7.39 (m, 4 H), 7.36-7.34 (m, 1 H), 6.45 (d, 1 H, J=15.9 Hz), 4.42-4.39 (m, 1 H), 3.87-3.82 (m, 2 H), 3.53-3.50 (m, 1 H), 3.07-3.01 (m, 1 H), 2.83-2.77 (m, 2 H), 2.73-2.68 (m, 4 H), 2.57 (s, 1 H), 1.29 (m, 2 H), 1.15-1.11 (m, 9 H), 0.93-0.88 (m, 3 H); LRMS (ES) m/z 479.2 (M$^+$+1).

Example 237

Synthesis of Compound 520

(3-(((3R,5S)-4-benzyl-3,5-dimethylpiperazin-1-yl) methyl)-N-hydroxy-1H-indole-6-carboxamide)

Step 1: Synthesis of Methyl 3-(((3R,5S)-4-benzyl-3, 5-dimethylpiperazin-1-yl)methyl)-1H-indole-6-carboxylate Methyl 3-formyl-1H-indole-6-carboxylate (formula 8-4, 0.500 g, 2.461 mmol), (2S,6R)-1-benzyl-2,6-dimethylpiperazine (0.553 g, 2.707 mmol) and STAB (0.782 g, 3.691 mmol) were dissolved in methylene chloride (20 mL) at room temperature, and the solution was stirred at the same temperature for 5 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 12 g cartridge; ethyl acetate/hexane=from 0% to 30%) and concentrated to afford the desired compound (0.551 g, 57.2%) as an ivory solid.

Step 2: Synthesis of Compound 520

Methyl 3-(((3R,5S)-4-benzyl-3,5-dimethylpiperazin-1-yl)methyl)-1H-indole-6-carboxylate (formula 8-5, 0.150 g, 0.383 mmol), hydroxylamine (50.00% aqueous solution, 0.234 mL, 3.831 mmol) and potassium hydroxide (0.215 g, 3.831 mmol) were dissolved in methylene chloride (10 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 520 (0.149 g, 99.4%) as a white solid.

$^1$H-NMR (400 MHz, CD$_3$OD) δ 7.80 (s, 1 H), 7.56 (d, 2 H, J=8.3 Hz), 7.42 (d, 1 H, J=8.3 Hz), 7.34-7.25 (m, 5 H), 7.16 (t, 1 H, J=7.2 Hz), 3.70 (s, 2 H), 3.55 (s, 2 H), 2.72 (d, 2 H, J=10.0 Hz), 2.55-2.53 (m, 2 H), 1.78 (t, 2 H, J=10.6 Hz), 0.89 (s, 3 H), 0.87 (s, 3 H); LRMS (ES) m/z 393.0 (M$^+$+1).

Example 238

Synthesis of Compound 569

(5-(((3R,5S)-4-benzyl-3,5-dimethylpiperazin-1-yl)methyl)-N-hydroxy-1H-indole-2-carboxamide)

Step 1: Synthesis of 1-(tert-butyl) 2-ethyl 5-(((3R,5S)-4-benzyl-3,5-dimethylpiperazin-1-yl)methyl)-1H-indole-1,2-dicarboxylate 1-(tert-butyl) 2-ethyl 5-(bromomethyl)-1H-indole-1,2-dicarboxylate (formula 22-1, 2.000 g, 5.232 mmol), DIPEA (2.779 mL, 15.697 mmol) and (2S,6R)-1-benzyl-2,6-dimethylpiperazine (1.069 g, 5.232 mmol) were dissolved in methylene chloride (10 mL) at room temperature, and the solution was stirred at the same temperature for 1 hour. The precipitated solid was filtered, washed with acetonitrile, and dried to yield the desired compound (1.100 g, 41.6%) as a white solid.

Step 2: Synthesis of Ethyl 5-(((3R,5S)-4-benzyl-3,5-dimethylpiperazin-1-yl)methyl)-1H-indole-2-carboxylate 1-(tert-butyl) 2-ethyl 5-(((3R,5S)-4-benzyl-3,5-dimethylpiperazin-1-yl)methyl)-1H-indole-1,2-dicarboxylate (formula 22-2, 1.100 g, 2.175 mmol) and hydrochloric acid (4.00 M 1,4-dioxane solution, 2.719 mL, 10.877 mmol) were mixed in 1,4-dioxane (2 mL) at room temperature, and the mixture was stirred at the same temperature for 16 hours. Then, the reaction mixture was concentrated under reduced pressure to remove the solvent, and diethyl ether (20 mL) was added to the concentrate, followed by stirring. The precipitated solid was filtered, washed with diethyl ether, and dried to yield the desired compound (0.832 g, 94.3%) as a pale pink solid.

Step 3: Synthesis of Compound 569

Ethyl 5-(((3R,5S)-4-benzyl-3,5-dimethylpiperazin-1-yl)methyl)-1H-indole-2-carboxylate (formula 22-3, 0.100 g, 0.247 mmol), hydroxylamine (50.00% aqueous solution, 0.151 mL, 2.466 mmol) and potassium hydroxide (0.138 g, 2.466 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 569 (0.079 g, 81.6%) as a white solid.

$^1$H-NMR (400 MHz, CD$_3$OD) δ 7.46 (s, 1 H), 7.38-7.28 (m, 5 H), 7.24-7.20 (m, 1 H), 7.11 (dd, 1 H, J=8.4, 1.3 Hz), 6.79 (s, 1 H), 3.91 (s, 2 H), 3.53 (s, 2 H), 2.79 (d, 2 H, J=11.0 Hz), 2.72-2.68 (m, 2 H), 1.93 (t, 2 H, J=11.1 Hz), 1.11 (s, 3 H), 1.10 (s, 3 H); LRMS (ES) m/z 393.0 (M$^+$+1).

Example 239

Synthesis of Compound 571

(5-(((3R,5S)-4-benzyl-3,5-dimethylpiperazin-1-yl)methyl)-N-hydroxybenzofuran-2-carboxamide)

Step 1: Synthesis of Methyl 5-(((3R,5S)-4-benzyl-3,5-dimethylpiperazin-1-yl)methyl)benzofuran-2-carboxylate Methyl 5-(bromomethyl)benzofuran-2-carboxylate (formula 8-4, 0.500 g, 1.858 mmol), DIPEA (0.720 g, 5.574 mmol) and (2S,6R)-1-benzyl-2,6-dimethylpiperazine (0.380 g, 1.858 mmol) were dissolved in acetonitrile (10 mL) at room temperature, and the solution was stirred at the same temperature for 1 hour. The reaction mixture was concentrated under reduced pressure to remove the solvent, and the precipitated solid was filtered, washed with acetonitrile, and dried to yield the desired compound (0.200 g, 27.4%) as a white solid.

Step 2: Synthesis of Compound 571

Methyl 5-(((3R,5S)-4-benzyl-3,5-dimethylpiperazin-1-yl)methyl)benzofuran-2-carboxylate (formula 8-5, 0.050 g, 0.127 mmol), hydroxylamine (50.00% aqueous solution, 0.078 mL, 1.274 mmol) and potassium hydroxide (0.071 g, 1.274 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 571 (0.010 g, 19.4%) as a pale pink solid.

$^1$H-NMR (400 MHz, CD$_3$OD) δ 7.60 (s, 1 H), 7.49 (d, 1 H, J=8.4 Hz), 7.38-7.34 (m, 3 H), 7.31 (t, 1 H, J=7.5 Hz), 7.25-7.21 (m, 2 H), 3.92 (s, 2 H), 3.56 (s, 2 H), 2.77 (d, 2 H, J=10.8 Hz), 2.73-2.66 (m, 2 H), 1.94 (t, 2 H, J=10.9 Hz), 1.12 (s, 3 H), 1.10 (s, 3 H); LRMS (ES) m/z 392.2 (M$^+$-1).

Example 240

Synthesis of Compound 573

(6-(((3R,5S)-4-benzyl-3,5-dimethylpiperazin-1-yl)methyl)-N-hydroxy-1H-indole-2-carboxamide)

Step 1: Synthesis of 1-(tert-butyl) 2-methyl 6-(((3R,5S)-4-benzyl-3,5-dimethylpiperazin-1-yl)methyl)-1H-indole-1,2-dicarboxylate 1-(tert-butyl) 2-methyl 6-(bromomethyl)-1H-indole-1,2-dicarboxylate (formula 22-1, 0.410 g, 1.113 mmol), DIPEA (0.432 g, 3.340 mmol) and (2S,6R)-1-benzyl-2, 6-dimethylpiperazine (0.227 g, 1.113 mmol) were dissolved in acetonitrile (10 mL) at room temperature, and the solution was stirred at the same temperature for 16 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 40 g cartridge; ethyl acetate/hexane=from 0% to 20%) and concentrated to afford the desired compound (0.224 g, 40.9%) as a yellow liquid.

Step 2: Synthesis of Methyl 6-(((3R,5S)-4-benzyl-3, 5-dimethylpiperazin-1-yl)methyl)-1H-indole-2-carboxylate (hydrochloride salt)

1-(tert-butyl) 2-methyl 6-(((3R,5S)-4-benzyl-3,5-dimethylpiperazin-1-yl)methyl)-1H-indole-1,2-dicarboxylate (formula 22-2, 0.224 g, 0.456 mmol) and hydrochloric acid (4.00 M 1,4-dioxane solution, 0.570 mL, 2.278 mmol) were dissolved in 1,4-dioxane (2 mL) at room temperature, and the solution was stirred at the same temperature for 16 hours. Then, the reaction mixture was concentrated under reduced pressure to remove the solvent, and diethyl ether (20 mL) was added to the concentrate, followed by stirring. The precipitated solid was filtered, washed with diethyl ether, and dried to yield the desired compound (0.167 g, 85.6%) as a ocher solid.

Step 3: Synthesis of Compound 573

Methyl 6-(((3R,5S)-4-benzyl-3,5-dimethylpiperazin-1-yl)methyl)-1H-indole-2-carboxylate (formula 22-3, 0.050 g, 0.117 mmol), hydroxylamine (50.00% aqueous solution, 0.071 mL, 1.168 mmol) and potassium hydroxide (0.066 g, 1.168 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 573 (0.025 g, 53.4%) as a yellow solid.
[1] H-NMR (400 MHz, CD$_3$OD) δ 7.49 (d, 1 H, J=8.3 Hz), 7.37 (d, 2 H, J=7.4 Hz), 7.31 (t, 3 H, J=7.5 Hz), 7.23 (t, 1 H, J=7.4 Hz), 7.00 (d, 1 H, J=8.2 Hz), 6.81 (s, 1 H), 3.91 (s, 2 H), 3.55 (s, 2 H), 2.79 (d, 2 H, J=10.9 Hz), 2.71-2.68 (m, 2 H), 1.93 (t, 2 H, J=10.7 Hz), 1.11 (s, 3 H), 1.10 (s, 3 H); LRMS (ES) m/z 391.2 (M$^+$−1)

Example 241

Synthesis of Compound 574

(2-(((3R,5S)-4-benzyl-3,5-dimethylpiperazin-1-yl)methyl)-N-hydroxybenzofuran-5-carboxamide)

Step 1: Synthesis of Methyl 2-(((3R,5S)-4-benzyl-3, 5-dimethylpiperazin-1-yl)methyl)benzofuran-5-carboxylate Methyl 2-(bromomethyl)benzofuran-5-carboxylate (formula 8-4, 0.691 g, 2.568 mmol), DIPEA (1.364 mL, 7.704 mmol) and (2S,6R)-1-benzyl-2,6-dimethylpiperazine (0.525 g, 2.568 mmol) were dissolved in acetonitrile (10 mL) at room temperature, and the solution was stirred at the same temperature for 16 hours. Water was added to the reaction mixture, which was then extracted with ethylacetate. The organic layer was washed with a saturated aqueous solution of sodium chloride, dried with anhydrous magnesium sulfate, filtered, and then concentrated under reduced pressure. The concentrate was purified by column chromatography (silicon dioxide, 40 g cartridge; ethyl acetate/hexane=from 0% to 20%) and concentrated to afford the desired compound (0.460 g, 45.6%) as an ivory solid.

Step 2: Synthesis of Compound 574

Methyl 2-(((3R,5S)-4-benzyl-3,5-dimethylpiperazin-1-yl)methyl)benzofuran-5-carboxylate (formula 8-5, 0.100 g, 0.254 mmol), hydroxylamine (50.00% aqueous solution, 0.155 mL, 2.541 mmol) and potassium hydroxide (0.143 g, 2.541 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 574 (0.013 g, 13.0%) as a pale pink solid.
[1] H-NMR (400 MHz, CD$_3$OD) δ 8.00 (d, 1 H, J=1.4 Hz), 7.72 (dd, 1 H, J=8.6, 1.8 Hz), 7.50 (d, 1 H, J=8.7 Hz), 7.38-7.20 (m, 5 H), 6.80 (s, 1 H), 3.90 (s, 2 H), 3.70 (s, 2 H), 2.85 (d, 1 H, J=10.7 Hz), 2.76-2.71 (m, 2 H), 2.07 (t, 2 H, J=11.0 Hz), 1.12 (s, 3 H), 1.10 (s, 3 H); LRMS (ES) m/z 394.0 (M$^+$+1)

Example 242

Synthesis of Compound 609

(5-(((3R,5S)-3,5-dimethyl-4-(3-(morpholinomethyl)benzyl)piperazin-1-yl)methyl)-N-hydroxypicolinamide)

Step 1: Synthesis of Tert-Butyl (3R,5S)-4-(3-formylbenzyl)-3,5-dimethylpiperazine-1-carboxylate (3R,5S)-tert-butyl 3,5-dimethylpiperazine-1-carboxylate (formula 8-1, 2.730 g, 12.739 mmol), 3-(bromomethyl)benzaldehyde (2.789 g, 14.013 mmol) and Cs$_2$CO$_3$ (8.301 g, 25.478 mmol) were mixed in acetonitrile (50 mL) at room temperature, and the mixture was stirred at the same temperature for 18 hours. The reaction mixture was filtered through a paper filter to remove solids, and the filtrate was purified by column chromatography (silicon dioxide, 120 g cartridge; ethyl acetate/hexane=from 5% to 30%) and concentrated to afford the desired compound (2.730 g, 64.5%) as a yellow oil.

Step 2: Synthesis of Tert-Butyl (3R,5S)-3,5-dimethyl-4-(3-(morpholinomethyl)benzyl)piperazine-1-carboxylate Tert-butyl (3R,5S)-4-(3-formylbenzyl)-3,5-dimethylpiperazine-1-carboxylate (formula 23-1, 1.246 g, 3.749 mmol), morpholine (0.656 mL, 7.497 mmol) and acetic acid (0.429 mL, 7.497 mmol) were mixed in methylene chloride (15 mL), and the mixture was stirred at room temperature for 1 hour. Na(CN)BH$_3$ (0.942 g, 14.995 mmol) was added to thereaction mixture, which was then further stirred at the same temperature for 4 hours. Then, a saturated aqueous solution of sodium hydrogen carbonate was added to the reaction mixture, followed by extraction with methylene chloride. The organic layer was washed with a saturated aqueous solution of sodium hydrogen carbonate, dried with anhydrous magnesium sulfate, filtered, and then concentrated under reduced pressure. The concentrate was purified by column chromatography (silicon dioxide, 24 g cartridge; methanol/methylene chloride=from 0% to 10%) and concentrated to afford the desired compound (1.272 g, 84.0%) as a yellow oil.

Step 3: Synthesis of 4-(3-(((2S,6R)-2,6-dimethylpiperazin-1-yl)methyl)benzyl)morpholine (hydrochloride salt)

Tert-Butyl (3R,5S)-3,5-dimethyl-4-(3-(morpholinomethyl)benzyl)piperazine-1-carboxylate (formula 23-2, 1.270 g, 3.147 mmol) and HCl (4.00 M 1,4-dioxane solution, 3.934 mL, 15.735 mmol) were dissolved in methylene chloride (15 mL) at room temperature, and the solution was stirred at the same temperature for 18 hours. Then, the reaction mixture was concentrated under reduced pressure to remove the solvent, and a saturated aqueous solution of sodium hydrogen carbonate was added to the resulting concentrate, followed by extraction with ethyl acetate. The organic layer was washed with a saturated aqueous solution of sodium chloride, dried with anhydrous magnesium sulfate, filtered, and then concentrated under reduced pressure. The product was used without additional purification (0.855 g, 89.5%, yellow oil).

Step 4: Synthesis of Methyl 5-(((3R,5S)-3,5-dimethyl-4-(3-(morpholinomethyl)benzyl)piperazin-1-yl)methyl)picolinate Methyl 5-formylpicolinate (0.200 g, 1.211 mmol), 4-(3-(((2S,6R)-2,6-dimethylpiperazin-1-yl)methyl)benzyl)morpholine (0.735 g, 2.422 mmol) and acetic acid (0.139 mL, 2.422 mmol) were mixed in methylene chloride (8 mL), and the mixture was stirred at room temperature for 1 hour. Na(CN)BH$_3$ (0.304 g, 4.844 mmol) was added to the reaction mixture, which was then further stirred at the same temperature for 15 hours. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 12 g cartridge; ethyl acetate/hexane=from 60% to 100%) and concentrated to afford the desired compound (0.317 g, 57.8%) as a yellow oil.

Step 5: Synthesis of Compound 609

Methyl 5-(((3R,5S)-3,5-dimethyl-4-(3-(morpholinomethyl)benzyl)piperazin-1-yl)methyl)picolinate (formula 23-4, 0.059 g, 0.130 mmol) and hydroxylamine (0.333 mL, 2.594 mmol, 50.00% aqueous solution) were mixed in methanol (1 mL), and potassium hydroxide (0.130 mL, 1.297 mmol, 10.00 M aqueous solution) was added thereto at 0° C. Then, the mixture was stirred at the same temperature for 5 minutes, and then stirred at room temperature for 15 hours. The reaction mixture was concentrated under reduced pressure, and the concentrate was purified by column chromatography (Waters, C18; 0.1%-formic acid (methanoic acid) aqueous solution/acetonitrile=from 5% to 30%), after which it was passed through a SPE cartridge (PL-HCO$_3$ MP SPE) and concentrated to afford compound 609 (0.006 g, 10.2%) as a brown oil.

$^1$H NMR (400 MHz, CD$_3$OD) δ 8.52 (s, 1 H), 7.99-7.87 (m, 2 H), 7.36 (s, 1 H), 7.28-7.27 (m, 2 H), 7.21-7.20 (m, 1 H), 3.90 (s, 2 H), 3.69-3.67 (m, 4 H), 3.54-3.52 (m, 4 H), 2.73-2.65 (m, 4 H), 2.45 (s, 4 H), 1.96 (t, 2 H, J=10.6 Hz), 1.09 (d, 6 H, J=6.0 Hz); LRMS (ES) m/z 454.5 (M$^+$+1).

Example 243

Synthesis of Compound 652

(4-(((3R,5S)-4-benzyl-3,5-dimethylpiperazin-1-yl)methyl)-N,2-dihydroxybenzamide)

Step 1: Synthesis of Methyl 4-(((3R,5S)-4-benzyl-3,5-dimethylpiperazin-1-yl)methyl)-2-hydroxybenzoate Methyl 4-(bromomethyl)-2-hydroxybenzoate (formula 8-4, 1.144 g, 4.668 mmol), TEA (0.776 mL, 5.602 mmol) and (2S,6R)-1-benzyl-2, 6-dimethylpiperazine (0.954 g, 4.668 mmol) were dissolved in acetonitrile (10 mL) at room temperature, and the solution was stirred at the same temperature for 16 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 40 g cartridge; ethyl acetate/hexane=from 0% to 20%) and concentrated to afford the desired compound (0.583 g, 33.9%) as a yellow liquid.

Step 2: Synthesis of Compound 652

Methyl 4-(((3R,5S)-4-benzyl-3,5-dimethylpiperazin-1-yl)methyl)-2-hydroxybenzoate (formula 8-5, 0.050 g, 0.136 mmol), hydroxylamine (50.00% aqueous solution, 0.083 mL, 1.357 mmol) and potassium hydroxide (0.076 g, 1.357 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 652 (0.035 g, 70.0%) as a pink solid.

$^1$H-NMR (400 MHz, CD$_3$OD) δ 7.61 (d, 1 H, J=8.1 Hz), 7.39 (d, 2 H, J=7.1 Hz), 7.33 (t, 2 H, J=7.5 Hz), 7.25 (t, 1 H, J=7.2 Hz), 6.90 (s, 1 H), 6.86 (d, 1 H, J=8.1 Hz), 3.96 (s, 2 H), 3.45 (s, 2 H), 2.78-2.72 (m, 4 H), 1.99-1.94 (m, 4 H), 1.15 (s, 3 H), 1.32 (s, 3 H); LRMS (ES) m/z 370.2 (M$^+$+1).

Example 244

Synthesis of Compound 653

(4-(((3R,5S)-3,5-dimethyl-4-(3-(morpholinomethyl)benzyl)piperazin-1-yl)methyl)-N,2-dihydroxybenzamide)

Step 1: Synthesis of Tert-Butyl (3R,5S)-3,5-dimethyl-4-(3-(morpholinomethyl)benzyl)piperazine-1-carboxylate Tert-butyl (3R,5S)-4-(3-formylbenzyl)-3,5-dimethylpiperazine-1-carboxylate (formula 23-1, 10.439 g, 31.401 mmol) was dissolved in methylene chloride (150 mL) at room temperature, and morpholine (2.747 mL, 31.401 mmol) was added to the solution, followed by stirring at the same temperature for 1 hour. STAB (13.310 g, 62.802 mmol) was added to the reaction mixture, which was then further stirred at the same temperature for 16 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 80 g cartridge; ethyl acetate/hexane=from 0% to 80%) and concentrated to afford the desired compound (11.080 g, 87.4%) as a colorless liquid.

Step 2: Synthesis of 4-(3-(((2S,6R)-2,6-dimethylpiperazin-1-yl)methyl)benzyl)morpholine (hydrochloride salt)

Tert-butyl (3R,5S)-3,5-dimethyl-4-(3-(morpholinomethyl)benzyl)piperazine-1-carboxylate (formula 23-2, 11.080 g, 27.456 mmol) and hydrochloric acid (4.00 M 1,4-dioxane solution, 34.320 mL, 137.278 mmol) were dissolved in 1,4-dioxane (2 mL) at room temperature, and the solution was stirred at the same temperature for 16 hours. Then, the reaction mixture was concentrated under reduced pressure to remove the solvent, and diethyl ether (150 mL) was added to the concentrate, followed by stirring. The precipitated solid was filtered and dried to yield the desired compound (7.800 g, 83.6%) as a white solid.

Step 3: Synthesis of Methyl 4-(((3R,5S)-3,5-dimethyl-4-(3-(morpholinomethyl)benzyl)piperazin-1-yl)methyl)-2-hydroxybenzoate 4-(3-(((2S,6R)-2,6-dimethylpiperazin-1-yl)methyl)benzyl)morpholine hydrochloride (formula 23-3, 0.832 g, 2.448 mmol) and methyl 4-(bromomethyl)-2-hydroxybenzoate (0.600 g, 2.448 mmol), TEA (0.407 mL, 2.938 mmol) were dissolved in acetonitrile (10 mL) at room temperature, and the solution was stirred at the same temperature for 16 hours. Water was added to the reaction solution, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 40 g cartridge; ethyl acetate/hexane=from 0% to 50%) and concentrated to afford the desired compound (0.441 g, 38.5%) as a yellow liquid.

Step 4: Synthesis of Compound 653

Methyl 4-(((3R,5S)-3,5-dimethyl-4-(3-(morpholinomethyl)benzyl)piperazin-1-yl)methyl)-2-hydroxybenzoate (formula 23-4, 0.050 g, 0.107 mmol), hydroxylamine (50.00% aqueous solution, 0.065 mL, 1.069 mmol) and potassium hydroxide (0.060 g, 1.069 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 653 (0.033 g, 83.7%) as a reddish brown solid.

$^1$H-NMR (400 MHz, CD$_3$OD) δ 7.65 (d, 1 H, J=8.0 Hz), 7.38 (s, 1 H), 7.30 (d, 2 H, J=5.2 Hz), 7.23-7.22 (m, 1 H), 6.81 (s, 1 H), 6.74 (d, 2 H, J=7.8 Hz), 3.92 (s, 2 H), 3.71-3.69 (m, 4 H), 3.54 (s, 2 H), 3.41 (s, 2 H), 2.77-2.67 (m, 4 H), 2.47 (m, 4 H), 1.93-1.90 (m, 2 H), 1.11 (s, 3 H), 1.10 (s, 3 H); LRMS (ES) m/z 469.3 (M$^+$+1).

Example 245

Synthesis of Compound 696

(4-(((3R,5S)-3,5-dimethyl-4-(3-(morpholinomethyl)benzyl)piperazin-1-yl)methyl)-3-fluoro-N-hydroxybenzamide)

Step 1: Synthesis of Methyl 4-(((3R,5S)-3,5-dimethyl-4-(3-(morpholinomethyl)benzyl)piperazin-1-yl)methyl)-3-fluorobenzoate 4-(3-(((2S,6R)-2,6-dimethylpiperazin-1-yl)methyl)benzyl)morpholine (formula 23-3, 1.376 g, 4.048 mmol), TEA (0.673 mL, 4.857 mmol) and methyl 4-(bromomethyl)-3-fluorobenzoate (1.000 g, 4.048 mmol) were dissolved in acetonitrile (150 mL) at room temperature, and the solution was stirred at the same temperature for 16 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 80 g cartridge; ethyl acetate/hexane=from 0% to 20%) and concentrated to afford the desired compound (0.438 g, 35.5%) as a yellow liquid.

Step 2: Synthesis of Compound 696

Methyl 4-(((3R,5S)-3,5-dimethyl-4-(3-(morpholinomethyl)benzyl)piperazin-1-yl)methyl)-3-fluorobenzoate (formula 23-4, 0.100 g, 0.213 mmol), hydroxylamine (0.070 g, 2.130 mmol) and potassium hydroxide (0.119 g, 2.130 mmol) were dissolved in methanol (2 mL) at room temperature, and the solution was stirred at the same temperature for 3 hours. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 696 (0.025 g, 25.0%) as a yellow solid.

$^1$H-NMR (400 MHz, CD$_3$OD) δ 7.58-7.20 (m, 7 H), 3.90 (s, 2 H), 3.71-3.68 (m, 4 H), 3.57 (s, 2 H), 3.53 (s, 2 H), 2.77 (d, 2 H, J-=10.2 Hz), 2.71-2.67 (m, 2 H), 2.46-2.45 (m, 4 H), 1.99 (t, 2 H, J=10.8 Hz), 1.10 (s, 3 H), 1.09 (s, 3 H); LRMS (ES) m/z 471.2 (M$^+$+1).

Example 246

Synthesis of Compound 812

(5-(((3R,5S)-4-benzyl-3,5-dimethylpiperazin-1-yl)methyl)-N-hydroxypicolinamide)

Step 1: Synthesis of Methyl 5-(((3R,5S)-4-benzyl-3,5-dimethylpiperazin-1-yl)methyl)picolinate Methyl 5-formylpicolinate (formula 8-4, 0.200 g, 0.831 mmol), (2S,6R)-1-benzyl-2,6-dimethylpiperazine (0.151 g, 0.914 mmol) and STAB (0.264 g, 1.246 mmol) were dissolved in methylene chloride (5 mL) at room temperature, and the solution was stirred at the same temperature for 16 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 12 g cartridge; ethyl acetate/hexane=from 0% to 20%) and concentrated to afford the desired compound (0.116 g, 39.5%) as a yellow liquid.

Step 2: Synthesis of Compound 812

Methyl 5-(((3R,5S)-4-benzyl-3,5-dimethylpiperazin-1-yl)methyl)picolinate (formula 8-5, 0.116 g, 0.328 mmol), hydroxylamine (50.00% aqueous solution, 0.100 mL, 1.641 mmol) and potassium hydroxide (0.092 g, 1.641 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 812 (0.088 g, 75.7%) as a white solid.
$^1$H-NMR (400 MHz, CDCl$_3$) δ 8.47 (s, 1 H), 8.07 (d, 1 H, J=7.9 Hz), 7.83 (d, 1 H, J=7.9 Hz), 7.38-7.24 (m, 5 H), 3.91 (s, 2H), 3.53 (s, 2 H), 2.75-2.68 (m, 4 H), 2.09-2.03 (m, 2 H), 1.11 (s, 3 H), 1.10 (s, 3 H); LRMS (ES) m/z 353.1 (M$^+$+1).

Example 247

Synthesis of Compound 813

(4-(((3R,5S)-4-benzyl-3,5-dimethylpiperazin-1-yl)methyl)-3-fluoro-N-hydroxybenzamide)

Step 1: Synthesis of Methyl 4-(((3R,5S)-4-benzyl-3,5-dimethylpiperazin-1-yl)methyl)-3-fluorobenzoate Methyl 4-(bromomethyl)-3-fluorobenzoate (formula 8-4, 0.200 g, 0.831 mmol), (2S,6R)-1-benzyl-2,6-dimethylpiperazine (0.226 g, 0.914 mmol) and sodium carbonate (0.230 g, 1.661 mmol) were dissolved in acetonitrile (5 mL) at room temperature, and the solution was stirred at the same temperature for 16 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 12 g cartridge; ethyl acetate/hexane=from 0% to 20%) and concentrated to afford the desired compound (0.135 g, 43.9%) as an ivory solid.

Step 2: Synthesis of Compound 813

Methyl 4-(((3R,5S)-4-benzyl-3,5-dimethylpiperazin-1-yl)methyl)-3-fluorobenzoate (formula 8-5, 0.135 g, 0.364 mmol), hydroxylamine (50.00% aqueous solution, 0.111 mL, 1.822 mmol) and potassium hydroxide (0.102 g, 1.822 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 813 (0.087 g, 64.3%) as an ivory solid.
$^1$H-NMR (400 MHz, CDCl$_3$) δ 8.47 (s, 1 H), 8.07 (d, 1 H, J=7.9 Hz), 7.83 (d, 2 H, J=8.2 Hz), 7.38-7.24 (m, 5 H), 3.91 (s, 2 H), 3.53 (s, 2 H), 2.75-2.68 (m, 4 H), 2.10-2.04 (m, 2 H), 1.11 (s, 3 H), 1.10 (s, 3 H); LRMS (ES) m/z 372.1 (M$^+$+1).

Example 248

Synthesis of Compound 814

(4-((3R,5S)-4-benzyl-3,5-dimethylpiperazine-1-carbonyl)-N-hydroxybenzamide)

Step 1: Synthesis of Methyl 4-((3R,5S)-4-benzyl-3,5-dimethylpiperazine-1-carbonyl)benzoate Methyl 4-(chlorocarbonyl)benzoate (formula 8-4, 0.200 g, 0.831 mmol), (2S,6R)-1-benzyl-2,6-dimethylpiperazine (0.181 g, 0.914 mmol) and TEA (0.232 mL, 1.661 mmol) were dissolved in methylene chloride (5 mL) at room temperature, and the solution was stirred at the same temperature for 16 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 12 g cartridge; ethyl acetate/hexane=from 0% to 20%) and concentrated to afford the desired compound (0.152 g, 49.9%) as a white solid.

Step 2: Synthesis of Compound 814

Methyl 4-((3R,5S)-4-benzyl-3,5-dimethylpiperazine-1-carbonyl)benzoate (formula 8-4, 0.152 g, 0.415 mmol), hydroxylamine (50.00% aqueous solution, 0.127 mL, 2.074 mmol) and potassium hydroxide (0.116 g, 2.074 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 814 (0.118 g, 77.4%) as a white solid.
$^1$H-NMR (400 MHz, CDCl$_3$) δ 7.66 (d, 2 H, J=6.7 Hz), 7.20-6.99 (m, 7 H), 3.61 (s, 2 H), 2.74-2.68 (m, 2 H), 2.49 (m, 2 H), 2.37-2.33 (m, 2 H), 0.92 (s, 3 H), 0.71 (s, 3 H); LRMS (ES) m/z 368.1 (M$^+$+1)

Example 249

Synthesis of Compound 818

(4-(((3R,5S)-4-benzyl-3,5-dimethylpiperazin-1-yl)sulfonyl)-N-hydroxybenzamide)

Step 1: Synthesis of Methyl 4-(((3R,5S)-4-benzyl-3,5-dimethylpiperazin-1-yl)sulfonyl)benzoate Methyl 4-(chlorosulfonyl)benzoate (formula 8-4, 0.200 g, 0.852 mmol), (2S,6R)-1-benzyl-2,6-dimethylpiperazine (0.186 g, 0.938 mmol) and TEA (0.236 mL, 1.705 mmol)

were dissolved in methylene chloride (10 mL) at room temperature, and the solution was stirred at the same temperature for 1 hour. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; ethyl acetate/hexane=from 0% to 50%) and concentrated to afford the desired compound (0.181 g, 52.8%) as a white solid.

Step 2: Synthesis of Compound 818

Methyl 4-(((3R,5S)-4-benzyl-3,5-dimethylpiperazin-1-yl)sulfonyl)benzoate (formula 8-5, 0.100 g, 0.248 mmol), hydroxylamine (50.00% aqueous solution, 0.076 mL, 1.242 mmol) and potassium hydroxide (0.070 g, 1.242 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 818 (0.042 g, 41.9%) as an ivory solid.

$^1$H-NMR (400 MHz, CD$_3$OD)) δ 8.00 (d, 2 H, J=8.3 Hz), 7.81 (d, 2 H, J=8.4 Hz), 7.32-7.25 (m, 4 H), 7.19 (t, 1 H, J=7.0 Hz), 3.82 (s, 2 H), 3.52 (d, 2 H, J=11.2 Hz), 2.73-2.68 (m, 2 H), 2.19 (t, 2 H, J=10.6 Hz), 1.07 (s, 3 H), 1.05 (s, 3 H); LRMS (ES) m/z 404.1 (M$^+$+1).

Example 250

Synthesis of Compound 820

(2-(4-(((3R,5S)-4-benzyl-3,5-dimethylpiperazin-1-yl)sulfonyl)phenyl)-N-hydroxyacetamide)

Step 1: Synthesis of Methyl 2-(4-(((3R,5S)-4-benzyl-3,5-dimethylpiperazin-1-yl)sulfonyl)phenyl)acetate Methyl 2-(4-(chlorosulfonyl)phenyl)acetate (formula 8-4, 0.200 g, 0.804 mmol), (2S,6R)-1-benzyl-2,6-dimethylpiperazine (0.176 g, 0.885 mmol) and TEA (0.223 mL, 1.608 mmol) were dissolved in methylene chloride (10 mL) at room temperature, and the solution was stirred at the same temperature for 1 hour. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; ethyl acetate/hexane=from 0% to 20%) and concentrated to afford the desired compound (0.198 g, 59.2%) as a colorless liquid.

Step 2: Synthesis of Compound 820

Methyl 2-(4-(((3R,5S)-4-benzyl-3,5-dimethylpiperazin-1-yl)sulfonyl)phenyl)acetate (formula 8-5, 0.198 g, 0.475 mmol), hydroxylamine (50.00% aqueous solution, 0.145 mL, 2.377 mmol) and potassium hydroxide (0.133 g, 2.377 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 820 (0.124 g, 62.5%) as a white solid.

$^1$H-NMR (400 MHz, CDCl$_3$) δ 7.67 (d, 2 H, J=7.6 Hz), 7.37-7.15 (m, 7 H), 3.74 (s, 2 H), 3.49 (d, 2 H, J=7.8 Hz), 3.21 (s, 2 H), 2.74 (m, 2 H), 2.23-2.18 (m, 2 H), 0.99 (s, 3 H), 0.98 (s, 3 H); LRMS (ES) m/z 418.1 (M$^+$+1).

Example 251

Synthesis of Compound 822

(4-(((3R,5S)-4-benzyl-3,5-dimethylpiperazin-1-yl)methyl)-N-hydroxycyclohexane-1-carboxamide)

Step 1: Synthesis of Methyl 4-(((3R,5S)-4-benzyl-3,5-dimethylpiperazin-1-yl)methyl)cyclohexane-1-carboxylate Methyl 4-formylcyclohexane-1-carboxylate (formula 8-4, 0.150 g, 0.881 mmol), (2S,6R)-1-benzyl-2,6-dimethylpiperazine (0.212 g, 0.881 mmol) and STAB (0.280 g, 1.322 mmol) were dissolved in methylene chloride (10 mL) at room temperature, and the solution was stirred at the same temperature for 16 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; ethyl acetate/hexane=from 0% to 50%) and concentrated to afford the desired compound (0.175 g, 55.4%) as a colorless liquid.

Step 2: Synthesis of Compound 822

Methyl 4-(((3R,5S)-4-benzyl-3,5-dimethylpiperazin-1-yl)methyl)cyclohexane-1-carboxylate (formula 8-5, 0.175 g, 0.488 mmol), hydroxylamine (50.00% aqueous solution, 0.149 mL, 2.441 mmol) and potassium hydroxide (0.137 g, 2.441 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 822 (0.050 g, 28.5%) as a white solid.

$^1$H-NMR (400 MHz, CDCl$_3$) δ 7.38 (d, 2 H, J=7.4 Hz), 7.32-7.28 (m, 2 H), 7.21 (t, 1 H, J=7.3 Hz), 3.82 (s, 2 H), 2.72-2.67 (m, 4 H), 2.19-1.96 (m, 3 H), 1.83-1.67 (m, 6 H), 1.48-1.45 (m, 5 H), 1.03 (s, 6 H); LRMS (ES) m/z 360.2 (M$^+$+1).

Example 252

Synthesis of Compound 823

(2-(4-((3R,5S)-4-benzyl-3,5-dimethylpiperazine-1-carbonyl)phenyl)-N-hydroxyacetamide)

Step 1: Synthesis of Methyl 2-(4-((3R,5S)-4-benzyl-3,5-dimethylpiperazine-1-carbonyl)phenyl)acetate 4-(2-methoxy-2-oxoethyl)benzoic acid (formula 8-4, 0.150 g, 0.772 mmol), (2S,6R)-1-benzyl-2,6-dimethylpiperazine (0.186 g, 0.772 mmol), EDC (0.296 g, 1.545 mmol), HOBt (0.237 g, 1.545 mmol) and DIPEA (0.684 mL, 3.862 mmol) were dissolved in methylene chloride (10 mL) at room temperature, and the solution was stirred at the same temperature for 16 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; ethyl acetate/hexane=from 0% to 50%) and concentrated to afford the desired compound (0.133 g, 45.3%) as a colorless liquid.

Step 2: Synthesis of Compound 823

Methyl 2-(4-((3R,5S)-4-benzyl-3,5-dimethylpiperazine-1-carbonyl)phenyl)acetate (formula 8-5, 0.133 g, 0.350 mmol), hydroxylamine (50.00% aqueous solution, 0.107 mL, 1.748 mmol) and potassium hydroxide (0.098 g, 1.748 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 823 (0.015 g, 11.2%) as a white solid.

$^1$H-NMR (400 MHz, CDCl$_3$) δ 7.36 (d, 2 H, J=7.5 Hz), 7.30 (t, 3 H, J=7.5 Hz), 7.25-7.21 (m, 5 H), 4.44 (d, 1 H, J=9.6 Hz), 3.84-3.75 (m, 2 H), 3.51 (d, 1 H, J=11.2 Hz), 3.23 (m, 2 H), 2.95-2.88 (m, 1 H), 2.69 (m, 1 H), 2.53 (m, 1 H), 1.11 (s, 3 H), 0.88 (s, 3 H); LRMS (ES) m/z 382.2 (M$^+$+1).

Example 253

Synthesis of Compound 824

(3-(4-((3R,5S)-4-benzyl-3,5-dimethylpiperazine-1-carbonyl)phenyl)-N-hydroxypropanamide)

Step 1: Synthesis of Methyl 3-(4-((3R,5S)-4-benzyl-3,5-dimethylpiperazine-1-carbonyl)phenyl)propanoate 4-(3-methoxy-3-oxopropyl)benzoic acid (formula 8-4, 0.150 g, 0.724 mmol), (2S,6R)-1-benzyl-2,6-dimethylpiperazine (0.174 g, 0.724 mmol), EDC (0.278 g, 1.448 mmol), HOBt (0.222 g, 1.448 mmol) and DIPEA (0.641 mL, 3.620 mmol) were dissolved in methylene chloride (10 mL) at room temperature, and the solution was stirred at the same temperature for 16 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (silicon dioxide, 4 g cartridge; ethyl acetate/hexane=from 0% to 50%) and concentrated to afford the desired compound (0.089 g, 31.2%) as a clear liquid.

Step 2: Synthesis of Compound 824

Methyl 3-(4-((3R,5S)-4-benzyl-3,5-dimethylpiperazine-1-carbonyl)phenyl)propanoate (formula 8-5, 0.089 g, 0.226 mmol), hydroxylamine (50.00% aqueous solution, 0.069 mL, 1.128 mmol) and potassium hydroxide (0.063 g, 1.128 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield compound 824 (0.052 g, 58.3%) as a white solid.

$^1$H-NMR (400 MHz, CDCl$_3$) δ 7.36 (d, 2 H, J=7.4 Hz), 7.30 (t, 2 H, J=7.5 Hz), 7.24 (t, 3 H, J=8.6 Hz), 7.26-7.22 (m, 3 H), 7.18 (d, 2 H, J=7.8 Hz), 4.44 (d, 1 H, J=8.0 Hz), 3.85-3.76 (m, 2 H), 3.53 (d, 1 H, J=9.0 Hz), 2.92-2.87 (m, 3 H), 2.69 (m, 2 H), 2.53 (m, 1 H), 2.30 (m, 2 H), 1.11 (s, 3 H), 0.90 (s, 3 H); LRMS (ES) m/z 396.2 (M$^+$+1).

The structural formulas of compounds 080 to 824 prepared as described above are shown in Table 16 below.

TABLE 16

Structural formulas of dimethylpiperazine derivative compounds

| Compound | Formula |
|---|---|
| 080 | |
| 081 | |

TABLE 16-continued
Structural formulas of dimethylpiperazine derivative compounds
| Compound | Formula |
|---|---|
| 082 | 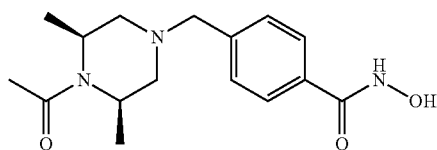 [SMILES: CC(=O)N1[C@H](C)CN(Cc2ccc(C(=O)NO)cc2)C[C@@H]1C] |
| 083 | 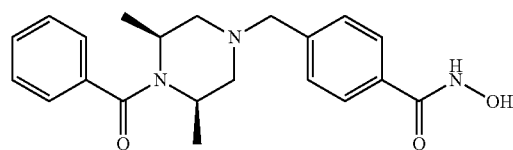 [SMILES: C[C@@H]1CN(Cc2ccc(C(=O)NO)cc2)C[C@H](C)N1C(=O)c1ccccc1] |
| 084 | 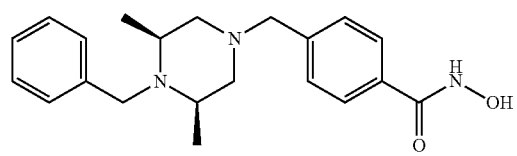 [SMILES: C[C@@H]1CN(Cc2ccc(C(=O)NO)cc2)C[C@H](C)N1Cc1ccccc1] |
| 098 | 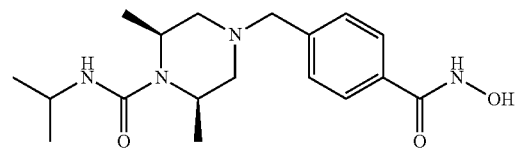 [SMILES: CC(C)NC(=O)N1[C@H](C)CN(Cc2ccc(C(=O)NO)cc2)C[C@@H]1C] |
| 099 | 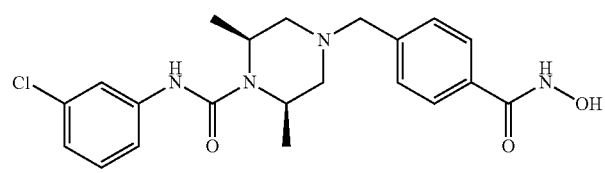 [SMILES: C[C@@H]1CN(Cc2ccc(C(=O)NO)cc2)C[C@H](C)N1C(=O)Nc1cccc(Cl)c1] |
| 100 | 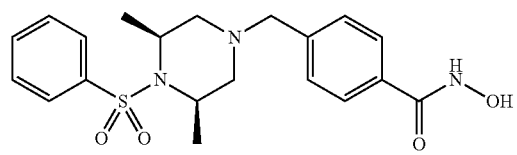 [SMILES: C[C@@H]1CN(Cc2ccc(C(=O)NO)cc2)C[C@H](C)N1S(=O)(=O)c1ccccc1] |
| 103 | 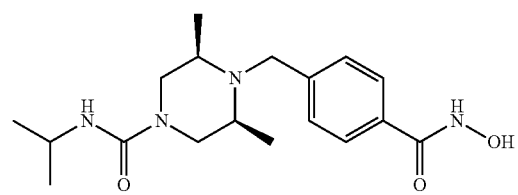 [SMILES: CC(C)NC(=O)N1C[C@@H](C)N(Cc2ccc(C(=O)NO)cc2)[C@@H](C)C1] |
| 104 | 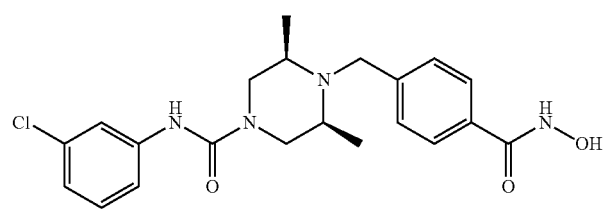 [SMILES: C[C@@H]1CN(C(=O)Nc2cccc(Cl)c2)C[C@H](C)N1Cc1ccc(C(=O)NO)cc1] |

TABLE 16-continued
Structural formulas of dimethylpiperazine derivative compounds
| Compound | Formula |
|---|---|
| 105 | 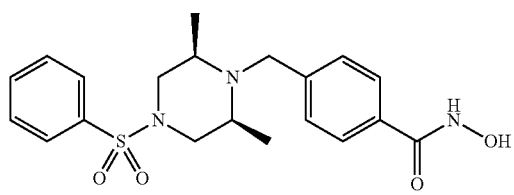 [SMILES: C[C@@H]1CN(S(=O)(=O)c2ccccc2)C[C@H](C)N1Cc1ccc(C(=O)NO)cc1] |
| 106 | 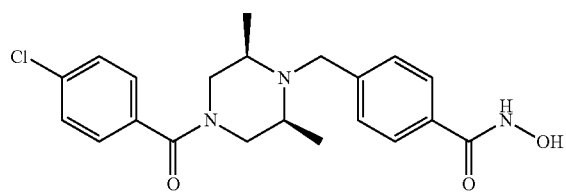 [SMILES: C[C@@H]1CN(C(=O)c2ccc(Cl)cc2)C[C@H](C)N1Cc1ccc(C(=O)NO)cc1] |
| 107 | 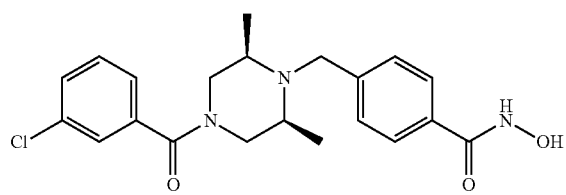 [SMILES: C[C@@H]1CN(C(=O)c2cccc(Cl)c2)C[C@H](C)N1Cc1ccc(C(=O)NO)cc1] |
| 108 | 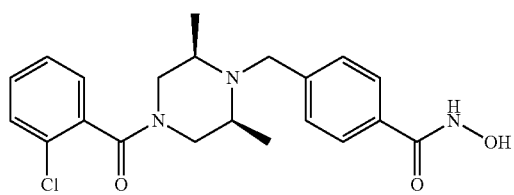 [SMILES: C[C@@H]1CN(C(=O)c2ccccc2Cl)C[C@H](C)N1Cc1ccc(C(=O)NO)cc1] |
| 109 | 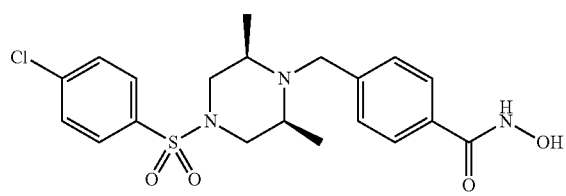 [SMILES: C[C@@H]1CN(S(=O)(=O)c2ccc(Cl)cc2)C[C@H](C)N1Cc1ccc(C(=O)NO)cc1] |
| 110 | 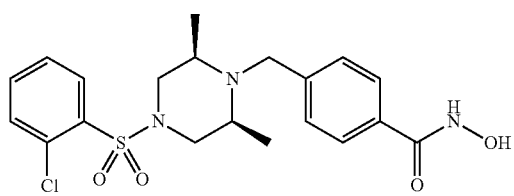 [SMILES: C[C@@H]1CN(S(=O)(=O)c2ccccc2Cl)C[C@H](C)N1Cc1ccc(C(=O)NO)cc1] |
| 111 | 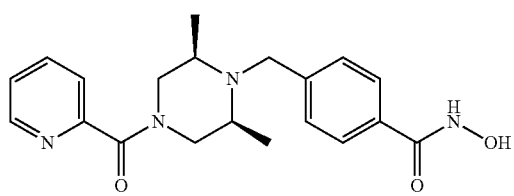 [SMILES: C[C@@H]1CN(C(=O)c2ccccn2)C[C@H](C)N1Cc1ccc(C(=O)NO)cc1] |

TABLE 16-continued

Structural formulas of dimethylpiperazine derivative compounds

| Compound | Formula |
| --- | --- |
| 112 | |
| 113 | |
| 114 | |
| 115 | |
| 118 | |
| 119 | |
| 120 | |
| 121 | |

TABLE 16-continued

Structural formulas of dimethylpiperazine derivative compounds

| Compound | Formula |
|---|---|
| 122 | |
| 123 | |
| 125 | |
| 126 | |
| 127 | |
| 128 | |
| 145 | |
| 146 | |
| 147 | |

TABLE 16-continued

Structural formulas of dimethylpiperazine derivative compounds

| Compound | Formula |
|---|---|
| 148 | |
| 149 | |
| 154 | |
| 159 | |
| 160 | |
| 161 | |
| 162 | |
| 163 | |
| 164 | |

TABLE 16-continued

Structural formulas of dimethylpiperazine derivative compounds

| Compound | Formula |
|---|---|
| 165 | |
| 166 | |
| 167 | |
| 168 | |
| 171 | |
| 172 | |
| 173 | |
| 174 | |

TABLE 16-continued

Structural formulas of dimethylpiperazine derivative compounds

| Compound | Formula |
|---|---|
| 175 | |
| 176 | |
| 177 | |
| 183 | |
| 184 | |
| 185 | |
| 186 | |

TABLE 16-continued

Structural formulas of dimethylpiperazine derivative compounds

| Compound | Formula |
|---|---|
| 187 | |
| 188 | |
| 189 | |
| 193 | |
| 194 | |
| 195 | |
| 196 | |
| 197 | |

TABLE 16-continued
Structural formulas of dimethylpiperazine derivative compounds
| Compound | Formula |
|---|---|
| 198 | 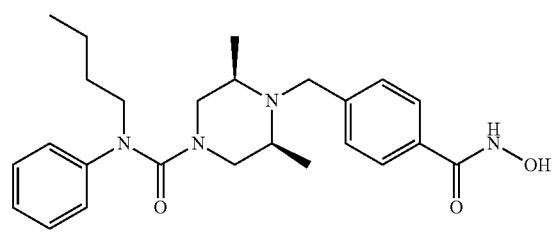 [SMILES: CCCCN(C(=O)N1C[C@@H](C)N(Cc2ccc(C(=O)NO)cc2)[C@@H](C)C1)c1ccccc1] |
| 204 | 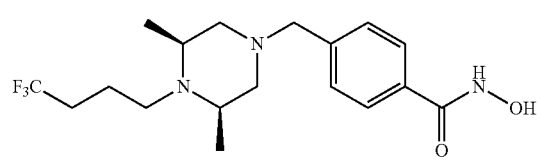 [SMILES: C[C@@H]1CN(Cc2ccc(C(=O)NO)cc2)C[C@H](C)N1CCCC(F)(F)F] |
| 211 | 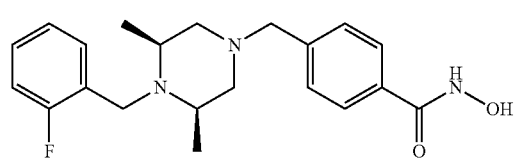 [SMILES: C[C@@H]1CN(Cc2ccc(C(=O)NO)cc2)C[C@H](C)N1Cc1ccccc1F] |
| 212 | 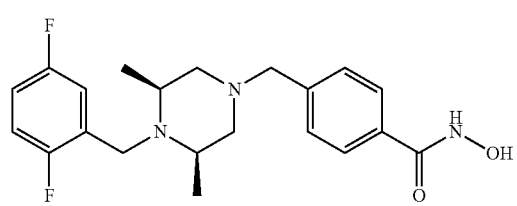 [SMILES: C[C@@H]1CN(Cc2ccc(C(=O)NO)cc2)C[C@H](C)N1Cc1cc(F)ccc1F] |
| 213 | 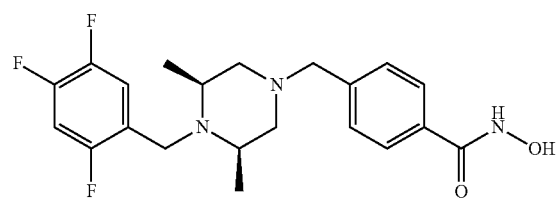 [SMILES: C[C@@H]1CN(Cc2ccc(C(=O)NO)cc2)C[C@H](C)N1Cc1cc(F)c(F)cc1F] |
| 214 | 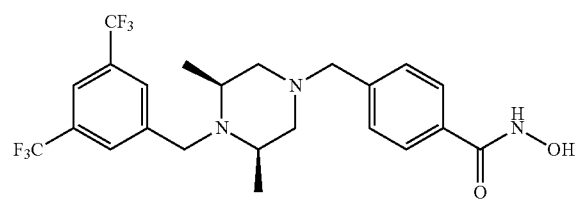 [SMILES: C[C@@H]1CN(Cc2ccc(C(=O)NO)cc2)C[C@H](C)N1Cc1cc(C(F)(F)F)cc(C(F)(F)F)c1] |
| 215 | 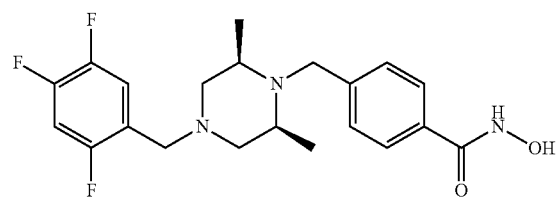 [SMILES: C[C@@H]1CN(Cc2cc(F)c(F)cc2F)C[C@H](C)N1Cc1ccc(C(=O)NO)cc1] |

TABLE 16-continued

Structural formulas of dimethylpiperazine derivative compounds

| Compound | Formula |
|---|---|
| 218 | |
| 219 | |
| 220 | |
| 222 | |
| 223 | |
| 224 | |
| 225 | |
| 230 | |

TABLE 16-continued

Structural formulas of dimethylpiperazine derivative compounds

| Compound | Formula |
|---|---|
| 231 | |
| 232 | |
| 233 | |
| 234 | |
| 242 | |
| 243 | |
| 244 | |

TABLE 16-continued
Structural formulas of dimethylpiperazine derivative compounds
| Compound | Formula |
|---|---|
| 245 | 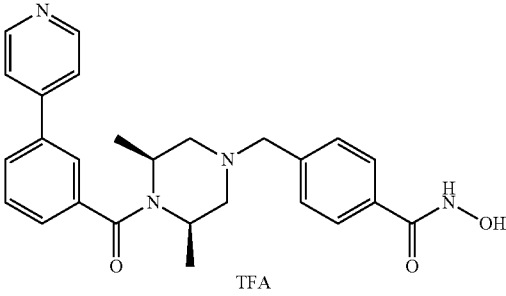 TFA |
| 246 | 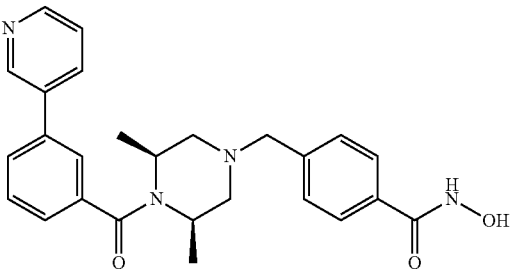 |
| 247 | 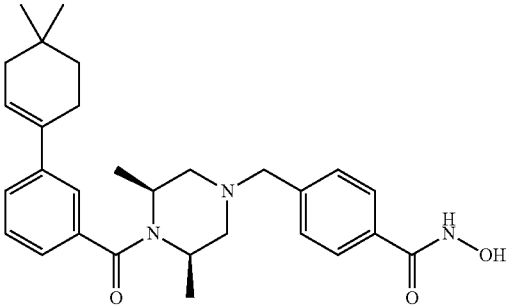 |
| 248 | 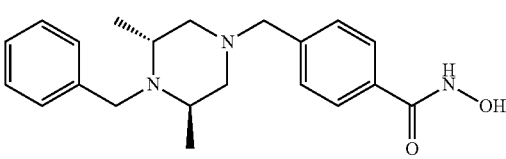 |
| 249 | 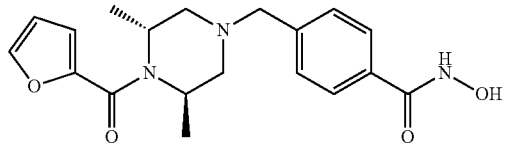 |
| 250 | 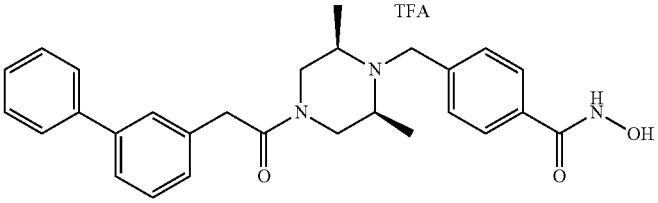 TFA |

TABLE 16-continued
Structural formulas of dimethylpiperazine derivative compounds
| Compound | Formula |
|---|---|
| 251 | 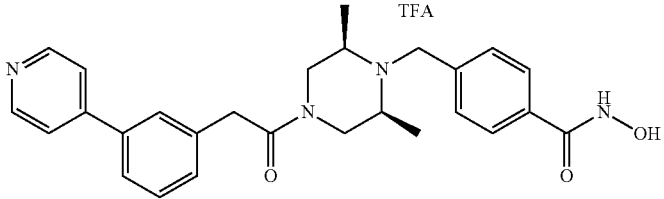 [SMILES: C[C@@H]1CN(C(=O)Cc2cccc(-c3ccncc3)c2)C[C@H](C)N1Cc1ccc(C(=O)NO)cc1] |
| 252 | 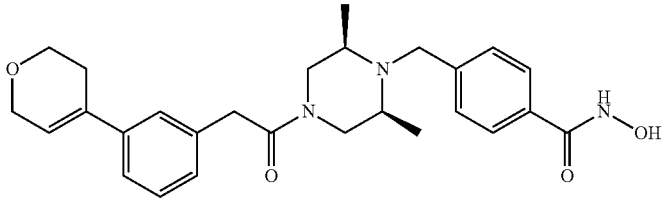 [SMILES: C[C@@H]1CN(C(=O)Cc2cccc(C3=CCOCC3)c2)C[C@H](C)N1Cc1ccc(C(=O)NO)cc1] |
| 253 | 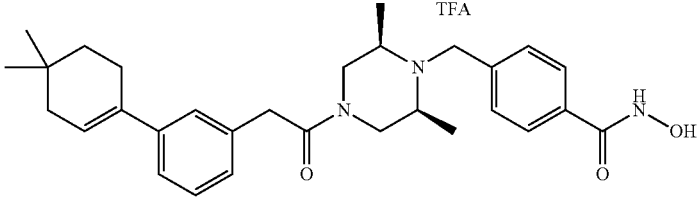 [SMILES: C[C@@H]1CN(C(=O)Cc2cccc(C3=CCC(C)(C)CC3)c2)C[C@H](C)N1Cc1ccc(C(=O)NO)cc1] |
| 255 | 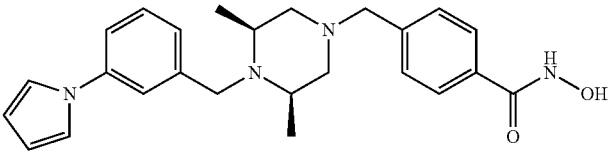 [SMILES: C[C@@H]1CN(Cc2ccc(C(=O)NO)cc2)C[C@H](C)N1Cc1cccc(-n2cccc2)c1] |
| 256 | 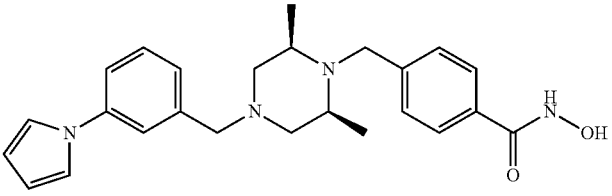 [SMILES: C[C@@H]1CN(Cc2cccc(-n3cccc3)c2)C[C@H](C)N1Cc1ccc(C(=O)NO)cc1] |
| 257 | 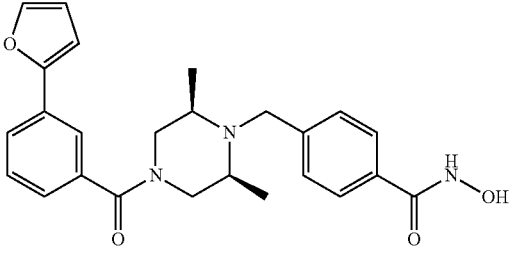 [SMILES: C[C@@H]1CN(C(=O)c2cccc(-c3ccco3)c2)C[C@H](C)N1Cc1ccc(C(=O)NO)cc1] |
| 258 | 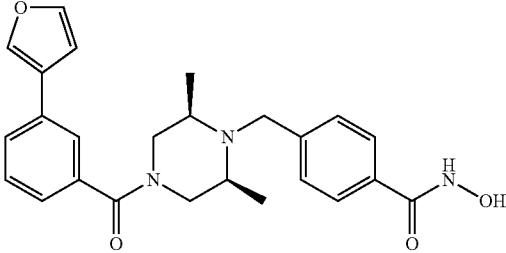 [SMILES: C[C@@H]1CN(C(=O)c2cccc(-c3ccoc3)c2)C[C@H](C)N1Cc1ccc(C(=O)NO)cc1] |

TABLE 16-continued
Structural formulas of dimethylpiperazine derivative compounds
| Compound | Formula |
|---|---|
| 259 | 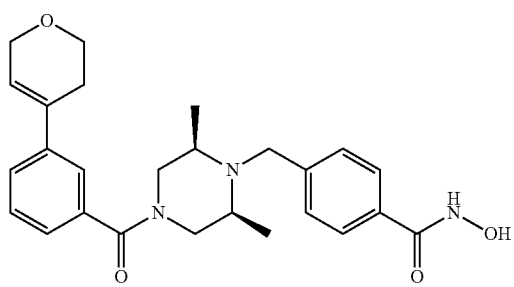 [SMILES: C[C@@H]1CN(C(=O)c2cccc(C3=CCOCC3)c2)C[C@H](C)N1Cc1ccc(C(=O)NO)cc1] |
| 260 | 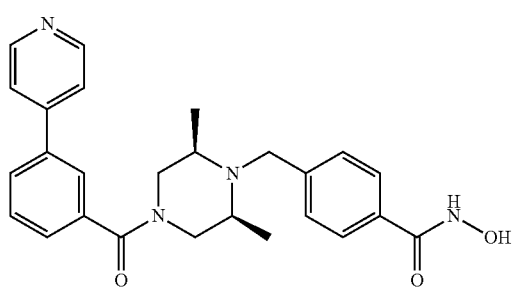 [SMILES: C[C@@H]1CN(C(=O)c2cccc(-c3ccncc3)c2)C[C@H](C)N1Cc1ccc(C(=O)NO)cc1] |
| 261 | 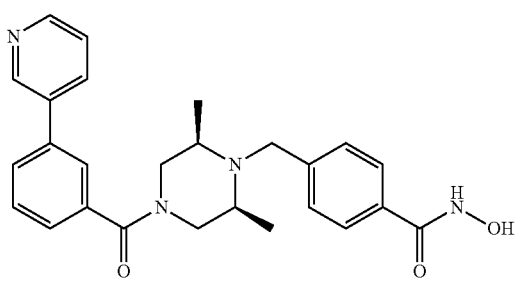 [SMILES: C[C@@H]1CN(C(=O)c2cccc(-c3cccnc3)c2)C[C@H](C)N1Cc1ccc(C(=O)NO)cc1] |
| 262 | 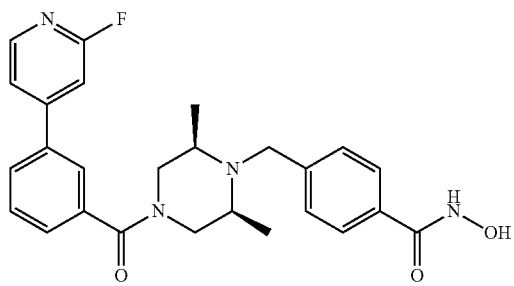 [SMILES: C[C@@H]1CN(C(=O)c2cccc(-c3ccnc(F)c3)c2)C[C@H](C)N1Cc1ccc(C(=O)NO)cc1] |
| 263 | 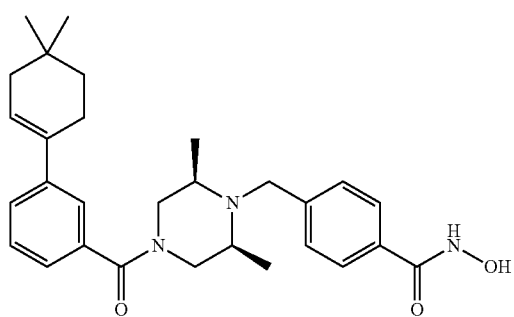 [SMILES: C[C@@H]1CN(C(=O)c2cccc(C3=CCC(C)(C)CC3)c2)C[C@H](C)N1Cc1ccc(C(=O)NO)cc1] |

TABLE 16-continued

Structural formulas of dimethylpiperazine derivative compounds

| Compound | Formula |
|---|---|
| 265 | (structure) |
| 266 | TFA (structure) |
| 267 | (structure) |
| 268 | (structure) |
| 270 | TFA (structure) |
| 271 | TFA (structure) |
| 272 | (structure) |
| 273 | TFA (structure) |

TABLE 16-continued
Structural formulas of dimethylpiperazine derivative compounds
| Compound | Formula |
|---|---|
| 274 | 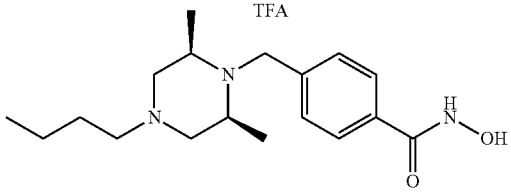 |
| 275 | 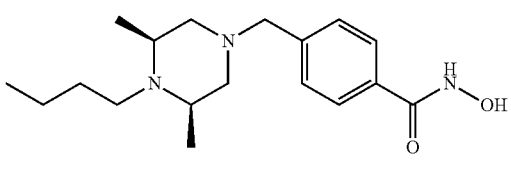 [SMILES: CC(C)=CCN1[C@H](C)CN(Cc2ccc(C(=O)NO)cc2)C[C@@H]1C] |
| 276 | 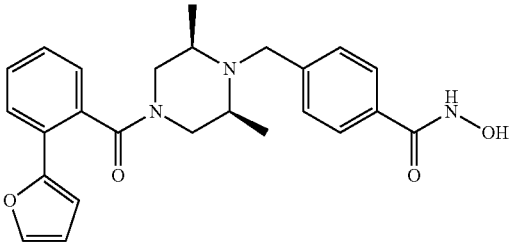 [SMILES: C[C@@H]1CN(C(=O)c2ccccc2-c2ccco2)C[C@H](C)N1Cc1ccc(C(=O)NO)cc1] |
| 277 | 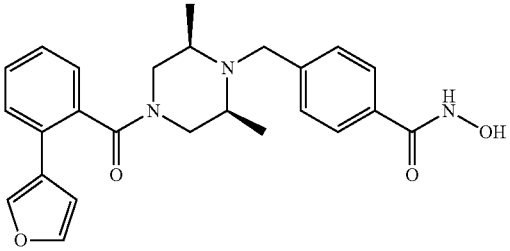 [SMILES: C[C@@H]1CN(C(=O)c2ccccc2-c2ccoc2)C[C@H](C)N1Cc1ccc(C(=O)NO)cc1] |
| 278 | 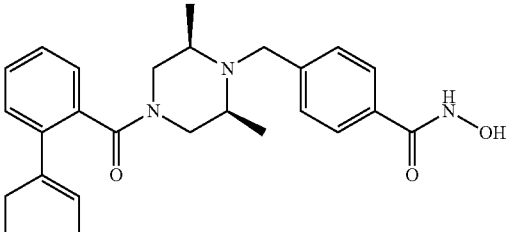 |
| 279 | 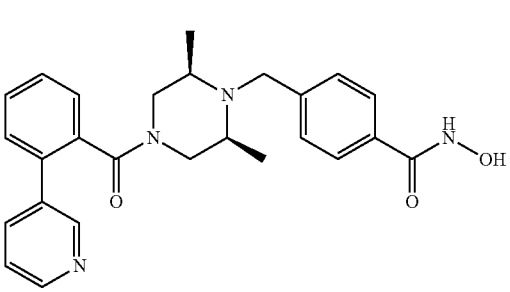 [SMILES: C[C@@H]1CN(C(=O)c2ccccc2-c2cccnc2)C[C@H](C)N1Cc1ccc(C(=O)NO)cc1] |

TABLE 16-continued
Structural formulas of dimethylpiperazine derivative compounds
| Compound | Formula |
| --- | --- |
| 280 | 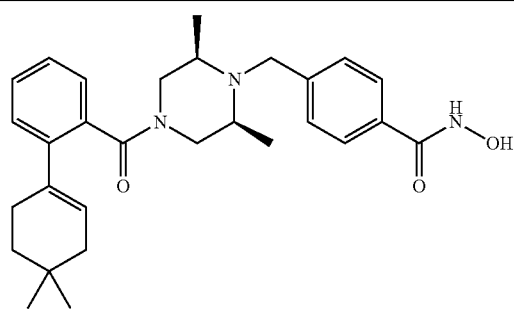 |
| 283 | 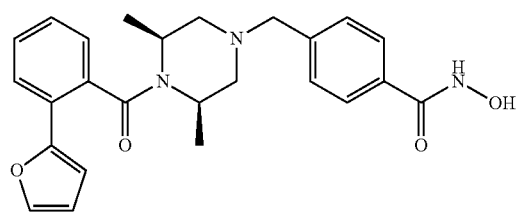 [SMILES: C[C@@H]1CN(Cc2ccc(C(=O)NO)cc2)C[C@H](C)N1C(=O)c1ccccc1-c1ccco1] |
| 284 | 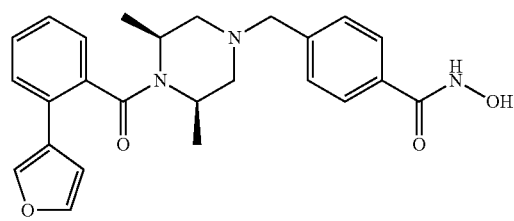 [SMILES: C[C@@H]1CN(Cc2ccc(C(=O)NO)cc2)C[C@H](C)N1C(=O)c1ccccc1-c1ccoc1] |
| 285 | 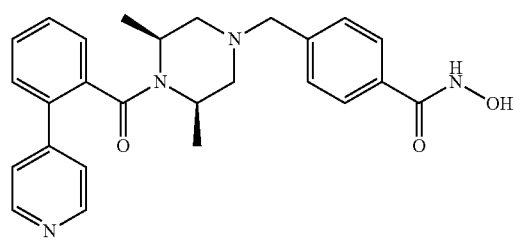 [SMILES: C[C@@H]1CN(Cc2ccc(C(=O)NO)cc2)C[C@H](C)N1C(=O)c1ccccc1-c1ccncc1] |
| 286 | 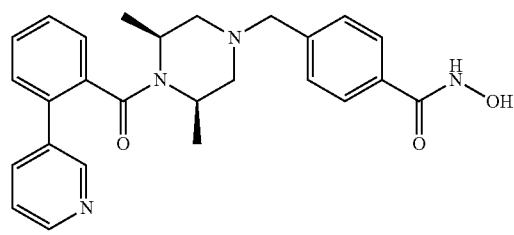 [SMILES: C[C@@H]1CN(Cc2ccc(C(=O)NO)cc2)C[C@H](C)N1C(=O)c1ccccc1-c1cccnc1] |
| 288 | 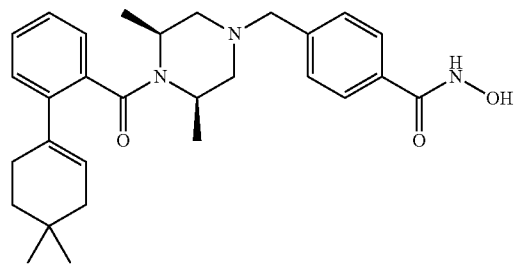 [SMILES: C[C@@H]1CN(Cc2ccc(C(=O)NO)cc2)C[C@H](C)N1C(=O)c1ccccc1C1=CCC(C)(C)CC1] |

TABLE 16-continued
Structural formulas of dimethylpiperazine derivative compounds
| Compound | Formula |
|---|---|
| 290 | 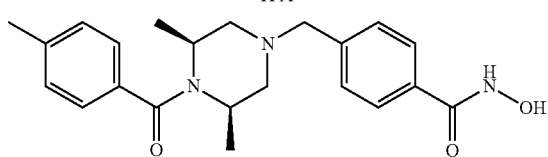 TFA |
| 291 | 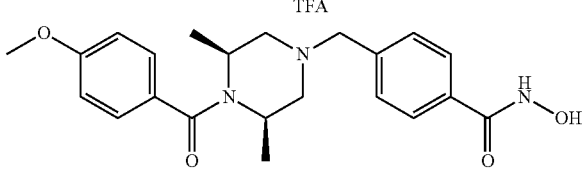 TFA |
| 292 | 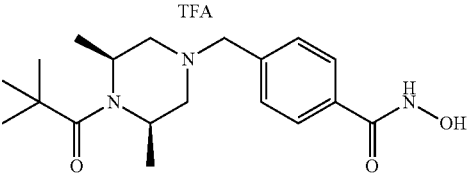 TFA |
| 293 | 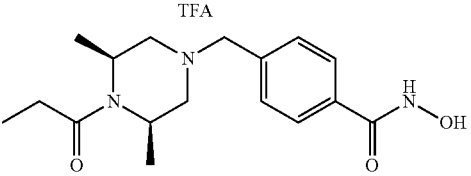 TFA |
| 294 | 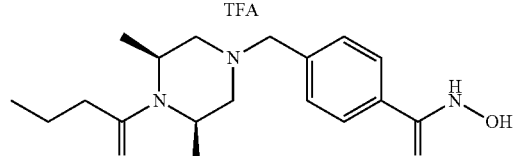 TFA |
| 295 | 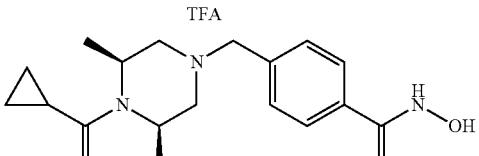 TFA |
| 296 | 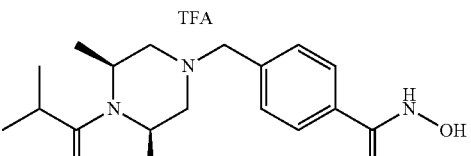 TFA |
| 297 | 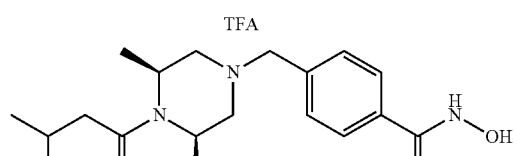 TFA |

TABLE 16-continued

Structural formulas of dimethylpiperazine derivative compounds

| Compound | Formula |
|---|---|
| 298 | |
| 299 | |
| 300 | |
| 301 | |
| 302 | |
| 303 | |
| 304 | |

TABLE 16-continued
Structural formulas of dimethylpiperazine derivative compounds
| Compound | Formula |
|---|---|
| 305 | 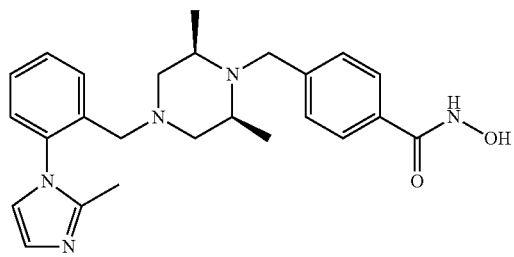 [SMILES: Cc1nccn1-c1ccccc1CN1C[C@@H](C)N(Cc2ccc(C(=O)NO)cc2)[C@@H](C)C1] |
| 309 | 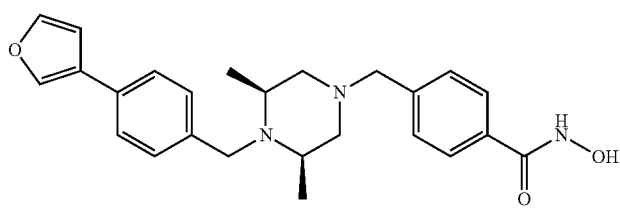 [SMILES: C[C@@H]1CN(Cc2ccc(C(=O)NO)cc2)C[C@H](C)N1Cc1ccc(-c2ccoc2)cc1] |
| 321 | 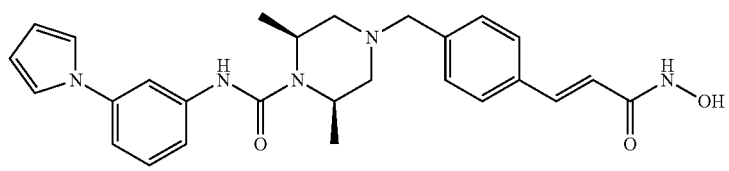 [SMILES: C[C@@H]1CN(Cc2ccc(/C=C/C(=O)NO)cc2)C[C@H](C)N1C(=O)Nc1cccc(-n2cccc2)c1] |
| 322 | 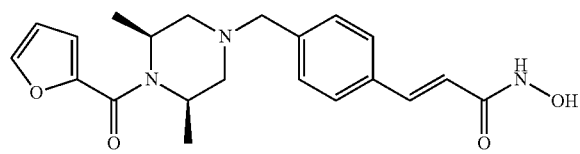 [SMILES: C[C@@H]1CN(Cc2ccc(/C=C/C(=O)NO)cc2)C[C@H](C)N1C(=O)c1ccco1] |
| 323 | 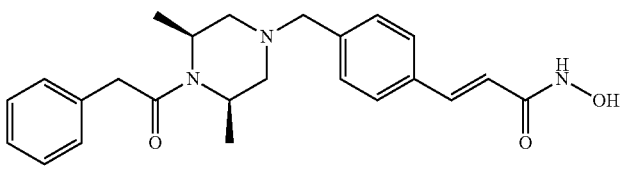 [SMILES: C[C@@H]1CN(Cc2ccc(/C=C/C(=O)NO)cc2)C[C@H](C)N1C(=O)Cc1ccccc1] |
| 326 | 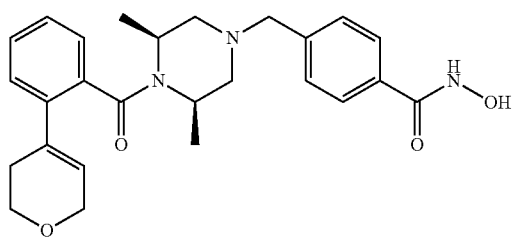 [SMILES: C[C@@H]1CN(Cc2ccc(C(=O)NO)cc2)C[C@H](C)N1C(=O)c1ccccc1C1=CCOCC1] |
| 327 | 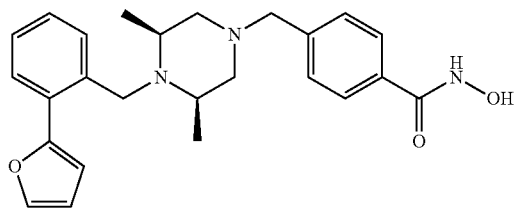 [SMILES: C[C@@H]1CN(Cc2ccc(C(=O)NO)cc2)C[C@H](C)N1Cc1ccccc1-c1ccco1] |

TABLE 16-continued

Structural formulas of dimethylpiperazine derivative compounds

| Compound | Formula |
|---|---|
| 328 | |
| 329 | |
| 330 | |
| 331 | |
| 332 | |
| 340 | |

TABLE 16-continued

Structural formulas of dimethylpiperazine derivative compounds

| Compound | Formula |
|---|---|
| 342 | |
| 343 | |
| 344 | |
| 345 | |
| 346 | |
| 347 | |
| 348 | |

TABLE 16-continued

Structural formulas of dimethylpiperazine derivative compounds

| Compound | Formula |
|---|---|
| 349 | |
| 350 | |
| 351 | |
| 352 | |
| 354 | |
| 355 | |

TABLE 16-continued
Structural formulas of dimethylpiperazine derivative compounds
| Compound | Formula |
|---|---|
| 356 | 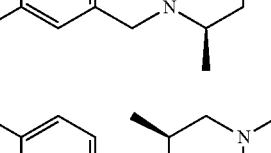 |
| 376 | 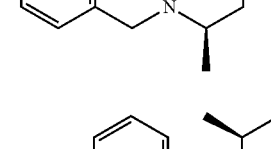 |
| 380 | 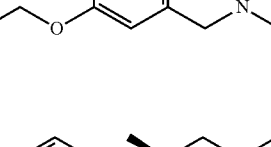 |
| 382 | 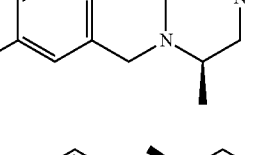 |
| 383 | 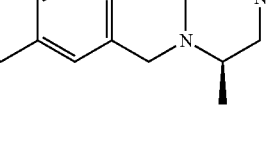 |
| 384 | 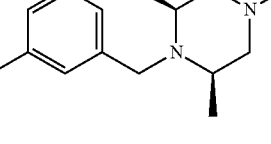 |
| 385 | 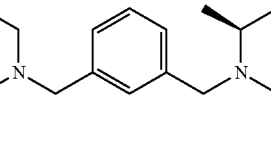 |
| 386 | 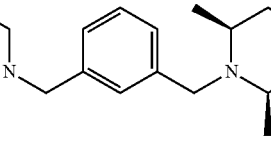 |
| 387 | 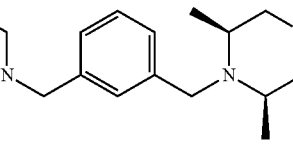 |

TABLE 16-continued
Structural formulas of dimethylpiperazine derivative compounds
| Compound | Formula |
|---|---|
| 388 | 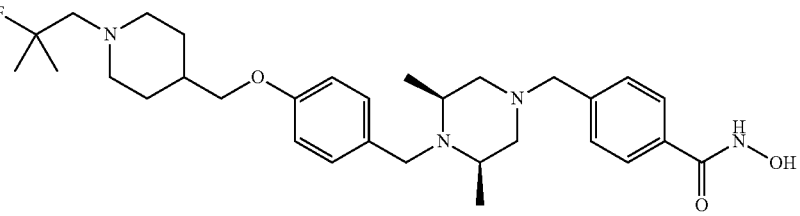 |
| 396 | 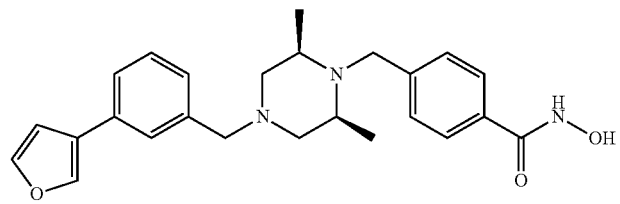 [SMILES: C[C@@H]1CN(Cc2cccc(-c3ccoc3)c2)C[C@H](C)N1Cc1ccc(C(=O)NO)cc1] |
| 400 | 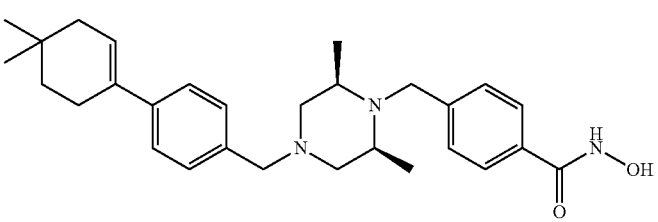 [SMILES: C[C@@H]1CN(Cc2ccc(C3=CCC(C)(C)CC3)cc2)C[C@H](C)N1Cc1ccc(C(=O)NO)cc1] |
| 401 | 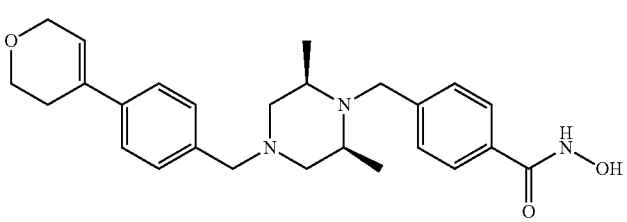 [SMILES: C[C@@H]1CN(Cc2ccc(C3=CCOCC3)cc2)C[C@H](C)N1Cc1ccc(C(=O)NO)cc1] |
| 402 | 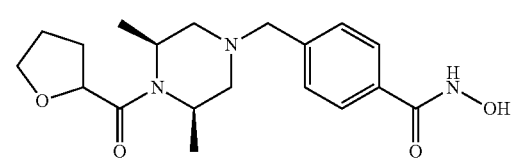 [SMILES: C[C@@H]1CN(Cc2ccc(C(=O)NO)cc2)C[C@H](C)N1C(=O)C1CCCO1] |
| 403 | 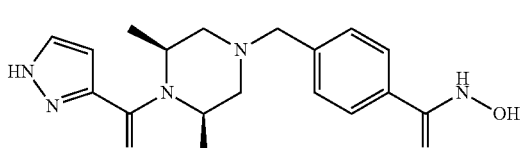 |
| 404 | 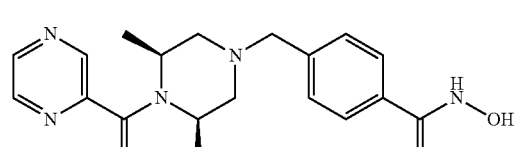 |
| 405 | 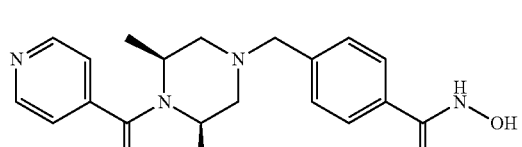 |

TABLE 16-continued

Structural formulas of dimethylpiperazine derivative compounds

| Compound | Formula |
|---|---|
| 411 | |
| 412 | |
| 413 | |
| 423 | |
| 424 | |
| 425 | |
| 426 | |
| 427 | |
| 428 | |

TABLE 16-continued

Structural formulas of dimethylpiperazine derivative compounds

| Compound | Formula |
|---|---|
| 429 | |
| 430 | |
| 431 | |
| 432 | |
| 433 | |
| 434 | |
| 435 | |
| 439 | |

TABLE 16-continued

Structural formulas of dimethylpiperazine derivative compounds

| Compound | Formula |
|---|---|
| 440 | |
| 441 | |
| 442 | |
| 443 | |
| 444 | |
| 446 | |
| 452 | |
| 453 | |

TABLE 16-continued

Structural formulas of dimethylpiperazine derivative compounds

| Compound | Formula |
|---|---|
| 454 | |
| 455 | |
| 456 | |
| 457 | |
| 458 | |
| 459 | |
| 460 | |
| 461 | |

TABLE 16-continued

Structural formulas of dimethylpiperazine derivative compounds

| Compound | Formula |
|---|---|
| 462 | |
| 463 | |
| 466 | |
| 467 | |
| 468 | |
| 472 | |
| 475 | |
| 476 | |
| 477 | |

TABLE 16-continued

Structural formulas of dimethylpiperazine derivative compounds

| Compound | Formula |
|---|---|
| 478 | |
| 479 | |
| 480 | |
| 481 | |
| 482 | |
| 483 | |

TABLE 16-continued

Structural formulas of dimethylpiperazine derivative compounds

| Compound | Formula |
|---|---|
| 484 | |
| 485 | |
| 486 | |
| 487 | |
| 520 | |
| 569 | |
| 571 | |

TABLE 16-continued
Structural formulas of dimethylpiperazine derivative compounds
| Compound | Formula |
|---|---|
| 573 | 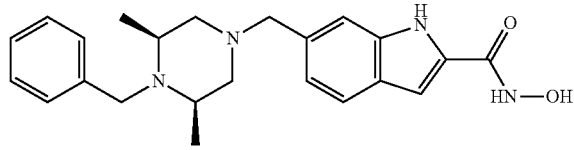 [SMILES: C[C@@H]1CN(Cc2ccc3cc(C(=O)NO)[nH]c3c2)C[C@H](C)N1Cc1ccccc1] |
| 574 | 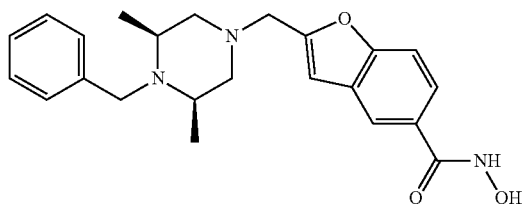 [SMILES: C[C@@H]1CN(Cc2cc3cc(C(=O)NO)ccc3o2)C[C@H](C)N1Cc1ccccc1] |
| 609 | 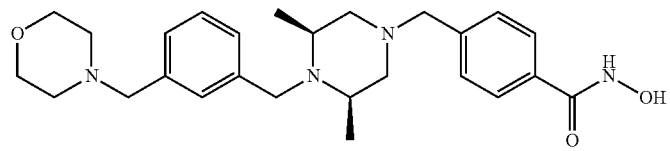 [SMILES: C[C@@H]1CN(Cc2ccc(C(=O)NO)cc2)C[C@H](C)N1Cc1cccc(CN2CCOCC2)c1] |
| 652 | 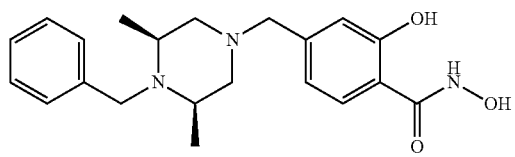 [SMILES: C[C@@H]1CN(Cc2ccc(C(=O)NO)c(O)c2)C[C@H](C)N1Cc1ccccc1] |
| 653 | 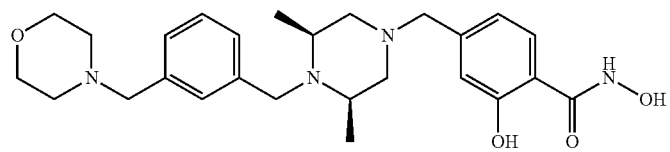 [SMILES: C[C@@H]1CN(Cc2ccc(C(=O)NO)c(O)c2)C[C@H](C)N1Cc1cccc(CN2CCOCC2)c1] |
| 696 | 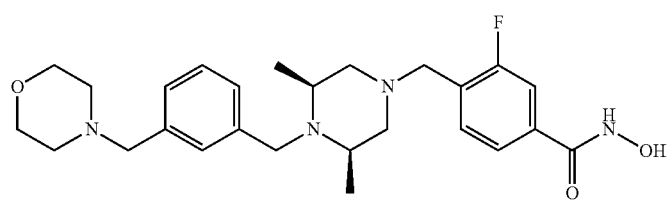 [SMILES: C[C@@H]1CN(Cc2ccc(C(=O)NO)cc2F)C[C@H](C)N1Cc1cccc(CN2CCOCC2)c1] |
| 812 | 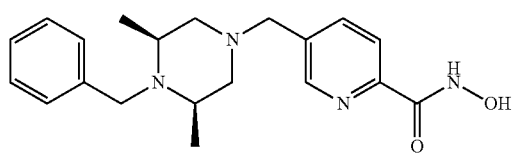 [SMILES: C[C@@H]1CN(Cc2ccc(C(=O)NO)nc2)C[C@H](C)N1Cc1ccccc1] |
| 813 | 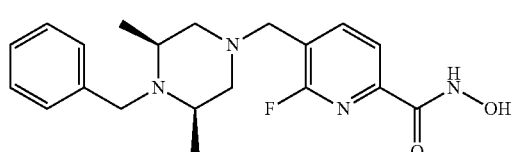 |

TABLE 16-continued

Structural formulas of dimethylpiperazine derivative compounds

| Compound | Formula |
|---|---|
| 814 | |
| 818 | |
| 820 | |
| 822 | |
| 823 | |
| 824 | |

Experimental Example 1

HDAC Enzyme Activity Inhibition Assays (In Vitro)

In order to examine the HDAC6 selectivity of the compounds of formula 1 of the present invention by HDAC1 and HDAC6 enzymatic activity inhibition assays, an experiment was performed using a conventional substance as a control.

HDAC enzyme activity was measured using a HDAC Fluorimetric Drug Discovery Kit (BML-AK511, 516, Enzo Life Science). For the HDAC1 enzyme activity test, human recombinant HDAC1 (BML-SE456) was used as an enzyme source, and Fluor de Lys®-"SIRT1 (BNL-KI177) was used as a substrate. A 5-fold dilution of the compound was seeded into a 96-well plate, and then 0.3 µg of the enzyme and 10 µM of the substrate were added to each well of the plate and allowed to react at 30° C. for 60 minutes. Then, Fluor de Lys® Developer II (BML-KI176) was added thereto and allowed to react for 30 minutes, after which the fluorescence value (Ex 360, Em 460) was measured using a multi-plate reader (Flexstation 3, Molecular Device). The HDAC6 enzyme was tested using human recombinant HDAC6 (382180) (Calbiochem) according to the same protocol as the HDAC1 enzyme activity test method. Based on the resulting values, each $IC_{50}$ value was calculated using GraphPad Prism4.0 program.

TABLE 17

Results of HDAC enzyme activity inhibition assays

| Compound | HDAC1 (uM) | HDAC6 (uM) | HDAC6 selectivity (fold) |
| --- | --- | --- | --- |
| 080 | 6.6 | 0.179 | 37 |
| 081 | 11.2 | 0.144 | 78 |
| 082 | 12.5 | 0.034 | 369 |
| 083 | 2.0 | 0.010 | 201 |
| 084 | 11.9 | 0.023 | 517 |
| 098 | >10 | 0.075 | >133 |
| 099 | 12.4 | 0.242 | 51 |
| 100 | >10 | 0.095 | >105 |
| 103 | 2.6 | 0.173 | 15 |
| 104 | 0.7 | 0.082 | 9 |
| 105 | 1.6 | 0.060 | 27 |
| 106 | 7.3 | 0.119 | 61 |
| 107 | 8.3 | 0.103 | 81 |
| 108 | 13.1 | 0.166 | 79 |
| 109 | 5.1 | 0.075 | 67 |
| 110 | 5.0 | 0.085 | 59 |
| 111 | >10 | 0.461 | >22 |
| 112 | >10 | 0.154 | >65 |
| 113 | 2.8 | 0.104 | 27 |
| 114 | 2.4 | 0.185 | 13 |
| 115 | 3.2 | 0.181 | 18 |
| 118 | 5.5 | 0.113 | 48 |
| 119 | 8.2 | 0.309 | 26 |
| 120 | 5.5 | 0.018 | 304 |
| 121 | 11.8 | 0.029 | 407 |
| 122 | 3.6 | 0.005 | 717 |
| 123 | 15.5 | 0.006 | 2584 |
| 125 | >10 | 0.003 | >3333 |
| 126 | 6.1 | 0.004 | 1525 |
| 127 | >10 | 0.011 | >909 |
| 128 | 11.1 | 0.002 | 5540 |
| 145 | 17.1 | 0.033 | 519 |
| 146 | 6.0 | 0.019 | 314 |
| 147 | >10 | 0.111 | >90 |
| 148 | 15.4 | 0.117 | 132 |
| 149 | >10 | 0.080 | >125 |
| 154 | 8.4 | 0.193 | 44 |
| 159 | 3.6 | 0.033 | 109 |
| 160 | 8.8 | 0.050 | 177 |
| 161 | 2.9 | 0.016 | 182 |
| 162 | 0.4 | 0.079 | 5 |
| 163 | 1.1 | 0.497 | 2 |
| 164 | 0.5 | 0.135 | 4 |
| 165 | 1.4 | 0.560 | 2 |
| 166 | 4.3 | 0.452 | 10 |
| 167 | 0.8 | 0.077 | 10 |
| 168 | 2.2 | 0.316 | 7 |
| 171 | ND | 0.039 | >256 |
| 172 | 1.3 | 0.038 | 35 |
| 173 | 7.2 | 0.085 | 85 |
| 174 | >10 | 0.097 | >103 |
| 175 | 6.1 | 0.068 | 90 |
| 176 | ND | 0.429 | >23 |
| 177 | 5.8 | 0.031 | 186 |
| 183 | >10 | 0.500 | >20 |
| 184 | ND | 0.249 | >40 |
| 185 | 0.8 | 0.249 | 3 |
| 186 | 0.3 | 0.005 | 65 |
| 187 | 1.1 | 0.239 | 5 |
| 188 | 13.6 | 0.191 | 71 |
| 189 | 3.0 | 0.303 | 10 |
| 193 | 16.3 | 0.271 | 60 |
| 194 | 24.8 | 0.082 | 303 |
| 195 | 22.4 | 0.410 | 55 |
| 196 | 14.4 | 0.148 | 97 |
| 197 | 2.1 | 0.177 | 12 |
| 198 | 12.2 | 0.241 | 51 |
| 204 | >10 | 0.807 | >12 |
| 211 | >10 | 0.065 | >154 |
| 212 | >10 | 0.358 | >28 |
| 213 | >10 | 0.349 | >29 |
| 214 | >10 | 0.165 | >61 |
| 215 | >10 | 0.523 | 2 |
| 218 | 11.1 | 0.749 | 15 |
| 219 | >10 | 0.170 | >59 |
| 220 | 15.9 | 1.231 | 13 |
| 222 | 1.6 | 0.100 | 16 |
| 223 | 0.9 | 0.118 | 8 |
| 224 | 1.7 | 0.120 | 14 |
| 225 | 1.9 | 0.052 | 36 |
| 230 | 2.4 | 0.687 | 3 |
| 231 | 1.5 | 0.763 | 2 |
| 232 | 7.9 | 0.286 | 28 |
| 233 | 16.9 | 1.476 | 11 |
| 234 | 8.9 | 0.512 | 17 |
| 242 | 2.4 | 0.098 | 24 |
| 243 | 3.0 | 0.074 | 40 |
| 244 | 3.4 | 0.097 | 35 |
| 245 | 3.6 | 0.116 | 31 |
| 246 | 3.4 | 0.129 | 26 |
| 247 | 13.3 | 0.441 | 30 |
| 248 | 8.5 | 0.089 | 96 |
| 249 | 15.6 | 0.120 | 130 |
| 250 | 9.5 | 0.168 | 57 |
| 251 | 13.7 | 0.242 | 57 |
| 252 | 17.5 | 0.221 | 79 |
| 253 | 22.6 | 1.535 | 15 |
| 255 | 8.5 | 0.024 | 354 |
| 256 | 4.6 | 0.303 | 15 |
| 257 | 1.6 | 0.255 | 6 |
| 258 | 1.7 | 0.258 | 7 |
| 259 | 2.5 | 0.400 | 6 |
| 260 | 1.7 | 0.529 | 3 |
| 261 | 2.0 | 0.577 | 3 |
| 262 | 2.4 | 0.727 | 3 |
| 263 | 6.8 | >1.000 | <7 |
| 265 | 6.2 | 0.074 | 84 |
| 266 | 19.1 | 0.282 | 68 |
| 267 | 14.2 | 0.188 | 75 |
| 268 | 2.8 | 1.267 | 2 |
| 270 | >10 | 2.217 | >5 |
| 271 | 12.5 | >1.000 | <13 |
| 272 | 12.2 | 0.182 | 67 |
| 273 | 13.7 | 0.441 | 31 |
| 274 | 13.5 | 0.378 | 36 |
| 275 | >10 | 0.475 | >21 |
| 276 | 12.3 | 0.337 | 36 |
| 277 | 10.4 | 0.455 | 23 |
| 278 | 14.4 | 0.911 | 16 |
| 279 | >10 | 0.769 | >13 |
| 280 | 17.7 | 0.388 | 46 |
| 283 | 3.5 | 0.023 | 154 |
| 284 | 5.7 | 0.068 | 84 |
| 285 | 7.0 | 0.093 | 75 |
| 286 | 13.1 | 0.161 | 81 |
| 288 | 10.7 | 0.326 | 33 |
| 290 | 3.8 | 0.079 | 48 |
| 291 | 1.3 | 0.055 | 24 |
| 292 | 5.6 | 0.074 | 76 |
| 293 | 5.8 | 0.131 | 44 |
| 294 | 8.2 | 0.220 | 37 |
| 295 | 5.7 | 0.079 | 72 |
| 296 | 6.9 | 0.204 | 34 |
| 297 | 5.6 | 0.090 | 62 |
| 298 | 5.5 | 0.369 | 15 |
| 299 | 1.2 | 0.243 | 5 |
| 300 | 3.7 | 0.530 | 7 |
| 301 | 2.8 | 0.253 | 11 |
| 302 | 3.6 | 1.126 | 3 |
| 303 | 2.9 | 1.106 | 3 |
| 304 | 2.3 | 0.280 | 8 |
| 305 | 5.6 | 0.032 | 174 |
| 309 | 1.6 | 0.073 | 21 |
| 321 | 1.1 | 0.125 | 8 |
| 322 | 1.1 | 0.175 | 6 |
| 323 | >10 | 0.921 | >11 |
| 326 | >10 | 0.058 | >172 |
| 327 | >10 | 0.235 | >43 |

TABLE 17-continued

Results of HDAC enzyme activity inhibition assays

| Compound | HDAC1 (uM) | HDAC6 (uM) | HDAC6 selectivity (fold) |
|---|---|---|---|
| 328 | 18.7 | 0.102 | 183 |
| 329 | 14.6 | 0.052 | 280 |
| 330 | 18.0 | 0.024 | 749 |
| 331 | ND | 0.731 | 13 |
| 332 | 21.9 | 0.106 | 207 |
| 340 | 1.6 | 0.606 | 3 |
| 342 | 8.7 | 0.019 | 456 |
| 343 | 8.8 | 0.027 | 328 |
| 344 | 5.8 | 0.012 | 481 |
| 345 | 5.5 | 0.016 | 341 |
| 346 | 8.3 | 0.025 | 332 |
| 347 | >10 | 0.408 | >25 |
| 348 | 4.7 | 0.843 | 6 |
| 349 | 5.0 | 0.005 | 1000 |
| 350 | 3.3 | 0.194 | 17 |
| 351 | 5.1 | 0.351 | 15 |
| 352 | 13.8 | 1.059 | >13 |
| 354 | >10 | 0.005 | >2000 |
| 355 | 21.0 | 1.060 | 20 |
| 356 | 12.3 | 0.022 | 558 |
| 376 | >10 | 0.084 | >119 |
| 380 | >10 | 0.162 | >62 |
| 382 | >10 | 0.083 | >120 |
| 383 | >10 | 0.098 | >102 |
| 384 | >10 | 0.106 | >94 |
| 385 | >10 | 0.189 | >53 |
| 386 | >10 | 0.130 | >77 |
| 387 | >10 | 0.085 | >118 |
| 388 | 9.0 | 0.083 | 109 |
| 396 | 1.7 | 0.406 | 4 |
| 400 | 11.3 | 2.822 | 4 |
| 401 | 2.0 | 0.301 | 7 |
| 402 | 5.2 | 0.161 | 32 |
| 403 | 3.2 | 0.061 | 53 |
| 404 | 5.5 | 0.182 | 30 |
| 405 | 4.3 | 0.248 | 17 |
| 411 | 4.3 | 0.008 | 538 |
| 412 | 1.1 | 0.032 | 36 |
| 413 | >10 | 0.013 | >769 |
| 423 | 1.0 | 0.046 | 22 |
| 424 | 1.2 | 0.043 | 27 |
| 425 | 1.5 | 0.086 | 17 |
| 426 | 5.0 | 0.142 | 35 |
| 427 | 6.0 | 0.152 | 40 |
| 428 | 4.7 | 0.117 | 41 |
| 429 | 4.4 | 0.100 | 44 |
| 430 | 4.5 | 0.082 | 55 |
| 431 | 13.4 | 0.022 | 611 |
| 432 | 3.4 | 0.042 | 81 |
| 433 | 3.5 | 0.049 | 71 |
| 434 | 3.7 | 0.060 | 61 |
| 435 | 5.1 | 0.090 | 57 |
| 439 | 10.9 | 0.104 | 105 |
| 440 | 5.6 | 0.078 | 71 |
| 441 | 5.4 | 0.035 | 154 |
| 442 | 7.8 | 0.120 | 65 |
| 443 | 9.6 | 0.141 | 68 |
| 444 | 8.5 | 0.058 | 146 |
| 446 | 3.8 | 0.114 | 33 |
| 452 | 9.1 | 0.065 | 140 |
| 453 | 11.9 | 0.077 | 154 |
| 454 | ND | 0.044 | >237 |
| 455 | 9.6 | 0.103 | 93 |
| 456 | 11.1 | 0.144 | 77 |
| 457 | 0.3 | 0.146 | 2 |
| 458 | 6.1 | 0.286 | 21 |
| 459 | 3.8 | 0.149 | 25 |
| 460 | 4.4 | 0.219 | 20 |
| 461 | 4.2 | 0.238 | 18 |
| 462 | 3.2 | 0.264 | 12 |
| 463 | 4.7 | 0.256 | 18 |
| 466 | 0.7 | 0.019 | 35 |
| 467 | >10 | 0.049 | 204 |
| 468 | 20 | 0.029 | 690 |
| 472 | 0.2 | 0.055 | 3 |
| 475 | 0.8 | 0.114 | 7 |
| 476 | 0.9 | 0.142 | 6 |
| 477 | 2.7 | 0.253 | 11 |
| 478 | 6.57 | 0.64 | 10 |
| 479 | 5.3 | 0.433 | 12 |
| 480 | 1.0 | 0.467 | 2 |
| 481 | 16.2 | 0.106 | 153 |
| 482 | 12.5 | 0.103 | 121 |
| 483 | 17.1 | 0.103 | 166 |
| 484 | 19.6 | 0.130 | 151 |
| 485 | 14.7 | 0.145 | 101 |
| 486 | >10 | 0.126 | >79 |
| 487 | 1.1 | 0.296 | 4 |
| 520 | >10 | 0.86 | >11 |
| 569 | >10 | 0.84 | 82 |
| 571 | 10.0 | 0.21 | 48 |
| 573 | >10 | 1.44 | 36 |
| 574 | 3.9 | 0.81 | 4 |
| 609 | >10 | 0.754 | >13.3 |
| 652 | >10 | 0.88 | >11 |
| 653 | >10 | 0.42 | >23 |
| 696 | >10 | 0.01 | >1000 |
| 812 | >10 | 1.54 | >6 |
| 813 | 17.2 | 0.01 | 1720 |
| 814 | 20.6 | 0.99 | 20 |
| 818 | >10 | 0.87 | >11 |
| 820 | 2.25 | 0.25 | 9 |
| 822 | >10 | 0.28 | >35 |
| 823 | 2.7 | 0.04 | 66 |
| 824 | 4.1 | 0.18 | 22 |

As can be seen in Table 16 above, the dimethylpiperazine hydroxamic acid derivative compounds of the present invention showed about 2 to about 5500 times higher selective HDAC6 inhibitory activities in the HDAC1 and HDAC6 activity inhibition assays.

INDUSTRIAL APPLICABILITY

The compounds represented by formula I, isomers thereof or pharmaceutically acceptable salts thereof can be used for prevention or treatment of histone deacetylase 6 activity-associated diseases.

The invention claimed is:
1. A compound represented by the following formula I, a stereoisomer thereof, or a pharmaceutically acceptable salt thereof:

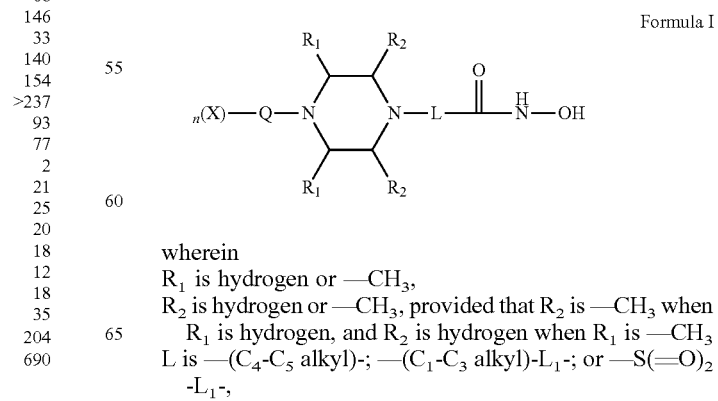

Formula I wherein
$R_1$ is hydrogen or —$CH_3$,
$R_2$ is hydrogen or —$CH_3$, provided that $R_2$ is —$CH_3$ when $R_1$ is hydrogen, and $R_2$ is hydrogen when $R_1$ is —$CH_3$
L is —($C_4$-$C_5$ alkyl)-; —($C_1$-$C_3$ alkyl)-$L_1$-; or —$S(=O)_2$-$L_1$-;

wherein —(C₄-C₅ alkyl)- and —(C₁-C₃ alkyl)- may be unsubstituted or substituted with —CH₃,
L₁ is —(C₃-C₆)cycloalkyl-;

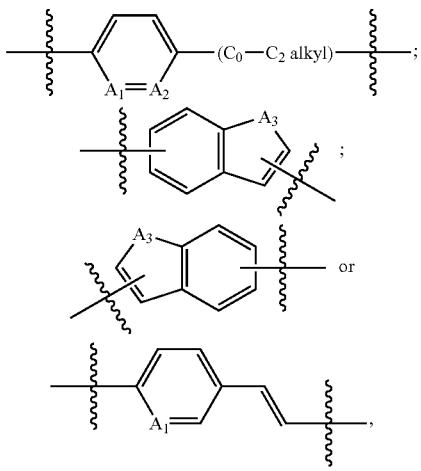

A₁ and A₂ are each independently —N— or —CR₃—, provided that both A₁ and A₂ cannot be —N—,
R₃ is hydrogen; —F, —Cl, —Br, —I or —OH, and
A₃ is —NH— or —O—,
Q is selected from the group consisting of —(C₁-C₆)alkyl-; —(C₂-C₆)alkenyl-; —C(=O)—; —C(=S)— or

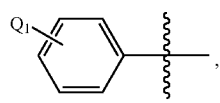

wherein —(C₁-C₆)alkyl- and —(C₂-C₆)alkenyl- may be unsubstituted or each independently substituted 1 to 3 —CH₃ groups or halogen atoms,
Q₁ is hydrogen; —F, —Cl, —Br or —I,
n is an integer of 0, 1 or 2, provided that n is 0 when Q is

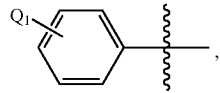

n is 1 when Q is —C(=O)— or —C(=S)—, and n is 1 or 2 when Q is —(C₁-C₆)alkyl- or —(C₂-C₆)alkenyl-, and
X may be selected from the group consisting of —C₁-C₆ alkyl; —C₃-C₆ cycloalkyl; —C₂-C₆ alkenyl; —C₃-C₆ cycloalkenyl; —(C₀-C₂ alkyl)Ar; —OAr; —(C₀-C₂ alkyl)Het; naphthyl and following groups:

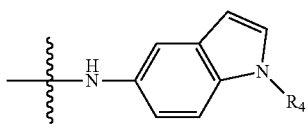

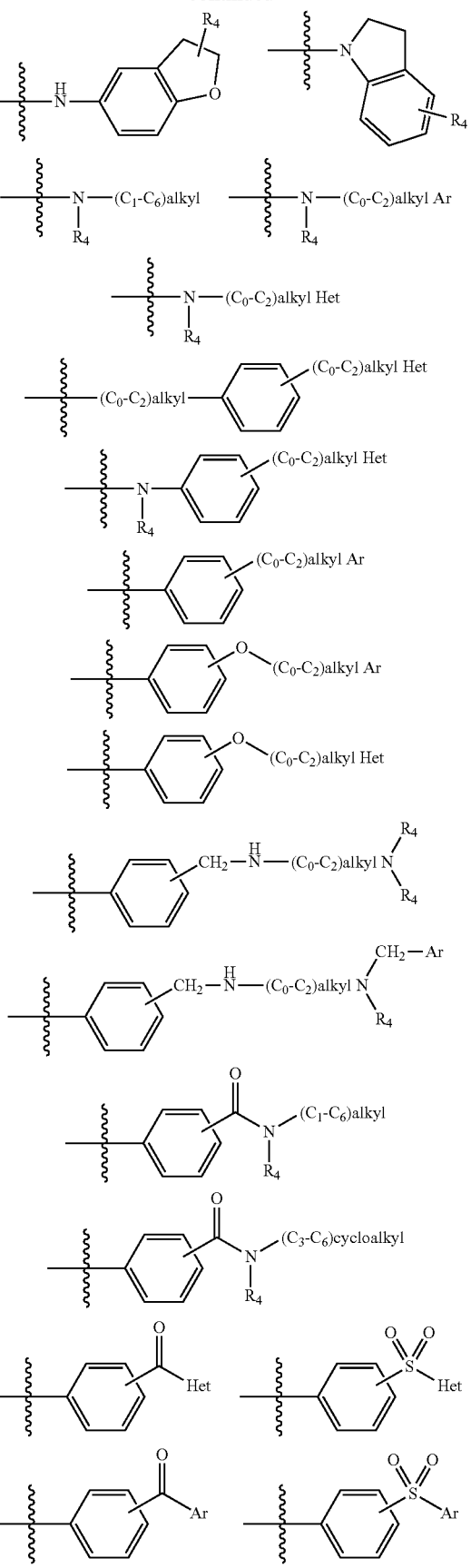

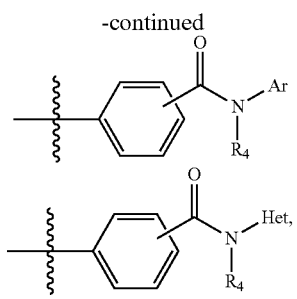

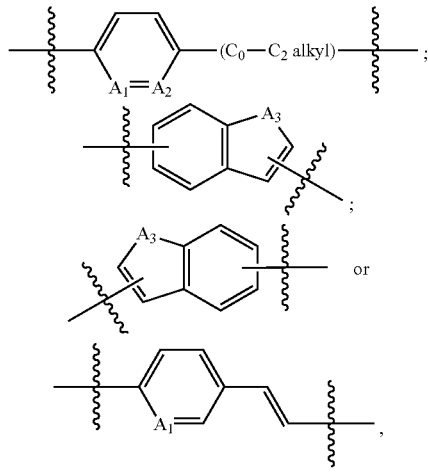

wherein $R_4$ is H or —$C_1$-$C_4$ alkyl,

—$C_0$-$C_2$ alkyl, —$C_2$-$C_6$ alkenyl and —$C_1$-$C_6$ alkyl may be unsubstituted or substituted with 1 to 2 —$CH_3$ groups; 1 to 3 —F groups, or a combination thereof, Ar is a $C_6$ monocyclic aromatic compound, which may be unsubstituted or substituted with one or more halogen atoms; —OH; —$NH_2$; —$C_1$-$C_6$ alkyl; —O($C_1$-$C_6$) alkyl; —$C_3$-$C_6$ cycloalkenyl; —NH($C_1$-$C_6$ alkyl); —N($C_1$-$C_3$ alkyl)$_2$; —$CH_2$N($C_1$-$C_3$ alkyl)$_2$; —S(=O)$_2$—($C_1$-$C_3$ alkyl) or phenyl groups, wherein —$C_1$-$C_3$ alkyl; —$C_1$-$C_6$ alkyl and —$C_3$-$C_6$ cycloalkenyl may be each independently substituted with 1 to 5 —F or —$CH_3$ groups, and Het is a 4- to 6-membered heteroaromatic or non-aromatic ring compound containing 1 to 3 elements selected from the group consisting of N, O and S while having 0 to 3 double bonds, and may be unsubstituted or substituted with one or more halogen atoms; —$C_1$-$C_6$ alkyl; —C(=O)($C_1$-$C_3$ alkyl); —S(=O)$_2$($C_1$-$C_3$ alkyl) or benzyl groups, wherein —$C_1$-$C_3$ alkyl and —$C_1$-$C_6$ alkyl may be each independently substituted with —OH; 1 to 5 —F or —$CH_3$ groups.

2. The compound represented by formula I, stereoisomer thereof or pharmaceutically acceptable salt thereof according to claim 1, wherein the compound represented by formula I is a compound represented by the following formula II or formula III:

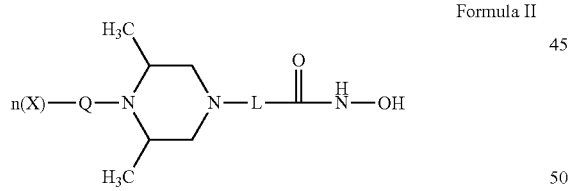

Formula II

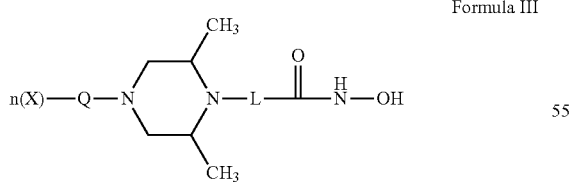

Formula III wherein

L is —($C_5$ alkyl)-; —($C_1$-$C_2$ alkyl)-$L_1$-; or —S(=O)$_2$-$L_1$-, wherein —($C_5$ alkyl)- and —($C_1$-$C_2$ alkyl)- are straight-chain and may be unsubstituted or substituted with —$CH_3$, $L_1$ is —($C_3$-$C_6$) cycloalkyl-;

$A_1$ and $A_2$ are each independently —N— or —$CR_3$—, provided that both $A_1$ and $A_2$ cannot be —N—, $R_3$ is hydrogen; —F or —OH, and $A_3$ is —NH— or —O—, Q is selected from the group consisting of —($C_1$-$C_3$) alkyl-; —C(=O)—; —C(=S)— or

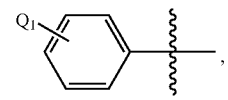

wherein —($C_1$-$C_3$)alkyl- may be unsubstituted or substituted with 1 to 3 —$CH_3$ groups or halogen atoms, $Q_1$ is hydrogen; —F or —Cl, n is an integer of 0 or 1, provided that n is 0 when Q is

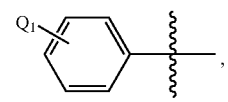

and n is 1 when Q is —C(=O)—, —C(=S)— or —($C_1$-$C_3$)alkyl-, and

X may be selected from the group consisting of —$C_1$-$C_6$ alkyl; —$C_3$-$C_6$ cycloalkyl; —$C_2$-$C_6$ alkenyl; —$C_3$-$C_6$ cycloalkenyl; —($C_0$-$C_2$ alkyl)Ar; —OAr; —($C_0$-$C_2$ alkyl)Het; naphthyl; and following groups:

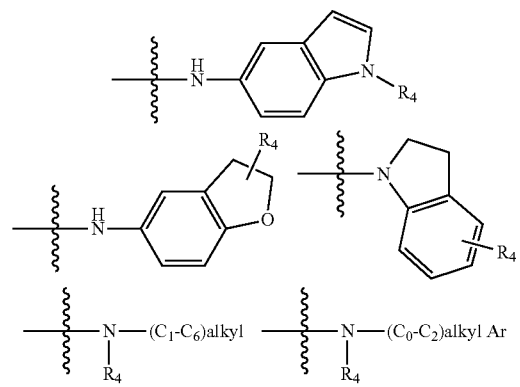

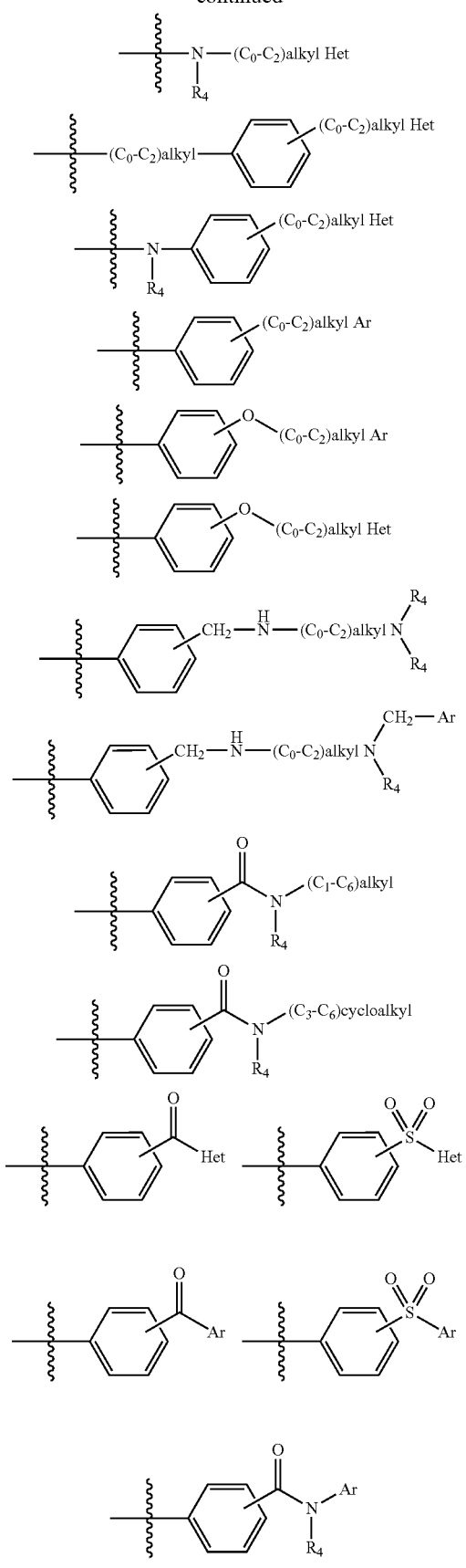

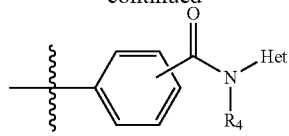

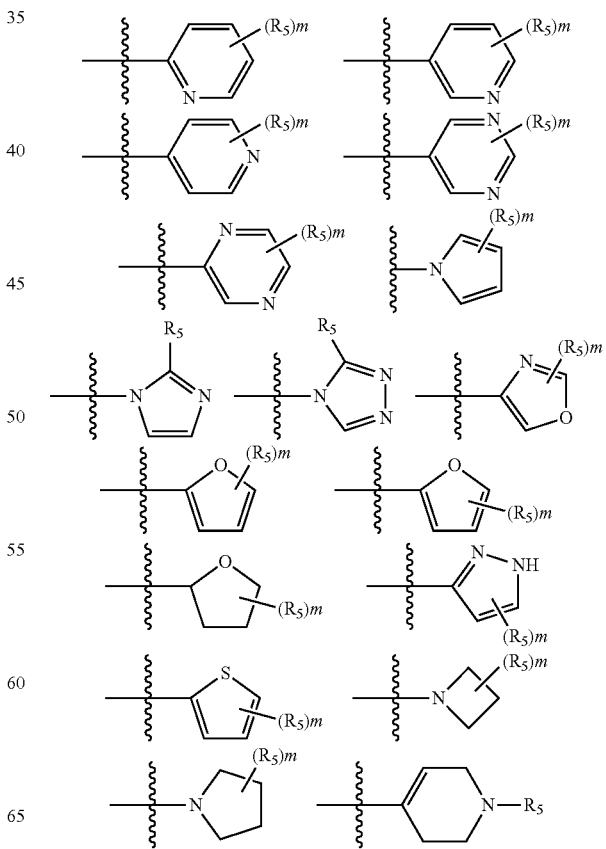

wherein $R_4$ is H or —$C_1$-$C_4$ alkyl,
—$C_0$-$C_2$ alkyl; —$C_2$-$C_6$ alkenyl and —$C_1$-$C_6$ alkyl may be unsubstituted or substituted with 1 or 2 —$CH_3$ groups or 1 to 3 —F groups, Ar is a $C_6$ monocyclic aromatic compound, which may be unsubstituted or substituted with one or more halogen atoms; —OH; —$NH_2$; —$C_1$-$C_6$ alkyl; —O($C_1$-$C_6$) alkyl; —$C_3$-$C_6$ cycloalkenyl; —NH($C_1$-$C_6$ alkyl); —N($C_1$-$C_3$ alkyl)$_2$; —$CH_2$N($C_1$-$C_3$ alkyl)$_2$; —S(=O)$_2$—($C_1$-$C_3$ alkyl) or phenyl groups, wherein —$C_1$-$C_3$ alkyl; —$C_1$-$C_6$ alkyl and —$C_3$-$C_6$ cycloalkenyl may be each independently substituted with 1 to 5 —F or —$CH_3$ groups, and Het is a 4- to 6-membered heteroaromatic or non-aromatic ring compound containing 1 to 3 elements selected from the group consisting of N; O and S while having 0 to 3 double bonds, and may be unsubstituted or substituted with one or more halogen atoms; —$C_1$-$C_6$ alkyl; —C(=O)($C_1$-$C_3$ alkyl); —S(=O)$_2$($C_1$-$C_3$ alkyl) or benzyl groups, wherein —$C_1$-$C_3$ alkyl and —$C_1$-$C_6$ alkyl may be each independently substituted with —OH; or 1 to 5 —F or —$CH_3$ groups.

3. The compound represented by formula I, stereoisomer thereof or pharmaceutically acceptable salt thereof according to claim 1, wherein Het is selected from following groups:

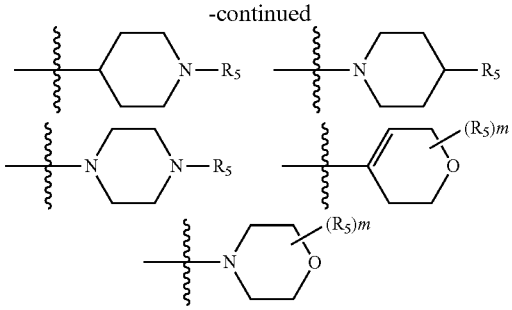

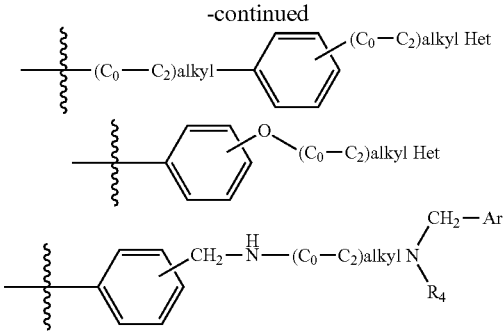

wherein $R_5$ are each independently hydrogen; —F; —Cl; —$C_1$-$C_6$ alkyl; —C(=O)($C_1$-$C_3$ alkyl); —S(=O)$_2$($C_1$-$C_3$ alkyl) or benzyl, wherein —$C_1$-$C_3$ alkyl and —$C_1$-$C_6$ alkyl may be each independently substituted with —OH; 1 to 5 —F or —$CH_3$ groups, m is an integer of 0, 1, 2 or 3, and Het is unsubstituted when m is 0, and Het may be substituted with independent $R_5$ when m is 1, 2 or 3.

4. The compound represented by formula I, stereoisomer thereof or pharmaceutically acceptable salt thereof according to claim 1, wherein L, $L_1$, $A_1$, $A_2$, $A_3$, $R_3$, $R_4$, Q and X are defined as follows:

L is —$CH_2$-$L_1$-, wherein $L_1$ is

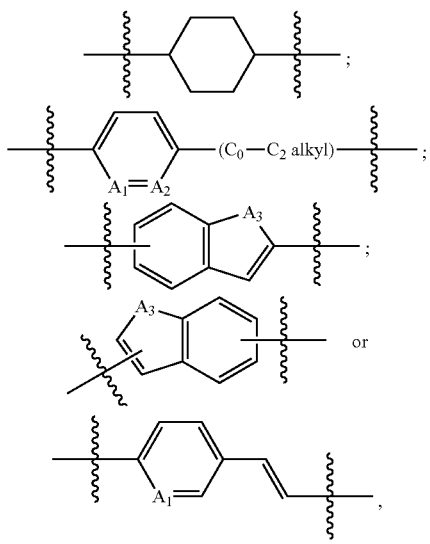

$A_1$ and $A_2$ are each independently —N— or —$CR_3$—, provided that both $A_1$ and $A_2$ cannot be —N—, $R_3$ is hydrogen; —F or —OH, and $A_3$ is —NH— or —O—, Q is —$CH_2$— or —C(=O)—, and X may be selected from the group consisting of —$C_1$-$C_6$ alkyl; —($C_0$-$C_2$ alkyl)Ar; —($C_0$-$C_2$ alkyl)Het; —OAr; or following groups:

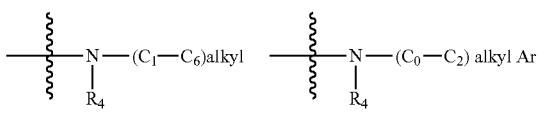

wherein $R_4$ is H or —$C_1$-$C_4$ alkyl,

—$C_0$-$C_2$ alkyl and —$C_1$-$C_6$ alkyl may be unsubstituted or substituted with 1 or 2 —$CH_3$ groups and/or 1 to 3 —F groups, and Ar and Het is each independently as defined in formula I.

5. The compound represented by formula I, stereoisomer thereof or pharmaceutically acceptable salt thereof according to claim 1, wherein the compound represented by formula I is any one of compounds set forth in the following table:

| No. | Name of Compound |
|---|---|
| 080 | 4-(((2S,6R)-4-benzoyl-2,6-dimethylpiperazin-1-yl)methyl)-N-hydroxybenzamide |
| 081 | 4-(((2S,6R)-4-benzyl-2,6-dimethylpiperazin-1-yl)methyl)-N-hydroxybenzamide |
| 082 | 4-(((3R,5S)-4-acetyl-3,5-dimethylpiperazin-1-yl)methyl)-N-hydroxybenzamide |
| 083 | 4-(((3R,5S)-4-benzoyl-3,5-dimethylpiperazin-1-yl)methyl)-N-hydroxybenzamide |
| 084 | 4-(((3R,5S)-4-benzyl-3,5-dimethylpiperazin-1-yl)methyl)-N-hydroxybenzamide |
| 098 | (2S,6R)-4-(4-(hydroxycarbamoyl)benzyl)-N-isopropyl-2,6-dimethylpiperazine-1-carboxamide |
| 099 | (2S,6R)-N-(3-chlorophenyl)-4-(4-(hydroxycarbamoyl)benzyl)-2,6-dimethylpiperazine-1-carboxamide |
| 100 | 4-(((3R,5S)-3,5-dimethyl-4-(phenylsulfonyl)piperazin-1-yl)methyl)-N-hydroxybenzamide |
| 103 | (3R,5S)-4-(4-(hydroxycarbamoyl)benzyl)-N-isopropyl-3,5-dimethylpiperazine-1-carboxamide |
| 104 | (3R,5S)-N-(3-chlorophenyl)-4-(4-(hydroxycarbamoyl)benzyl)-3,5-dimethylpiperazine-1-carboxamide |
| 105 | 4-(((2S,6R)-2,6-dimethyl-4-(phenylsulfonyl)piperazin-1-yl)methyl)-N-hydroxybenzamide |
| 106 | 4-(((2S,6R)-4-(4-chlorobenzoyl)-2,6-dimethylpiperazin-1-yl)methyl)-N-hydroxybenzamide |
| 107 | 4-(((2S,6R)-4-(3-chlorobenzoyl)-2,6-dimethylpiperazin-1-yl)methyl)-N-hydroxybenzamide |
| 108 | 4-(((2S,6R)-4-(2-chlorobenzoyl)-2,6-dimethylpiperazin-1-yl)methyl)-N-hydroxybenzamide |
| 109 | 4-(((2S,6R)-4-((4-chlorophenyl)sulfonyl)-2,6-dimethylpiperazin-1-yl)methyl)-N-hydroxybenzamide |
| 110 | 4-(((2S,6R)-4-((2-chlorophenyl)sulfonyl)-2,6-dimethylpiperazin-1-yl)methyl)-N-hydroxybenzamide |
| 111 | 4-(((2S,6R)-2,6-dimethyl-4-picolinoylpiperazin-1-yl)methyl)-N-hydroxybenzamide |
| 112 | 4-(((2S,6R)-2,6-dimethyl-4-nicotinoylpiperazin-1-yl)methyl)-N-hydroxybenzamide |
| 113 | 4-(((2S,6R)-2,6-dimethyl-4-(pyridin-3-ylsulfonyl)piperazin-1-yl)methyl)-N-hydroxybenzamide |
| 114 | 4-(((2S,6R)-2,6-dimethyl-4-(thiophene-2-carbonyl)piperazin-1-yl)methyl)-N-hydroxybenzamide |
| 115 | 4-(((2S,6R)-4-(furan-2-carbonyl)-2,6-dimethylpiperazin-1-yl)methyl)-N-hydroxybenzamide |
| 118 | 4-(((2S,6R)-4-(2-chlorobenzyl)-2,6-dimethylpiperazin-1-yl)methyl)-N-hydroxybenzamide |
| 119 | 4-(((2R,6S)-4-(4-fluorophenyl)-2,6-dimethylpiperazin-1-yl)methyl)-N-hydroxybenzamide |

| No. | Name of Compound |
|---|---|
| 120 | 4-(((3R,5S)-4-(2-chlorobenzoyl)-3,5-dimethylpiperazin-1-yl)methyl)-N-hydroxybenzamide |
| 121 | 4-(((3R,5S)-4-(3-chlorobenzoyl)-3,5-dimethylpiperazin-1-yl)methyl)-N-hydroxybenzamide |
| 122 | 4-(((3R,5S)-4-(4-chlorobenzoyl)-3,5-dimethylpiperazin-1-yl)methyl)-N-hydroxybenzamide |
| 123 | 4-(((3R,5S)-3,5-dimethyl-4-picolinoylpiperazin-1-yl)methyl)-N-hydroxybenzamide |
| 125 | 4-(((3R,5S)-4-(furan-2-carbonyl)-3,5-dimethylpiperazin-1-yl)methyl)-N-hydroxybenzamide |
| 126 | 4-(((3R,5S)-3,5-dimethyl-4-(thiophene-2-carbonyl)piperazin-1-yl)methyl)-N-hydroxybenzamide |
| 127 | 4-(((3R,5S)-4-(2-chlorobenzyl)-3,5-dimethylpiperazin-1-yl)methyl)-N-hydroxybenzamide |
| 128 | 4-(((3R,5S)-4-(3-chlorobenzyl)-3,5-dimethylpiperazin-1-yl)methyl)-N-hydroxybenzamide |
| 145 | 4-(((3R,5S)-4-(furan-2-ylmethyl)-3,5-dimethylpiperazin-1-yl)methyl)-N-hydroxybenzamide |
| 146 | 4-(((3R,5S)-3,5-dimethyl-4-(2-phenylacetyl)piperazin-1-yl)methyl)-N-hydroxybenzamide |
| 147 | 4-(((3R,5S)-4-ethyl-3,5-dimethylpiperazin-1-yl)methyl)-N-hydroxybenzamide |
| 148 | 4-(((3R,5S)-3,5-dimethyl-4-propylpiperazin-1-yl)methyl)-N-hydroxybenzamide |
| 149 | 4-(((3R,5S)-3,5-dimethyl-4-(2,2,2-trifluoroethyl)piperazin-1-yl)methyl)-N-hydroxybenzamide |
| 154 | 6-((3R,5S)-4-benzyl-3,5-dimethylpiperazin-1-yl)-N-hydroxyhexanamide |
| 159 | (2S,6R)-4-(4-(hydroxycarbamoyl)benzyl)-2,6-dimethyl-N-phenylpiperazine-1-carboxamide |
| 160 | (2S,6R)-4-(4-(hydroxycarbamoyl)benzyl)-2,6-dimethyl-N-(o-tolyl)piperazine-1-carboxamide |
| 161 | (2S,6R)-N-benzyl-4-(4-(hydroxycarbamoyl)benzyl)-2,6-dimethylpiperazine-1-carboxamide |
| 162 | (3R,5S)-4-(4-(hydroxycarbamoyl)benzyl)-3,5-dimethyl-N-phenylpiperazine-1-carboxamide |
| 163 | (3R,5S)-4-(4-(hydroxycarbamoyl)benzyl)-N-(2-methoxyphenyl)-3,5-dimethylpiperazine-1-carboxamide |
| 164 | (3R,5S)-4-(4-(hydroxycarbamoyl)benzyl)-N-(3-methoxyphenyl)-3,5-dimethylpiperazine-1-carboxamide |
| 165 | (3R,5S)-4-(4-(hydroxycarbamoyl)benzyl)-N-(4-methoxyphenyl)-3,5-dimethylpiperazine-1-carboxamide |
| 166 | (3R,5S)-4-(4-(hydroxycarbamoyl)benzyl)-3,5-dimethyl-N-(o-tolyl)piperazine-1-carboxamide |
| 167 | (3R,5S)-4-(4-(hydroxycarbamoyl)benzyl)-3,5-dimethyl-N-(m-tolyl)piperazine-1-carboxamide |
| 168 | (3R,5S)-N-benzyl-4-(4-(hydroxycarbamoyl)benzyl)-3,5-dimethylpiperazine-1-carboxamide |
| 171 | 4-(((3R,5S)-4-benzyl-3,5-dimethylpiperazin-1-yl)methyl)-2-fluoro-N-hydroxybenzamide |
| 172 | (E)-3-(4-(((3R,5S)-4-benzyl-3,5-dimethylpiperazin-1-yl)methyl)phenyl)-N-hydroxyacrylamide |
| 173 | 2-(4-(((3R,5S)-4-benzyl-3,5-dimethylpiperazin-1-yl)methyl)phenyl)-N-hydroxyacetamide |
| 174 | 4-(((2S,6R)-4-benzyl-2,6-dimethylpiperazin-1-yl)methyl)-2-fluoro-N-hydroxybenzamide |
| 175 | (E)-3-(4-(((2S,6R)-4-benzyl-2,6-dimethylpiperazin-1-yl)methyl)phenyl)-N-hydroxyacrylamide |
| 176 | 2-(4-(((2S,6R)-4-benzyl-2,6-dimethylpiperazin-1-yl)methyl)phenyl)-N-hydroxyacetamide |
| 177 | phenyl (2S,6R)-4-(4-(hydroxycarbamoyl)benzyl)-2,6-dimethylpiperazine-1-carboxylate |
| 183 | 4-(((2S,6R)-2,6-dimethyl-4-phenethylpiperazin-1-yl)methyl)-N-hydroxybenzamide |
| 184 | 4-(((3R,5S)-3,5-dimethyl-4-phenethylpiperazin-1-yl)methyl)-N-hydroxybenzamide |
| 185 | (3R,5S)-4-(4-(hydroxycarbamoyl)benzyl)-3,5-dimethyl-N-(1-methyl-1H-indol-5-yl)piperazine-1-carboxamide |
| 186 | (3R,5S)-N-(3-(1H-pyrrol-1-yl)phenyl)-4-(4-(hydroxycarbamoyl)benzyl)-3,5-dimethylpiperazine-1-carboxamide |
| 187 | (3R,5S)-N-(2,3-dihydrobenzofuran-5-yl)-4-(4-(hydroxycarbamoyl)benzyl)-3,5-dimethylpiperazine-1-carboxamide |
| 188 | 4-(((3R,5S)-3,5-dimethyl-4-(3-phenylpropanoyl)piperazin-1-yl)methyl)-N-hydroxybenzamide |
| 189 | 4-(((2S,6R)-2,6-dimethyl-4-(m-tolylcarbamothioyl)piperazin-1-yl)methyl)-N-hydroxybenzamide |
| 193 | 4-(((2S,6R)-4-(2-fluoro-2-methylpropyl)-2,6-dimethylpiperazin-1-yl)methyl)-N-hydroxybenzamide |
| 194 | 6-(((3R,5S)-4-benzyl-3,5-dimethylpiperazin-1-yl)methyl)-N-hydroxynicotinamide |
| 195 | 6-(((2S,6R)-4-benzyl-2,6-dimethylpiperazin-1-yl)methyl)-N-hydroxynicotinamide |
| 196 | (3R,5S)-4-(4-(hydroxycarbamoyl)benzyl)-N,3,5-trimethyl-N-phenylpiperazine-1-carboxamide |
| 197 | N-hydroxy-4-(((2S,6R)-4-(indoline-1-carbonyl)-2,6-dimethylpiperazin-1-yl)methyl)benzamide |
| 198 | (3R,5S)-N-butyl-4-(4-(hydroxycarbamoyl)benzyl)-3,5-dimethyl-N-phenylpiperazine-1-carboxamide |
| 204 | 4-(((3R,5S)-3,5-dimethyl-4-(4,4,4-trifluorobutyl)piperazin-1-yl)methyl)-N-hydroxybenzamide |
| 211 | 4-(((3R,5S)-4-(2-fluorobenzyl)-3,5-dimethylpiperazin-1-yl)methyl)-N-hydroxybenzamide |
| 212 | 4-(((3R,5S)-4-(2,5-difluorobenzyl)-3,5-dimethylpiperazin-1-yl)methyl)-N-hydroxybenzamide |
| 213 | 4-(((3R,5S)-3,5-dimethyl-4-(2,4,5-trifluorobenzyl)piperazin-1-yl)methyl)-N-hydroxybenzamide |
| 214 | 4-(((3R,5S)-4-(3,5-bis(trifluoromethyl)benzyl)-3,5-dimethylpiperazin-1-yl)methyl)-N-hydroxybenzamide |
| 215 | 4-(((2S,6R)-2,6-dimethyl-4-(2,4,5-trifluorobenzyl)piperazin-1-yl)methyl)-N-hydroxybenzamide |
| 218 | 4-(2-((3S,5S)-4-benzyl-3,5-dimethylpiperazin-1-yl)ethyl)-N-hydroxybenzamide |
| 219 | 4-(1-((3R,5S)-4-benzyl-3,5-dimethylpiperazin-1-yl)ethyl)-N-hydroxybenzamide |
| 220 | 4-(((2S,6R)-2,6-dimethyl-4-(1-phenylethyl)piperazin-1-yl)methyl)-N-hydroxybenzamide |
| 222 | 4-(((3R,5S)-4-(2-(3-fluorophenyl)acetyl)-3,5-dimethylpiperazin-1-yl)methyl)-N-hydroxybenzamide |
| 223 | 4-(((3R,5S)-3,5-dimethyl-4-(2-(3-(trifluoromethyl)phenyl)acetyl)piperazin-1-yl)methyl)-N-hydroxybenzamide |
| 224 | 4-(((3R,5S)-4-(2-(3-chlorophenyl)acetyl)-3,5-dimethylpiperazin-1-yl)methyl)-N-hydroxybenzamide |
| 225 | 4-(((3R,5S)-4-(3-fluorobenzyl)-3,5-dimethylpiperazin-1-yl)methyl)-N-hydroxybenzamide |
| 230 | (3R,5S)-4-(4-(hydroxycarbamoyl)benzyl)-N-(3-methoxybenzyl)-3,5-dimethylpiperazine-1-carboxamide (Trifluoroacetic acid salt) |
| 231 | (3R,5S)-N-(3-fluorobenzyl)-4-(4-(hydroxycarbamoyl)benzyl)-3,5-dimethylpiperazine-1-carboxamide |
| 232 | (2S,6R)-N-(3-fluorobenzyl)-4-(4-(hydroxycarbamoyl)benzyl)-2,6-dimethylpiperazine-1-carboxamide |
| 233 | 4-(((2S,6R)-4-(2-(3-chlorophenyl)acetyl)-2,6-dimethylpiperazin-1-yl)methyl)-N-hydroxybenzamide |
| 234 | 4-(((3R,5S)-4-(2-([1,1'-biphenyl]-3-yl)acetyl)-3,5-dimethylpiperazin-1-yl)methyl)-N-hydroxybenzamide |
| 242 | 4-(((3R,5S)-4-(3-(furan-2-yl)benzoyl)-3,5-dimethylpiperazin-1-yl)methyl)-N-hydroxybenzamide |
| 243 | 4-(((3R,5S)-4-(3-(furan-3-yl)benzoyl)-3,5-dimethylpiperazin-1-yl)methyl)-N-hydroxybenzamide |
| 244 | 4-(((3R,5S)-4-(3-(3,6-dihydro-2H-pyran-4-yl)benzoyl)-3,5-dimethylpiperazin-1-yl)methyl)-N-hydroxybenzamide |
| 245 | 4-(((3R,5S)-3,5-dimethyl-4-(3-(pyridin-4-yl)benzoyl)piperazin-1-yl)methyl)-N-hydroxybenzamide (Trifluoroacetic acid salt) |
| 246 | 4-(((3R,5S)-3,5-dimethyl-4-(3-(pyridin-3-yl)benzoyl)piperazin-1-yl)methyl)-N-hydroxybenzamide |
| 247 | 4-(((3R,5S)-4-(4',4'-dimethyl-2',3',4',5'-tetrahydro-[1,1'-biphenyl]-3-carbonyl)-3,5-dimethylpiperazin-1-yl)methyl)-N-hydroxybenzamide |
| 248 | 4-(((3R,5R)-4-benzyl-3,5-dimethylpiperazin-1-yl)methyl)-N-hydroxybenzamide |

| No. | Name of Compound |
|---|---|
| 249 | 4-(((3R,5R)-4-(furan-2-carbonyl)-3,5-dimethylpiperazin-1-yl)methyl)-N-hydroxybenzamide |
| 250 | 4-(((2S,6R)-4-(2-([1,1'-biphenyl]-3-yl)acetyl)-2,6-dimethylpiperazin-1-yl)methyl)-N-hydroxybenzamide (Trifluoroacetic acid salt) |
| 251 | 4-(((2S,6R)-2,6-dimethyl-4-(2-(3-(pyridin-4-yl)phenyl)acetyl)piperazin-1-yl)methyl)-N-hydroxybenzamide (Trifluoroacetic acid salt) |
| 252 | 4-(((2S,6R)-4-(2-(3-(3,6-dihydro-2H-pyran-4-yl)phenyl)acetyl)-2,6-dimethylpiperazin-1-yl)methyl)-N-hydroxybenzamide |
| 253 | 4-(((2S,6R)-4-(2-(4',4'-dimethyl-2',3',4',5'-tetrahydro-[1,1'-biphenyl]-3-yl)acetyl)-2,6-dimethylpiperazin-1-yl)methyl)-N-hydroxybenzamide (Trifluoroacetic acid salt) |
| 255 | 4-(((3R,5S)-4-(3-(1H-pyrrol-1-yl)benzyl)-3,5-dimethylpiperazin-1-yl)methyl)-N-hydroxybenzamide |
| 256 | 4-(((2S,6R)-4-(3-(1H-pyrrol-1-yl)benzyl)-2,6-dimethylpiperazin-1-yl)methyl)-N-hydroxybenzamide |
| 257 | 4-(((2S,6R)-4-(3-(furan-2-yl)benzoyl)-2,6-dimethylpiperazin-1-yl)methyl)-N-hydroxybenzamide |
| 258 | 4-(((2S,6R)-4-(3-(furan-3-yl)benzoyl)-2,6-dimethylpiperazin-1-yl)methyl)-N-hydroxybenzamide |
| 259 | 4-(((2S,6R)-4-(3-(3,6-dihydro-2H-pyran-4-yl)benzoyl)-2,6-dimethylpiperazin-1-yl)methyl)-N-hydroxybenzamide |
| 260 | 4-(((2S,6R)-2,6-dimethyl-4-(3-(pyridin-4-yl)benzoyl)piperazin-1-yl)methyl)-N-hydroxybenzamide |
| 261 | 4-(((2S,6R)-2,6-dimethyl-4-(3-(pyridin-3-yl)benzoyl)piperazin-1-yl)methyl)-N-hydroxybenzamide |
| 262 | 4-(((2S,6R)-4-(3-(2-fluoropyridin-4-yl)benzoyl)-2,6-dimethylpiperazin-1-yl)methyl)-N-hydroxybenzamide |
| 263 | 4-(((2S,6R)-4-(4',4'-dimethyl-2',3',4',5'-tetrahydro-[1,1'-biphenyl]-3-carbonyl)-2,6-dimethylpiperazin-1-yl)methyl)-N-hydroxybenzamide |
| 265 | 4-(((3R,5S)-3,5-dimethyl-4-(naphthalen-2-ylmethyl)piperazin-1-yl)methyl)-N-hydroxybenzamide |
| 266 | 4-(((3R,5S)-3,5-dimethyl-4-(pyridin-4-ylmethyl)piperazin-1-yl)methyl)-N-hydroxybenzamide (Trifluoroacetic acid salt) |
| 267 | 4-(((3R,5S)-4-(3-chloro-2-(trifluoromethyl)benzyl)-3,5-dimethylpiperazin-1-yl)methyl)-N-hydroxybenzamide |
| 268 | 4-(((2S,6R)-2,6-dimethyl-4-(naphthalen-2-ylmethyl)piperazin-1-yl)methyl)-N-hydroxybenzamide |
| 270 | N-hydroxy-4-(((3R,5S)-4-isopentyl-3,5-dimethylpiperazin-1-yl)methyl)benzamide (Trifluoroacetic acid salt) |
| 271 | N-hydroxy-4-(((2S,6R)-4-isopentyl-2,6-dimethylpiperazin-1-yl)methyl)benzamide (Trifluoroacetic acid salt) |
| 272 | 4-(((3R,5S)-3,5-dimethyl-4-(3-methylbut-2-en-1-yl)piperazin-1-yl)methyl)-N-hydroxybenzamide |
| 273 | N-hydroxy-4-(((2S,6R)-4-isopropyl-2,6-dimethylpiperazin-1-yl)methyl)benzamide (Trifluoroacetic acid salt) |
| 274 | 4-(((2S,6R)-4-butyl-2,6-dimethylpiperazin-1-yl)methyl)-N-hydroxybenzamide (Trifluoroacetic acid salt) |
| 275 | 4-(((3R,5S)-4-butyl-3,5-dimethylpiperazin-1-yl)methyl)-N-hydroxybenzamide (Trifluoroacetic acid salt) |
| 276 | 4-(((2S,6R)-4-(2-(furan-2-yl)benzoyl)-2,6-dimethylpiperazin-1-yl)methyl)-N-hydroxybenzamide |
| 277 | 4-(((2S,6R)-4-(2-(furan-3-yl)benzoyl)-2,6-dimethylpiperazin-1-yl)methyl)-N-hydroxybenzamide |
| 278 | 4-(((2S,6R)-4-(2-(3,6-dihydro-2H-pyran-4-yl)benzoyl)-2,6-dimethylpiperazin-1-yl)methyl)-N-hydroxybenzamide |
| 279 | 4-(((2S,6R)-2,6-dimethyl-4-(2-(pyridin-3-yl)benzoyl)piperazin-1-yl)methyl)-N-hydroxybenzamide |
| 280 | 4-(((2S,6R)-4-(4',4'-dimethyl-2',3',4',5'-tetrahydro-[1,1'-biphenyl]-2-carbonyl)-2,6-dimethylpiperazin-1-yl)methyl)-N-hydroxybenzamide |
| 283 | 4-(((3R,5S)-4-(2-(furan-2-yl)benzoyl)-3,5-dimethylpiperazin-1-yl)methyl)-N-hydroxybenzamide |
| 284 | 4-(((3R,5S)-4-(2-(furan-3-yl)benzoyl)-3,5-dimethylpiperazin-1-yl)methyl)-N-hydroxybenzamide |
| 285 | 4-(((3R,5S)-3,5-dimethyl-4-(2-(pyridin-4-yl)benzoyl)piperazin-1-yl)methyl)-N-hydroxybenzamide |
| 286 | 4-(((3R,5S)-3,5-dimethyl-4-(2-(pyridin-3-yl)benzoyl)piperazin-1-yl)methyl)-N-hydroxybenzamide |
| 288 | 4-(((3R,5S)-4-(4',4'-dimethyl-2',3',4',5'-tetrahydro-[1,1'-biphenyl]-2-carbonyl)-3,5-dimethylpiperazin-1-yl)methyl)-N-hydroxybenzamide |
| 290 | 4-(((3R,5S)-3,5-dimethyl-4-(4-methylbenzoyl)piperazin-1-yl)methyl)-N-hydroxybenzamide (Trifluoroacetic acid salt) |
| 291 | N-hydroxy-4-(((3R,5S)-4-(4-methoxybenzoyl)-3,5-dimethylpiperazin-1-yl)methyl)benzamide (Trifluoroacetic acid salt) |
| 292 | 4-(((3R,5S)-3,5-dimethyl-4-pivaloylpiperazin-1-yl)methyl)-N-hydroxybenzamide (Trifluoroacetic acid salt) |
| 293 | 4-(((3R,5S)-3,5-dimethyl-4-propionylpiperazin-1-yl)methyl)-N-hydroxybenzamide (Trifluoroacetic acid salt) |
| 294 | 4-(((3R,5S)-4-butyryl-3,5-dimethylpiperazin-1-yl)methyl)-N-hydroxybenzamide (Trifluoroacetic acid salt) |
| 295 | 4-(((3R,5S)-4-(cyclopropanecarbonyl)-3,5-dimethylpiperazin-1-yl)methyl)-N-hydroxybenzamide (Trifluoroacetic acid salt) |
| 296 | N-hydroxy-4-(((3R,5S)-4-isobutyryl-3,5-dimethylpiperazin-1-yl)methyl)benzamide (Trifluoroacetic acid salt) |
| 297 | 4-(((3R,5S)-3,5-dimethyl-4-(3-methylbutanoyl)piperazin-1-yl)methyl)-N-hydroxybenzamide (Trifluoroacetic acid salt) |
| 298 | 4-(((2S,6R)-2,6-dimethyl-4-(3-(trifluoromethyl)benzyl)piperazin-1-yl)methyl)-N-hydroxybenzamide |
| 299 | 4-(((2S,6R)-4-(4-(dimethylamino)benzyl)-2,6-dimethylpiperazin-1-yl)methyl)-N-hydroxybenzamide |
| 300 | 4-(((2S,6R)-2,6-dimethyl-4-(4-(methylsulfonyl)benzyl)piperazin-1-yl)methyl)-N-hydroxybenzamide |
| 301 | 4-(((2S,6R)-4-(4-(1H-imidazol-1-yl)benzyl)-2,6-dimethylpiperazin-1-yl)methyl)-N-hydroxybenzamide |
| 302 | 4-(((2S,6R)-2,6-dimethyl-4-(4-(thiophen-2-yl)benzyl)piperazin-1-yl)methyl)-N-hydroxybenzamide |
| 303 | 4-(((2S,6R)-4-(4-(furan-2-yl)benzyl)-2,6-dimethylpiperazin-1-yl)methyl)-N-hydroxybenzamide |
| 304 | 4-(((2S,6R)-4-(4-(4H-1,2,4-triazol-4-yl)benzyl)-2,6-dimethylpiperazin-1-yl)methyl)-N-hydroxybenzamide |
| 305 | 4-(((2S,6R)-2,6-dimethyl-4-(2-(2-methyl-1H-imidazol-1-yl)benzyl)piperazin-1-yl)methyl)-N-hydroxybenzamide |
| 309 | 4-(((3R,5S)-4-(4-(furan-3-yl)benzyl)-3,5-dimethylpiperazin-1-yl)methyl)-N-hydroxybenzamide |
| 321 | (2S,6R)-N-(3-(1H-pyrrol-1-yl)phenyl)-4-(4-((E)-3-(hydroxyamino)-3-oxoprop-1-en-1-yl)benzyl)-2,6-dimethylpiperazine-1-carboxamide |
| 322 | (E)-3-(4-(((3R,5S)-4-(furan-2-carbonyl)-3,5-dimethylpiperazin-1-yl)methyl)phenyl)-N-hydroxyacrylamide |
| 323 | (E)-3-(4-(((3R,5S)-3,5-dimethyl-4-(2-phenylacetyl)piperazin-1-yl)methyl)phenyl)-N-hydroxyacrylamide |
| 326 | 4-(((3R,5S)-4-(2-(3,6-dihydro-2H-pyran-4-yl)benzoyl)-3,5-dimethylpiperazin-1-yl)methyl)-N-hydroxybenzamide |
| 327 | 4-(((3R,5S)-4-(2-(furan-2-yl)benzyl)-3,5-dimethylpiperazin-1-yl)methyl)-N-hydroxybenzamide |
| 328 | 4-(((3R,5S)-4-(2-(furan-3-yl)benzyl)-3,5-dimethylpiperazin-1-yl)methyl)-N-hydroxybenzamide |
| 329 | 4-(((3R,5S)-3,5-dimethyl-4-(2-(pyridin-4-yl)benzyl)piperazin-1-yl)methyl)-N-hydroxybenzamide |
| 330 | 4-(((3R,5S)-3,5-dimethyl-4-(2-(pyridin-3-yl)benzyl)piperazin-1-yl)methyl)-N-hydroxybenzamide |
| 331 | 4-(((3R,5S)-4-((4',4'-dimethyl-2',3',4',5'-tetrahydro-[1,1'-biphenyl]-2-yl)methyl)-3,5-dimethylpiperazin-1-yl)methyl)-N-hydroxybenzamide |
| 332 | 4-(((3R,5S)-4-(2-(3,6-dihydro-2H-pyran-4-yl)benzyl)-3,5-dimethylpiperazin-1-yl)methyl)-N-hydroxybenzamide |
| 340 | 4-(((3R,5S)-4-(4-(furan-2-yl)benzoyl)-3,5-dimethylpiperazin-1-yl)methyl)-N-hydroxybenzamide |
| 342 | 4-(((3R,5S)-4-(3-(furan-2-yl)benzyl)-3,5-dimethylpiperazin-1-yl)methyl)-N-hydroxybenzamide |

| No. | Name of Compound |
|---|---|
| 343 | 4-(((3R,5S)-4-(3-(furan-3-yl)benzyl)-3,5-dimethylpiperazin-1-yl)methyl)-N-hydroxybenzamide |
| 344 | 4-(((3R,5S)-3,5-dimethyl-4-(3-(pyridin-3-yl)benzyl)piperazin-1-yl)methyl)-N-hydroxybenzamide |
| 345 | 4-(((3R,5S)-3,5-dimethyl-4-(3-(pyridin-4-yl)benzyl)piperazin-1-yl)methyl)-N-hydroxybenzamide |
| 346 | 4-(((3R,5S)-4-(3-(3,6-dihydro-2H-pyran-4-yl)benzyl)-3,5-dimethylpiperazin-1-yl)methyl)-N-hydroxybenzamide |
| 347 | 4-(((3R,5S)-4-((4',4'-dimethyl-2',3',4',5'-tetrahydro-[1,1'-biphenyl]-3-yl)methyl)-3,5-dimethylpiperazin-1-yl)methyl)-N-hydroxybenzamide |
| 348 | 4-(((2S,6R)-4-(2-(furan-3-yl)benzyl)-2,6-dimethylpiperazin-1-yl)methyl)-N-hydroxybenzamide |
| 349 | 4-(((2S,6R)-2,6-dimethyl-4-(2-(pyridin-3-yl)benzyl)piperazin-1-yl)methyl)-N-hydroxybenzamide |
| 350 | 4-(((2S,6R)-2,6-dimethyl-4-(2-(pyridin-4-yl)benzyl)piperazin-1-yl)methyl)-N-hydroxybenzamide |
| 351 | 4-(((2S,6R)-4-(2-(3,6-dihydro-2H-pyran-4-yl)benzyl)-2,6-dimethylpiperazin-1-yl)methyl)-N-hydroxybenzamide |
| 352 | 4-(((2S,6R)-4-((4',4'-dimethyl-2',3',4',5'-tetrahydro-[1,1'-biphenyl]-2-yl)methyl)-2,6-dimethylpiperazin-1-yl)methyl)-N-hydroxybenzamide |
| 354 | 4-(((3R,5S)-3,5-dimethyl-4-(oxazol-4-ylmethyl)piperazin-1-yl)methyl)-N-hydroxybenzamide |
| 355 | 4-(((3R,5S)-3,5-dimethyl-4-(pyrimidin-5-ylmethyl)piperazin-1-yl)methyl)-N-hydroxybenzamide |
| 356 | 4-(((3R,5S)-3,5-dimethyl-4-(3-(morpholinomethyl)benzyl)piperazin-1-yl)methyl)-N-hydroxybenzamide |
| 376 | 4-(((3R,5S)-3,5-dimethyl-4-(4-(morpholinomethyl)benzyl)piperazin-1-yl)methyl)-N-hydroxybenzamide |
| 380 | 4-(((3R,5S)-4-(3-((1-(2-fluoro-2-methylpropyl)piperidin-4-yl)methoxy)benzyl)-3,5-dimethylpiperazin-1-yl)methyl)-N-hydroxybenzamide |
| 382 | 4-(((3R,5S)-3,5-dimethyl-4-(3-(piperidin-1-ylmethyl)benzyl)piperazin-1-yl)methyl)-N-hydroxybenzamide |
| 383 | 4-(((3R,5S)-4-(3-(((R)-3-fluoropyrrolidin-1-yl)methyl)benzyl)-3,5-dimethylpiperazin-1-yl)methyl)-N-hydroxybenzamide |
| 384 | 4-(((3R,5S)-4-(3-((3,3-difluoroazetidin-1-yl)methyl)benzyl)-3,5-dimethylpiperazin-1-yl)methyl)-N-hydroxybenzamide |
| 385 | 4-(((3R,5S)-4-(3-((4-benzylpiperazin-1-yl)methyl)benzyl)-3,5-dimethylpiperazin-1-yl)methyl)-N-hydroxybenzamide |
| 386 | N-hydroxy-4-(((3R,5S)-4-(3-((4-(2-hydroxy-2-methylpropyl)piperazin-1-yl)methyl)benzyl)-3,5-dimethylpiperazin-1-yl)methyl)benzamide |
| 387 | 4-(((3R,5S)-4-(3-((4-(2-fluoro-2-methylpropyl)piperazin-1-yl)methyl)benzyl)-3,5-dimethylpiperazin-1-yl)methyl)-N-hydroxybenzamide |
| 388 | 4-(((3R,5S)-4-(4-((1-(2-fluoro-2-methylpropyl)piperidin-4-yl)methoxy)benzyl)-3,5-dimethylpiperazin-1-yl)methyl)-N-hydroxybenzamide |
| 396 | 4-(((2S,6R)-4-(3-(furan-3-yl)benzyl)-2,6-dimethylpiperazin-1-yl)methyl)-N-hydroxybenzamide |
| 400 | 4-(((2S,6R)-4-((4',4'-dimethyl-2',3',4',5'-tetrahydro-[1,1'-biphenyl]-4-yl)methyl)-2,6-dimethylpiperazin-1-yl)methyl)-N-hydroxybenzamide |
| 401 | 4-(((2S,6R)-4-(4-(3,6-dihydro-2H-pyran-4-yl)benzyl)-2,6-dimethylpiperazin-1-yl)methyl)-N-hydroxybenzamide |
| 402 | 4-(((3R,5S)-3,5-dimethyl-4-(tetrahydrofuran-2-carbonyl)piperazin-1-yl)methyl)-N-hydroxybenzamide |
| 403 | 4-(((3R,5S)-3,5-dimethyl-4-(1H-pyrazole-3-carbonyl)piperazin-1-yl)methyl)-N-hydroxybenzamide |
| 404 | 4-(((3R,5S)-3,5-dimethyl-4-(pyrazine-2-carbonyl)piperazin-1-yl)methyl)-N-hydroxybenzamide |
| 405 | N-hydroxy-4-(((3R,5S)-4-isonicotinoyl-3,5-dimethylpiperazin-1-yl)methyl)benzamide |
| 411 | 4-(((3R,5S)-4-(4-(((R)-3-fluoropyrrolidin-1-yl)methyl)benzyl)-3,5-dimethylpiperazin-1-yl)methyl)-N-hydroxybenzamide |
| 412 | 4-(((3R,5S)-4-(4-((3,3-difluoroazetidin-1-yl)methyl)benzyl)-3,5-dimethylpiperazin-1-yl)methyl)-N-hydroxybenzamide |
| 413 | 4-(((3R,5S)-4-(4-((4-benzylpiperazin-1-yl)methyl)benzyl)-3,5-dimethylpiperazin-1-yl)methyl)-N-hydroxybenzamide |
| 423 | 4-(((3R,5S)-3,5-dimethyl-4-(3-(pyrrolidin-1-ylmethyl)benzoyl)piperazin-1-yl)methyl)-N-hydroxybenzamide |
| 424 | 4-(((3R,5S)-3,5-dimethyl-4-(3-(piperidin-1-ylmethyl)benzoyl)piperazin-1-yl)methyl)-N-hydroxybenzamide |
| 425 | 4-(((3R,5S)-4-(3-((diethylamino)methyl)benzoyl)-3,5-dimethylpiperazin-1-yl)methyl)-N-hydroxybenzamide |
| 426 | 4-(((3R,5S)-4-(3-((diethylamino)methyl)benzyl)-3,5-dimethylpiperazin-1-yl)methyl)-N-hydroxybenzamide |
| 427 | 4-(((3R,5S)-3,5-dimethyl-4-(3-(pyrrolidin-1-ylmethyl)benzyl)piperazin-1-yl)methyl)-N-hydroxybenzamide |
| 428 | 4-(((3R,5S)-3,5-dimethyl-4-(3-((4-methylpiperazin-1-yl)methyl)benzyl)piperazin-1-yl)methyl)-N-hydroxybenzamide |
| 429 | 4-(((3R,5S)-4-(3-((4-ethylpiperazin-1-yl)methyl)benzyl)-3,5-dimethylpiperazin-1-yl)methyl)-N-hydroxybenzamide |
| 430 | N-hydroxy-4-(((3R,5S)-4-(3-((4-isopropylpiperazin-1-yl)methyl)benzyl)-3,5-dimethylpiperazin-1-yl)methyl)benzamide |
| 431 | 4-(((3R,5S)-4-(3-((4-acetylpiperazin-1-yl)methyl)benzyl)-3,5-dimethylpiperazin-1-yl)methyl)-N-hydroxybenzamide |
| 432 | 4-(((3R,5S)-3,5-dimethyl-4-(3-((4-methylpiperazin-1-yl)methyl)benzoyl)piperazin-1-yl)methyl)-N-hydroxybenzamide |
| 433 | 4-(((3R,5S)-4-(3-((4-ethylpiperazin-1-yl)methyl)benzoyl)-3,5-dimethylpiperazin-1-yl)methyl)-N-hydroxybenzamide |
| 434 | N-hydroxy-4-(((3R,5S)-4-(3-((4-isopropylpiperazin-1-yl)methyl)benzoyl)-3,5-dimethylpiperazin-1-yl)methyl)benzamide |
| 435 | 4-(((3R,5S)-4-(3-((4-acetylpiperazin-1-yl)methyl)benzoyl)-3,5-dimethylpiperazin-1-yl)methyl)-N-hydroxybenzamide |
| 439 | 4-(((3R,5S)-3,5-dimethyl-4-(3-(morpholinomethyl)benzoyl)piperazin-1-yl)methyl)-N-hydroxybenzamide |
| 440 | 4-(((3R,5S)-4-(3-(((1-(diethylamino)propan-2-yl)amino)methyl)benzoyl)-3,5-dimethylpiperazin-1-yl)methyl)-N-hydroxybenzamide |
| 441 | 4-(((3R,5S)-4-(3-(((1-(benzyl(methyl)amino)propan-2-yl)amino)methyl)benzoyl)-3,5-dimethylpiperazin-1-yl)methyl)-N-hydroxybenzamide |
| 442 | N-hydroxy-4-(((3R,5S)-4-(3-((4-isopentylpiperazin-1-yl)methyl)benzoyl)-3,5-dimethylpiperazin-1-yl)methyl)benzamide |
| 443 | 4-(((3R,5S)-3,5-dimethyl-4-(3-((4-(2,2,2-trifluoroethyl)piperazin-1-yl)methyl)benzoyl)piperazin-1-yl)methyl)-N-hydroxybenzamide |
| 444 | 4-(((3R,5S)-3,5-dimethyl-4-(3-((4-(methylsulfonyl)piperazin-1-yl)methyl)benzoyl)piperazin-1-yl)methyl)-N-hydroxybenzamide |
| 446 | 4-(((3R,5S)-3,5-dimethyl-4-(3-(morpholine-4-carbonyl)benzyl)piperazin-1-yl)methyl)-N-hydroxybenzamide |
| 452 | 4-(((3R,5S)-3,5-dimethyl-4-(3-((4-(methylsulfonyl)piperazin-1-yl)methyl)benzyl)piperazin-1-yl)methyl)-N-hydroxybenzamide |
| 453 | 4-(((3R,5S)-3,5-dimethyl-4-(3-((4-(2,2,2-trifluoroethyl)piperazin-1-yl)methyl)benzyl)piperazin-1-yl)methyl)-N-hydroxybenzamide |
| 454 | N-hydroxy-4-(((3R,5S)-4-(3-((4-isopentylpiperazin-1-yl)methyl)benzyl)-3,5-dimethylpiperazin-1-yl)methyl)benzamide |
| 455 | 4-(((3R,5S)-4-(3-(((1-(diethylamino)propan-2-yl)amino)methyl)benzyl)-3,5-dimethylpiperazin-1-yl)methyl)-N-hydroxybenzamide |

| No. | Name of Compound |
|---|---|
| 456 | 4-(((3R,5S)-4-(3-(((1-(benzyl(methyl)amino)propan-2-yl)amino)methyl)benzyl)-3,5-dimethylpiperazin-1-yl)methyl)-N-hydroxybenzamide |
| 457 | 4-(((3R,5S)-3,5-dimethyl-4-(2-(morpholinomethyl)benzyl)piperazin-1-yl)methyl)-N-hydroxybenzamide |
| 458 | 4-(((3R,5S)-3,5-dimethyl-4-(4-(morpholinomethyl)benzoyl)piperazin-1-yl)methyl)-N-hydroxybenzamide |
| 459 | 4-(((3R,5S)-3,5-dimethyl-4-(4-(piperidin-1-ylmethyl)benzoyl)piperazin-1-yl)methyl)-N-hydroxybenzamide |
| 460 | 4-(((3R,5S)-4-(4-(((R)-3-fluoropyrrolidin-1-yl)methyl)benzoyl)-3,5-dimethylpiperazin-1-yl)methyl)-N-hydroxybenzamide |
| 461 | 4-(((3R,5S)-3,5-dimethyl-4-(4-(pyrrolidin-1-ylmethyl)benzoyl)piperazin-1-yl)methyl)-N-hydroxybenzamide |
| 462 | 4-(((3R,5S)-3,5-dimethyl-4-(4-((4-methylpiperazin-1-yl)methyl)benzoyl)piperazin-1-yl)methyl)-N-hydroxybenzamide |
| 463 | 4-(((3R,5S)-3,5-dimethyl-4-(4-((4-(methylsulfonyl)piperazin-1-yl)methyl)benzoyl)piperazin-1-yl)methyl)-N-hydroxybenzamide |
| 466 | 4-(((3R,5S)-3,5-dimethyl-4-(4-(pyrrolidin-1-ylmethyl)benzyl)piperazin-1-yl)methyl)-N-hydroxybenzamide |
| 467 | 4-(((3R,5S)-3,5-dimethyl-4-(4-(piperidin-1-ylmethyl)benzyl)piperazin-1-yl)methyl)-N-hydroxybenzamide |
| 468 | 4-(((3R,5S)-3,5-dimethyl-4-(4-((4-methylpiperazin-1-yl)methyl)benzyl)piperazin-1-yl)methyl)-N-hydroxybenzamide |
| 472 | (E)-3-(4-(((3R,5S)-3,5-dimethyl-4-(3-(morpholinomethyl)benzyl)piperazin-1-yl)methyl)phenyl)-N-hydroxyacrylamide |
| 475 | (E)-3-(4-(((2S,6R)-2,6-dimethyl-4-(3-(pyrrolidin-1-ylmethyl)benzyl)piperazin-1-yl)methyl)phenyl)-N-hydroxyacrylamide |
| 476 | (E)-3-(4-(((2S,6R)-4-(3-((diethylamino)methyl)benzyl)-2,6-dimethylpiperazin-1-yl)methyl)phenyl)-N-hydroxyacrylamide |
| 477 | (E)-3-(4-(((2S,6R)-4-(4-(furan-2-yl)benzyl)-2,6-dimethylpiperazin-1-yl)methyl)phenyl)-N-hydroxyacrylamide |
| 478 | 4-(((2S,6R)-4-(3-((diethylamino)methyl)benzyl)-2,6-dimethylpiperazin-1-yl)methyl)-N-hydroxybenzamide (hydrochloride salt) |
| 479 | 4-(((2S,6R)-2,6-dimethyl-4-(3-(pyrrolidin-1-ylmethyl)benzyl)piperazin-1-yl)methyl)-N-hydroxybenzamide |
| 480 | (E)-3-(4-(((2S,6R)-2,6-dimethyl-4-(3-(pyrrolidin-1-ylmethyl)benzoyl)piperazin-1-yl)methyl)phenyl)-N-hydroxyacrylamide |
| 481 | 4-(((3R,5S)-3,5-dimethyl-4-(2-(1-(methylsulfonyl)-1,2,3,6-tetrahydropyridin-4-yl)benzyl)piperazin-1-yl)methyl)-N-hydroxybenzamide |
| 482 | 4-(((3R,5S)-4-(2-(1-acetyl-1,2,3,6-tetrahydropyridin-4-yl)benzyl)-3,5-dimethylpiperazin-1-yl)methyl)-N-hydroxybenzamide |
| 483 | 4-(((3R,5S)-3,5-dimethyl-4-(2-(1-(2,2,2-trifluoroethyl)-1,2,3,6-tetrahydropyridin-4-yl)benzyl)piperazin-1-yl)methyl)-N-hydroxybenzamide |
| 484 | N-hydroxy-4-(((3R,5S)-4-(2-(1-isopropyl-1,2,3,6-tetrahydropyridin-4-yl)benzyl)-3,5-dimethylpiperazin-1-yl)methyl)benzamide |
| 485 | 4-(((3R,5S)-4-(2-(1-ethyl-1,2,3,6-tetrahydropyridin-4-yl)benzyl)-3,5-dimethylpiperazin-1-yl)methyl)-N-hydroxybenzamide |
| 486 | 4-(((3R,5S)-4-(4-((4-acetylpiperazin-1-yl)methyl)benzyl)-3,5-dimethylpiperazin-1-yl)methyl)-N-hydroxybenzamide (hydrochloride salt) |
| 487 | (E)-3-(4-(((2S,6R)-4-(3-((diethylamino)methyl)benzoyl)-2,6-dimethylpiperazin-1-yl)methyl)phenyl)-N-hydroxyacrylamide |
| 520 | 3-(((3R,5S)-4-benzyl-3,5-dimethylpiperazin-1-yl)methyl)-N-hydroxy-1H-indole-6-carboxamide |
| 569 | 5-(((3R,5S)-4-benzyl-3,5-dimethylpiperazin-1-yl)methyl)-N-hydroxy-1H-indole-2-carboxamide |
| 571 | 5-(((3R,5S)-4-benzyl-3,5-dimethylpiperazin-1-yl)methyl)-N-hydroxybenzofuran-2-carboxamide |
| 573 | 6-(((3R,5S)-4-benzyl-3,5-dimethylpiperazin-1-yl)methyl)-N-hydroxy-1H-indole-2-carboxamide |
| 574 | 2-(((3R,5S)-4-benzyl-3,5-dimethylpiperazin-1-yl)methyl)-N-hydroxybenzofuran-5-carboxamide |
| 609 | 5-(((3R,5S)-3,5-dimethyl-4-(3-(morpholinomethyl)benzyl)piperazin-1-yl)methyl)-N-hydroxypicolinamide |
| 652 | 4-(((3R,5S)-4-benzyl-3,5-dimethylpiperazin-1-yl)methyl)-N,2-dihydroxybenzamide |
| 653 | 4-(((3R,5S)-3,5-dimethyl-4-(3-(morpholinomethyl)benzyl)piperazin-1-yl)methyl)-N,2-dihydroxybenzamide |
| 696 | 4-(((3R,5S)-3,5-dimethyl-4-(3-(morpholinomethyl)benzyl)piperazin-1-yl)methyl)-3-fluoro-N-hydroxybenzamide |
| 812 | 5-(((3R,5S)-4-benzyl-3,5-dimethylpiperazin-1-yl)methyl)-N-hydroxypicolinamide |
| 813 | 4-(((3R,5S)-4-benzyl-3,5-dimethylpiperazin-1-yl)methyl)-3-fluoro-N-hydroxybenzamide |
| 818 | 4-(((3R,5S)-4-benzyl-3,5-dimethylpiperazin-1-yl)sulfonyl)-N-hydroxybenzamide |
| 820 | 2-(4-(((3R,5S)-4-benzyl-3,5-dimethylpiperazin-1-yl)sulfonyl)phenyl)-N-hydroxyacetamide |
| 822 | 4-(((3R,5S)-4-benzyl-3,5-dimethylpiperazin-1-yl)methyl)-N-hydroxycyclohexane-1-carboxamide. |

6. The compound represented by formula I, stereoisomer thereof or pharmaceutically acceptable salt thereof according to claim 5, wherein the compound represented by formula I is any one of compounds set forth in the following table:

| No. | Name of Compound |
|---|---|
| 081 | 4-(((2S,6R)-4-benzyl-2,6-dimethylpiperazin-1-yl)methyl)-N-hydroxybenzamide |
| 082 | 4-(((3R,5S)-4-acetyl-3,5-dimethylpiperazin-1-yl)methyl)-N-hydroxybenzamide |
| 083 | 4-(((3R,5S)-4-benzoyl-3,5-dimethylpiperazin-1-yl)methyl)-N-hydroxybenzamide |
| 084 | 4-(((3R,5S)-4-benzyl-3,5-dimethylpiperazin-1-yl)methyl)-N-hydroxybenzamide |
| 098 | (2S,6R)-4-(4-(hydroxycarbamoyl)benzyl)-N-isopropyl-2,6-dimethylpiperazine-1-carboxamide |
| 099 | (2S,6R)-N-(3-chlorophenyl)-4-(4-(hydroxycarbamoyl)benzyl)-2,6-dimethylpiperazine-1-carboxamide |
| 100 | 4-(((3R,5S)-3,5-dimethyl-4-(phenylsulfonyl)piperazin-1-yl)methyl)-N-hydroxybenzamide |
| 106 | 4-(((2S,6R)-4-(4-chlorobenzoyl)-2,6-dimethylpiperazin-1-yl)methyl)-N-hydroxybenzamide |
| 107 | 4-(((2S,6R)-4-(3-chlorobenzoyl)-2,6-dimethylpiperazin-1-yl)methyl)-N-hydroxybenzamide |
| 108 | 4-(((2S,6R)-4-(2-chlorobenzoyl)-2,6-dimethylpiperazin-1-yl)methyl)-N-hydroxybenzamide |
| 109 | 4-(((2S,6R)-4-((4-chlorophenyl)sulfonyl)-2,6-dimethylpiperazin-1-yl)methyl)-N-hydroxybenzamide |
| 110 | 4-(((2S,6R)-4-((2-chlorophenyl)sulfonyl)-2,6-dimethylpiperazin-1-yl)methyl)-N-hydroxybenzamide |
| 112 | 4-(((2S,6R)-2,6-dimethyl-4-nicotinoylpiperazin-1-yl)methyl)-N-hydroxybenzamide |
| 120 | 4-(((3R,5S)-4-(2-chlorobenzoyl)-3,5-dimethylpiperazin-1-yl)methyl)-N-hydroxybenzamide |
| 121 | 4-(((3R,5S)-4-(3-chlorobenzoyl)-3,5-dimethylpiperazin-1-yl)methyl)-N-hydroxybenzamide |
| 122 | 4-(((3R,5S)-4-(4-chlorobenzoyl)-3,5-dimethylpiperazin-1-yl)methyl)-N-hydroxybenzamide |
| 123 | 4-(((3R,5S)-3,5-dimethyl-4-picolinoylpiperazin-1-yl)methyl)-N-hydroxybenzamide |

| No. | Name of Compound |
|---|---|
| 125 | 4-(((3R,5S)-4-(furan-2-carbonyl)-3,5-dimethylpiperazin-1-yl)methyl)-N-hydroxybenzamide |
| 126 | 4-(((3R,5S)-3,5-dimethyl-4-(thiophene-2-carbonyl)piperazin-1-yl)methyl)-N-hydroxybenzamide |
| 127 | 4-(((3R,5S)-4-(2-chlorobenzyl)-3,5-dimethylpiperazin-1-yl)methyl)-N-hydroxybenzamide |
| 128 | 4-(((3R,5S)-4-(3-chlorobenzyl)-3,5-dimethylpiperazin-1-yl)methyl)-N-hydroxybenzamide |
| 145 | 4-(((3R,5S)-4-(furan-2-ylmethyl)-3,5-dimethylpiperazin-1-yl)methyl)-N-hydroxybenzamide |
| 146 | 4-(((3R,5S)-3,5-dimethyl-4-(2-phenylacetyl)piperazin-1-yl)methyl)-N-hydroxybenzamide |
| 147 | 4-(((3R,5S)-4-ethyl-3,5-dimethylpiperazin-1-yl)methyl)-N-hydroxybenzamide |
| 148 | 4-(((3R,5S)-3,5-dimethyl-4-propylpiperazin-1-yl)methyl)-N-hydroxybenzamide |
| 149 | 4-(((3R,5S)-3,5-dimethyl-4-(2,2,2-trifluoroethyl)piperazin-1-yl)methyl)-N-hydroxybenzamide |
| 159 | (2S,6R)-4-(4-(hydroxycarbamoyl)benzyl)-2,6-dimethyl-N-phenylpiperazine-1-carboxamide |
| 160 | (2S,6R)-4-(4-(hydroxycarbamoyl)benzyl)-2,6-dimethyl-N-(o-tolyl)piperazine-1-carboxamide |
| 161 | (2S,6R)-N-benzyl-4-(4-(hydroxycarbamoyl)benzyl)-2,6-dimethylpiperazine-1-carboxamide |
| 171 | 4-(((3R,5S)-4-benzyl-3,5-dimethylpiperazin-1-yl)methyl)-2-fluoro-N-hydroxybenzamide |
| 173 | 2-(4-(((3R,5S)-4-benzyl-3,5-dimethylpiperazin-1-yl)methyl)phenyl)-N-hydroxyacetamide |
| 174 | 4-(((2S,6R)-4-benzyl-2,6-dimethylpiperazin-1-yl)methyl)-2-fluoro-N-hydroxybenzamide |
| 175 | (E)-3-(4-(((2S,6R)-4-benzyl-2,6-dimethylpiperazin-1-yl)methyl)phenyl)-N-hydroxyacrylamide |
| 177 | phenyl (2S,6R)-4-(4-(hydroxycarbamoyl)benzyl)-2,6-dimethylpiperazine-1-carboxylate |
| 186 | (3R,5S)-N-(3-(1H-pyrrol-1-yl)phenyl)-4-(4-(hydroxycarbamoyl)benzyl)-3,5-dimethylpiperazine-1-carboxamide |
| 188 | 4-(((3R,5S)-3,5-dimethyl-4-(3-phenylpropanoyl)piperazin-1-yl)methyl)-N-hydroxybenzamide |
| 193 | 4-(((2S,6R)-4-(2-fluoro-2-methylpropyl)-2,6-dimethylpiperazin-1-yl)methyl)-N-hydroxybenzamide |
| 194 | 6-(((3R,5S)-4-benzyl-3,5-dimethylpiperazin-1-yl)methyl)-N-hydroxynicotinamide |
| 195 | 6-(((2S,6R)-4-benzyl-2,6-dimethylpiperazin-1-yl)methyl)-N-hydroxynicotinamide |
| 196 | (3R,5S)-4-(4-(hydroxycarbamoyl)benzyl)-N,3,5-trimethyl-N-phenylpiperazine-1-carboxamide |
| 198 | (3R,5S)-N-butyl-4-(4-(hydroxycarbamoyl)benzyl)-3,5-dimethyl-N-phenylpiperazine-1-carboxamide |
| 211 | 4-(((3R,5S)-4-(2-fluorobenzyl)-3,5-dimethylpiperazin-1-yl)methyl)-N-hydroxybenzamide |
| 214 | 4-(((3R,5S)-4-(3,5-bis(trifluoromethyl)benzyl)-3,5-dimethylpiperazin-1-yl)methyl)-N-hydroxybenzamide |
| 219 | 4-(1-((3R,5S)-4-benzyl-3,5-dimethylpiperazin-1-yl)ethyl)-N-hydroxybenzamide |
| 248 | 4-(((3R,5R)-4-benzyl-3,5-dimethylpiperazin-1-yl)methyl)-N-hydroxybenzamide |
| 249 | 4-(((3R,5R)-4-(furan-2-carbonyl)-3,5-dimethylpiperazin-1-yl)methyl)-N-hydroxybenzamide |
| 250 | 4-(((2S,6R)-4-(2-([1,1'-biphenyl]-3-yl)acetyl)-2,6-dimethylpiperazin-1-yl)methyl)-N-hydroxybenzamide (Trifluoroacetic acid salt) |
| 251 | 4-(((2S,6R)-2,6-dimethyl-4-(2-(3-(pyridin-4-yl)phenyl)acetyl)piperazin-1-yl)methyl)-N-hydroxybenzamide (Trifluoroacetic acid salt) |
| 252 | 4-(((2S,6R)-4-(2-(3-(3,6-dihydro-2H-pyran-4-yl)phenyl)acetyl)-2,6-dimethylpiperazin-1-yl)methyl)-N-hydroxybenzamide |
| 255 | 4-(((3R,5S)-4-(3-(1H-pyrrol-1-yl)benzyl)-3,5-dimethylpiperazin-1-yl)methyl)-N-hydroxybenzamide |
| 265 | 4-(((3R,5S)-3,5-dimethyl-4-(naphthalen-2-ylmethyl)piperazin-1-yl)methyl)-N-hydroxybenzamide |
| 266 | 4-(((3R,5S)-3,5-dimethyl-4-(pyridin-4-ylmethyl)piperazin-1-yl)methyl)-N-hydroxybenzamide (Trifluoroacetic acid salt) |
| 267 | 4-(((3R,5S)-4-(3-chloro-2-(trifluoromethyl)benzyl)-3,5-dimethylpiperazin-1-yl)methyl)-N-hydroxybenzamide |
| 272 | 4-(((3R,5S)-3,5-dimethyl-4-(3-methylbut-2-en-1-yl)piperazin-1-yl)methyl)-N-hydroxybenzamide |
| 283 | 4-(((3R,5S)-4-(2-(furan-2-yl)benzoyl)-3,5-dimethylpiperazin-1-yl)methyl)-N-hydroxybenzamide |
| 284 | 4-(((3R,5S)-4-(2-(furan-3-yl)benzoyl)-3,5-dimethylpiperazin-1-yl)methyl)-N-hydroxybenzamide |
| 285 | 4-(((3R,5S)-3,5-dimethyl-4-(2-(pyridin-4-yl)benzoyl)piperazin-1-yl)methyl)-N-hydroxybenzamide |
| 286 | 4-(((3R,5S)-3,5-dimethyl-4-(2-(pyridin-3-yl)benzoyl)piperazin-1-yl)methyl)-N-hydroxybenzamide |
| 292 | 4-(((3R,5S)-3,5-dimethyl-4-pivaloylpiperazin-1-yl)methyl)-N-hydroxybenzamide (Trifluoroacetic acid salt) |
| 295 | 4-(((3R,5S)-4-(cyclopropanecarbonyl)-3,5-dimethylpiperazin-1-yl)methyl)-N-hydroxybenzamide (Trifluoroacetic acid salt) |
| 297 | 4-(((3R,5S)-3,5-dimethyl-4-(3-methylbutanoyl)piperazin-1-yl)methyl)-N-hydroxybenzamide (Trifluoroacetic acid salt) |
| 305 | 4-(((2S,6R)-2,6-dimethyl-4-(2-(2-methyl-1H-imidazol-1-yl)benzyl)piperazin-1-yl)methyl)-N-hydroxybenzamide |
| 326 | 4-(((3R,5S)-4-(2-(3,6-dihydro-2H-pyran-4-yl)benzoyl)-3,5-dimethylpiperazin-1-yl)methyl)-N-hydroxybenzamide |
| 328 | 4-(((3R,5S)-4-(2-(furan-3-yl)benzyl)-3,5-dimethylpiperazin-1-yl)methyl)-N-hydroxybenzamide |
| 329 | 4-(((3R,5S)-3,5-dimethyl-4-(2-(pyridin-4-yl)benzyl)piperazin-1-yl)methyl)-N-hydroxybenzamide |
| 330 | 4-(((3R,5S)-3,5-dimethyl-4-(2-(pyridin-3-yl)benzyl)piperazin-1-yl)methyl)-N-hydroxybenzamide |
| 332 | 4-(((3R,5S)-4-(2-(3,6-dihydro-2H-pyran-4-yl)benzyl)-3,5-dimethylpiperazin-1-yl)methyl)-N-hydroxybenzamide |
| 342 | 4-(((3R,5S)-4-(3-(furan-2-yl)benzyl)-3,5-dimethylpiperazin-1-yl)methyl)-N-hydroxybenzamide |
| 343 | 4-(((3R,5S)-4-(3-(furan-3-yl)benzyl)-3,5-dimethylpiperazin-1-yl)methyl)-N-hydroxybenzamide |
| 344 | 4-(((3R,5S)-3,5-dimethyl-4-(3-(pyridin-3-yl)benzyl)piperazin-1-yl)methyl)-N-hydroxybenzamide |
| 345 | 4-(((3R,5S)-3,5-dimethyl-4-(3-(pyridin-4-yl)benzyl)piperazin-1-yl)methyl)-N-hydroxybenzamide |
| 346 | 4-(((3R,5S)-4-(3-(3,6-dihydro-2H-pyran-4-yl)benzyl)-3,5-dimethylpiperazin-1-yl)methyl)-N-hydroxybenzamide |
| 349 | 4-(((2S,6R)-2,6-dimethyl-4-(2-(pyridin-3-yl)benzyl)piperazin-1-yl)methyl)-N-hydroxybenzamide |
| 354 | 4-(((3R,5S)-3,5-dimethyl-4-(oxazol-4-ylmethyl)piperazin-1-yl)methyl)-N-hydroxybenzamide |
| 356 | 4-(((3R,5S)-3,5-dimethyl-4-(3-(morpholinomethyl)benzyl)piperazin-1-yl)methyl)-N-hydroxybenzamide |
| 376 | 4-(((3R,5S)-3,5-dimethyl-4-(4-(morpholinomethyl)benzyl)piperazin-1-yl)methyl)-N-hydroxybenzamide |
| 380 | 4-(((3R,5S)-4-(3-((1-(2-fluoro-2-methylpropyl)piperidin-4-yl)methoxy)benzyl)-3,5-dimethylpiperazin-1-yl)methyl)-N-hydroxybenzamide |
| 382 | 4-(((3R,5S)-3,5-dimethyl-4-(3-(piperidin-1-ylmethyl)benzyl)piperazin-1-yl)methyl)-N-hydroxybenzamide |
| 383 | 4-(((3R,5S)-4-(3-(((R)-3-fluoropyrrolidin-1-yl)methyl)benzyl)-3,5-dimethylpiperazin-1-yl)methyl)-N-hydroxybenzamide |
| 384 | 4-(((3R,5S)-4-(3-((3,3-difluoroazetidin-1-yl)methyl)benzyl)-3,5-dimethylpiperazin-1-yl)methyl)-N-hydroxybenzamide |
| 385 | 4-(((3R,5S)-4-(3-((4-benzylpiperazin-1-yl)methyl)benzyl)-3,5-dimethylpiperazin-1-yl)methyl)-N-hydroxybenzamide |
| 386 | N-hydroxy-4-(((3R,5S)-4-(3-((4-(2-hydroxy-2-methylpropyl)piperazin-1-yl)methyl)benzyl)-3,5-dimethylpiperazin-1-yl)methyl)benzamide |
| 387 | 4-(((3R,5S)-4-(3-((4-(2-fluoro-2-methylpropyl)piperazin-1-yl)methyl)benzyl)-3,5-dimethylpiperazin-1-yl)methyl)-N-hydroxybenzamide |
| 388 | 4-(((3R,5S)-4-(4-((1-(2-fluoro-2-methylpropyl)piperidin-4-yl)methoxy)benzyl)-3,5-dimethylpiperazin-1-yl)methyl)-N-hydroxybenzamide |

| No. | Name of Compound |
|---|---|
| 403 | 4-(((3R,5S)-3,5-dimethyl-4-(1H-pyrazole-3-carbonyl)piperazin-1-yl)methyl)-N-hydroxybenzamide |
| 411 | 4-(((3R,5S)-4-(4-(((R)-3-fluoropyrrolidin-1-yl)methyl)benzyl)-3,5-dimethylpiperazin-1-yl)methyl)-N-hydroxybenzamide |
| 413 | 4-(((3R,5S)-4-(4-((4-benzylpiperazin-1-yl)methyl)benzyl)-3,5-dimethylpiperazin-1-yl)methyl)-N-hydroxybenzamide |
| 430 | N-hydroxy-4-(((3R,5S)-4-(3-((4-isopropylpiperazin-1-yl)methyl)benzyl)-3,5-dimethylpiperazin-1-yl)methyl)benzamide |
| 431 | 4-(((3R,5S)-4-(3-((4-acetylpiperazin-1-yl)methyl)benzyl)-3,5-dimethylpiperazin-1-yl)methyl)-N-hydroxybenzamide |
| 432 | 4-(((3R,5S)-3,5-dimethyl-4-((4-methylpiperazin-1-yl)methyl)benzoyl)piperazin-1-yl)methyl)-N-hydroxybenzamide |
| 433 | 4-(((3R,5S)-4-(3-((4-ethylpiperazin-1-yl)methyl)benzoyl)-3,5-dimethylpiperazin-1-yl)methyl)-N-hydroxybenzamide |
| 434 | N-hydroxy-4-(((3R,5S)-4-(3-((4-isopropylpiperazin-1-yl)methyl)benzoyl)-3,5-dimethylpiperazin-1-yl)methyl)benzamide |
| 435 | 4-(((3R,5S)-4-(3-((4-acetylpiperazin-1-yl)methyl)benzoyl)-3,5-dimethylpiperazin-1-yl)methyl)-N-hydroxybenzamide |
| 439 | 4-(((3R,5S)-3,5-dimethyl-4-(3-(morpholinomethyl)benzoyl)piperazin-1-yl)methyl)-N-hydroxybenzamide |
| 440 | 4-(((3R,5S)-4-(3-(((1-(diethylamino)propan-2-yl)amino)methyl)benzoyl)-3,5-dimethylpiperazin-1-yl)methyl)-N-hydroxybenzamide |
| 441 | 4-(((3R,5S)-4-(3-(((1-(benzyl(methyl)amino)propan-2-yl)amino)methyl)benzoyl)-3,5-dimethylpiperazin-1-yl)methyl)-N-hydroxybenzamide |
| 442 | N-hydroxy-4-(((3R,5S)-4-(3-((4-isopentylpiperazin-1-yl)methyl)benzoyl)-3,5-dimethylpiperazin-1-yl)methyl)benzamide |
| 443 | 4-(((3R,5S)-3,5-dimethyl-4-(3-((4-(2,2,2-trifluoroethyl)piperazin-1-yl)methyl)benzoyl)piperazin-1-yl)methyl)-N-hydroxybenzamide |
| 444 | 4-(((3R,5S)-3,5-dimethyl-4-(3-((4-(methylsulfonyl)piperazin-1-yl)methyl)benzoyl)piperazin-1-yl)methyl)-N-hydroxybenzamide |
| 452 | 4-(((3R,5S)-3,5-dimethyl-4-(3-((4-(methylsulfonyl)piperazin-1-yl)methyl)benzyl)piperazin-1-yl)methyl)-N-hydroxybenzamide |
| 453 | 4-(((3R,5S)-3,5-dimethyl-4-(3-((4-(2,2,2-trifluoroethyl)piperazin-1-yl)methyl)benzyl)piperazin-1-yl)methyl)-N-hydroxybenzamide |
| 454 | N-hydroxy-4-(((3R,5S)-4-(3-((4-isopentylpiperazin-1-yl)methyl)benzyl)-3,5-dimethylpiperazin-1-yl)methyl)benzamide |
| 455 | 4-(((3R,5S)-4-(3-(((1-(diethylamino)propan-2-yl)amino)methyl)benzyl)-3,5-dimethylpiperazin-1-yl)methyl)-N-hydroxybenzamide |
| 456 | 4-(((3R,5S)-4-(3-(((1-(benzyl(methyl)amino)propan-2-yl)amino)methyl)benzyl)-3,5-dimethylpiperazin-1-yl)methyl)-N-hydroxybenzamide |
| 467 | 4-(((3R,5S)-3,5-dimethyl-4-(4-(piperidin-1-ylmethyl)benzyl)piperazin-1-yl)methyl)-N-hydroxybenzamide |
| 468 | 4-(((3R,5S)-3,5-dimethyl-4-(4-((4-methylpiperazin-1-yl)methyl)benzyl)piperazin-1-yl)methyl)-N-hydroxybenzamide |
| 481 | 4-(((3R,5S)-3,5-dimethyl-4-(2-(1-(methylsulfonyl)-1,2,3,6-tetrahydropyridin-4-yl)benzyl)piperazin-1-yl)methyl)-N-hydroxybenzamide |
| 482 | 4-(((3R,5S)-4-(2-(1-acetyl-1,2,3,6-tetrahydropyridin-4-yl)benzyl)-3,5-dimethylpiperazin-1-yl)methyl)-N-hydroxybenzamide |
| 483 | 4-(((3R,5S)-3,5-dimethyl-4-(2-(1-(2,2,2-trifluoroethyl)-1,2,3,6-tetrahydropyridin-4-yl)benzyl)piperazin-1-yl)methyl)-N-hydroxybenzamide |
| 484 | N-hydroxy-4-(((3R,5S)-4-(2-(1-isopropyl-1,2,3,6-tetrahydropyridin-4-yl)benzyl)-3,5-dimethylpiperazin-1-yl)methyl)benzamide |
| 485 | 4-(((3R,5S)-4-(2-(1-ethyl-1,2,3,6-tetrahydropyridin-4-yl)benzyl)-3,5-dimethylpiperazin-1-yl)methyl)-N-hydroxybenzamide |
| 486 | 4-(((3R,5S)-4-(4-((4-acetylpiperazin-1-yl)methyl)benzyl)-3,5-dimethylpiperazin-1-yl)methyl)-N-hydroxybenzamide (hydrochloride salt) |
| 569 | 5-(((3R,5S)-4-benzyl-3,5-dimethylpiperazin-1-yl)methyl)-N-hydroxy-1H-indole-2-carboxamide |
| 696 | 4-(((3R,5S)-3,5-dimethyl-4-(3-(morpholinomethyl)benzyl)piperazin-1-yl)methyl)-3-fluoro-N-hydroxybenzamide |
| 813 | 4-(((3R,5S)-4-benzyl-3,5-dimethylpiperazin-1-yl)methyl)-3-fluoro-N-hydroxybenzamide. |

7. The compound represented by formula I, stereoisomer thereof or pharmaceutically acceptable salt thereof according to claim 6, wherein the compound represented by formula I is any one of compounds set forth in the following table:

| No. | Name of Compound |
|---|---|
| 082 | 4-(((3R,5S)-4-acetyl-3,5-dimethylpiperazin-1-yl)methyl)-N-hydroxybenzamide |
| 083 | 4-(((3R,5S)-4-benzoyl-3,5-dimethylpiperazin-1-yl)methyl)-N-hydroxybenzamide |
| 084 | 4-(((3R,5S)-4-benzyl-3,5-dimethylpiperazin-1-yl)methyl)-N-hydroxybenzamide |
| 098 | (2S,6R)-4-(4-(hydroxycarbamoyl)benzyl)-N-isopropyl-2,6-dimethylpiperazine-1-carboxamide |
| 100 | 4-(((3R,5S)-3,5-dimethyl-4-(phenylsulfonyl)piperazin-1-yl)methyl)-N-hydroxybenzamide |
| 120 | 4-(((3R,5S)-4-(2-chlorobenzoyl)-3,5-dimethylpiperazin-1-yl)methyl)-N-hydroxybenzamide |
| 121 | 4-(((3R,5S)-4-(3-chlorobenzoyl)-3,5-dimethylpiperazin-1-yl)methyl)-N-hydroxybenzamide |
| 122 | 4-(((3R,5S)-4-(4-chlorobenzoyl)-3,5-dimethylpiperazin-1-yl)methyl)-N-hydroxybenzamide |
| 123 | 4-(((3R,5S)-3,5-dimethyl-4-picolinoylpiperazin-1-yl)methyl)-N-hydroxybenzamide |
| 125 | 4-(((3R,5S)-4-(furan-2-carbonyl)-3,5-dimethylpiperazin-1-yl)methyl)-N-hydroxybenzamide |
| 126 | 4-(((3R,5S)-3,5-dimethyl-4-(thiophene-2-carbonyl)piperazin-1-yl)methyl)-N-hydroxybenzamide |
| 127 | 4-(((3R,5S)-4-(2-chlorobenzyl)-3,5-dimethylpiperazin-1-yl)methyl)-N-hydroxybenzamide |
| 128 | 4-(((3R,5S)-4-(3-chlorobenzyl)-3,5-dimethylpiperazin-1-yl)methyl)-N-hydroxybenzamide |
| 145 | 4-(((3R,5S)-4-(furan-2-ylmethyl)-3,5-dimethylpiperazin-1-yl)methyl)-N-hydroxybenzamide |
| 146 | 4-(((3R,5S)-3,5-dimethyl-4-(2-phenylacetyl)piperazin-1-yl)methyl)-N-hydroxybenzamide |
| 148 | 4-(((3R,5S)-3,5-dimethyl-4-propylpiperazin-1-yl)methyl)-N-hydroxybenzamide |
| 149 | 4-(((3R,5S)-3,5-dimethyl-4-(2,2,2-trifluoroethyl)piperazin-1-yl)methyl)-N-hydroxybenzamide |
| 159 | (2S,6R)-4-(4-(hydroxycarbamoyl)benzyl)-2,6-dimethyl-N-phenylpiperazine-1-carboxamide |
| 160 | (2S,6R)-4-(4-(hydroxycarbamoyl)benzyl)-2,6-dimethyl-N-(o-tolyl)piperazine-1-carboxamide |
| 161 | (2S,6R)-N-benzyl-4-(4-(hydroxycarbamoyl)benzyl)-2,6-dimethylpiperazine-1-carboxamide |
| 171 | 4-(((3R,5S)-4-benzyl-3,5-dimethylpiperazin-1-yl)methyl)-2-fluoro-N-hydroxybenzamide |
| 174 | 4-(((2S,6R)-4-benzyl-2,6-dimethylpiperazin-1-yl)methyl)-2-fluoro-N-hydroxybenzamide |

| No. | Name of Compound |
|---|---|
| 177 | phenyl (2S,6R)-4-(4-(hydroxycarbamoyl)benzyl)-2,6-dimethylpiperazine-1-carboxylate |
| 194 | 6-(((3R,5S)-4-benzyl-3,5-dimethylpiperazin-1-yl)methyl)-N-hydroxynicotinamide |
| 211 | 4-(((3R,5S)-4-(2-fluorobenzyl)-3,5-dimethylpiperazin-1-yl)methyl)-N-hydroxybenzamide |
| 249 | 4-(((3R,5R)-4-(furan-2-carbonyl)-3,5-dimethylpiperazin-1-yl)methyl)-N-hydroxybenzamide |
| 255 | 4-(((3R,5S)-4-(3-(1H-pyrrol-1-yl)benzyl)-3,5-dimethylpiperazin-1-yl)methyl)-N-hydroxybenzamide |
| 283 | 4-(((3R,5S)-4-(2-(furan-2-yl)benzoyl)-3,5-dimethylpiperazin-1-yl)methyl)-N-hydroxybenzamide |
| 305 | 4-(((2S,6R)-2,6-dimethyl-4-(2-(2-methyl-1H-imidazol-1-yl)benzyl)piperazin-1-yl)methyl)-N-hydroxybenzamide |
| 326 | 4-(((3R,5S)-4-(2-(3,6-dihydro-2H-pyran-4-yl)benzoyl)-3,5-dimethylpiperazin-1-yl)methyl)-N-hydroxybenzamide |
| 328 | 4-(((3R,5S)-4-(2-(furan-3-yl)benzyl)-3,5-dimethylpiperazin-1-yl)methyl)-N-hydroxybenzamide |
| 329 | 4-(((3R,5S)-3,5-dimethyl-4-(2-(pyridin-4-yl)benzyl)piperazin-1-yl)methyl)-N-hydroxybenzamide |
| 330 | 4-(((3R,5S)-3,5-dimethyl-4-(2-(pyridin-3-yl)benzyl)piperazin-1-yl)methyl)-N-hydroxybenzamide |
| 332 | 4-(((3R,5S)-4-(2-(3,6-dihydro-2H-pyran-4-yl)benzyl)-3,5-dimethylpiperazin-1-yl)methyl)-N-hydroxybenzamide |
| 342 | 4-(((3R,5S)-4-(3-(furan-2-yl)benzyl)-3,5-dimethylpiperazin-1-yl)methyl)-N-hydroxybenzamide |
| 343 | 4-(((3R,5S)-4-(3-(furan-3-yl)benzyl)-3,5-dimethylpiperazin-1-yl)methyl)-N-hydroxybenzamide |
| 344 | 4-(((3R,5S)-3,5-dimethyl-4-(3-(pyridin-3-yl)benzyl)piperazin-1-yl)methyl)-N-hydroxybenzamide |
| 345 | 4-(((3R,5S)-3,5-dimethyl-4-(3-(pyridin-4-yl)benzyl)piperazin-1-yl)methyl)-N-hydroxybenzamide |
| 346 | 4-(((3R,5S)-4-(3-(3,6-dihydro-2H-pyran-4-yl)benzyl)-3,5-dimethylpiperazin-1-yl)methyl)-N-hydroxybenzamide |
| 349 | 4-(((2S,6R)-2,6-dimethyl-4-(2-(pyridin-3-yl)benzyl)piperazin-1-yl)methyl)-N-hydroxybenzamide |
| 354 | 4-(((3R,5S)-3,5-dimethyl-4-(oxazol-4-ylmethyl)piperazin-1-yl)methyl)-N-hydroxybenzamide |
| 356 | 4-(((3R,5S)-3,5-dimethyl-4-(3-(morpholinomethyl)benzyl)piperazin-1-yl)methyl)-N-hydroxybenzamide |
| 376 | 4-(((3R,5S)-3,5-dimethyl-4-(4-(morpholinomethyl)benzyl)piperazin-1-yl)methyl)-N-hydroxybenzamide |
| 382 | 4-(((3R,5S)-3,5-dimethyl-4-(3-(piperidin-1-ylmethyl)benzyl)piperazin-1-yl)methyl)-N-hydroxybenzamide |
| 383 | 4-(((3R,5S)-4-(3-(((R)-3-fluoropyrrolidin-1-yl)methyl)benzyl)-3,5-dimethylpiperazin-1-yl)methyl)-N-hydroxybenzamide |
| 387 | 4-(((3R,5S)-4-(3-((4-(2-fluoro-2-methylpropyl)piperazin-1-yl)methyl)benzyl)-3,5-dimethylpiperazin-1-yl)methyl)-N-hydroxybenzamide |
| 388 | 4-(((3R,5S)-4-(4-((1-(2-fluoro-2-methylpropyl)piperidin-4-yl)methoxy)benzyl)-3,5-dimethylpiperazin-1-yl)methyl)-N-hydroxybenzamide |
| 411 | 4-(((3R,5S)-4-(4-(((R)-3-fluoropyrrolidin-1-yl)methyl)benzyl)-3,5-dimethylpiperazin-1-yl)methyl)-N-hydroxybenzamide |
| 413 | 4-(((3R,5S)-4-(4-((4-benzylpiperazin-1-yl)methyl)benzyl)-3,5-dimethylpiperazin-1-yl)methyl)-N-hydroxybenzamide |
| 431 | 4-(((3R,5S)-4-(3-((4-acetylpiperazin-1-yl)methyl)benzyl)-3,5-dimethylpiperazin-1-yl)methyl)-N-hydroxybenzamide |
| 439 | 4-(((3R,5S)-3,5-dimethyl-4-(3-(morpholinomethyl)benzoyl)piperazin-1-yl)methyl)-N-hydroxybenzamide |
| 441 | 4-(((3R,5S)-4-(3-(((1-(benzyl(methyl)amino)propan-2-yl)amino)methyl)benzoyl)-3,5-dimethylpiperazin-1-yl)methyl)-N-hydroxybenzamide |
| 444 | 4-(((3R,5S)-3,5-dimethyl-4-(3-((4-(methylsulfonyl)piperazin-1-yl)methyl)benzoyl)piperazin-1-yl)methyl)-N-hydroxybenzamide |
| 452 | 4-(((3R,5S)-3,5-dimethyl-4-(3-((4-(methylsulfonyl)piperazin-1-yl)methyl)benzyl)piperazin-1-yl)methyl)-N-hydroxybenzamide |
| 453 | 4-(((3R,5S)-3,5-dimethyl-4-(3-((4-(2,2,2-trifluoroethyl)piperazin-1-yl)methyl)benzyl)piperazin-1-yl)methyl)-N-hydroxybenzamide |
| 454 | N-hydroxy-4-(((3R,5S)-4-(3-((4-isopentylpiperazin-1-yl)methyl)benzyl)-3,5-dimethylpiperazin-1-yl)methyl)benzamide |
| 467 | 4-(((3R,5S)-3,5-dimethyl-4-(4-(piperidin-1-ylmethyl)benzyl)piperazin-1-yl)methyl)-N-hydroxybenzamide |
| 468 | 4-(((3R,5S)-3,5-dimethyl-4-(4-((4-methylpiperazin-1-yl)methyl)benzyl)piperazin-1-yl)methyl)-N-hydroxybenzamide |
| 481 | 4-(((3R,5S)-3,5-dimethyl-4-(2-(1-(methylsulfonyl)-1,2,3,6-tetrahydropyridin-4-yl)benzyl)piperazin-1-yl)methyl)-N-hydroxybenzamide |
| 482 | 4-(((3R,5S)-4-(2-(1-acetyl-1,2,3,6-tetrahydropyridin-4-yl)benzyl)-3,5-dimethylpiperazin-1-yl)methyl)-N-hydroxybenzamide |
| 483 | 4-(((3R,5S)-3,5-dimethyl-4-(2-(1-(2,2,2-trifluoroethyl)-1,2,3,6-tetrahydropyridin-4-yl)benzyl)piperazin-1-yl)methyl)-N-hydroxybenzamide |
| 484 | N-hydroxy-4-(((3R,5S)-4-(2-(1-isopropyl-1,2,3,6-tetrahydropyridin-4-yl)benzyl)-3,5-dimethylpiperazin-1-yl)methyl)benzamide |
| 485 | 4-(((3R,5S)-4-(2-(1-ethyl-1,2,3,6-tetrahydropyridin-4-yl)benzyl)-3,5-dimethylpiperazin-1-yl)methyl)-N-hydroxybenzamide |
| 696 | 4-(((3R,5S)-3,5-dimethyl-4-(3-(morpholinomethyl)benzyl)piperazin-1-yl)methyl)-3-fluoro-N-hydroxybenzamide |
| 813 | 4-(((3R,5S)-4-benzyl-3,5-dimethylpiperazin-1-yl)methyl)-3-fluoro-N-hydroxybenzamide. |

8. A pharmaceutical composition comprising a compound represented by formula I, stereoisomer thereof or pharmaceutically acceptable salt thereof according to claim 1.

* * * * *